United States Patent
Arya et al.

(10) Patent No.: US 12,398,385 B2
(45) Date of Patent: Aug. 26, 2025

(54) RNA-GUIDED NUCLEASES AND ACTIVE FRAGMENTS AND VARIANTS THEREOF AND METHODS OF USE

(71) Applicant: Life Edit Therapeutics, Inc., Durham, NC (US)

(72) Inventors: Gunjan H. Arya, Cary, NC (US); Michael Coyle, Chapel Hill, NC (US); Alexandra Briner Crawley, Cary, NC (US); Tedd D. Elich, Durham, NC (US); Joel S. Parker, Apex, NC (US)

(73) Assignee: Life Edit Therapeutics, Inc., Durham, NC (US)

( * ) Notice: Subject to any disclaimer, the term of this patent is extended or adjusted under 35 U.S.C. 154(b) by 0 days.

(21) Appl. No.: 18/781,694

(22) Filed: Jul. 23, 2024

(65) Prior Publication Data

US 2024/0376455 A1 Nov. 14, 2024

Related U.S. Application Data

(63) Continuation of application No. PCT/IB2023/050560, filed on Jan. 23, 2023.

(60) Provisional application No. 63/386,061, filed on Dec. 5, 2022, provisional application No. 63/302,271, filed on Jan. 24, 2022.

(51) Int. Cl.
| | |
|---|---|
| *C12N 15/62* | (2006.01) |
| *A61K 48/00* | (2006.01) |
| *C12N 9/12* | (2006.01) |
| *C12N 9/22* | (2006.01) |
| *C12N 9/78* | (2006.01) |
| *C12N 15/11* | (2006.01) |
| *C12N 15/63* | (2006.01) |
| *C12N 15/90* | (2006.01) |
| *A61K 38/00* | (2006.01) |

(52) U.S. Cl.
CPC .............. *C12N 9/22* (2013.01); *A61K 48/005* (2013.01); *C12N 9/1252* (2013.01); *C12N 9/1276* (2013.01); *C12N 9/78* (2013.01); *C12N 15/11* (2013.01); *C12N 15/111* (2013.01); *C12N 15/63* (2013.01); *C12N 15/907* (2013.01); *A61K 38/00* (2013.01); *C12N 2310/20* (2017.05); *C12Y 305/04001* (2013.01); *C12Y 305/04002* (2013.01)

(58) Field of Classification Search
CPC ........ C12N 9/22; C12N 15/11; C12N 15/113; C12N 2310/20; C12Y 305/04004; C12Y 305/04005; C12Y 305/04001; C12Y 207/07049; C12Y 207/11
USPC ........................................................ 435/462
See application file for complete search history.

(56) References Cited

U.S. PATENT DOCUMENTS

2010/0192451 A1 8/2010 Ponnusamy et al.

FOREIGN PATENT DOCUMENTS

| WO | WO 2020/139783 A2 | 7/2020 |
|---|---|---|
| WO | WO 2022/150790 A2 | 7/2022 |

OTHER PUBLICATIONS

Database UniProtKB, Database Accession No. A0A413AJC9,"CRISPR-associated endonuclease Cas9", 2019, 4 pages.
Liu, L., et al., "Genome-Based Taxonomy of *Brevundimonas* with Reporting *Brevundimonas huaxiensis* sp. nov.," *Microbiology Spectrum*, 2021, vol. 9(1), pp. 1-12.
Lekota Kgaugelo Edward et al. "Whole genome sequencing and identification of Bacillus endophyticus and B. anthracis isolated from anthrax outbreaks in South Africa", BMC Microbiology, vol. 18, No. 1, Jul. 9, 2018 (Jul. 9, 2018), XP093228051, GB ISSN: 1471-2180, DOI: 10.1186/a12866-018-1205-9.

*Primary Examiner* — Robert B Mondesi
*Assistant Examiner* — Mohammad Y Meah
(74) *Attorney, Agent, or Firm* — Womble Bond Dickinson (US) LLP

(57) ABSTRACT

Compositions and methods for binding to a target sequence of interest are provided. The compositions find use in cleaving or modifying a target sequence of interest, visualization of a target sequence of interest, and modifying the expression of a sequence of interest. Compositions comprise RNA-guided nuclease (RGN) polypeptides, CRISPR RNAs, trans-activating CRISPR RNAs, guide RNAs, and nucleic acid molecules encoding the same. Vectors and host cells comprising the nucleic acid molecules are also provided. Further provided are RGN systems for binding a target sequence of interest, wherein the RGN system comprises an RNA-guided nuclease polypeptide and one or more guide RNAs.

29 Claims, 5 Drawing Sheets
Specification includes a Sequence Listing.

SEQUENCE LISTING

```
Sequence total quantity: 712
SEQ ID NO: 1            moltype = AA  length = 1055
FEATURE                 Location/Qualifiers
source                  1..1055
                        mol_type = protein
                        organism = Brevundimonas vesicularis
REGION                  1..1055
                        note = LPG10134
SEQUENCE: 1
MTTRLGLDVG TNSIGWALID KDSARIIDLG SRIFSDGRDP KSGASLAVDR REARAARRRR    60
DRYLGRRSAF LETLIQHGLM PERADDAKLV AAKDPYALRA RALDEPLEPH EIGRALFHLN   120
QRRGFKSNRK AERGRKENED GKIESGAKAL DTAMTVAKAR TLGEFLHTQN AKRVRMGGDN   180
QTYDFYPQRR HVETEFAVLW AAQKAHHPAL LTDAAEEALH RILFFQRDLK DQEVGLCTFA   240
GWNDVPENER RLPKTHPLFQ ERRLYEEVNH LKIVSPGAKD RDLTLAERDA VLLKLRDTRK   300
SSFSALGKLI KLGEGERFNK ESETRKDLLG DEVRAELADK KRFGARWTFF DIAEQLKIID   360
RIQNEADPEV LLDWLKAEYG LDDASAVAVS KARLPEGYGR FGETATRRLI DALKAQVVTY   420
DKAALAAGFH HSDRRTGEVW ERLPYYGQIL TTEIAPGKAE HGDDNERRFG KITNPTVHIE   480
LRQLEKLVNA VITVHGRPDE IVVELARELK LNEEDRKKHD ARIRRDTAAA IARGEKLEAE   540
GIPDTGANRH AMRMWEDLNP GNPLDRRCPY CAEVIGIRAL FSGEADIDHI IPYSQSLDDS   600
AGNKVVAHRH CNRAKGNKTP YERWGHDEAR WEIISAQVAR MHRSKQWRFG PEARERLEKE   660
GGFIARQLTD TQYLSRATAK YLSSLYTPDE GRRVYALPGR MTAMLRRLWG LNSLLPDHNF   720
VENEHSNAPK NRLDHRHHTI DGAVAAVTDA SLMQRIATVA ARAEENELDR LFEDLAPPWP   780
TFREELKERL ARVTVSHKPD HGRKGRPDRT RDVTAGRLHN DTAYGFTGQV AADGKTPIVV   840
HRVPFASLKP ADILDPTRIP DTALREALFE ATRDLTGKSY DQAMARFAKQ HPVFKGIRRV   900
RVREALNVIP IRSKEGRPYK AYKGDSNARY DVWRLPNGKW VTDIVSMFDA HSPEASDRRP   960
HPAAKKVLSL RQNDMLAIER DGGEAQIVRV VKFSRSGLIL AGQNEAGPLK ARDAAPNETD  1020
PFRYISASAS SLKRDNARQI RIDPLGRVFD PGPRD                            1055

SEQ ID NO: 2            moltype = AA  length = 1079
FEATURE                 Location/Qualifiers
source                  1..1079
                        mol_type = protein
                        organism = Bacillus endophyticus
REGION                  1..1079
                        note = LPG10136
SEQUENCE: 2
MKDLDYRIGL DIGTNSIGWS IIKLQFNDTT QRYEKSGIID LGVRMFDKAE IPKTGASLSE    60
PRRLARSSRR RLKRKSERKQ IIRRLLVDFD ILSQEELDHL FPLPKDSVDI WDIRLEGLER   120
VLNRFEWARL LLHLAQRRGF KSNRKSQRNE TETGKMLASI YDKNRLSAY  RTVGEMWMKD   180
KKFAQYDKRR NSPDEYIFNV SRDDLEKEIM TLFEAQRKFL SEYASEQLQE AYLKVWSHQL   240
```

```
PFASGNDILK KVGHCSLEKN ERRIPKATYT FQYFAALDKI NNLRLGDYVQ PLRQEQQKLL  300
LKKMFERIDF VKKKSIPIIK YSDLRKWLKL DESICFKGLT YNPNEKLSKV EKKEFINLKP  360
YYEMKKVISK HYEKHENIYE VADFDTFGYA LTIYKNDQDI RSYLRNSNNI GKKVYDEALI  420
EDLLNLSYTK FGHLSFKALQ NLIPIMEEGK SFVDATKELS YDTTGLKKTK KSRLLPPIPD  480
DITNPIVKRS LTQSRKVVNS IIKTYGPPLS IHIELARELS KDHEERRKIS KTQDENYRRN  540
KGAIEVLLEN GIINPKGYDI VRYKLWKEQR ECCAYSLKKI PADVFFSELR RERGSSPILE  600
VDHILPYSQS FMDSYHNKVL VYSDENRKKG DLIPYDYIKG EEQRWKDFES YVQTNNLFSK  660
KKREYLLKKE YTSRESDMVK ERHLNDTRYA TRFFKNFMEQ RLLFKEAKVS MKKRVQTVNG  720
IITSHFRSRW GLEKVREDTY LHHALDAVVV ACTDHHMVTR VTEYYKHKES SLKSRKPFFP  780
WPWKGFRDEL LTRLTSQPVP DKISEALQLG TSLPDYRIVS RMPKRSITGA AHKETIMMKG  840
GIDEKTGKTI IVKRVALKDI KFDKNGDFEM VGKEQDMATY TAIKERYLQH KKNAEKAFEK  900
PIYKPSKKGR GNPIKRVKVV FESKAFVREV NGGVANNEKL VRVDLFEKDG KYSMVPIYVM  960
DTVTEKLPDK IVTIGKGHHQ WRRLDESYTF LFSLHPYDLV RVRSEEADTF FYFGSIDINS  1020
NRIHFKHVNH PTKPNELRYA LGKIDLLEKY EIGLLGDIKQ VKKETRNTFH QPKKQLTME  1079

SEQ ID NO: 3          moltype = AA   length = 1081
FEATURE               Location/Qualifiers
source                1..1081
                      mol_type = protein
                      organism = Bacillus megaterium
REGION                1..1081
                      note = LPG10138
SEQUENCE: 3
MKNLDYRIGL DIGTNSVGWS VIELNFNQTT NRYEKVGIID FNVRMFNKAE IPKTGASLAE  60
PRRQFRSTRR QLKRKSIRKQ KIRKLLIAQD VISQQELDNL YPLSKGSVDI WDIRVEGLDR  120
YLNKIEWSRL LLHLAQRRGF KSNRKSDNQE TEQGKVLPII QENKQLLCSY RTVGEMWMKD  180
EKFATSDKRK NTNDNYLFNV SREDLKQEIQ LLFQQQRQFG SLYASEQTEK EYLDIWEHQL  240
PPFASGHDILK KVGYCSLEPK ERRIPKATYT FQYFTVIDKL NNLRLGSHFE PLTKDQRDIL  300
LQKIMERTDF INKKTIPSIR YSDIRKWLAL DDSIQFKGLI YEPNEKTQKI EKKEFVNLKP  360
YYEIKKVILL HSEKTGETYT NMDIDTIGYA LTVYKTDKDI RAYFRNSHNL SQKVFDDALI  420
DELLNLSYTK FGHLSIKALR RLLPYLEEGL SYAEAVNKVG YDTTNLKGKK KERLLPKIPD  480
DITNPIVKRS LTQARKVVNA IIRKYGSPLT VHIELARELS KNTNERKKLS KAQTKNYERN  540
QDAIAILVEN GILNPTGYDI VRYKLWKEQD ERCMYSLRKI PAEQFFAELR RERGSTPLLD  600
VDHILPYSQS FLDGYDNKVL VFSDENRKKG SRIPFYYLQE NPKKWLDFEA YVQSNEKLSK  660
KKRGYLVKKV YTARESDDVK ERHLNDTRYA TRFLKNFIEQ FLVFKEAQIP MKKRVQTLNG  720
RITSHFRSRW GFEKLREDTY LHHAVDAVVV ACTDQHMVNK VTDYYKSEQ SLKSNAPYFP  780
WPWERFRDEM LTRLHAQPVP DQIKQAITGY SPLSDYRLVS RMSKHSVTGA AHKETIMMNG  840
GENNKTGKTI IVKRMLLKEI KFDNNGDFKM VGKEQDPATY QAIKQRYLSY DKDAEKAFEK  900
PLYKPSKKGH SNLIKRVKVE IQEKTFVREV NGGVAENGDL VRIDLFKKED TYYMIPIYVL  960
DTSSPELPDH IVTSGKGYKL WKKLDESYTF QFSLTPYDLI RVKINEKDQF LYFSTIDISN  1020
NRIICKHVNK PSVPKECTYS LTKIEIIEKC KVGILSDVSF VKNEKRRSFG HPAKKVALQT  1080
R                                                                 1081

SEQ ID NO: 4          moltype = AA   length = 1081
FEATURE               Location/Qualifiers
source                1..1081
                      mol_type = protein
                      organism = Bacillus megaterium
REGION                1..1081
                      note = LPG10139
SEQUENCE: 4
MRNLDYRIGL DIGTNSVGWS VIELNFNQTT NRYEKVGIID FNVRMFNKAE IPKTGASLAE  60
PRRQFRSTRR QLKRKSIRKQ KIRQLLVTHD VISQQELDNL YPLSKGSIDI WDIRVEGLDR  120
YLNKIEWSRL LLHLAQRRGF KSNRKSDNQE TEQGKILPII QENKQLLCSY RTVGEMWMKD  180
EKFATSDKRK NTNDNYLFNV SREDLKREIQ LLFQQQRQFG SLYASEQTEK EYLDIWEHQL  240
PPFASGHDVLK KVGYCSLEPK ERRVPKATYT FQYFTVIDKL NNLRLGSHFE PLTKEQRDIL  300
LQKIMERTDF INKKTTPSIR YSDIRKWLTL DDSIQFKGLI YEPDEKTQKI EKKEFVNLKS  360
YYEIKKVILL HSEKTGETYT NMDLDTIGYA LTVYKTDKDI RAYLRNPHNL SQKVFDDVLI  420
DELLNLSYTK FGHLSIKALH RLLPYLEEGL SYAEAVNKVG YDTTNLKGKK KERLLPKIPD  480
DITNPVVKRS LTQARKVVNA IIRKYGSPLS VHIELARELS KNASERKKLS KAQTKNYERN  540
QGAIAILVEN GILNPTGYDI VRYKLWKEQD ERCMYSLRKI PSEQFFAELR RERGSTPLLD  600
VDHILPYSQS FLDGYDNKVL VFSDENRKKG DRIPFDYLQE NPKKWLDFEA YVQSNEKLSK  660
KKRGYLVKKV YTARESDDVK ERHLNDTRYA TRFLKNFIEQ FLFFKEAQIP MKKRVQTLNG  720
RITSHFRSRW GFKKIREDTY LHHAVDAVVV ACTDQHMVNK VTDYYKSEQ SLKSNAPYFP  780
WPWEGFRDEV LTRLHAQPVP DQIKQAITSY SPLPNYRLVS RMSKHSVTGA AHKETIMMNG  840
GENNKTGKTI IVKRMLLREI KFDDNGDFKM VGKEQDPATY QAIKQRYLSY DKDAKKAFDK  900
PLYKPSKKGH SNPIKRVKVE VQEKTFVREV NGGVAENGDL VRIDLFKKED TYYMIPIYVL  960
DTSSPELPDH IVTSGKGYKL WKKLDESYTF QFSLTPYDLI RVKINEKDQF LYFSTIDISN  1020
NRIICKHVNK PSVPKECTYS LTKIEVIEKC KVGILSDVSF VKNETRRSFG QPTKKVALQT  1080
R                                                                 1081

SEQ ID NO: 5          moltype = AA   length = 1103
FEATURE               Location/Qualifiers
source                1..1103
                      mol_type = protein
                      organism = Bosea thiooxidans
REGION                1..1103
                      note = LPG10141
SEQUENCE: 5
```

```
MDWRFGGDLG  TNSIGWAAAE  LVLVDGVWTP  KRVVAAGSRI  FSDGREPKSG  ASLAGARRDA    60
RAMRRRRDRF  KQRQAALLKY  LTLAGFFPSD  AEERRKLAEV  DPYELRARAL  DEALPHPHLG   120
RALFHLNQRR  GFKSNRKADR  GRNDDDSGKI  RIGVRELHAQ  MDAAGARTLG  EFLHGRRAGA   180
DQNAIPLVRT  RIVAHLAEDG  KASEAYNFYP  DRRMLEDEFE  AVWEAQIPHH  PDALTPERKA   240
QPFHEIIFHQR PLKEPKIGYC  TLRPPEPRLP  KAHPLFQRRR  LLEEVNALKI  VLPGAEARAL   300
EKPERDSLLS  KLAAKKTVAY  ASLRKALKLD  PDARFNKESD  NRKDMKGDEV  AAEMSHAKRF   360
GKAWLGMSPE  TQWQVVDRLR  QLESDEQVAD  FEAWLRERHG  LSHEQAQAVT  GARLPEGYGR   420
FGETATRALI  EALKEKVIVY  SEAVTEAGLG  HHSDFRDGQV  WQDEKGNPAL  PYYGEILERH   480
ILPGTADPAD  DDVVSRIGRL  TNPTVHIGLN  QLRRVLNTLI  RRYGPPLEIA  IELARELKLD   540
EERKREINTR  NRENREAAEK  RSKKLNELGQ  ADKGGNRALL  KLWEELNRDN  VLDRRCVYSG   600
RKISMEMLFS  GAVEVDHILP  FSATLDDSGG  NRILCLREVN  RIKRKRTPWE  AQADLRAHFG   660
PDAEWEAIAA  RAARLPKEKR  WRFEPDAIHR  FDAQGGFLAR  HLTDTQHLSR  LAREYLSALY   720
PERGEGSSHV  WVSPGRLTEM  LRRAWSLNHH  LPDHNLAGHA  SQPKNRKDHR  HHAIDAIVVA   780
VTDRSLLNRI  AREAGRHGHE  EASRVVADIP  EPWDGFSDEV  GRVLRSIVVS  HRPDHGTASK   840
AGLARQKDAT  AARLHNETAY  GLTGEKDARG  LDIVVTRKPL  SSFRKPADLD  AIRDEDLKRK   900
LKDWTAGKEG  GAFEQAMRAF  GHLERGPRSY  PGLRRIRVVE  PLSVIPIKDR  EGRAYKAYKG   960
DSNHRFDMWE  LTNGKWKDEV  VSMFEAHQRD  WVSPIRAANP  TARKVLSLQQ  NDVIAIEQED  1020
GRKLMRVVKF  SAGTLVLALP  QEAGSLKTRD  ADKDDPFRYV  YGSPSSLLRW  KARQVRIDEI  1080
GRVLDPGFPA  RKPRAGKTRG  EEA                                             1103

SEQ ID NO: 6            moltype = AA  length = 1130
FEATURE                 Location/Qualifiers
source                  1..1130
                        mol_type = protein
                        organism = unidentified
REGION                  1..1130
                        note = LPG10145
SEQUENCE: 6
MSKVAKNMTR  VNLGFDIGIA  SVGWSVLDNQ  TGKILETGVS  IFPSGSASRN  EERRSFRQSR    60
RLIRRKKARI  CDMDHLLKKN  GFPFPGNTGA  NPYEIRVKLG  TEKLSREELA  IALHHLVKRR   120
GISYDLKDVE  DESAGGTNYQ  ESIAVNQRLL  KKETPAEIQL  ARLTECGKVR  GQVKSLGEDN   180
TATTLLNVFP  NAAYQEEMVK  LLLKKQQEFYG EIDDPFMETA  IGILSRKREY  FIGPGSEKSR   240
TDYGIYRTDG  TTLKNLFEIL  VGKDKIFPDQ  YRAAGNSYTA  QLYNLLNDLN  NLEVDATEDG   300
KLTTAHKEQI  IEELTTTTGN  VNMLKLIAKV  AGTSPAGIKK  YRVDREGKEP  FHSLAIYRRL   360
RKKLGEAGFE  INEWPPEFFD  DYGPIVTLNT  ESGELRKWLA  EEGSRKYDFL  TEPVIEAILA   420
NKSAFDSVGK  NKWHRFSLKT  MQLLIPELLH  TFKEQMTILA  EMGLLHENKK  DYGDQNKVDV   480
KYLTENLYNP  VVRKSVKQAM  DIFNALFEKY  ANIDYVVIEM  PRDDAEDELE  QKKQFQKFQL   540
KNEKEKDASL  KEFQELAGVS  DLQLEAQLRK  RKKLRQKIRM  WYQQRGKCPY  SGKTIAAVDL   600
FHQDNQFEID  HIIPLSVSFD  DGQNNKVLCY  SEMNQEKGKQ  TPYAFMSRGG  GQGFSALQAY   660
VKSNNRLENA  KKRNLLFTED  INDLEVRRKF  IARNLVDTRY  ASRIVLNELQ  QFVRSKELDT   720
RVTVIRGKLT  SKLRDRWRLN  KSRETHHHHA  VDAAVIAVSP  MLKMWEKNAE  IIPLKVDENT   780
VDLKSGEIIT  DQEYAAQMYE  LPYARFLEQM  PELHKKIKPH  HQVDKKMNRK  VSDATLYSTR   840
KAKVGTDKKE  QEYVIGKIKD  IYQFDQYKKF  KKLYDGDKSK  FLMQRLDPQT  FAKLEKIMED   900
YPAKIDATQP  NGTIKLVDIS  PFELYRREHG  PVTKYAKKNN  GPAIKSLKFY  DSIVGSSVKI   960
TPKNAKGKEV  ILKSLKPWRT  DVYYNHEKEQ  YEIMGIKYAD  LKFKGDNYGI  TKARYQEIKE  1020
EEGVSEESEF  LFSLYRGDRI  QVSNGEDKID  LLFLSRSNPA  KKGYVELKPI  DRNQLNGKEV  1080
VSVYGAASGG  RLKKQFVKKN  HTLHKVNTDI  LGNPFYIKKE  SDQPKNILDL              1130

SEQ ID NO: 7            moltype = AA  length = 1158
FEATURE                 Location/Qualifiers
source                  1..1158
                        mol_type = protein
                        organism = Bifidobacterium thermacidophilum
REGION                  1..1158
                        note = LPG10146
SEQUENCE: 7
MTPLAKKGIS  MSDKTYRIGI  DVGLYSVGLS  AIQVNDDDDP  VRILNAQSVI  HDGGVDPNAQ    60
KSADSRRAQS  GIARRTRRMR  RNKKRLKRL  DQLLVESGFP  VSGENDLEGF  EPWLLRAQAA   120
DALIEDEDVR  KRAISVSCRH  IARHRGWRNP  YLDVRTLLTV  DSPSSAFYDK  LVENAALEMD   180
GQMPDSDAAP  AQIVRDVLEY  KRGGAAIRLR  KSTAENKKDR  FALFPEKMMQ  DDYAYELRLI   240
LAKQAVPKDI  ARKLILAVFQ  SQSPKGSAEK  RVGKDPLDPS  QPRALKASLA  FQEYRILNIL   300
TNLRLRDGGM  ERRLSIEEKQ  KLYKMLVEDT  GREKKYETWT  DIASAMEWKR  NWLKGVGSLT   360
ADGDDRVTSR  PPHIDIVEKL  NGIKDTKFRK  SILSWWKSAS  TANREAMIAL  LSNTVDIAKK   420
QDDPDFSSAV  DFIDSMDDND  LQIILDTISIQ PGRAAYSSRT  LRALSEQMYS  TDDDLHEARK   480
HVFGVDDSWC  PPQPAIGAPL  GNPSVDRVAK  IVNRWLLACQ  SRWGNPLSIQ  IEHVRDALSS   540
AATATADKRA  YERALGKRNA  EKMEIKNQLR  QQGLDEPHES  DIRRQEAITR  QQGKCLYCGD   600
DIKFSTCEMD  HIVPRKGPGS  TNTRDNFAAV  CITCNRQKSN  MPFAVWCQTP  EAKSRGVSLE   660
DAIQRVRGFF  TESKELKGRQ  AKAFISSMIM  RLKQTTADDP  IDSRSIESVA  WMADELHRRI   720
DWHFNGSTSE  SDHDRKVQVV  VYQGRITSEA  RNVMRFQADG  DFHFVGGHGK  TRLDRRHHAV   780
DASVIAMMTP  AAAHTLAERI  NIRDSQRFIG  RLEEDEVDWK  QWPSKPTEKY  QQWLNRGKRL   840
FVLINEALDN  DRIPITHWQR  YALGNSIAHD  ATIHPLQKIP  LGSAIDNESI  RRAATPALYC   900
ALTRCPEYSV  NDGLPENKQR  HITVNGKVYG  PEDEVEFFAS  TAAQIAIQGG  SADIGSAIHH   960
ARIYRCYTVN  GKVKRWFYG   MIRVFQTDLI  HARHDNLFAY  PLPPQSISMR  YAEPRTAQAV  1020
LDGRAEYLGN  LVVGDEIDIP  SGGKFTGQIK  TYLDFIEQLP  GNYKLVEKWS  VDGFMTNSKL  1080
RMHPLCLAGE  GLKKMEDILE  KEAPADVQKV  LIHPGWLPSV  DIVFSKNPQV  IRRNTLGEPR  1140
WKSRSGMPIS  WQVTGSEA                                                   1158

SEQ ID NO: 8            moltype = AA  length = 1268
FEATURE                 Location/Qualifiers
```

| source | 1..1268 |
| --- | --- |
| | mol_type = protein |
| | organism = unidentified |
| REGION | 1..1268 |
| | note = LPG10147 |

SEQUENCE: 8

```
MKQILGLDLG TNSIGWALVE IDENCTPLRI IAMGSRIIPL STDDRTQFER GQSISKNQDR    60
TIARTQRKGY DRKQLKKSDD FKYSLKKELK KYNIFPDVNL LNLPMLDLWK LRSDASSEPI   120
DAKQLGRILY MLNQKRGYKS ARSEANADKK DTDYVAEVKG RYSLLKESNL TIGQHFYKEL   180
SFANSNSSYY RIREQVYPRE AYIEEFDVIM NEQKKHHSFL TNDVIERLRD NIIYYQRKLK   240
SQKGLVSICD FEGFEKEIFD TKKQNKISF  VGPKVAPKTS PISQLCKIWE VVNTITLKVK   300
NPEGSKYKWS DRFPTIEEKK IISEHLSKNA LLSFNDLLKI LNLKKDEVYA NKQILKGIQG   360
NITFNEIHKI TGDTEWLDFN LISIESNEDA LLVDKKTGEI LEEKKRLLID ASFEKEPFYQ   420
LWHTIYSIKD LDECKSALVK RFDFTEEIAN KLSKIDFNKQ AFGNKSVKAM RKILPYLMQG   480
FDYSQACSLA GYNHSNSLTT EEKNQKELKD KLDLLPKNSL RQPVVEKIIN QMINVVNAII   540
GRYGKPNEIR VELARELKQS KDERDAADKS NSNNKKQNEM IAKRLESMGI SASKKYIQKY   600
KFIFPAKDKK WKEADVVNQC IYCGEHFNLS EALTGDNFDV DHIVPKALLF DDSQMNKVLV   660
HRHCNSSKLD KTAYDYLAAK GEQTLNSYLK RVDDWYARGI LSYGKMERLK VSFVEYQERK   720
KLKKETEADK KLWESFIDRQ LRETQYIAKK SRQILEQICQ NVTVTEGNVT AKLRKLWGWD   780
DVLMNLQMDK YRELGQTEWK EWTSEHGKRK HKKEEISNWT KRDDHRHHAI DALVIACTKQ   840
GFIQRINTLN ASDVKDEMQK DIEKSKIIFN EKLNTLDKYL VSQKPFTTAE VEKEADKVLI   900
SPKAGKKVAT ISKFKAKGKN IDTGVIVPRG ALHEQFVYGK NKRIMKTEQN LKYLFENTND   960
IVSSKIKTLV ESRINQFSGD IKLALSSLRK SPIYLDNNTK VLEKACYEI  ATVLKYPLST  1020
ITSKQVDDIV DKQVRELVRE RLFVFGNKEK EAFKDILWFN EAKQIPIKTV RIYARPDANS  1080
IRVVKRDENG KEIGFAVLGN NHHIAIYKDK EEKLVQHSCT FWHAVERKKN KLPVVISNTS  1140
ELWDSLDSSA LDQSFLEDLP EDGLKLSFSM QQNEMFILGM SQEEFNDALK TNDKAILSKH  1200
LYLVWSISES NYWFRHHLET KNSELKKTEG VKESKRLYNI RSLGALFTLN PIKVRTNHLG  1260
EIIQVGEY                                                          1268
```

| SEQ ID NO: 9 | moltype = AA length = 1395 |
| --- | --- |
| FEATURE | Location/Qualifiers |
| source | 1..1395 |
| | mol_type = protein |
| | organism = unidentified |
| REGION | 1..1395 |
| | note = LPG10150 |

SEQUENCE: 9

```
MAKNILGLDL GVSSIGWAVV QEDSKNPENN KIIKLGVRVN PLTVDEQLNF EKGKPITTNA    60
GRTLARSARR NLQRFKLRRV NLIDVLKKNN ILKETDLLTE VGKNSTFQTQ KIRAISARQK   120
IELSEFVRVL LLINKKRGYK SSRKAKNEED GQIIDGMSVA KKLYEENRTP GEYSYQLLQE   180
GKKQLPDFYR SDLQAEFDKI WNFQKQFNPE IFTNELYERL QGKNRNATWK ELEIPFSLVG   240
IKQIGTMQEK KMERYLWRSD AVKRQLDFET LAVVFQEINS NLNNSSGYLG AISDRSKELY   300
FNNQTVGEYL YNQLKINPHT KLKNQVFYRQ DYLDEFEKIW ETQAKYHKEL TKELKEEIRD   360
IVIFYQRKLK SQKGLISICE FENREIEITE NGKTKKKTIG LKVAPKSSPL FQEFKIWQVL   420
NNLQFQNLET KEIFPIDLDF KQSIFDEVNI KGKLSAKDVL DIVGYSGKEW KTNFKDIEGN   480
YTNENFYTAF LKIIASEGIE FPKEFKLTID DEIKVSKINA SAEIIKLFVK EKLSELGINT   540
SVSDFNPELD GSDFEKQASY QLWHLLYSYE GDDSPSGNEK LYELLEKKFG FKKEHSKILA   600
EIGFPQDYGS LSSKAMRKIY PYIKEHKYSD ACNYAGYNHS KNSLTKEQLE NRVLKEQLDI   660
LPKNSLRNPV VEKILNQMIN LVNEVSKEYG RPDEIRIELA RELKNNAEER ANMTSEISKA   720
TLLHQKYAEI LKKEFGIPVP SRNDIIRYKL YLELANNGFK DLYTDIQIKK EELFTDKYDI   780
DHIIPQSRFF DDSFSNKVLV PRGANLKKGN FTAFDYLEIE EKEKLEKFLN VIKELYDKGA   840
ITKAKYEKLQ KKGIEIGDGF IERDLRNTQY IAKKAKEILF GITNSVISTS GRITDKLRED   900
WNLINTMKEL NLEKYRKLGL TETVINSKGE EKQRIIDWTK RNDHRHHAMD ALTVAFTTHN   960
HIQYLNYLNA RKDEKHKEHQ NIFAIENLIT KVFEKKNGSK ERRFKEPIKN FRIDAKKHLD  1020
EVLISHKAKN KVVTKNINKI KKKGSVIAKT ELTPRGQLHK ETIYGSSKFL KTKEEKVSGK  1080
FDLETINKVQ NEKFRNALLL RLQEFDGDSK KAFTGKNVIS KNPIFLNKEK TEQLPETVTL  1140
AWYETAYTIR KVVNPDNFKD YKNIEKVIDK GVREVLMNRL KECNGNSKEA FSDLDKNPIW  1200
LNKSKGIAVK TVTINGINNA EALHYKKDHF GKEILDENGN KIAVDFVSTG NNHHVAIYED  1260
DRGNLQEKVV SFYEAVERVN QGLTIIDKDY NADLGWKFLF TMKQNEMFLF PSEDFNPKEI  1320
DFFFDEKNLGL ISKNLFRVQK IATKDYFFRH HLETTVEDNS ALKGITWRRE GLNGIREILK  1380
VRLNHLGKIV YIGEY                                                  1395
```

| SEQ ID NO: 10 | moltype = AA length = 1439 |
| --- | --- |
| FEATURE | Location/Qualifiers |
| source | 1..1439 |
| | mol_type = protein |
| | organism = Chryseobacterium geocarposphaerae |
| REGION | 1..1439 |
| | note = LPG10155 |

SEQUENCE: 10

```
MAKNILGLDL GTNSIGWALI NQDFDKKEGK ILGMGSRIIP MSQDILGEFG KGNSVSQTAT    60
RTDYRGVRRL RERFLLRRER LHRVLNILSF LPEHYASQID FEKRFGKFKE DTEPKLAYNK   120
NGFIFKNSFE EMLSDFKKHQ PQLLENDKKI PYDWTIYFLR NKALTQKIEK EELAWILLNF   180
NQKRGYYQLR GEEEEENPNK LVEFYFLKIV DVLADEPQKG KSDIWYSLIL ENGWIYRRSS   240
KIPLFNWKDK TRDFIVTTDL NDDGSIKTDK DGNEKRSFRA PSENDWTLVK KKTEQEIDQS   300
HKTVGTYIYE TLLQNPKQKI KGKLVRTIER KFYKDELKQI LEKQKEFHPE LQNDDLYSDC   360
IRELYRNNEA HQLTLSKKDL VHLLMEDIIF YQRPLRSQKS SISNCTLEFR KYKDENGGEH   420
TQYLKAIPKS NPYYQEFRIW QWMYNLNIYK KDDDTNVTKE FLSLTKDFEN LFEFLNSRKE   480
VDQKALLKHF KLNNKTHRWN FVEDKKYPCN ETRIMISSRL DKVENISEDF LTREIEQKIW   540
```

```
HIIYSVNDKV EYEKALKSFA NKNNLDEISF FEAFKKFPPF KSEYGSFSEK AIKKLLPLMR    600
LGKYWNYADI DKNSKDRIQK IINGEYDENI KDKVREKAVH LTAENDFQGL QLWSAQYIVY    660
ERHSEASMIG KWNSADDLEE FLKDFKQHSL RNSIVEQVIT ETLRVVKDIW LKYGNGAKDF    720
FNEIHIELGR EMKLPADDRK KLTNQISENE NTNLRIKALL AEMMNDHSVE NVRPFSPMQQ    780
EILKIYEDGV LNSGIEIEDE YLKISKTAQP SSSDLKRYKL WLEQKYKSPY TGQIIPLNKL    840
FTPEYEIEHI IPQSRYFDDS FSNKIICESA VNKLKDNYIG LGFIKQFGGT IVELGFGKSV    900
KVFEAAEEYED FVKKNYANNR SKRNKLLLED IPEKMIERQL NDTRHISKYI SGLLSNIVRV    960
EDGTDEGINS KNIVHGNGKI TTQLKDDWGL NDVWNELILP RFERMNQLTN STDFTAWNEN   1020
HQKYLPTVPI EYSKGFSKKR IDHRHHALDA LVIACATKDH VNLLNNQSAK SETKRYDLKV   1080
KLMKFEKVSY IHTQTGEKIE KEVPKQFLKP WENFTVEAKN SLEKIIVSFK QNLRVINKAT   1140
NYYEKYVEKD GLKIKERVEQ TATNWAIRKP MHKDTVSGKI DLPWVKVPKG KILTATRKAL   1200
DTSFDLKSIN SITDTGIQKI LKNYLDFKGS PELAFSPEGI EDLNKNIEKY NDGKPHQPIN   1260
KVRVFELGSK FQVGQTGNKK AKYVEAAKGT NLFFVVYEDK NGERSYETIP LNEIIERQKQ   1320
GLSVVDLRGT NDFYLCPNDL VYIPSGDKIE NKNNIDFGNL AKENIEKIYK VVSFSGGQIF   1380
FIRQDIATSI VNKAEFSTLN KMERAMDGSM VKELCIKLNV DRLGNFKSIV YDHPLHLHR    1439

SEQ ID NO: 11           moltype = AA  length = 1461
FEATURE                 Location/Qualifiers
source                  1..1461
                        mol_type = protein
                        organism = synthetic construct
REGION                  1..1461
                        note = LPG10159
SEQUENCE: 11
MTKTILGLDL GTNSIGWALI KQDFENKQGI ILGLGSRIIP MSQDILGEFG KGNALSQTAE     60
RTGYRSTRRI RERFLLRRER LHRVLNILGF LPAHYSAKID FEKAIGKFVN HSEPQICYDN    120
GFIFSASYEE MLHDFKQNYP DYFVDENGKP RLVPHAWTLY YLRKKATRHK ISKQELAWIL    180
LNFNQKRGYY QLRGEEEEEN QHRLVEFHSL RVVNVIADAQ KNNKGESWYS LTLENGWTYR    240
RSSKIPLDDW NGKVKDFIVT TDLNDDGSEK RDRDGEIKRT FRAPGPDDWS LLKKKTEFEI    300
EQSQETVGAY IYDSLLRDPK QKIKGKLVRT IERKFYKSEL KRILTKQAEF HPEFSDQDLL    360
TDCARELYRN NEQHRQQLES KDLIHLLMND IIFYQRPLRS QKSGIGRCSL EYKSYKAKDQ    420
HGHPLQDADG NVIEKRAYAP AIAKSNPYYQ EFRLLQWMSN LAFYQKDSDE SITAHLIPDI    480
ETYERLFDFL KERKEIKQDT LIKFLLGQKG LKGKDLTNES AKLRWNYVED KLYPCYETRA    540
LITSRLDKIS NLPQHFLTTE KELALWHILY SVNDKVEMEK ALKTFAEKNR LNEDEFVAAF    600
RKFPPIQSDY GSLSERAIKK LLPLMRFGSY WSWDLIDEYT KNRIDKVLTG EYDEKIKARV    660
REKAQHLSTE HDFQKLPLWL AQYIVYDRHA EAADLGKWTS IADLAQFISD FKQHSLRNPI    720
VEQIVTETLR VVKDIWMSYG AGAPDFFDEI HIELGREMKN PADERKRLTN AMTENENTNL    780
RIKSLLAELA YDQEIVNRVP YSPMQQELLK IYEEGVLNSG IAIDDDILKI SKTAQPSSAD    840
LKRYKLWLEQ KYRSPYTGLP IPLNQLFTPA YEIEHIIPQS LYFDDSMSNK VICESAVNKL    900
KDNKIGLSFI QAHQGQMVDC GFGKLVRISE VRDYEQFVEN CYAKNRSKRN KLLLTDIPEK    960
MIERQLNDTR YISKYITGLL SNIVRDNREN GKDDGVNSKY VLPGNGKVTS RLKQDWGLND   1020
VWNNLILPRF ERMNKLTNST SFTSWNENHQ KYLPTVPEL SKGFSKKRID HRHHAMDALV   1080
IACATRDHIN LLNNESAKNS VKRHDLNRKL RSYEKVTYAD ARSGAIIARE VPKGFLKPWN   1140
NFTADARTAL NDIVVSFKQN NRVINKATNY YESYTDEDGN LRLDKNNKPL KGLVAQKGTN   1200
WAIRKSLHKE TVSGKVNLPG IKLAKGKILT ATRKPLDASF NLKSILSITD TGIQKILQNY   1260
LKAKDNKSEI AFSPEGIDEL NQNIAFYNDG KQHQPIKKVR IFEQGSKFSL GETGTKSTKY   1320
VEAAKGTNLF FAIYADADGK RNYATIPLNI VIERQKQGLP SVPETNEKGN RLLFSLSPND   1380
LVMITPVDSD NWPVSDRIYK VMSFTGNQAF FIKHAVSTSI VNKGEFSTLN KSERSIEGLM   1440
IKEGCEKINL DRLGKIVKIE P                                             1461

SEQ ID NO: 12           moltype = AA  length = 1462
FEATURE                 Location/Qualifiers
source                  1..1462
                        mol_type = protein
                        organism = Chryseobacterium ureilyticum
REGION                  1..1462
                        note = LPG10160
SEQUENCE: 12
MFSQRNNPYC ELLFKIISTN IEEKIFTIIM GIHNSDVFFI SIFIWYHKII TMNKHILGLD     60
LGTNSIGWAL IKQNSESRQG SVLGMGTRVL PMSQDILGDF GKGNSVSQTA ARTGYRGVRR    120
LRERFLLRRE RLHRVLNILG FLPEYYASQI DFDKRFGKFR EETEPKLPYN NEGFIFKNSF    180
EEMLLDFKIS QSELLSGNKK VPYDWTIYYL RKKAVYQKIE KEELAWILLN FNQKRGYYQL    240
RGEDFDEEKD KTFVTLDVEK VIDSGEKIKE NVLFDVYFTN GWKYEKQITK PQDWIGRTKE    300
FIITESTLKN GDIKRTFKAV DSEKDWIAIK AKTEQEIDSS HKTVGSYIYD AILQNPKQKI    360
RGKLVRTIER KFYKEELKQI LEKQKEFYPE LQNNDLYNDC VRELYRNNEA HQLNLAKKDF    420
VHLFLEDIIF YQRPLRSQKS SVSNCTLEFR KYKDGNGVDR IQFLKVIPKS NPYYQEFRIW    480
QWMFNLSIYR RDDDINITSD HLKTIEDYER LFEFLNNRKE VDQKALLKHF KLNDKTHQWR    540
YVEDKRYPCN ETRAMIIACL GKTETNTVEF LTRKIEQEIW HIIYSVNDKT EYEKALKSFA    600
KKNHLDENSF FEVFRKFPPF ISEYGSYSEK AIKRLLPLMR TGKYWSWEDI DAKSKNRIQK    660
IITGEYDEDI KDNIREKTRT LQKESDFQGL PLWLAQYVVY GRHSEASLTG KWNSVDDIEE    720
YLREFKQHSL RNPIVEQVIT ETLRVVKDIW MKYGNGVKDF FSEIHIELAR EMKLPAKERN    780
KMTQRISENE NTNLRIKALL AEMVNDSEVR NVRPYSPMQQ EILKIYEDGV LNSEISMDDD    840
ILKISKTAQP SSSDLKKYKL WLEQKYRSPY TGEIIPLNKL FTPEYEIEHI IPQSRYFDDS    900
FTNKVICESA VNKLKDNYIG LGFIKQFHGY KISDRIKVFE VEEYEDFVKK NYSNNRTKRS    960
KLLLEEIPED MIERQLNDTR YISKFISGIL SNIVRKEVND DGVNSNDIIP SNGKITSELK   1020
QDWGLNDVWN ELILPRFERM NLLTKSNDYT VWNEKYQKPL PTVPIEFSKG FSKKRIDHRH   1080
HALDALVIAC ATRDHINLLN NQSAKSEMKR YDLKRKLMKF EKKIYQHPQT GEKIERDIPK   1140
QFLKPWEKFT VEAKDNLDKI IVSFKQNLRV INKATNHYEK WIEKDSIKVK GLVEQEGLNW   1200
AIRKPLHKDT VAGKVELPWI KVPRGKILTA TRKSLDTSFD LKNISSITDT GIQKILKNYL   1260
```

```
EYKGSSEEAF SPEGIEDMNR NIEKFNDGKP HQPIIKVRFF ELGSKFPLGQ IGNKKHKYVE    1320
TAKGTNLFFA VYEGDKDKRT YETISLNEVI ERQKQGLSPV ALKSKNDFYL CPNDLVYVAA    1380
EDELVDSFDF QTISKENINN VYKVVSFSGS QIFFVRQNVA VSIVNKTEFS TLNKMEKAVD    1440
GRMIKESCVK LKIDRLGNIT NS                                            1462

SEQ ID NO: 13              moltype = RNA   length = 25
FEATURE                    Location/Qualifiers
source                     1..25
                           mol_type = other RNA
                           organism = Brevundimonas vesicularis
misc_feature               1..25
                           note = LPG10134 crRNA
SEQUENCE: 13
gttgccgctg gccttcgatt tctga                                           25

SEQ ID NO: 14              moltype = RNA   length = 14
FEATURE                    Location/Qualifiers
source                     1..14
                           mol_type = other RNA
                           organism = Bacillus endophyticus
misc_feature               1..14
                           note = LPG10136 crRNA
SEQUENCE: 14
gtcatagttc cact                                                       14

SEQ ID NO: 15              moltype = RNA   length = 25
FEATURE                    Location/Qualifiers
source                     1..25
                           mol_type = other RNA
                           organism = Bacillus megaterium
misc_feature               1..25
                           note = LPG10138 crRNA
SEQUENCE: 15
gtcatagtcc catcatatcc attgc                                           25

SEQ ID NO: 16              moltype = RNA   length = 24
FEATURE                    Location/Qualifiers
source                     1..24
                           mol_type = other RNA
                           organism = Bacillus megaterium
misc_feature               1..24
                           note = LPG10139 crRNA
SEQUENCE: 16
gtcatagtcc catcatatcc attg                                            24

SEQ ID NO: 17              moltype = RNA   length = 25
FEATURE                    Location/Qualifiers
source                     1..25
                           mol_type = other RNA
                           organism = Bosea thiooxidans
misc_feature               1..25
                           note = LPG10141 crRNA
SEQUENCE: 17
gttgccgctg gaccgcgatc tctga                                           25

SEQ ID NO: 18              moltype = RNA   length = 24
FEATURE                    Location/Qualifiers
source                     1..24
                           mol_type = other RNA
                           organism = unidentified
misc_feature               1..24
                           note = LPG10145 crRNA
SEQUENCE: 18
gttttttgtac tctcaaggaa tcag                                           24

SEQ ID NO: 19              moltype = RNA   length = 20
FEATURE                    Location/Qualifiers
source                     1..20
                           mol_type = other RNA
                           organism = Bifidobacterium thermacidophilum
misc_feature               1..20
                           note = LPG10146 crRNA
SEQUENCE: 19
gctgagaatt agcatccttc                                                 20

SEQ ID NO: 20              moltype = RNA   length = 16
FEATURE                    Location/Qualifiers
source                     1..16
                           mol_type = other RNA
```

```
                        organism = unidentified
misc_feature            1..16
                        note = LPG10147 crRNA
SEQUENCE: 20
gttgtgaatt cctttc                                                          16

SEQ ID NO: 21           moltype = RNA   length = 16
FEATURE                 Location/Qualifiers
source                  1..16
                        mol_type = other RNA
                        organism = unidentified
misc_feature            1..16
                        note = LPG10150 crRNA
SEQUENCE: 21
gttgtgaatt gctttc                                                          16

SEQ ID NO: 22           moltype = RNA   length = 16
FEATURE                 Location/Qualifiers
source                  1..16
                        mol_type = other RNA
                        organism = Chryseobacterium geocarposphaerae
misc_feature            1..16
                        note = LPG10155 crRNA
SEQUENCE: 22
gttgtgaatt gctttc                                                          16

SEQ ID NO: 23           moltype = RNA   length = 15
FEATURE                 Location/Qualifiers
source                  1..15
                        mol_type = other RNA
                        organism = synthetic construct
misc_feature            1..15
                        note = LPG10159 crRNA
SEQUENCE: 23
gttgtgaatt gcttt                                                           15

SEQ ID NO: 24           moltype = RNA   length = 15
FEATURE                 Location/Qualifiers
source                  1..15
                        mol_type = other RNA
                        organism = Chryseobacterium ureilyticum
misc_feature            1..15
                        note = LPG10160 crRNA
SEQUENCE: 24
gttgtgattt gcttt                                                           15

SEQ ID NO: 25           moltype = RNA   length = 80
FEATURE                 Location/Qualifiers
source                  1..80
                        mol_type = other RNA
                        organism = Brevundimonas vesicularis
misc_feature            1..80
                        note = LPG10134 tracrRNA
SEQUENCE: 25
tgtcagaaat cgaaggctgg ctgttaacaa gcagctagac tgcaccaaat aagggcgggg          60
ctacggcccc gtcttttttt                                                      80

SEQ ID NO: 26           moltype = RNA   length = 89
FEATURE                 Location/Qualifiers
source                  1..89
                        mol_type = other RNA
                        organism = Bacillus endophyticus
misc_feature            1..89
                        note = LPG10136 tracrRNA
SEQUENCE: 26
acagcaatgg ctttgatgtt tctatgataa gggtttcgac ccgtggcgtt ggggatcgcc          60
tgcccatttc gatgggcgtc tccccattt                                            89

SEQ ID NO: 27           moltype = RNA   length = 102
FEATURE                 Location/Qualifiers
source                  1..102
                        mol_type = other RNA
                        organism = Bacillus megaterium
misc_feature            1..102
                        note = LPG10138 tracrRNA
SEQUENCE: 27
acagcaatgg atatgatgtt tctatgataa gggctctcta agagagacct gtggcgttgg          60
ggatcgcctg cccgtttcga cgggtgtctc cccatttcat tt                            102
```

-continued

```
SEQ ID NO: 28                moltype = RNA  length = 102
FEATURE                      Location/Qualifiers
source                       1..102
                             mol_type = other RNA
                             organism = Bacillus megaterium
misc_feature                 1..102
                             note = LPG10139 tracrRNA
SEQUENCE: 28
acagcaatgg atatgatgtt tctatgataa gggctctcta agagagacct gtggcgttgg    60
ggatcgcctg cccgtttcga cgggtgtctc cccatttcat tt                      102

SEQ ID NO: 29                moltype = RNA  length = 77
FEATURE                      Location/Qualifiers
source                       1..77
                             mol_type = other RNA
                             organism = Bosea thiooxidans
misc_feature                 1..77
                             note = LPG10141 tracrRNA
SEQUENCE: 29
tcagagatcg cggtctggct gttaacaagc agtcaagtct gcaccagata agggcgacgc    60
tccggcgtcg cctttt                                                   77

SEQ ID NO: 30                moltype = RNA  length = 85
FEATURE                      Location/Qualifiers
source                       1..85
                             mol_type = other RNA
                             organism = unidentified
misc_feature                 1..85
                             note = LPG10145 tracrRNA
SEQUENCE: 30
taccattact gattccttga gaatctacaa aaataaggct ttatgccgaa attcccactc    60
ttaacggagt gggttttta ttttt                                          85

SEQ ID NO: 31                moltype = RNA  length = 97
FEATURE                      Location/Qualifiers
source                       1..97
                             mol_type = other RNA
                             organism = Bifidobacterium thermacidophilum
misc_feature                 1..97
                             note = LPG10146 tracrRNA
SEQUENCE: 31
gaagaagcta attctcagta agtacagcaa tttatagctg tatctgaatg ctaagcggtt    60
agccgcaggg gagagcttcg gctctccccg ttctttt                            97

SEQ ID NO: 32                moltype = RNA  length = 76
FEATURE                      Location/Qualifiers
source                       1..76
                             mol_type = other RNA
                             organism = unidentified
misc_feature                 1..76
                             note = LPG10147 tracrRNA
SEQUENCE: 32
tttgtaacga aaggaattca caataaggat tattccgttg tgaaaacatt taaggtgggg    60
taactcgcct tttttt                                                   76

SEQ ID NO: 33                moltype = RNA  length = 72
FEATURE                      Location/Qualifiers
source                       1..72
                             mol_type = other RNA
                             organism = unidentified
misc_feature                 1..72
                             note = LPG10150 tracrRNA
SEQUENCE: 33
gaaagcaatt cacaataagg attattccgt tgtgaaaaca tttagcgcct cgcctatctg    60
cggggtattt tt                                                       72

SEQ ID NO: 34                moltype = RNA  length = 72
FEATURE                      Location/Qualifiers
source                       1..72
                             mol_type = other RNA
                             organism = Chryseobacterium geocarposphaerae
misc_feature                 1..72
                             note = LPG10155 tracrRNA
SEQUENCE: 34
gaaagcaatt cacaataagg attattccgt tgtgaaaaca tttagcgcct cgcctatctg    60
cggggtattt tt                                                       72

SEQ ID NO: 35                moltype = RNA  length = 75
FEATURE                      Location/Qualifiers
```

```
source                  1..75
                        mol_type = other RNA
                        organism = synthetic construct
misc_feature            1..75
                        note = LPG10159 tracrRNA
SEQUENCE: 35
gaaagcaatt cacaataagg attattccgt tgtgaaaaca tctagcgcct cgtctatcta    60
cggggcattt ttttt                                                    75

SEQ ID NO: 36           moltype = RNA  length = 88
FEATURE                 Location/Qualifiers
source                  1..88
                        mol_type = other RNA
                        organism = Chryseobacterium ureilyticum
misc_feature            1..88
                        note = LPG10160 tracrRNA
SEQUENCE: 36
taataatttt gaaaagcaat tcacaataag gattattccg ttgtgaaaac atttaagccc    60
cctcgtctta caatacgggg atttttttt                                     88

SEQ ID NO: 37           moltype = RNA  length = 104
FEATURE                 Location/Qualifiers
source                  1..104
                        mol_type = other RNA
                        organism = synthetic construct
misc_feature            1..104
                        note = LPG10134 sgRNA
SEQUENCE: 37
gttgccgctg gccttcgatt tctgaaaagt cagaaatcga aggctggctg ttaacaagca    60
gctagactgc accaaataag ggcggggcta cggccccgtc tttt                    104

SEQ ID NO: 38           moltype = RNA  length = 111
FEATURE                 Location/Qualifiers
source                  1..111
                        mol_type = other RNA
                        organism = synthetic construct
misc_feature            1..111
                        note = LPG10136 sgRNA
SEQUENCE: 38
gtcatagttc cactaaagcc attaaagaat ggctttgatg tttctatgat aagggtttcg    60
acccgtggcg ttggggatcg cctgcccatt tcgatgggcg tctccccatt t            111

SEQ ID NO: 39           moltype = RNA  length = 123
FEATURE                 Location/Qualifiers
source                  1..123
                        mol_type = other RNA
                        organism = synthetic construct
misc_feature            1..123
                        note = LPG10138 sgRNA
SEQUENCE: 39
gtcatagtcc catcatatcc attgcaaagg caatggatat gatgtttcta tgataagggc    60
tctctaagag agacctgtgg cgttggggat cgcctgcccg tttcgacggg tgtctcccca    120
ttt                                                                 123

SEQ ID NO: 40           moltype = RNA  length = 121
FEATURE                 Location/Qualifiers
source                  1..121
                        mol_type = other RNA
                        organism = synthetic construct
misc_feature            1..121
                        note = LPG10139 sgRNA
SEQUENCE: 40
gtcatagtcc catcatatcc attgaaagca atggatatga tgtttctatg ataagggctc    60
tctaagagag acctgtggcg ttggggatcg cctgcccgtt tcgacgggtg tctccccatt    120
t                                                                   121

SEQ ID NO: 41           moltype = RNA  length = 105
FEATURE                 Location/Qualifiers
source                  1..105
                        mol_type = other RNA
                        organism = synthetic construct
misc_feature            1..105
                        note = LPG10141 sgRNA
SEQUENCE: 41
gttgccgctg gaccgcgatc tctgaaaagt cagagatcgc ggtctggctg ttaacaagca    60
gtcaagtctg caccagataa gggcgacgct ccggcgtcgc ctttt                   105

SEQ ID NO: 42           moltype = RNA  length = 98
FEATURE                 Location/Qualifiers
```

```
source                       1..98
                             mol_type = other RNA
                             organism = synthetic construct
misc_feature                 1..98
                             note = LPG10145 sgRNA
SEQUENCE: 42
gttattgtac tctcaaggaa tcagaaagac tgattccttg agaatctaca ataataaggc    60
tttatgccga aattcccact cttaacggag tgggtttt                           98

SEQ ID NO: 43                moltype = RNA   length = 121
FEATURE                      Location/Qualifiers
source                       1..121
                             mol_type = other RNA
                             organism = synthetic construct
misc_feature                 1..121
                             note = LPG10146 sgRNA
SEQUENCE: 43
gctgagaatt agcatccttc aaaggaagaa gctaattctc agtaagtaca gcaattaata    60
gctgtatctg aatgctaagc ggttagccgc aggggagagc ttcggctctc ccgttctttt   120
t                                                                   121

SEQ ID NO: 44                moltype = RNA   length = 85
FEATURE                      Location/Qualifiers
source                       1..85
                             mol_type = other RNA
                             organism = synthetic construct
misc_feature                 1..85
                             note = LPG10147 sgRNA
SEQUENCE: 44
gttgtgaatt cctttcaaag gaaaggaatt cacaataagg attattccgt tgtgaaaaca    60
tttaaggtgg ggtaactcgc ctttt                                         85

SEQ ID NO: 45                moltype = RNA   length = 89
FEATURE                      Location/Qualifiers
source                       1..89
                             mol_type = other RNA
                             organism = synthetic construct
misc_feature                 1..89
                             note = LPG10150 sgRNA
SEQUENCE: 45
gttgtgaatt gctttaaaga aagcaattca caataaggat tattccgttg tgaaaacatc    60
tagcgcctcg tctatctacg gggcatttt                                     89

SEQ ID NO: 46                moltype = RNA   length = 89
FEATURE                      Location/Qualifiers
source                       1..89
                             mol_type = other RNA
                             organism = synthetic construct
misc_feature                 1..89
                             note = LPG10155 sgRNA
SEQUENCE: 46
gttgtgaatt gctttaaaga aagcaattca caataaggat tattccgttg tgaaaacatc    60
tagcgcctcg tctatctacg gggcatttt                                     89

SEQ ID NO: 47                moltype = RNA   length = 89
FEATURE                      Location/Qualifiers
source                       1..89
                             mol_type = other RNA
                             organism = synthetic construct
misc_feature                 1..89
                             note = LPG10159 sgRNA
SEQUENCE: 47
gttgtgaatt gctttaaaga aagcaattca caataaggat tattccgttg tgaaaacatc    60
tagcgcctcg tctatctacg gggcatttt                                     89

SEQ ID NO: 48                moltype = RNA   length = 91
FEATURE                      Location/Qualifiers
source                       1..91
                             mol_type = other RNA
                             organism = synthetic construct
misc_feature                 1..91
                             note = LPG10160 sgRNA
SEQUENCE: 48
gttgtgattt gctttaaaga aagcaattca caataaggat tattccgttg tgaaaacatt    60
taagccccct cgtcttacaa tacggggatt t                                  91

SEQ ID NO: 49                moltype = RNA   length = 134
FEATURE                      Location/Qualifiers
source                       1..134
```

```
                        mol_type = other RNA
                        organism = synthetic construct
misc_feature            1..134
                        note = LPG10134 sgRNA L1
SEQUENCE: 49
gttgccgctg gccttcgatt tctgaaaagt cagaaatcga aggctggctg ttaacaagca   60
gctagactgc accaaataag ggcggggcta cggccccgtc ttttgagcgg acagcagctt  120
cctatatctc gtac                                                    134

SEQ ID NO: 50           moltype = RNA  length = 111
FEATURE                 Location/Qualifiers
source                  1..111
                        mol_type = other RNA
                        organism = synthetic construct
misc_feature            1..111
                        note = LPG10136 sgRNA L1
SEQUENCE: 50
gtcatagttc cactaaagcc attaaagaat ggctttgatg tttctatgat aagggtttcg   60
acccgtggcg ttggggatcg cctgcccatt tcgatgggcg tctccccatt t           111

SEQ ID NO: 51           moltype = RNA  length = 123
FEATURE                 Location/Qualifiers
source                  1..123
                        mol_type = other RNA
                        organism = synthetic construct
misc_feature            1..123
                        note = LPG10138 sgRNA L1
SEQUENCE: 51
gtcatagtcc catcatatcc attgcaaagg caatggatat gatgtttcta tgataagggc   60
tctctaagag agacctgtgg cgttggggat cgcctgcccg tttcgacggg tgtctcccca  120
ttt                                                                123

SEQ ID NO: 52           moltype = RNA  length = 121
FEATURE                 Location/Qualifiers
source                  1..121
                        mol_type = other RNA
                        organism = synthetic construct
misc_feature            1..121
                        note = LPG10139 sgRNA L1
SEQUENCE: 52
gtcatagtcc catcatatcc attgaaagca atggatatga tgtttctatg ataagggctc   60
tctaagagag acctgtggcg ttggggatcg cctgcccgtt tcgacgggtg tctccccatt  120
t                                                                  121

SEQ ID NO: 53           moltype = RNA  length = 105
FEATURE                 Location/Qualifiers
source                  1..105
                        mol_type = other RNA
                        organism = synthetic construct
misc_feature            1..105
                        note = LPG10141 sgRNA L1
SEQUENCE: 53
gttgccgctg gaccgcgatc tctgaaaagt cagagatcgc ggtctggctg ttaacaagca   60
gtcaagtctg caccagataa gggcgacgct ccggcgtcgc ctttt                  105

SEQ ID NO: 54           moltype = RNA  length = 98
FEATURE                 Location/Qualifiers
source                  1..98
                        mol_type = other RNA
                        organism = synthetic construct
misc_feature            1..98
                        note = LPG10145 sgRNA L1
SEQUENCE: 54
gttattgtac tctcaaggaa tcagaaagac tgattccttg agaatctaca ataataaggc   60
tttatgccga aattcccact cttaacggag tgggtttt                          98

SEQ ID NO: 55           moltype = RNA  length = 121
FEATURE                 Location/Qualifiers
source                  1..121
                        mol_type = other RNA
                        organism = synthetic construct
misc_feature            1..121
                        note = LPG10146 sgRNA L1
SEQUENCE: 55
gctgagaatt agcatccttc aaaggaagaa gctaattctc agtaagtaca gcaattaata   60
gctgtatctg aatgctaagc ggttagccgc aggggagagc ttcggctctc cccgttcttt  120
t                                                                  121

SEQ ID NO: 56           moltype = RNA  length = 85
```

```
FEATURE              Location/Qualifiers
source               1..85
                     mol_type = other RNA
                     organism = synthetic construct
misc_feature         1..85
                     note = LPG10147 sgRNA L1
SEQUENCE: 56
gttgtgaatt cctttcaaag gaaaggaatt cacaataagg attattccgt tgtgaaaaca    60
tttaaggtgg ggtaactcgc ctttt                                         85

SEQ ID NO: 57        moltype = RNA   length = 89
FEATURE              Location/Qualifiers
source               1..89
                     mol_type = other RNA
                     organism = synthetic construct
misc_feature         1..89
                     note = LPG10150 sgRNA L1
SEQUENCE: 57
gttgtgaatt gctttaaaga aagcaattca caataaggat tattccgttg tgaaaacatc    60
tagcgcctcg tctatctacg gggcatttt                                     89

SEQ ID NO: 58        moltype = RNA   length = 89
FEATURE              Location/Qualifiers
source               1..89
                     mol_type = other RNA
                     organism = synthetic construct
misc_feature         1..89
                     note = LPG10155 sgRNA L1
SEQUENCE: 58
gttgtgaatt gctttaaaga aagcaattca caataaggat tattccgttg tgaaaacatc    60
tagcgcctcg tctatctacg gggcatttt                                     89

SEQ ID NO: 59        moltype = RNA   length = 89
FEATURE              Location/Qualifiers
source               1..89
                     mol_type = other RNA
                     organism = synthetic construct
misc_feature         1..89
                     note = LPG10159 sgRNA L1
SEQUENCE: 59
gttgtgaatt gctttaaaga aagcaattca caataaggat tattccgttg tgaaaacatc    60
tagcgcctcg tctatctacg gggcatttt                                     89

SEQ ID NO: 60        moltype = RNA   length = 91
FEATURE              Location/Qualifiers
source               1..91
                     mol_type = other RNA
                     organism = synthetic construct
misc_feature         1..91
                     note = LPG10160 sgRNA L1
SEQUENCE: 60
gttgtgatttgctttaaaga aagcaattca caataaggat tattccgttg tgaaaacatt    60
taagcccct cgtcttacaa tacggggatt t                                  91

SEQ ID NO: 61        moltype = RNA   length = 134
FEATURE              Location/Qualifiers
source               1..134
                     mol_type = other RNA
                     organism = synthetic construct
misc_feature         1..134
                     note = LPG10134 sgRNA L2
SEQUENCE: 61
ccatgatata gacgttgtgg ctgttgtagt gttgccgctg gccttcgatt tctgaaaagt    60
cagaaatcga aggctggctg ttaacaagca gctagactgc accaaataag gcgggggcta   120
cggccccgtc tttt                                                    134

SEQ ID NO: 62        moltype = RNA   length = 111
FEATURE              Location/Qualifiers
source               1..111
                     mol_type = other RNA
                     organism = synthetic construct
misc_feature         1..111
                     note = LPG10136 sgRNA L2
SEQUENCE: 62
gtcatagttc cactaaagcc attaaagaat ggctttgatg tttctatgat aagggtttcg    60
acccgtggcg ttggggatcg cctgcccatt tcgatgggcg tctccccatt t            111

SEQ ID NO: 63        moltype = RNA   length = 123
FEATURE              Location/Qualifiers
```

```
source                   1..123
                         mol_type = other RNA
                         organism = synthetic construct
misc_feature             1..123
                         note = LPG10138 sgRNA L2
SEQUENCE: 63
gtcatagtcc catcatatcc attgcaaagg caatggatat gatgtttcta tgataagggc    60
tctctaagag agacctgtgg cgttggggat cgcctgcccg tttcgacggg tgtctcccca   120
ttt                                                                 123

SEQ ID NO: 64            moltype = RNA   length = 121
FEATURE                  Location/Qualifiers
source                   1..121
                         mol_type = other RNA
                         organism = synthetic construct
misc_feature             1..121
                         note = LPG10139 sgRNA L2
SEQUENCE: 64
gtcatagtcc catcatatcc attgaaagca atggatatga tgtttctatg ataagggctc    60
tctaagagag acctgtggcg ttggggatcg cctgcccgtt tcgacgggtg tctcccatt    120
t                                                                   121

SEQ ID NO: 65            moltype = RNA   length = 105
FEATURE                  Location/Qualifiers
source                   1..105
                         mol_type = other RNA
                         organism = synthetic construct
misc_feature             1..105
                         note = LPG10141 sgRNA L2
SEQUENCE: 65
gttgccgctg gaccgcgatc tctgaaaagt cagagatcgc ggtctggctg ttaacaagca    60
gtcaagtctg caccagataa gggcgacgct ccggcgtcgc ctttt                   105

SEQ ID NO: 66            moltype = RNA   length = 98
FEATURE                  Location/Qualifiers
source                   1..98
                         mol_type = other RNA
                         organism = synthetic construct
misc_feature             1..98
                         note = LPG10145 sgRNA L2
SEQUENCE: 66
gttattgtac tctcaaggaa tcagaaagac tgattccttg agaatctaca ataataaggc    60
tttatgccga aattcccact cttaacggag tgggtttt                            98

SEQ ID NO: 67            moltype = RNA   length = 121
FEATURE                  Location/Qualifiers
source                   1..121
                         mol_type = other RNA
                         organism = synthetic construct
misc_feature             1..121
                         note = LPG10146 sgRNA L2
SEQUENCE: 67
gctgagaatt agcatccttc aaaggaagaa gctaattctc agtaagtaca gcaattaata    60
gctgtatctg aatgctaagc ggttagccgc aggggagagc ttcggctctc ccgttctttt   120
t                                                                   121

SEQ ID NO: 68            moltype = RNA   length = 85
FEATURE                  Location/Qualifiers
source                   1..85
                         mol_type = other RNA
                         organism = synthetic construct
misc_feature             1..85
                         note = LPG10147 sgRNA L2
SEQUENCE: 68
gttgtgaatt cctttcaaag gaaaggaatt cacaataagg attattccgt tgtgaaaaca    60
tttaaggtgg ggtaactcgc ctttt                                          85

SEQ ID NO: 69            moltype = RNA   length = 89
FEATURE                  Location/Qualifiers
source                   1..89
                         mol_type = other RNA
                         organism = synthetic construct
misc_feature             1..89
                         note = LPG10150 sgRNA L2
SEQUENCE: 69
gttgtgaatt gctttaaaga aagcaattca caataaggat tattccgttg tgaaaacatc    60
tagcgcctcg tctatctacg gggcatttt                                      89

SEQ ID NO: 70            moltype = RNA   length = 89
```

```
FEATURE                 Location/Qualifiers
source                  1..89
                        mol_type = other RNA
                        organism = synthetic construct
misc_feature            1..89
                        note = LPG10155 sgRNA L2
SEQUENCE: 70
gttgtgaatt gctttaaaga aagcaattca caataaggat tattccgttg tgaaaacatc   60
tagcgcctcg tctatctacg gggcatttt                                    89

SEQ ID NO: 71           moltype = RNA   length = 89
FEATURE                 Location/Qualifiers
source                  1..89
                        mol_type = other RNA
                        organism = synthetic construct
misc_feature            1..89
                        note = LPG10159 sgRNA L2
SEQUENCE: 71
gttgtgaatt gctttaaaga aagcaattca caataaggat tattccgttg tgaaaacatc   60
tagcgcctcg tctatctacg gggcatttt                                    89

SEQ ID NO: 72           moltype = RNA   length = 91
FEATURE                 Location/Qualifiers
source                  1..91
                        mol_type = other RNA
                        organism = synthetic construct
misc_feature            1..91
                        note = LPG10160 sgRNA L2
SEQUENCE: 72
gttgtgatttt gctttaaaga aagcaattca caataaggat tattccgttg tgaaaacatt  60
taagccccct cgtcttacaa tacggggatt t                                 91

SEQ ID NO: 73           moltype =       length =
SEQUENCE: 73
000

SEQ ID NO: 74           moltype =       length =
SEQUENCE: 74
000

SEQ ID NO: 75           moltype =       length =
SEQUENCE: 75
000

SEQ ID NO: 76           moltype =       length =
SEQUENCE: 76
000

SEQ ID NO: 77           moltype =       length =
SEQUENCE: 77
000

SEQ ID NO: 78           moltype =       length =
SEQUENCE: 78
000

SEQ ID NO: 79           moltype =       length =
SEQUENCE: 79
000

SEQ ID NO: 80           moltype =       length =
SEQUENCE: 80
000

SEQ ID NO: 81           moltype =       length =
SEQUENCE: 81
000

SEQ ID NO: 82           moltype =       length =
SEQUENCE: 82
000

SEQ ID NO: 83           moltype =       length =
SEQUENCE: 83
000

SEQ ID NO: 84           moltype =       length =
SEQUENCE: 84
000
```

```
SEQ ID NO: 85            moltype = DNA  length = 20
FEATURE                  Location/Qualifiers
source                   1..20
                         mol_type = other DNA
                         organism = Homo sapiens
misc_feature             1..20
                         note = ABCA4 target sequence
SEQUENCE: 85
gcagagtacc cacctctcca                                                    20

SEQ ID NO: 86            moltype = DNA  length = 20
FEATURE                  Location/Qualifiers
source                   1..20
                         mol_type = other DNA
                         organism = Homo sapiens
misc_feature             1..20
                         note = ABCA4 target sequence
SEQUENCE: 86
ggcgaactct gacacacagc                                                    20

SEQ ID NO: 87            moltype = DNA  length = 20
FEATURE                  Location/Qualifiers
source                   1..20
                         mol_type = other DNA
                         organism = Homo sapiens
misc_feature             1..20
                         note = ABCA4 target sequence
SEQUENCE: 87
gagttcgccc tggagaggtg                                                    20

SEQ ID NO: 88            moltype = DNA  length = 25
FEATURE                  Location/Qualifiers
source                   1..25
                         mol_type = other DNA
                         organism = Homo sapiens
misc_feature             1..25
                         note = ABCA4 target sequence
SEQUENCE: 88
gctgtgtgtc agagttcgcc ctgga                                              25

SEQ ID NO: 89            moltype = DNA  length = 20
FEATURE                  Location/Qualifiers
source                   1..20
                         mol_type = other DNA
                         organism = Homo sapiens
misc_feature             1..20
                         note = ABCA4 target sequence
SEQUENCE: 89
agagttcgcc ctggagaggt                                                    20

SEQ ID NO: 90            moltype = DNA  length = 20
FEATURE                  Location/Qualifiers
source                   1..20
                         mol_type = other DNA
                         organism = Homo sapiens
misc_feature             1..20
                         note = ABCA4 target sequence
SEQUENCE: 90
ggaagtagga ctgttggaaa                                                    20

SEQ ID NO: 91            moltype = DNA  length = 20
FEATURE                  Location/Qualifiers
source                   1..20
                         mol_type = other DNA
                         organism = Homo sapiens
misc_feature             1..20
                         note = ABCA4 target sequence
SEQUENCE: 91
gtttcagacg ctgctcaggt                                                    20

SEQ ID NO: 92            moltype = DNA  length = 25
FEATURE                  Location/Qualifiers
source                   1..25
                         mol_type = other DNA
                         organism = Homo sapiens
misc_feature             1..25
                         note = ABCA4 target sequence
SEQUENCE: 92
```

```
                                            -continued
ctacttccct gtttcagacg ctgct                                               25

SEQ ID NO: 93          moltype = DNA   length = 25
FEATURE                Location/Qualifiers
source                 1..25
                       mol_type = other DNA
                       organism = Homo sapiens
misc_feature           1..25
                       note = ABCA4 target sequence
SEQUENCE: 93
gtctgaaaca gggaagtagg actgt                                               25

SEQ ID NO: 94          moltype = DNA   length = 25
FEATURE                Location/Qualifiers
source                 1..25
                       mol_type = other DNA
                       organism = Homo sapiens
misc_feature           1..25
                       note = ABCA4 target sequence
SEQUENCE: 94
ggggtggggt ttgccccgtt tccaa                                               25

SEQ ID NO: 95          moltype = DNA   length = 25
FEATURE                Location/Qualifiers
source                 1..25
                       mol_type = other DNA
                       organism = Homo sapiens
misc_feature           1..25
                       note = ABCA4 target sequence
SEQUENCE: 95
gtgagagcat ctgggcccca cctgc                                               25

SEQ ID NO: 96          moltype = DNA   length = 20
FEATURE                Location/Qualifiers
source                 1..20
                       mol_type = other DNA
                       organism = Homo sapiens
misc_feature           1..20
                       note = ABCA4 target sequence
SEQUENCE: 96
gggcccacc tgctgaagag                                                      20

SEQ ID NO: 97          moltype = DNA   length = 20
FEATURE                Location/Qualifiers
source                 1..20
                       mol_type = other DNA
                       organism = Homo sapiens
misc_feature           1..20
                       note = ACADM target sequence
SEQUENCE: 97
gtgacagagc tggtttcaaa                                                     20

SEQ ID NO: 98          moltype = DNA   length = 25
FEATURE                Location/Qualifiers
source                 1..25
                       mol_type = other DNA
                       organism = Homo sapiens
misc_feature           1..25
                       note = ACADM target sequence
SEQUENCE: 98
ggtgacagag ctggtttcaa agttg                                               25

SEQ ID NO: 99          moltype = DNA   length = 20
FEATURE                Location/Qualifiers
source                 1..20
                       mol_type = other DNA
                       organism = Homo sapiens
misc_feature           1..20
                       note = ACADVL target sequence
SEQUENCE: 99
tttgcggtgg agaggggctt                                                     20

SEQ ID NO: 100         moltype = DNA   length = 20
FEATURE                Location/Qualifiers
source                 1..20
                       mol_type = other DNA
                       organism = Homo sapiens
misc_feature           1..20
                       note = ACADVL target sequence
```

```
SEQUENCE: 100
gtgagtgaat ttgggttggg                                                        20

SEQ ID NO: 101           moltype = DNA   length = 25
FEATURE                  Location/Qualifiers
source                   1..25
                         mol_type = other DNA
                         organism = Homo sapiens
misc_feature             1..25
                         note = ACADVL target sequence
SEQUENCE: 101
gcattaccca gtgagtgaat ttggg                                                  25

SEQ ID NO: 102           moltype = DNA   length = 25
FEATURE                  Location/Qualifiers
source                   1..25
                         mol_type = other DNA
                         organism = Homo sapiens
misc_feature             1..25
                         note = ACADVL target sequence
SEQUENCE: 102
agcagacatc ttcacggtct ttgcc                                                  25

SEQ ID NO: 103           moltype = DNA   length = 20
FEATURE                  Location/Qualifiers
source                   1..20
                         mol_type = other DNA
                         organism = Homo sapiens
misc_feature             1..20
                         note = ACADVL target sequence
SEQUENCE: 103
gaagatcaca gcttttgcgg                                                        20

SEQ ID NO: 104           moltype = DNA   length = 20
FEATURE                  Location/Qualifiers
source                   1..20
                         mol_type = other DNA
                         organism = Homo sapiens
misc_feature             1..20
                         note = ADSL target sequence
SEQUENCE: 104
gcatatccag gttgatgcct                                                        20

SEQ ID NO: 105           moltype = DNA   length = 20
FEATURE                  Location/Qualifiers
source                   1..20
                         mol_type = other DNA
                         organism = Homo sapiens
misc_feature             1..20
                         note = AGXT target sequence
SEQUENCE: 105
gcttcaggga actctgccac                                                        20

SEQ ID NO: 106           moltype = DNA   length = 20
FEATURE                  Location/Qualifiers
source                   1..20
                         mol_type = other DNA
                         organism = Homo sapiens
misc_feature             1..20
                         note = AGXT target sequence
SEQUENCE: 106
gaactctgcc acaggtgagc                                                        20

SEQ ID NO: 107           moltype = DNA   length = 20
FEATURE                  Location/Qualifiers
source                   1..20
                         mol_type = other DNA
                         organism = Homo sapiens
misc_feature             1..20
                         note = AGXT target sequence
SEQUENCE: 107
gaactctgcc acaggtgagc                                                        20

SEQ ID NO: 108           moltype = DNA   length = 25
FEATURE                  Location/Qualifiers
source                   1..25
                         mol_type = other DNA
                         organism = Homo sapiens
misc_feature             1..25
```

```
                            note = AGXT target sequence
SEQUENCE: 108
ggtggactgg agcacagctc agagc                                          25

SEQ ID NO: 109         moltype = DNA  length = 20
FEATURE                Location/Qualifiers
source                 1..20
                       mol_type = other DNA
                       organism = Homo sapiens
misc_feature           1..20
                       note = AGXT target sequence
SEQUENCE: 109
gcttcaggga actctgccac                                                20

SEQ ID NO: 110         moltype = DNA  length = 20
FEATURE                Location/Qualifiers
source                 1..20
                       mol_type = other DNA
                       organism = Homo sapiens
misc_feature           1..20
                       note = ALPL target sequence
SEQUENCE: 110
ggccttgagc cagggctgta                                                20

SEQ ID NO: 111         moltype = DNA  length = 20
FEATURE                Location/Qualifiers
source                 1..20
                       mol_type = other DNA
                       organism = Homo sapiens
misc_feature           1..20
                       note = ALPL target sequence
SEQUENCE: 111
gctggtaggc gatgtcctta                                                20

SEQ ID NO: 112         moltype = DNA  length = 20
FEATURE                Location/Qualifiers
source                 1..20
                       mol_type = other DNA
                       organism = Homo sapiens
misc_feature           1..20
                       note = ALPL target sequence
SEQUENCE: 112
ggccttgagc cagggctgta                                                20

SEQ ID NO: 113         moltype = DNA  length = 25
FEATURE                Location/Qualifiers
source                 1..25
                       mol_type = other DNA
                       organism = Homo sapiens
misc_feature           1..25
                       note = ALPL target sequence
SEQUENCE: 113
gtcccggtca gccgagtggg cgtag                                          25

SEQ ID NO: 114         moltype = DNA  length = 20
FEATURE                Location/Qualifiers
source                 1..20
                       mol_type = other DNA
                       organism = Homo sapiens
misc_feature           1..20
                       note = ARSA target sequence
SEQUENCE: 114
ggtggttcct atctggtcgt                                                20

SEQ ID NO: 115         moltype = DNA  length = 20
FEATURE                Location/Qualifiers
source                 1..20
                       mol_type = other DNA
                       organism = Homo sapiens
misc_feature           1..20
                       note = ARSA target sequence
SEQUENCE: 115
gataggaacc acccgggccc                                                20

SEQ ID NO: 116         moltype = DNA  length = 20
FEATURE                Location/Qualifiers
source                 1..20
                       mol_type = other DNA
                       organism = Homo sapiens
```

```
misc_feature          1..20
                      note = ARSA target sequence
SEQUENCE: 116
gaccagatag gaaccacccg                                                    20

SEQ ID NO: 117        moltype = DNA  length = 25
FEATURE               Location/Qualifiers
source                1..25
                      mol_type = other DNA
                      organism = Homo sapiens
misc_feature          1..25
                      note = ARSA target sequence
SEQUENCE: 117
ggcccggtg gttcctatct ggtcg                                               25

SEQ ID NO: 118        moltype = DNA  length = 25
FEATURE               Location/Qualifiers
source                1..25
                      mol_type = other DNA
                      organism = Homo sapiens
misc_feature          1..25
                      note = ARSA target sequence
SEQUENCE: 118
accagatagg aaccacccgg gccct                                              25

SEQ ID NO: 119        moltype = DNA  length = 20
FEATURE               Location/Qualifiers
source                1..20
                      mol_type = other DNA
                      organism = Homo sapiens
misc_feature          1..20
                      note = ARSA target sequence
SEQUENCE: 119
ggctggggga ctttgggagg                                                    20

SEQ ID NO: 120        moltype = DNA  length = 20
FEATURE               Location/Qualifiers
source                1..20
                      mol_type = other DNA
                      organism = Homo sapiens
misc_feature          1..20
                      note = BRCA1 target sequence
SEQUENCE: 120
gatgcctaga cagaggacaa                                                    20

SEQ ID NO: 121        moltype = DNA  length = 20
FEATURE               Location/Qualifiers
source                1..20
                      mol_type = other DNA
                      organism = Homo sapiens
misc_feature          1..20
                      note = BRCA1 target sequence
SEQUENCE: 121
acagaggaca atggcttcca                                                    20

SEQ ID NO: 122        moltype = DNA  length = 20
FEATURE               Location/Qualifiers
source                1..20
                      mol_type = other DNA
                      organism = Homo sapiens
misc_feature          1..20
                      note = BRCA1 target sequence
SEQUENCE: 122
gacaatggct tccatggtaa                                                    20

SEQ ID NO: 123        moltype = DNA  length = 20
FEATURE               Location/Qualifiers
source                1..20
                      mol_type = other DNA
                      organism = Homo sapiens
misc_feature          1..20
                      note = BRCA1 target sequence
SEQUENCE: 123
gcctagacag aggacaatgg                                                    20

SEQ ID NO: 124        moltype = DNA  length = 25
FEATURE               Location/Qualifiers
source                1..25
                      mol_type = other DNA
```

```
                          organism = Homo sapiens
misc_feature              1..25
                          note = BRCA1 target sequence
SEQUENCE: 124
gcctagacag aggacaatgg cttcc                                              25

SEQ ID NO: 125            moltype = DNA   length = 25
FEATURE                   Location/Qualifiers
source                    1..25
                          mol_type = other DNA
                          organism = Homo sapiens
misc_feature              1..25
                          note = BRCA1 target sequence
SEQUENCE: 125
ttgtcctctg tctaggcatc tggct                                              25

SEQ ID NO: 126            moltype = DNA   length = 20
FEATURE                   Location/Qualifiers
source                    1..20
                          mol_type = other DNA
                          organism = Homo sapiens
misc_feature              1..20
                          note = BRCA2 target sequence
SEQUENCE: 126
tgactcatac cctccaatga                                                    20

SEQ ID NO: 127            moltype = DNA   length = 25
FEATURE                   Location/Qualifiers
source                    1..25
                          mol_type = other DNA
                          organism = Homo sapiens
misc_feature              1..25
                          note = BRCA2 target sequence
SEQUENCE: 127
ggtggatgac tcatccctc caatg                                               25

SEQ ID NO: 128            moltype = DNA   length = 25
FEATURE                   Location/Qualifiers
source                    1..25
                          mol_type = other DNA
                          organism = Homo sapiens
misc_feature              1..25
                          note = BRCA2 target sequence
SEQUENCE: 128
ctgatggtgg atgactcata ccctc                                              25

SEQ ID NO: 129            moltype = DNA   length = 25
FEATURE                   Location/Qualifiers
source                    1..25
                          mol_type = other DNA
                          organism = Homo sapiens
misc_feature              1..25
                          note = BRCA2 target sequence
SEQUENCE: 129
ggatgactca taccctccaa tgatg                                              25

SEQ ID NO: 130            moltype = DNA   length = 25
FEATURE                   Location/Qualifiers
source                    1..25
                          mol_type = other DNA
                          organism = Homo sapiens
misc_feature              1..25
                          note = BRCA2 target sequence
SEQUENCE: 130
ctgatggtgg atgactcata ccctc                                              25

SEQ ID NO: 131            moltype = DNA   length = 20
FEATURE                   Location/Qualifiers
source                    1..20
                          mol_type = other DNA
                          organism = Homo sapiens
misc_feature              1..20
                          note = BRCA2 target sequence
SEQUENCE: 131
tgactcatac cctccaatga                                                    20

SEQ ID NO: 132            moltype = DNA   length = 20
FEATURE                   Location/Qualifiers
source                    1..20
```

```
                           mol_type = other DNA
                           organism = Homo sapiens
misc_feature               1..20
                           note = BRCA2 target sequence
SEQUENCE: 132
tcttcatgga gcagaactgg                                                     20

SEQ ID NO: 133             moltype = DNA  length = 20
FEATURE                    Location/Qualifiers
source                     1..20
                           mol_type = other DNA
                           organism = Homo sapiens
misc_feature               1..20
                           note = BRCA2 target sequence
SEQUENCE: 133
tcttcatgga gcagaactgg                                                     20

SEQ ID NO: 134             moltype = DNA  length = 20
FEATURE                    Location/Qualifiers
source                     1..20
                           mol_type = other DNA
                           organism = Homo sapiens
misc_feature               1..20
                           note = CBS target sequence
SEQUENCE: 134
gtccatcctc gcagagccgg                                                     20

SEQ ID NO: 135             moltype = DNA  length = 20
FEATURE                    Location/Qualifiers
source                     1..20
                           mol_type = other DNA
                           organism = Homo sapiens
misc_feature               1..20
                           note = CBS target sequence
SEQUENCE: 135
tcactggggt ggatcccgaa                                                     20

SEQ ID NO: 136             moltype = DNA  length = 20
FEATURE                    Location/Qualifiers
source                     1..20
                           mol_type = other DNA
                           organism = Homo sapiens
misc_feature               1..20
                           note = CBS target sequence
SEQUENCE: 136
ggtggatccc gaagggtcca                                                     20

SEQ ID NO: 137             moltype = DNA  length = 25
FEATURE                    Location/Qualifiers
source                     1..25
                           mol_type = other DNA
                           organism = Homo sapiens
misc_feature               1..25
                           note = CBS target sequence
SEQUENCE: 137
gttcagctcc tccggctctg cgagg                                               25

SEQ ID NO: 138             moltype = DNA  length = 25
FEATURE                    Location/Qualifiers
source                     1..25
                           mol_type = other DNA
                           organism = Homo sapiens
misc_feature               1..25
                           note = CBS target sequence
SEQUENCE: 138
ggctcaaggc cagcaaaagc cccgc                                               25

SEQ ID NO: 139             moltype = DNA  length = 25
FEATURE                    Location/Qualifiers
source                     1..25
                           mol_type = other DNA
                           organism = Homo sapiens
misc_feature               1..25
                           note = CBS target sequence
SEQUENCE: 139
gcagatcact ggggtggatc ccgaa                                               25

SEQ ID NO: 140             moltype = DNA  length = 25
FEATURE                    Location/Qualifiers
```

```
                                 source                       1..25
                                                              mol_type = other DNA
                                                              organism = Homo sapiens
                                 misc_feature                 1..25
                                                              note = CBS target sequence
SEQUENCE: 140
ctctgcagat cactggggtg gatcc                                                           25

SEQ ID NO: 141                   moltype = DNA   length = 20
FEATURE                          Location/Qualifiers
source                           1..20
                                                              mol_type = other DNA
                                                              organism = Homo sapiens
misc_feature                     1..20
                                                              note = CBS target sequence
SEQUENCE: 141
ccacccagt gatctgcaga                                                                  20

SEQ ID NO: 142                   moltype = DNA   length = 20
FEATURE                          Location/Qualifiers
source                           1..20
                                                              mol_type = other DNA
                                                              organism = Homo sapiens
misc_feature                     1..20
                                                              note = CBS target sequence
SEQUENCE: 142
ggtaggtcga gtccagagcc                                                                 20

SEQ ID NO: 143                   moltype = DNA   length = 20
FEATURE                          Location/Qualifiers
source                           1..20
                                                              mol_type = other DNA
                                                              organism = Homo sapiens
misc_feature                     1..20
                                                              note = CBS target sequence
SEQUENCE: 143
gctggacagg acggtaggtc                                                                 20

SEQ ID NO: 144                   moltype = DNA   length = 20
FEATURE                          Location/Qualifiers
source                           1..20
                                                              mol_type = other DNA
                                                              organism = Homo sapiens
misc_feature                     1..20
                                                              note = CBS target sequence
SEQUENCE: 144
ggatcagcta cgacttcatc                                                                 20

SEQ ID NO: 145                   moltype = DNA   length = 25
FEATURE                          Location/Qualifiers
source                           1..25
                                                              mol_type = other DNA
                                                              organism = Homo sapiens
misc_feature                     1..25
                                                              note = CBS target sequence
SEQUENCE: 145
gtcgtagctg atcccttcca cctcg                                                           25

SEQ ID NO: 146                   moltype = DNA   length = 20
FEATURE                          Location/Qualifiers
source                           1..20
                                                              mol_type = other DNA
                                                              organism = Homo sapiens
misc_feature                     1..20
                                                              note = CBS target sequence
SEQUENCE: 146
cagctacgac ttcatcccca                                                                 20

SEQ ID NO: 147                   moltype = DNA   length = 20
FEATURE                          Location/Qualifiers
source                           1..20
                                                              mol_type = other DNA
                                                              organism = Homo sapiens
misc_feature                     1..20
                                                              note = CFTR target sequence
SEQUENCE: 147
gtggagatca acgagcaaga                                                                 20

SEQ ID NO: 148                   moltype = DNA   length = 25
```

```
FEATURE                 Location/Qualifiers
source                  1..25
                        mol_type = other DNA
                        organism = Homo sapiens
misc_feature            1..25
                        note = CFTR target sequence
SEQUENCE: 148
acactgagtg gagatcaacg agcaa                                              25

SEQ ID NO: 149          moltype = DNA   length = 20
FEATURE                 Location/Qualifiers
source                  1..20
                        mol_type = other DNA
                        organism = Homo sapiens
misc_feature            1..20
                        note = CFTR target sequence
SEQUENCE: 149
taagagaggc tgtactgctt                                                    20

SEQ ID NO: 150          moltype = DNA   length = 20
FEATURE                 Location/Qualifiers
source                  1..20
                        mol_type = other DNA
                        organism = Homo sapiens
misc_feature            1..20
                        note = CFTR target sequence
SEQUENCE: 150
gaggaacact ctatcgcgat                                                    20

SEQ ID NO: 151          moltype = DNA   length = 25
FEATURE                 Location/Qualifiers
source                  1..25
                        mol_type = other DNA
                        organism = Homo sapiens
misc_feature            1..25
                        note = CFTR target sequence
SEQUENCE: 151
gtgttcctcc ttgttatccg ggtca                                              25

SEQ ID NO: 152          moltype = DNA   length = 20
FEATURE                 Location/Qualifiers
source                  1..20
                        mol_type = other DNA
                        organism = Homo sapiens
misc_feature            1..20
                        note = CFTR target sequence
SEQUENCE: 152
agcagtacag cctctcttac                                                    20

SEQ ID NO: 153          moltype = DNA   length = 20
FEATURE                 Location/Qualifiers
source                  1..20
                        mol_type = other DNA
                        organism = Homo sapiens
misc_feature            1..20
                        note = ELP1 target sequence
SEQUENCE: 153
gtacaatggc gcttacttgt                                                    20

SEQ ID NO: 154          moltype = DNA   length = 20
FEATURE                 Location/Qualifiers
source                  1..20
                        mol_type = other DNA
                        organism = Homo sapiens
misc_feature            1..20
                        note = ELP1 target sequence
SEQUENCE: 154
ggcgcttact tgtccaacca                                                    20

SEQ ID NO: 155          moltype = DNA   length = 25
FEATURE                 Location/Qualifiers
source                  1..25
                        mol_type = other DNA
                        organism = Homo sapiens
misc_feature            1..25
                        note = ELP1 target sequence
SEQUENCE: 155
ccgaatctga gctaaaacca gggct                                              25
```

```
SEQ ID NO: 156         moltype = DNA   length = 20
FEATURE                Location/Qualifiers
source                 1..20
                       mol_type = other DNA
                       organism = Homo sapiens
misc_feature           1..20
                       note = FAH target sequence
SEQUENCE: 156
gtgaatatct ggctgcactg                                                    20

SEQ ID NO: 157         moltype = DNA   length = 20
FEATURE                Location/Qualifiers
source                 1..20
                       mol_type = other DNA
                       organism = Homo sapiens
misc_feature           1..20
                       note = FAH target sequence
SEQUENCE: 157
gcccacgcag agcatccctg                                                    20

SEQ ID NO: 158         moltype = DNA   length = 20
FEATURE                Location/Qualifiers
source                 1..20
                       mol_type = other DNA
                       organism = Homo sapiens
misc_feature           1..20
                       note = FAH target sequence
SEQUENCE: 158
gtgaatatct ggctgcactg                                                    20

SEQ ID NO: 159         moltype = DNA   length = 25
FEATURE                Location/Qualifiers
source                 1..25
                       mol_type = other DNA
                       organism = Homo sapiens
misc_feature           1..25
                       note = FAH target sequence
SEQUENCE: 159
gggccggtga atatctggct gcact                                              25

SEQ ID NO: 160         moltype = DNA   length = 20
FEATURE                Location/Qualifiers
source                 1..20
                       mol_type = other DNA
                       organism = Homo sapiens
misc_feature           1..20
                       note = GJB2 target sequence
SEQUENCE: 160
tggccatgca cgtggcctac                                                    20

SEQ ID NO: 161         moltype = DNA   length = 20
FEATURE                Location/Qualifiers
source                 1..20
                       mol_type = other DNA
                       organism = Homo sapiens
misc_feature           1..20
                       note = GJB2 target sequence
SEQUENCE: 161
cgctcccagt ggccatgcac                                                    20

SEQ ID NO: 162         moltype = DNA   length = 20
FEATURE                Location/Qualifiers
source                 1..20
                       mol_type = other DNA
                       organism = Homo sapiens
misc_feature           1..20
                       note = GJB2 target sequence
SEQUENCE: 162
cgctcccagt ggccatgcac                                                    20

SEQ ID NO: 163         moltype = DNA   length = 25
FEATURE                Location/Qualifiers
source                 1..25
                       mol_type = other DNA
                       organism = Homo sapiens
misc_feature           1..25
                       note = GJB2 target sequence
SEQUENCE: 163
gccagcgctc ccagtggcca tgcac                                              25
```

```
SEQ ID NO: 164           moltype = DNA  length = 25
FEATURE                  Location/Qualifiers
source                   1..25
                         mol_type = other DNA
                         organism = Homo sapiens
misc_feature             1..25
                         note = GJB2 target sequence
SEQUENCE: 164
tgcatggcca ctgggagcgc tggcg                                          25

SEQ ID NO: 165           moltype = DNA  length = 25
FEATURE                  Location/Qualifiers
source                   1..25
                         mol_type = other DNA
                         organism = Homo sapiens
misc_feature             1..25
                         note = GJB2 target sequence
SEQUENCE: 165
tgcatggcca ctgggagcgc tggcg                                          25

SEQ ID NO: 166           moltype = DNA  length = 25
FEATURE                  Location/Qualifiers
source                   1..25
                         mol_type = other DNA
                         organism = Homo sapiens
misc_feature             1..25
                         note = GJB2 target sequence
SEQUENCE: 166
gccactggga gcgctggcgt ggaca                                          25

SEQ ID NO: 167           moltype = DNA  length = 20
FEATURE                  Location/Qualifiers
source                   1..20
                         mol_type = other DNA
                         organism = Homo sapiens
misc_feature             1..20
                         note = GJB2 target sequence
SEQUENCE: 167
gctcaccgtc ctcttcattt                                                20

SEQ ID NO: 168           moltype = DNA  length = 25
FEATURE                  Location/Qualifiers
source                   1..25
                         mol_type = other DNA
                         organism = Homo sapiens
misc_feature             1..25
                         note = GJB2 target sequence
SEQUENCE: 168
ggtgagctag atctttccaa tgctg                                          25

SEQ ID NO: 169           moltype = DNA  length = 25
FEATURE                  Location/Qualifiers
source                   1..25
                         mol_type = other DNA
                         organism = Homo sapiens
misc_feature             1..25
                         note = GJB2 target sequence
SEQUENCE: 169
gccacaacga ggatcataat gcgaa                                          25

SEQ ID NO: 170           moltype = DNA  length = 20
FEATURE                  Location/Qualifiers
source                   1..20
                         mol_type = other DNA
                         organism = Homo sapiens
misc_feature             1..20
                         note = GJB2 target sequence
SEQUENCE: 170
ctagatcttt ccaatgctgg                                                20

SEQ ID NO: 171           moltype = DNA  length = 20
FEATURE                  Location/Qualifiers
source                   1..20
                         mol_type = other DNA
                         organism = Homo sapiens
misc_feature             1..20
                         note = GNE target sequence
SEQUENCE: 171
```

```
cgtgctggca gcacccagca                                                    20

SEQ ID NO: 172           moltype = DNA  length = 20
FEATURE                  Location/Qualifiers
source                   1..20
                         mol_type = other DNA
                         organism = Homo sapiens
misc_feature             1..20
                         note = GNE target sequence
SEQUENCE: 172
gacatggacc ttctctccag                                                    20

SEQ ID NO: 173           moltype = DNA  length = 25
FEATURE                  Location/Qualifiers
source                   1..25
                         mol_type = other DNA
                         organism = Homo sapiens
misc_feature             1..25
                         note = GNE target sequence
SEQUENCE: 173
gagagaaggt ccatgtctgt tcctg                                              25

SEQ ID NO: 174           moltype = DNA  length = 25
FEATURE                  Location/Qualifiers
source                   1..25
                         mol_type = other DNA
                         organism = Homo sapiens
misc_feature             1..25
                         note = GNE target sequence
SEQUENCE: 174
tgctgccagc acggttctgg actac                                              25

SEQ ID NO: 175           moltype = DNA  length = 20
FEATURE                  Location/Qualifiers
source                   1..20
                         mol_type = other DNA
                         organism = Homo sapiens
misc_feature             1..20
                         note = GNE target sequence
SEQUENCE: 175
cgtgctggca gcacccagca                                                    20

SEQ ID NO: 176           moltype = DNA  length = 20
FEATURE                  Location/Qualifiers
source                   1..20
                         mol_type = other DNA
                         organism = Homo sapiens
misc_feature             1..20
                         note = IDUA target sequence
SEQUENCE: 176
gctctaggcc gaagtgtcgc                                                    20

SEQ ID NO: 177           moltype = DNA  length = 20
FEATURE                  Location/Qualifiers
source                   1..20
                         mol_type = other DNA
                         organism = Homo sapiens
misc_feature             1..20
                         note = IDUA target sequence
SEQUENCE: 177
ggacagcaac cacacggtgg                                                    20

SEQ ID NO: 178           moltype = DNA  length = 20
FEATURE                  Location/Qualifiers
source                   1..20
                         mol_type = other DNA
                         organism = Homo sapiens
misc_feature             1..20
                         note = IDUA target sequence
SEQUENCE: 178
gctctaggcc gaagtgtcgc                                                    20

SEQ ID NO: 179           moltype = DNA  length = 25
FEATURE                  Location/Qualifiers
source                   1..25
                         mol_type = other DNA
                         organism = Homo sapiens
misc_feature             1..25
                         note = IDUA target sequence
```

```
SEQUENCE: 179
ggagcagctc taggccgaag tgtcg                                              25

SEQ ID NO: 180           moltype = DNA   length = 25
FEATURE                  Location/Qualifiers
source                   1..25
                         mol_type = other DNA
                         organism = Homo sapiens
misc_feature             1..25
                         note = IDUA target sequence
SEQUENCE: 180
gctctaggcc gaagtgtcgc aggcc                                              25

SEQ ID NO: 181           moltype = DNA   length = 20
FEATURE                  Location/Qualifiers
source                   1..20
                         mol_type = other DNA
                         organism = Homo sapiens
misc_feature             1..20
                         note = IDUA target sequence
SEQUENCE: 181
taggccgaag tgtcgcaggc                                                    20

SEQ ID NO: 182           moltype = DNA   length = 20
FEATURE                  Location/Qualifiers
source                   1..20
                         mol_type = other DNA
                         organism = Homo sapiens
misc_feature             1..20
                         note = LDLR target sequence
SEQUENCE: 182
gggcaaccgg aagaccatct                                                    20

SEQ ID NO: 183           moltype = DNA   length = 20
FEATURE                  Location/Qualifiers
source                   1..20
                         mol_type = other DNA
                         organism = Homo sapiens
misc_feature             1..20
                         note = LDLR target sequence
SEQUENCE: 183
gagtcaaccc agtagaggcg                                                    20

SEQ ID NO: 184           moltype = DNA   length = 25
FEATURE                  Location/Qualifiers
source                   1..25
                         mol_type = other DNA
                         organism = Homo sapiens
misc_feature             1..25
                         note = LDLR target sequence
SEQUENCE: 184
caacgagggc aaccggaaga ccatc                                              25

SEQ ID NO: 185           moltype = DNA   length = 25
FEATURE                  Location/Qualifiers
source                   1..25
                         mol_type = other DNA
                         organism = Homo sapiens
misc_feature             1..25
                         note = LDLR target sequence
SEQUENCE: 185
atcgatgtca acgagggcaa ccgga                                              25

SEQ ID NO: 186           moltype = DNA   length = 20
FEATURE                  Location/Qualifiers
source                   1..20
                         mol_type = other DNA
                         organism = Homo sapiens
misc_feature             1..20
                         note = LDLR target sequence
SEQUENCE: 186
gggcaaccgg aagaccatct                                                    20

SEQ ID NO: 187           moltype = DNA   length = 20
FEATURE                  Location/Qualifiers
source                   1..20
                         mol_type = other DNA
                         organism = Homo sapiens
misc_feature             1..20
```

```
                              note = MEFV target sequence
SEQUENCE: 187
cagctctgta gtccacgaag                                              20

SEQ ID NO: 188        moltype = DNA   length = 20
FEATURE               Location/Qualifiers
source                1..20
                      mol_type = other DNA
                      organism = Homo sapiens
misc_feature          1..20
                      note = MEFV target sequence
SEQUENCE: 188
gatgcccaca cgcttgggag                                              20

SEQ ID NO: 189        moltype = DNA   length = 25
FEATURE               Location/Qualifiers
source                1..25
                      mol_type = other DNA
                      organism = Homo sapiens
misc_feature          1..25
                      note = MEFV target sequence
SEQUENCE: 189
actacagagc tggaagcatc tcctt                                        25

SEQ ID NO: 190        moltype = DNA   length = 25
FEATURE               Location/Qualifiers
source                1..25
                      mol_type = other DNA
                      organism = Homo sapiens
misc_feature          1..25
                      note = MEFV target sequence
SEQUENCE: 190
gagatgcttc cagctctgta gtcca                                        25

SEQ ID NO: 191        moltype = DNA   length = 25
FEATURE               Location/Qualifiers
source                1..25
                      mol_type = other DNA
                      organism = Homo sapiens
misc_feature          1..25
                      note = MEFV target sequence
SEQUENCE: 191
ggggcccaga gaaagagcag ctggc                                        25

SEQ ID NO: 192        moltype = DNA   length = 20
FEATURE               Location/Qualifiers
source                1..20
                      mol_type = other DNA
                      organism = Homo sapiens
misc_feature          1..20
                      note = MEFV target sequence
SEQUENCE: 192
gggctgaaga taggttgaag                                              20

SEQ ID NO: 193        moltype = DNA   length = 20
FEATURE               Location/Qualifiers
source                1..20
                      mol_type = other DNA
                      organism = Homo sapiens
misc_feature          1..20
                      note = MEFV target sequence
SEQUENCE: 193
ggacacatga tggagggaag                                              20

SEQ ID NO: 194        moltype = DNA   length = 25
FEATURE               Location/Qualifiers
source                1..25
                      mol_type = other DNA
                      organism = Homo sapiens
misc_feature          1..25
                      note = MEFV target sequence
SEQUENCE: 194
ccatcatgtg tcccagggct gaaga                                        25

SEQ ID NO: 195        moltype = DNA   length = 25
FEATURE               Location/Qualifiers
source                1..25
                      mol_type = other DNA
                      organism = Homo sapiens
```

```
misc_feature            1..25
                        note = MEFV target sequence
SEQUENCE: 195
gccccttcaa cctatcttca gccct                                              25

SEQ ID NO: 196          moltype = DNA  length = 25
FEATURE                 Location/Qualifiers
source                  1..25
                        mol_type = other DNA
                        organism = Homo sapiens
misc_feature            1..25
                        note = MEFV target sequence
SEQUENCE: 196
gccccttcaa cctatcttca gccct                                              25

SEQ ID NO: 197          moltype = DNA  length = 25
FEATURE                 Location/Qualifiers
source                  1..25
                        mol_type = other DNA
                        organism = Homo sapiens
misc_feature            1..25
                        note = MEFV target sequence
SEQUENCE: 197
ttccctccat catgtgtccc agggc                                              25

SEQ ID NO: 198          moltype = DNA  length = 20
FEATURE                 Location/Qualifiers
source                  1..20
                        mol_type = other DNA
                        organism = Homo sapiens
misc_feature            1..20
                        note = MVK target sequence
SEQUENCE: 198
gcatctccat ccactcagcc                                                    20

SEQ ID NO: 199          moltype = DNA  length = 20
FEATURE                 Location/Qualifiers
source                  1..20
                        mol_type = other DNA
                        organism = Homo sapiens
misc_feature            1..20
                        note = MVK target sequence
SEQUENCE: 199
gcatctccat ccactcagcc                                                    20

SEQ ID NO: 200          moltype = DNA  length = 25
FEATURE                 Location/Qualifiers
source                  1..25
                        mol_type = other DNA
                        organism = Homo sapiens
misc_feature            1..25
                        note = MVK target sequence
SEQUENCE: 200
ggtgccccecg gcatctccat ccact                                             25

SEQ ID NO: 201          moltype = DNA  length = 20
FEATURE                 Location/Qualifiers
source                  1..20
                        mol_type = other DNA
                        organism = Homo sapiens
misc_feature            1..20
                        note = MYBPC3 target sequence
SEQUENCE: 201
gggaggagac cttcaaatac                                                    20

SEQ ID NO: 202          moltype = DNA  length = 20
FEATURE                 Location/Qualifiers
source                  1..20
                        mol_type = other DNA
                        organism = Homo sapiens
misc_feature            1..20
                        note = MYBPC3 target sequence
SEQUENCE: 202
gaccagggag gagaccttca                                                    20

SEQ ID NO: 203          moltype = DNA  length = 20
FEATURE                 Location/Qualifiers
source                  1..20
                        mol_type = other DNA
```

```
                           organism = Homo sapiens
misc_feature               1..20
                           note = MYBPC3 target sequence
SEQUENCE: 203
gaccagggag gagaccttca                                                        20

SEQ ID NO: 204             moltype = DNA  length = 25
FEATURE                    Location/Qualifiers
source                     1..25
                           mol_type = other DNA
                           organism = Homo sapiens
misc_feature               1..25
                           note = MYBPC3 target sequence
SEQUENCE: 204
ggagaccttc aaataccggt tcaag                                                  25

SEQ ID NO: 205             moltype = DNA  length = 25
FEATURE                    Location/Qualifiers
source                     1..25
                           mol_type = other DNA
                           organism = Homo sapiens
misc_feature               1..25
                           note = MYBPC3 target sequence
SEQUENCE: 205
tggagctgac cagggaggag acctt                                                  25

SEQ ID NO: 206             moltype = DNA  length = 25
FEATURE                    Location/Qualifiers
source                     1..25
                           mol_type = other DNA
                           organism = Homo sapiens
misc_feature               1..25
                           note = MYBPC3 target sequence
SEQUENCE: 206
gtggagctga ccagggagga gacct                                                  25

SEQ ID NO: 207             moltype = DNA  length = 25
FEATURE                    Location/Qualifiers
source                     1..25
                           mol_type = other DNA
                           organism = Homo sapiens
misc_feature               1..25
                           note = MYBPC3 target sequence
SEQUENCE: 207
gtggagctga ccagggagga gacct                                                  25

SEQ ID NO: 208             moltype = DNA  length = 25
FEATURE                    Location/Qualifiers
source                     1..25
                           mol_type = other DNA
                           organism = Homo sapiens
misc_feature               1..25
                           note = MYBPC3 target sequence
SEQUENCE: 208
ggagctgacc agggaggaga ccttc                                                  25

SEQ ID NO: 209             moltype = DNA  length = 20
FEATURE                    Location/Qualifiers
source                     1..20
                           mol_type = other DNA
                           organism = Homo sapiens
misc_feature               1..20
                           note = MYBPC3 target sequence
SEQUENCE: 209
tgtccaaggt gagggggccc                                                        20

SEQ ID NO: 210             moltype = DNA  length = 20
FEATURE                    Location/Qualifiers
source                     1..20
                           mol_type = other DNA
                           organism = Homo sapiens
misc_feature               1..20
                           note = MYBPC3 target sequence
SEQUENCE: 210
gtgtctgtcc tgggctcggg                                                        20

SEQ ID NO: 211             moltype = DNA  length = 20
FEATURE                    Location/Qualifiers
source                     1..20
```

```
                        mol_type = other DNA
                        organism = Homo sapiens
misc_feature            1..20
                        note = MYBPC3 target sequence
SEQUENCE: 211
gggccctggt gtctgtcctg                                               20

SEQ ID NO: 212          moltype = DNA  length = 25
FEATURE                 Location/Qualifiers
source                  1..25
                        mol_type = other DNA
                        organism = Homo sapiens
misc_feature            1..25
                        note = MYBPC3 target sequence
SEQUENCE: 212
ggagcccgag cccaggacag acacc                                         25

SEQ ID NO: 213          moltype = DNA  length = 25
FEATURE                 Location/Qualifiers
source                  1..25
                        mol_type = other DNA
                        organism = Homo sapiens
misc_feature            1..25
                        note = MYBPC3 target sequence
SEQUENCE: 213
gccccctcac cttggacagt gagat                                         25

SEQ ID NO: 214          moltype = DNA  length = 20
FEATURE                 Location/Qualifiers
source                  1..20
                        mol_type = other DNA
                        organism = Homo sapiens
misc_feature            1..20
                        note = MYBPC3 target sequence
SEQUENCE: 214
tgtccaaggt gaggggggccc                                              20

SEQ ID NO: 215          moltype = DNA  length = 20
FEATURE                 Location/Qualifiers
source                  1..20
                        mol_type = other DNA
                        organism = Homo sapiens
misc_feature            1..20
                        note = MYH7 target sequence
SEQUENCE: 215
ggtgagcaca cctcgggact                                               20

SEQ ID NO: 216          moltype = DNA  length = 20
FEATURE                 Location/Qualifiers
source                  1..20
                        mol_type = other DNA
                        organism = Homo sapiens
misc_feature            1..20
                        note = MYH7 target sequence
SEQUENCE: 216
gaaacctcct cttgagatct                                               20

SEQ ID NO: 217          moltype = DNA  length = 20
FEATURE                 Location/Qualifiers
source                  1..20
                        mol_type = other DNA
                        organism = Homo sapiens
misc_feature            1..20
                        note = MYH7 target sequence
SEQUENCE: 217
gctgctggaa cgtaggtgag                                               20

SEQ ID NO: 218          moltype = DNA  length = 25
FEATURE                 Location/Qualifiers
source                  1..25
                        mol_type = other DNA
                        organism = Homo sapiens
misc_feature            1..25
                        note = MYH7 target sequence
SEQUENCE: 218
gtactccatt ctggtgagca cacct                                         25

SEQ ID NO: 219          moltype = DNA  length = 25
FEATURE                 Location/Qualifiers
```

```
source                      1..25
                            mol_type = other DNA
                            organism = Homo sapiens
misc_feature                1..25
                            note = MYH7 target sequence
SEQUENCE: 219
tactccattc tggtgagcac acctc                                              25

SEQ ID NO: 220              moltype = DNA  length = 25
FEATURE                     Location/Qualifiers
source                      1..25
                            mol_type = other DNA
                            organism = Homo sapiens
misc_feature                1..25
                            note = MYH7 target sequence
SEQUENCE: 220
gaggtgtgct caccagaatg gagta                                              25

SEQ ID NO: 221              moltype = DNA  length = 20
FEATURE                     Location/Qualifiers
source                      1..20
                            mol_type = other DNA
                            organism = Homo sapiens
misc_feature                1..20
                            note = MYH7 target sequence
SEQUENCE: 221
ccattctggt gagcacacct                                                    20

SEQ ID NO: 222              moltype = DNA  length = 20
FEATURE                     Location/Qualifiers
source                      1..20
                            mol_type = other DNA
                            organism = Homo sapiens
misc_feature                1..20
                            note = MYH7 target sequence
SEQUENCE: 222
ggtggagagc aagttggtca                                                    20

SEQ ID NO: 223              moltype = DNA  length = 20
FEATURE                     Location/Qualifiers
source                      1..20
                            mol_type = other DNA
                            organism = Homo sapiens
misc_feature                1..20
                            note = MYL2 target sequence
SEQUENCE: 223
gttcaaacag acccaaatcc                                                    20

SEQ ID NO: 224              moltype = DNA  length = 20
FEATURE                     Location/Qualifiers
source                      1..20
                            mol_type = other DNA
                            organism = Homo sapiens
misc_feature                1..20
                            note = MYL2 target sequence
SEQUENCE: 224
gggtctgttt gaacatggag                                                    20

SEQ ID NO: 225              moltype = DNA  length = 25
FEATURE                     Location/Qualifiers
source                      1..25
                            mol_type = other DNA
                            organism = Homo sapiens
misc_feature                1..25
                            note = MYL2 target sequence
SEQUENCE: 225
ggagaacacg ttggagttgg cgccc                                              25

SEQ ID NO: 226              moltype = DNA  length = 25
FEATURE                     Location/Qualifiers
source                      1..25
                            mol_type = other DNA
                            organism = Homo sapiens
misc_feature                1..25
                            note = MYL2 target sequence
SEQUENCE: 226
cccccggctc tcttctttgc tttct                                              25

SEQ ID NO: 227              moltype = DNA  length = 25
```

```
FEATURE                 Location/Qualifiers
source                  1..25
                        mol_type = other DNA
                        organism = Homo sapiens
misc_feature            1..25
                        note = MYL2 target sequence
SEQUENCE: 227
gctattgaat catccgcctg gatgg                                              25

SEQ ID NO: 228          moltype = DNA  length = 20
FEATURE                 Location/Qualifiers
source                  1..20
                        mol_type = other DNA
                        organism = Homo sapiens
misc_feature            1..20
                        note = MYL2 target sequence
SEQUENCE: 228
gttcaaacag acccaaatcc                                                    20

SEQ ID NO: 229          moltype = DNA  length = 20
FEATURE                 Location/Qualifiers
source                  1..20
                        mol_type = other DNA
                        organism = Homo sapiens
misc_feature            1..20
                        note = NPC1 target sequence
SEQUENCE: 229
ttacagccag taatgtcacc                                                    20

SEQ ID NO: 230          moltype = DNA  length = 20
FEATURE                 Location/Qualifiers
source                  1..20
                        mol_type = other DNA
                        organism = Homo sapiens
misc_feature            1..20
                        note = NPC1 target sequence
SEQUENCE: 230
ggtctgcagc acggtgtggt                                                    20

SEQ ID NO: 231          moltype = DNA  length = 25
FEATURE                 Location/Qualifiers
source                  1..25
                        mol_type = other DNA
                        organism = Homo sapiens
misc_feature            1..25
                        note = NPC1 target sequence
SEQUENCE: 231
cgacttacag ccagtaatgt caccg                                              25

SEQ ID NO: 232          moltype = DNA  length = 25
FEATURE                 Location/Qualifiers
source                  1..25
                        mol_type = other DNA
                        organism = Homo sapiens
misc_feature            1..25
                        note = NPC1 target sequence
SEQUENCE: 232
ccgacttaca gccagtaatg tcacc                                              25

SEQ ID NO: 233          moltype = DNA  length = 25
FEATURE                 Location/Qualifiers
source                  1..25
                        mol_type = other DNA
                        organism = Homo sapiens
misc_feature            1..25
                        note = NPC1 target sequence
SEQUENCE: 233
cccgacttac agccagtaat gtcac                                              25

SEQ ID NO: 234          moltype = DNA  length = 20
FEATURE                 Location/Qualifiers
source                  1..20
                        mol_type = other DNA
                        organism = Homo sapiens
misc_feature            1..20
                        note = PAH target sequence
SEQUENCE: 234
ggagaagaca gccatccaaa                                                    20
```

```
SEQ ID NO: 235            moltype = DNA   length = 25
FEATURE                   Location/Qualifiers
source                    1..25
                          mol_type = other DNA
                          organism = Homo sapiens
misc_feature              1..25
                          note = PAH target sequence
SEQUENCE: 235
cttctccccc tggagctgga gaaga                                               25

SEQ ID NO: 236            moltype = DNA   length = 20
FEATURE                   Location/Qualifiers
source                    1..20
                          mol_type = other DNA
                          organism = Homo sapiens
misc_feature              1..20
                          note = PAH target sequence
SEQUENCE: 236
ggacagtact cacggtttgg                                                     20

SEQ ID NO: 237            moltype = DNA   length = 20
FEATURE                   Location/Qualifiers
source                    1..20
                          mol_type = other DNA
                          organism = Homo sapiens
misc_feature              1..20
                          note = PAH target sequence
SEQUENCE: 237
gtactgtcct ccagctacca                                                     20

SEQ ID NO: 238            moltype = DNA   length = 20
FEATURE                   Location/Qualifiers
source                    1..20
                          mol_type = other DNA
                          organism = Homo sapiens
misc_feature              1..20
                          note = PAH target sequence
SEQUENCE: 238
gtactgtcct ccagctacca                                                     20

SEQ ID NO: 239            moltype = DNA   length = 25
FEATURE                   Location/Qualifiers
source                    1..25
                          mol_type = other DNA
                          organism = Homo sapiens
misc_feature              1..25
                          note = PAH target sequence
SEQUENCE: 239
gctggaggac agtactcacg gtttg                                               25

SEQ ID NO: 240            moltype = DNA   length = 25
FEATURE                   Location/Qualifiers
source                    1..25
                          mol_type = other DNA
                          organism = Homo sapiens
misc_feature              1..25
                          note = PAH target sequence
SEQUENCE: 240
cccccaaacc gtgagtactg tcctc                                               25

SEQ ID NO: 241            moltype = DNA   length = 25
FEATURE                   Location/Qualifiers
source                    1..25
                          mol_type = other DNA
                          organism = Homo sapiens
misc_feature              1..25
                          note = PAH target sequence
SEQUENCE: 241
acggtttggg ggtatacatg ggctt                                               25

SEQ ID NO: 242            moltype = DNA   length = 20
FEATURE                   Location/Qualifiers
source                    1..20
                          mol_type = other DNA
                          organism = Homo sapiens
misc_feature              1..20
                          note = PAH target sequence
SEQUENCE: 242
tgagaaactt cttccagctg                                                     20
```

```
SEQ ID NO: 243           moltype = DNA  length = 20
FEATURE                  Location/Qualifiers
source                   1..20
                         mol_type = other DNA
                         organism = Homo sapiens
misc_feature             1..20
                         note = PAH target sequence
SEQUENCE: 243
gccattgacc ctgatgtgga                                                    20

SEQ ID NO: 244           moltype = DNA  length = 25
FEATURE                  Location/Qualifiers
source                   1..25
                         mol_type = other DNA
                         organism = Homo sapiens
misc_feature             1..25
                         note = PAH target sequence
SEQUENCE: 244
gcaggaactg agaaacttct tccag                                              25

SEQ ID NO: 245           moltype = DNA  length = 25
FEATURE                  Location/Qualifiers
source                   1..25
                         mol_type = other DNA
                         organism = Homo sapiens
misc_feature             1..25
                         note = PAH target sequence
SEQUENCE: 245
ctgagaaact tcttccagct gggga                                              25

SEQ ID NO: 246           moltype = DNA  length = 25
FEATURE                  Location/Qualifiers
source                   1..25
                         mol_type = other DNA
                         organism = Homo sapiens
misc_feature             1..25
                         note = PAH target sequence
SEQUENCE: 246
aactgagaaa cttcttccag ctggg                                              25

SEQ ID NO: 247           moltype = DNA  length = 20
FEATURE                  Location/Qualifiers
source                   1..20
                         mol_type = other DNA
                         organism = Homo sapiens
misc_feature             1..20
                         note = PAH target sequence
SEQUENCE: 247
tgagaaactt cttccagctg                                                    20

SEQ ID NO: 248           moltype = DNA  length = 20
FEATURE                  Location/Qualifiers
source                   1..20
                         mol_type = other DNA
                         organism = Homo sapiens
misc_feature             1..20
                         note = PAH target sequence
SEQUENCE: 248
gctacaaccc atacacccaa                                                    20

SEQ ID NO: 249           moltype = DNA  length = 20
FEATURE                  Location/Qualifiers
source                   1..20
                         mol_type = other DNA
                         organism = Homo sapiens
misc_feature             1..20
                         note = PAH target sequence
SEQUENCE: 249
tgggttgtag cgaactgaga                                                    20

SEQ ID NO: 250           moltype = DNA  length = 20
FEATURE                  Location/Qualifiers
source                   1..20
                         mol_type = other DNA
                         organism = Homo sapiens
misc_feature             1..20
                         note = PAH target sequence
SEQUENCE: 250
```

```
gggttgtagc gaactgagaa                                               20

SEQ ID NO: 251         moltype = DNA   length = 25
FEATURE                Location/Qualifiers
source                 1..25
                       mol_type = other DNA
                       organism = Homo sapiens
misc_feature           1..25
                       note = PAH target sequence
SEQUENCE: 251
gcgaactgag aagggccgag gtatt                                         25

SEQ ID NO: 252         moltype = DNA   length = 25
FEATURE                Location/Qualifiers
source                 1..25
                       mol_type = other DNA
                       organism = Homo sapiens
misc_feature           1..25
                       note = PAH target sequence
SEQUENCE: 252
ctcagttcgc tacaacccat acacc                                         25

SEQ ID NO: 253         moltype = DNA   length = 20
FEATURE                Location/Qualifiers
source                 1..20
                       mol_type = other DNA
                       organism = Homo sapiens
misc_feature           1..20
                       note = PEX1 target sequence
SEQUENCE: 253
tactatccag ttacctgcca                                               20

SEQ ID NO: 254         moltype = DNA   length = 20
FEATURE                Location/Qualifiers
source                 1..20
                       mol_type = other DNA
                       organism = Homo sapiens
misc_feature           1..20
                       note = PEX1 target sequence
SEQUENCE: 254
gtaacccatc aatcttgtcc                                               20

SEQ ID NO: 255         moltype = DNA   length = 20
FEATURE                Location/Qualifiers
source                 1..20
                       mol_type = other DNA
                       organism = Homo sapiens
misc_feature           1..20
                       note = PEX1 target sequence
SEQUENCE: 255
gggttacatg aagttaggca                                               20

SEQ ID NO: 256         moltype = DNA   length = 25
FEATURE                Location/Qualifiers
source                 1..25
                       mol_type = other DNA
                       organism = Homo sapiens
misc_feature           1..25
                       note = PEX1 target sequence
SEQUENCE: 256
gtaacccatc aatcttgtcc caacc                                         25

SEQ ID NO: 257         moltype = DNA   length = 25
FEATURE                Location/Qualifiers
source                 1..25
                       mol_type = other DNA
                       organism = Homo sapiens
misc_feature           1..25
                       note = PEX1 target sequence
SEQUENCE: 257
agacctgggt tgggacaaga ttgat                                         25

SEQ ID NO: 258         moltype = DNA   length = 25
FEATURE                Location/Qualifiers
source                 1..25
                       mol_type = other DNA
                       organism = Homo sapiens
misc_feature           1..25
                       note = PEX1 target sequence
```

-continued

```
SEQUENCE: 258
taacccatca atcttgtccc aaccc                                              25

SEQ ID NO: 259           moltype = DNA  length = 20
FEATURE                  Location/Qualifiers
source                   1..20
                         mol_type = other DNA
                         organism = Homo sapiens
misc_feature             1..20
                         note = PEX1 target sequence
SEQUENCE: 259
ataaacctag agacctgggt                                                    20

SEQ ID NO: 260           moltype = DNA  length = 20
FEATURE                  Location/Qualifiers
source                   1..20
                         mol_type = other DNA
                         organism = Homo sapiens
misc_feature             1..20
                         note = PIK3CD target sequence
SEQUENCE: 260
gggcttcgtt aaacttcact                                                    20

SEQ ID NO: 261           moltype = DNA  length = 20
FEATURE                  Location/Qualifiers
source                   1..20
                         mol_type = other DNA
                         organism = Homo sapiens
misc_feature             1..20
                         note = PIK3CD target sequence
SEQUENCE: 261
ggccagccag ttcactttgg                                                    20

SEQ ID NO: 262           moltype = DNA  length = 20
FEATURE                  Location/Qualifiers
source                   1..20
                         mol_type = other DNA
                         organism = Homo sapiens
misc_feature             1..20
                         note = PIK3CD target sequence
SEQUENCE: 262
gtttaacgaa gccctccgtg                                                    20

SEQ ID NO: 263           moltype = DNA  length = 22
FEATURE                  Location/Qualifiers
source                   1..22
                         mol_type = other DNA
                         organism = Homo sapiens
misc_feature             1..22
                         note = PIK3CD target sequence
SEQUENCE: 263
gttgtgggcc agccagttca ct                                                 22

SEQ ID NO: 264           moltype = DNA  length = 25
FEATURE                  Location/Qualifiers
source                   1..25
                         mol_type = other DNA
                         organism = Homo sapiens
misc_feature             1..25
                         note = PIK3CD target sequence
SEQUENCE: 264
ggaaaaccaa agtgaactgg ctggc                                              25

SEQ ID NO: 265           moltype = DNA  length = 25
FEATURE                  Location/Qualifiers
source                   1..25
                         mol_type = other DNA
                         organism = Homo sapiens
misc_feature             1..25
                         note = PIK3CD target sequence
SEQUENCE: 265
taacgaagcc ctccgtgaga gctgg                                              25

SEQ ID NO: 266           moltype = DNA  length = 25
FEATURE                  Location/Qualifiers
source                   1..25
                         mol_type = other DNA
                         organism = Homo sapiens
misc_feature             1..25
```

```
                               note = PIK3CD target sequence
SEQUENCE: 266
gaggaggcac tgaagcactt ccgag                                           25

SEQ ID NO: 267         moltype = DNA  length = 20
FEATURE                Location/Qualifiers
source                 1..20
                       mol_type = other DNA
                       organism = Homo sapiens
misc_feature           1..20
                       note = PIK3CD target sequence
SEQUENCE: 267
acgaagccct ccgtgagagc                                                 20

SEQ ID NO: 268         moltype = DNA  length = 20
FEATURE                Location/Qualifiers
source                 1..20
                       mol_type = other DNA
                       organism = Homo sapiens
misc_feature           1..20
                       note = POLG target sequence
SEQUENCE: 268
gatctgacca atgatgcctg                                                 20

SEQ ID NO: 269         moltype = DNA  length = 25
FEATURE                Location/Qualifiers
source                 1..25
                       mol_type = other DNA
                       organism = Homo sapiens
misc_feature           1..25
                       note = POLG target sequence
SEQUENCE: 269
ggcaggcatc attggtcaga tccat                                           25

SEQ ID NO: 270         moltype = DNA  length = 20
FEATURE                Location/Qualifiers
source                 1..20
                       mol_type = other DNA
                       organism = Homo sapiens
misc_feature           1..20
                       note = POLG target sequence
SEQUENCE: 270
ggctcaccgc cagcaatgcc                                                 20

SEQ ID NO: 271         moltype = DNA  length = 20
FEATURE                Location/Qualifiers
source                 1..20
                       mol_type = other DNA
                       organism = Homo sapiens
misc_feature           1..20
                       note = POLG target sequence
SEQUENCE: 271
gggctgtgga gcccacatgg                                                 20

SEQ ID NO: 272         moltype = DNA  length = 25
FEATURE                Location/Qualifiers
source                 1..25
                       mol_type = other DNA
                       organism = Homo sapiens
misc_feature           1..25
                       note = POLG target sequence
SEQUENCE: 272
gcccgggtat gtgacctctg tacct                                           25

SEQ ID NO: 273         moltype = DNA  length = 20
FEATURE                Location/Qualifiers
source                 1..20
                       mol_type = other DNA
                       organism = Homo sapiens
misc_feature           1..20
                       note = POLG target sequence
SEQUENCE: 273
gtgctggcag tcaccacttg                                                 20

SEQ ID NO: 274         moltype = DNA  length = 20
FEATURE                Location/Qualifiers
source                 1..20
                       mol_type = other DNA
                       organism = Homo sapiens
```

```
misc_feature          1..20
                      note = PRKAG2 target sequence
SEQUENCE: 274
gtgtccaagc agcgccactg                                               20

SEQ ID NO: 275        moltype = DNA   length = 20
FEATURE               Location/Qualifiers
source                1..20
                      mol_type = other DNA
                      organism = Homo sapiens
misc_feature          1..20
                      note = PRKAG2 target sequence
SEQUENCE: 275
gcgctgcttg gacaccgttg                                               20

SEQ ID NO: 276        moltype = DNA   length = 20
FEATURE               Location/Qualifiers
source                1..20
                      mol_type = other DNA
                      organism = Homo sapiens
misc_feature          1..20
                      note = PRKAG2 target sequence
SEQUENCE: 276
gcgctgcttg gacaccgttg                                               20

SEQ ID NO: 277        moltype = DNA   length = 25
FEATURE               Location/Qualifiers
source                1..25
                      mol_type = other DNA
                      organism = Homo sapiens
misc_feature          1..25
                      note = PRKAG2 target sequence
SEQUENCE: 277
gacaccgttg gctaccaaag caaag                                         25

SEQ ID NO: 278        moltype = DNA   length = 25
FEATURE               Location/Qualifiers
source                1..25
                      mol_type = other DNA
                      organism = Homo sapiens
misc_feature          1..25
                      note = PRKAG2 target sequence
SEQUENCE: 278
cacagtggcg ctgcttggac accgt                                         25

SEQ ID NO: 279        moltype = DNA   length = 25
FEATURE               Location/Qualifiers
source                1..25
                      mol_type = other DNA
                      organism = Homo sapiens
misc_feature          1..25
                      note = PRKAG2 target sequence
SEQUENCE: 279
gcgctgcttg gacaccgttg gctac                                         25

SEQ ID NO: 280        moltype = DNA   length = 20
FEATURE               Location/Qualifiers
source                1..20
                      mol_type = other DNA
                      organism = Homo sapiens
misc_feature          1..20
                      note = PRKAG2 target sequence
SEQUENCE: 280
gtgtccaagc agcgccactg                                               20

SEQ ID NO: 281        moltype = DNA   length = 20
FEATURE               Location/Qualifiers
source                1..20
                      mol_type = other DNA
                      organism = Homo sapiens
misc_feature          1..20
                      note = SBDS target sequence
SEQUENCE: 281
gggtaacagc tgcagcatag                                               20

SEQ ID NO: 282        moltype = DNA   length = 20
FEATURE               Location/Qualifiers
source                1..20
                      mol_type = other DNA
```

```
                            organism = Homo sapiens
misc_feature                1..20
                            note = SBDS target sequence
SEQUENCE: 282
gggtaacagc tgcagcatag                                                20

SEQ ID NO: 283              moltype = DNA  length = 20
FEATURE                     Location/Qualifiers
source                      1..20
                            mol_type = other DNA
                            organism = Homo sapiens
misc_feature                1..20
                            note = SCN5A target sequence
SEQUENCE: 283
gctgaagttc tccaggatga                                                20

SEQ ID NO: 284              moltype = DNA  length = 20
FEATURE                     Location/Qualifiers
source                      1..20
                            mol_type = other DNA
                            organism = Homo sapiens
misc_feature                1..20
                            note = SCN5A target sequence
SEQUENCE: 284
ggggcttggt gctctcctcc                                                20

SEQ ID NO: 285              moltype = DNA  length = 20
FEATURE                     Location/Qualifiers
source                      1..20
                            mol_type = other DNA
                            organism = Homo sapiens
misc_feature                1..20
                            note = SCN5A target sequence
SEQUENCE: 285
gggagaaatt tgacccagag                                                20

SEQ ID NO: 286              moltype = DNA  length = 25
FEATURE                     Location/Qualifiers
source                      1..25
                            mol_type = other DNA
                            organism = Homo sapiens
misc_feature                1..25
                            note = SCN5A target sequence
SEQUENCE: 286
ggccacgctg aagttctcca ggatg                                          25

SEQ ID NO: 287              moltype = DNA  length = 25
FEATURE                     Location/Qualifiers
source                      1..25
                            mol_type = other DNA
                            organism = Homo sapiens
misc_feature                1..25
                            note = SCN5A target sequence
SEQUENCE: 287
gagatctggg agaaatttga cccag                                          25

SEQ ID NO: 288              moltype = DNA  length = 25
FEATURE                     Location/Qualifiers
source                      1..25
                            mol_type = other DNA
                            organism = Homo sapiens
misc_feature                1..25
                            note = SCN5A target sequence
SEQUENCE: 288
gaggagagca ccaagcccct gagtg                                          25

SEQ ID NO: 289              moltype = DNA  length = 20
FEATURE                     Location/Qualifiers
source                      1..20
                            mol_type = other DNA
                            organism = Homo sapiens
misc_feature                1..20
                            note = SERPINA1 target sequence
SEQUENCE: 289
gaaagggact gaagctgctg                                                20

SEQ ID NO: 290              moltype = DNA  length = 20
FEATURE                     Location/Qualifiers
source                      1..20
```

```
                            mol_type = other DNA
                            organism = Homo sapiens
misc_feature                1..20
                            note = SERPINA1 target sequence
SEQUENCE: 290
gaggccatac ccatgtctat                                                   20

SEQ ID NO: 291              moltype = DNA  length = 20
FEATURE                     Location/Qualifiers
source                      1..20
                            mol_type = other DNA
                            organism = Homo sapiens
misc_feature                1..20
                            note = SERPINA1 target sequence
SEQUENCE: 291
gaaagggact gaagctgctg                                                   20

SEQ ID NO: 292              moltype = DNA  length = 20
FEATURE                     Location/Qualifiers
source                      1..20
                            mol_type = other DNA
                            organism = Homo sapiens
misc_feature                1..20
                            note = SERPINA1 target sequence
SEQUENCE: 292
ctggagggga gagaagcaga                                                   20

SEQ ID NO: 293              moltype = DNA  length = 25
FEATURE                     Location/Qualifiers
source                      1..25
                            mol_type = other DNA
                            organism = Homo sapiens
misc_feature                1..25
                            note = SERPINA1 target sequence
SEQUENCE: 293
gtcgatggtc agcacagcct tatgc                                             25

SEQ ID NO: 294              moltype = DNA  length = 20
FEATURE                     Location/Qualifiers
source                      1..20
                            mol_type = other DNA
                            organism = Homo sapiens
misc_feature                1..20
                            note = SERPINA1 target sequence
SEQUENCE: 294
aagaaaggga ctgaagctgc                                                   20

SEQ ID NO: 295              moltype = DNA  length = 20
FEATURE                     Location/Qualifiers
source                      1..20
                            mol_type = other DNA
                            organism = Homo sapiens
misc_feature                1..20
                            note = SGSH target sequence
SEQUENCE: 295
gtcggccaca tggaccaagg                                                   20

SEQ ID NO: 296              moltype = DNA  length = 20
FEATURE                     Location/Qualifiers
source                      1..20
                            mol_type = other DNA
                            organism = Homo sapiens
misc_feature                1..20
                            note = SGSH target sequence
SEQUENCE: 296
gtcggccaca tggaccaagg                                                   20

SEQ ID NO: 297              moltype = DNA  length = 25
FEATURE                     Location/Qualifiers
source                      1..25
                            mol_type = other DNA
                            organism = Homo sapiens
misc_feature                1..25
                            note = SGSH target sequence
SEQUENCE: 297
ggtgggcttg cagaaccggg cactg                                             25

SEQ ID NO: 298              moltype = DNA  length = 20
FEATURE                     Location/Qualifiers
```

```
source                       1..20
                             mol_type = other DNA
                             organism = Homo sapiens
misc_feature                 1..20
                             note = SGSH target sequence
SEQUENCE: 298
ttggtccatg tggccgacgg                                                      20

SEQ ID NO: 299               moltype = DNA  length = 20
FEATURE                      Location/Qualifiers
source                       1..20
                             mol_type = other DNA
                             organism = Homo sapiens
misc_feature                 1..20
                             note = TSC2 target sequence
SEQUENCE: 299
gcatccagct gcaggtatgg                                                      20

SEQ ID NO: 300               moltype = DNA  length = 20
FEATURE                      Location/Qualifiers
source                       1..20
                             mol_type = other DNA
                             organism = Homo sapiens
misc_feature                 1..20
                             note = TSC2 target sequence
SEQUENCE: 300
ggttgcgcag ccagttcctg                                                      20

SEQ ID NO: 301               moltype = DNA  length = 25
FEATURE                      Location/Qualifiers
source                       1..25
                             mol_type = other DNA
                             organism = Homo sapiens
misc_feature                 1..25
                             note = TSC2 target sequence
SEQUENCE: 301
gcatccagct gcaggtatgg tggct                                                25

SEQ ID NO: 302               moltype = DNA  length = 20
FEATURE                      Location/Qualifiers
source                       1..20
                             mol_type = other DNA
                             organism = Homo sapiens
misc_feature                 1..20
                             note = TSC2 target sequence
SEQUENCE: 302
ggggttgcgc agccagttcc                                                      20

SEQ ID NO: 303               moltype = DNA  length = 20
FEATURE                      Location/Qualifiers
source                       1..20
                             mol_type = other DNA
                             organism = Homo sapiens
misc_feature                 1..20
                             note = TTR target sequence
SEQUENCE: 303
ggctgtcgac accaatccca                                                      20

SEQ ID NO: 304               moltype = DNA  length = 20
FEATURE                      Location/Qualifiers
source                       1..20
                             mol_type = other DNA
                             organism = Homo sapiens
misc_feature                 1..20
                             note = TTR target sequence
SEQUENCE: 304
acaccaatcc caaggaatga                                                      20

SEQ ID NO: 305               moltype = DNA  length = 25
FEATURE                      Location/Qualifiers
source                       1..25
                             mol_type = other DNA
                             organism = Homo sapiens
misc_feature                 1..25
                             note = TTR target sequence
SEQUENCE: 305
gctgtcgaca ccaatcccaa ggaat                                                25

SEQ ID NO: 306               moltype = DNA  length = 25
```

```
FEATURE                 Location/Qualifiers
source                  1..25
                        mol_type = other DNA
                        organism = Homo sapiens
misc_feature            1..25
                        note = TTR target sequence
SEQUENCE: 306
tgtcgacacc aatcccaagg aatga                                               25

SEQ ID NO: 307          moltype = DNA   length = 25
FEATURE                 Location/Qualifiers
source                  1..25
                        mol_type = other DNA
                        organism = Homo sapiens
misc_feature            1..25
                        note = TTR target sequence
SEQUENCE: 307
cacggctgtc gacaccaatc ccaag                                               25

SEQ ID NO: 308          moltype = DNA   length = 20
FEATURE                 Location/Qualifiers
source                  1..20
                        mol_type = other DNA
                        organism = Homo sapiens
misc_feature            1..20
                        note = TTR target sequence
SEQUENCE: 308
gggattggtg tcgacagccg                                                     20

SEQ ID NO: 309          moltype = DNA   length = 20
FEATURE                 Location/Qualifiers
source                  1..20
                        mol_type = other DNA
                        organism = Homo sapiens
misc_feature            1..20
                        note = VWF target sequence
SEQUENCE: 309
gatgccacgt gctccacgat                                                     20

SEQ ID NO: 310          moltype = DNA   length = 20
FEATURE                 Location/Qualifiers
source                  1..20
                        mol_type = other DNA
                        organism = Homo sapiens
misc_feature            1..20
                        note = VWF target sequence
SEQUENCE: 310
ggacctgaag tggaactgca                                                     20

SEQ ID NO: 311          moltype = DNA   length = 20
FEATURE                 Location/Qualifiers
source                  1..20
                        mol_type = other DNA
                        organism = Homo sapiens
misc_feature            1..20
                        note = VWF target sequence
SEQUENCE: 311
gtcctgacag acactaggag                                                     20

SEQ ID NO: 312          moltype = DNA   length = 25
FEATURE                 Location/Qualifiers
source                  1..25
                        mol_type = other DNA
                        organism = Homo sapiens
misc_feature            1..25
                        note = VWF target sequence
SEQUENCE: 312
gtcctgacag acactaggag cagtc                                               25

SEQ ID NO: 313          moltype = DNA   length = 25
FEATURE                 Location/Qualifiers
source                  1..25
                        mol_type = other DNA
                        organism = Homo sapiens
misc_feature            1..25
                        note = VWF target sequence
SEQUENCE: 313
gaccatgtgt gtgatgccac gtgct                                               25
```

```
SEQ ID NO: 314          moltype = DNA  length = 25
FEATURE                 Location/Qualifiers
source                  1..25
                        mol_type = other DNA
                        organism = Homo sapiens
misc_feature            1..25
                        note = VWF target sequence
SEQUENCE: 314
tgtcaggacc tgaagtggaa ctgca                                          25

SEQ ID NO: 315          moltype = AA  length = 82
FEATURE                 Location/Qualifiers
source                  1..82
                        mol_type = protein
                        organism = synthetic construct
REGION                  1..82
                        note = UGI domain
SEQUENCE: 315
TNLSDHEKET GKQLVIQESI LMLPEEVEEV IGNKPESDIL VHTAYDESTD ENVMLLTSDA    60
PEYKPWALVI QDSNGENKIK ML                                             82

SEQ ID NO: 316          moltype = AA  length = 7
FEATURE                 Location/Qualifiers
source                  1..7
                        mol_type = protein
                        organism = synthetic construct
REGION                  1..7
                        note = SV40 Nuclear Localization Signal
SEQUENCE: 316
PKKKRKV                                                               7

SEQ ID NO: 317          moltype = AA  length = 16
FEATURE                 Location/Qualifiers
source                  1..16
                        mol_type = protein
                        organism = synthetic construct
REGION                  1..16
                        note = Nucleoplasmin Nuclear Localization Signal
SEQUENCE: 317
KRPAATKKAG QAKKKK                                                    16

SEQ ID NO: 318          moltype =     length =
SEQUENCE: 318
000

SEQ ID NO: 319          moltype =     length =
SEQUENCE: 319
000

SEQ ID NO: 320          moltype =     length =
SEQUENCE: 320
000

SEQ ID NO: 321          moltype =     length =
SEQUENCE: 321
000

SEQ ID NO: 322          moltype =     length =
SEQUENCE: 322
000

SEQ ID NO: 323          moltype =     length =
SEQUENCE: 323
000

SEQ ID NO: 324          moltype = AA  length = 1493
FEATURE                 Location/Qualifiers
source                  1..1493
                        mol_type = protein
                        organism = synthetic construct
REGION                  1..1493
                        note = CSB
SEQUENCE: 324
MPNEGIPHSS QTQEQDCLQS QPVSNNEEMA IKQESGGDGE VEEYLSFRSV GDGLSTSAVG    60
CASAAPRRGP ALLHIDRHQI QAVEPSAQAL ELQGLGVDVY DQDVLEQGVL QQVDNAIHEA   120
SRASQLVDVE KEYRSVLDDL TSCTTSLRQI NKIIEQLSPQ AATSRDINRK LDSVKRQKYN   180
KEQQLKKITA KQKHLQAILG GAEVKIELDH ASLEEDAEPG PSSLGSMLMP VQETAWEELI   240
RTGQMTPFGT QIPQKQEKKP RKIMLNEASG FEKYLADQAK LSFERKKQGC NKRAARKAPA   300
PVTPPAPVQN KNKPNKKARV LSKKEERLKK HIKKLQKRAL QFQGKVGLPK ARRPWESDMR   360
```

```
PEAEGDSEGE ESEYFPTEEE EEEEDDEVEG AEADLSGDGT DYELKPLPKG GKRQKKVPVQ     420
EIDDDFFPSS GEEAEAASVG EGGGGGRKVG RYRDDGDEDY YKQRLRRWNK LRLQDKEKRL     480
KLEDDSEESD AEFDEGFKVP GFLFKKLFKY QQTGVRWLWE LHCQQAGGIL GDEMGLGKTI     540
QIIAFLAGLS YSKIRTRGSN YRFEGLGPTV IVCPTTVMHQ WVKEFHTWWP PFRVAILHET     600
GSYTHKKEKL IRDVAHCHGI LITSYSYIRL MQDDISRYDW HYVILDEGHK IRNPNAAVTL     660
ACKQFRTPHR IILSGSPMQN NLRELWSLFD FIFPGKLGTL PVFMEQFSVP ITMGGYSNAS     720
PVQVKTAYKC ACVLRDTINP YLLRRMKSDV KMSLSLPDKN EQVLFCRLTD EQHKVYQNFV     780
DSKEVYRILN GEMQIFSGLI ALRKICNHPD LFSGGPKNLK GLPDDELEED QFGYWKRSGK     840
MIVVESLLKI WHKQGQRVLL FSQSRQMLDI LEVFLRAQKY TYLKMDGTTT IASRQPLITR     900
YNEDTSIFVF LLTTRVGGLG VNLTGANRVV IYDPDWNPST DTQARERAWR IGQKKQVTVY     960
RLLTAGTIEE KIYHRQIFKQ FLTNRVLKDP KQRRFFKSND LYELFTLTSP DASQTETSA     1020
IFAGTGSDVQ TPKCHLKRRI QPAFGADHDV PKRKKFPASN ISVNDATSSE EKSEAKGAEV    1080
NAVTSNRSDP LKDDPHMSSN VTSNDRLGEE TNAVSGPEEL SVISGNGECS NSSGTGKTSM    1140
PSGDESIDEK LGLSYKRERP SQAQTEAFWE NKQMENNFYK HKSKTKHHSV AEEETLEKHL    1200
RPKQKPKNSK HCRDAKFEGT RIPHLVKKRR YQKQDSENKS EAKEQSNDDY VLEKLFKKSV    1260
GVHSVMKHDA IMDGASPDYV LVEAEANRVA QDALKALRLS RQRCLGAVSG VPTWTGHRGI    1320
SGAPAGKKSR FGKKRNSNFS VQHPSSTSPT EKCQDGIMKK EGKDNVPEHF SGRAEDADSS    1380
SGPLASSSLL AKMRARNHLI LPERLESESG HLQEASALLP TTEHDDLLVE MRNFIAFQAH    1440
TDGQASTREI LQEFESKLSA SQSCVFRELL RNLCTFHRTS GGEGIWKLKP EYC           1493

SEQ ID NO: 325          moltype = AA  length = 116
FEATURE                 Location/Qualifiers
source                  1..116
                        mol_type = protein
                        organism = synthetic construct
REGION                  1..116
                        note = USP2
SEQUENCE: 325
MKTTTQELKQ YITRLFQLSN NETWECEALE EAAENILPER FINNSLLAHL TLNTYTYYND    60
ELHELSIYPF LMYANDQLIS IGYLDHFDMD FLYLTDTKNT IIDERHLLKQ GENNHE        116

SEQ ID NO: 326          moltype = AA  length = 16
FEATURE                 Location/Qualifiers
source                  1..16
                        mol_type = protein
                        organism = synthetic construct
REGION                  1..16
                        note = 3xFLAG tag
SEQUENCE: 326
DYKDHDGDYK DHDIDY                                                    16

SEQ ID NO: 327          moltype = DNA  length = 203
FEATURE                 Location/Qualifiers
source                  1..203
                        mol_type = other DNA
                        organism = synthetic construct
misc_feature            1..203
                        note = cytomegalovirus promoter
SEQUENCE: 327
tgatgcggtt ttggcagtac atcaatgggc gtggatagcg gtttgactca cggggatttc    60
caagtctcca ccccattgac gtcaatggga gtttgttttg gcaccaaaat caacgggact    120
ttccaaaatg tcgtaacaac tccgccccat tgacgcaaat gggcggtagg cgtgtacggt    180
gggaggtcta tataagcaga gct                                            203

SEQ ID NO: 328          moltype = DNA  length = 304
FEATURE                 Location/Qualifiers
source                  1..304
                        mol_type = other DNA
                        organism = synthetic construct
misc_feature            1..304
                        note = CMV transcription enhancer
SEQUENCE: 328
cgttacataa cttacggtaa atggcccgcc tggctgaccg cccaacgacc cccgcccatt    60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catg                                                                 304

SEQ ID NO: 329          moltype = RNA  length = 318
FEATURE                 Location/Qualifiers
source                  1..318
                        mol_type = other RNA
                        organism = Homo sapiens
misc_feature            1..318
                        note = human RNA polymerase III U6 promoter
SEQUENCE: 329
tgtacaaaaa agcaggcttt aaaggaacca attcagtcga ctggatccgg taccaaggtc    60
gggcaggaag agggcctatt tcccatgatt ccttcatatt tgcatatacg atacaaggct    120
```

```
gttagagaga taattagaat taatttgact gtaaacacaa agatattagt acaaaatacg    180
tgacgtagaa agtaataatt tcttgggtag tttgcagttt taaaattatg ttttaaaatg    240
gactatcata tgcttaccgt aacttgaaag tatttcgatt tcttggcttt atatatcttg    300
tggaaaggac gaaacacc                                                  318
```

| | | |
|---|---|---|
| SEQ ID NO: 330 | moltype = DNA length = 20 | |
| FEATURE | Location/Qualifiers | |
| source | 1..20 | |
| | mol_type = other DNA | |
| | organism = Homo sapiens | |
| misc_feature | 1..20 | |
| | note = VWF target sequence | |

SEQUENCE: 330
```
ttcaggtcct gacagacact                                                20
```

| | | |
|---|---|---|
| SEQ ID NO: 331 | moltype = length = | |

SEQUENCE: 331
000

| | | |
|---|---|---|
| SEQ ID NO: 332 | moltype = length = | |

SEQUENCE: 332
000

| | | |
|---|---|---|
| SEQ ID NO: 333 | moltype = AA length = 168 | |
| FEATURE | Location/Qualifiers | |
| source | 1..168 | |
| | mol_type = protein | |
| | organism = synthetic construct | |
| REGION | 1..168 | |
| | note = LPG50148 | |

SEQUENCE: 333
```
MSNPEFTHEY WMRHALTLAR RARDEGEVPV GAVLVLNNQV IGEGWNRAIG LHDPTAHAEI    60
MALRQGGLVL QNYRLIDTTL YVTFEPCVMC SGAMVHSRIG TLVFGVRNSK RGAAGSLMNV   120
LNYPGMNHQV KTIGGVLAPE CSGLLCDFYR MPRQVFNQQK AELKSIND               168
```

| | | |
|---|---|---|
| SEQ ID NO: 334 | moltype = DNA length = 3846 | |
| FEATURE | Location/Qualifiers | |
| source | 1..3846 | |
| | mol_type = other DNA | |
| | organism = synthetic construct | |
| misc_feature | 1..3846 | |
| | note = SV40- LPG50148-Linker-d LPG10134 -Linker-Nuc | |

SEQUENCE: 334
```
ccaaagaaga agcggaaagt catgagcaac cccgagttca cacacgagta ctggatgcgg    60
cacgccctga cactggcccg cagagccaga gatgagggcg aagtgcctgt gggcgccgtg   120
ctggtcctga caaccaggt gatcggcgaa ggctggaacc gggccattgg actgcatgac   180
cccaccgccc acgccgaaat catggccctg agacaggcg gcggtgct gcagaactac   240
cggctgatcg acaccaccct gtacgtgaca ttcgagccat gtgtgatgtg tagcggcgct   300
atggtccatt ctagaatcgg caccctggtt ttcggcgtgc ggaacagcaa gagaggagct   360
gctggcagcc tgatgaacgt gctgaattat cctggaatga atcaccaggt gaagaccatc   420
ggcggcgtgc tcgcccctga atgcagcggc ctgctgtgcg acttctacag aatgcctaga   480
caagtgttta accagcagaa agccgagctg aagtccatca cgactccgg cgggtcttcc   540
ggcggctcta gtgggagtga gacgccagga acgtctgaat ctgctactcc gaatctagc   600
ggcggatcca gtggcggtag tatgaccact cgcctgggcc tggctgttgg tacgaactct   660
attggttggg ccctgatcga taaagatagc gcgcgtataa ttgacctggg ctctcgcatc   720
ttctctgacg gccgcgaccc taaatccggt gcctctctgg cagttgatcg ccgtgaagca   780
cgtgcggcac gtcgccgtcg cgatcgctat ctgggtcgcc gttctgcttt cctgaaaacc   840
ctgatccagc atggcctgat gccggagcgc gcagatgacg ctaaactggt ggcggctaag   900
gacccttatg cgctgcgtgc tcgtgcactg gacgaaccgc tggaaccgca tgaaattggc   960
cgtgcgctgt tccacctgaa ccagcgtcgc ggcttcaaaa gcaatcgtaa ggcggaaccg  1020
ggccgcaaag agaacgagga tggtaagatt gaaagcggcg ctaaagctct ggatactgcg  1080
atgactgtag caaaagctcg taccctgggt gagtttctgc atacgcagaa cgctaaacgc  1140
gtccgtatgg gtggcgacaa ccagacgtat gacttctacc gcagcgtcg ccacgtgaaa  1200
accggagttcg cagttctgtg ggctgcgcag aaggctcatc accggcgact cctgaccgcc  1260
gctgcggagg aagctctgca ccgcattctg ttttttccagc gcgacctgaa agaccaggaa  1320
gttggtctgt gtacctttgc tggctggaac gacgtgccgg aaaacgaacg tcgcctgccg  1380
aagacccacc cgctgttcca agaacgccgt ctctatgagg aagtcaacca cctgaaaatc  1440
gttagcccgg gcgcgaaaga ccgtgacctg acccgtgcgg aacgtgacgc ggtgctcctg  1500
aagctgcgcg atactcgtaa aagctctttc tccgctcgtg ccaaactgaa caactgggc  1560
gaaggtgaac gttttaacaa agagtctgaa actcgtaaag atctcctggg tgatgaggtc  1620
cgtgcagaac tggctgacaa aaagcgcttc ggtgcacgtt ggacgttttt cgatatcgct  1680
gaacaactca aaattatcga tcgtattcag aacgaagcag atccggaagt tctcctggac  1740
tggctgaaag cagagtatgg tctggacgat gcaagcgctg tggcggtatc caagcgcgt  1800
ctgcctgaag gttatgccgg tttggcgaa accgcctgat tgatgcctta  1860
aaagcgcagg ttgtaaccta cgacaaagcg gcactggctg cgggtttcca tcacagcgat  1920
cgccgtaccg gcgaagtgtg ggagcgtctg ccatattacg tcagatcct gaccgccgaa  1980
attgcaccag gtaaagcgga gcacggcgat gacaacgaac gccgttttgg caaaatcacc  2040
aatccgaccg ttcacattga actcgtcag ctggaaaaac tcgttaacgc agttatcacc  2100
gtgcacggcc gtcctgatga atcgtcgtt gaactggcgc gtgaactcaa actgaatgag  2160
```

```
gaagaccgca aaaagcacga tgcgcgtatt cgtcgcgata ccgcggccgc tatcgcccgt  2220
ggtgaaaaac tggaggcgga aggtatcccg gacaccggcg caaaccgtat ggcgatgcgt  2280
atgtgggaag atctgaaccc tggcaacccg ctggatcgcc gttgcccgta ttgcgcagaa  2340
gttatcggta tccgtgctct gttttccggt gaagcagata tcgacgccat tatcccgtac  2400
tcccagagcc tggatgacag cgcggcaac aaagtcgtgg cccatccgcca ttgtaaccgc  2460
gcgaaaggca acaagactcc gtatgaacgc tggggtcacg atgaggcacg ttgggaaatt  2520
atctctgctc aggtagcacg catgcaccgc tccaaacagt ggcgtttcgg cccagaagcg  2580
cgtgaacgtc tggagaagga gggtggcttc atcgctcgtc agctgaccga cacccagtac  2640
ctcagccgcg ctactgcgaa atatctgtcc tctctgtata ccccggacga aggtcgtcgc  2700
gtttacgctc tgccgggtcg tatgaccgcg atgctgcgcc gtctgtgggg cctgaactct  2760
ctcctgccgg accacaattt cgttgaaaac gaacactcca acgctccgaa aaaccgtctg  2820
gaccaccgcc atcacactat cgatggtgca gttgcggctg taaccgacgc ttccctgatg  2880
cagcgtattg cgaccgttgc agcgcgtgct gaagagaacg aactggatcg tctgttcgaa  2940
gatctggctc cgccttggcc aacttccgt gaggaactga aagaacgtct ggcgcgtgtc  3000
acggtgtctc ataaaccgga ccatggtcgc aagggtcgtc cggaccgcac ccgcgatgtt  3060
actgccggtc gtctgcacaa cgataccgct tacggtttta cgggtcaagt agctgcgagc  3120
ggcaaaacgc cgatcgttgt gcatcgcgtg ccttttcgcaa gcctgaaacc agcggacatc  3180
ctcgacccga cccgtatccc ggacaccgcg ctgcgcgaa ctctctttga agctactcgt  3240
gatctgaccg gtaaatccta cgaccaagca atggcgcgct cgcaaaaca gcacccggtt  3300
tttaaaggca ttcgtcgcgt tcgtgtgcgt gaggctctga acgttatccc gatccgttct  3360
aaagaaggtc gtccgtacaa agcttacaaa ggtgattcca acgctcgtta tgacgtgtgg  3420
cgtctgccga atggcaagtg ggtgaccgac atttgtttcca tgttcgacgc tcacagcccg  3480
gaagcgagcg atcgtcgccc tcatccggcg gccaagaaag tcctgtctct gcgtcaaaac  3540
gacatgctgg caatcgaacg tgatggcggt gaagcacaga tcgttcgcgt ggtcaaattc  3600
agccgctctg gcctgattct ggccggccaa aacgaagcag gtccgctgaa agctcgtgac  3660
gcggctccga acgaaacgga cccattccgc tacatttccgtc tagccgtgaaa  3720
cgcgataacg cccgtcagat ccgtattgat ccgctgggtc gtgttttcga tccgggtccg  3780
cgcgatagcg gcggaagcaa aagacctgcc gctacaagaa aggccggcca ggccaagaaa  3840
aagaag                                                            3846

SEQ ID NO: 335          moltype = DNA   length = 4071
FEATURE                 Location/Qualifiers
source                  1..4071
                        mol_type = other DNA
                        organism = synthetic construct
misc_feature            1..4071
                        note = SV40- LPG50148-Linker-d LPG10145 -Linker-Nuc
SEQUENCE: 335
ccaaagaaga agcggaaagt catgagcaac cccgagttca cacacgagta ctggatgcgg    60
cacgccctga cactgcccg cagagccaga gatgagggcg aagtgcctgt gggcgccgtg   120
ctggtcctga caaccaggt gatcggcgaa ggctggaacc gggccattgg actgcatgac   180
cccaccgcc acgccgaaat catggccctg agacaggggcg gactggtgct gcagaactac   240
cggctgatcg acaccaccct gtacgtgaca ttcgagccat ggtgatgtg tagcggcgct   300
atggtccatt ctagaatcgg caccctggtt ttcggcgtgc ggaacagcaa gagaggagct   360
gctggcagcc tgatgaacgt gctgaattat cctggaatga atcaccaggt gaagaccatc   420
ggcggcgtgc tcgcccctga atgcagcggc ctgctgtgcg acttctacag aatgcctaga   480
caagtgttta accagcagaa agccgagctg aagtccatca acgactccgg cgggtcttcc   540
ggcggctcta gtgggagtga gacgccagga acgtctgaat ctgctactcc cgaatctagc   600
ggcggatcca gtgcgcggtag tatgtccaaa gtggcaaaaa acatgacccg tgtaaacctg   660
ggttccgcta tcggtatcgc gagcgtaggc tggtctgtgc tcgataacca gaccggtaag   720
atcctggaaa ccggcgtgag catcttcccg tctggtacgc cgagccgtaa cgaggaaccg   780
cgctctttcc gtcagtctcg ccgtctgatt cgtcgcaaga aagcccgtat ctgcgacatg   840
gatcacctcc tgaagaaaaa cggcttcccg ttcccgggta acactggcgc aaatccgtac   900
gaaattcgcg tcaaaggcct gaccgagaaa ctgtctcgtg aagagctggc tatcgcgctg   960
catccctgg taaacgccg tggcatcagc tatgacctga aagatgttga ggacgaaagc  1020
gcaggcggta ccaactatca ggaaagcatt gcagttaatc agcgtctgct caagaaagaa  1080
actccggcgg agattcagct ggccgcct accgaatgcg gtaaagtgcg tggcaggta  1140
aaatccctgg gcgaagacaa caccgccact accctcctga cgtgttccc gaacgccgcg  1200
tatcaggaga agatggttaa actcctgaag aacaacagga aattctacgg tgagattgat  1260
gacccgttca tggagaccgc gatcggcatc ctgtctcgca aacgtgaata cttcattggt  1320
ccgggctccg agaaaagccg cactgactat ggcatctacc gtactgacgg taccactctg  1380
aaaaacctgt cgaaattct ggttggtaag gacaagatt ttccggacca gtaccgcgcg  1440
gcaggtaaca gctacaccgc ccagctgtat aacctcctga tgacctgaa taacctggaa  1500
gtagatccga ccgaagacgg caaactgact accgcacata aagaacagat cattgaggaa  1560
ctgactacca ctaccggcaa cgtgaacatg ctgaaactga tcgccaaagt cgctggcacc  1620
tctccggctg gtatcaagaa ataccgtgtc gaccgtgaag gtaaacctga attccactct  1680
ctggctatct accgcgtct gcgcaagaaa ctgggtgaag ctggtttcga attaacgaa  1740
tggcctccgg aattttttcga tgactatggt ccgatcgtta cgctgaacac cgaatccggc  1800
gaactgcgta agtggctggc cgaagagggc tctcgcaaat acgattcct gaccgagccg  1860
gtcattgaag caattctcgc taataaatct gcttttgact ccgtgggtaa aaacaaatgg  1920
caccgttct ccctgaaaac catgcagctc ctgatcccgg aactcctgca caccttaag  1980
gaacagatga ccattctggc tgaaatgggc ctcctgcatg aaaacaagaa agattatgc  2040
gaccaaaata aagttgatgt taaatatctg acggaaaaacc tgtacaaccc agtagtgcgt  2100
aaaagcgtga agcaggccat ggatatcttc aacgctcgt tcgagaaata cgctaacatc  2160
gattatgtgg ttatcgaaat gccgcgtgac gatgccgaga acgaactgga acagaaaaag  2220
cagtttcaga aatttcaact caaaaacgag aagaaaaaga tgcgtctct gaaagaattt  2280
caagaactgc cggtgtatc cgatctgcag ctggaagcgc agctgcgtaa gcgtaagaaa  2340
ctgcgccaga agatccgtat gtggatcaa cagcgtggta aatgtccgta ttctggcaag  2400
accatcgcgg ctgtggacct gttccaccag gataaccat tgaaatcga tgcgattatc  2460
```

```
ccgctgagcg tgtctttcga cgatggccag aataacaaag tactgtgcta tagcgaaatg  2520
aaccaggaaa aagtaaaaca aacgccgtac gcgttcatgt cccgtggtgg cggtcagggt  2580
tttccgcac tgcaggccta cgtgaaatcc aataaccgtc tcgaaaatgc taagaaacgc   2640
aatctcctgt ttacgaaga cattaacgac ctcgaggttc gcaaacgctt catcgctcgc   2700
aacctggtgg acacgcgtta tgcttctcgt atcgttctga atgaactgca acagttcgtg  2760
cgtagcaaag aactggacac ccgtgtaact gttatccgcg gcaaactgac ttctaagctg  2820
cgtgatcgtt ggcgtctgaa caaaagccgt gaaacgcacc atcaccatgc tgtagacgcc  2880
gctgtaatcg ctgtcagccc gatgctgaaa atgtgggaga gaacgcgga aattatccct   2940
ctgaaagttg atgaaaacac cgtagatctg aaaagcggtg aaatcattac tgatcaggag  3000
tatgcagctc agatgtatga actgccttac gcgcgtttcc tggagcagat gcctgaactg  3060
cacaagaaaa tcaaatttca tcaccaggtg gataagaaaa tgaaccgcaa agtgtctgac  3120
gccactctgt acagcacccg caaagccaag gtaggcactg acaaaaagga acaggagtat  3180
gttattggca aaatttaaga tatctaccag ttcgatcagt ataagaaatt caagaaactc  3240
tatgacggtg ataaatctaa attcctgatg cagcgcctgg atccacagac tttcgcgaaa  3300
ctggagaaaa tcatggaaga ttacccggca aaaattgacg cgactcaacc gaatggcact  3360
atcaaactgg tcgatatctc tccgttcgaa ctgtaccgtc gcgaacacgg cccggttacc  3420
aaatacgcaa agaaaaataa cggtccggct atcaagtccc tgaaattcta tgattctatc  3480
gtcggtagct ctgtaaaaat cacgccgaaa aacgctaaag gtaaggaagt gatcctcaaa  3540
agcctgaaac cgtggcgcac tgacgtgtat tacaaccatg agaaagaaca atacgagatc  3600
atgggcatta aatacgcgga cctgaaattc aaaggcgata actacggtat caccaaagct  3660
cgctaccaag aaatcaaaga ggaagagggt gtgtccgagg aaagcgagtt cctgttttct  3720
ctgtatcgcg gcgaccgtat ccaggtatct aacggcgaaa acaaaattga cctcctgttc  3780
ctgtctcgtt ctaatccggc gaagaaaggt tatgttgagc tgaaaccgat cgaccgtaat  3840
caactgaacg gtaaagaggt agtttctgta tatggtgctg cctctggcgg tcgcctgaaa  3900
aagcagttcg ttaagaaaaa ccacaccctc cataaagtaa acaccgacat cctcggcaac  3960
ccattttata tcaagaaaga aagcgaccag ccgaagaaca ttctggatct gagcggcgga  4020
agcaaaagac ctgccgctac aaagaaggcc ggccaggcca agaaaaagaa g           4071
SEQ ID NO: 336          moltype = DNA   length = 3918
FEATURE                 Location/Qualifiers
source                  1..3918
                        mol_type = other DNA
                        organism = synthetic construct
misc_feature            1..3918
                        note = SV40- LPG50148-Linker-d LPG10136 -Linker-Nuc
SEQUENCE: 336
ccaaagaaga agcggaaagt catgagcaac cccgagttca cacgagta ctggatgcgn    60
cacgccctga cactggcccg cagagccaga gatgagggcg aagtgcctgt gggcgccgtg  120
ctggtcctga caaccaggt gatcggcgaa ggctgaacc gggccattgg actgcatgac    180
cccaccgccc acgccgaaat catggccctg agacagggcg gactggtgct gcagaactac  240
cggctgatcg acaccaccct gtacgtgaca ttcgagccat gtgtgatgtg tagcggcgct  300
atggtccatt ctagaatcgg caccctggtt ttcggcgtgc ggaacagcaa gagagggagct 360
gctggcagcc tgatgaacgt gctgaattat cctggaatga atcaccaggt gagaccatc   420
ggcggcgtgc tcgcccctga atgcagcggc ctgctgtgcg acttctacag aatgcctaga  480
caagtgtttta accagcagaa agccgagctg aagtccatca cgactccgg cgggtcttcc  540
ggcggctcta gtgggagtga gacgccagga acgtctgaat ctgctactcc gaatctagc   600
ggcggatcca gtggcggtag tatgaaagat ctggactatc gatcggcct ggcgatcggc   660
accaacagca ttggctggtc catcattaag ctgcagttta atgatactac ccagcgttac  720
gagaaatccg gcattatcga cctggtgtgt cgtatgttcg acaaagctga atccctaag   780
acgggcgcga gcctgtctga accgcgtcgc ctggcgcgtt ctagccgccg tcgcctgaaa  840
cgcaaaagcg agcgtaaaca gattatccgc cgtctcctcg tagacttcga cattctcagc  900
caggaggaac tggatcacct gttttcctctg ccaaaggata gcgtagatat ttgggatatc  960
cgtctggaag gtctgagcg tgttctgaac cgtttcgagt gggcgcgtct gctcctgcac  1020
ctggcacagc gtcgcggttt caaaagcaac cgtaaatctc agcgcaatga aaccgagact 1080
ggcaaaatgc tggcaagcat ctacgacaat aaaaatcgtc tgtctgcgta ccgtaccgtc  1140
ggcgaaatgt ggatgaaaga caagaaattc gcgcagtatg acaaacgccg taactctccg  1200
gacgaatata tttttaacgt gtctcgtgac gatctggaaa agaaattat gactctgttt  1260
gaagcacagc gcaaattcct gtctgagtac gcaagcgaac aactgcagga agcgtatctg  1320
aaagtatgga gccatcagct gccgttcgcg tctggtaatg acatcctgag gaaagtgggt  1380
cactgcagcc tggagaaaaa cgaacgtcgc atcccgaaag caacctacac gtttcagtac  1440
ttcgcggccc tcgataagat caataacctg cgcctcggtg attacgttca gccgctcgcg  1500
caggagcaac agaaactgct cctgaagaaa atgttcgaac gtatcgattt cgttaagaaa  1560
aagtctattc cgatcattaa atattctgac ctgcgtaaat ggctgaaact ggacgaatct  1620
atttgcttca aggcctgac ttcaaacccg aacgagaaac tgtccaaagt agaaaagaaa  1680
gagtttatca acctgaaacc gtattacgag atgaagaaag tgatcagcaa acactacgaa  1740
aaacatgaaa acatctatga agtagcggac tttgacacct tcggctacgc tctgaccatt  1800
tacaaaaacg atcaagatat ccgtagctac ctgcgcaact ctaataacat cggtaagaaa  1860
gttttacgatg aagctctgat cgaagacctc ctgaacctgt cttataccaa attccggtcac  1920
ctctctttca aagcactgca gaacctgatc ccgattattg aggaaggtaa atccttcgta  1980
gacgccacca agaactgtc ttacgatacc actggtctga gaaaactaa aaagagccgt    2040
ctcctgcctc cgattccgga cgatattacc aacccgattg taaaacgttc tgacccagag  2100
tctcgtaaag tagttaactc tattatcaag acctatggtc accgctctc tatccatatc   2160
gaactggcac gtgaactgtc caaagatcac gaggaacgtc gcaaactc taaacccaa     2220
gacgaaaact accgccgtaa caaggtgcg attgaagtgc tgggaaaa cggtattatc     2280
aacccgaaag ttacgacat tgtacgttat aaactgtgga agaacagcg tgagtgctgt    2340
gcatactccc tgaagaaaat cccggctgat gttttttct ctgaactgcg ccgtgaacgt   2400
ggctcctctc cgatcctcga agttgacgct atcctgcctt acagccagtc ctttatggac  2460
tcctaccata caaagtgct ggtttactct gacgaaaacc gtaagaaagg cgacctgatc   2520
ccgtatgatt acatcaaagg tgaagagcag cgttggaaaga atttcgaaag ctatgtacag  2580
```

```
accaataacc tgttttctaa aaagaaacgt gaatacctgc tcaagaaaga atacacctcc  2640
cgtgaaagcg acatggttaa agaacgtcac ctgaatgaca cccgttatgc gacccgtttt  2700
ttcaaaaact tcatggaaca acgtctcctg ttcaaagaag cgaaagttag catgaagaaa  2760
cgcgttcaga ccgttaacgg catcattacc tcccatttcc gcagccgttg gggcctggaa  2820
aaagtacgcg aagacaccta cctgcatcac gctctgtagc ctgttgtggt tgcctgcact  2880
gatcatcaca tggtaacccg cgtgaccgaa tactataaac acaaagaatc cagcctgaaa  2940
tctcgtaaac cgttttccc gtggccttgg aagggtttcc gtgatgaact cctgacccgt  3000
ctgacctccc aaccagtacc ggataaaatc agcgaagctc tgcagctggg tacctctctg  3060
ccggactacc gtatcgtgtc ccgtatgcct aaacgctcca ttactggtgc ggctcacaag  3120
gagaccatta tgatgaaggg cggtatcgac gaaaaaactg gcaaaaccat cattgtaaaa  3180
cgcgtagcac tgaaagatat caaattcgac aaaaacggtg acttcgaaat ggtgggtaaa  3240
gagcaggata tggcgactta cactgcgatc aaggaacgtt atctgcagca caagaaaaac  3300
gctgaaaaag catttgaaaa accgatctac aaaccgtcta aaagggccg cggcaaccca  3360
attaagcgtg tgaaggtggt tttcgaaagc aaagcgtttg tgcgtgaggt taacggcggt  3420
gtcgctaata acgaaaagct ggtccgcgtt gacctgttcg aaaaagacgg taagtactcc  3480
atggtcccga tctatgtcat ggataccgtg actgaaaagc tgccggataa aattgttacc  3540
atcggtaaag gccatcacca tggcgccgt ctggacgaat cttataccttt ctgttcagc  3600
ctgcacccgt acgatctggt tcgcgttcgt tctgaggaag ctgacacgtt tttctatttc  3660
ggtagcattg acatcaacag caaccgcatc cacttcaaac acgtgaacca cccgactaaa  3720
ccgaacgaac tgcgttacgc cctgggcaaa atcgacctgc tcgaaaaata cgaaattggt  3780
ctcctgggtg acatcaagca ggtcaagaaa gaaactcgca cacgttttca ccagcctaag  3840
aaacaactga ctatggagag cggcggaagc aaaagacctg ccgctacaaa gaaggccggc  3900
caggccaaga aaagaag                                                  3918

SEQ ID NO: 337         moltype = DNA   length = 3924
FEATURE                Location/Qualifiers
source                 1..3924
                       mol_type = other DNA
                       organism = synthetic construct
misc_feature           1..3924
                       note = SV40- LPG50148-Linker-d LPG10139 -Linker-Nuc
SEQUENCE: 337
ccaaagaaga agcggaaagt catgagcaac cccgagttca cacacgagta ctggatgcgn  60
cacgccctga cactggcccg cagagccaga gatgagggcg aagtgcctgt gggcgccgtg  120
ctggtcctga acaaccaggt gatcggcgaa ggctggaacc gggccattgg actgcatgac  180
cccaccgccc acgccgaaat catggccctg acacagggcg gactggtgct gcagaactac  240
cggctgatcg acaccaccct gtacgtgaca ttcgagccat gtgtgatgtg tagcggcgct  300
atggtccatt ctagaatcgg caccctggtt tcggcgtgc ggaacagcaa gagaggagct  360
gctggcagcc tgatgaacgt gctgaattat cctggaatga atcaccaggt gaagaccatc  420
ggcggcgtgc tcgcccctga atgcagcggc ctgctgtgcg acttctacag aatgcctaga  480
caagtgtttta accagcagaa agcgagctg aagtccatca acgactccgg cgggtcttcc  540
ggcggctcta gtgggagtga gacgccagga acgtctgaat ctgctactcc gaatctagc  600
ggcggatcca gtgggcggtag tatgcgtaac ctggactatc gtattggtct ggctatcggt  660
accaacagcg ttggctggtc tgttatcgaa ctgaacttta accagactac caaccgttac  720
gaaaaagtcg gcatcattga cttcaacgtt cgtatgttca caaggcgga aatcccgaaa  780
accggcgcat ccctggccga accgcgccgt cagttccgtt ccacgcgtcg ccaactgaaa  840
cgtaaaagca tccgcaagca gaaaatccgc caactcctga tgactcacga tgttatctcc  900
cagcaagaac tggacaatct gtatccgctc agcaaaggtt ctatcgacat ctgggacatt  960
cgtgtcgagg gcctggaccg ttacctgaac aaaatcgagt ggtctcgcct gctcctgcat  1020
ctggctcagc gccgtggctt caaatccaac cgcaaatccg ataaccaaga aaccgaacag  1080
ggtaaaatcc tgccgatcat tcaggagaac aacagctcc tgtgtctccta ccgtactgtg  1140
ggcgaaatgt ggatgaaaga cgagaaattt gcgaccagcg ataaacgtaa aaacaccaac  1200
gataactatc tgtttaatgt gagccgtgag gacctgaaac gtgaaatcca gctcctgttt  1260
cagcaacagc gtcaatttgg ttctctgtac gcttccgaac agactgaaaa agaatatctg  1320
gatatctggg aacaccagct gccgtttgct tctggccatg acgtactgaa aaaggtgggc  1380
tactgctctc tggagccgaa agagcgcgcg ttccgaaag caacctatac cttccaatac  1440
ttcaccgtaa tcgacaaact gaataacctg cgcctgggta gccatttgaa gccgctgacc  1500
aaggaacaac gcgacatcct gctccagaag atcatggaac gtacggattt catcaataag  1560
aaaactaccc cgtccattcg ctattccgac atccgtaaat ggctgacct ggatgactcc  1620
atccagttca aggtctgat ctatgagcca gacgaaaaaa ctcgaaaat tgagaagaaa  1680
gaattcgtaa acctgaaatc ctactatgaa attaagaaag taatcctcct gcatagcgag  1740
aaaaccggtg agacctatac caatatggat ctggatacca tcgttatgc actgactgtt  1800
tacaacacgg acaaagacat ccgtgcatac ctgcgtaacc cgcacaacct gtcagaaa  1860
gttttttgatg acgttctgat cgatgagctc cttacactaa atttggtcac  1920
ctgtctatca aagccctgca ccgtctcctg ccgtacctgg aggaaggtct gtcttacgcc  1980
gaagctgtaa acaagttgg ctacgacacg accaatctga agggtaaaaa gaagaacgt  2040
ctcctgccga agatccccgga cgatatcacc aatccggttg tgaaacgttc cctgactcag  2100
gcgcgtaagg tcgttaacgc gattatccgt aaatatggtt ctccgctgtc cgtgcacatt  2160
gaactggccg cgtgaacgtc taaaaacgcg tccgaacgta agaatctg taaggcccaa  2220
actaaaaact acgaacgtaa ccagggtgcg attgctatcc tggttgaaaa cggtattctc  2280
aatccgaccg gctatgacat cgtccgttac aaactgtgga agaacagga tgaacgctgc  2340
atgtattctc tgcgtaaaat cccgtctgaa cagttttttcg ctgaactgcg tcgcgaacgt  2400
ggctccactc cgctcctgga cgttgatgcg atcctgccgt actcccagtc tttcctcgat  2460
ggttacgaca atatttct ggtattctct gacgagaacc gcaagaaagg cgatcgcatc  2520
ccgtttgact acctgcagga aaacccaaaa aagtggctgg acttcgaggc gtacgttcag  2580
agcaacgaaa aactgtccaa aaagaaacgt ggctacctgg tgaagaaagt atatactgct  2640
cgcgaatctg acgatgtgaa agaacgtcac ctgaacgaca ctcgttacgc gacccgtttc  2700
ctgaaaaatt ttatcgagca gttcctgttt ttcaaagagg ctcagatccc tatgaagaaa  2760
cgtgttcaga ccctgaacgg tcgtatcacc tcccactttc gttcccgttg gggttttaag  2820
```

```
aaaattcgcg aggatactta cctgcaccat gcagttgacg cagtcgttgt ggcatgtact  2880
gaccaacata tggtaaacaa agttaccgat tattacaaat ccaaagaaca gtctctgaaa  2940
tccaacgccc catatttccc gtggccgtgg gaaggtttcc gtgatgaagt actgacccgc  3000
ctgcacgctc agccggttcc ggaccagatc aagcaggcca tcacctctta ctccccgctg  3060
cctaactacc gtctggtgtc ccgtatgtct aaacactctg tgaccggcgc agctcacaaa  3120
gaaacgatca tgatgaacgg cggtgagaac aataaaaccg gtaaaaccat tatcgttaaa  3180
cgtatgctcc tgcgtgaaat caaattcgat gacaacggcg acttcaaaat ggttggtaaa  3240
gaacaggacc cggctaccta ccaggctatt aaacaacgct atctgtctta cgacaaagat  3300
gcgaagaaag cattcgacaa accgctctat aagccgacaa aaagggcca ttccaaccgg  3360
atcaagcgcg tcaaggtgga agtccaagaa aaaactttcg tgcgtgaagt gaacggcggt  3420
gttgctgaaa atggtgatct ggttcgtatc gacctcttca agaaagagga tacctattac  3480
atgatcccga tctatgtact cgacacctcc agcccagaac tgccggatca tatcgtaacc  3540
tccggtaaag gctataaact gtggaagaaa ctggacgagt cctatacttt ccagttctct  3600
ctgactccgt acgacctgat tcgtgtgaag attaatgaga aagatcagtt tctgtacttc  3660
agcaccatcg acatctctaa taaccgcatt atctgtaaac atgtcaacaa gccgtctgtt  3720
ccgaaagaat gtacttactc cctgacgaaa atcgaagtaa ttgagaaatg taaagtcggc  3780
atcctgtctg acgtttcctt cgtaaaaaac gaaacccgtc gcagcttcgg tcagccgacc  3840
aagaaagttg cgctgcagac ccgtagcggc ggaagcaaaa gacctgccgc tacaaagaag  3900
gccggccagg ccaagaaaaa gaag                                         3924

SEQ ID NO: 338         moltype = RNA   length = 124
FEATURE                Location/Qualifiers
source                 1..124
                       mol_type = other RNA
                       organism = synthetic construct
misc_feature           1..124
                       note = Hurler guide LPG10134
SEQUENCE: 338
gctctaggcc gaagtgtcgc gttgccgctg gccttcgatt tctgaaaagt cagaaatcga   60
aggctggctg ttaacaagca gctagactgc accaaataag ggcgggggcta cggccccgtc  120
tttt                                                                124

SEQ ID NO: 339         moltype = RNA   length = 118
FEATURE                Location/Qualifiers
source                 1..118
                       mol_type = other RNA
                       organism = synthetic construct
misc_feature           1..118
                       note = Hurler guide LPG10145
SEQUENCE: 339
agctctaggc cgaagtgtcg gttattgtac tctcaaggaa tcagaaagac tgattccttg   60
agaatctaca ataataaggc tttatgccga aattcccact cttaacgagt gggtttt     118

SEQ ID NO: 340         moltype = RNA   length = 131
FEATURE                Location/Qualifiers
source                 1..131
                       mol_type = other RNA
                       organism = synthetic construct
misc_feature           1..131
                       note = Hurler guide LPG10136
SEQUENCE: 340
agctctaggc cgaagtgtcg gtcatagttc cactaaagcc attaaagaat ggctttgatg   60
tttctatgat aagggtttcg acccgtggcg ttggggatcg cctgcccatt tcgatgggcg  120
tctccccatt t                                                        131

SEQ ID NO: 341         moltype = RNA   length = 141
FEATURE                Location/Qualifiers
source                 1..141
                       mol_type = other RNA
                       organism = synthetic construct
misc_feature           1..141
                       note = Hurler guide LPG10139
SEQUENCE: 341
agctctaggc cgaagtgtcg gtcatagtcc catcatatcc attgaaagca atggatatga   60
tgtttctatg ataagggctc tctaagagag acctgtggcg ttggggatcg cctgcccgtt  120
tcgacgggtg tctccccatt t                                             141

SEQ ID NO: 342         moltype = DNA   length = 15
FEATURE                Location/Qualifiers
source                 1..15
                       mol_type = other DNA
                       organism = synthetic construct
misc_feature           1..15
                       note = Forward Amplification Primer
SEQUENCE: 342
gactccttca ccaag                                                    15

SEQ ID NO: 343         moltype = DNA   length = 14
FEATURE                Location/Qualifiers
```

```
source                  1..14
                        mol_type = other DNA
                        organism = synthetic construct
misc_feature            1..14
                        note = Reverse Amplification Primer
SEQUENCE: 343
gtagatcagc accg                                                              14

SEQ ID NO: 344          moltype = DNA  length = 14
FEATURE                 Location/Qualifiers
source                  1..14
                        mol_type = other DNA
                        organism = synthetic construct
misc_feature            1..14
                        note = Wild Type Probe
SEQUENCE: 344
ctctgggccg aagt                                                              14

SEQ ID NO: 345          moltype = DNA  length = 14
FEATURE                 Location/Qualifiers
source                  1..14
                        mol_type = other DNA
                        organism = synthetic construct
misc_feature            1..14
                        note = W402X Probe
SEQUENCE: 345
ctctaggccg aagt                                                              14

SEQ ID NO: 346          moltype = DNA  length = 13
FEATURE                 Location/Qualifiers
source                  1..13
                        mol_type = other DNA
                        organism = synthetic construct
misc_feature            1..13
                        note = Forward primer
SEQUENCE: 346
acttcctcca gcc                                                               13

SEQ ID NO: 347          moltype = DNA  length = 13
FEATURE                 Location/Qualifiers
source                  1..13
                        mol_type = other DNA
                        organism = synthetic construct
misc_feature            1..13
                        note = Reverse primer
SEQUENCE: 347
gaacccggc tta                                                                13

SEQ ID NO: 348          moltype = DNA  length = 20
FEATURE                 Location/Qualifiers
source                  1..20
                        mol_type = other DNA
                        organism = Homo sapiens
misc_feature            1..20
                        note = LPG10134 5-prime Genome Target Sequence FA
SEQUENCE: 348
gcccataatc tcagcacttt                                                        20

SEQ ID NO: 349          moltype = DNA  length = 20
FEATURE                 Location/Qualifiers
source                  1..20
                        mol_type = other DNA
                        organism = Homo sapiens
misc_feature            1..20
                        note = LPG10134 5-prime Genome Target Sequence FA
SEQUENCE: 349
ctaggaaggt ggatcacctg                                                        20

SEQ ID NO: 350          moltype = DNA  length = 20
FEATURE                 Location/Qualifiers
source                  1..20
                        mol_type = other DNA
                        organism = Homo sapiens
misc_feature            1..20
                        note = LPG10134 3-prime Genome Target Sequence FA
SEQUENCE: 350
tgtaatccca gctactccag                                                        20

SEQ ID NO: 351          moltype = DNA  length = 20
```

```
FEATURE             Location/Qualifiers
source              1..20
                    mol_type = other DNA
                    organism = Homo sapiens
misc_feature        1..20
                    note = LPG10134 3-prime Genome Target Sequence FA
SEQUENCE: 351
gcaggagaat cgcttgagcc                                              20

SEQ ID NO: 352      moltype = DNA   length = 20
FEATURE             Location/Qualifiers
source              1..20
                    mol_type = other DNA
                    organism = Homo sapiens
misc_feature        1..20
                    note = LPG10145 5-prime Genome Target Sequence FA
SEQUENCE: 352
tctcagcact ttgggaggcc                                              20

SEQ ID NO: 353      moltype = DNA   length = 20
FEATURE             Location/Qualifiers
source              1..20
                    mol_type = other DNA
                    organism = Homo sapiens
misc_feature        1..20
                    note = LPG10145 5-prime Genome Target Sequence FA
SEQUENCE: 353
gaaggtggat cacctgaggt                                              20

SEQ ID NO: 354      moltype = DNA   length = 20
FEATURE             Location/Qualifiers
source              1..20
                    mol_type = other DNA
                    organism = Homo sapiens
misc_feature        1..20
                    note = LPG10145 3-prime Genome Target Sequence FA
SEQUENCE: 354
tcccagctac tccagaggct                                              20

SEQ ID NO: 355      moltype = DNA   length = 20
FEATURE             Location/Qualifiers
source              1..20
                    mol_type = other DNA
                    organism = Homo sapiens
misc_feature        1..20
                    note = LPG10145 3-prime Genome Target Sequence FA
SEQUENCE: 355
tcgcttgagc ccgggaggca                                              20

SEQ ID NO: 356      moltype = DNA   length = 20
FEATURE             Location/Qualifiers
source              1..20
                    mol_type = other DNA
                    organism = Homo sapiens
misc_feature        1..20
                    note = LPG10136 5-prime Genome Target Sequence FA
SEQUENCE: 356
ccataatctc agcactttgg                                              20

SEQ ID NO: 357      moltype = DNA   length = 20
FEATURE             Location/Qualifiers
source              1..20
                    mol_type = other DNA
                    organism = Homo sapiens
misc_feature        1..20
                    note = LPG10136 5-prime Genome Target Sequence FA
SEQUENCE: 357
tgggaggcct aggaaggtgg                                              20

SEQ ID NO: 358      moltype = DNA   length = 20
FEATURE             Location/Qualifiers
source              1..20
                    mol_type = other DNA
                    organism = Homo sapiens
misc_feature        1..20
                    note = LPG10136 3-prime Genome Target Sequence FA
SEQUENCE: 358
cgcgcgcctg taatcccagc                                              20
```

```
SEQ ID NO: 359           moltype = DNA   length = 20
FEATURE                  Location/Qualifiers
source                   1..20
                         mol_type = other DNA
                         organism = Homo sapiens
misc_feature             1..20
                         note = LPG10136 3-prime Genome Target Sequence FA
SEQUENCE: 359
ccgggaggca gaggttgcat                                                 20

SEQ ID NO: 360           moltype = DNA   length = 20
FEATURE                  Location/Qualifiers
source                   1..20
                         mol_type = other DNA
                         organism = Homo sapiens
misc_feature             1..20
                         note = LPG10139 5-prime Genome Target Sequence FA
SEQUENCE: 360
ctaggaaggt ggatcacctg                                                 20

SEQ ID NO: 361           moltype = DNA   length = 20
FEATURE                  Location/Qualifiers
source                   1..20
                         mol_type = other DNA
                         organism = Homo sapiens
misc_feature             1..20
                         note = LPG10139 5-prime Genome Target Sequence FA
SEQUENCE: 361
ctgaggtccg gagttcaaga                                                 20

SEQ ID NO: 362           moltype = DNA   length = 20
FEATURE                  Location/Qualifiers
source                   1..20
                         mol_type = other DNA
                         organism = Homo sapiens
misc_feature             1..20
                         note = LPG10139 3-prime Genome Target Sequence FA
SEQUENCE: 362
gctgcggcag gagaatcgct                                                 20

SEQ ID NO: 363           moltype = DNA   length = 20
FEATURE                  Location/Qualifiers
source                   1..20
                         mol_type = other DNA
                         organism = Homo sapiens
misc_feature             1..20
                         note = LPG10139 3-prime Genome Target Sequence FA
SEQUENCE: 363
agaggttgca ttaagccaag                                                 20

SEQ ID NO: 364           moltype = DNA   length = 500
FEATURE                  Location/Qualifiers
source                   1..500
                         mol_type = other DNA
                         organism = Homo sapiens
misc_feature             1..500
                         note = BCL11A enhancer region
SEQUENCE: 364
aaaaatggac aattatgagg aggggagagt gcagacaggg gaagcttcac ctcctttaca     60
attttgggag tccacacggc atggcataca aattatttca ttcccattga gaaataaaat   120
ccaattctcc atcaccaaga gagccttccg aaagaggccc ccctgggcaa acggccaccg   180
atggagaggt ctgccagtcc tcttctaccc cacccacgcc cccacctaa tcagaggca    240
aaccttcct ggagcctgtg ataaaagcaa ctgttagctt gcactagact agcttcaaag   300
ttgtattgac cctggtgtgt tatgtctaag agtagatgct atatctcttt tctggcctat   360
gttattacct gtatggactt tgcactggaa tcagctatct gctcttactt atgcacacct   420
ggggcataga gccagccctg tatcgctttt cagccatctc actacagata actcccaagt   480
cctgtctagc tgccttcctt                                              500

SEQ ID NO: 365           moltype = DNA   length = 20
FEATURE                  Location/Qualifiers
source                   1..20
                         mol_type = other DNA
                         organism = Homo sapiens
misc_feature             1..20
                         note = LPG10134  BCL11A target
SEQUENCE: 365
atcagaggcc aaacccttcc                                                 20

SEQ ID NO: 366           moltype = DNA   length = 20
```

```
FEATURE              Location/Qualifiers
source               1..20
                     mol_type = other DNA
                     organism = Homo sapiens
misc_feature         1..20
                     note = LPG10134  BCL11A target
SEQUENCE: 366
cacaggctcc aggaagggtt                                                    20

SEQ ID NO: 367       moltype = DNA  length = 20
FEATURE              Location/Qualifiers
source               1..20
                     mol_type = other DNA
                     organism = Homo sapiens
misc_feature         1..20
                     note = LPG10134  BCL11A target
SEQUENCE: 367
ctaacagttg cttttatcac                                                    20

SEQ ID NO: 368       moltype = DNA  length = 20
FEATURE              Location/Qualifiers
source               1..20
                     mol_type = other DNA
                     organism = Homo sapiens
misc_feature         1..20
                     note = LPG10145  BCL11A target
SEQUENCE: 368
gctaacagtt gcttttatca                                                    20

SEQ ID NO: 369       moltype = DNA  length = 20
FEATURE              Location/Qualifiers
source               1..20
                     mol_type = other DNA
                     organism = Homo sapiens
misc_feature         1..20
                     note = LPG10145  BCL11A target
SEQUENCE: 369
gttgctttta tcacaggctc                                                    20

SEQ ID NO: 370       moltype = DNA  length = 20
FEATURE              Location/Qualifiers
source               1..20
                     mol_type = other DNA
                     organism = Homo sapiens
misc_feature         1..20
                     note = LPG10145  BCL11A target
SEQUENCE: 370
aatcagaggc caaacccttc                                                    20

SEQ ID NO: 371       moltype = DNA  length = 20
FEATURE              Location/Qualifiers
source               1..20
                     mol_type = other DNA
                     organism = Homo sapiens
misc_feature         1..20
                     note = LPG10136 BCL11A target
SEQUENCE: 371
accctaatca gaggccaaac                                                    20

SEQ ID NO: 372       moltype = DNA  length = 20
FEATURE              Location/Qualifiers
source               1..20
                     mol_type = other DNA
                     organism = Homo sapiens
misc_feature         1..20
                     note = LPG10136 BCL11A target
SEQUENCE: 372
tcagaggcca aacccttcct                                                    20

SEQ ID NO: 373       moltype = DNA  length = 20
FEATURE              Location/Qualifiers
source               1..20
                     mol_type = other DNA
                     organism = Homo sapiens
misc_feature         1..20
                     note = LPG10136 BCL11A target
SEQUENCE: 373
taacagttgc ttttatcaca                                                    20
```

-continued

```
SEQ ID NO: 374            moltype = DNA  length = 20
FEATURE                   Location/Qualifiers
source                    1..20
                          mol_type = other DNA
                          organism = Homo sapiens
misc_feature              1..20
                          note = LPG10139 BCL11A target
SEQUENCE: 374
accctaatca gaggccaaac                                                 20

SEQ ID NO: 375            moltype = DNA  length = 20
FEATURE                   Location/Qualifiers
source                    1..20
                          mol_type = other DNA
                          organism = Homo sapiens
misc_feature              1..20
                          note = LPG10139 BCL11A target
SEQUENCE: 375
tcagaggcca aaccctttcct                                                20

SEQ ID NO: 376            moltype = DNA  length = 20
FEATURE                   Location/Qualifiers
source                    1..20
                          mol_type = other DNA
                          organism = Homo sapiens
misc_feature              1..20
                          note = LPG10139 BCL11A target
SEQUENCE: 376
taacagttgc ttttatcaca                                                 20

SEQ ID NO: 377            moltype = AA  length = 192
FEATURE                   Location/Qualifiers
source                    1..192
                          mol_type = protein
                          organism = synthetic construct
REGION                    1..192
                          note = APG00868 deaminase
SEQUENCE: 377
MEPWRPSPRN PMDRIDPNTF RFHFPNLLYA SGRKLCYLCF QVETGDYFSC DDSDRGVFRN     60
KVHPWARCHA EQCFLSWFRD QYPCRDEYYN VTWFLSWSPC PTCAEEVVEF LEEYRNLTLS    120
IFTSRLYYFY HPNYQQGLRK LWDAGVQLDI MSCDDFEHCW DNFVDHKGMR FQRRNLLKDY    180
DFLAAELQEI LR                                                        192

SEQ ID NO: 378            moltype = AA  length = 373
FEATURE                   Location/Qualifiers
source                    1..373
                          mol_type = protein
                          organism = synthetic construct
REGION                    1..373
                          note = APG02316 deaminase
SEQUENCE: 378
MIENPALKIS KRDRIKISNL KDLKNALKNE NYNIKANDKE KFKDEVKKVF NINDDIFERL     60
DKCLNRDITY KVDNVEDFID YIKKIMIFED KHEIICEKLK RIKKLYINRE EYEREKSTRD    120
NVEHIIEVIE KTKENVSRKI SLEELERLEI LEEELEDKYL FAKDIEFLKK MILGNCKNVI    180
ESYNETKIK TLKMKIPKEI NYSYIKAKEG SVEYHQYLNN NINRMNRLIK SIDKYIEHYK    240
DDIFNINQSL ALQDSINIAL ATFDNKEFKA ISGKNDIEDY CKVIPIEKSR FKSRKVNKLG    300
ELGIGYNRIN DSEKKILEEI HEKIKQKILK DRGNLTLYTK WEPCPSCYFV ISQFCEKYPN    360
IKVEVKYNKK YGE                                                       373

SEQ ID NO: 379            moltype = AA  length = 235
FEATURE                   Location/Qualifiers
source                    1..235
                          mol_type = protein
                          organism = synthetic construct
REGION                    1..235
                          note = APG05241 deaminase
SEQUENCE: 379
MNSKTGPSVG DATLRRRIKP WEFVAFFNPQ ELRKETCLLY EIKWGNQNIW RHSNQNTSQH     60
AEINFMEKFT AERHFNSSVR CSITWFLSWS PCWECSKAIR KFLDHYPNVT LAIFISRLYW    120
HMDQQHRQGL KELVHSGVTI QIMSYSEYHY CWRNFVDYPQ GEEDYWPKYP YLWIMLYVLE    180
LHCIILGLPP CLKISGSHSN QLALFSLDLQ DCHYQKIPYN VLVATGLVQP FVTWR         235

SEQ ID NO: 380            moltype = AA  length = 201
FEATURE                   Location/Qualifiers
source                    1..201
                          mol_type = protein
                          organism = synthetic construct
REGION                    1..201
                          note = APG05840 deaminase
```

```
SEQUENCE: 380
MEASPASRPR PLMDPHMFTG NFTNNPRVFG LHQTYLCYEV KRQGPDGTRD LMNEQRDFLC     60
NQAKNHFSGS EDHHAERCFL DRIPSWQLDP AQTYRVTCFI SWSPCFSCAQ EVAEFLHENP    120
HVNLRIFAAR IYDYLPRYEE GLQMLQNAGA QVSIMTSEEF GHCWDTFVDR QGHPFQPWEG    180
LDEHSQALSG RLQAILQNQG N                                             201

SEQ ID NO: 381           moltype = AA   length = 262
FEATURE                  Location/Qualifiers
source                   1..262
                         mol_type = protein
                         organism = synthetic construct
REGION                   1..262
                         note = APG07280 deaminase
SEQUENCE: 381
MHHSARLPPN CIVSRYANAP WTVLPLPLPP TEAPATGDDT LRRRIEPWEF EAFFNPQELR     60
REACLLYQIT WSSHKVWRET AKNTVDSHVE VNFIQNLTAG RYCRPSTRCS ILWFLSWSPC    120
SSCSKAIRLF LSQHPGVSLV IYVARLFQHM DPQNRQGLRE LIHSGVTIQV MRPQEYDYCW    180
KNFVNYPPGQ EEHWPRYPVQ CMTLYNLELY CIIHNLPPCV RISKQRQSQL AFFSLGLENV    240
HYQRIPPPLL LLTGLVFVFP WK                                            262

SEQ ID NO: 382           moltype = AA   length = 395
FEATURE                  Location/Qualifiers
source                   1..395
                         mol_type = protein
                         organism = synthetic construct
REGION                   1..395
                         note = APG07386 deaminase
SEQUENCE: 382
MNPQIRNPME GMDRHAFNYN FENEPILYGR SYTWLCYEVK IRKDPSKLPW DTGVFRGQVR     60
PKLQSNRRYE LSNWECRKHV YFQPQYHAEM CFLSWFCGNQ LPAHKRFQIT WFVSWTPCPD    120
CVAKVTEFLA EHPNVTLTIS VARLYYYRGK DWRRALCRLH QAGARVKIMD YEEFAYCWEN    180
FVYNEGQSFM PWDKFDDNYA FLHHKLKEIL RNPMEATYPH IFYFHFPKNLR KAYGRNETWL    240
CFTMEIIKQH STVFWETGVF RNQVYPESLC HAERCFLSWF CEDILSPNTD YRVTWYTSWS    300
PCLDCAGEVA EFLARHSNVK LAIFAARLYY FWDPHYQQGL RSLSEKGASV EIMGYKDFKY    360
CWENFVYNGD EPFKPWKGLK YNFLFLDSKL QEILQ                              395

SEQ ID NO: 383           moltype = AA   length = 234
FEATURE                  Location/Qualifiers
source                   1..234
                         mol_type = protein
                         organism = synthetic construct
REGION                   1..234
                         note = APG08360 deaminase
SEQUENCE: 383
MDPQRLRQWP GPGPASRGGY GQRPRIRNPE EWFHELSPRT FSFHFRNLRF ASGRNRSYIC     60
CQVEGKNCFF QGIFQNQKKR HAEIRFIDKI NSLNLDQNQC YRIICYVTWS PCHNCAKELV    120
DFISNRHHLS LQLFASRLYF HWVRCYQRGL QRLQANRSVV AVMKGPEFKD CWEKFVDHQG    180
ESFPSWEKLE QYSESISRRL SRILRFANQN NLEDSFRDLR LGSPSPSSSR SDSR          234

SEQ ID NO: 384           moltype = AA   length = 211
FEATURE                  Location/Qualifiers
source                   1..211
                         mol_type = protein
                         organism = synthetic construct
REGION                   1..211
                         note = APG09260 deaminase
SEQUENCE: 384
MEDFHCVCVY CPLQVSVMSD YQAASSSPDC PQCPQHILTG AEAAVSYSQF CETFGFHMGP     60
SGARALLLFY ELWGPSGTLV QRGQASNLLE VCEEVLYSNY MPCQECSQTL ISFLLRYPWV    120
RLDLLFSQLY HTAPSQTHSL DNQTGLRSLA VLTLSPNSGA AWGHLLRCFV RDVPPSALQL    180
PLLPERVEAD RVNAIHISAT TGIGPAFWTS H                                  211

SEQ ID NO: 385           moltype = AA   length = 267
FEATURE                  Location/Qualifiers
source                   1..267
                         mol_type = protein
                         organism = synthetic construct
REGION                   1..267
                         note = APG09688 deaminase
SEQUENCE: 385
MGTPKDTKSR HLAGRCHELH NSRGRSPESD TMASEKGPSN KDYTLRRRIE PWEFEVFFDP     60
QELRKEACLL YEIKWGASSK TWRSSGKNTT NHVEVNFLEK LTSEGRLGPS TCCSITWFLS    120
WSPCWECSTA IREFLSQHPG VTLVIFVARL FQHMDRRNRQ GLKDLVTSGV TVQVMSVSEY    180
CYCWENFVNY PPGKAAQWPR YPPRWMLMYA LELYCIILGL PPCLKISRRH QKQLTFFSLT    240
PQYCHYKMIP PYILLATGLL QPSVPWR                                       267

SEQ ID NO: 386           moltype = AA   length = 230
FEATURE                  Location/Qualifiers
source                   1..230
```

```
                          mol_type = protein
                          organism = synthetic construct
REGION                    1..230
                          note = APG09980 deaminase
SEQUENCE: 386
MAAGPAPEAR SLMDEQTFLD NFNNLKYPRK TYLCYEVELL VGENHIPLDD YKGFVHNEGF      60
DMGLERCHAE LIFLERMASW NLDTELRYRI TVFISWSPCP ECADELVKFL RENRHVNLRI     120
FAARIYDWYQ GYEAGLRALK AAGAEVAMMT LHEFEYCWNN FVDHQQDEDT PFPPWDNLVA     180
RSEELSQRLE GILQPSVLVF CWPSQVSVTA AHSDIMSQAS RAWEKRRDPP                230

SEQ ID NO: 387            moltype = AA  length = 169
FEATURE                   Location/Qualifiers
source                    1..169
                          mol_type = protein
                          organism = synthetic construct
REGION                    1..169
                          note = APG09982 deaminase
SEQUENCE: 387
MSDLELNHEY WMRHALQLAK RARDEGEVPV GAVLVLNNQV IGEGWNRAIG LHDPTAHAEI      60
MALRQGGLVL QNYRLYDTTL YSTFEPCVMC SGAMVHSRIG TLVFGVRNEK TGAAGSLMDV     120
LRHPGMNHQV QIIDGVLAPE CSGLLCRFFR MPRRVFNQQK AESTSSPGD                 169

SEQ ID NO: 388            moltype = AA  length = 164
FEATURE                   Location/Qualifiers
source                    1..164
                          mol_type = protein
                          organism = synthetic construct
REGION                    1..164
                          note = APG03724 deaminase
SEQUENCE: 388
MSNPELTHEH WMRYALTLAK RAREEGEVPV GAVLVLNNQV IGEGWNRAIG LHDPTAHAEI      60
MALRQGGLVL QNYRLYDTTL YSTFEPCVMC AGAMVHSRIG QLVFGVRNAK TGAAGSLMDV     120
LHHPGMNHRI EFTEGVLRDE CAAMLCRFFR QPRRVFNALK TGNA                      164

SEQ ID NO: 389            moltype = AA  length = 169
FEATURE                   Location/Qualifiers
source                    1..169
                          mol_type = protein
                          organism = synthetic construct
REGION                    1..169
                          note = APG09949 deaminase
SEQUENCE: 389
MSIPELNHDV WMRHALTLAK RAREEGEVPV GAVLVLNGQV IGEGWNRAIG LHDPTAHAEI      60
MALRQGGLVL QNYRLYDTTL YSTFEPCVMC AGAMVHSRIG QLVFGVRNAK TGAAGSLIDV     120
LHHPGMNHRV AITEGVLREE CAAMLCRFFR QPRRVFNALK KPAGDPTAF                 169

SEQ ID NO: 390            moltype = AA  length = 172
FEATURE                   Location/Qualifiers
source                    1..172
                          mol_type = protein
                          organism = synthetic construct
REGION                    1..172
                          note = APG08196 deaminase
SEQUENCE: 390
MSNPELNHEY WMRYALTLAK RARDEGEVPV GAVLVLNDQV IGEGWNRAIG LHDPTAHAEI      60
MALRQGGLVL QNYRLYDTTL YSTFEPCVMC AGAMVHSRIG RLVFGVRNAK TGAAGSLLDV     120
LHHPGMNHHI EMEEGVLRDE CAAMLCRFFR QPRRVFNALK KSPPDSPNLQ AR             172

SEQ ID NO: 391            moltype = AA  length = 169
FEATURE                   Location/Qualifiers
source                    1..169
                          mol_type = protein
                          organism = synthetic construct
REGION                    1..169
                          note = APG06333 deaminase
SEQUENCE: 391
MSNPELTHDH WMRHALTLAQ RARNEGEVPV GAVLVLNGQV IGEGWNRAIG LHDPTAHAEI      60
MALRQGGLVL QNYRLYDTVL YSTFEPCVMC AGAMVHSRIG QLVFGVRNAK TGAAGSLIDV     120
LHHPGMNHRV EIIEGVLRDE CAAMLCRFFR HPRRVFNALK KNAGTSPTQ                 169

SEQ ID NO: 392            moltype = AA  length = 166
FEATURE                   Location/Qualifiers
source                    1..166
                          mol_type = protein
                          organism = synthetic construct
REGION                    1..166
                          note = APG06489 deaminase
SEQUENCE: 392
MSDTELNHEY WMRHALMLAK RARDEGEVPV GAVLVLKNQV IGEGWNRAIG LHDPTAHAEI      60
```

```
MALRQGGLVL QNYRLYDTTL YSTFEPCVMC AGAMVHSRIG NLVFGVRNAK TGAAGSLIDV    120
LHHPGMNHRV EIAEGVLADE CSAMLCRFFR HPRRVFNALK QAAKHD                  166

SEQ ID NO: 393          moltype = AA  length = 171
FEATURE                 Location/Qualifiers
source                  1..171
                        mol_type = protein
                        organism = synthetic construct
REGION                  1..171
                        note = APG08449 deaminase
SEQUENCE: 393
MSDIELNHEY WMRHALMLAK RAREEGEVPV GAVLVLNNQV IGEGWNRAIG LHDPTAHAEI    60
MALRQGGLVL QNYRLYDTTL YSTFEPCVMC AGAMVHSRIG HLVFGVRNAK TGAAGSLIDV    120
LHHPGMNHRI EFTEGVLADE CSGMLCRFFR YPRRVFNTLK QAAKANPPAA Q             171

SEQ ID NO: 394          moltype = AA  length = 173
FEATURE                 Location/Qualifiers
source                  1..173
                        mol_type = protein
                        organism = synthetic construct
REGION                  1..173
                        note = APG05174 deaminase
SEQUENCE: 394
MSIPELNHDV WMRHALTLAK RAREEGEVPV GAVLVLNGQV IGEGWNRAIG LHDPTAHAEI    60
MALRQGGLVL QNYRLYDTTL YSTFEPCVMC AGAMVHSRIG QLVFGVRNAK TGAAGSLMDV    120
LHHPGMNHRV EITEGVLRDE CAAMLCRFFR QPRRVFNALK KPAGDPSALQ NNR           173

SEQ ID NO: 395          moltype = AA  length = 168
FEATURE                 Location/Qualifiers
source                  1..168
                        mol_type = protein
                        organism = synthetic construct
REGION                  1..168
                        note = APG09102 deaminase
SEQUENCE: 395
MSNPEFTHEY WMRHALTLAR RARDEGEVPV GAVLVLNNQV IGEGWNRAIG LHDPTAHAEI    60
MALRQGGLVL QNYRLYDTTL YSTFEPCVMC SGAMVHSRIG TLVFGVRNEK TGAAGSLMDV    120
LGHPGMNHQV KTIGGVLAPE CSGLLCRFFR MPRRVFNQQK AELKSSGD                 168

SEQ ID NO: 396          moltype = AA  length = 167
FEATURE                 Location/Qualifiers
source                  1..167
                        mol_type = protein
                        organism = synthetic construct
REGION                  1..167
                        note = APG05723 deaminase
SEQUENCE: 396
MSDAELTHEY WMRHALTLAQ RARDEGEVPV GAVLVLNNQV IGEGWNRAIG LHDPTAHAEI    60
MALRQGGLVQ QNYRLYDTTL YSTFEPCVMC AGAMVHSRIG RLIFGVRNAK TGAAGSLIDV    120
LHHPGMNHRV EVVEGILRDE CAGMLCRFFR QPRRVFNALK KGATDVL                  167

SEQ ID NO: 397          moltype = AA  length = 169
FEATURE                 Location/Qualifiers
source                  1..169
                        mol_type = protein
                        organism = synthetic construct
REGION                  1..169
                        note = LPG50140 deaminase
SEQUENCE: 397
MSDLELNHEY WMRHALQLAK RARDEGEVPV GAVLVLNNQV IGEGWNRAIG LHDPTAHAEI    60
MALRQGGLVL QNYRLIDTTL YVTFEPCVMC SGAMVHSRIG TLVFGVRNSK RGAAGSLMNV    120
LNYPGMNHQV QIIDGVLAPE CSGLLCDFYR MPRQVFNQQK AESTSINGD                169

SEQ ID NO: 398          moltype = AA  length = 164
FEATURE                 Location/Qualifiers
source                  1..164
                        mol_type = protein
                        organism = synthetic construct
REGION                  1..164
                        note = LPG50141 deaminase
SEQUENCE: 398
MSNPELTHEH WMRYALTLAK RAREEGEVPV GAVLVLNNQV IGEGWNRAIG LHDPTAHAEI    60
MALRQGGLVL QNYRLIDTTL YVTFEPCVMC AGAMVHSRIG QLVFGVRNSK RGAAGSLMNV    120
LNYPGMNHRI EFTEGVLRDE CAAMLCDFYR QPRQVFNALK TGNA                     164

SEQ ID NO: 399          moltype = AA  length = 169
FEATURE                 Location/Qualifiers
source                  1..169
                        mol_type = protein
```

```
                        organism = synthetic construct
REGION                  1..169
                        note = LPG50142 deaminase
SEQUENCE: 399
MSIPELNHDV WMRHALTLAK RAREEGEVPV GAVLVLNGQV IGEGWNRAIG LHDPTAHAEI   60
MALRQGGLVL QNYRLIDTTL YVTFEPCVMC AGAMVHSRIG QLVFGVRNSK RGAAGSLINV  120
LNYPGMNHRV AITEGVLREE CAAMLCDFYR QPRQVFNALK KPAGDINAF              169

SEQ ID NO: 400          moltype = AA  length = 172
FEATURE                 Location/Qualifiers
source                  1..172
                        mol_type = protein
                        organism = synthetic construct
REGION                  1..172
                        note = LPG50143 deaminase
SEQUENCE: 400
MSNPELNHEY WMRYALTLAK RARDEGEVPV GAVLVLNDQV IGEGWNRAIG LHDPTAHAEI   60
MALRQGGLVL QNYRLIDTTL YVTFEPCVMC AGAMVHSRIG RLVFGVRNSK RGAAGSLLNV  120
LNYPGMNHHI EMEEGVLRDE CAAMLCDFYR QPRQVFNALK KSPPDINNLQ AR          172

SEQ ID NO: 401          moltype = AA  length = 169
FEATURE                 Location/Qualifiers
source                  1..169
                        mol_type = protein
                        organism = synthetic construct
REGION                  1..169
                        note = LPG50144 deaminase
SEQUENCE: 401
MSNPELTHDH WMRHALTLAQ RARNEGEVPV GAVLVLNGQV IGEGWNRAIG LHDPTAHAEI   60
MALRQGGLVL QNYRLIDTVL YVTFEPCVMC AGAMVHSRIG QLVFGVRNSK RGAAGSLINV  120
LNYPGMNHRV EIIEGVLRDE CAAMLCDFYR HPRQVFNALK KNAGTINTQ              169

SEQ ID NO: 402          moltype = AA  length = 166
FEATURE                 Location/Qualifiers
source                  1..166
                        mol_type = protein
                        organism = synthetic construct
REGION                  1..166
                        note = LPG50145 deaminase
SEQUENCE: 402
MSDTELNHEY WMRHALMLAK RARDEGEVPV GAVLVLKNQV IGEGWNRAIG LHDPTAHAEI   60
MALRQGGLVL QNYRLIDTTL YVTFEPCVMC AGAMVHSRIG NLVFGVRNSK RGAAGSLINV  120
LNYPGMNHRV EIAEGVLADE CSAMLCDFYR HPRQVFNALK QAAKHI                 166

SEQ ID NO: 403          moltype = AA  length = 171
FEATURE                 Location/Qualifiers
source                  1..171
                        mol_type = protein
                        organism = synthetic construct
REGION                  1..171
                        note = LPG50146 deaminase
SEQUENCE: 403
MSDIELNHEY WMRHALMLAK RAREEGEVPV GAVLVLNNQV IGEGWNRAIG LHDPTAHAEI   60
MALRQGGLVL QNYRLIDTTL YVTFEPCVMC AGAMVHSRIG HLVFGVRNSK RGAAGSLINV  120
LNYPGMNHRI EFTEGVLADE CSGMLCDFYR YPRQVFNTLK QAAKAINPAA Q           171

SEQ ID NO: 404          moltype = AA  length = 173
FEATURE                 Location/Qualifiers
source                  1..173
                        mol_type = protein
                        organism = synthetic construct
REGION                  1..173
                        note = LPG50147 deaminase
SEQUENCE: 404
MSIPELNHDV WMRHALTLAK RAREEGEVPV GAVLVLNGQV IGEGWNRAIG LHDPTAHAEI   60
MALRQGGLVL QNYRLIDTTL YVTFEPCVMC AGAMVHSRIG QLVFGVRNSK RGAAGSLMNV  120
LNYPGMNHRV EITEGVLRDE CAAMLCDFYR QPRQVFNALK KPAGDINALQ NNR         173

SEQ ID NO: 405          moltype = AA  length = 168
FEATURE                 Location/Qualifiers
source                  1..168
                        mol_type = protein
                        organism = synthetic construct
REGION                  1..168
                        note = LPG50148 deaminase
SEQUENCE: 405
MSNPEFTHEY WMRHALTLAR RARDEGEVPV GAVLVLNNQV IGEGWNRAIG LHDPTAHAEI   60
MALRQGGLVL QNYRLIDTTL YVTFEPCVMC SGAMVHSRIG TLVFGVRNSK RGAAGSLMNV  120
LNYPGMNHQV KTIGGVLAPE CSGLLCDFYR MPRQVFNQQK AELKSIND               168
```

```
SEQ ID NO: 406          moltype = AA   length = 167
FEATURE                 Location/Qualifiers
source                  1..167
                        mol_type = protein
                        organism = synthetic construct
REGION                  1..167
                        note = LPG50149 deaminase
SEQUENCE: 406
MSDAELTHEY WMRHALTLAQ RARDEGEVPV GAVLVLNNQV IGEGWNRAIG LHDPTAHAEI    60
MALRQGGLVQ QNYRLIDTTL YVTFEPCVMC AGAMVHSRIG RLIFGVRNSK RGAAGSLINV   120
LNYPGMNHRV EVVEGILRDE CAGMLCDFYR QPRQVFNALK KGATDIN                 167

SEQ ID NO: 407          moltype = AA   length = 167
FEATURE                 Location/Qualifiers
source                  1..167
                        mol_type = protein
                        organism = synthetic construct
REGION                  1..167
                        note = LPG50150 deaminase
SEQUENCE: 407
MSDAELTHEY WMRHALTLAQ RARDEGEVPV GAVLVLNNQV IGEGWNRAIG LHDPTAHAEI    60
MALRQGGLVQ QNYRLLDTTL YVTFEPCVMC AGAMVHSRIG RLIFGVRNSK RGAAGSLINV   120
LNYPGMNHRV EVVEGILRDE CAGMLCAFYR QPRAVKNALK KGATDVL                 167

SEQ ID NO: 408          moltype = AA   length = 169
FEATURE                 Location/Qualifiers
source                  1..169
                        mol_type = protein
                        organism = synthetic construct
REGION                  1..169
                        note = LPG50151 deaminase
SEQUENCE: 408
MSDLELNHEY WMRHALQLAQ RARDEGEVPV GAVLVYNNQV IGEGWNRAIG LHDPTAHAEI    60
MALRQGGLVL QNYRLLDTTL YVTFEPCVMC SGAMVHSRIG TLVFGVRNEK RGAAGSLMNV   120
LRYPGMNHQV QIIDGVLAPE CSGLLCDFYR MPRQQKNQQK AESTSSPGD               169

SEQ ID NO: 409          moltype = AA   length = 167
FEATURE                 Location/Qualifiers
source                  1..167
                        mol_type = protein
                        organism = synthetic construct
REGION                  1..167
                        note = LPG50152 deaminase
SEQUENCE: 409
MSDNELNHEY WMRHALGLAK RAREEGEVPV GAVLVLNNQV IGEGWNRAIG LHDPTAHAEI    60
MALRQGGLVL QNYRLTDTTL YVTFEPCVMC AGAMVHSRIG TLVFGVRNSK RGAAGSLMNV   120
LNYPGMNHRV EIVEGILSES CAAMLCDFYR QPRAVKNALK KAADPAA                 167

SEQ ID NO: 410          moltype = AA   length = 164
FEATURE                 Location/Qualifiers
source                  1..164
                        mol_type = protein
                        organism = synthetic construct
REGION                  1..164
                        note = LPG50153 deaminase
SEQUENCE: 410
MSDTEFTHEH WMRHALTLAQ RARDEGEVPV GAVLVLNNQV IGEGWNRAIG LHDPTAHAEI    60
MALRQGGLVL QNYRLLDTTL YVTFEPCVMC AGAMVHSRIG HLVFGVRNSK RGAIGSLMNV   120
LGYPGMNHQV QVSEGVLATE CSAMLCDFYR APRLVKNALK EKAR                    164

SEQ ID NO: 411          moltype = AA   length = 171
FEATURE                 Location/Qualifiers
source                  1..171
                        mol_type = protein
                        organism = synthetic construct
REGION                  1..171
                        note = LPG50154 deaminase
SEQUENCE: 411
MSESEFTHEH WMRHALTLAR RAREEGEVPV GAVLVLNNQV IGEGWNRAIG LHDPTAHAEI    60
MALRQGGLVL QNYRLLDSTL YVTFEPCVMC AGAMVHGRIG NLVFGVRNSK RGAIGSLMNV   120
VGYPGMNHQI NVIEGVLAEE CSAMLCDFYR APRLVKNALK EKARNGNNPN K            171

SEQ ID NO: 412          moltype = AA   length = 164
FEATURE                 Location/Qualifiers
source                  1..164
                        mol_type = protein
                        organism = synthetic construct
REGION                  1..164
```

```
                        note = LPG50155 deaminase
SEQUENCE: 412
MSNPELTHEH WMRYALTLAK RAREEGEVPV GAVLVLNNQV IGEGWNRAIG LHDPTAHAEI    60
MALRQGGLVL QNYRLIDTTL YVTFEPCVMC AGAMVHSRIG QLVFGVRNSK RGAAGSLMNV   120
LNYPGMNHRI EFTEGVLRDE CAAMLCDFYR QPRLVKNALK TGNA                   164

SEQ ID NO: 413          moltype = AA   length = 166
FEATURE                 Location/Qualifiers
source                  1..166
                        mol_type = protein
                        organism = synthetic construct
REGION                  1..166
                        note = LPG50156 deaminase
SEQUENCE: 413
MSDPELNHEY WMRHALQLAK RAREEGEVPV GAVLVLNNQV IGEGWNRAIG LHDPTAHAEI    60
MALRQGGLVL QNYRLLDTTL YVTFEPCVMC SGAMIHSRIG TVVFGVRNEK RGAAGSLLNV   120
LRYPGMNHQV NVLGGVLAPA CSEMLCEFYR MPRQQKNRQK AESKLS                 166

SEQ ID NO: 414          moltype = AA   length = 166
FEATURE                 Location/Qualifiers
source                  1..166
                        mol_type = protein
                        organism = synthetic construct
REGION                  1..166
                        note = LPG50157 deaminase
SEQUENCE: 414
MSDNELNHEH WMRHALTLAQ RAREEGEVPV GAVLVLQNQV IGEGWNRAIG LHDPTAHAEI    60
MALRQGGMVL QNYRLIDTTL YVTFEPCVMC AGAMVHSRIG QLVFGVRNSK RGAAGSLINV   120
LNYPGMNHRV EITEGVLADD CSSMLCDFYR HPREQKNALK RAAHSN                 166

SEQ ID NO: 415          moltype = AA   length = 168
FEATURE                 Location/Qualifiers
source                  1..168
                        mol_type = protein
                        organism = synthetic construct
REGION                  1..168
                        note = LPG50158 deaminase
SEQUENCE: 415
MSNPEHNHEY WMRHALTLAQ RARDEGEVPV GAVLVYNNQV IGEGWNRAIG LHDPTAHAEI    60
MALRQGGLVL QNYRLLDTTL YVTFEPCVMC SGAMVHSRIG TLVFGVRNEK RGAAGSLMNV   120
LGYPGMNHQV QTIGGVLAPE CSGLLCDFYR MPRQQKNQQK AELNQPGD               168

SEQ ID NO: 416          moltype = AA   length = 168
FEATURE                 Location/Qualifiers
source                  1..168
                        mol_type = protein
                        organism = synthetic construct
REGION                  1..168
                        note = LPG50159 deaminase
SEQUENCE: 416
MSDLELNHEY WMRHALSLAK RARDEGEVPV GAVLVLNNQV IGEGWNRAIG LHDPTAHAEI    60
MALRQGGLVL QNYRLLDTTL YVTFEPCVMC SGAMVHSRIG TLVYGVRNEK RGAAGSLMNV   120
LGYPGMNHQV QIIGGVLAPD CSGLLCDFYR MPRQQKNQQK AELKSSGD               168

SEQ ID NO: 417          moltype = AA   length = 166
FEATURE                 Location/Qualifiers
source                  1..166
                        mol_type = protein
                        organism = synthetic construct
REGION                  1..166
                        note = LPG50160 deaminase
SEQUENCE: 417
MSDHEFNDEY WMRHALTLAK RAREEGEVPV GAVLVLNNQV IGEGWNRAIG LHDPTAHAEI    60
MALRQGGLVL QNYRLIDATL YVTFEPCVMC AGAMVHSRIS RLVFGVRNSK RGAAGSLINV   120
LNYPGMNHRV EITEGILAES CSAMLCDFYR WPREVKNALK KARQEE                 166

SEQ ID NO: 418          moltype = AA   length = 166
FEATURE                 Location/Qualifiers
source                  1..166
                        mol_type = protein
                        organism = synthetic construct
REGION                  1..166
                        note = LPG50161 deaminase
SEQUENCE: 418
MSQTELTHEY WMRHALTLAQ RARDEGEVPV GAVLVLNNQV IGEGWNRAIG LHDPTAHAEI    60
MALRQGGLVL QNYRLLDTTL YVTFEPCVMC AGAMVHGRIG TLVFGVRNSK RGAVGSLMNI   120
TGYPGMNHQV QVIEGILATE CSAMLCAFYR QPRLVKNALK EAAKTA                 166

SEQ ID NO: 419          moltype = AA   length = 167
```

| FEATURE | Location/Qualifiers |
|---|---|
| source | 1..167 |
| | mol_type = protein |
| | organism = synthetic construct |
| REGION | 1..167 |
| | note = LPG50162 deaminase |

SEQUENCE: 419

```
MSNPELNHDY WMRHALSLAK RAREEGEVPV GAVLVRNNEV IGEGWNRAIG LHDPTAHAEI    60
MALRQGGMVL QNYRLIDTTL YVTFEPCVMC AGAMVHSRIG QLVFGVRNSK RGAAGSLMNV  120
LNYPGMNHRV EIVEGVLRDE CAGMLCDFYR QPRLVKNAQK KGAEPLI               167
```

| SEQ ID NO: 420 | moltype = AA   length = 172 |
|---|---|
| FEATURE | Location/Qualifiers |
| source | 1..172 |
| | mol_type = protein |
| | organism = synthetic construct |
| REGION | 1..172 |
| | note = LPG50163 deaminase |

SEQUENCE: 420

```
MSNPELNHEY WMRYALTLAK RARDEGEVPV GAVLVYNDQV IGEGWNRAIG LHDPTAHAEI    60
MALRQGGLVL QNYRLIDTTL YVTFEPCVMC AGAMVHSRIG RLVFGVRNSK RGAAGSLLNV  120
LNYPGMNHHI EMEEGVLRDE CAAMLCDFYR QPRMVKNALK KSPPDSPNLQ AR          172
```

| SEQ ID NO: 421 | moltype = AA   length = 168 |
|---|---|
| FEATURE | Location/Qualifiers |
| source | 1..168 |
| | mol_type = protein |
| | organism = synthetic construct |
| REGION | 1..168 |
| | note = LPG50164 deaminase |

SEQUENCE: 421

```
MSNPEFTHEY WMRHALTLAR RARDEGEVPV GAVLVLNNQV IGEGWNRAIG LHDPTAHAEI    60
MALRQGGLVL QNYRLLDTTL YVTFEPCVMC SGAMVHSRIG TLVFGVRNEK RGAAGSLMNV  120
LGYPGMNHQV KTIGGVLAPE CSGLLCDFYR MPRQQKNQQK AELKSSGD              168
```

| SEQ ID NO: 422 | moltype = AA   length = 165 |
|---|---|
| FEATURE | Location/Qualifiers |
| source | 1..165 |
| | mol_type = protein |
| | organism = synthetic construct |
| REGION | 1..165 |
| | note = LPG50165 deaminase |

SEQUENCE: 422

```
MSDNEFNHEY WMRHALTLAQ RARDEGEVPV GAVLVLDNQV IGEGWNRAIG LHDPTAHAEI    60
MALRQGGMVL QNYRLINATL YVTFEPCVMC AGAMVHSRIG HVVFGVRNSK RGAAGSLMNV  120
LNYPGMNHRV EVTEGVLREQ CAGMLCDFYR EPREQFNALR KAQKA                 165
```

| SEQ ID NO: 423 | moltype = AA   length = 170 |
|---|---|
| FEATURE | Location/Qualifiers |
| source | 1..170 |
| | mol_type = protein |
| | organism = synthetic construct |
| REGION | 1..170 |
| | note = LPG50166 deaminase |

SEQUENCE: 423

```
MSDNELNHEY WMRHALTLAQ RARDEGEVPV GAVLVLNNQV IGEGWNRAIG LHDPTAHAEI    60
MALRQGGMVL QNYRLIDATL YVTFEPCIMC AGAMVHSRIG QVVFGVRNSK RGAAGSLINI  120
LNYPGMNHRV DVTEGVLSER CANMLCDFYR EPRLQFNAQR KAEKAGNAAA            170
```

| SEQ ID NO: 424 | moltype = AA   length = 169 |
|---|---|
| FEATURE | Location/Qualifiers |
| source | 1..169 |
| | mol_type = protein |
| | organism = synthetic construct |
| REGION | 1..169 |
| | note = LPG50167 deaminase |

SEQUENCE: 424

```
MSNPELTHDH WMRHALTLAQ RARNEGEVPV GAVLVLNGQV IGEGWNRAIG LHDPTAHAEI    60
MALRQGGLVL QNYRLIDTVL YVTFEPCVMC AGAMVHSRIG QLVFGVRNSK RGAAGSLINV  120
LNYPGMNHRV EIIEGVLRDE CAAMLCDFYR HPRLVKNALK KNAGTSPTQ             169
```

| SEQ ID NO: 425 | moltype = AA   length = 166 |
|---|---|
| FEATURE | Location/Qualifiers |
| source | 1..166 |
| | mol_type = protein |
| | organism = synthetic construct |
| REGION | 1..166 |
| | note = LPG50168 deaminase |

SEQUENCE: 425

```
MSDTELNHEY WMRHALMLAK RARDEGEVPV GAVLVLKNQV IGEGWNRAIG LHDPTAHAEI    60
MALRQGGLVL QNYRLIDTTL YVTFEPCVMC AGAMVHSRIG NLVFGVRNSK RGAAGSLINV   120
LNYPGMNHRV EIAEGVLADE CSAMLCDFYR HPRQQQNALK QAAKHD                 166

SEQ ID NO: 426         moltype = AA   length = 171
FEATURE                Location/Qualifiers
source                 1..171
                       mol_type = protein
                       organism = synthetic construct
REGION                 1..171
                       note = LPG50169 deaminase
SEQUENCE: 426
MSDIELNHEY WMRHALMLAK RAREEGEVPV GAVLVLNNQV IGEGWNRAIG LHDPTAHAEI    60
MALRQGGLVL QNYRLIDTTL YVTFEPCVMC AGAMVHSRIG HLVFGVRNSK RGAAGSLINV   120
LNYPGMNHRI EFTEGVLADE CSGMLCDFYR YPRQQQNTLK QAAKANPPAA Q            171

SEQ ID NO: 427         moltype = AA   length = 165
FEATURE                Location/Qualifiers
source                 1..165
                       mol_type = protein
                       organism = synthetic construct
REGION                 1..165
                       note = LPG50170 deaminase
SEQUENCE: 427
MSDNELNHER WMRHALTLAQ RARDEGEVPV GAVLVYQNQV IGEGWNRAIG LHDPTAHAEI    60
MALRQGGLVL QNYRLIDTTL YVTFEPCVMC AGAMVHSRIG QLVFGVRNSK RGAAGSLINV   120
LNYPGMNHRV AITEGVLAES CSAMLCDFYR HPREQKNALR RAAQS                  165

SEQ ID NO: 428         moltype = AA   length = 166
FEATURE                Location/Qualifiers
source                 1..166
                       mol_type = protein
                       organism = synthetic construct
REGION                 1..166
                       note = LPG50171 deaminase
SEQUENCE: 428
MSDLELNDEY WMRHALTLAK RAREEGEVPV GAVLVLNNQV IGEGWNRAIG LHDPTAHAEI    60
MALRQGGLVL QNYRLIDATL YVTFEPCVMC AGAMVHSRIA RLVFGVRNSK RGAAGSLMNV   120
LNYPGMNHRV EISEGVLAES CSAMLCDFYR WPREVKNALK KAREQN                 166

SEQ ID NO: 429         moltype = AA   length = 169
FEATURE                Location/Qualifiers
source                 1..169
                       mol_type = protein
                       organism = synthetic construct
REGION                 1..169
                       note = LPG50172 deaminase
SEQUENCE: 429
MSDLELDHEY WMRHALLLAK RARDEGEVPV GAVLVLNNQV IGEGWNRAIG LHDPTAHAEI    60
MALRQGGLVL QNYRLLDTTL YVTFEPCVMC SGAMVHSRIG TLVYGVRNEK RGAAGSLMNV   120
LGYPGMNHQV QVIDGVLAPE CSGLLCDFYR MPRQQKNQQK AESTSSRGD              169

SEQ ID NO: 430         moltype = AA   length = 162
FEATURE                Location/Qualifiers
source                 1..162
                       mol_type = protein
                       organism = synthetic construct
REGION                 1..162
                       note = LPG50173 deaminase
SEQUENCE: 430
MSDTELTHEY WMRHALMLAQ RARDEGEVPV GAVLVLNNRV IGEGWNRAIG LHDPTAHAEI    60
MALRQGGLVL QNYRLLDTTL YVTFEPCVMC AGAMVHGRIG TLVFGVRNLK RGAAGSLMNV   120
LNYPGMNHRV EIVEGTLSDE CSGMLCEFYR QPRLAFNAQK QA                     162

SEQ ID NO: 431         moltype = AA   length = 173
FEATURE                Location/Qualifiers
source                 1..173
                       mol_type = protein
                       organism = synthetic construct
REGION                 1..173
                       note = LPG50174 deaminase
SEQUENCE: 431
MSIPELNHDV WMRHALTLAK RAREEGEVPV GAVLVLNGQV IGEGWNRAIG LHDPTAHAEI    60
MALRQGGLVL QNYRLIDTTL YVTFEPCVMC AGAMVHSRIG QLVFGVRNSK RGAAGSLMNV   120
LNYPGMNHRV EITEGVLRDE CAAMLCDFYR QPRLVKNALK KPAGDPSALQ NNR          173

SEQ ID NO: 432         moltype = AA   length = 166
FEATURE                Location/Qualifiers
source                 1..166
```

```
                          mol_type = protein
                          organism = synthetic construct
REGION                    1..166
                          note = LPG50175 deaminase
SEQUENCE: 432
MSDLELNDEY WMRHALTLAK RAREEGEVPV GAVLVLNNQV IGEGWNRAIG LHDPTAHAEI    60
MALRQGGLVL QNYRLIDATL YVTFEPCVMC AGAMVHSRIA RLVFGVRNSK RGAAGSLMNV   120
LNYPGMNHRV EISEGVLAGS CSAMLCDFYR WPREVKNALK KAREQN                 166

SEQ ID NO: 433            moltype = AA   length = 153
FEATURE                   Location/Qualifiers
source                    1..153
                          mol_type = protein
                          organism = synthetic construct
REGION                    1..153
                          note = LPG50176 deaminase
SEQUENCE: 433
MSDIEQNHEY WMRHALVLAK RAREEGEVPV GAVLVLNNQV IGEGWNRAIG LHDPTAHAEI    60
MALRQGGLVL QNYRLIDTTL YVTFEPCVMC AGAMVHGRIG SLVFGVRNSK RGAAGSLINV   120
LNYPGMNHRV EMTEGVLADE CSAMLCDFYR HPR                                153

SEQ ID NO: 434            moltype = AA   length = 168
FEATURE                   Location/Qualifiers
source                    1..168
                          mol_type = protein
                          organism = synthetic construct
REGION                    1..168
                          note = LPG50177 deaminase
SEQUENCE: 434
MCNPERDHEY WMRHALTLAQ RARDEGEVPV GAVLVLNNQV IGEGWNRAIG LHDPTAHAEI    60
MALRQGGMVL QNYRLLDTTL YVTFEPCVMC SGAMVHSRIG TLVFGVRNEK RGAAGSLLNV   120
LGYPGMNHQV KTIGGVLAPA CSALLCDFYR MPRQQKNQQK AELKLSND                168

SEQ ID NO: 435            moltype = AA   length = 162
FEATURE                   Location/Qualifiers
source                    1..162
                          mol_type = protein
                          organism = synthetic construct
REGION                    1..162
                          note = LPG50178 deaminase
SEQUENCE: 435
MSAIELNHEY WMRHALGLAQ RARDEGEVPV GAVLVYQNQV IGEGWNRAIG LHDPTAHAEI    60
MALRQGGLVL QNYRLIDTTL YVTFEPCVMC AGAMVHSRIG RVVFGVRNSK RGAAGSLMNV   120
LNYPGMNHRV EVTEGVLAGE CSAMLCDFYR APRAQFNAQK RP                      162

SEQ ID NO: 436            moltype = AA   length = 169
FEATURE                   Location/Qualifiers
source                    1..169
                          mol_type = protein
                          organism = synthetic construct
REGION                    1..169
                          note = LPG50179 deaminase
SEQUENCE: 436
MSNPELNHEY WMRYALTLAK RAREEGEVPV GAVLVLNERV IGEGWNRAIG LHDPTAHAEI    60
MALRQGGMVL QNYRLIDTTL YVTFEPCVMC AGAMVHSRIG HLVFGVRNSK RGAAGSLMNV   120
LNYPGMNHRV AITEGVLRDE CAAMLCDFYR QPRQVKNALK KTLSDSQEQ               169

SEQ ID NO: 437            moltype = AA   length = 168
FEATURE                   Location/Qualifiers
source                    1..168
                          mol_type = protein
                          organism = synthetic construct
REGION                    1..168
                          note = LPG50180 deaminase
SEQUENCE: 437
MSNPEHDHEY WMRHALNLAQ RARDEGEVPV GAVLVLNNQV IGEGWNRAIG LHDPTAHAEI    60
MALRQGGLVL QNYRLLDTTL YVTFEPCVMC SGAMVHSRIG TLVYGVRNEK RGAAGSLMNV   120
LGYPGMNHQV NVIGGVLAQD CSARLCDFYR MPRQQKNQQR AELKAQGD                168

SEQ ID NO: 438            moltype = AA   length = 168
FEATURE                   Location/Qualifiers
source                    1..168
                          mol_type = protein
                          organism = synthetic construct
REGION                    1..168
                          note = LPG50181 deaminase
SEQUENCE: 438
MSDPELNHEY WMRHALQLAQ RARDEGEVPV GAVLVLNNQV IGEGWNRAIG LHDPTAHAEI    60
MALRQGGLVL QNYRLLDTTL YVTFEPCVMC SGAMIHSRIG TVVYGVRNEK RGAAGSLLNV   120
```

```
LSYPGMNHQV KVIGEVLAPA CSAMLCDFYR MPRQQKNQQK AEWKLSGE              168

SEQ ID NO: 439            moltype = AA   length = 171
FEATURE                   Location/Qualifiers
source                    1..171
                          mol_type = protein
                          organism = synthetic construct
REGION                    1..171
                          note = LPG50182 deaminase
SEQUENCE: 439
MSNPELNHEY WMRYALTLAK RARDEGEVPV GAVLVYHDQV IGEGWNRAIG LHDPTAHAEI   60
MALRQGGLVL QNYRLIDTTL YVTFEPCVMC AGAMVHSRIG RLVFGVRNSK RGAAGSLLNV  120
LNYPGMNHQI DMEEGVLRDE CAAMLCDFYR LPRIVKNALK QSPPDSTNLH A          171

SEQ ID NO: 440            moltype = AA   length = 182
FEATURE                   Location/Qualifiers
source                    1..182
                          mol_type = protein
                          organism = synthetic construct
REGION                    1..182
                          note = APG09980.1 deaminase
SEQUENCE: 440
MDEQTFLDNF NNLKYPRKTY LCYEVELLVG ENHIPLDDYK GFVHNEGFDM GLERCHAELI   60
FLERMASWNL DTELRYRITV FISWSPCPEC ADELVKFLRE NRHVNLRIFA ARIYDWYQGY  120
EAGLRALKAA GAEVAMMTLH EFEYCWNNFV DHQQDEDTPF PPWDNLVARS EELSQRLEGI  180
LQ                                                                182

SEQ ID NO: 441            moltype = AA   length = 185
FEATURE                   Location/Qualifiers
source                    1..185
                          mol_type = protein
                          organism = synthetic construct
REGION                    1..185
                          note = APG05840.1 deaminase
SEQUENCE: 441
MDPHMFTGNF TNNPRVFGLH QTYLCYEVKR QGPDGTRDLM NEQRDFLCNQ AKNHFSGSED   60
HHAERCFLDR IPSWQLDPAQ TYRVTCFISW SPCFSCAQEV AEFLHENPHV NLRIFAARIY  120
DYLPRYEEGL QMLQNAGAQV SIMTSEEFGH CWDTFVDRQG HPFQPWEGLD EHSQALSGRL  180
QAILQ                                                             185

SEQ ID NO: 442            moltype = AA   length = 178
FEATURE                   Location/Qualifiers
source                    1..178
                          mol_type = protein
                          organism = synthetic construct
REGION                    1..178
                          note = APG00868.1 deaminase
SEQUENCE: 442
MDPNTFRFHF PNLLYASGRK LCYLCFQVET GDYFSCDDSD RGVFRNKVHP WARCHAEQCF   60
LSWFRDQYPC RDEYYNVTWF LSWSPCPTCA EEVVEFLEEY RNLTLSIFTS RLYYFYHPNY  120
QQGLRKLWDA GVQLDIMSCD DFEHCWDNFV DHKGMRFQRR NLLKDYDFLA AELQEILR    178

SEQ ID NO: 443            moltype = AA   length = 152
FEATURE                   Location/Qualifiers
source                    1..152
                          mol_type = protein
                          organism = synthetic construct
REGION                    1..152
                          note = APG30125 deaminase
SEQUENCE: 443
MINLVQTPYD LNSGYPIVRR TLEDKKKLVK HEGFGPESCC ATIEYTLRGN SRYAFGNSQM   60
QVEMPPNIYA HNWVKLHGEM TALVAAIRRI ERVDSTSAVL PITSAYIELR PCEASCLPAL  120
HNMLPDNITV YFSFLHPTQV DQWKQSARAL CA                               152

SEQ ID NO: 444            moltype = AA   length = 152
FEATURE                   Location/Qualifiers
source                    1..152
                          mol_type = protein
                          organism = synthetic construct
REGION                    1..152
                          note = APG30126 deaminase
SEQUENCE: 444
MPVLIKVPYD INSANGVVQA CLRKKREVVQ SKDNGGITGI GAGSCCSFVV YMKHGGDVDN   60
VFGNSRIRIP FKVNGIEIAN ACAHGELTAL WNAIADEPSI PTILAMYIEM SPCTKCQSAL  120
DNLLQPGQEI YYSFDHPGEV KAWQAAAKHL CA                               152

SEQ ID NO: 445            moltype = AA   length = 148
FEATURE                   Location/Qualifiers
source                    1..148
```

```
                        mol_type = protein
                        organism = synthetic construct
REGION                  1..148
                        note = APG30127 deaminase
SEQUENCE: 445
MIKTEYSLSS GYPIVRRTLE DKKNLVKQPG FGPESCCAVV QYRLRGNIRY AFGNSRMQIS   60
MPPGIYTHNW VRLHGEMAAL VAAINRIERY STDDVIPITA AYIELRPCEA NCMQALRNIL  120
PEDACVYYSF DHPTQVDEWK LRANELCS                                    148

SEQ ID NO: 446          moltype = AA  length = 147
FEATURE                 Location/Qualifiers
source                  1..147
                        mol_type = protein
                        organism = synthetic construct
REGION                  1..147
                        note = APG30128 deaminase
SEQUENCE: 446
MIKTEYTLRS GYPIVRRTLE NKKNLVKQPG FGPESCCAVV EYRLRGNIRY AFGNSRMQVS   60
VPPGIYTNNW VRLHGEMAAL VAAIERIERF SSDDVIPITA AYIELRPCEA NCMQALHNIL  120
PENANVYYSF DHPTQVEEWK LRAHELC                                     147

SEQ ID NO: 447          moltype = AA  length = 147
FEATURE                 Location/Qualifiers
source                  1..147
                        mol_type = protein
                        organism = synthetic construct
REGION                  1..147
                        note = APG30129 deaminase
SEQUENCE: 447
MIKTEYALNS GYPIVRRTLE DKKKLVKQPG FGPESCCAVV EYRLRGNIRY AFGNSQMHVS   60
MPPGIYTHNW VKLHGEMAAL VAAINRIERF STDDVIPITG AYIELRPCEA NCLQALHNIL  120
PEDANVYYSF DHPTQLDEWK LRAHELC                                     147

SEQ ID NO: 448          moltype = AA  length = 147
FEATURE                 Location/Qualifiers
source                  1..147
                        mol_type = protein
                        organism = synthetic construct
REGION                  1..147
                        note = APG30130 deaminase
SEQUENCE: 448
MIQLVQAEYS IKSGYPIVRR TLEDKKKLIE KPGFGPESCC ATIEYQLRGS TRYAFGNSQM   60
KMEMPPDIYT HNWVKLHAEM AALVAAIRRI ERFDADKEQV PITNVYIELR PCEANCMQAL  120
QNILPDGTTV YYSFLHPTEV EEWKRSA                                     147

SEQ ID NO: 449          moltype = DNA  length = 300
FEATURE                 Location/Qualifiers
source                  1..300
                        mol_type = other DNA
                        organism = synthetic construct
misc_feature            1..300
                        note = NC_041760 promoter
SEQUENCE: 449
agctccacgg caagagaatt caaagccgcg ggcctgggtt ccacgcgggg ccccttaccc   60
aaggtgcccc gggcgctcat ttgcatgtcc cacccaacag gtaaacctga caggtcagtc  120
gcggccgggt acggcctggc ggtcagagca ccaaacgtac gagccttgtg atgcggttcc  180
attgcatgaa attctcctaa aggccccaag atgaacggga aagcgcgcgg ttcgctcacc  240
gtaactaaaa caggtgagag actcccgtgc cttataaggc ctgtggacgg aggcagttgc  300

SEQ ID NO: 450          moltype = DNA  length = 300
FEATURE                 Location/Qualifiers
source                  1..300
                        mol_type = other DNA
                        organism = synthetic construct
misc_feature            1..300
                        note = NW_004848155 promoter
SEQUENCE: 450
tgttctccga acagtacttg taatatacag gttccccgat ccaccaccgt ctgcgggtgg   60
cggtacagcc tctcccagtg tgctttgcgc tcatttgcat agagcacggc accgaacgca  120
gccactgtcc cccgcgtccg ctgtcccccg tgcaggccaa acccgggcgc ggccccgccg  180
acggtgggta cagagagtgg tcggctcggc accggctgct gcgcggcacc ggcactcacc  240
ctgtcccttat ggagccctaa ctccatggct ataaatatct aaggggagga agggtagatc  300

SEQ ID NO: 451          moltype = DNA  length = 300
FEATURE                 Location/Qualifiers
source                  1..300
                        mol_type = other DNA
                        organism = synthetic construct
misc_feature            1..300
```

```
                              note = LR738627 promoter
SEQUENCE: 451
agcgctccgc ggagacttct gggacgcggc ggctccgact ccgccccgct tccggcttat    60
ttgcatacag caattcctag caggcccgtgt gctgaattta gtcggaaaac taccatgttc   120
agtcgaaaaa gcaaatactt ttgtcagata tggccaaaaa cttcacttga cttagccgtg   180
tttcatgtaa agcattaaaa ggatggagtg attgttcaaa tttcataaga agaattcacc   240
ttcagtttaa ggtggttcgc tttctgcact tcaaataccg cggtggacag accctgtttc   300

SEQ ID NO: 452                moltype = DNA  length = 300
FEATURE                       Location/Qualifiers
source                        1..300
                              mol_type = other DNA
                              organism = synthetic construct
misc_feature                  1..300
                              note = NC_044556 promoter
SEQUENCE: 452
gcctgagtcg cgccgccgcc tcccaaagac ttctgggaag gcggtgcggc tcaggctccg    60
ccccgcttcc ggggatattt gcatacgagc attcccagta attcccagca gccactgtag   120
ctatatttgg tagaataacg agcactttct gaactccagt taataactgc gttagttgcg   180
ttacacattg gactaaaaca aatagaagtt gaatctctag agcagtggag ataagtcgcc   240
gtatgtgtac agaaattgct tccgggggct ataaatagct ggtagtgggg ctagaacgtc   300

SEQ ID NO: 453                moltype = DNA  length = 300
FEATURE                       Location/Qualifiers
source                        1..300
                              mol_type = other DNA
                              organism = synthetic construct
misc_feature                  1..300
                              note = XM_030845548 promoter
SEQUENCE: 453
cgccgcgcca gcgcagccgc ttcccagaga cttctgggac ggcagcggct gcggctccgc    60
ccctcttcca gtataatttg catgcgacca tggattccca gcagccacct gagtcatatt   120
tggtggaaca aaaaccactt tctcaatttc agtgaatgac cccatttggt taaggtattg   180
ttgcacaaat atcataaaag aagggacgaa tggctgaacc ggttttttaat ggagttcgc    240
cttagcgtaa aagagtttat tctatgccct ctaaatagtt ctgggatcaa ccgtactact   300

SEQ ID NO: 454                moltype = DNA  length = 111
FEATURE                       Location/Qualifiers
source                        1..111
                              mol_type = other DNA
                              organism = synthetic construct
misc_feature                  1..111
                              note = Mini NC_041760 promoter
SEQUENCE: 454
cccccttaccc aaggtgcccc gggcgctcat ttgcatgtcc caccgctcac cgtaactaaa    60
acaggtgaga gactcccgtg ccttataagg cctgtggacg gaggcagttg c             111

SEQ ID NO: 455                moltype = DNA  length = 111
FEATURE                       Location/Qualifiers
source                        1..111
                              mol_type = other DNA
                              organism = synthetic construct
misc_feature                  1..111
                              note = Mini NW_004848155 promoter
SEQUENCE: 455
acagcctctc ccagtgtgct ttgcgctcat ttgcatagag cacgactcac cctgtcctta    60
tggagcccta actccatggc tataaatatc taagggggagg aagggtagat c             111

SEQ ID NO: 456                moltype = DNA  length = 111
FEATURE                       Location/Qualifiers
source                        1..111
                              mol_type = other DNA
                              organism = synthetic construct
misc_feature                  1..111
                              note = Mini LR738627 promoter
SEQUENCE: 456
ggctccgact ccgccccgct tccggcttat ttgcatacag caatattcac cttcagttta    60
aggtggttcg cttctgcac ttcaaatacc gcggtggaca gaccctgttt c              111

SEQ ID NO: 457                moltype = DNA  length = 111
FEATURE                       Location/Qualifiers
source                        1..111
                              mol_type = other DNA
                              organism = synthetic construct
misc_feature                  1..111
                              note = Mini NC_044556 promoter
SEQUENCE: 457
gctcaggctc cgccccgctt ccggggatat ttgcatacga gcatagtcgc cgtatgtgta    60
cagaaattgc ttccgggggc tataaatagc tggtagtggg gctagaacgt c             111
```

```
SEQ ID NO: 458          moltype = DNA   length = 111
FEATURE                 Location/Qualifiers
source                  1..111
                        mol_type = other DNA
                        organism = synthetic construct
misc_feature            1..111
                        note = Mini XM_030845548 promoter
SEQUENCE: 458
gctgcggctc cgcccctctt ccagtataat ttgcatgcga ccatgttcgc ccttagcgta    60
aaagagttta ttctatgccc tctaaatagt tctgggatca accgtactac t            111

SEQ ID NO: 459          moltype = DNA   length = 26
FEATURE                 Location/Qualifiers
source                  1..26
                        mol_type = other DNA
                        organism = synthetic construct
misc_feature            1..26
                        note = Library 1 Target Sequence
SEQUENCE: 459
ggacagcagc ttcctatatc tcgtac                                         26

SEQ ID NO: 460          moltype = DNA   length = 26
FEATURE                 Location/Qualifiers
source                  1..26
                        mol_type = other DNA
                        organism = synthetic construct
misc_feature            1..26
                        note = Library 2 Target Sequence
SEQUENCE: 460
gatatagacg ttgtggctgt tgtagt                                         26

SEQ ID NO: 461          moltype =    length =
SEQUENCE: 461
000

SEQ ID NO: 462          moltype =    length =
SEQUENCE: 462
000

SEQ ID NO: 463          moltype =    length =
SEQUENCE: 463
000

SEQ ID NO: 464          moltype =    length =
SEQUENCE: 464
000

SEQ ID NO: 465          moltype =    length =
SEQUENCE: 465
000

SEQ ID NO: 466          moltype =    length =
SEQUENCE: 466
000

SEQ ID NO: 467          moltype =    length =
SEQUENCE: 467
000

SEQ ID NO: 468          moltype =    length =
SEQUENCE: 468
000

SEQ ID NO: 469          moltype =    length =
SEQUENCE: 469
000

SEQ ID NO: 470          moltype =    length =
SEQUENCE: 470
000

SEQ ID NO: 471          moltype =    length =
SEQUENCE: 471
000

SEQ ID NO: 472          moltype = DNA   length = 2536
FEATURE                 Location/Qualifiers
source                  1..2536
```

|  |  | mol_type = other DNA |  |
|  |  | organism = synthetic construct |  |
| misc_feature |  | 1..2536 |  |
|  |  | note = In vitro cleavage plasmid sequence |  |

SEQUENCE: 472

```
gtcttggaga ttgtcggata gcaagcttgt ctcgtgggct cggagcgtgg catccaccat   60
cgccatgata tagacgttgt ggctgttgta gtacggattc cagacttatc acttagcctg  120
tgatgataat gggtgataga caaattgagg agcggacagc agcttcctat atctcgtaca  180
cggattccaa catggttgat ttaccgctag gtgctactga ggacagggtg ctgacgctgc  240
cgacgaggat ccactggccg tcgttttact cagagcgtca ctgcgagtag taatatgtat  300
ccgctcatga gacaaaggct aggtggaggc tcagtgatga taagtctgcg atggtggatg  360
catgtgtcat ggtcatagct gtttcctgtg tgaaattgtt atccgctcag agggcacaat  420
cctattccgc gctatccgac aatctccaag acattaggtg gagttcagtt cggcgtatgg  480
catatgtcgc tggaaagaac atgtgagcaa aaggccagca aaaggccagg aaccgtaaaa  540
aggccgcgtt gctggcgttt ttccataggc tccgcccccc tgacgagcat cacaaaaatc  600
gacgctcaag tcagaggtgg cgaaacccga caggactata agataccagg cgtttccccc  660
ctggaagctc cctcgtgcgc tctcctgttc cgaccctgcc gcttaccgga tacctgtccg  720
cctttctccc ttcgggaagc gtggcgcttt ctcatagctc acgctgtagg tatctcagtt  780
cggtgtaggt cgttcgctcc aagctgggct gtgtgcacga accccccgtt cagcccgacc  840
gctgcgcctt atccggtaac tatcgtcttg agtccaaccc ggtaagacac gacttatcgc  900
cactggcagc agccactggt aacaggatta gcagagcgag gtatgtaggc ggtgctacag  960
agttcttgaa gtggtggcct aactacggct acactagaag aacagtattt ggtatctgcg 1020
ctctgctgaa gccagttacc ttcggaaaaa gagttggtag ctcttgatcc ggcaaacaaa 1080
ccaccgctgg tagcggtggt ttttttgttt gcaagcagca gattacgcgc agaaaaaaag 1140
gatctcaaga agatcctttg atcttttcta cggggtctga cgctctattc aacaaagcca 1200
ccgtccccgtc aagtcagcgt aaatgggtag ggggcttcaa atcgtcctcg tgataccaat 1260
tcggagcctg ctttttttgta caaacttgtt gataatggca attcaaggat cttcacctag 1320
atccttttaa attaaaaatg aagttttaaa tcaatctaaa gtatatatga gtaaacttgg 1380
tctgacagtt accaatgctt aatcagtgag gcacctatct cagcgatctg tctatttcgt 1440
tcatccatag ttgcctgact ccccgtcgtg tagataacta cgatacggga ggcttacca  1500
tctggcccca gtgctgcaat gataccgcga gagccacgct caccggctcc agatttatca 1560
gcaataaacc agccagccgg aagggccgag cgcagaagtg gtcctgcaac tttatccgcc 1620
tccatccagt ctattaattg ttgccgggaa gctagagtaa gtagttcgcc agttaatagt 1680
ttgcgcaacg ttgttgccat tgctacaggc atcgtggtgt cacgctcgtc gtttggtatg 1740
gcttcattca gctccggttc ccaacgatca aggcgagtta catgatcccc catgttgtgc 1800
aaaaaagcgg ttagctcctt cggtcctccg atcgttgtca gaagtaagtt ggccgcagtg 1860
ttatcactca tggttatggc agcactgcat aattctctta ctgtcatgcc atccgtaaga 1920
tgcttttctg tgactggtga gtactcaacc aagtcattct gagaatagtg tatgcggcga 1980
ccgagttgct cttgcccggc gtcaatacgg gataataccg cgccacatag cagaacttta 2040
aaagtgctca tcattggaaa acgttcttcg gggcgaaaac tctcaaggat cttaccgctg 2100
ttgagatcca gttcgatgta acccactcgt gcacccaact gatcttcagc atcttttact 2160
ttcaccagcg tttctgggtg agcaaaaaca ggaaggcaaa atgccgcaaa aaagggaata 2220
agggcgacac ggaaatgttg aatactcata ctcttccttt ttcaatatta ttgaagcatt 2280
tatcagggtt attgtctcat gagcggatac atatttgaat gtatttagaa aaataaacaa 2340
ataggggttc cgcgcacatt tccccgaaaa gtgccagata cctgaaacaa acccatcgt  2400
acggccaagg aagtctccaa taactgtgat ccaccacaag cgcagggtt tcccagtca  2460
cgacgttgta aaacgacggc cagtcatgca taatccgcac gcatctggaa taaggaagtg 2520
ccattccgcc tgacct                                                  2536
```

| SEQ ID NO: 473 |  | moltype = RNA length = 124 |
| FEATURE |  | Location/Qualifiers |
| source |  | 1..124 |
|  |  | mol_type = other RNA |
|  |  | organism = synthetic construct |
| misc_feature |  | 1..124 |
|  |  | note = sgRNA for Library 1 protospacer |

SEQUENCE: 473

```
ggacagcagc ttcctatatc tcgtacgttt ttgtactctc aaggaatcag aaagactgat   60
tccttgagaa tctacaaaaa taaggcttta tgccgaaatt cccactctta acggagtggg  120
tttt                                                                124
```

| SEQ ID NO: 474 |  | moltype = RNA length = 124 |
| FEATURE |  | Location/Qualifiers |
| source |  | 1..124 |
|  |  | mol_type = other RNA |
|  |  | organism = synthetic construct |
| misc_feature |  | 1..124 |
|  |  | note = sgRNA for Library 2 protospacer |

SEQUENCE: 474

```
gatatagacg ttgtggctgt tgtagtgttt ttgtactctc aaggaatcag aaagactgat   60
tccttgagaa tctacaaaaa taaggcttta tgccgaaatt cccactctta acggagtggg  120
tttt                                                                124
```

| SEQ ID NO: 475 |  | moltype = DNA length = 48 |
| FEATURE |  | Location/Qualifiers |
| source |  | 1..48 |
|  |  | mol_type = other DNA |
|  |  | organism = synthetic construct |
| misc_feature |  | 1..48 |

```
                        note = Adapter Ligation-F
SEQUENCE: 475
cacagcttaa ccaccgcttc agagtgattt agcgtgacag ccgcaggt               48

SEQ ID NO: 476          moltype = DNA   length = 47
FEATURE                 Location/Qualifiers
source                  1..47
                        mol_type = other DNA
                        organism = synthetic construct
misc_feature            1..47
                        note = Adapter Ligation-R
SEQUENCE: 476
cctgcggctg tcacgctaaa tcactctgaa gcggtggtta agctgtg                47

SEQ ID NO: 477          moltype = DNA   length = 20
FEATURE                 Location/Qualifiers
source                  1..20
                        mol_type = other DNA
                        organism = synthetic construct
misc_feature            1..20
                        note = SGN003014 target sequence
SEQUENCE: 477
gcgcgagcac agctaaggcc                                              20

SEQ ID NO: 478          moltype = DNA   length = 20
FEATURE                 Location/Qualifiers
source                  1..20
                        mol_type = other DNA
                        organism = synthetic construct
misc_feature            1..20
                        note = SGN003015 target sequence
SEQUENCE: 478
gactcacgct ggatagcctc                                              20

SEQ ID NO: 479          moltype = DNA   length = 20
FEATURE                 Location/Qualifiers
source                  1..20
                        mol_type = other DNA
                        organism = synthetic construct
misc_feature            1..20
                        note = SGN003016 target sequence
SEQUENCE: 479
cgctactctc tctttctggc                                              20

SEQ ID NO: 480          moltype = DNA   length = 20
FEATURE                 Location/Qualifiers
source                  1..20
                        mol_type = other DNA
                        organism = synthetic construct
misc_feature            1..20
                        note = SGN003017 target sequence
SEQUENCE: 480
aggccacgga gcgagacatc                                              20

SEQ ID NO: 481          moltype = DNA   length = 20
FEATURE                 Location/Qualifiers
source                  1..20
                        mol_type = other DNA
                        organism = synthetic construct
misc_feature            1..20
                        note = SGN003018 target sequence
SEQUENCE: 481
agagtagcgc gagcacagct                                              20

SEQ ID NO: 482          moltype = DNA   length = 20
FEATURE                 Location/Qualifiers
source                  1..20
                        mol_type = other DNA
                        organism = synthetic construct
misc_feature            1..20
                        note = SGN003019 target sequence
SEQUENCE: 482
tctctcagct ggtacacggc                                              20

SEQ ID NO: 483          moltype = DNA   length = 20
FEATURE                 Location/Qualifiers
source                  1..20
                        mol_type = other DNA
                        organism = synthetic construct
```

```
misc_feature            1..20
                        note = SGN003020 target sequence
SEQUENCE: 483
agctggtaca cggcagggtc                                            20

SEQ ID NO: 484          moltype = DNA   length = 20
FEATURE                 Location/Qualifiers
source                  1..20
                        mol_type = other DNA
                        organism = synthetic construct
misc_feature            1..20
                        note = SGN003021 target sequence
SEQUENCE: 484
tgagaatcaa aatcggtgaa                                            20

SEQ ID NO: 485          moltype = DNA   length = 20
FEATURE                 Location/Qualifiers
source                  1..20
                        mol_type = other DNA
                        organism = synthetic construct
misc_feature            1..20
                        note = SGN003022 target sequence
SEQUENCE: 485
gtcagggttc tggatatctg                                            20

SEQ ID NO: 486          moltype = DNA   length = 20
FEATURE                 Location/Qualifiers
source                  1..20
                        mol_type = other DNA
                        organism = synthetic construct
misc_feature            1..20
                        note = SGN003023 target sequence
SEQUENCE: 486
ataggcagac agacttgtca                                            20

SEQ ID NO: 487          moltype = DNA   length = 24
FEATURE                 Location/Qualifiers
source                  1..24
                        mol_type = other DNA
                        organism = synthetic construct
misc_feature            1..24
                        note = SGN005117 target sequence
SEQUENCE: 487
gtgaataggc agacagactt gtca                                       24

SEQ ID NO: 488          moltype = DNA   length = 23
FEATURE                 Location/Qualifiers
source                  1..23
                        mol_type = other DNA
                        organism = synthetic construct
misc_feature            1..23
                        note = SGN005118 target sequence
SEQUENCE: 488
tgaataggca gacagacttg tca                                        23

SEQ ID NO: 489          moltype = DNA   length = 22
FEATURE                 Location/Qualifiers
source                  1..22
                        mol_type = other DNA
                        organism = synthetic construct
misc_feature            1..22
                        note = SGN005119 target sequence
SEQUENCE: 489
gaataggcag acagacttgt ca                                         22

SEQ ID NO: 490          moltype = DNA   length = 21
FEATURE                 Location/Qualifiers
source                  1..21
                        mol_type = other DNA
                        organism = synthetic construct
misc_feature            1..21
                        note = SGN005120 target sequence
SEQUENCE: 490
aataggcaga cagacttgtc a                                          21

SEQ ID NO: 491          moltype = DNA   length = 24
FEATURE                 Location/Qualifiers
source                  1..24
                        mol_type = other DNA
```

```
SEQ ID NO: 491    moltype = DNA   length = 24
FEATURE           Location/Qualifiers
source            1..24
                  mol_type = other DNA
                  organism = synthetic construct
misc_feature      1..24
                  note = SGN005121 target sequence
SEQUENCE: 491
agagagagta gcgcgagcac agct                                          24

SEQ ID NO: 492    moltype = DNA   length = 23
FEATURE           Location/Qualifiers
source            1..23
                  mol_type = other DNA
                  organism = synthetic construct
misc_feature      1..23
                  note = SGN005122 target sequence
SEQUENCE: 492
gagagagtag cgcgagcaca gct                                           23

SEQ ID NO: 493    moltype = DNA   length = 22
FEATURE           Location/Qualifiers
source            1..22
                  mol_type = other DNA
                  organism = synthetic construct
misc_feature      1..22
                  note = SGN005123 target sequence
SEQUENCE: 493
agagagtagc gcgagcacag ct                                            22

SEQ ID NO: 494    moltype = DNA   length = 21
FEATURE           Location/Qualifiers
source            1..21
                  mol_type = other DNA
                  organism = synthetic construct
misc_feature      1..21
                  note = SGN005124 target sequence
SEQUENCE: 494
gagagtagcg cgagcacagc t                                             21

SEQ ID NO: 495    moltype = DNA   length = 17
FEATURE           Location/Qualifiers
source            1..17
                  mol_type = other DNA
                  organism = synthetic construct
misc_feature      1..17
                  note = SGN007076 target sequence
SEQUENCE: 495
gtagcgcgag cacagct                                                  17

SEQ ID NO: 496    moltype = DNA   length = 18
FEATURE           Location/Qualifiers
source            1..18
                  mol_type = other DNA
                  organism = synthetic construct
misc_feature      1..18
                  note = SGN007077 target sequence
SEQUENCE: 496
agtagcgcga gcacagct                                                 18

SEQ ID NO: 497    moltype = DNA   length = 19
FEATURE           Location/Qualifiers
source            1..19
                  mol_type = other DNA
                  organism = synthetic construct
misc_feature      1..19
                  note = SGN007078 target sequence
SEQUENCE: 497
gagtagcgcg agcacagct                                                19

SEQ ID NO: 498    moltype = DNA   length = 26
FEATURE           Location/Qualifiers
source            1..26
                  mol_type = other DNA
                  organism = synthetic construct
misc_feature      1..26
                  note = SGN007079 target sequence
SEQUENCE: 498
aaagagagag tagcgcgagc acagct                                        26

SEQ ID NO: 499    moltype = DNA   length = 27
FEATURE           Location/Qualifiers
source            1..27
```

```
                        mol_type = other DNA
                        organism = synthetic construct
misc_feature            1..27
                        note = SGN007080 target sequence
SEQUENCE: 499
gaaagagaga gtagcgcgag cacagct                                              27

SEQ ID NO: 500          moltype = DNA   length = 17
FEATURE                 Location/Qualifiers
source                  1..17
                        mol_type = other DNA
                        organism = synthetic construct
misc_feature            1..17
                        note = SGN007081 target sequence
SEQUENCE: 500
ggcagacaga cttgtca                                                         17

SEQ ID NO: 501          moltype = DNA   length = 18
FEATURE                 Location/Qualifiers
source                  1..18
                        mol_type = other DNA
                        organism = synthetic construct
misc_feature            1..18
                        note = SGN007082 target sequence
SEQUENCE: 501
aggcagacag acttgtca                                                        18

SEQ ID NO: 502          moltype = DNA   length = 19
FEATURE                 Location/Qualifiers
source                  1..19
                        mol_type = other DNA
                        organism = synthetic construct
misc_feature            1..19
                        note = SGN007083 target sequence
SEQUENCE: 502
taggcagaca gacttgtca                                                       19

SEQ ID NO: 503          moltype = DNA   length = 26
FEATURE                 Location/Qualifiers
source                  1..26
                        mol_type = other DNA
                        organism = synthetic construct
misc_feature            1..26
                        note = SGN007084 target sequence
SEQUENCE: 503
cggtgaatag gcagacagac ttgtca                                               26

SEQ ID NO: 504          moltype = DNA   length = 27
FEATURE                 Location/Qualifiers
source                  1..27
                        mol_type = other DNA
                        organism = synthetic construct
misc_feature            1..27
                        note = SGN007085 target sequence
SEQUENCE: 504
tcggtgaata ggcagacaga cttgtca                                              27

SEQ ID NO: 505          moltype = DNA   length = 25
FEATURE                 Location/Qualifiers
source                  1..25
                        mol_type = other DNA
                        organism = synthetic construct
misc_feature            1..25
                        note = SGN002654 target seq
SEQUENCE: 505
cattcgggcc gagatgtctc gctcc                                                25

SEQ ID NO: 506          moltype = DNA   length = 25
FEATURE                 Location/Qualifiers
source                  1..25
                        mol_type = other DNA
                        organism = synthetic construct
misc_feature            1..25
                        note = SGN002655 target seq
SEQUENCE: 506
gctgtgctcg cgctactctc tcttt                                                25

SEQ ID NO: 507          moltype = DNA   length = 25
FEATURE                 Location/Qualifiers
```

```
                         source          1..25
                                         mol_type = other DNA
                                         organism = synthetic construct
                         misc_feature    1..25
                                         note = SGN002656 target seq
SEQUENCE: 507
tgacagcatt cgggccgaga tgtct                                               25

SEQ ID NO: 508           moltype = DNA   length = 25
FEATURE                  Location/Qualifiers
source                   1..25
                         mol_type = other DNA
                         organism = synthetic construct
misc_feature             1..25
                         note = SGN002657 target seq
SEQUENCE: 508
ctccaaagat tcaggtttac tcacg                                               25

SEQ ID NO: 509           moltype = DNA   length = 25
FEATURE                  Location/Qualifiers
source                   1..25
                         mol_type = other DNA
                         organism = synthetic construct
misc_feature             1..25
                         note = SGN002658 target seq
SEQUENCE: 509
tttctatctc ttgtactaca ctgaa                                               25

SEQ ID NO: 510           moltype = DNA   length = 25
FEATURE                  Location/Qualifiers
source                   1..25
                         mol_type = other DNA
                         organism = synthetic construct
misc_feature             1..25
                         note = SGN002659 target seq
SEQUENCE: 510
atccagtgac aagtctgtct gccta                                               25

SEQ ID NO: 511           moltype = DNA   length = 25
FEATURE                  Location/Qualifiers
source                   1..25
                         mol_type = other DNA
                         organism = synthetic construct
misc_feature             1..25
                         note = SGN002660 target seq
SEQUENCE: 511
gtgcaaacgc cttcaacaac agcat                                               25

SEQ ID NO: 512           moltype = DNA   length = 25
FEATURE                  Location/Qualifiers
source                   1..25
                         mol_type = other DNA
                         organism = synthetic construct
misc_feature             1..25
                         note = SGN002661 target seq
SEQUENCE: 512
tcttgtccca cagatatcca gaacc                                               25

SEQ ID NO: 513           moltype = DNA   length = 25
FEATURE                  Location/Qualifiers
source                   1..25
                         mol_type = other DNA
                         organism = synthetic construct
misc_feature             1..25
                         note = SGN002662 target seq
SEQUENCE: 513
tgatcctctt gtcccacaga tatcc                                               25

SEQ ID NO: 514           moltype = DNA   length = 25
FEATURE                  Location/Qualifiers
source                   1..25
                         mol_type = other DNA
                         organism = synthetic construct
misc_feature             1..25
                         note = SGN002663 target seq
SEQUENCE: 514
tgccgtgtac cagctgagag actct                                               25

SEQ ID NO: 515           moltype = DNA   length = 25
```

```
FEATURE                 Location/Qualifiers
source                  1..25
                        mol_type = other DNA
                        organism = synthetic construct
misc_feature            1..25
                        note = SGN002699 target seq
SEQUENCE: 515
ggagagactc acgctggata gcctc                                               25

SEQ ID NO: 516          moltype = DNA  length = 25
FEATURE                 Location/Qualifiers
source                  1..25
                        mol_type = other DNA
                        organism = synthetic construct
misc_feature            1..25
                        note = SGN002702 target seq
SEQUENCE: 516
aagagagagt agcgcgagca cagct                                               25

SEQ ID NO: 517          moltype = DNA  length = 25
FEATURE                 Location/Qualifiers
source                  1..25
                        mol_type = other DNA
                        organism = synthetic construct
misc_feature            1..25
                        note = SGN002707 target seq
SEQUENCE: 517
ggtgaatagg cagacagact tgtca                                               25

SEQ ID NO: 518          moltype = DNA  length = 24
FEATURE                 Location/Qualifiers
source                  1..24
                        mol_type = other DNA
                        organism = synthetic construct
misc_feature            1..24
                        note = SGN003017 3017-1 off-target seq
SEQUENCE: 518
tgtccacgga gcgagacagg gagg                                                24

SEQ ID NO: 519          moltype = DNA  length = 23
FEATURE                 Location/Qualifiers
source                  1..23
                        mol_type = other DNA
                        organism = synthetic construct
misc_feature            1..23
                        note = SGN003023 3023-1 off-target seq
SEQUENCE: 519
ataggcagac aaacttgtat agg                                                 23

SEQ ID NO: 520          moltype = DNA  length = 23
FEATURE                 Location/Qualifiers
source                  1..23
                        mol_type = other DNA
                        organism = synthetic construct
misc_feature            1..23
                        note = SGN003023 3023-2 off-target seq
SEQUENCE: 520
ataggcagac agacttgcag agg                                                 23

SEQ ID NO: 521          moltype = DNA  length = 24
FEATURE                 Location/Qualifiers
source                  1..24
                        mol_type = other DNA
                        organism = synthetic construct
misc_feature            1..24
                        note = SGN003023 3023-3 off-target seq
SEQUENCE: 521
acaggcagac agatttgtca gagg                                                24

SEQ ID NO: 522          moltype = DNA  length = 24
FEATURE                 Location/Qualifiers
source                  1..24
                        mol_type = other DNA
                        organism = synthetic construct
misc_feature            1..24
                        note = SGN003023 3023-4 off-target seq
SEQUENCE: 522
aaaggcagac agacatgtca gtgg                                                24
```

```
SEQ ID NO: 523          moltype = DNA   length = 26
FEATURE                 Location/Qualifiers
source                  1..26
                        mol_type = other DNA
                        organism = synthetic construct
misc_feature            1..26
                        note = SGN003023 3023-5 off-target seq
SEQUENCE: 523
ctaggcagac agacttcctt cctagg                                        26

SEQ ID NO: 524          moltype = DNA   length = 25
FEATURE                 Location/Qualifiers
source                  1..25
                        mol_type = other DNA
                        organism = synthetic construct
misc_feature            1..25
                        note = SGN003023 3023-6 off-target seq
SEQUENCE: 524
atgggcaga cagacttgtc acagg                                          25

SEQ ID NO: 525          moltype = DNA   length = 24
FEATURE                 Location/Qualifiers
source                  1..24
                        mol_type = other DNA
                        organism = synthetic construct
misc_feature            1..24
                        note = SGN003023 3023-7off-target seq
SEQUENCE: 525
acaggcagac agacttgcat ttgg                                          24

SEQ ID NO: 526          moltype = DNA   length = 24
FEATURE                 Location/Qualifiers
source                  1..24
                        mol_type = other DNA
                        organism = synthetic construct
misc_feature            1..24
                        note = SGN003023 3023-8 off-target seq
SEQUENCE: 526
ataggcagac agacttgtta gaag                                          24

SEQ ID NO: 527          moltype = DNA   length = 24
FEATURE                 Location/Qualifiers
source                  1..24
                        mol_type = other DNA
                        organism = synthetic construct
misc_feature            1..24
                        note = SGN003023 3023-9 off-target seq
SEQUENCE: 527
ataggtagac agacttgtca gtga                                          24

SEQ ID NO: 528          moltype = DNA   length = 53
FEATURE                 Location/Qualifiers
source                  1..53
                        mol_type = other DNA
                        organism = synthetic construct
misc_feature            1..53
                        note = 3017-1 Left Primer
SEQUENCE: 528
tcgtcggcag cgtcagatgt gtataagaga cagtcttcgc ctgtgatctc tga          53

SEQ ID NO: 529          moltype = DNA   length = 54
FEATURE                 Location/Qualifiers
source                  1..54
                        mol_type = other DNA
                        organism = synthetic construct
misc_feature            1..54
                        note = 3017-1 Right Primer
SEQUENCE: 529
gtctcgtggg ctcggagatg tgtataagag acagttggat gggatgtcct gagg         54

SEQ ID NO: 530          moltype = DNA   length = 53
FEATURE                 Location/Qualifiers
source                  1..53
                        mol_type = other DNA
                        organism = synthetic construct
misc_feature            1..53
                        note = 3023-1 Left Primer
SEQUENCE: 530
tcgtcggcag cgtcagatgt gtataagaga caggctagtt ccagctgcct agg          53
```

```
SEQ ID NO: 531           moltype = DNA   length = 54
FEATURE                  Location/Qualifiers
source                   1..54
                         mol_type = other DNA
                         organism = synthetic construct
misc_feature             1..54
                         note = 3023-1 Right Primer
SEQUENCE: 531
gtctcgtggg ctcggagatg tgtataagag acagcagtgc gtttctctgg tcct        54

SEQ ID NO: 532           moltype = DNA   length = 53
FEATURE                  Location/Qualifiers
source                   1..53
                         mol_type = other DNA
                         organism = synthetic construct
misc_feature             1..53
                         note = 3023-2 Left Primer
SEQUENCE: 532
tcgtcggcag cgtcagatgt gtataagaga cagtgagccc ttcttctgtg ctg         53

SEQ ID NO: 533           moltype = DNA   length = 54
FEATURE                  Location/Qualifiers
source                   1..54
                         mol_type = other DNA
                         organism = synthetic construct
misc_feature             1..54
                         note = 3023-2 Right Primer
SEQUENCE: 533
gtctcgtggg ctcggagatg tgtataagag acagcctcca gatccccact acca        54

SEQ ID NO: 534           moltype = DNA   length = 53
FEATURE                  Location/Qualifiers
source                   1..53
                         mol_type = other DNA
                         organism = synthetic construct
misc_feature             1..53
                         note = 3023-3 Left Primer
SEQUENCE: 534
tcgtcggcag cgtcagatgt gtataagaga cagagtgcta gagtgatgtg gga         53

SEQ ID NO: 535           moltype = DNA   length = 54
FEATURE                  Location/Qualifiers
source                   1..54
                         mol_type = other DNA
                         organism = synthetic construct
misc_feature             1..54
                         note = 3023-3 Right Primer
SEQUENCE: 535
gtctcgtggg ctcggagatg tgtataagag acagaggtca cctttgttgc catc        54

SEQ ID NO: 536           moltype = DNA   length = 53
FEATURE                  Location/Qualifiers
source                   1..53
                         mol_type = other DNA
                         organism = synthetic construct
misc_feature             1..53
                         note = 3023-4 Left Primer
SEQUENCE: 536
tcgtcggcag cgtcagatgt gtataagaga cagatctccc tcagtccagt ccc         53

SEQ ID NO: 537           moltype = DNA   length = 54
FEATURE                  Location/Qualifiers
source                   1..54
                         mol_type = other DNA
                         organism = synthetic construct
misc_feature             1..54
                         note = 3023-4 Right Primer
SEQUENCE: 537
gtctcgtggg ctcggagatg tgtataagag acagccatct catccagtgc cctc        54

SEQ ID NO: 538           moltype = DNA   length = 53
FEATURE                  Location/Qualifiers
source                   1..53
                         mol_type = other DNA
                         organism = synthetic construct
misc_feature             1..53
                         note = 3023-5 Left Primer
SEQUENCE: 538
```
tcgtcggcag cgtcagatgt gtataagaga cagccagaac atcagcagca agc         53

SEQ ID NO: 539           moltype = DNA   length = 54
FEATURE                  Location/Qualifiers
source                   1..54
                         mol_type = other DNA
                         organism = synthetic construct
misc_feature             1..54
                         note = 3023-5 Right Primer
SEQUENCE: 539
gtctcgtggg ctcggagatg tgtataagag acagcctggg tcacttcctg tcac        54

SEQ ID NO: 540           moltype = DNA   length = 53
FEATURE                  Location/Qualifiers
source                   1..53
                         mol_type = other DNA
                         organism = synthetic construct
misc_feature             1..53
                         note = 3023-6 Left Primer
SEQUENCE: 540
tcgtcggcag cgtcagatgt gtataagaga cagaaggtgg gactcactct gaa         53

SEQ ID NO: 541           moltype = DNA   length = 54
FEATURE                  Location/Qualifiers
source                   1..54
                         mol_type = other DNA
                         organism = synthetic construct
misc_feature             1..54
                         note = 3023-6 Right Primer
SEQUENCE: 541
gtctcgtggg ctcggagatg tgtataagag acagatttta ctcaaggccc aggc        54

SEQ ID NO: 542           moltype = DNA   length = 53
FEATURE                  Location/Qualifiers
source                   1..53
                         mol_type = other DNA
                         organism = synthetic construct
misc_feature             1..53
                         note = 3023-7 Left Primer
SEQUENCE: 542
tcgtcggcag cgtcagatgt gtataagaga cagccctcag ctctgactcc tct         53

SEQ ID NO: 543           moltype = DNA   length = 54
FEATURE                  Location/Qualifiers
source                   1..54
                         mol_type = other DNA
                         organism = synthetic construct
misc_feature             1..54
                         note = 3023-7 Right Primer
SEQUENCE: 543
gtctcgtggg ctcggagatg tgtataagag acagtgaact caggaccaca tggc        54

SEQ ID NO: 544           moltype = DNA   length = 53
FEATURE                  Location/Qualifiers
source                   1..53
                         mol_type = other DNA
                         organism = synthetic construct
misc_feature             1..53
                         note = 3023-8 Left Primer
SEQUENCE: 544
tcgtcggcag cgtcagatgt gtataagaga cagcctgtca agggagtgtt tct         53

SEQ ID NO: 545           moltype = DNA   length = 54
FEATURE                  Location/Qualifiers
source                   1..54
                         mol_type = other DNA
                         organism = synthetic construct
misc_feature             1..54
                         note = 3023-8 Right Primer
SEQUENCE: 545
gtctcgtggg ctcggagatg tgtataagag acagatcctt gcaatcctct gaaa        54

SEQ ID NO: 546           moltype = DNA   length = 53
FEATURE                  Location/Qualifiers
source                   1..53
                         mol_type = other DNA
                         organism = synthetic construct
misc_feature             1..53
                         note = 3023-9 Left Primer

```
SEQUENCE: 546
tcgtcggcag cgtcagatgt gtataagaga cagatgctcc gctccttgat ctg        53

SEQ ID NO: 547          moltype = DNA  length = 55
FEATURE                 Location/Qualifiers
source                  1..55
                        mol_type = other DNA
                        organism = synthetic construct
misc_feature            1..55
                        note = 3023-9 Right Primer
SEQUENCE: 547
gtctcgtggg ctcggagatg tgtataagag acagtcattc cctccccact ttctc      55

SEQ ID NO: 548          moltype = DNA  length = 31
FEATURE                 Location/Qualifiers
source                  1..31
                        mol_type = other DNA
                        organism = Homo sapiens
misc_feature            1..31
                        note = Human IDUA W402X
SEQUENCE: 548
ggagcagctc taggccgaag tgtcgcaggc c                                 31

SEQ ID NO: 549          moltype = DNA  length = 31
FEATURE                 Location/Qualifiers
source                  1..31
                        mol_type = other DNA
                        organism = Mus musculus
misc_feature            1..31
                        note = Mouse IDUA W392X
SEQUENCE: 549
agaacaactc taggcagagg tctcaaaggc t                                 31

SEQ ID NO: 550          moltype = DNA  length = 31
FEATURE                 Location/Qualifiers
source                  1..31
                        mol_type = other DNA
                        organism = synthetic construct
misc_feature            1..31
                        note = Humanized mouse IDUA
SEQUENCE: 550
ggagcagctc taggccgaag tgtcgcaggc c                                 31

SEQ ID NO: 551          moltype = AA  length = 1130
FEATURE                 Location/Qualifiers
source                  1..1130
                        mol_type = protein
                        organism = synthetic construct
REGION                  1..1130
                        note = LPG10145 D16A nickase
SEQUENCE: 551
MSKVAKNMTR VNLGFAIGIA SVGWSVLDNQ TGKILETGVS IFPSGSASRN EERRSFRQSR   60
RLIRRKKARI CDMDHLLKKN GFPFPGNTGA NPYEIRVKGL TEKLSREELA IALHHLVKRR  120
GISYDLKDVE DESAGGTNYQ ESIAVNQRLL KKETPAEIQL ARLTECGKVR GQVKSLGEDN  180
TATTLLNVFP NAAYQEEMVK LLKKQQEFYG EIDDPFMETA IGILSRKREY FIGPGSEKSR  240
TDYGIYRTDG TTLKNLFEIL VGKDKIFPDQ YRAAGNSYTA QLYNLLNDLN NLEVDATEDG  300
KLTTAHKEQI IEELTTTTGN VNMLKLIAKV AGTSPAGIKK YRVDREGKPE PHSLAIYRRL  360
RKKLGEAGFE INEWPPEFFD DYGPIVTLNT ESGELRKWLA EEGSRKYDFL TEPVIEAILA  420
NKSAFDSVGK NKWHRFSLKT MQLLIPELLH TFKEQMTILA EMGLLHENKK DYGDQNKVDV  480
KYLTENLYNP VVRKSVKQAM DIFNALFEKY ANIDYVVIEM PRDDAEDELE QKKQFQKFQL  540
KNEKEKDASL KEFQELAGVS DLQLEAQLRK RKKLRQKIRM WYQQRGKCPY SGKTIAAVDL  600
FHQDNQFEID HIIPLSVSFD DGQNNKVLCY SEMNQEKGKQ TPYAFMSRGG GQGFSALQAY  660
VKSNNRLENA KKRNLLFTED INDLEVRKRF IARNLVDTRY ASRIVLNELQ QFVRSKELDT  720
RVTVIRGKLT SKLRDRWRLN KSRETHHHHA VDAAVIAVSP MLKMWEKNAE IIPLKVDENT  780
VDLKSGEIIT DQEYAAQMYE LPYARFLEQM PELHKKIKFH HQVDKKMNRK VSDATLYSTR  840
KAKVGTDKKE QEYVIGKIKD IYQFDQYKKF KKLYDGDKSK FLMQRLDPQT FAKLEKIMED  900
YPAKIDATQP NGTIKLVDIS PFELYRREHG PVTKYAKKNN GPAIKSLKFY DSIVGSSVKI  960
TPKNAKGKEV ILKSLKPWRT DVYYNHEKEQ YEIMGIKYAD LKPFKGDNYGI TKARYQEIKE 1020
EEGVSEESEF LFSLYRGDRI QVSNGEDKID LLFLSRSNPA KKGYVELKPI DRNQLNGKEV 1080
VSVYGAASGG RLKKQFVKKN HTLHKVNTDI LGNPFYIKKE SDQPKNILDL           1130

SEQ ID NO: 552          moltype = AA  length = 1130
FEATURE                 Location/Qualifiers
source                  1..1130
                        mol_type = protein
                        organism = synthetic construct
REGION                  1..1130
                        note = LPG10145 H611A nickase
SEQUENCE: 552
```

```
MSKVAKNMTR VNLGFDIGIA SVGWSVLDNQ TGKILETGVS IFPSGSASRN EERRSFRQSR    60
RLIRRKKARI CDMDHLLKKN GFPFPGNTGA NPYEIRVKGL TEKLSREELA IALHHLVKRR   120
GISYDLKDVE DESAGGTNYQ ESIAVNQRLL KKETPAEIQL ARLTECGKVR GQVKSLGEDN   180
TATTLLNVFP NAAYQEEMVK LLKKQQEFYG EIDDPFMETA IGILSRKREY FIGPGSEKSR   240
TDYGIYRTDG TTLKNLFEIL VGKDKIFPDQ YRAAGNSYTA QLYNLLNDLN NLEVDATEDG   300
KLTTAHKEQI IEELTTTGN  VNMLKLIAKV AGTSPAGIKK YRVDREGKPE FHSLAIYRRL   360
RKKLGEAGFE INEWPPEFFD DYGPIVTLNT ESGELRKWLA EEGSRKYDFL TEPVIEAILA   420
NKSAFDSVGK NKWHRFSLKT MQLLIPELLH TFKEQMTILA EMGLLHENKK DYGDQNKVDV   480
KYLTENLYNP VVRKSVKQAM DIFNALFEKY ANIDYVVIEM PRDDAEDELE QKKQFQKFQL   540
KNEKEKDASL KEFQELAGVS DLQLEAQLRK RKKLRQKIRM WYQQRGKCPY SGKTIAAVDL   600
FHQDNQFEID AIIPLSVSFD DGQNNKVLCY SEMNQEKGKQ TPYAFMSRGG GQGFSALQAY   660
VKSNNRLENA KKRNLLFTED INDLEVRKRF IARNLVDTRY ASRIVLNELQ QFVRSKELDT   720
RVTVIRGKLT SKLRDRWRLN KSRETHHHHA VDAAVIAVSP MLKMWEKNAE IIPLKVDENT   780
VDLKSGEIIT DQEYAAQMYE LPYARFLEQM PELHKKIKFH HQVDKKMNRK VSDATLYSTR   840
KAKVGTDKKE QEYVIGKIKD IYQFDQYKKF KKLYDGDKSK FLMQRLDPQT FAKLEKIMED   900
YPAKIDATQP NGTIKLVDIS PFELYRREHG PVTKYAKKNN GPAIKSLKFY DSIVGSSVKI   960
TPKNAKGKEV ILKSLKPWRT DVYYNHEKEQ YEIMGIKYAD LKFKGDNYGI TKARYQEIKE  1020
EEGVSEESEF LFSLYRGDRI QVSNGEDKID LLFLSRSNPA KKGYVELKPI DRNQLNGKEV  1080
VSVYGAASGG RLKKQFVKKN HTLHKVNTDI LGNPFYIKKE SDQPKNILDL            1130

SEQ ID NO: 553          moltype = AA   length = 1130
FEATURE                 Location/Qualifiers
source                  1..1130
                        mol_type = protein
                        organism = synthetic construct
REGION                  1..1130
                        note = dLPG10145 (D16A H611A)
SEQUENCE: 553
MSKVAKNMTR VNLGFAIGIA SVGWSVLDNQ TGKILETGVS IFPSGSASRN EERRSFRQSR    60
RLIRRKKARI CDMDHLLKKN GFPFPGNTGA NPYEIRVKGL TEKLSREELA IALHHLVKRR   120
GISYDLKDVE DESAGGTNYQ ESIAVNQRLL KKETPAEIQL ARLTECGKVR GQVKSLGEDN   180
TATTLLNVFP NAAYQEEMVK LLKKQQEFYG EIDDPFMETA IGILSRKREY FIGPGSEKSR   240
TDYGIYRTDG TTLKNLFEIL VGKDKIFPDQ YRAAGNSYTA QLYNLLNDLN NLEVDATEDG   300
KLTTAHKEQI IEELTTTGN  VNMLKLIAKV AGTSPAGIKK YRVDREGKPE FHSLAIYRRL   360
RKKLGEAGFE INEWPPEFFD DYGPIVTLNT ESGELRKWLA EEGSRKYDFL TEPVIEAILA   420
NKSAFDSVGK NKWHRFSLKT MQLLIPELLH TFKEQMTILA EMGLLHENKK DYGDQNKVDV   480
KYLTENLYNP VVRKSVKQAM DIFNALFEKY ANIDYVVIEM PRDDAEDELE QKKQFQKFQL   540
KNEKEKDASL KEFQELAGVS DLQLEAQLRK RKKLRQKIRM WYQQRGKCPY SGKTIAAVDL   600
FHQDNQFEID AIIPLSVSFD DGQNNKVLCY SEMNQEKGKQ TPYAFMSRGG GQGFSALQAY   660
VKSNNRLENA KKRNLLFTED INDLEVRKRF IARNLVDTRY ASRIVLNELQ QFVRSKELDT   720
RVTVIRGKLT SKLRDRWRLN KSRETHHHHA VDAAVIAVSP MLKMWEKNAE IIPLKVDENT   780
VDLKSGEIIT DQEYAAQMYE LPYARFLEQM PELHKKIKFH HQVDKKMNRK VSDATLYSTR   840
KAKVGTDKKE QEYVIGKIKD IYQFDQYKKF KKLYDGDKSK FLMQRLDPQT FAKLEKIMED   900
YPAKIDATQP NGTIKLVDIS PFELYRREHG PVTKYAKKNN GPAIKSLKFY DSIVGSSVKI   960
TPKNAKGKEV ILKSLKPWRT DVYYNHEKEQ YEIMGIKYAD LKFKGDNYGI TKARYQEIKE  1020
EEGVSEESEF LFSLYRGDRI QVSNGEDKID LLFLSRSNPA KKGYVELKPI DRNQLNGKEV  1080
VSVYGAASGG RLKKQFVKKN HTLHKVNTDI LGNPFYIKKE SDQPKNILDL            1130

SEQ ID NO: 554          moltype = DNA   length = 25
FEATURE                 Location/Qualifiers
source                  1..25
                        mol_type = other DNA
                        organism = Homo sapiens
misc_feature            1..25
                        note = SGN002644 target seq
SEQUENCE: 554
agagagagta gcgcgagcac agcta                                            25

SEQ ID NO: 555          moltype = DNA   length = 25
FEATURE                 Location/Qualifiers
source                  1..25
                        mol_type = other DNA
                        organism = Homo sapiens
misc_feature            1..25
                        note = SGN002645 target seq
SEQUENCE: 555
ctcgcgctac tctctctttc tggcc                                            25

SEQ ID NO: 556          moltype = DNA   length = 25
FEATURE                 Location/Qualifiers
source                  1..25
                        mol_type = other DNA
                        organism = Homo sapiens
misc_feature            1..25
                        note = SGN002646 target seq
SEQUENCE: 556
gagagactca cgctggatag cctcc                                            25

SEQ ID NO: 557          moltype = DNA   length = 25
```

```
FEATURE                 Location/Qualifiers
source                  1..25
                        mol_type = other DNA
                        organism = Homo sapiens
misc_feature            1..25
                        note = SGN002647 target seq
SEQUENCE: 557
gatgacgtga gtaaacctga atctt                                               25

SEQ ID NO: 558          moltype = DNA   length = 25
FEATURE                 Location/Qualifiers
source                  1..25
                        mol_type = other DNA
                        organism = Homo sapiens
misc_feature            1..25
                        note = SGN002648 target seq
SEQUENCE: 558
tcagtaagtc aacttcaatg tcgga                                               25

SEQ ID NO: 559          moltype = DNA   length = 20
FEATURE                 Location/Qualifiers
source                  1..20
                        mol_type = other DNA
                        organism = Homo sapiens
misc_feature            1..20
                        note = SGN002649 target seq
SEQUENCE: 559
agagcaacag tgctgtggcc                                                     20

SEQ ID NO: 560          moltype = DNA   length = 25
FEATURE                 Location/Qualifiers
source                  1..25
                        mol_type = other DNA
                        organism = Homo sapiens
misc_feature            1..25
                        note = SGN002650 target seq
SEQUENCE: 560
ctctcagctg gtacacggca gggtc                                               25

SEQ ID NO: 561          moltype = DNA   length = 25
FEATURE                 Location/Qualifiers
source                  1..25
                        mol_type = other DNA
                        organism = Homo sapiens
misc_feature            1..25
                        note = SGN002651 target seq
SEQUENCE: 561
gcagggtcag ggttctggat atctg                                               25

SEQ ID NO: 562          moltype = DNA   length = 25
FEATURE                 Location/Qualifiers
source                  1..25
                        mol_type = other DNA
                        organism = Homo sapiens
misc_feature            1..25
                        note = SGN002652 target seq
SEQUENCE: 562
tagagtctct cagctggtac acggc                                               25

SEQ ID NO: 563          moltype = DNA   length = 25
FEATURE                 Location/Qualifiers
source                  1..25
                        mol_type = other DNA
                        organism = Homo sapiens
misc_feature            1..25
                        note = SGN002653 target seq
SEQUENCE: 563
tgtttgagaa tcaaaatcgg tgaat                                               25

SEQ ID NO: 564          moltype = DNA   length = 25
FEATURE                 Location/Qualifiers
source                  1..25
                        mol_type = other DNA
                        organism = Homo sapiens
misc_feature            1..25
                        note = SGN002654 target seq
SEQUENCE: 564
cattcgggcc gagatgtctc gctcc                                               25
```

```
SEQ ID NO: 565          moltype = DNA   length = 25
FEATURE                 Location/Qualifiers
source                  1..25
                        mol_type = other DNA
                        organism = Homo sapiens
misc_feature            1..25
                        note = SGN002655 target seq
SEQUENCE: 565
gctgtgctcg cgctactctc tcttt                                               25

SEQ ID NO: 566          moltype = DNA   length = 25
FEATURE                 Location/Qualifiers
source                  1..25
                        mol_type = other DNA
                        organism = Homo sapiens
misc_feature            1..25
                        note = SGN002656 target seq
SEQUENCE: 566
tgacagcatt cgggccgaga tgtct                                               25

SEQ ID NO: 567          moltype = DNA   length = 25
FEATURE                 Location/Qualifiers
source                  1..25
                        mol_type = other DNA
                        organism = Homo sapiens
misc_feature            1..25
                        note = SGN002657 target seq
SEQUENCE: 567
ctccaaagat tcaggtttac tcacg                                               25

SEQ ID NO: 568          moltype = DNA   length = 25
FEATURE                 Location/Qualifiers
source                  1..25
                        mol_type = other DNA
                        organism = Homo sapiens
misc_feature            1..25
                        note = SGN002658 target seq
SEQUENCE: 568
tttctatctc ttgtactaca ctgaa                                               25

SEQ ID NO: 569          moltype = DNA   length = 25
FEATURE                 Location/Qualifiers
source                  1..25
                        mol_type = other DNA
                        organism = Homo sapiens
misc_feature            1..25
                        note = SGN002659 target seq
SEQUENCE: 569
atccagtgac aagtctgtct gccta                                               25

SEQ ID NO: 570          moltype = DNA   length = 25
FEATURE                 Location/Qualifiers
source                  1..25
                        mol_type = other DNA
                        organism = Homo sapiens
misc_feature            1..25
                        note = SGN002660 target seq
SEQUENCE: 570
gtgcaaacgc cttcaacaac agcat                                               25

SEQ ID NO: 571          moltype = DNA   length = 25
FEATURE                 Location/Qualifiers
source                  1..25
                        mol_type = other DNA
                        organism = Homo sapiens
misc_feature            1..25
                        note = SGN002661 target seq
SEQUENCE: 571
tcttgtccca cagatatcca gaacc                                               25

SEQ ID NO: 572          moltype = DNA   length = 25
FEATURE                 Location/Qualifiers
source                  1..25
                        mol_type = other DNA
                        organism = Homo sapiens
misc_feature            1..25
                        note = SGN002662 target seq
SEQUENCE: 572
tgatcctctt gtcccacaga tatcc                                               25
```

```
SEQ ID NO: 573          moltype = DNA  length = 25
FEATURE                 Location/Qualifiers
source                  1..25
                        mol_type = other DNA
                        organism = Homo sapiens
misc_feature            1..25
                        note = SGN002663 target seq
SEQUENCE: 573
tgccgtgtac cagctgagag actct                                              25

SEQ ID NO: 574          moltype = DNA  length = 25
FEATURE                 Location/Qualifiers
source                  1..25
                        mol_type = other DNA
                        organism = Homo sapiens
misc_feature            1..25
                        note = SGN002664 target seq
SEQUENCE: 574
cattcgggcc gagatgtctc gctcc                                              25

SEQ ID NO: 575          moltype = DNA  length = 25
FEATURE                 Location/Qualifiers
source                  1..25
                        mol_type = other DNA
                        organism = Homo sapiens
misc_feature            1..25
                        note = SGN002665 target seq
SEQUENCE: 575
gagagactca cgctggatag cctcc                                              25

SEQ ID NO: 576          moltype = DNA  length = 25
FEATURE                 Location/Qualifiers
source                  1..25
                        mol_type = other DNA
                        organism = Homo sapiens
misc_feature            1..25
                        note = SGN002666 target seq
SEQUENCE: 576
gctgtgctcg cgctactctc tcttt                                              25

SEQ ID NO: 577          moltype = DNA  length = 25
FEATURE                 Location/Qualifiers
source                  1..25
                        mol_type = other DNA
                        organism = Homo sapiens
misc_feature            1..25
                        note = SGN002667 target seq
SEQUENCE: 577
tgacagcatt cgggccgaga tgtct                                              25

SEQ ID NO: 578          moltype = DNA  length = 25
FEATURE                 Location/Qualifiers
source                  1..25
                        mol_type = other DNA
                        organism = Homo sapiens
misc_feature            1..25
                        note = SGN002668 target seq
SEQUENCE: 578
tttctatctc ttgtactaca ctgaa                                              25

SEQ ID NO: 579          moltype = DNA  length = 25
FEATURE                 Location/Qualifiers
source                  1..25
                        mol_type = other DNA
                        organism = Homo sapiens
misc_feature            1..25
                        note = SGN002669 target seq
SEQUENCE: 579
gctgagagac tctaaatcca gtgac                                              25

SEQ ID NO: 580          moltype = DNA  length = 25
FEATURE                 Location/Qualifiers
source                  1..25
                        mol_type = other DNA
                        organism = Homo sapiens
misc_feature            1..25
                        note = SGN002670 target seq
SEQUENCE: 580
```

```
ggatttagag tctctcagct ggtac                                              25

SEQ ID NO: 581           moltype = DNA  length = 25
FEATURE                  Location/Qualifiers
source                   1..25
                         mol_type = other DNA
                         organism = Homo sapiens
misc_feature             1..25
                         note = SGN002671 target seq
SEQUENCE: 581
tcttgtccca cagatatcca gaacc                                              25

SEQ ID NO: 582           moltype = DNA  length = 25
FEATURE                  Location/Qualifiers
source                   1..25
                         mol_type = other DNA
                         organism = Homo sapiens
misc_feature             1..25
                         note = SGN002672 target seq
SEQUENCE: 582
tgatcctctt gtcccacaga tatcc                                              25

SEQ ID NO: 583           moltype = DNA  length = 25
FEATURE                  Location/Qualifiers
source                   1..25
                         mol_type = other DNA
                         organism = Homo sapiens
misc_feature             1..25
                         note = SGN002673 target seq
SEQUENCE: 583
tgccgtgtac cagctgagag actct                                              25

SEQ ID NO: 584           moltype = DNA  length = 25
FEATURE                  Location/Qualifiers
source                   1..25
                         mol_type = other DNA
                         organism = Homo sapiens
misc_feature             1..25
                         note = SGN002674 target seq
SEQUENCE: 584
cattcgggcc gagatgtctc gctcc                                              25

SEQ ID NO: 585           moltype = DNA  length = 25
FEATURE                  Location/Qualifiers
source                   1..25
                         mol_type = other DNA
                         organism = Homo sapiens
misc_feature             1..25
                         note = SGN002675 target seq
SEQUENCE: 585
gagagactca cgctggatag cctcc                                              25

SEQ ID NO: 586           moltype = DNA  length = 25
FEATURE                  Location/Qualifiers
source                   1..25
                         mol_type = other DNA
                         organism = Homo sapiens
misc_feature             1..25
                         note = SGN002676 target seq
SEQUENCE: 586
gctgtgctcg cgctactctc tcttt                                              25

SEQ ID NO: 587           moltype = DNA  length = 25
FEATURE                  Location/Qualifiers
source                   1..25
                         mol_type = other DNA
                         organism = Homo sapiens
misc_feature             1..25
                         note = SGN002677 target seq
SEQUENCE: 587
tgacagcatt cgggccgaga tgtct                                              25

SEQ ID NO: 588           moltype = DNA  length = 25
FEATURE                  Location/Qualifiers
source                   1..25
                         mol_type = other DNA
                         organism = Homo sapiens
misc_feature             1..25
                         note = SGN002678 target seq
```

```
SEQUENCE: 588
tttctatctc ttgtactaca ctgaa                                              25

SEQ ID NO: 589          moltype = DNA  length = 25
FEATURE                 Location/Qualifiers
source                  1..25
                        mol_type = other DNA
                        organism = Homo sapiens
misc_feature            1..25
                        note = SGN002679 target seq
SEQUENCE: 589
gctgagagac tctaaatcca gtgac                                              25

SEQ ID NO: 590          moltype = DNA  length = 25
FEATURE                 Location/Qualifiers
source                  1..25
                        mol_type = other DNA
                        organism = Homo sapiens
misc_feature            1..25
                        note = SGN002680 target seq
SEQUENCE: 590
ggatttagag tctctcagct ggtac                                              25

SEQ ID NO: 591          moltype = DNA  length = 25
FEATURE                 Location/Qualifiers
source                  1..25
                        mol_type = other DNA
                        organism = Homo sapiens
misc_feature            1..25
                        note = SGN002681 target seq
SEQUENCE: 591
tcttgtccca cagatatcca gaacc                                              25

SEQ ID NO: 592          moltype = DNA  length = 25
FEATURE                 Location/Qualifiers
source                  1..25
                        mol_type = other DNA
                        organism = Homo sapiens
misc_feature            1..25
                        note = SGN002682 target seq
SEQUENCE: 592
tgatcctctt gtcccacaga tatcc                                              25

SEQ ID NO: 593          moltype = DNA  length = 25
FEATURE                 Location/Qualifiers
source                  1..25
                        mol_type = other DNA
                        organism = Homo sapiens
misc_feature            1..25
                        note = SGN002683 target seq
SEQUENCE: 593
tgccgtgtac cagctgagag actct                                              25

SEQ ID NO: 594          moltype = DNA  length = 25
FEATURE                 Location/Qualifiers
source                  1..25
                        mol_type = other DNA
                        organism = Homo sapiens
misc_feature            1..25
                        note = SGN002684 target seq
SEQUENCE: 594
agtagcgcga gcacagctaa ggcca                                              25

SEQ ID NO: 595          moltype = DNA  length = 25
FEATURE                 Location/Qualifiers
source                  1..25
                        mol_type = other DNA
                        organism = Homo sapiens
misc_feature            1..25
                        note = SGN002685 target seq
SEQUENCE: 595
ctcgcgctac tctctctttc tggcc                                              25

SEQ ID NO: 596          moltype = DNA  length = 25
FEATURE                 Location/Qualifiers
source                  1..25
                        mol_type = other DNA
                        organism = Homo sapiens
misc_feature            1..25
```

```
                        note = SGN002686 target seq
SEQUENCE: 596
acattgaagt tgacttactg aagaa                                               25

SEQ ID NO: 597          moltype = DNA  length = 25
FEATURE                 Location/Qualifiers
source                  1..25
                        mol_type = other DNA
                        organism = Homo sapiens
misc_feature            1..25
                        note = SGN002687 target seq
SEQUENCE: 597
atgaaaccca gacacatagc aattc                                               25

SEQ ID NO: 598          moltype = DNA  length = 25
FEATURE                 Location/Qualifiers
source                  1..25
                        mol_type = other DNA
                        organism = Homo sapiens
misc_feature            1..25
                        note = SGN002688 target seq
SEQUENCE: 598
gatgacgtga gtaaacctga atctt                                               25

SEQ ID NO: 599          moltype = DNA  length = 20
FEATURE                 Location/Qualifiers
source                  1..20
                        mol_type = other DNA
                        organism = Homo sapiens
misc_feature            1..20
                        note = SGN002689 target seq
SEQUENCE: 599
agagcaacag tgctgtggcc                                                     20

SEQ ID NO: 600          moltype = DNA  length = 25
FEATURE                 Location/Qualifiers
source                  1..25
                        mol_type = other DNA
                        organism = Homo sapiens
misc_feature            1..25
                        note = SGN002690 target seq
SEQUENCE: 600
cttcaagagc aacagtgctg tggcc                                               25

SEQ ID NO: 601          moltype = DNA  length = 25
FEATURE                 Location/Qualifiers
source                  1..25
                        mol_type = other DNA
                        organism = Homo sapiens
misc_feature            1..25
                        note = SGN002691 target seq
SEQUENCE: 601
gatttagagt ctctcagctg gtaca                                               25

SEQ ID NO: 602          moltype = DNA  length = 25
FEATURE                 Location/Qualifiers
source                  1..25
                        mol_type = other DNA
                        organism = Homo sapiens
misc_feature            1..25
                        note = SGN002692 target seq
SEQUENCE: 602
gcagggtcag ggttctggat atctg                                               25

SEQ ID NO: 603          moltype = DNA  length = 25
FEATURE                 Location/Qualifiers
source                  1..25
                        mol_type = other DNA
                        organism = Homo sapiens
misc_feature            1..25
                        note = SGN002693 target seq
SEQUENCE: 603
tgtttgagaa tcaaaatcgg tgaat                                               25

SEQ ID NO: 604          moltype = DNA  length = 25
FEATURE                 Location/Qualifiers
source                  1..25
                        mol_type = other DNA
                        organism = Homo sapiens
```

```
misc_feature           1..25
                       note = SGN002698 target seq
SEQUENCE: 604
gagtagcgcg agcacagcta aggcc                                              25

SEQ ID NO: 605         moltype = DNA  length = 25
FEATURE                Location/Qualifiers
source                 1..25
                       mol_type = other DNA
                       organism = Homo sapiens
misc_feature           1..25
                       note = SGN002699 target seq
SEQUENCE: 605
ggagagactc acgctggata gcctc                                              25

SEQ ID NO: 606         moltype = DNA  length = 25
FEATURE                Location/Qualifiers
source                 1..25
                       mol_type = other DNA
                       organism = Homo sapiens
misc_feature           1..25
                       note = SGN002700 target seq
SEQUENCE: 606
gctcgcgcta ctctctcttt ctggc                                              25

SEQ ID NO: 607         moltype = DNA  length = 25
FEATURE                Location/Qualifiers
source                 1..25
                       mol_type = other DNA
                       organism = Homo sapiens
misc_feature           1..25
                       note = SGN002701 target seq
SEQUENCE: 607
agctaaggcc acggagcgag acatc                                              25

SEQ ID NO: 608         moltype = DNA  length = 25
FEATURE                Location/Qualifiers
source                 1..25
                       mol_type = other DNA
                       organism = Homo sapiens
misc_feature           1..25
                       note = SGN002702 target seq
SEQUENCE: 608
aagagagagt agcgcgagca cagct                                              25

SEQ ID NO: 609         moltype = DNA  length = 25
FEATURE                Location/Qualifiers
source                 1..25
                       mol_type = other DNA
                       organism = Homo sapiens
misc_feature           1..25
                       note = SGN002703 target seq
SEQUENCE: 609
tagagtctct cagctggtac acggc                                              25

SEQ ID NO: 610         moltype = DNA  length = 25
FEATURE                Location/Qualifiers
source                 1..25
                       mol_type = other DNA
                       organism = Homo sapiens
misc_feature           1..25
                       note = SGN002704 target seq
SEQUENCE: 610
ctctcagctg gtacacggca gggtc                                              25

SEQ ID NO: 611         moltype = DNA  length = 25
FEATURE                Location/Qualifiers
source                 1..25
                       mol_type = other DNA
                       organism = Homo sapiens
misc_feature           1..25
                       note = SGN002705 target seq
SEQUENCE: 611
ttgtttgaga atcaaaatcg gtgaa                                              25

SEQ ID NO: 612         moltype = DNA  length = 25
FEATURE                Location/Qualifiers
source                 1..25
                       mol_type = other DNA
```

```
                            organism = Homo sapiens
misc_feature                1..25
                            note = SGN002706 target seq
SEQUENCE: 612
gcagggtcag ggttctggat atctg                                         25

SEQ ID NO: 613              moltype = DNA   length = 25
FEATURE                     Location/Qualifiers
source                      1..25
                            mol_type = other DNA
                            organism = Homo sapiens
misc_feature                1..25
                            note = SGN002707 target seq
SEQUENCE: 613
ggtgaatagg cagacagact tgtca                                         25

SEQ ID NO: 614              moltype = DNA   length = 25
FEATURE                     Location/Qualifiers
source                      1..25
                            mol_type = other DNA
                            organism = Homo sapiens
misc_feature                1..25
                            note = SGN002708 target seq
SEQUENCE: 614
gcgcgagcac agctaaggcc acgga                                         25

SEQ ID NO: 615              moltype = DNA   length = 25
FEATURE                     Location/Qualifiers
source                      1..25
                            mol_type = other DNA
                            organism = Homo sapiens
misc_feature                1..25
                            note = SGN002709 target seq
SEQUENCE: 615
tcgctccgtg gccttagctg tgctc                                         25

SEQ ID NO: 616              moltype = DNA   length = 25
FEATURE                     Location/Qualifiers
source                      1..25
                            mol_type = other DNA
                            organism = Homo sapiens
misc_feature                1..25
                            note = SGN002710 target seq
SEQUENCE: 616
agagagagta gcgcgagcac agcta                                         25

SEQ ID NO: 617              moltype = DNA   length = 25
FEATURE                     Location/Qualifiers
source                      1..25
                            mol_type = other DNA
                            organism = Homo sapiens
misc_feature                1..25
                            note = SGN002711 target seq
SEQUENCE: 617
tccaggccag aaagagagag tagcg                                         25

SEQ ID NO: 618              moltype = DNA   length = 25
FEATURE                     Location/Qualifiers
source                      1..25
                            mol_type = other DNA
                            organism = Homo sapiens
misc_feature                1..25
                            note = SGN002712 target seq
SEQUENCE: 618
gcgctactct ctctttctgg cctgg                                         25

SEQ ID NO: 619              moltype = DNA   length = 25
FEATURE                     Location/Qualifiers
source                      1..25
                            mol_type = other DNA
                            organism = Homo sapiens
misc_feature                1..25
                            note = SGN002713 target seq
SEQUENCE: 619
cctgatcctc ttgtcccaca gatat                                         25

SEQ ID NO: 620              moltype = DNA   length = 25
FEATURE                     Location/Qualifiers
source                      1..25
```

```
                        mol_type = other DNA
                        organism = Homo sapiens
misc_feature            1..25
                        note = SGN002714 target seq
SEQUENCE: 620
ctggtacacg gcagggtcag ggttc                                         25

SEQ ID NO: 621          moltype = DNA  length = 25
FEATURE                 Location/Qualifiers
source                  1..25
                        mol_type = other DNA
                        organism = Homo sapiens
misc_feature            1..25
                        note = SGN002715 target seq
SEQUENCE: 621
accctgaccc tgccgtgtac cagct                                         25

SEQ ID NO: 622          moltype = DNA  length = 25
FEATURE                 Location/Qualifiers
source                  1..25
                        mol_type = other DNA
                        organism = Homo sapiens
misc_feature            1..25
                        note = SGN002716 target seq
SEQUENCE: 622
tgtaccagct gagagactct aaatc                                         25

SEQ ID NO: 623          moltype = DNA  length = 25
FEATURE                 Location/Qualifiers
source                  1..25
                        mol_type = other DNA
                        organism = Homo sapiens
misc_feature            1..25
                        note = SGN002717 target seq
SEQUENCE: 623
gcatgtgcaa acgccttcaa caaca                                         25

SEQ ID NO: 624          moltype = DNA  length = 25
FEATURE                 Location/Qualifiers
source                  1..25
                        mol_type = other DNA
                        organism = Homo sapiens
misc_feature            1..25
                        note = SGN002718 target seq
SEQUENCE: 624
acgtcatcca gcagagaatg gaaag                                         25

SEQ ID NO: 625          moltype = DNA  length = 25
FEATURE                 Location/Qualifiers
source                  1..25
                        mol_type = other DNA
                        organism = Homo sapiens
misc_feature            1..25
                        note = SGN002719 target seq
SEQUENCE: 625
tgaaacccag acacatagca attca                                         25

SEQ ID NO: 626          moltype = DNA  length = 25
FEATURE                 Location/Qualifiers
source                  1..25
                        mol_type = other DNA
                        organism = Homo sapiens
misc_feature            1..25
                        note = SGN002720 target seq
SEQUENCE: 626
cctgccgtgt accagctgag agact                                         25

SEQ ID NO: 627          moltype = DNA  length = 25
FEATURE                 Location/Qualifiers
source                  1..25
                        mol_type = other DNA
                        organism = Homo sapiens
misc_feature            1..25
                        note = SGN002721 target seq
SEQUENCE: 627
cctattcacc gattttgatt ctcaa                                         25

SEQ ID NO: 628          moltype = DNA  length = 25
FEATURE                 Location/Qualifiers
```

```
source                   1..25
                         mol_type = other DNA
                         organism = Homo sapiens
misc_feature             1..25
                         note = SGN002722 target seq
SEQUENCE: 628
ctttgtgaca catttgtttg agaat                                                25

SEQ ID NO: 629           moltype = DNA  length = 25
FEATURE                  Location/Qualifiers
source                   1..25
                         mol_type = other DNA
                         organism = Homo sapiens
misc_feature             1..25
                         note = SGN002723 target seq
SEQUENCE: 629
agcaacagtg ctgtggcctg gagca                                                25

SEQ ID NO: 630           moltype = DNA  length = 25
FEATURE                  Location/Qualifiers
source                   1..25
                         mol_type = other DNA
                         organism = Homo sapiens
misc_feature             1..25
                         note = SGN002724 target seq
SEQUENCE: 630
gcgagcacag ctaaggccac ggagc                                                25

SEQ ID NO: 631           moltype = DNA  length = 25
FEATURE                  Location/Qualifiers
source                   1..25
                         mol_type = other DNA
                         organism = Homo sapiens
misc_feature             1..25
                         note = SGN002725 target seq
SEQUENCE: 631
ttctggcctg gaggctatcc agcgt                                                25

SEQ ID NO: 632           moltype = DNA  length = 25
FEATURE                  Location/Qualifiers
source                   1..25
                         mol_type = other DNA
                         organism = Homo sapiens
misc_feature             1..25
                         note = SGN002726 target seq
SEQUENCE: 632
tctgctggat gacgtgagta aacct                                                25

SEQ ID NO: 633           moltype = DNA  length = 25
FEATURE                  Location/Qualifiers
source                   1..25
                         mol_type = other DNA
                         organism = Homo sapiens
misc_feature             1..25
                         note = SGN002727 target seq
SEQUENCE: 633
ctcacgtcat ccagcagaga atgga                                                25

SEQ ID NO: 634           moltype = DNA  length = 25
FEATURE                  Location/Qualifiers
source                   1..25
                         mol_type = other DNA
                         organism = Homo sapiens
misc_feature             1..25
                         note = SGN002728 target seq
SEQUENCE: 634
aagtcaactt caatgtcgga tggat                                                25

SEQ ID NO: 635           moltype = DNA  length = 25
FEATURE                  Location/Qualifiers
source                   1..25
                         mol_type = other DNA
                         organism = Homo sapiens
misc_feature             1..25
                         note = SGN002729 target seq
SEQUENCE: 635
tgatcctctt gtcccacaga tatcc                                                25

SEQ ID NO: 636           moltype = DNA  length = 25
```

```
FEATURE                 Location/Qualifiers
source                  1..25
                        mol_type = other DNA
                        organism = Homo sapiens
misc_feature            1..25
                        note = SGN002730 target seq
SEQUENCE: 636
cctgaccctg ccgtgtacca gctga                                              25

SEQ ID NO: 637          moltype = DNA  length = 25
FEATURE                 Location/Qualifiers
source                  1..25
                        mol_type = other DNA
                        organism = Homo sapiens
misc_feature            1..25
                        note = SGN002731 target seq
SEQUENCE: 637
agagtctctc agctggtaca cggca                                              25

SEQ ID NO: 638          moltype = DNA  length = 25
FEATURE                 Location/Qualifiers
source                  1..25
                        mol_type = other DNA
                        organism = Homo sapiens
misc_feature            1..25
                        note = SGN002732 target seq
SEQUENCE: 638
tgccgtgtac cagctgagag actct                                              25

SEQ ID NO: 639          moltype = DNA  length = 25
FEATURE                 Location/Qualifiers
source                  1..25
                        mol_type = other DNA
                        organism = Homo sapiens
misc_feature            1..25
                        note = SGN002733 target seq
SEQUENCE: 639
gccttcaaca acagcattat tccag                                              25

SEQ ID NO: 640          moltype = DNA  length = 25
FEATURE                 Location/Qualifiers
source                  1..25
                        mol_type = other DNA
                        organism = Homo sapiens
misc_feature            1..25
                        note = SGN002734 target seq
SEQUENCE: 640
acgtcatcca gcagagaatg gaaag                                              25

SEQ ID NO: 641          moltype = DNA  length = 25
FEATURE                 Location/Qualifiers
source                  1..25
                        mol_type = other DNA
                        organism = Homo sapiens
misc_feature            1..25
                        note = SGN002735 target seq
SEQUENCE: 641
tgaaacccag acacatagca attca                                              25

SEQ ID NO: 642          moltype = DNA  length = 25
FEATURE                 Location/Qualifiers
source                  1..25
                        mol_type = other DNA
                        organism = Homo sapiens
misc_feature            1..25
                        note = SGN002736 target seq
SEQUENCE: 642
cctgccgtgt accagctgag agact                                              25

SEQ ID NO: 643          moltype = DNA  length = 25
FEATURE                 Location/Qualifiers
source                  1..25
                        mol_type = other DNA
                        organism = Homo sapiens
misc_feature            1..25
                        note = SGN002737 target seq
SEQUENCE: 643
cctattcacc gattttgatt ctcaa                                              25
```

```
SEQ ID NO: 644            moltype = DNA   length = 25
FEATURE                   Location/Qualifiers
source                    1..25
                          mol_type = other DNA
                          organism = Homo sapiens
misc_feature              1..25
                          note = SGN002738 target seq
SEQUENCE: 644
ctttgtgaca catttgtttg agaat                                               25

SEQ ID NO: 645            moltype = DNA   length = 25
FEATURE                   Location/Qualifiers
source                    1..25
                          mol_type = other DNA
                          organism = Homo sapiens
misc_feature              1..25
                          note = SGN002739 target seq
SEQUENCE: 645
agcaacagtg ctgtggcctg gagca                                               25

SEQ ID NO: 646            moltype = DNA   length = 25
FEATURE                   Location/Qualifiers
source                    1..25
                          mol_type = other DNA
                          organism = Homo sapiens
misc_feature              1..25
                          note = SGN002740 target seq
SEQUENCE: 646
ctcacgctgg atagcctcca ggcca                                               25

SEQ ID NO: 647            moltype = DNA   length = 25
FEATURE                   Location/Qualifiers
source                    1..25
                          mol_type = other DNA
                          organism = Homo sapiens
misc_feature              1..25
                          note = SGN002741 target seq
SEQUENCE: 647
actcacgctg gatagcctcc aggcc                                               25

SEQ ID NO: 648            moltype = DNA   length = 25
FEATURE                   Location/Qualifiers
source                    1..25
                          mol_type = other DNA
                          organism = Homo sapiens
misc_feature              1..25
                          note = SGN002742 target seq
SEQUENCE: 648
ttactcacgt catccagcag agaat                                               25

SEQ ID NO: 649            moltype = DNA   length = 25
FEATURE                   Location/Qualifiers
source                    1..25
                          mol_type = other DNA
                          organism = Homo sapiens
misc_feature              1..25
                          note = SGN002743 target seq
SEQUENCE: 649
tgaaacccag acacatagca attca                                               25

SEQ ID NO: 650            moltype = DNA   length = 25
FEATURE                   Location/Qualifiers
source                    1..25
                          mol_type = other DNA
                          organism = Homo sapiens
misc_feature              1..25
                          note = SGN002744 target seq
SEQUENCE: 650
taagtcaact tcaatgtcgg atgga                                               25

SEQ ID NO: 651            moltype = DNA   length = 25
FEATURE                   Location/Qualifiers
source                    1..25
                          mol_type = other DNA
                          organism = Homo sapiens
misc_feature              1..25
                          note = SGN002745 target seq
SEQUENCE: 651
ttttgattct caaacaaatg tgtca                                               25
```

```
SEQ ID NO: 652          moltype = DNA  length = 25
FEATURE                 Location/Qualifiers
source                  1..25
                        mol_type = other DNA
                        organism = Homo sapiens
misc_feature            1..25
                        note = SGN002746 target seq
SEQUENCE: 652
ctttgtgaca catttgtttg agaat                                               25

SEQ ID NO: 653          moltype = DNA  length = 25
FEATURE                 Location/Qualifiers
source                  1..25
                        mol_type = other DNA
                        organism = Homo sapiens
misc_feature            1..25
                        note = SGN002747 target seq
SEQUENCE: 653
ctccaggcca cagcactgtt gctct                                               25

SEQ ID NO: 654          moltype = DNA  length = 25
FEATURE                 Location/Qualifiers
source                  1..25
                        mol_type = other DNA
                        organism = Homo sapiens
misc_feature            1..25
                        note = SGN002748 target seq
SEQUENCE: 654
ctgttgttga aggcgtttgc acatg                                               25

SEQ ID NO: 655          moltype = DNA  length = 25
FEATURE                 Location/Qualifiers
source                  1..25
                        mol_type = other DNA
                        organism = Homo sapiens
misc_feature            1..25
                        note = SGN002749 target seq
SEQUENCE: 655
acgccttcaa caacagcatt attcc                                               25

SEQ ID NO: 656          moltype = DNA  length = 25
FEATURE                 Location/Qualifiers
source                  1..25
                        mol_type = other DNA
                        organism = Homo sapiens
misc_feature            1..25
                        note = SGN002750 target seq
SEQUENCE: 656
tctgctggat gacgtgagta aacct                                               25

SEQ ID NO: 657          moltype = DNA  length = 25
FEATURE                 Location/Qualifiers
source                  1..25
                        mol_type = other DNA
                        organism = Homo sapiens
misc_feature            1..25
                        note = SGN002751 target seq
SEQUENCE: 657
aggtttactc acgtcatcca gcaga                                               25

SEQ ID NO: 658          moltype = DNA  length = 25
FEATURE                 Location/Qualifiers
source                  1..25
                        mol_type = other DNA
                        organism = Homo sapiens
misc_feature            1..25
                        note = SGN002752 target seq
SEQUENCE: 658
gtcatccagc agagaatgga aagtc                                               25

SEQ ID NO: 659          moltype = DNA  length = 25
FEATURE                 Location/Qualifiers
source                  1..25
                        mol_type = other DNA
                        organism = Homo sapiens
misc_feature            1..25
                        note = SGN002753 target seq
SEQUENCE: 659
```
aaacccagac acatagcaat tcagg					25

SEQ ID NO: 660			moltype = DNA   length = 25
FEATURE				Location/Qualifiers
source				1..25
				mol_type = other DNA
				organism = Homo sapiens
misc_feature			1..25
				note = SGN002754 target seq
SEQUENCE: 660
tctccattct tcagtaagtc aactt					25

SEQ ID NO: 661			moltype = DNA   length = 25
FEATURE				Location/Qualifiers
source				1..25
				mol_type = other DNA
				organism = Homo sapiens
misc_feature			1..25
				note = SGN002755 target seq
SEQUENCE: 661
tgccgtgtac cagctgagag actct					25

SEQ ID NO: 662			moltype = DNA   length = 25
FEATURE				Location/Qualifiers
source				1..25
				mol_type = other DNA
				organism = Homo sapiens
misc_feature			1..25
				note = SGN002756 target seq
SEQUENCE: 662
tattcaccga ttttgattct caaac					25

SEQ ID NO: 663			moltype = DNA   length = 25
FEATURE				Location/Qualifiers
source				1..25
				mol_type = other DNA
				organism = Homo sapiens
misc_feature			1..25
				note = SGN002757 target seq
SEQUENCE: 663
ttgtgacaca tttgtttgag aatca					25

SEQ ID NO: 664			moltype = DNA   length = 25
FEATURE				Location/Qualifiers
source				1..25
				mol_type = other DNA
				organism = Homo sapiens
misc_feature			1..25
				note = SGN002758 target seq
SEQUENCE: 664
caacagtgct gtggcctgga gcaac					25

SEQ ID NO: 665			moltype = DNA   length = 25
FEATURE				Location/Qualifiers
source				1..25
				mol_type = other DNA
				organism = Homo sapiens
misc_feature			1..25
				note = SGN002759 target seq
SEQUENCE: 665
gggctgggga agaaggtgtc ttctg					25

SEQ ID NO: 666			moltype = DNA   length = 47
FEATURE				Location/Qualifiers
source				1..47
				mol_type = other DNA
				organism = Homo sapiens
misc_feature			1..47
				note = LPG10136 wt target sequence
SEQUENCE: 666
ctcaggtact ccaaagattc aggtttactc acgtcatcca gcagaga				47

SEQ ID NO: 667			moltype = DNA   length = 43
FEATURE				Location/Qualifiers
source				1..43
				mol_type = other DNA
				organism = synthetic construct
misc_feature			1..43
				note = LPG10136 indel 1

```
SEQUENCE: 667
ctcaggtact ccaaagattc aggtttacgt catccagcag aga                    43

SEQ ID NO: 668          moltype = DNA   length = 42
FEATURE                 Location/Qualifiers
source                  1..42
                        mol_type = other DNA
                        organism = synthetic construct
misc_feature            1..42
                        note = LPG10136 indel 2
SEQUENCE: 668
ctcaggtact ccaaagattc aggtttactc atccagcaga ga                     42

SEQ ID NO: 669          moltype = DNA   length = 37
FEATURE                 Location/Qualifiers
source                  1..37
                        mol_type = other DNA
                        organism = synthetic construct
misc_feature            1..37
                        note = LPG10136 indel 3
SEQUENCE: 669
ctcaggtact ccaaagattc acgtcatcca gcagaga                           37

SEQ ID NO: 670          moltype = DNA   length = 46
FEATURE                 Location/Qualifiers
source                  1..46
                        mol_type = other DNA
                        organism = synthetic construct
misc_feature            1..46
                        note = LPG10136 indel 4
SEQUENCE: 670
ctcaggtact ccaaagattc aggtttacta cgtcatccag cagaga                 46

SEQ ID NO: 671          moltype = DNA   length = 47
FEATURE                 Location/Qualifiers
source                  1..47
                        mol_type = other DNA
                        organism = synthetic construct
misc_feature            1..47
                        note = LPG10136 indel 5
SEQUENCE: 671
ctcaggtact ccaaagattc aggtttactc aacgtcatcc agcagag                47

SEQ ID NO: 672          moltype = DNA   length = 39
FEATURE                 Location/Qualifiers
source                  1..39
                        mol_type = other DNA
                        organism = synthetic construct
misc_feature            1..39
                        note = LPG10136 indel 6
SEQUENCE: 672
ctcaggtact ccaaagattc aggtttactc cagcagaga                         39

SEQ ID NO: 673          moltype = DNA   length = 45
FEATURE                 Location/Qualifiers
source                  1..45
                        mol_type = other DNA
                        organism = synthetic construct
misc_feature            1..45
                        note = LPG10136 indel 7
SEQUENCE: 673
ctcaggtact ccaaagattc aggtttactc gtcatccagc agaga                  45

SEQ ID NO: 674          moltype = DNA   length = 33
FEATURE                 Location/Qualifiers
source                  1..33
                        mol_type = other DNA
                        organism = synthetic construct
misc_feature            1..33
                        note = LPG10136 indel 8
SEQUENCE: 674
ctcaggtact ccaaagacgt catccagcag aga                               33

SEQ ID NO: 675          moltype = DNA   length = 47
FEATURE                 Location/Qualifiers
source                  1..47
                        mol_type = other DNA
                        organism = synthetic construct
misc_feature            1..47
```

-continued

```
                        note = LPG10136 indel 9
SEQUENCE: 675
ctcaggtact ccaaagattc aggtttactc cacgtcatcc agcagag             47

SEQ ID NO: 676          moltype = DNA   length = 38
FEATURE                 Location/Qualifiers
source                  1..38
                        mol_type = other DNA
                        organism = synthetic construct
misc_feature            1..38
                        note = LPG10136 indel 10
SEQUENCE: 676
ctcaggtact ccaaagattc aggtttactc agcagaga                       38

SEQ ID NO: 677          moltype = DNA   length = 38
FEATURE                 Location/Qualifiers
source                  1..38
                        mol_type = other DNA
                        organism = synthetic construct
misc_feature            1..38
                        note = LPG10136 indel 11
SEQUENCE: 677
ctcaggtact ccaaagattc aacgtcatcc agcagaga                       38

SEQ ID NO: 678          moltype = DNA   length = 17
FEATURE                 Location/Qualifiers
source                  1..17
                        mol_type = other DNA
                        organism = synthetic construct
misc_feature            1..17
                        note = LPG10136 indel 12
SEQUENCE: 678
ctcaggtact ccaaaga                                              17

SEQ ID NO: 679          moltype = DNA   length = 32
FEATURE                 Location/Qualifiers
source                  1..32
                        mol_type = other DNA
                        organism = synthetic construct
misc_feature            1..32
                        note = LPG10136 indel 13
SEQUENCE: 679
ctcaggtact ccaaagattc atccagcaga ga                             32

SEQ ID NO: 680          moltype = DNA   length = 45
FEATURE                 Location/Qualifiers
source                  1..45
                        mol_type = other DNA
                        organism = synthetic construct
misc_feature            1..45
                        note = LPG10136 indel 14
SEQUENCE: 680
ctcaggtact ccaaagattc aggtttacac gtcatccagc agaga               45

SEQ ID NO: 681          moltype = DNA   length = 35
FEATURE                 Location/Qualifiers
source                  1..35
                        mol_type = other DNA
                        organism = synthetic construct
misc_feature            1..35
                        note = LPG10136 indel 15
SEQUENCE: 681
ctcaggtact ccaaagatac gtcatccagc agaga                          35

SEQ ID NO: 682          moltype = DNA   length = 37
FEATURE                 Location/Qualifiers
source                  1..37
                        mol_type = other DNA
                        organism = synthetic construct
misc_feature            1..37
                        note = LPG10136 indel 16
SEQUENCE: 682
ctcaggtact ccaaagattc aggtcatcca gcagaga                        37

SEQ ID NO: 683          moltype = DNA   length = 46
FEATURE                 Location/Qualifiers
source                  1..46
                        mol_type = other DNA
                        organism = synthetic construct
```

```
misc_feature            1..46
                        note = LPG10136 indel 17
SEQUENCE: 683
ctcaggtact ccaaagattc aggtttactc cgtcatccag cagaga                    46

SEQ ID NO: 684          moltype = DNA   length = 42
FEATURE                 Location/Qualifiers
source                  1..42
                        mol_type = other DNA
                        organism = synthetic construct
misc_feature            1..42
                        note = LPG10136 indel 18
SEQUENCE: 684
ctcaggtact ccaaagattc aggttacgtc atccagcaga ga                        42

SEQ ID NO: 685          moltype = DNA   length = 26
FEATURE                 Location/Qualifiers
source                  1..26
                        mol_type = other DNA
                        organism = synthetic construct
misc_feature            1..26
                        note = LPG10136 indel 19
SEQUENCE: 685
ctcaggtact ccaaagattc aggttt                                          26

SEQ ID NO: 686          moltype = DNA   length = 44
FEATURE                 Location/Qualifiers
source                  1..44
                        mol_type = other DNA
                        organism = synthetic construct
misc_feature            1..44
                        note = LPG10136 indel 20
SEQUENCE: 686
ctcaggtact ccaaagattc aggtttaacg tcatccagca gaga                      44

SEQ ID NO: 687          moltype = DNA   length = 47
FEATURE                 Location/Qualifiers
source                  1..47
                        mol_type = other DNA
                        organism = Homo sapiens
misc_feature            1..47
                        note = LPG10145 wt target sequence
SEQUENCE: 687
atgtctcgct ccgtggcctt agctgtgctc gcgctactct ctctttc                   47

SEQ ID NO: 688          moltype = DNA   length = 46
FEATURE                 Location/Qualifiers
source                  1..46
                        mol_type = other DNA
                        organism = synthetic construct
misc_feature            1..46
                        note = LPG10145 indel 1
SEQUENCE: 688
atgtctcgct ccgtggctta gctgtgctcg cgctactctc tctttc                    46

SEQ ID NO: 689          moltype = DNA   length = 45
FEATURE                 Location/Qualifiers
source                  1..45
                        mol_type = other DNA
                        organism = synthetic construct
misc_feature            1..45
                        note = LPG10145 indel 2
SEQUENCE: 689
atgtctcgct ccgtggctag ctgtgctcgc gctactctct ctttc                     45

SEQ ID NO: 690          moltype = DNA   length = 41
FEATURE                 Location/Qualifiers
source                  1..41
                        mol_type = other DNA
                        organism = synthetic construct
misc_feature            1..41
                        note = LPG10145 indel 3
SEQUENCE: 690
atgtctcgct ccgtggctgt gctcgcgcta ctctctcttt c                         41

SEQ ID NO: 691          moltype = DNA   length = 37
FEATURE                 Location/Qualifiers
source                  1..37
                        mol_type = other DNA
```

```
                        organism = synthetic construct
misc_feature            1..37
                        note = LPG10145 indel 4
SEQUENCE: 691
atgtctcgct ccgtggcctc gcgctactct ctctttc                                37

SEQ ID NO: 692          moltype = DNA   length = 47
FEATURE                 Location/Qualifiers
source                  1..47
                        mol_type = other DNA
                        organism = synthetic construct
misc_feature            1..47
                        note = LPG10145 indel 5
SEQUENCE: 692
atgtctcgct ccgtggcact tagctgtgct cgcgctactc tctcttt                     47

SEQ ID NO: 693          moltype = DNA   length = 36
FEATURE                 Location/Qualifiers
source                  1..36
                        mol_type = other DNA
                        organism = synthetic construct
misc_feature            1..36
                        note = LPG10145 indel 6
SEQUENCE: 693
atgtctcgct ccgtggctcg cgctactctc tctttc                                 36

SEQ ID NO: 694          moltype = DNA   length = 38
FEATURE                 Location/Qualifiers
source                  1..38
                        mol_type = other DNA
                        organism = synthetic construct
misc_feature            1..38
                        note = LPG10145 indel 7
SEQUENCE: 694
atgtctcgct tagctgtgct cgcgctactc tctctttc                               38

SEQ ID NO: 695          moltype = DNA   length = 28
FEATURE                 Location/Qualifiers
source                  1..28
                        mol_type = other DNA
                        organism = synthetic construct
misc_feature            1..28
                        note = LPG10145 indel 8
SEQUENCE: 695
atgtctcgct cgcgctactc tctctttc                                          28

SEQ ID NO: 696          moltype = DNA   length = 43
FEATURE                 Location/Qualifiers
source                  1..43
                        mol_type = other DNA
                        organism = synthetic construct
misc_feature            1..43
                        note = LPG10145 indel 9
SEQUENCE: 696
atgtctcgct ccgtggcgct gtgctcgcgc tactctctct ttc                         43

SEQ ID NO: 697          moltype = DNA   length = 42
FEATURE                 Location/Qualifiers
source                  1..42
                        mol_type = other DNA
                        organism = synthetic construct
misc_feature            1..42
                        note = LPG10145 indel 10
SEQUENCE: 697
atgtctcgct ccgtggcctg tgctcgcgct actctctctt tc                          42

SEQ ID NO: 698          moltype = DNA   length = 44
FEATURE                 Location/Qualifiers
source                  1..44
                        mol_type = other DNA
                        organism = synthetic construct
misc_feature            1..44
                        note = LPG10145 indel 11
SEQUENCE: 698
atgtctcgct ccgtggcagc tgtgctcgcg ctactctctc tttc                        44

SEQ ID NO: 699          moltype = DNA   length = 32
FEATURE                 Location/Qualifiers
source                  1..32
```

```
                       mol_type = other DNA
                       organism = synthetic construct
misc_feature           1..32
                       note = LPG10145 indel 12
SEQUENCE: 699
atgtctcgct ccgtggcgct actctctctt tc                                      32

SEQ ID NO: 700         moltype = DNA   length = 39
FEATURE                Location/Qualifiers
source                 1..39
                       mol_type = other DNA
                       organism = synthetic construct
misc_feature           1..39
                       note = LPG10145 indel 13
SEQUENCE: 700
atgtctcgct ccgtggctgc tcgcgctact ctctctttc                               39

SEQ ID NO: 701         moltype = DNA   length = 24
FEATURE                Location/Qualifiers
source                 1..24
                       mol_type = other DNA
                       organism = synthetic construct
misc_feature           1..24
                       note = LPG10145 indel 14
SEQUENCE: 701
atgtctcgcg ctactctctc tttc                                               24

SEQ ID NO: 702         moltype = DNA   length = 38
FEATURE                Location/Qualifiers
source                 1..38
                       mol_type = other DNA
                       organism = synthetic construct
misc_feature           1..38
                       note = LPG10145 indel 15
SEQUENCE: 702
atgtctcgct ccgtggcgct cgcgctactc tctctttc                                38

SEQ ID NO: 703         moltype = DNA   length = 47
FEATURE                Location/Qualifiers
source                 1..47
                       mol_type = other DNA
                       organism = synthetic construct
misc_feature           1..47
                       note = LPG10145 indel 16
SEQUENCE: 703
atgtctcgct ccgtggcttc ttagctgtgc tcgcgctact ctctctt                      47

SEQ ID NO: 704         moltype = DNA   length = 40
FEATURE                Location/Qualifiers
source                 1..40
                       mol_type = other DNA
                       organism = synthetic construct
misc_feature           1..40
                       note = LPG10145 indel 17
SEQUENCE: 704
atgtctcgct ccgtggcgtg ctcgcgctac tctctctttc                              40

SEQ ID NO: 705         moltype = DNA   length = 33
FEATURE                Location/Qualifiers
source                 1..33
                       mol_type = other DNA
                       organism = synthetic construct
misc_feature           1..33
                       note = LPG10145 indel 18
SEQUENCE: 705
atgtctcgct gtgctcgcgc tactctctct ttc                                     33

SEQ ID NO: 706         moltype = DNA   length = 45
FEATURE                Location/Qualifiers
source                 1..45
                       mol_type = other DNA
                       organism = synthetic construct
misc_feature           1..45
                       note = LPG10145 indel 19
SEQUENCE: 706
atgtctcgct ccgtggcgag ctgtgctcgc gctactctct ctttc                        45

SEQ ID NO: 707         moltype = DNA   length = 47
FEATURE                Location/Qualifiers
```

```
                                    371                                                           372
                                                              -continued source                  1..47
                        mol_type = other DNA
                        organism = synthetic construct
misc_feature            1..47
                        note = LPG10145 indel 20
SEQUENCE: 707
atgtctcgct ccgtggccgt ttccccctgg aagctccctc gtgcgct                              47

SEQ ID NO: 708          moltype = DNA  length = 41
FEATURE                 Location/Qualifiers
source                  1..41
                        mol_type = other DNA
                        organism = synthetic construct
misc_feature            1..41
                        note = LPG10145 indel 21
SEQUENCE: 708
atgtctcgct ccgtagctgt gctcgcgcta ctctctcttt c                                    41

SEQ ID NO: 709          moltype =    length =
SEQUENCE: 709
000

SEQ ID NO: 710          moltype = DNA  length = 30
FEATURE                 Location/Qualifiers
source                  1..30
                        mol_type = other DNA
                        organism = synthetic construct
misc_feature            1..30
                        note = LPG10145 indel 23
SEQUENCE: 710
atgtctcgct ccgtggctac tctctctttc                                                 30

SEQ ID NO: 711          moltype = DNA  length = 35
FEATURE                 Location/Qualifiers
source                  1..35
                        mol_type = other DNA
                        organism = synthetic construct
misc_feature            1..35
                        note = LPG10145 indel 24
SEQUENCE: 711
atgtctcgct ccgtggccgc gctactctct ctttc                                           35

SEQ ID NO: 712          moltype = DNA  length = 42
FEATURE                 Location/Qualifiers
source                  1..42
                        mol_type = other DNA
                        organism = synthetic construct
misc_feature            1..42
                        note = LPG10145 indel 25
SEQUENCE: 712
atgtctcgct cccttagctg tgctcgcgct actctctctt tc                                   42
```

RNA-GUIDED NUCLEASES AND ACTIVE FRAGMENTS AND VARIANTS THEREOF AND METHODS OF USE

CROSS-REFERENCE TO RELATED APPLICATION

This application is a continuation of International Application No. PCT/IB2023/050560, filed Jan. 23, 2023, and claims priority to U.S. Provisional Patent Application Nos. 63/302,271, filed Jan. 24, 2022, and 63/386,061, filed Dec. 5, 2022, each of which is fully incorporated by reference herein

REFERENCE TO A SEQUENCE LISTING SUBMITTED ELECTRONICALLY AS AN XML FILE

The instant application contains a Sequence Listing which has been submitted in xml format via USPTO Patent Center and is hereby incorporated by reference in its entirety. Said xml copy, created on Jan. 23, 2023, is named L103438_1260WO_Seq_List.xml, and is 905 KB in size.

FIELD OF THE INVENTION

The present invention relates to the field of molecular biology and gene editing.

BACKGROUND OF THE INVENTION

Targeted genome editing or modification is rapidly becoming an important tool for basic and applied research. Initial methods involved engineering nucleases such as meganucleases, zinc finger fusion proteins or TALENs, requiring the generation of chimeric nucleases with engineered, programmable, sequence-specific DNA-binding domains specific for each particular target sequence. RNA-guided nucleases, such as the Clustered Regularly Interspaced Short Palindromic Repeats (CRISPR)-associated (Cas) proteins of the CRISPR-Cas bacterial system, allow for the targeting of specific sequences by complexing the nucleases with guide RNA that specifically hybridizes with a particular target sequence. Producing target-specific guide RNAs is less costly and more efficient than generating chimeric nucleases for each target sequence. Such RNA-guided nucleases can be used to edit genomes optionally through the introduction of a sequence-specific, double-stranded break that is repaired via error-prone non-homologous end-joining (NHEJ) to introduce a mutation at a specific genomic location. Alternatively, heterologous DNA may be introduced into the genomic site via homology-directed repair. RNA-guided nucleases (RGNs) can also be used for base editing when fused with a deaminase.

BRIEF SUMMARY OF THE INVENTION

Compositions and methods for binding a target sequence of interest are provided. The compositions find use in cleaving or modifying a target sequence of interest, detection of a target sequence of interest, and modifying the expression of a sequence of interest. Compositions comprise RNA-guided nuclease (RGN) polypeptides, CRISPR RNAs (crRNAs), trans-activating CRISPR RNAs (tracrRNAs), guide RNAs (gRNAs), nucleic acid molecules encoding the same, and vectors and host cells comprising the nucleic acid molecules. Also provided are RGN systems for binding a target sequence of interest, wherein the RGN system comprises an RNA-guided nuclease polypeptide and one or more guide RNAs. Thus, methods disclosed herein are drawn to binding a target sequence of interest, and in some embodiments, cleaving or modifying the target sequence of interest. The target sequence of interest can be modified, for example, as a result of non-homologous end joining, homology-directed repair with an introduced donor sequence, or base editing.

In a first aspect, the present disclosure provides a nucleic acid molecule comprising a polynucleotide encoding an RNA-guided nuclease (RGN) polypeptide, wherein the polynucleotide comprises a nucleotide sequence encoding an RGN polypeptide comprising an amino acid sequence having at least 90% sequence identity to any one of SEQ ID NOs: 1-12; wherein the RGN polypeptide is capable of binding a target DNA sequence in an RNA-guided sequence specific manner when bound to a guide RNA (gRNA) capable of hybridizing to the target DNA sequence. In some embodiments, the RGN polypeptide comprises an amino acid sequence having 90% sequence identity to SEQ ID NO: 6. In some embodiments of the above aspect, the RGN polypeptide comprises an amino acid sequence having at least 91%, at least 92%, at least 93%, at least 94%, at least 95%, at least 96%, at least 97%, at least 98%, at least 99%, or 100% sequence identity to any one of SEQ ID NOs: 1-12. In some embodiments, the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 6.

In some embodiments of the above aspect, the polynucleotide encoding an RGN polypeptide is operably linked to a promoter heterologous to the polynucleotide.

In some embodiments of the above aspect, the RGN polypeptide is capable of cleaving the target DNA sequence upon binding.

In some embodiments of the above aspect, the RGN polypeptide is capable of generating a double-stranded break.

In some embodiments of the above aspect, the RGN polypeptide is capable of generating a single-stranded break.

In some embodiments of the above aspect, the RGN polypeptide is nuclease inactive or is a nickase.

In some embodiments of the above aspect, the RGN polypeptide is operably linked to a prime editing polypeptide. In some embodiments, the prime editing polypeptide comprises a DNA polymerase. In some embodiments, the prime editing polypeptide comprises a reverse transcriptase. In some embodiments of the above aspect, the RGN polypeptide is operably linked to a base-editing polypeptide. In some embodiments, the base-editing polypeptide is a deaminase. In some embodiments, the deaminase is a cytosine deaminase or an adenine deaminase. In some embodiments, the deaminase has at least 90% sequence identity to an amino acid sequence of any one of SEQ ID NOs: 377-448. In some embodiments of the above aspect, the deaminase has at least 91%, at least 92%, at least 93%, at least 94%, at least 95%, at least 96%, at least 97%, at least 98%, at least 99%, or 100% sequence identity to an amino acid sequence of any one of SEQ ID NOs: 377-448.

In some embodiments of the above aspect, the RGN polypeptide comprises one or more nuclear localization signals.

In some embodiments of the above aspect, the RGN polypeptide is codon optimized for expression in a eukaryotic cell.

In some embodiments of the above aspect, the target DNA sequence is located adjacent to a protospacer adjacent motif (PAM).

In another aspect, the present disclosure provides a vector comprising a nucleic acid molecule described hereinabove.

In some embodiments of the above aspect, the vector further comprises at least one nucleotide sequence encoding the gRNA capable of hybridizing to the target DNA sequence.

In some embodiments of the above aspect, the guide RNA is selected from the group consisting of: a) a guide RNA comprising a CRISPR RNA comprising a CRISPR repeat sequence having at least 90% sequence identity to SEQ ID NO: 13, and a tracrRNA having at least 90% sequence identity to SEQ ID NO: 25, wherein the RGN polypeptide comprises an amino acid sequence having at least 90% sequence identity to SEQ ID NO: 1; b) a guide RNA comprising a CRISPR RNA comprising a CRISPR repeat sequence having at least 90% sequence identity to SEQ ID NO: 14, and a tracrRNA having at least 90% sequence identity to SEQ ID NO: 26, wherein the RGN polypeptide comprises an amino acid sequence having at least 90% sequence identity to SEQ ID NO: 2; c) a guide RNA comprising a CRISPR RNA comprising a CRISPR repeat sequence having at least 90% sequence identity to SEQ ID NO: 15, and a tracrRNA having at least 90% sequence identity to SEQ ID NO: 27, wherein the RGN polypeptide comprises an amino acid sequence having at least 90% sequence identity to SEQ ID NO: 3; d) a guide RNA comprising a CRISPR RNA comprising a CRISPR repeat sequence having at least 90% sequence identity to SEQ ID NO: 16, and a tracrRNA having at least 90% sequence identity to SEQ ID NO: 28, wherein the RGN polypeptide comprises an amino acid sequence having at least 90% sequence identity to SEQ ID NO: 4; e) a guide RNA comprising a CRISPR RNA comprising a CRISPR repeat sequence having at least 90% sequence identity to SEQ ID NO: 17, and a tracrRNA having at least 90% sequence identity to SEQ ID NO: 29, wherein the RGN polypeptide comprises an amino acid sequence having at least 90% sequence identity to SEQ ID NO: 5; f) a guide RNA comprising a CRISPR RNA comprising a CRISPR repeat sequence having at least 90% sequence identity to SEQ ID NO: 18, and a tracrRNA having at least 90% sequence identity to SEQ ID NO: 30, wherein the RGN polypeptide comprises an amino acid sequence having at least 90% sequence identity to SEQ ID NO: 6; g) a guide RNA comprising a CRISPR RNA comprising a CRISPR repeat sequence having at least 90% sequence identity to SEQ ID NO: 19, and a tracrRNA having at least 90% sequence identity to SEQ ID NO: 31, wherein the RGN polypeptide comprises an amino acid sequence having at least 90% sequence identity to SEQ ID NO: 7; h) a guide RNA comprising a CRISPR RNA comprising a CRISPR repeat sequence having at least 90% sequence identity to SEQ ID NO: 20, and a tracrRNA having at least 90% sequence identity to SEQ ID NO: 32, wherein the RGN polypeptide comprises an amino acid sequence having at least 90% sequence identity to SEQ ID NO: 8; i) a guide RNA comprising a CRISPR RNA comprising a CRISPR repeat sequence having at least 90% sequence identity to SEQ ID NO: 21, and a tracrRNA having at least 90% sequence identity to SEQ ID NO: 33, wherein the RGN polypeptide comprises an amino acid sequence having at least 90% sequence identity to SEQ ID NO: 9; j) a guide RNA comprising a CRISPR RNA comprising a CRISPR repeat sequence having at least 90% sequence identity to SEQ ID NO: 22, and a tracrRNA having at least 90% sequence identity to SEQ ID NO: 34, wherein the RGN polypeptide comprises an amino acid sequence having at least 90% sequence identity to SEQ ID NO: 10; a guide RNA comprising a CRISPR RNA comprising a CRISPR repeat sequence having at least 90% sequence identity to SEQ ID NO: 23, and a tracrRNA having at least 90% sequence identity to SEQ ID NO: 35, wherein the RGN polypeptide comprises an amino acid sequence having at least 90% sequence identity to SEQ ID NO: 11; and 1) a guide RNA comprising a CRISPR RNA comprising a CRISPR repeat sequence having at least 90% sequence identity to SEQ ID NO: 24, and a tracrRNA having at least 90% sequence identity to SEQ ID NO: 36, wherein the RGN polypeptide comprises an amino acid sequence having at least 90% sequence identity to SEQ ID NO: 12.

In some embodiments of the above aspect, the guide RNA is selected from the group consisting of: a) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 13, and a tracrRNA having at least 91%, at least 92%, at least 93%, at least 94%, at least 95%, at least 96%, at least 97%, at least 98%, at least 99%, or 100% sequence identity to SEQ ID NO: 25, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 1; b) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 14, and a tracrRNA having at least 91%, at least 92%, at least 93%, at least 94%, at least 95%, at least 96%, at least 97%, at least 98%, at least 99%, or 100% sequence identity to SEQ ID NO: 26, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 2; c) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 15, and a tracrRNA having at least 91%, at least 92%, at least 93%, at least 94%, at least 95%, at least 96%, at least 97%, at least 98%, at least 99%, or 100% sequence identity to SEQ ID NO: 27, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 3; d) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 16, and a tracrRNA having at least 91%, at least 92%, at least 93%, at least 94%, at least 95%, at least 96%, at least 97%, at least 98%, at least 99%, or 100% sequence identity to SEQ ID NO: 28, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 4; e) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 17, and a tracrRNA having at least 91%, at least 92%, at least 93%, at least 94%, at least 95%, at least 96%, at least 97%, at least 98%, at least 99%, or 100% sequence identity to SEQ ID NO: 29, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 5; f) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 18, and a tracrRNA having at least 91%, at least 92%, at least 93%, at least 94%, at least 95%, at least 96%, at least 97%, at least 98%, at least 99%, or 100% sequence identity to SEQ ID NO: 30, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 6; g) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 19, and a tracrRNA having at least 91%, at least 92%, at least 93%, at least 94%, at least 95%, at least 96%, at least 97%, at least 98%, at least 99%, or 100% sequence identity to SEQ ID NO: 31, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 7; h) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 20, and a tracrRNA having at least 91%, at least 92%, at least 93%, at least 94%, at least 95%, at least 96%, at least 97%, at least 98%, at least 99%, or 100% sequence identity to SEQ ID NO: 32, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 8; i) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 21, and a tracrRNA having at least 91%, at least 92%, at least 93%, at least 94%, at least 95%, at least 96%, at least 97%, at least 98%, at least 99%, or 100% sequence identity to SEQ ID NO: 33, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 9; j) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 22, and a tracrRNA having at least 91%, at least 92%, at least 93%, at least 94%, at least 95%, at least 96%, at least 97%, at least 98%, at least 99%, or 100% sequence identity to SEQ ID NO: 34, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 10; k) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 23, and a tracrRNA having at least 91%, at least 92%, at least 93%, at least 94%, at least 95%, at least 96%, at least 97%, at least 98%, at least 99%, or 100% sequence identity to SEQ ID NO: 35, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 11; and l) a guide RNA comprising a CRISPR RNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 24, and a tracrRNA having at least 91%, at least 92%, at least 93%, at least 94%, at least 95%, at least 96%, at least 97%, at least 98%, at least 99%, or 100% sequence identity to SEQ ID NO: 36, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 12.

In some embodiments of the above aspect, the gRNA is a single guide RNA. In some embodiments, the single guide RNA further comprises an extension comprising an edit template for prime editing.

In some embodiments of the above aspect, the gRNA is a dual-guide RNA.

In another aspect, the present disclosure provides a cell comprising a nucleic acid molecule described hereinabove or a vector described hereinabove. In yet another aspect, the present disclosure provides a method for making an RGN polypeptide comprising culturing a cell described hereinabove under conditions in which the RGN polypeptide is expressed.

In another aspect, the present disclosure provides a method for making an RGN polypeptide comprising introducing into a cell a heterologous nucleic acid molecule comprising a nucleotide sequence encoding an RNA-guided nuclease (RGN) polypeptide comprising an amino acid sequence having at least 90% sequence identity to any one of SEQ ID NOs: 1-12; wherein the RGN polypeptide is capable of binding a target DNA sequence in an RNA-guided sequence specific manner when bound to a guide RNA (gRNA) capable of hybridizing to the target DNA sequence; and culturing the cell under conditions in which the RGN polypeptide is expressed. In some embodiments, the RGN polypeptide comprises an amino acid sequence having at least 90% sequence identity to SEQ ID NO: 6. In some embodiments, the RGN polypeptide comprises an amino acid sequence having at least 91%, at least 92%, at least 93%, at least 94%, at least 95%, at least 96%, at least 97%, at least 98%, at least 99%, or 100% sequence identity to any one of SEQ ID NOs: 1-12. In some embodiments, the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 6.

In some embodiments of the above aspect, the method further comprises purifying the RGN polypeptide.

In some embodiments of the above aspect, the cell further expresses one or more guide RNAs capable of binding to the RGN polypeptide to form an RGN ribonucleoprotein complex.

In some embodiments of the above aspect, the method further comprises purifying the RGN ribonucleoprotein complex.

In still another aspect, the present disclosure provides an RNA-guided nuclease (RGN) polypeptide, wherein the RGN polypeptide comprises an amino acid sequence having at least 90% sequence identity to any one of SEQ ID NOs: 1-12, and wherein the RGN polypeptide is capable of binding a target DNA sequence of a DNA molecule in an RNA-guided sequence specific manner when bound to a guide RNA (gRNA) capable of hybridizing to the target DNA sequence. In some embodiments, the RGN polypeptide comprises an amino acid sequence having at least 90% sequence identity to SEQ ID NO: 6. In some embodiments, the RGN polypeptide comprises an amino acid sequence having at least 91%, at least 92%, at least 93%, at least 94%, at least 95%, at least 96%, at least 97%, at least 98%, at least 99%, or 100% sequence identity to any one of SEQ ID NOs: 1-12. In some embodiments, the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 6. In some embodiments of the above aspect, the RGN polypeptide is an isolated RGN polypeptide.

In some embodiments of the above aspect, the RGN polypeptide is capable of cleaving the target DNA sequence upon binding.

In some embodiments of the above aspect, cleavage by the RGN polypeptide generates a double-stranded break.

In some embodiments of the above aspect, cleavage by the RGN polypeptide generates a single-stranded break.

In some embodiments of the above aspect, the RGN polypeptide is nuclease inactive or a nickase.

In some embodiments of the above aspect, the RGN polypeptide is operably linked to a prime editing polypeptide. In some embodiments, the prime editing polypeptide comprises a DNA polymerase. In some embodiments, the prime editing polypeptide comprises a reverse transcriptase.

In some embodiments of the above aspect, the RGN polypeptide is operably linked to a base-editing polypeptide. In some embodiments, the base-editing polypeptide is a deaminase. In some embodiments, the deaminase is a cytosine deaminase or an adenine deaminase. In some embodiments, the deaminase has at least 90% sequence identity to an amino acid sequence of any one of SEQ ID NOs: 377-448. In some embodiments, the deaminase has at least 91%, at least 92%, at least 93%, at least 94%, at least 95%, at least 96%, at least 97%, at least 98%, at least 99%, or 100% sequence identity to an amino acid sequence of any one of SEQ ID NOs: 377-448.

In some embodiments of the above aspect, the target DNA sequence is located adjacent to a protospacer adjacent motif (PAM).

In some embodiments of the above aspect, the RGN polypeptide comprises one or more nuclear localization signals.

In another aspect, the present disclosure provides a ribonucleoprotein (RNP) complex comprising a RGN polypeptide described hereinabove and the guide RNA bound to the RGN polypeptide. In some embodiments, the guide RNA is a single guide RNA. In some embodiments, the single guide RNA comprises an extension comprising an edit template for prime editing. In yet another aspect, the present disclosure provides a system for binding a target DNA sequence of a DNA molecule, wherein the system comprises: a) one or more guide RNAs capable of hybridizing to the target DNA sequence or one or more polynucleotides comprising one or more nucleotide sequences encoding the one or more guide RNAs (gRNAs); and b) an RNA-guided nuclease (RGN) polypeptide comprising an amino acid sequence having at least 90% sequence identity to any one of SEQ ID NOS: 1-12 or a polynucleotide comprising a nucleotide sequence encoding the RGN polypeptide;
wherein the one or more guide RNAs are capable of hybridizing to the target DNA sequence, and wherein the one or more guide RNAs are capable of forming a complex with the RGN polypeptide in order to direct the RGN polypeptide to bind to the target DNA sequence of the DNA molecule.

In some embodiments of the above aspect, the RGN polypeptide comprises an amino acid sequence having at least 90% sequence identity to SEQ ID NO: 6.

In some embodiments of the above aspect, at least one of the nucleotide sequences encoding the one or more guide RNAs and the nucleotide sequence encoding the RGN polypeptide is operably linked to a promoter heterologous to the nucleotide sequence.

In some embodiments of the above aspect, the nucleotide sequences encoding the one or more guide RNAs and the nucleotide sequence encoding the RGN polypeptide are located on one vector.

In still another aspect, the present disclosure provides a system for binding a target DNA sequence of a DNA molecule, wherein the system comprises: a) one or more guide RNAs capable of hybridizing to the target DNA sequence or one or more polynucleotides comprising one or more nucleotide sequences encoding the one or more guide RNAs (gRNAs); and b) an RNA-guided nuclease (RGN) polypeptide comprising an amino acid sequence having at least 90% sequence identity to any one of SEQ ID NOs: 1-12; wherein the one or more guide RNAs are capable of hybridizing to the target DNA sequence, and wherein the one or more guide RNAs are capable of forming a complex with the RGN polypeptide in order to direct the RGN polypeptide to bind to the target DNA sequence of the DNA molecule.

In some embodiments of the above aspect, the RGN polypeptide comprises an amino acid sequence having at least 90% sequence identity to SEQ ID NO: 6.

In some embodiments of the above aspect, the RGN polypeptide comprises an amino acid sequence having at least 91%, at least 92%, at least 93%, at least 94%, at least 95%, at least 96%, at least 97%, at least 98%, at least 99%, or 100% sequence identity to any one of SEQ ID NOs: 1-12. In some embodiments, the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 6.

In some embodiments of the above aspect, at least one of the nucleotides sequences encoding the one or more guide RNAs is operably linked to a promoter heterologous to the nucleotide sequence.

In some embodiments of the above aspect, the RGN polypeptide and the one or more guide RNAs are not found complexed to one another in nature.

In some embodiments of the above aspect, the target DNA sequence is a eukaryotic target DNA sequence.

In some embodiments of the above aspect, the gRNA is a single guide RNA (sgRNA). In some embodiments, the sgRNA comprises an extension comprising an edit template for prime editing.

In some embodiments of the above aspect, the gRNA is a dual-guide RNA.

In some embodiments of the above aspect, the gRNA is selected from the group consisting of: a) a gRNA comprising a CRISPR repeat sequence having at least 90% sequence identity to SEQ ID NO: 13 and a tracrRNA having at least 90% sequence identity to SEQ ID NO: 25, wherein the RGN polypeptide comprises an amino acid sequence having at least 90% sequence identity to SEQ ID NO: 1; b) a gRNA comprising a CRISPR repeat sequence having at least 90% sequence identity to SEQ ID NO: 14 and a tracrRNA having at least 90% sequence identity to SEQ ID NO: 26, wherein the RGN polypeptide comprises an amino acid sequence having at least 90% sequence identity to SEQ ID NO: 2; c) a gRNA comprising a CRISPR repeat sequence having at least 90% sequence identity to SEQ ID NO: 15 and a tracrRNA having at least 90% sequence identity to SEQ ID NO: 27, wherein the RGN polypeptide comprises an amino acid sequence having at least 90% sequence identity to SEQ ID NO: 3; d) a gRNA comprising a CRISPR repeat sequence having at least 90% sequence identity to SEQ ID NO: 16 and a tracrRNA having at least 90% sequence identity to SEQ ID NO: 28, wherein the RGN polypeptide comprises an amino acid sequence having at least 90% sequence identity to SEQ ID NO: 4; e) a gRNA comprising a CRISPR repeat sequence having at least 90% sequence identity to SEQ ID NO: 17 and a tracrRNA having at least 90% sequence identity to SEQ ID NO: 29, wherein the RGN polypeptide comprises an amino acid sequence having at least 90% sequence identity to SEQ ID NO: 5; f) a gRNA comprising a CRISPR repeat sequence having at least 90% sequence identity to SEQ ID NO: 18 and a tracrRNA having at least 90% sequence identity to SEQ ID NO: 30, wherein the RGN polypeptide comprises an amino acid sequence having at least 90% sequence identity to SEQ ID NO: 6; g) a gRNA comprising a CRISPR repeat sequence having at least 90% sequence identity to SEQ ID NO: 19 and a tracrRNA having at least 90% sequence identity to SEQ ID NO: 31, wherein the RGN polypeptide comprises an amino acid sequence having at least 90% sequence identity to SEQ ID NO: 7; h) a gRNA comprising a CRISPR repeat sequence having at least 90% sequence identity to SEQ ID NO: 20 and a tracrRNA having at least 90% sequence identity to SEQ ID NO: 32, wherein the RGN polypeptide comprises an amino acid sequence having at least 90% sequence identity to SEQ ID NO: 8; i) a gRNA comprising a CRISPR repeat sequence having at least 90% sequence identity to SEQ ID NO: 21 and a tracrRNA having at least 90% sequence identity to SEQ ID NO: 33, wherein the RGN polypeptide comprises an amino acid sequence having at least 90% sequence identity to SEQ ID NO: 9; j) a gRNA comprising a CRISPR repeat sequence having at least 90% sequence identity to SEQ ID NO: 22 and a tracrRNA having at least 90% sequence identity to SEQ ID NO: 34, wherein the RGN polypeptide comprises an amino acid sequence having at least 90% sequence identity to SEQ ID NOs: 10; k) a gRNA comprising a CRISPR repeat sequence having at least 90% sequence identity to SEQ ID NO: 23 and a tracrRNA having at least 90% sequence identity to SEQ ID NO: 35, wherein the RGN polypeptide comprises an amino acid sequence having at least 90% sequence identity to SEQ ID NO: 11; and 1) a gRNA comprising a CRISPR repeat sequence having at least 90% sequence identity to SEQ ID NO: 24 and a tracrRNA having at least 90% sequence identity to SEQ ID NO: 36, wherein the RGN polypeptide comprises an amino acid sequence having at least 90% sequence identity to SEQ ID NO: 12. In some embodiments, the gRNA comprises a CRISPR repeat sequence having at least 90% sequence identity to SEQ ID NO: 18 and a tracrRNA having at least 90% sequence identity to SEQ ID NO: 30.

In some embodiments of the above aspect, the gRNA is selected from the group consisting of: a) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 13 and a tracrRNA having at least 91%, at least 92%, at least 93%, at least 94%, at least 95%, at least 96%, at least 97%, at least 98%, at least 99%, or 100% sequence identity to SEQ ID NO: 25, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 1; b) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 14 and a tracrRNA having at least 91%, at least 92%, at least 93%, at least 94%, at least 95%, at least 96%, at least 97%, at least 98%, at least 99%, or 100% sequence identity to SEQ ID NO: 26, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 2; c) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 15 and a tracrRNA having at least 91%, at least 92%, at least 93%, at least 94%, at least 95%, at least 96%, at least 97%, at least 98%, at least 99%, or 100% sequence identity to SEQ ID NO: 27, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 3; d) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 16 and a tracrRNA having at least 91%, at least 92%, at least 93%, at least 94%, at least 95%, at least 96%, at least 97%, at least 98%, at least 99%, or 100% sequence identity to SEQ ID NO: 28, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 4; e) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 17 and a tracrRNA having at least 91%, at least 92%, at least 93%, at least 94%, at least 95%, at least 96%, at least 97%, at least 98%, at least 99%, or 100% sequence identity to SEQ ID NO: 29, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 5; f) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 18 and a tracrRNA having at least 91%, at least 92%, at least 93%, at least 94%, at least 95%, at least 96%, at least 97%, at least 98%, at least 99%, or 100% sequence identity to SEQ ID NO: 30, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 6; g) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 19 and a tracrRNA having at least 91%, at least 92%, at least 93%, at least 94%, at least 95%, at least 96%, at least 97%, at least 98%, at least 99%, or 100% sequence identity to SEQ ID NO: 31, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 7; h) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 20 and a tracrRNA having at least 91%, at least 92%, at least 93%, at least 94%, at least 95%, at least 96%, at least 97%, at least 98%, at least 99%, or 100% sequence identity to SEQ ID NO: 32, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 8; i) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 21 and a tracrRNA having at least 91%, at least 92%, at least 93%, at least 94%, at least 95%, at least 96%, at least 97%, at least 98%, at least 99%, or 100% sequence identity to SEQ ID NO: 33, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 9; j) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 22 and a tracrRNA having at least 91%, at least 92%, at least 93%, at least 94%, at least 95%, at least 96%, at least 97%, at least 98%, at least 99%, or 100% sequence identity to SEQ ID NO: 34, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NOs: 10; k) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 23 and a tracrRNA having at least 91%, at least 92%, at least 93%, at least 94%, at least 95%, at least 96%, at least 97%, at least 98%, at least 99%, or 100% sequence identity to SEQ ID NO: 35, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 11; and l) a gRNA comprising a CRISPR repeat sequence having at least 91%, at least 92%, at least 93%, at least 94%, at least 95%, at least 96%, at least 97%, at least 98%, at least 99%, or 100% sequence identity to SEQ ID NO: 24 and a tracrRNA having at least 91%, at least 92%, at least 93%, at least 94%, at least 95%, at least 96%, at least 97%, at least 98%, at least 99%, or 100% sequence identity to SEQ ID NO: 36, wherein the RGN polypeptide comprises an amino acid sequence having at least 91%, at least 92%, at least 93%, at least 94%, at least 95%, at least 96%, at least 97%, at least 98%, at least 99%, or 100% sequence identity to SEQ ID NO: 12. In some embodiments, the gRNA comprises a CRISPR repeat sequence having at least 91%, at least 92%, at least 93%, at least 94%, at least 95%, at least 96%, at least 97%, at least 98%, at least 99%, or 100% sequence identity to SEQ ID NO: 18 and a tracrRNA having at least 91%, at least 92%, at least 93%, at least 94%, at least 95%, at least 96%, at least 97%, at least 98%, at least 99%, or 100% sequence identity to SEQ ID NO: 30.

In some embodiments of the above aspect, the target DNA sequence is located adjacent to a protospacer adjacent motif (PAM).

In some embodiments of the above aspect, the target DNA sequence is within a cell.

In some embodiments of the above aspect, the one or more guide RNAs is capable of hybridizing to the target DNA sequence and the guide RNA is capable of forming a complex with the RGN polypeptide to direct cleavage of the target DNA sequence.

In some embodiments of the above aspect, the cleavage generates a double-stranded break.

In some embodiments of the above aspect, the cleavage generates a single-stranded break.

In some embodiments of the above aspect, the RGN polypeptide is nuclease inactive or is a nickase.

In some embodiments of the above aspect, the RGN polypeptide is operably linked to a prime editing polypeptide. In some embodiments, the prime editing polypeptide comprises a DNA polymerase. In some embodiments, the prime editing polypeptide comprises a reverse transcriptase.

In some embodiments of the above aspect, the RGN polypeptide is operably linked to a base-editing polypeptide.

In some embodiments of the above aspect, the base-editing polypeptide is a deaminase. In some embodiments, the deaminase is a cytosine deaminase or an adenine deaminase. In some embodiments, the deaminase has at least 90% sequence identity to an amino acid sequence of any one of SEQ ID NOs: 377-448. In some embodiments, the deaminase has at least 91%, at least 92%, at least 93%, at least 94%, at least 95%, at least 96%, at least 97%, at least 98%, at least 99%, or 100% sequence identity to an amino acid sequence of any one of SEQ ID NOs: 377-448.

In some embodiments of the above aspect, the RGN polypeptide comprises one or more nuclear localization signals.

In some embodiments of the above aspect, the RGN polypeptide is codon optimized for expression in a eukaryotic cell.

In some embodiments of the above aspect, the system further comprises one or more donor polynucleotides.

In another aspect, the present disclosure provides a cell comprising a system described hereinabove.

In yet another aspect, the present disclosure provides a pharmaceutical composition comprising a nucleic acid molecule, a vector, a cell, a RGN polypeptide, a RNP complex, or a system described hereinabove, and a pharmaceutically acceptable carrier.

In still another aspect, the present disclosure provides a method for binding a target DNA sequence of a DNA molecule comprising delivering a system described hereinabove to the target DNA sequence or a cell comprising the target DNA sequence.

In some embodiments of the above aspect, the RGN polypeptide or the guide RNA further comprises a detectable label, thereby allowing for detection of the target DNA sequence.

In some embodiments of the above aspect, the guide RNA or the RGN polypeptide further comprises an expression modulator, thereby modulating expression of the target DNA sequence or a gene under transcriptional control by the target DNA sequence.

In another aspect, the present disclosure provides a method for cleaving and/or modifying a target DNA sequence of a DNA molecule comprising delivering a system described hereinabove to the target DNA sequence or a cell comprising the DNA molecule, wherein cleavage or modification of the target DNA sequence occurs.

In some embodiments of the above aspect, the modified target DNA sequence comprises insertion of heterologous DNA into the target DNA sequence.

In some embodiments of the above aspect, the modified target DNA sequence comprises deletion of at least one nucleotide from the target DNA sequence.

In some embodiments of the above aspect, the modified target DNA sequence comprises mutation of at least one nucleotide in the target DNA sequence.

In another aspect, the present disclosure provides a method for binding a target DNA sequence of a DNA molecule comprising: a) assembling an RNA-guided nuclease (RGN) ribonucleotide complex by combining one or more guide RNAs capable of hybridizing to the target DNA sequence, and an RGN polypeptide comprising an amino acid sequence having at least 90% sequence identity to any one of SEQ ID NOs: 1-12 under conditions suitable for formation of the RGN ribonucleotide complex; and b) contacting the target DNA sequence or a cell comprising the target DNA sequence with the assembled RGN ribonucleotide complex; wherein the one or more guide RNAs hybridize to the target DNA sequence, thereby directing the RGN polypeptide to bind to the target DNA sequence. In some embodiments, the RGN polypeptide has at least 90% sequence identity to SEQ ID NO: 6.

In some embodiments of the above aspect, the RGN polypeptide comprises an amino acid sequence having at least 91%, at least 92%, at least 93%, at least 94%, at least 95%, at least 96%, at least 97%, at least 98%, at least 99%, or 100% sequence identity to any one of SEQ ID NOs: 1-12. In some embodiments, the RGN polypeptide has at least 91%, at least 92%, at least 93%, at least 94%, at least 95%, at least 96%, at least 97%, at least 98%, at least 99%, or 100% sequence identity to SEQ ID NO: 6.

In some embodiments of the above aspect, the method is performed in vitro, in vivo, or ex vivo.

In some embodiments of the above aspect, the RGN polypeptide or the guide RNA further comprises a detectable label, thereby allowing for detection of the target DNA sequence.

In some embodiments of the above aspect, the guide RNA or the RGN polypeptide further comprises an expression modulator, thereby allowing for the modulation of expression of the target DNA sequence.

In some embodiments of the above aspect, the RGN polypeptide is operably linked to a prime editing polypeptide, thereby allowing for the modification of the target DNA sequence. In some embodiments, the prime editing polypeptide comprises a DNA polymerase. In some embodiments, the prime editing polypeptide comprises a reverse transcriptase.

In some embodiments of the above aspect, the RGN polypeptide is operably linked to a base-editing polypeptide, thereby allowing for the modification of the target DNA sequence. In some embodiments, the base-editing polypeptide comprises a deaminase. In some embodiments, the deaminase is a cytosine deaminase or an adenine deaminase. In some embodiments of the above aspect, the RGN polypeptide is capable of cleaving the target DNA sequence, thereby allowing for the cleaving and/or modifying of the target DNA sequence.

In another aspect, the present disclosure provides a method for cleaving and/or modifying a target DNA sequence of a DNA molecule, comprising contacting the DNA molecule with: a) an RNA-guided nuclease (RGN) polypeptide, wherein the RGN comprises an amino acid sequence having at least 90% sequence identity to any one of SEQ ID NOs: 1-12; and b) one or more guide RNAs capable of targeting the RGN of (a) to the target DNA sequence, wherein the one or more guide RNAs hybridize to the target DNA sequence, thereby directing the RGN polypeptide to bind to the target DNA sequence and cleavage and/or modification of the target DNA sequence occurs. In some embodiments, the RGN polypeptide has at least 90% sequence identity to SEQ ID NO: 6.

In some embodiments of the above aspect, the RGN polypeptide comprises an amino acid sequence having at least 91%, at least 92%, at least 93%, at least 94%, at least 95%, at least 96%, at least 97%, at least 98%, at least 99%, or 100% sequence identity to any one of SEQ ID NOs: 1-12. In some embodiments, the RGN polypeptide has at least 91%, at least 92%, at least 93%, at least 94%, at least 95%, at least 96%, at least 97%, at least 98%, at least 99%, or 100% sequence identity to SEQ ID NO: 6.

In some embodiments of the above aspect, cleavage by the RGN polypeptide generates a double-stranded break.

In some embodiments of the above aspect, cleavage by the RGN polypeptide generates a single-stranded break.

In some embodiments of the above aspect, the RGN polypeptide is nuclease inactive or a nickase.

In some embodiments of the above aspect, the RGN polypeptide is operably linked to a prime editing polypeptide, thereby allowing for the modification of the target DNA sequence. In some embodiments, the prime editing polypeptide comprises a DNA polymerase. In some embodiments, the prime editing polypeptide comprises a reverse transcriptase.

In some embodiments of the above aspect, the RGN polypeptide is operably linked to a base-editing polypeptide.

In some embodiments of the above aspect, the base-editing polypeptide is a deaminase. In some embodiments, the deaminase is a cytosine deaminase or an adenine deaminase. In some embodiments, the deaminase has at least 90% sequence identity to an amino acid sequence of any one of SEQ ID NOs: 377-448. In some embodiments, the deaminase has at least 91%, at least 92%, at least 93%, at least 94%, at least 95%, at least 96%, at least 97%, at least 98%, at least 99%, or 100% sequence identity to an amino acid sequence of any one of SEQ ID NOs: 377-448.

In some embodiments of the above aspect, the modified target DNA sequence comprises insertion of heterologous DNA into the target DNA sequence.

In some embodiments of the above aspect, the modified target DNA sequence comprises deletion of at least one nucleotide from the target DNA sequence.

In some embodiments of the above aspect, the modified target DNA sequence comprises mutation of at least one nucleotide in the target DNA sequence.

In some embodiments of the above aspect, the target DNA sequence is located adjacent to a protospacer adjacent motif (PAM).

In some embodiments of the above aspect, the target DNA sequence is a eukaryotic target DNA sequence.

In some embodiments of the above aspect, the gRNA is a single guide RNA (sgRNA). In some embodiments, the sgRNA comprises an extension comprising an edit template for prime editing.

In some embodiments of the above aspect, the gRNA is a dual-guide RNA.

In some embodiments of the above aspect, the RGN, the guide RNA, and the tracrRNA is selected from the group consisting of: a) an RGN having at least 90% sequence identity to SEQ ID NO: 1, a guide RNA comprising a crRNA repeat sequence having at least 90% sequence identity to SEQ ID NO: 13 and a tracrRNA having at least 90% sequence identity to SEQ ID NO: 25; b) an RGN having at least 90% sequence identity to SEQ ID NO: 2, a guide RNA comprising a crRNA repeat sequence having at least 90% sequence identity to SEQ ID NO: 14 and a tracrRNA having at least 90% sequence identity to SEQ ID NO: 26; c) an RGN having at least 90% sequence identity to SEQ ID NO: 3, a guide RNA comprising a crRNA repeat sequence having at least 90% sequence identity to SEQ ID NO: 15 and a tracrRNA having at least 90% sequence identity to SEQ ID NO: 27; d) an RGN having at least 90% sequence identity to SEQ ID NO: 4, a guide RNA comprising a crRNA repeat sequence having at least 90% sequence identity to SEQ ID NO: 16 and a tracrRNA having at least 90% sequence identity to SEQ ID NO: 28; e) an RGN having at least 90% sequence identity to SEQ ID NO: 5, a guide RNA comprising a crRNA repeat sequence having at least 90% sequence identity to SEQ ID NO: 17 and a tracrRNA having at least 90% sequence identity to SEQ ID NO: 29; f) an RGN having at least 90% sequence identity to SEQ ID NO: 6, a guide RNA comprising a crRNA repeat sequence having at least 90% sequence identity to SEQ ID NO: 18 and a tracrRNA having at least 90% sequence identity to SEQ ID NO: 30; g) an RGN having at least 90% sequence identity to SEQ ID NO: 7, a guide RNA comprising a crRNA repeat sequence having at least 90% sequence identity to SEQ ID NO: 19 and a tracrRNA having at least 90% sequence identity to SEQ ID NO: 31; h) an RGN having at least 90% sequence identity to SEQ ID NO: 8, a guide RNA comprising a crRNA repeat sequence having at least 90% sequence identity to SEQ ID NO: 20 and a tracrRNA having at least 90% sequence identity to SEQ ID NO: 32; i) an RGN having at least 90% sequence identity to SEQ ID NO: 9, a guide RNA comprising a crRNA repeat sequence having at least 90% sequence identity to SEQ ID NO: 21 and a tracrRNA having at least 90% sequence identity to SEQ ID NO: 33; j) an RGN having at least 90% sequence identity to SEQ ID NO: 10, a guide RNA comprising a crRNA repeat sequence having at least 90% sequence identity to SEQ ID NO: 22 and a tracrRNA having at least 90% sequence identity to SEQ ID NO:34; k) an RGN having at least 90% sequence identity to SEQ ID NO: 11, a guide RNA comprising a crRNA repeat sequence having at least 90% sequence identity to SEQ ID NO: 23 and a tracrRNA having at least 90% sequence identity to SEQ ID NO: 35; and l) an RGN having at least 90% sequence identity to SEQ ID NO: 12, a guide RNA comprising a crRNA repeat sequence having at least 90% sequence identity to SEQ ID NO: 24 and a tracrRNA having at least 90% sequence identity to SEQ ID NO: 36. In some embodiments, the RGN has at least 90% sequence identity to SEQ ID NO: 6, the guide RNA comprises a crRNA repeat sequence having at least 90% sequence identity to SEQ ID NO: 18 and the tracrRNA has at least 90% sequence identity to SEQ ID NO: 30.

In some embodiments of the above aspect, the RGN, the guide RNA, and the tracrRNA is selected from the group consisting of: a) an RGN having at least 91%, at least 92%, at least 93%, at least 94%, at least 95%, at least 96%, at least 97%, at least 98%, at least 99%, or 100% sequence identity to SEQ ID NO: 1, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 13 and a tracrRNA having at least 91%, at least 92%, at least 93%, at least 94%, at least 95%, at least 96%, at least 97%, at least 98%, at least 99%, or 100% sequence identity to SEQ ID NO: 25; b) an RGN having at least 91%, at least 92%, at least 93%, at least 94%, at least 95%, at least 96%, at least 97%, at least 98%, at least 99%, or 100% sequence identity to SEQ ID NO: 2, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 14 and a tracrRNA having at least 91%, at least 92%, at least 93%, at least 94%, at least 95%, at least 96%, at least 97%, at least 98%, at least 99%, or 100% sequence identity to SEQ ID NO: 26; c) an RGN having at least 91%, at least 92%, at least 93%, at least 94%, at least 95%, at least 96%, at least 97%, at least 98%, at least 99%, or 100% sequence identity to SEQ ID NO: 3, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 15 and a tracrRNA having at least 91%, at least 92%, at least 93%, at least 94%, at least 95%, at least 96%, at least 97%, at least 98%, at least 99%, or 100% sequence identity to SEQ ID NO: 27; d) an RGN having at least 91%, at least 92%, at least 93%, at least 94%, at least 95%, at least 96%, at least 97%, at least 98%, at least 99%, or 100% sequence identity to SEQ ID NO: 4, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 16 and a tracrRNA having at least 91%, at least 92%, at least 93%, at least 94%, at least 95%, at least 96%, at least 97%, at least 98%, at least 99%, or 100% sequence identity to SEQ ID NO: 28; e) an RGN having at least 91%, at least 92%, at least 93%, at least 94%, at least 95%, at least 96%, at least 97%, at least 98%, at least 99%, or 100% sequence identity to SEQ ID NO: 5, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 17 and a tracrRNA having at least 91%, at least 92%, at least 93%, at least 94%, at least 95%, at least 96%, at least 97%, at least 98%, at least 99%, or 100% sequence identity to SEQ ID NO: 29; f) an RGN having at least 91%, at least 92%, at least 93%, at least 94%, at least 95%, at least 96%, at least 97%, at least 98%, at least 99%, or 100% sequence identity to SEQ ID NO: 6, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 18 and a tracrRNA having at least 91%, at least 92%, at least 93%, at least 94%, at least 95%, at least 96%, at least 97%, at least 98%, at least 99%, or 100% sequence identity to SEQ ID NO: 30; g) an RGN having at least 91%, at least 92%, at least 93%, at least 94%, at least 95%, at least 96%, at least 97%, at least 98%, at least 99%, or 100% sequence identity to SEQ ID NO: 7, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 19 and a tracrRNA having at least 91%, at least 92%, at least 93%, at least 94%, at least 95%, at least 96%, at least 97%, at least 98%, at least 99%, or 100% sequence identity to SEQ ID NO: 31; h) an RGN having at least 91%, at least 92%, at least 93%, at least 94%, at least 95%, at least 96%, at least 97%, at least 98%, at least 99%, or 100% sequence identity to SEQ ID NO: 8, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 20 and a tracrRNA having at least 91%, at least 92%, at least 93%, at least 94%, at least 95%, at least 96%, at least 97%, at least 98%, at least 99%, or 100% sequence identity to SEQ ID NO: 32; i) an RGN having at least 91%, at least 92%, at least 93%, at least 94%, at least 95%, at least 96%, at least 97%, at least 98%, at least 99%, or 100% sequence identity to SEQ ID NO: 9, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 21 and a tracrRNA having at least 91%, at least 92%, at least 93%, at least 94%, at least 95%, at least 96%, at least 97%, at least 98%, at least 99%, or 100% sequence identity to SEQ ID NO: 33; j) an RGN having at least 91%, at least 92%, at least 93%, at least 94%, at least 95%, at least 96%, at least 97%, at least 98%, at least 99%, or 100% sequence identity to SEQ ID NO: 10, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 22 and a tracrRNA having at least 91%, at least 92%, at least 93%, at least 94%, at least 95%, at least 96%, at least 97%, at least 98%, at least 99%, or 100% sequence identity to SEQ ID NO:34; k) an RGN having at least 91%, at least 92%, at least 93%, at least 94%, at least 95%, at least 96%, at least 97%, at least 98%, at least 99%, or 100% sequence identity to SEQ ID NO: 11, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 23 and a tracrRNA having at least 91%, at least 92%, at least 93%, at least 94%, at least 95%, at least 96%, at least 97%, at least 98%, at least 99%, or 100% sequence identity to SEQ ID NO: 35; and l) an RGN having at least 91%, at least 92%, at least 93%, at least 94%, at least 95%, at least 96%, at least 97%, at least 98%, at least 99%, or 100% sequence identity to SEQ ID NO: 12, a guide RNA comprising a crRNA repeat sequence having at least 91%, at least 92%, at least 93%, at least 94%, at least 95%, at least 96%, at least 97%, at least 98%, at least 99%, or 100% sequence identity to SEQ ID NO: 24 and a tracrRNA having at least 91%, at least 92%, at least 93%, at least 94%, at least 95%, at least 96%, at least 97%, at least 98%, at least 99%, or 100% sequence identity to SEQ ID NO: 36. In some embodiments, the RGN has at least 91%, at least 92%, at least 93%, at least 94%, at least 95%, at least 96%, at least 97%, at least 98%, at least 99%, or 100% sequence identity to SEQ ID NO: 6, the guide RNA comprises a crRNA repeat sequence having at least 91%, at least 92%, at least 93%, at least 94%, at least 95%, at least 96%, at least 97%, at least 98%, at least 99%, or 100% sequence identity to SEQ ID NO: 18 and the tracrRNA has at least 91%, at least 92%, at least 93%, at least 94%, at least 95%, at least 96%, at least 97%, at least 98%, at least 99%, or 100% sequence identity to SEQ ID NO: 30.

In some embodiments of the above aspect, the target DNA sequence is within a cell.

In some embodiments of the above aspect, the method further comprises culturing the cell under conditions in which the RGN polypeptide is expressed and cleaves and modifies the target DNA sequence to produce a DNA molecule comprising a modified target DNA sequence, and selecting a cell comprising the modified target DNA sequence.

In another aspect, the present disclosure provides a cell comprising a modified target DNA sequence according to the method described hereinabove.

In yet another aspect, the present disclosure provides a pharmaceutical composition comprising a cell described hereinabove and a pharmaceutically acceptable carrier.

In still another aspect, the present disclosure provides a method of treating a disease, disorder, or condition, comprising administering to a subject in need thereof an effective amount of a pharmaceutical composition described hereinabove.

In some embodiments of the above aspect, the disease is associated with a causal mutation and the effective amount of the pharmaceutical composition corrects or deletes the causal mutation.

In some embodiments of the above aspect, the subject is at risk of developing the disease, disorder, or condition.

In another aspect, the present disclosure provides a nucleic acid molecule comprising a CRISPR RNA (crRNA) or a polynucleotide encoding a crRNA, wherein the crRNA comprises a spacer sequence and a CRISPR repeat sequence, wherein the CRISPR repeat sequence comprises a nucleotide sequence having at least 90% sequence identity to any one of SEQ ID NOs: 13-24; wherein a guide RNA, comprising the crRNA and a trans-activating CRISPR RNA (tracrRNA) hybridized to the CRISPR repeat sequence of the crRNA, is capable of hybridizing to a target DNA sequence in a sequence specific manner through the spacer sequence of the crRNA when the guide RNA is bound to an RNA-guided nuclease (RGN) polypeptide. In some embodiments, the CRISPR repeat sequence comprises a nucleotide sequence having at least 90% sequence identity to SEQ ID NO: 18.

In some embodiments of the above aspect, the polynucleotide encoding a crRNA is operably linked to a promoter heterologous to the polynucleotide.

In some embodiments of the above aspect, the CRISPR repeat sequence comprises a nucleotide sequence having at least 91%, at least 92%, at least 93%, at least 94%, at least 95%, at least 96%, at least 97%, at least 98%, at least 99%, or 100% sequence identity to any one of SEQ ID NOs: 13-24. In some embodiments, the CRISPR repeat sequence comprises a nucleotide sequence having at least 91%, at least 92%, at least 93%, at least 94%, at least 95%, at least 96%, at least 97%, at least 98%, at least 99%, or 100% sequence identity to SEQ ID NO: 18.

In another aspect, the present disclosure provides a vector comprising a nucleic acid molecule comprising a polynucleotide encoding a crRNA described hereinabove.

In some embodiments of the above aspect, the vector further comprises a polynucleotide encoding the tracrRNA.

In some embodiments of the above aspect, the tracrRNA is selected from the group consisting of: a) a tracrRNA having at least 90% sequence identity to SEQ ID NO: 25, wherein the CRISPR repeat sequence has at least 90% sequence identity to SEQ ID NO: 13; b) a tracrRNA having at least 90% sequence identity to SEQ ID NO: 26, wherein the CRISPR repeat sequence has at least 90% sequence identity to SEQ ID NO: 14; c) a tracrRNA having at least 90% sequence identity to SEQ ID NO: 27, wherein the CRISPR repeat sequence has at least 90% sequence identity to SEQ ID NO: 15; d) a tracrRNA having at least 90% sequence identity to SEQ ID NO: 28, wherein the CRISPR repeat sequence has at least 90% sequence identity to SEQ ID NO: 16; e) a tracrRNA having at least 90% sequence identity to SEQ ID NO: 29, wherein the CRISPR repeat sequence has at least 90% sequence identity to SEQ ID NO: 17; f) a tracrRNA having at least 90% sequence identity to SEQ ID NO: 30, wherein the CRISPR repeat sequence has at least 90% sequence identity to SEQ ID NO: 18; g) a tracrRNA having at least 90% sequence identity to SEQ ID NO: 31, wherein the CRISPR repeat sequence has at least 90% sequence identity to SEQ ID NO: 19; h) a tracrRNA having at least 90% sequence identity to SEQ ID NO: 32, wherein the CRISPR repeat sequence has at least 90% sequence identity to SEQ ID NO: 20; i) a tracrRNA having at least 90% sequence identity to SEQ ID NO: 33, wherein the CRISPR repeat sequence has at least 90% sequence identity to SEQ ID NO: 21; j) a tracrRNA having at least 90% sequence identity to SEQ ID NO: 34, wherein the CRISPR repeat sequence has at least 90% sequence identity to SEQ ID NO: 22; k) a tracrRNA having at least 90% sequence identity to SEQ ID NO: 35, wherein the CRISPR repeat sequence has at least 90% sequence identity to SEQ ID NO: 23; and l) a tracrRNA having at least 90% sequence identity to SEQ ID NO: 36, wherein the CRISPR repeat sequence has at least 90% sequence identity to SEQ ID NO: 24. In some embodiments, the tracrRNA has at least 90% sequence identity to SEQ ID NO: 30 and the CRISPR repeat sequence has at least 90% sequence identity to SEQ ID NO: 18.

In some embodiments of the above aspect, the tracrRNA is selected from the group consisting of: a) a tracrRNA having at least 91%, at least 92%, at least 93%, at least 94%, at least 95%, at least 96%, at least 97%, at least 98%, at least 99%, or 100% sequence identity to SEQ ID NO: 25, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 13; b) a tracrRNA having at least 91%, at least 92%, at least 93%, at least 94%, at least 95%, at least 96%, at least 97%, at least 98%, at least 99%, or 100% sequence identity to SEQ ID NO: 26, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 14; c) a tracrRNA having at least 91%, at least 92%, at least 93%, at least 94%, at least 95%, at least 96%, at least 97%, at least 98%, at least 99%, or 100% sequence identity to SEQ ID NO: 27, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 15; d) a tracrRNA having at least 91%, at least 92%, at least 93%, at least 94%, at least 95%, at least 96%, at least 97%, at least 98%, at least 99%, or 100% sequence identity to SEQ ID NO: 28, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 16; e) a tracrRNA having at least 91%, at least 92%, at least 93%, at least 94%, at least 95%, at least 96%, at least 97%, at least 98%, at least 99%, or 100% sequence identity to SEQ ID NO: 29, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 17; f) a tracrRNA having at least 91%, at least 92%, at least 93%, at least 94%, at least 95%, at least 96%, at least 97%, at least 98%, at least 99%, or 100% sequence identity to SEQ ID NO: 30, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 18; g) a tracrRNA having at least 91%, at least 92%, at least 93%, at least 94%, at least 95%, at least 96%, at least 97%, at least 98%, at least 99%, or 100% sequence identity to SEQ ID NO: 31, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 19; h) a tracrRNA having at least 91%, at least 92%, at least 93%, at least 94%, at least 95%, at least 96%, at least 97%, at least 98%, at least 99%, or 100% sequence identity to SEQ ID NO: 32, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 20; i) a tracrRNA having at least 91%, at least 92%, at least 93%, at least 94%, at least 95%, at least 96%, at least 97%, at least 98%, at least 99%, or 100% sequence identity to SEQ ID NO: 33, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 21; j) a tracrRNA having at least 91%, at least 92%, at least 93%, at least 94%, at least 95%, at least 96%, at least 97%, at least 98%, at least 99%, or 100% sequence identity to SEQ ID NO: 34, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 22; k) a tracrRNA having at least 91%, at least 92%, at least 93%, at least 94%, at least 95%, at least 96%, at least 97%, at least 98%, at least 99%, or 100% sequence identity to SEQ ID NO: 35, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 23; and l) a tracrRNA having at least 91%, at least 92%, at least 93%, at least 94%, at least 95%, at least 96%, at least 97%, at least 98%, at least 99%, or 100% sequence identity to SEQ ID NO: 36, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 24. In some embodiments, the tracrRNA has 91%, at least 92%, at least 93%, at least 94%, at least 95%, at least 96%, at least 97%, at least 98%, at least 99%, or 100% sequence identity to SEQ ID NO: 30 and the CRISPR repeat sequence has 91%, at least 92%, at least 93%, at least 94%, at least 95%, at least 96%, at least 97%, at least 98%, at least 99%, or 100% sequence identity to SEQ ID NO: 18.

In some embodiments of the above aspect, the vector further comprises a polynucleotide encoding the RGN polypeptide.

In some embodiments of the above aspect, the RGN polypeptide is selected from the group consisting of: a) a RGN polypeptide having at least 90% sequence identity to SEQ ID NO: 1, wherein the CRISPR repeat sequence has at least 90% sequence identity to SEQ ID NO: 13 and the tracrRNA has at least 90% sequence identity to SEQ ID NO: 25; b) a RGN polypeptide having at least 90% sequence identity to SEQ ID NO: 2, wherein the CRISPR repeat sequence has at least 90% sequence identity to SEQ ID NO: 14 and the tracrRNA has at least 90% sequence identity to SEQ ID NO: 26; c) a RGN polypeptide having at least 90% sequence identity to SEQ ID NO: 3, wherein the CRISPR repeat sequence has at least 90% sequence identity to SEQ ID NO: 15 and the tracrRNA has at least 90% sequence identity to SEQ ID NO: 27; d) a RGN polypeptide having at least 90% sequence identity to SEQ ID NO: 4, wherein the CRISPR repeat sequence has at least 90% sequence identity to SEQ ID NO: 16 and the tracrRNA has at least 90% sequence identity to SEQ ID NO: 28; e) a RGN polypeptide having at least 90% sequence identity to SEQ ID NO: 5, wherein the CRISPR repeat sequence has at least 90% sequence identity to SEQ ID NO: 17 and the tracrRNA has at least 90% sequence identity to SEQ ID NO: 29; f) a RGN polypeptide having at least 90% sequence identity to SEQ ID NO: 6, wherein the CRISPR repeat sequence has at least 90% sequence identity to SEQ ID NO: 18 and the tracrRNA has at least 90% sequence identity to SEQ ID NO: 30; g) a RGN polypeptide having at least 90% sequence identity to SEQ ID NO: 7, wherein the CRISPR repeat sequence has at least 90% sequence identity to SEQ ID NO: 19 and the tracrRNA has at least 90% sequence identity to SEQ ID NO: 31; h) a RGN polypeptide having at least 90% sequence identity to SEQ ID NO: 8, wherein the CRISPR repeat sequence has at least 90% sequence identity to SEQ ID NO: 20 and the tracrRNA has at least 90% sequence identity to SEQ ID NO: 32; i) a RGN polypeptide having at least 90% sequence identity to SEQ ID NO: 9, wherein the CRISPR repeat sequence has at least 90% sequence identity to SEQ ID NO: 21 and the tracrRNA has at least 90% sequence identity to SEQ ID NO: 33; j) a RGN polypeptide having at least 90% sequence identity to SEQ ID NO: 10, wherein the CRISPR repeat sequence has at least 90% sequence identity to SEQ ID NO: 22 and the tracrRNA has at least 90% sequence identity to SEQ ID NO: 34; k) a RGN polypeptide having at least 90% sequence identity to SEQ ID NO: 11, wherein the CRISPR repeat sequence has at least 90% sequence identity to SEQ ID NO: 23 and the tracrRNA has at least 90% sequence identity to SEQ ID NO: 35; and l) a RGN polypeptide having at least 90% sequence identity to SEQ ID NO: 12, wherein the CRISPR repeat sequence has at least 90% sequence identity to SEQ ID NO: 24 and the tracrRNA has at least 90% sequence identity to SEQ ID NO: 36. In some embodiments, the RGN polypeptide has at least 90% sequence identity to SEQ ID NO: 6, the CRISPR repeat sequence has at least 90% sequence identity to SEQ ID NO: 18, and the tracrRNA has at least 90% sequence identity to SEQ ID NO: 30.

In some embodiments of the above aspect, the RGN polypeptide is selected from the group consisting of: a) a RGN polypeptide having at least 91%, at least 92%, at least 93%, at least 94%, at least 95%, at least 96%, at least 97%, at least 98%, at least 99%, or 100% sequence identity to SEQ ID NO: 1, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 13 and the tracrRNA has at least 91%, at least 92%, at least 93%, at least 94%, at least 95%, at least 96%, at least 97%, at least 98%, at least 99%, or 100% sequence identity to SEQ ID NO: 25; b) a RGN polypeptide having at least 91%, at least 92%, at least 93%, at least 94%, at least 95%, at least 96%, at least 97%, at least 98%, at least 99%, or 100% sequence identity to SEQ ID NO: 2, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 14 and the tracrRNA has at least 91%, at least 92%, at least 93%, at least 94%, at least 95%, at least 96%, at least 97%, at least 98%, at least 99%, or 100% sequence identity to SEQ ID NO: 26; c) a RGN polypeptide having at least 91%, at least 92%, at least 93%, at least 94%, at least 95%, at least 96%, at least 97%, at least 98%, at least 99%, or 100% sequence identity to SEQ ID NO: 3, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 15 and the tracrRNA has at least 91%, at least 92%, at least 93%, at least 94%, at least 95%, at least 96%, at least 97%, at least 98%, at least 99%, or 100% sequence identity to SEQ ID NO: 27; d) a RGN polypeptide having at least 91%, at least 92%, at least 93%, at least 94%, at least 95%, at least 96%, at least 97%, at least 98%, at least 99%, or 100% sequence identity to SEQ ID NO: 4, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 16 and the tracrRNA has at least 91%, at least 92%, at least 93%, at least 94%, at least 95%, at least 96%, at least 97%, at least 98%, at least 99%, or 100% sequence identity to SEQ ID NO: 28; e) a RGN polypeptide having at least 91%, at least 92%, at least 93%, at least 94%, at least 95%, at least 96%, at least 97%, at least 98%, at least 99%, or 100% sequence identity to SEQ ID NO: 5, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 17 and the tracrRNA has at least 91%, at least 92%, at least 93%, at least 94%, at least 95%, at least 96%, at least 97%, at least 98%, at least 99%, or 100% sequence identity to SEQ ID NO: 29; f) a RGN polypeptide having at least 91%, at least 92%, at least 93%, at least 94%, at least 95%, at least 96%, at least 97%, at least 98%, at least 99%, or 100% sequence identity to SEQ ID NO: 6, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 18 and the tracrRNA has at least 91%, at least 92%, at least 93%, at least 94%, at least 95%, at least 96%, at least 97%, at least 98%, at least 99%, or 100% sequence identity to SEQ ID NO: 30; g) a RGN polypeptide having at least 91%, at least 92%, at least 93%, at least 94%, at least 95%, at least 96%, at least 97%, at least 98%, at least 99%, or 100% sequence identity to SEQ ID NO: 7, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 19 and the tracrRNA has at least 91%, at least 92%, at least 93%, at least 94%, at least 95%, at least 96%, at least 97%, at least 98%, at least 99%, or 100% sequence identity to SEQ ID NO: 31; h) a RGN polypeptide having at least 91%, at least 92%, at least 93%, at least 94%, at least 95%, at least 96%, at least 97%, at least 98%, at least 99%, or 100% sequence identity to SEQ ID NO: 8, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 20 and the tracrRNA has at least 91%, at least 92%, at least 93%, at least 94%, at least 95%, at least 96%, at least 97%, at least 98%, at least 99%, or 100% sequence identity to SEQ ID NO: 32; i) a RGN polypeptide having at least 91%, at least 92%, at least 93%, at least 94%, at least 95%, at least 96%, at least 97%, at least 98%, at least 99%, or 100% sequence identity to SEQ ID NO: 9, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 21 and the tracrRNA has at least 91%, at least 92%, at least 93%, at least 94%, at least 95%, at least 96%, at least 97%, at least 98%, at least 99%, or 100% sequence identity to SEQ ID NO: 33; j) a RGN polypeptide having at least 91%, at least 92%, at least 93%, at least 94%, at least 95%, at least 96%, at least 97%, at least 98%, at least 99%, or 100% sequence identity to SEQ ID NO: 10, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 22 and the tracrRNA has at least 91%, at least 92%, at least 93%, at least 94%, at least 95%, at least 96%, at least 97%, at least 98%, at least 99%, or 100% sequence identity to SEQ ID NO: 34; k) a RGN polypeptide having at least 91%, at least 92%, at least 93%, at least 94%, at least 95%, at least 96%, at least 97%, at least 98%, at least 99%, or 100% sequence identity to SEQ ID NO: 11, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 23 and the tracrRNA has at least 91%, at least 92%, at least 93%, at least 94%, at least 95%, at least 96%, at least 97%, at least 98%, at least 99%, or 100% sequence identity to SEQ ID NO: 35; and l) a RGN polypeptide having at least 91%, at least 92%, at least 93%, at least 94%, at least 95%, at least 96%, at least 97%, at least 98%, at least 99%, or 100% sequence identity to SEQ ID NO: 12, wherein the CRISPR repeat sequence has at least 91%, at least 92%, at least 93%, at least 94%, at least 95%, at least 96%, at least 97%, at least 98%, at least 99%, or 100% sequence identity to SEQ ID NO: 24 and the tracrRNA has at least 91%, at least 92%, at least 93%, at least 94%, at least 95%, at least 96%, at least 97%, at least 98%, at least 99%, or 100% sequence identity to SEQ ID NO: 36. In some embodiments, the RGN polypeptide has at least 91%, at least 92%, at least 93%, at least 94%, at least 95%, at least 96%, at least 97%, at least 98%, at least 99%, or 100% sequence identity to SEQ ID NO: 6, the CRISPR repeat sequence has 91%, at least 92%, at least 93%, at least 94%, at least 95%, at least 96%, at least 97%, at least 98%, at least 99%, or 100% sequence identity to SEQ ID NO: 18, and the tracrRNA has 91%, at least 92%, at least 93%, at least 94%, at least 95%, at least 96%, at least 97%, at least 98%, at least 99%, or 100% sequence identity to SEQ ID NO: 30.

In another aspect, the present disclosure provides a nucleic acid molecule comprising a trans-activating CRISPR RNA (tracrRNA), or a polynucleotide encoding a tracrRNA comprising a nucleotide sequence having at least 90% sequence identity to any one of SEQ ID NOs: 25-36; wherein a guide RNA, comprising the tracrRNA and a crRNA comprising a spacer sequence and a CRISPR repeat sequence, wherein the tracrRNA hybridizes with the CRISPR repeat sequence of the crRNA, is capable of hybridizing to a target DNA sequence in a sequence specific manner through the spacer sequence of the crRNA when the guide RNA is bound to an RNA-guided nuclease (RGN) polypeptide. In some embodiments, the tracrRNA comprises a nucleotide sequence having at least 90% sequence identity to SEQ ID NO: 30.

In some embodiments of the above aspect, the polynucleotide encoding a tracrRNA is operably linked to a promoter heterologous to the polynucleotide.

In some embodiments of the above aspect, the tracrRNA comprises a nucleotide sequence having at least 91%, at least 92%, at least 93%, at least 94%, at least 95%, at least 96%, at least 97%, at least 98%, at least 99%, or 100% sequence identity to any one of SEQ ID NOs: 25-36. In some embodiments, the tracrRNA comprises a nucleotide sequence having at least 91%, at least 92%, at least 93%, at least 94%, at least 95%, at least 96%, at least 97%, at least 98%, at least 99%, or 100% sequence identity to SEQ ID NO: 30.

In another aspect, the present disclosure provides a vector comprising a nucleic acid molecule comprising a polynucleotide encoding a tracrRNA described hereinabove.

In yet another aspect, the present disclosure provides a single guide RNA comprising a nucleic acid molecule comprising a crRNA described hereinabove and a nucleic acid molecule comprising a tracrRNA described hereinabove.

In still another aspect, the present disclosure provides a double guide RNA comprising a nucleic acid molecule comprising a crRNA described hereinabove and a nucleic acid molecule comprising a tracrRNA described hereinabove.

In another aspect, the present disclosure provides a cell comprising a nucleic acid molecule, a single guide RNA, a double guide RNA, or a vector described hereinabove.

BRIEF DESCRIPTION OF THE FIGURES

FIG. 3B demonstrates dose dependence of increased editing activity with increasing amounts of RNPs comprising sgRNAs with two different spacer lengths (20 or 25 nucleotides).

DETAILED DESCRIPTION

Figure 1:
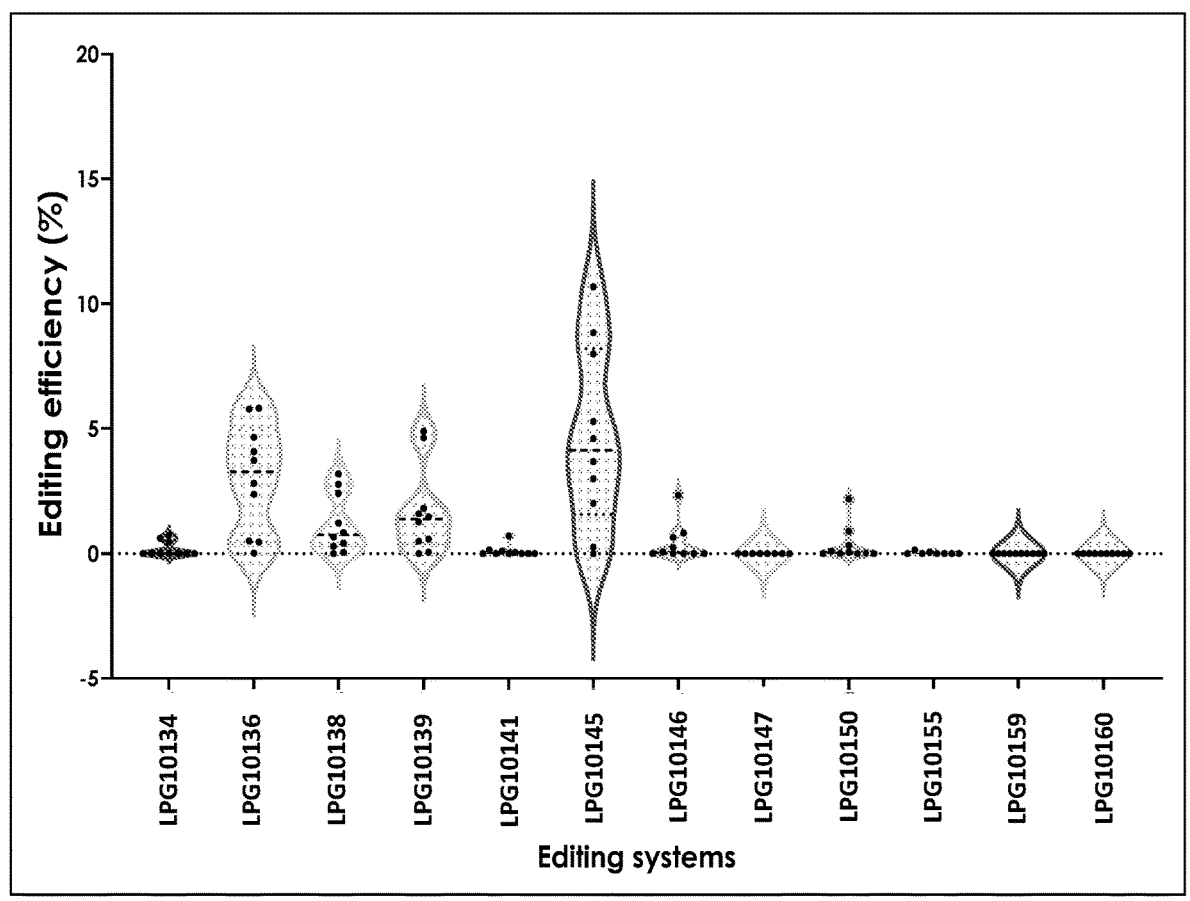
FIG. 1 provides the editing rates of LPG10134, LPG10136, LPG10138, LPG10139, LPG10141, LPG10145, LPG10146, LPG10147, LPG10150, LPG10155, LPG10159, and LPG10160 on multiple genes. Plasmids comprising expression cassettes for RGNs and guide RNAs were co-transfected into HEK293T cells.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

I. Overview

RNA-guided nucleases (RGNs) allow for the targeted manipulation of specific site(s) within a genome and are useful in the context of gene targeting for therapeutic and research applications. In a variety of organisms, including mammals, RNA-guided nucleases have been used for genome engineering by stimulating non-homologous end joining and homologous recombination, for example. The compositions and methods described herein are useful for creating single- or double-stranded breaks in polynucleotides, modifying polynucleotides, detecting a particular site within a polynucleotide, or modifying the expression of a particular gene.

The RNA-guided nucleases disclosed herein can alter gene expression by modifying a target sequence. In specific embodiments, the RNA-guided nucleases are directed to the target sequence by a guide RNA (gRNA) as part of a Clustered Regularly Interspaced Short Palindromic Repeats (CRISPR) RNA-guided nuclease system. The RGNs are considered "RNA-guided" because guide RNAs form a complex with the RNA-guided nucleases to direct the RNA-guided nuclease to bind to a target sequence and in some embodiments, introduce a single-stranded or double-stranded break at the target sequence. After the target sequence has been cleaved, the break can be repaired such that the DNA sequence of the target sequence is modified during the repair process. Thus, provided herein are methods for using the RNA-guided nucleases to modify a target sequence in the DNA of host cells. For example, RNA-guided nucleases can be used to modify a target sequence at a genomic locus of eukaryotic cells or prokaryotic cells.

II. RNA-Guided Nucleases

Provided herein are RNA-guided nucleases. The term RNA-guided nuclease (RGN) refers to a polypeptide that binds to a particular target nucleotide sequence in a sequence-specific manner and is directed to the target nucleotide sequence by a guide RNA molecule that is complexed with the polypeptide and hybridizes with the target sequence. Although an RNA-guided nuclease can be capable of cleaving the target sequence upon binding, the term RNA-guided nuclease also encompasses nuclease-dead RNA-guided nucleases that are capable of binding to, but not cleaving, a target sequence. Cleavage of a target sequence by an RNA-guided nuclease can result in a single- or double-stranded break. RNA-guided nucleases only capable of cleaving a single strand of a double-stranded nucleic acid molecule are referred to herein as nickases.

The RNA-guided nucleases disclosed herein include the LPG10134, LPG10136, LPG10138, LPG10139, LPG10141, LPG10145, LPG10146, LPG10147, LPG10150, LPG10155, LPG10159, and LPG10160 RNA-guided nucleases, the amino acid sequences of which are set forth, respectively, as SEQ ID NOs: 1-12, and active fragments or variants thereof that retain the ability to bind to a target nucleotide sequence in an RNA-guided sequence-specific manner. In some of these embodiments, the active fragment or variant of the LPG10134, LPG10136, LPG10138, LPG10139, LPG10141, LPG10145, LPG10146, LPG10147, LPG10150, LPG10155, LPG10159, or LPG10160 RGN is capable of cleaving a single- or double-stranded target sequence. In some embodiments, an active variant of the LPG10134, LPG10136, LPG10138, LPG10139, LPG10141, LPG10145, LPG10146, LPG10147, LPG10150, LPG10155, LPG10159, or LPG10160 RGN comprises an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth as any one of SEQ ID NOs: 1-12. In certain embodiments, an active fragment of the LPG10134, LPG10136, LPG10138, LPG10139, LPG10141, LPG10145, LPG10146, LPG10147, LPG10150, LPG10155, LPG10159, or LPG10160 RGN comprises at least 50, 100, 150, 200, 250, 300, 350, 400, 450, 500, 550, 600, 650, 700, 750, 800, 850, 900, 950, 1000, 1050 or more contiguous amino acid residues of the amino acid sequence set forth as any one of SEQ ID NOs: 1-12. RNA-guided nucleases provided herein can comprise at least one nuclease domain (e.g., DNase, RNase domain) and at least one RNA recognition and/or RNA binding domain to interact with guide RNAs. Further domains that can be found in RNA-guided nucleases provided herein include, but are not limited to: DNA binding domains, helicase domains, protein-protein interaction domains, and dimerization domains. In specific embodiments, the RNA-guided nucleases provided herein can comprise at least 70%, 75%, 80%, 85%, 90%, 91%, 92%, 93%, 94%, 95%, 96%, 97%, 98%, 99% or more sequence identity to one or more of a DNA binding domain, helicase domain, protein-protein interaction domain, and dimerization domain.

A target nucleotide sequence is bound by an RNA-guided nuclease provided herein and hybridizes with the guide RNA associated with the RNA-guided nuclease. The target sequence can then be subsequently cleaved by the RNA-guided nuclease if the polypeptide possesses nuclease activity. The terms "cleave" or "cleavage" refer to the hydrolysis of at least one phosphodiester bond within the backbone of a target nucleotide sequence that can result in either single-stranded or double-stranded breaks within the target sequence. The presently disclosed RGNs can cleave nucleotides within a polynucleotide, functioning as an endonuclease or can be an exonuclease, removing successive nucleotides from the end (the 5' and/or the 3' end) of a polynucleotide. In other embodiments, the disclosed RGNs can cleave nucleotides of a target sequence within any position of a polynucleotide and thus function as both an endonuclease and exonuclease. The cleavage of a target polynucleotide by the presently disclosed RGNs can result in staggered breaks or blunt ends.

The presently disclosed RNA-guided nucleases can be wild-type sequences derived from bacterial or archaeal species. Alternatively, the RNA-guided nucleases can be variants or fragments of wild-type polypeptides. The wild-type RGN can be modified to alter nuclease activity or alter PAM specificity, for example. In some embodiments, the RNA-guided nuclease is not naturally-occurring.

In certain embodiments, the RNA-guided nuclease functions as a nickase, only cleaving a single strand of the target nucleotide sequence. Such RNA-guided nucleases have a single functioning nuclease domain. In particular embodiments, the nickase is capable of cleaving the positive strand or negative strand. In some of these embodiments, additional nuclease domains have been mutated such that the nuclease activity is reduced or eliminated.

In other embodiments, the RNA-guided nuclease lacks nuclease activity altogether and is referred to herein as nuclease-dead or nuclease inactive. Any method known in the art for introducing mutations into an amino acid sequence, such as PCR-mediated mutagenesis and site-directed mutagenesis, can be used for generating nickases or nuclease-dead RGNs. See, e.g., U.S. Publ. No. 2014/0068797 and U.S. Pat. No. 9,790,490; each of which is incorporated by reference in its entirety. A non-limiting example of a nickase is the LPG10145 D16A nickase, which is set forth herein as SEQ ID NO: 551. Nickases which comprise a mutation in the RuvC domain and have a functional HNH domain are useful in base editing wherein the nickase is fused to a base editing polypeptide such as a deaminase. Another non-limiting example of a nickase is the LPG10145 H611A nickase, which is set forth herein as SEQ ID NO: 552. Nickases which comprise a mutation in the HNH domain and have a functional RuvC domain are useful in prime editing wherein the nickase is fused to a prime editing polypeptide such as a reverse transcriptase. A non-limiting example of a nuclease dead RGN is the LPG10145 D16A H611A sequence set forth as SEQ ID NO: 553.

RNA-guided nucleases that lack nuclease activity can be used to deliver a fused polypeptide, polynucleotide, or small molecule payload to a particular genomic location. In some of these embodiments, the RGN polypeptide or guide RNA can be fused to a detectable label to allow for detection of a particular sequence. As a non-limiting example, a nuclease-dead RGN can be fused to a detectable label (e.g., fluorescent protein) and targeted to a particular sequence associated with a disease to allow for detection of the disease-associated sequence.

Alternatively, nuclease-dead RGNs can be targeted to particular genomic locations to alter the expression of a desired sequence. In some embodiments, the binding of a nuclease-dead RNA-guided nuclease to a target sequence results in the reduction in expression of the target sequence or a gene under transcriptional control by the target sequence by interfering with the binding of RNA polymerase or transcription factors within the targeted genomic region. In other embodiments, the RGN (e.g., a nuclease-dead RGN) or its complexed guide RNA further comprises an expression modulator that, upon binding to a target sequence, serves to either repress or activate the expression of the target sequence or a gene under transcriptional control by the target sequence. In some of these embodiments, the expression modulator modulates the expression of the target sequence or regulated gene through epigenetic mechanisms.

In other embodiments, the nuclease-dead RGNs or an RGN with nickase activity can be targeted to particular genomic locations to modify the sequence of a target polynucleotide through fusion to a base-editing polypeptide, for example a deaminase polypeptide or active variant or fragment thereof, that directly chemically modifies (e.g., deaminates) a nucleobase, resulting in conversion from one nucleobase to another. The base-editing polypeptide can be fused to the RGN at its N-terminal or C-terminal end. Additionally, the base-editing polypeptide may be fused to the RGN via a peptide linker. A non-limiting example of a deaminase polypeptide that is useful for such compositions and methods includes a cytosine deaminase or an adenine deaminase (such as the adenine deaminase base editor described in Gaudelli et al. (2017) Nature 551:464-471, U.S. Publ. Nos. 2017/0121693 and 2018/0073012, and International Publ. No. WO 2018/027078, or any of the deaminases disclosed in International Publ. No. WO 2020/139873, U.S. Provisional Appl. Nos. 63/077,089 filed Sep. 11, 2020, 63/146,840 filed Feb. 8, 2021, and 63/164,273 filed Mar. 22, 2021, and International Appl. No. PCT/US2021/049853 filed Sep. 10, 2021, each of which is herein incorporated by reference in its entirety). In one embodiment, the deaminase polypeptide that is useful for such compositions and methods is a cytosine deaminase or an adenine deaminase comprising an amino acid sequence selected from any one of SEQ ID NOs: 377-448. In one embodiment, the deaminase polypeptide that is useful for such compositions and methods is a cytosine deaminase or an adenine deaminase having a sequence that is at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to any one of the amino acid sequences set forth as SEQ ID NOs: 377-448. In some embodiments, the deaminase polypeptide that is useful for such the presently disclosed compositions and methods is a deaminase disclosed in Table 17 of International Publ. No. WO 2020/139873, which is incorporated herein by reference in its entirety. Further, it is known in the art that certain fusion proteins between an RGN and a base-editing enzyme (e.g., cytosine deaminase) may also comprise at least one uracil stabilizing polypeptide that increases the mutation rate of a cytidine, deoxycytidine, or cytosine to a thymidine, deoxythymidine, or thymine in a nucleic acid molecule by a deaminase. Non-limiting examples of uracil stabilizing polypeptides include those disclosed in U.S. Provisional Appl. No. 63/052,175, filed Jul. 15, 2020, and International Appl. No. PCT/US2021/041809, filed Jul. 15, 2021 (each of which is herein incorporated by reference in its entirety), including USP2 (SEQ ID NO: 325), and a uracil glycosylase inhibitor (UGI) domain (SEQ ID NO: 315), which may increase base editing efficiency. Therefore, a fusion protein may comprise an RGN described herein or variant thereof, a deaminase, and optionally at least one uracil stabilizing polypeptide, such as UGI or USP2. In certain embodiments, the RGN that is fused to the base-editing polypeptide is a nickase that cleaves the DNA strand that is not acted upon by the base-editing polypeptide (e.g., deaminase).

In some embodiments, an RGN may be fused to a prime editing polypeptide. Prime editing is a versatile and precise genome editing method that directly writes new genetic information into a specified DNA site using a nucleic acid programmable DNA binding protein working in association with a polymerase. The prime editing system uses an RGN that is a nickase, and the system is programmed with a prime editing (PE) guide RNA ("PERNA"). The PEgRNA is a guide RNA that both specifies the target sequence and provides the template for polymerization of the replacement strand containing the edit by way of an extension engineered onto the guide RNA (e.g., at the 5' or 3' end, or at an internal portion of the guide RNA). The RGN nickase/prime editing polypeptide fusion is guided to the target sequence by the PEgRNA and nicks the target strand upstream of sequence to be edited and upstream of the PAM, creating a 3' flap on the target strand. The pegRNA includes a primer binding site (PBS) that is complementary to the 3' flap of the target strand. In some embodiments, a PBS is at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In certain embodiments, the pegRNA comprises a PBS that is at least 5 (e.g., at least 5, 6, 7, 8, 9, 10, 11, 12, 13, 14, 15, 16, 17, 28, 19, or 20) nucleotides in length. In some embodiments, the pegRNA may comprise a PBS that is at least 8 nucleotides in length. Hybridization of the PBS and 3' flap of the target strand allows polymerization of the replacement strand containing the edit using the extension of the PERNA as template. The extension of the PEgRNA can be formed from RNA or DNA. In the case of an RNA extension, the polymerase of the prime editor can be an RNA-dependent DNA polymerase (such as a reverse transcriptase). In the case of a DNA extension, the polymerase of the prime editor may be a DNA-dependent DNA polymerase.

The replacement strand containing the desired edit (e.g., a single nucleobase substitution) shares the same sequence as the target strand of the target sequence to be edited (with the exception that it includes the desired edit). Through DNA repair and/or replication machinery, the target strand of the target sequence is replaced by the newly synthesized replacement strand containing the desired edit. In some cases, prime editing may be thought of as a "search-and-replace" genome editing technology since the prime editors not only search and locate the desired target sequence to be edited, but at the same time, encode a replacement strand containing a desired edit which is installed in place of the corresponding target strand of the target sequence. Thus, in some embodiments, a guide RNA of the disclosure comprises an extension comprising an edit template for prime editing. In some embodiments, a prime editing polypeptide that can be fused to an RGN includes a DNA polymerase. In certain embodiments, the DNA polymerase is a reverse transcriptase. In certain embodiments, the RGN is a nickase.

RNA-guided nucleases that are fused to a polypeptide or domain can be separated or joined by a linker. The term "linker," as used herein, refers to a chemical group or a molecule linking two molecules or moieties, e.g., a binding domain and a cleavage domain of a nuclease. In some embodiments, a linker joins a gRNA binding domain of an RNA guided nuclease and a base-editing polypeptide, such as a deaminase. In some embodiments, a linker joins a nuclease-dead RGN and a deaminase. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The presently disclosed RNA-guided nucleases can comprise at least one nuclear localization signal (NLS) to enhance transport of the RGN to the nucleus of a cell. Nuclear localization signals are known in the art and generally comprise a stretch of basic amino acids (see, e.g., Lange et al., *J. Biol. Chem.* (2007) 282:5101-5105). In some embodiments, the RGN comprises 2, 3, 4, 5, 6 or more nuclear localization signals. The nuclear localization signal(s) can be a heterologous NLS. Non-limiting examples of nuclear localization signals useful for the presently disclosed RGNs are the nuclear localization signals of SV40 Large T-antigen, nucleoplasmin, and c-Myc (see, e.g., Ray et al. (2015) *Bioconjug Chem* 26 (6): 1004-7). In particular embodiments, the RGN comprises the NLS sequence set forth as SEQ ID NO: 316 or 317. The RGN can comprise one or more NLS sequences at its N-terminus, C-terminus, or both the N-terminus and C-terminus. For example, the RGN can comprise two NLS sequences at the N-terminal region and four NLS sequences at the C-terminal region.

Other localization signal sequences known in the art that localize polypeptides to particular subcellular location(s) can also be used to target the RGNs, including, but not limited to, plastid localization sequences, mitochondrial localization sequences, and dual-targeting signal sequences that target to both the plastid and mitochondria (see, e.g., Nassoury and Morse (2005) *Biochim Biophys Acta* 1743:5-19; Kunze and Berger (2015) *Front Physiol* dx.doi.org/10.3389/fphys.2015.00259; Herrmann and Neupert (2003) *IUBMB Life* 55:219-225; Soll (2002) *Curr Opin Plant Biol* 5:529-535; Carrie and Small (2013) *Biochim Biophys Acta* 1833:253-259; Carrie et al. (2009) *FEBS J* 276:1187-1195; Silva-Filho (2003) *Curr Opin Plant Biol* 6:589-595; Peeters and Small (2001) *Biochim Biophys Acta* 1541:54-63; Murcha et al. (2014) *J Exp Bot* 65:6301-6335; Mackenzie (2005) *Trends Cell Biol* 15:548-554; Glaser et al. (1998) *Plant Mol Biol* 38:311-338).

In certain embodiments, the presently disclosed RNA-guided nucleases comprise at least one cell-penetrating domain that facilitates cellular uptake of the RGN. Cell-penetrating domains are known in the art and generally comprise stretches of positively charged amino acid residues (i.e., polycationic cell-penetrating domains), alternating polar amino acid residues and non-polar amino acid residues (i.e., amphipathic cell-penetrating domains), or hydrophobic amino acid residues (i.e., hydrophobic cell-penetrating domains) (see, e.g., Milletti F. (2012) *Drug Discov Today* 17:850-860). A non-limiting example of a cell-penetrating domain is the trans-activating transcriptional activator (TAT) from the human immunodeficiency virus 1.

The nuclear localization signal, plastid localization signal, mitochondrial localization signal, dual-targeting localization signal, and/or cell-penetrating domain can be located at the amino-terminus (N-terminus), the carboxyl-terminus (C-terminus), or in an internal location of the RNA-guided nuclease.

The presently disclosed RGNs can be fused to an effector domain, such as a cleavage domain, a deaminase domain, or an expression modulator domain, either directly or indirectly via a linker peptide. Such a domain can be located at the N-terminus, the C-terminus, or an internal location of the RNA-guided nuclease. In some of these embodiments, the RGN component of the fusion protein is a nuclease-dead RGN or a nickase.

In some embodiments, the RGN fusion protein comprises a cleavage domain, which is any domain that is capable of cleaving a polynucleotide (i.e., RNA, DNA, or RNA/DNA hybrid) and includes, but is not limited to, restriction endonucleases and homing endonucleases, such as Type IIS endonucleases (e.g., FokI) (see, e.g., Belfort et al. (1997) *Nucleic Acids Res.* 25:3379-3388; Linn et al. (eds.) Nucleases, Cold Spring Harbor Laboratory Press, 1993).

In other embodiments, the RGN fusion protein comprises a deaminase domain that deaminates a nucleobase, resulting in conversion from one nucleobase to another, and includes, but is not limited to, a cytosine deaminase or an adenine deaminase (see, e.g., Gaudelli et al. (2017) Nature 551:464-471, U.S. Publ. Nos. 2017/0121693 and 2018/0073012, U.S. Pat. No. 9,840,699, and International Publ. No. WO/2018/027078, or any of the deaminases disclosed in International Publ. No. WO 2020/139873, U.S. Provisional Appl. Nos. 63/077,089 filed Sep. 11, 2020, 63/146,840 filed Feb. 8, 2021, and 63/164,273 filed Mar. 22, 2021, and International Appl. No. PCT/US2021/049853 filed Sep. 10, 2021, each of which is herein incorporated by reference in its entirety).

In some embodiments, the effector domain of the RGN fusion protein can be an expression modulator domain, which is a domain that either serves to upregulate or downregulate transcription. The expression modulator domain can be an epigenetic modification domain, a transcriptional repressor domain or a transcriptional activation domain.

In some of these embodiments, the expression modulator of the RGN fusion protein comprises an epigenetic modification domain that covalently modifies DNA or histone proteins to alter histone structure and/or chromosomal structure without altering the DNA sequence, leading to changes in gene expression (i.e., upregulation or downregulation). Non-limiting examples of epigenetic modifications include acetylation or methylation of lysine residues, arginine methylation, serine and threonine phosphorylation, and lysine ubiquitination and sumoylation of histone proteins, and methylation and hydroxymethylation of cytosine residues in DNA. Non-limiting examples of epigenetic modification domains include histone acetyltransferase domains, histone deacetylase domains, histone methyltransferase domains, histone demethylase domains, DNA methyltransferase domains, and DNA demethylase domains.

In other embodiments, the expression modulator of the fusion protein comprises a transcriptional repressor domain, which interacts with transcriptional control elements and/or transcriptional regulatory proteins, such as RNA polymerases and transcription factors, to reduce or terminate transcription of at least one gene. Transcriptional repressor domains are known in the art and include, but are not limited to, Sp1-like repressors, IκB, and Krüppel associated box (KRAB) domains.

In yet other embodiments, the expression modulator of the fusion protein comprises a transcriptional activation domain, which interacts with transcriptional control elements and/or transcriptional regulatory proteins, such as RNA polymerases and transcription factors, to increase or activate transcription of at least one gene. Transcriptional activation domains are known in the art and include, but are not limited to, a herpes simplex virus VP16 activation domain and an NFAT activation domain.

The presently disclosed RGN polypeptides can comprise a detectable label or a purification tag. The detectable label or purification tag can be located at the N-terminus, the C-terminus, or an internal location of the RNA-guided nuclease, either directly or indirectly via a linker peptide. In some of these embodiments, the RGN component of the fusion protein is a nuclease-dead RGN. In other embodiments, the RGN component of the fusion protein is an RGN with nickase activity.

A detectable label is a molecule that can be visualized or otherwise observed. The detectable label may be fused to the RGN as a fusion protein (e.g., fluorescent protein) or may be a small molecule conjugated to the RGN polypeptide that can be detected visually or by other means. Detectable labels that can be fused to the presently disclosed RGNs as a fusion protein include any detectable protein domain, including but not limited to, a fluorescent protein or a protein domain that can be detected with a specific antibody. Non-limiting examples of fluorescent proteins include green fluorescent proteins (e.g., GFP, EGFP, ZsGreen1) and yellow fluorescent proteins (e.g., YFP, EYFP, Zs Yellow1). Non-limiting examples of small molecule detectable labels include radioactive labels, such as $^3$H and $^{35}$S.

RGN polypeptides can also comprise a purification tag, which is any molecule that can be utilized to isolate a protein or fused protein from a mixture (e.g., biological sample, culture medium). Non-limiting examples of purification tags include biotin, myc, maltose binding protein (MBP), glutathione-S-transferase (GST), and 3×FLAG tag.

III. Guide RNA

The present disclosure provides guide RNAs and polynucleotides encoding the same. The term "guide RNA" refers to a nucleotide sequence having sufficient complementarity with a target nucleotide sequence to hybridize with the target sequence and direct sequence-specific binding of an associated RNA-guided nuclease to the target nucleotide sequence. Thus, an RGN's respective guide RNA is one or more RNA molecules (generally, one or two), that can bind to the RGN and guide the RGN to bind to a particular target nucleotide sequence, and in those embodiments wherein the RGN has nickase or nuclease activity, also cleave the target nucleotide sequence. In general, a guide RNA comprises a CRISPR RNA (crRNA) and a trans-activating CRISPR RNA (tracrRNA). Native guide RNAs that comprise both a crRNA and a tracrRNA generally comprise two separate RNA molecules that hybridize to each other through the repeat sequence of the crRNA and the anti-repeat sequence of the tracrRNA.

Native direct repeat sequences within a CRISPR array generally range in length from 28 to 37 base pairs, although the length can vary between about 23 bp to about 55 bp. Spacer sequences within a CRISPR array generally range from about 32 to about 38 bp in length, although the length can be between about 21 bp to about 72 bp. Each CRISPR array generally comprises less than 50 units of the CRISPR repeat-spacer sequence. The CRISPRs are transcribed as part of a long transcript termed the primary CRISPR transcript, which comprises much of the CRISPR array. The primary CRISPR transcript is cleaved by Cas proteins to produce crRNAs or in some cases, to produce pre-crRNAs that are further processed by additional Cas proteins into mature crRNAs. Mature crRNAs comprise a spacer sequence and a CRISPR repeat sequence. In some embodiments in which pre-crRNAs are processed into mature (or processed) crRNAs, maturation involves the removal of about one to about six or more 5', 3', or 5' and 3' nucleotides. For the purposes of genome editing or targeting a particular target nucleotide sequence of interest, these nucleotides that are removed during maturation of the pre-crRNA molecule are not necessary for generating or designing a guide RNA.

A CRISPR RNA (crRNA) comprises a spacer sequence and a CRISPR repeat sequence. The "spacer sequence" is the nucleotide sequence that directly hybridizes with the target nucleotide sequence of interest. The spacer sequence is engineered to be fully or partially complementary with the target sequence of interest. In various embodiments, the spacer sequence can comprise from about 8 nucleotides to about 30 nucleotides, or more. For example, the spacer sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the spacer sequence is 8, 9, 10, 11, 12, 13, 14, 15, 16, 17, 18, 19, 20, 21, 22, 23, 24, 25, 26, 27, 28, 29, 30, or more nucleotides in length. In some embodiments, the spacer sequence is about 10 to about 26 nucleotides in length, or about 12 to about 30 nucleotides in length. In some embodiments, the spacer sequence is 19-27 nucleotides in length. In certain embodiments, particularly when the RGN has the amino acid sequence set forth as SEQ ID NO: 6 or an active variant or fragment thereof, the spacer sequence is 21-24 nucleotides in length. In particular embodiments, the spacer sequence is about 30 nucleotides in length. In some embodiments, the spacer sequence is 30 nucleotides in length. In some embodiments, the degree of complementarity between a spacer sequence and its corresponding target sequence, when optimally aligned using a suitable alignment algorithm, is between 50% and 99% or more, including but not limited to about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the degree of complementarity between a spacer sequence and its corresponding target sequence, when optimally aligned using a suitable alignment algorithm, is 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more. In particular embodiments, the spacer sequence is free of secondary structure, which can be predicted using any suitable polynucleotide folding algorithm known in the art, including but not limited to mFold (see, e.g., Zuker and Stiegler (1981) *Nucleic Acids Res.* 9: 133-148) and RNAfold (see, e.g., Gruber et al. (2008) *Cell* 106 (1): 23-24).

The CRISPR RNA repeat sequence comprises a nucleotide sequence that forms a structure, either on its own or in concert with a hybridized tracrRNA, that is recognized by the RGN molecule. In various embodiments, the CRISPR RNA repeat sequence can comprise from about 8 nucleotides to about 30 nucleotides, or more. For example, the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In particular embodiments, the CRISPR repeat sequence is 8, 9, 10, 11, 12, 13, 14, 15, 16, 17, 18, 19, 20, 21, 22, 23, 24, 25, 26, 27, 28, 29, 30, or more nucleotides in length. In some embodiments, the degree of complementarity between a CRISPR repeat sequence and its corresponding tracrRNA sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the degree of complementarity between a CRISPR repeat sequence and its corresponding tracrRNA sequence, when optimally aligned using a suitable alignment algorithm, is 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more.

In particular embodiments, the CRISPR repeat sequence comprises the nucleotide sequence of any one of SEQ ID NOs: 13-24, or an active variant or fragment thereof that when comprised within a guide RNA, is capable of directing the sequence-specific binding of an associated RNA-guided nuclease provided herein to a target sequence of interest. In certain embodiments, an active CRISPR repeat sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of the nucleotide sequences set forth as SEQ ID NOS: 13-24.

In certain embodiments, an active CRISPR repeat sequence fragment of a wild-type sequence comprises at least 5, 6, 7, 8, 9, 10, 11, 12, 13, 14, 15, 16, 17, 18, 19, 20, 21, or 22 contiguous nucleotides of any one of the nucleotide sequences set forth as SEQ ID NOs: 13-24.

In certain embodiments, the crRNA is not naturally-occurring. In some of these embodiments, the specific CRISPR repeat sequence is not linked to the engineered spacer sequence in nature and the CRISPR repeat sequence is considered heterologous to the spacer sequence. In certain embodiments, the spacer sequence is an engineered sequence that is not naturally occurring.

A trans-activating CRISPR RNA or tracrRNA molecule comprises a nucleotide sequence comprising a region that has sufficient complementarity to hybridize to a CRISPR repeat sequence of a crRNA, which is referred to herein as the anti-repeat region. In some embodiments, the tracrRNA molecule further comprises a region with secondary structure (e.g., stem-loop) or forms secondary structure upon hybridizing with its corresponding crRNA. In particular embodiments, the region of the tracrRNA that is fully or partially complementary to a CRISPR repeat sequence is at the 5' end of the molecule and the 3' end of the tracrRNA comprises secondary structure. This region of secondary structure generally comprises several hairpin structures, including the nexus hairpin, which is found adjacent to the anti-repeat sequence. The nexus forms the core of the interactions between the guide RNA and the RGN, and is at the intersection between the guide RNA, the RGN, and the target DNA. The nexus hairpin often has a conserved nucleotide sequence in the base of the hairpin stem, with the motif UNANNC (SEQ ID NO: 318) found in many nexus hairpins in tracrRNAs. Interestingly, several of the RGNs of the invention use tracrRNAs that comprise non-canonical sequences in the base of the hairpin stem of their nexus hairpins, including UNANNA, UNANNG, and CNANNC (SEQ ID NOs: 319, 321, and 322, respectively). There are often terminal hairpins at the 3' end of the tracrRNA that can vary in structure and number, but often comprise a GC-rich Rho-independent transcriptional terminator hairpin followed by a string of U's at the 3' end. See, for example, Briner et al. (2014) *Molecular Cell* 56:333-339, Briner and Barrangou (2016) *Cold Spring Harb Protoc*; doi: 10.1101/pdb.top090902, and U.S. Publication No. 2017/0275648, each of which is herein incorporated by reference in its entirety.

In various embodiments, the anti-repeat region of the tracrRNA that is fully or partially complementary to the CRISPR repeat sequence comprises from about 8 nucleotides to about 30 nucleotides, or more. For example, the region of base pairing between the tracrRNA anti-repeat sequence and the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In particular embodiments, the region of base pairing between the tracrRNA anti-repeat sequence and the CRISPR repeat sequence is 6, 7, 8, 9, 10, 11, 12, 13, 14, 15, 16, 17, 18, 19, 20, 21, 22, 23, 24, 25, 26, 27, 28, 29, 30, or more nucleotides in length. In some embodiments, the degree of complementarity between a CRISPR repeat sequence and its corresponding tracrRNA anti-repeat sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the degree of complementarity between a CRISPR repeat sequence and its corresponding tracrRNA anti-repeat sequence, when optimally aligned using a suitable alignment algorithm, is 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more.

In various embodiments, the entire tracrRNA can comprise from about 60 nucleotides to more than about 210 nucleotides. For example, the tracrRNA can be about 60, about 65, about 70, about 75, about 80, about 85, about 90, about 95, about 100, about 105, about 110, about 115, about 120, about 125, about 130, about 135, about 140, about 150, about 160, about 170, about 180, about 190, about 200, about 210, or more nucleotides in length. In particular embodiments, the tracrRNA is 60, 65, 70, 75, 80, 85, 90, 95, 100, 105, 110, 115, 120, 125, 130, 135, 140, 150, 160, 170, 180, 190, 200, 210 or more nucleotides in length. In particular embodiments, the tracrRNA is about 70 to about 105 nucleotides in length, including about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, and about 105 nucleotides in length. In particular embodiments, the tracrRNA is 70 to 105 nucleotides in length, including 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, and 105 nucleotides in length.

In particular embodiments, the tracrRNA comprises the nucleotide sequence of any one of SEQ ID NOs: 25-36, or an active variant or fragment thereof that when comprised within a guide RNA is capable of directing the sequence-specific binding of an associated RNA-guided nuclease provided herein to a target sequence of interest. In certain embodiments, an active tracrRNA sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of the nucleotide sequences set forth as SEQ ID NOs: 25-36. In certain embodiments, an active tracrRNA sequence fragment of a wild-type sequence comprises at least 5, 10, 15, 20, 25, 30, 35, 40, 45, 50, 55, 60, 65, 70, 75, 80, or more contiguous nucleotides of any one of the nucleotide sequences set forth as SEQ ID NOs: 25-36.

Two polynucleotide sequences can be considered to be substantially complementary when the two sequences hybridize to each other under stringent conditions. Likewise, an RGN is considered to bind to a particular target sequence within a sequence-specific manner if the guide RNA bound to the RGN binds to the target sequence under stringent conditions. By "stringent conditions" or "stringent hybridization conditions" is intended conditions under which the two polynucleotide sequences will hybridize to each other to a detectably greater degree than to other sequences (e.g., at least 2-fold over background). Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3, and the temperature is at least about 30° C. for short sequences (e.g., 10 to 50 nucleotides) and at least about 60° C. for long sequences (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The Tm is the temperature (under defined ionic strength and pH) at which 50% of a complementary target sequence hybridizes to a perfectly matched sequence. For DNA-DNA hybrids, the Tm can be approximated from the equation of Meinkoth and Wahl (1984) Anal. Biochem. 138:267–284: Tm=81.5° C.+16.6 (log M)+0.41 (% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, New York).

The term "sequence specific" can also refer to the binding of a target sequence at a greater frequency than binding to a randomized background sequence.

The guide RNA can be a single guide RNA (sgRNA) or a dual-guide RNA system. A single guide RNA comprises the crRNA and tracrRNA on a single molecule of RNA, whereas a dual-guide RNA system comprises a crRNA and a tracrRNA present on two distinct RNA molecules, hybridized to one another through at least a portion of the CRISPR repeat sequence of the crRNA and at least a portion of the tracrRNA, which may be fully or partially complementary to the CRISPR repeat sequence of the crRNA. In some of those embodiments wherein the guide RNA is a single guide RNA, the crRNA and tracrRNA are separated by a linker nucleotide sequence. In general, the linker nucleotide sequence is one that does not include complementary bases in order to avoid the formation of secondary structure within or comprising nucleotides of the linker nucleotide sequence. In some embodiments, the linker nucleotide sequence between the crRNA and tracrRNA is at least 3, at least 4, at least 5, at least 6, at least 7, at least 8, at least 9, at least 10, at least 11, at least 12, or more nucleotides in length. In particular embodiments, the linker nucleotide sequence of a single guide RNA is at least 4 nucleotides in length. In certain embodiments, the linker nucleotide sequence is the nucleotide sequence set forth as SEQ ID NO: 323.

The single guide RNA or dual-guide RNA can be synthesized chemically or via in vitro transcription. Assays for determining sequence-specific binding between an RGN and a guide RNA are known in the art and include, but are not limited to, in vitro binding assays between an expressed RGN and the guide RNA, which can be tagged with a detectable label (e.g., biotin) and used in a pull-down detection assay in which the guide RNA: RGN complex is captured via the detectable label (e.g., with streptavidin beads). A control guide RNA with an unrelated sequence or structure to the guide RNA can be used as a negative control for non-specific binding of the RGN to RNA. In certain embodiments, the guide RNA is any one of SEQ ID NOs: 37-48, wherein the spacer sequence can be any sequence and is indicated as a poly-N sequence.

In certain embodiments, the guide RNA can be introduced into a target cell, organelle, or embryo as an RNA molecule. The guide RNA can be transcribed in vitro or chemically synthesized. In other embodiments, a nucleotide sequence encoding the guide RNA is introduced into the cell, organelle, or embryo. In some of these embodiments, the nucleotide sequence encoding the guide RNA is operably linked to a promoter (e.g., an RNA polymerase III promoter). The promoter can be a native promoter or heterologous to the guide RNA-encoding nucleotide sequence.

In various embodiments, the guide RNA can be introduced into a target cell, organelle, or embryo as a ribonucleoprotein complex, as described herein, wherein the guide RNA is bound to an RNA-guided nuclease polypeptide.

The guide RNA directs an associated RNA-guided nuclease to a particular target nucleotide sequence of interest through hybridization of the guide RNA to the target nucleotide sequence. A target nucleotide sequence can comprise DNA, RNA, or a combination of both and can be single-stranded or double-stranded. A target nucleotide sequence can be genomic DNA (i.e., chromosomal DNA), plasmid DNA, or an RNA molecule (e.g., messenger RNA, ribosomal RNA, transfer RNA, micro RNA, small interfering RNA). The target nucleotide sequence can be bound (and in some embodiments, cleaved) by an RNA-guided nuclease in vitro or in a cell. The chromosomal sequence targeted by the RGN can be a nuclear, plastid or mitochondrial chromosomal sequence. In some embodiments, the target nucleotide sequence is unique in the target genome.

The target nucleotide sequence is adjacent to a protospacer adjacent motif (PAM). A protospacer adjacent motif is generally within about 1 to about 10 nucleotides from the target nucleotide sequence, including about 1, about 2, about 3, about 4, about 5, about 6, about 7, about 8, about 9, or about 10 nucleotides from the target nucleotide sequence. In particular embodiments, a PAM is within 1 to 10 nucleotides from the target nucleotide sequence, including 1, 2, 3, 4, 5, 6, 7, 8, 9, or 10 nucleotides from the target nucleotide sequence. When not otherwise noted herein, the given PAM sequence for a presently disclosed RGN is immediately adjacent to the target nucleotide sequence. The PAM can be 5' or 3' of the target sequence. In some embodiments, the PAM is 3' of the target sequence for the presently disclosed RGNs. Generally, the PAM is a consensus sequence of about 3-4 nucleotides, but in particular embodiments it can be 2, 3, 4, 5, 6, 7, 8, 9, or more nucleotides in length. In various embodiments, the PAM sequence recognized by the presently disclosed RGNs comprises the consensus sequence set forth in any one of SEQ ID NOs: 73-84.

In particular embodiments, an RNA-guided nuclease having any one of SEQ ID NOs: 1-12 or an active variant or fragment thereof binds a target nucleotide sequence adjacent to a PAM sequence set forth as any one of SEQ ID NOs: 73-84. In some embodiments, the RGN binds to a guide sequence comprising a CRISPR repeat sequence set forth in any one of SEQ ID NOs: 13-24, respectively, or an active variant or fragment thereof, and a tracrRNA sequence set forth in any one of SEQ ID NOs: 25-36, respectively, or an active variant or fragment thereof. The RGN systems are described further in Examples 1-3 and Tables 1 and 2 of the present specification.

In some embodiments, an RNA-guided nuclease having SEQ ID NO: 1 or an active variant or fragment thereof binds a target nucleotide sequence adjacent to a PAM sequence set forth as SEQ ID NO: 73, when bound to a guide RNA comprising a CRISPR repeat sequence set forth as SEQ ID NO: 13 or an active variant or fragment thereof and a tracrRNA sequence set forth as SEQ ID NO: 25 or an active variant or fragment thereof.

In some embodiments, an RNA-guided nuclease having SEQ ID NO: 2 or an active variant or fragment thereof binds a target nucleotide sequence adjacent to a PAM sequence set forth as SEQ ID NO: 74, when bound to a guide RNA comprising a CRISPR repeat sequence set forth as SEQ ID NO: 14 or an active variant or fragment thereof and a tracrRNA sequence set forth as SEQ ID NO: 26 or an active variant or fragment thereof.

In some embodiments, an RNA-guided nuclease having SEQ ID NO: 3 or an active variant or fragment thereof binds a target nucleotide sequence adjacent to a PAM sequence set forth as SEQ ID NO: 75, when bound to a guide RNA comprising a CRISPR repeat sequence set forth as SEQ ID NO: 15 or an active variant or fragment thereof and a tracrRNA sequence set forth as SEQ ID NO: 27 or an active variant or fragment thereof.

In some embodiments, an RNA-guided nuclease having SEQ ID NO: 4 or an active variant or fragment thereof binds a target nucleotide sequence adjacent to a PAM sequence set forth as SEQ ID NO: 76, when bound to a guide RNA comprising a CRISPR repeat sequence set forth as SEQ ID NO: 16 or an active variant or fragment thereof and a tracrRNA sequence set forth as SEQ ID NO: 28 or an active variant or fragment thereof.

In some embodiments, an RNA-guided nuclease having SEQ ID NO: 5 or an active variant or fragment thereof binds a target nucleotide sequence adjacent to a PAM sequence set forth as SEQ ID NO: 77, when bound to a guide RNA comprising a CRISPR repeat sequence set forth as SEQ ID NO: 17 or an active variant or fragment thereof and a tracrRNA sequence set forth as SEQ ID NO: 29 or an active variant or fragment thereof.

In some embodiments, an RNA-guided nuclease having SEQ ID NO: 6 or an active variant or fragment thereof binds a target nucleotide sequence adjacent to a PAM sequence set forth as SEQ ID NO: 78, when bound to a guide RNA comprising a CRISPR repeat sequence set forth as SEQ ID NO: 18 or an active variant or fragment thereof and a tracrRNA sequence set forth as SEQ ID NO: 30 or an active variant or fragment thereof.

In some embodiments, an RNA-guided nuclease having SEQ ID NO: 7 or an active variant or fragment thereof binds a target nucleotide sequence adjacent to a PAM sequence set forth as SEQ ID NO: 79, when bound to a guide RNA comprising a CRISPR repeat sequence set forth as SEQ ID NO: 19 or an active variant or fragment thereof and a tracrRNA sequence set forth as SEQ ID NO: 31 or an active variant or fragment thereof.

In some embodiments, an RNA-guided nuclease having SEQ ID NO: 8 or an active variant or fragment thereof binds a target nucleotide sequence adjacent to a PAM sequence set forth as SEQ ID NO: 80, when bound to a guide RNA comprising a CRISPR repeat sequence set forth as SEQ ID NO: 20 or an active variant or fragment thereof and a tracrRNA sequence set forth as SEQ ID NO: 32 or an active variant or fragment thereof.

In some embodiments, an RNA-guided nuclease having SEQ ID NO: 9 or an active variant or fragment thereof binds a target nucleotide sequence adjacent to a PAM sequence set forth as SEQ ID NO: 81, when bound to a guide RNA comprising a CRISPR repeat sequence set forth as SEQ ID NO: 21 or an active variant or fragment thereof and a tracrRNA sequence set forth as SEQ ID NO: 33 or an active variant or fragment thereof.

In some embodiments, an RNA-guided nuclease having SEQ ID NO: 10 or an active variant or fragment thereof binds a target nucleotide sequence adjacent to a PAM sequence set forth as SEQ ID NO: 82, when bound to a guide RNA comprising a CRISPR repeat sequence set forth as SEQ ID NO: 22 or an active variant or fragment thereof and a tracrRNA sequence set forth as SEQ ID NO: 34 or an active variant or fragment thereof.

In some embodiments, an RNA-guided nuclease having SEQ ID NO: 11 or an active variant or fragment thereof binds a target nucleotide sequence adjacent to a PAM sequence set forth as SEQ ID NO: 83, when bound to a guide RNA comprising a CRISPR repeat sequence set forth as SEQ ID NO: 23 or an active variant or fragment thereof and a tracrRNA sequence set forth as SEQ ID NO: 35 or an active variant or fragment thereof.

In some embodiments, an RNA-guided nuclease having SEQ ID NO: 12 or an active variant or fragment thereof binds a target nucleotide sequence adjacent to a PAM sequence set forth as SEQ ID NO: 84, when bound to a guide RNA comprising a CRISPR repeat sequence set forth as SEQ ID NO: 24 or an active variant or fragment thereof and a tracrRNA sequence set forth as SEQ ID NO: 36 or an active variant or fragment thereof.

It is well-known in the art that PAM sequence specificity for a given nuclease enzyme is affected by enzyme concentration (see, e.g., Karvelis et al. (2015) *Genome Biol* 16:253), which may be modified by altering the promoter used to express the RGN, or the amount of ribonucleoprotein complex delivered to the cell, organelle, or embryo.

Upon recognizing its corresponding PAM sequence, the RGN can cleave the target nucleotide sequence at a specific cleavage site. As used herein, a cleavage site is made up of the two particular nucleotides within a target nucleotide sequence between which the nucleotide sequence is cleaved by an RGN. The cleavage site can comprise the $1^{st}$ and $2^{nd}$, $2^{nd}$ and $3^{rd}$, $3^{rd}$ and $4^{th}$, $4^{th}$ and $5^{th}$, $5^{th}$ and $6^{th}$, $7^{th}$ and $8^{th}$, or $8^{th}$ and $9^{th}$ nucleotides from the PAM in either the 5' or 3' direction. In some embodiments, the cleavage site may be over 10, 11, 12, 13, 14, 15, 16, 17, 18, 19, or 20 nucleotides from the PAM in either the 5' or 3' direction. In some embodiments, particularly those wherein the RGN has the amino acid sequence set forth as SEQ ID NO: 6 or an active variant or fragment thereof, the cleavage site of the RGN is between the $3^{rd}$ and $4^{th}$ nucleotides 5' of the PAM, generating blunt ends. As RGNs can cleave a target nucleotide sequence resulting in staggered ends, in some embodiments, the cleavage site is defined based on the distance of the two nucleotides from the PAM on the positive (+) strand of the polynucleotide and the distance of the two nucleotides from the PAM on the negative (−) strand of the polynucleotide.

IV. Nucleotides Encoding RNA-guided Nucleases, CRISPR RNA, and/or tracrRNA

The present disclosure provides polynucleotides comprising the presently disclosed CRISPR RNAs, tracrRNAs, and/or sgRNAs and polynucleotides comprising a nucleotide sequence encoding the presently disclosed RNA-guided nucleases, CRISPR RNAs, tracrRNAs, and/or sgRNAs. Presently disclosed polynucleotides include those comprising or encoding a CRISPR repeat sequence comprising any one of the nucleotide sequences set forth as SEQ ID NOs: 13-24, or an active variant or fragment thereof that when comprised within a guide RNA is capable of directing the sequence-specific binding of an associated RNA-guided nuclease to a target sequence of interest. Also disclosed are polynucleotides comprising or encoding a tracrRNA comprising any one of the nucleotide sequences set forth as SEQ ID NOs: 25-36, or an active variant or fragment thereof that when comprised within a guide RNA is capable of directing the sequence-specific binding of an associated RNA-guided nuclease to a target sequence of interest. Polynucleotides are also provided that encode an RNA-guided nuclease comprising any one of the amino acid sequences set forth as SEQ ID NOs: 1-12, and active fragments or variants thereof that retain the ability to bind to a target nucleotide sequence in an RNA-guided sequence-specific manner.

The use of the term "polynucleotide" or "nucleic acid molecule" is not intended to limit the present disclosure to polynucleotides comprising DNA. Those of ordinary skill in the art will recognize that polynucleotides can comprise ribonucleotides (RNA) and combinations of ribonucleotides and deoxyribonucleotides. Such deoxyribonucleotides and ribonucleotides include both naturally occurring molecules and synthetic analogues. These include peptide nucleic acids (PNAs), PNA-DNA chimers, locked nucleic acids (LNAs), and phosphothiorate linked sequences. The polynucleotides disclosed herein also encompass all forms of sequences including, but not limited to, single-stranded forms, double-stranded forms, DNA-RNA hybrids, triplex structures, stem-and-loop structures, and the like.

In some embodiments, the polynucleotide encoding a presently disclosed RGN is an mRNA (messenger RNA) molecule. An mRNA refers to any polynucleotide which encodes a polypeptide of interest and which is capable of being translated to produce the encoded polypeptide of interest in vitro, in vivo, in situ, or ex vivo. In embodiments, the basic components of an mRNA molecule include at least a coding region, a 5'UTR, a 3'UTR, a 5' cap and a poly-A tail. In embodiments, an mRNA encoding an RGN useful in the presently disclosed methods and compositions can include one or more structural and/or chemical modifications or alterations which impart useful properties to the polynucleotide. For instance, a useful property of an mRNA includes the lack of a substantial induction of the innate immune response of a cell into which the mRNA is introduced. A "structural" feature or modification is one in which two or more linked nucleotides are inserted, deleted, duplicated, inverted or randomized in an mRNA without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. Chemical modifications to mRNA can involve inclusion of 5-methylcytosine, N1-methyl-pseudouridine, pseudouridine, 2-thiouridine, 4-thiouridine, 5-methoxyuridine, 2'Fluoroguanosine, 2'Fluorouridine, 5-bromouridine, 5-(2-carbomethoxyvinyl) uridine, 5-[3 (1-E-propenylamino)]uridine, α-thiocytidine, N6-methyladenosine, 5-methylcytidine, N4-acetylcytidine, 5-formylcytidine, or combinations thereof, in an mRNA.

The nucleic acid molecules encoding RGNs can be codon optimized for expression in an organism of interest. A "codon-optimized" coding sequence is a polynucleotide coding sequence having its frequency of codon usage designed to mimic the frequency of preferred codon usage or transcription conditions of a particular host cell. Expression in the particular host cell or organism is enhanced as a result of the alteration of one or more codons at the nucleic acid level such that the translated amino acid sequence is not changed. Nucleic acid molecules can be codon optimized, either wholly or in part. Codon tables and other references providing preference information for a wide range of organisms are available in the art (see, e.g., Campbell and Gowri (1990) *Plant Physiol.* 92:1-11 for a discussion of plant-preferred codon usage). Methods are available in the art for synthesizing plant-preferred genes or mammalian (for example human) codon-optimized coding sequences. See, for example, U.S. Pat. Nos. 5,380,831, and 5,436,391, and Murray et al. (1989) *Nucleic Acids Res.* 17:477-498, herein incorporated by reference.

Polynucleotides encoding the RGNs, crRNAs, tracrRNAs, and/or sgRNAs provided herein can be provided in expression cassettes for in vitro expression or expression in a cell, organelle, embryo, or organism of interest. The cassette will include 5' and 3' regulatory sequences operably linked to a polynucleotide encoding an RGN, crRNA, tracrRNAs, and/or sgRNAs provided herein that allows for expression of the polynucleotide. The cassette may additionally contain at least one additional gene or genetic element to be cotransformed into the organism. Where additional genes or elements are included, the components are operably linked. The term "operably linked" is intended to mean a functional linkage between two or more elements. For example, an operable linkage between a promoter and a coding region of interest (e.g., region coding for an RGN, crRNA, tracrRNAs, and/or sgRNAs) is a functional link that allows for expression of the coding region of interest. Operably linked elements may be contiguous or non-contiguous. When used to refer to the joining of two protein coding regions, by operably linked is intended that the coding regions are in the same reading frame. Alternatively, the additional gene(s) or element(s) can be provided on multiple expression cassettes. For example, the nucleotide sequence encoding a presently disclosed RGN can be present on one expression cassette, whereas the nucleotide sequence encoding a crRNA, tracrRNA, or complete guide RNA can be on a separate expression cassette. Such an expression cassette is provided with a plurality of restriction sites and/or recombination sites for insertion of the polynucleotides to be under the transcriptional regulation of the regulatory regions. The expression cassette may additionally contain a selectable marker gene.

The expression cassette will include in the 5'-3' direction of transcription, a transcriptional (and, in some embodiments, translational) initiation region (i.e., a promoter), an RGN-, crRNA-, tracrRNA- and/or sgRNA-encoding polynucleotide of the invention, and a transcriptional (and in some embodiments, translational) termination region (i.e., termination region) functional in the organism of interest. The promoters of the invention are capable of directing or driving expression of a coding sequence in a host cell. The regulatory regions (e.g., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. As used herein, a chimeric gene comprises a coding sequence operably linked to a transcription initiation region that is heterologous to the coding sequence.

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional regulatory signals include, but are not limited to, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) Molecular Cloning: A Laboratory Manual, ed. Maniatis et al. (Cold Spring Harbor Laboratory Press, Cold Spring Harbor, N.Y.), hereinafter "Sambrook 11"; Davis et al., eds. (1980) Advanced Bacterial Genetics (Cold Spring Harbor Laboratory Press), Cold Spring Harbor, N. Y., and the references cited therein.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, growth stage-specific, cell type-specific, tissue-preferred, tissue-specific, or other promoters for expression in the organism of interest. See, for example, promoters set forth in WO 99/43838 and in U.S. Pat. Nos. 8,575,425; 7,790,846; 8,147,856; 8,586,832; 7,772,369; 7,534,939; 6,072,050; 5,659,026; 5,608,149; 5,608,144; 5,604,121; 5,569,597; 5,466,785; 5,399,680; 5,268,463; 5,608,142; and 6,177,611; herein incorporated by reference.

For expression in plants, constitutive promoters also include CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); and MAS (Velten et al. (1984) *EMBO J.* 3:2723-2730).

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the Axig1 promoter which is auxin induced and tapetum specific but also active in callus (PCT US01/22169), the steroid-responsive promoters (see, for example, the ERE promoter which is estrogen induced, and the glucocorticoid-inducible promoter in Schena et al. (1991) Proc. Natl. Acad. Sci. USA 88:10421-10425 and McNellis et al. (1998) Plant J. 14 (2): 247-257) and tetracycline-inducible and tetracycline-repressible promoters (see, for example, Gatz et al. (1991) Mol. Gen. Genet. 227:229-237, and U.S. Pat. Nos. 5,814,618 and 5,789,156), herein incorporated by reference.

Tissue-specific or tissue-preferred promoters can be utilized to target expression of an expression construct within a particular tissue. In certain embodiments, the tissue-specific or tissue-preferred promoters are active in plant tissue. Examples of promoters under developmental control in plants include promoters that initiate transcription preferentially in certain tissues, such as leaves, roots, fruit, seeds, or flowers. A "tissue specific" promoter is a promoter that initiates transcription only in certain tissues. Unlike constitutive expression of genes, tissue-specific expression is the result of several interacting levels of gene regulation. As such, promoters from homologous or closely related plant species can be preferable to use to achieve efficient and reliable expression of transgenes in particular tissues. In some embodiments, the expression comprises a tissue-preferred promoter. A "tissue preferred" promoter is a promoter that initiates transcription preferentially, but not necessarily entirely or solely in certain tissues.

In some embodiments, the nucleic acid molecules encoding an RGN, crRNA, and/or tracrRNA comprise a cell type-specific promoter. A "cell type specific" promoter is a promoter that primarily drives expression in certain cell types in one or more organs. Some examples of plant cells in which cell type specific promoters functional in plants may be primarily active include, for example, BETL cells, vascular cells in roots, leaves, stalk cells, and stem cells. The nucleic acid molecules can also include cell type preferred promoters. A "cell type preferred" promoter is a promoter that primarily drives expression mostly, but not necessarily entirely or solely in certain cell types in one or more organs. Some examples of plant cells in which cell type preferred promoters functional in plants may be preferentially active include, for example, BETL cells, vascular cells in roots, leaves, stalk cells, and stem cells.

The nucleic acid sequences encoding the RGNs, crRNAs, tracrRNAs, and/or sgRNAs can be operably linked to a promoter sequence that is recognized by a phage RNA polymerase for example, for in vitro mRNA synthesis. In such embodiments, the in vitro-transcribed RNA can be purified for use in the methods described herein. For example, the promoter sequence can be a T7, T3, or SP6 promoter sequence or a variation of a T7, T3, or SP6 promoter sequence. In such embodiments, the expressed protein and/or RNAs can be purified for use in the methods of genome modification described herein.

In certain embodiments, the polynucleotide encoding the RGN, crRNA, tracrRNA, and/or sgRNA also can be linked to a polyadenylation signal (e.g., SV40 polyA signal and other signals functional in plants) and/or at least one transcriptional termination sequence. Additionally, the sequence encoding the RGN also can be linked to sequence(s) encoding at least one nuclear localization signal, at least one cell-penetrating domain, and/or at least one signal peptide capable of trafficking proteins to particular subcellular locations, as described elsewhere herein.

The polynucleotide encoding the RGN, crRNA, tracrRNA, and/or sgRNA can be present in a vector or multiple vectors. A "vector" refers to a polynucleotide composition for transferring, delivering, or introducing a nucleic acid into a host cell. Suitable vectors include plasmid vectors, phagemids, cosmids, artificial/mini-chromosomes, transposons, and viral vectors (e.g., lentiviral vectors, adeno-associated viral vectors, baculoviral vector). The vector can comprise additional expression control sequences (e.g., enhancer sequences, Kozak sequences, polyadenylation sequences, transcriptional termination sequences), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001.

The vector can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D).

In some embodiments, the expression cassette or vector comprising the sequence encoding the RGN polypeptide can further comprise a sequence encoding a crRNA and/or a tracrRNA, or the crRNA and tracrRNA combined to create a sgRNA. The sequence(s) encoding the crRNA and/or tracrRNA can be operably linked to at least one transcriptional control sequence for expression of the crRNA and/or tracrRNA in the organism or host cell of interest. For example, the polynucleotide encoding the crRNA and/or tracrRNA can be operably linked to a promoter sequence that is recognized by RNA polymerase III (Pol III). Examples of suitable Pol III promoters include, but are not limited to, mammalian U6, U3, H1, and 7SL RNA promoters and rice U6 and U3 promoters, such as the human U6 promoter set forth as SEQ ID NO: 329, as well as the promoters disclosed in U.S. Provisional Appl. No. 63/209,660, filed Jun. 11, 2021, which is herein incorporated by reference in its entirety, including those set forth herein as SEQ ID NOs: 449-458.

As indicated, expression constructs comprising nucleotide sequences encoding the RGNs, crRNA, tracrRNA, and/or sgRNA can be used to transform organisms of interest. Methods for transformation involve introducing a nucleotide construct into an organism of interest. By "introducing" is intended to introduce the nucleotide construct to the host cell in such a manner that the construct gains access to the interior of the host cell. The methods of the invention do not require a particular method for introducing a nucleotide construct to a host organism, only that the nucleotide construct gains access to the interior of at least one cell of the host organism. The host cell can be a eukaryotic or prokaryotic cell. In particular embodiments, the eukaryotic host cell is a plant cell, a mammalian cell, an avian cell, or an insect cell. In some embodiments, the eukaryotic cell that comprises or expresses a presently disclosed RGN or that has been modified by a presently disclosed RGN is a human cell. In some embodiments, the eukaryotic cell that comprises or expresses a presently disclosed RGN or that has been modified by a presently disclosed RGN is a cell of hematopoietic origin, such as an immune cell (i.e., a cell of the innate or adaptive immune system) including but not limited to a B cell, a T cell, a natural killer (NK) cell, a pluripotent stem cell, an induced pluripotent stem cell, a chimeric antigen receptor T (CAR-T) cell, a monocyte, a macrophage, and a dendritic cell. In some embodiments, the eukaryotic cell that comprises or expresses a presently disclosed RGN or that has been modified by a presently disclosed RGN is an ocular cell, muscle cell (e.g., skeletal muscle cell), epithelial cell (e.g., lung epithelial cell), diseased cell (e.g., tumor cell).

Methods for introducing nucleotide constructs into plants and other host cells are known in the art including, but not limited to, stable transformation methods, transient transformation methods, and virus-mediated methods.

The methods result in a transformed organism, such as a plant, including whole plants, as well as plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic organisms" or "transformed organisms" or "stably transformed" organisms or cells or tissues refers to organisms that have incorporated or integrated a polynucleotide encoding an RGN, crRNA, and/or tracrRNA of the invention. It is recognized that other exogenous or endogenous nucleic acid sequences or DNA fragments may also be incorporated into the host cell. *Agrobacterium-* and biolistic-mediated transformation remain the two predominantly employed approaches for transformation of plant cells. However, transformation of a host cell may be performed by infection, transfection, microinjection, electroporation, microprojection, biolistics or particle bombardment, electroporation, silica/carbon fibers, ultrasound mediated, PEG mediated, calcium phosphate co-precipitation, polycation DMSO technique, DEAE dextran procedure, and viral mediated, liposome mediated and the like. Viral-mediated introduction of a polynucleotide encoding an RGN, crRNA, and/or tracrRNA includes retroviral, lentiviral, adenoviral, and adeno-associated viral mediated introduction and expression, as well as the use of Caulimoviruses, Geminiviruses, and RNA plant viruses.

Transformation protocols as well as protocols for introducing polypeptides or polynucleotide sequences into plants may vary depending on the type of host cell (e.g., monocot or dicot plant cell) targeted for transformation. Methods for transformation are known in the art and include those set forth in U.S. Pat. Nos. 8,575,425; 7,692,068; 8,802,934; 7,541,517; each of which is herein incorporated by reference. See, also, Rakoczy-Trojanowska, M. (2002) *Cell Mol Biol Lett.* 7:849-858; Jones et al. (2005) *Plant Methods* 1:5; Rivera et al. (2012) *Physics of Life Reviews* 9:308-345; Bartlett et al. (2008) *Plant Methods* 4:1-12; Bates, G. W. (1999) *Methods in Molecular Biology* 111:359-366; Binns and Thomashow (1988) *Annual Reviews in Microbiology* 42:575-606; Christou, P. (1992) *The Plant Journal* 2:275-281; Christou, P. (1995) *Euphytica* 85:13-27; Tzfira et al. (2004) *TRENDS in Genetics* 20:375-383; Yao et al. (2006) *Journal of Experimental Botany* 57:3737-3746; Zupan and Zambryski (1995) *Plant Physiology* 107:1041-1047; Jones et al. (2005) *Plant Methods* 1:5;

Transformation may result in stable or transient incorporation of the nucleic acid into the cell. "Stable transformation" is intended to mean that the nucleotide construct introduced into a host cell integrates into the genome of the host cell and is capable of being inherited by the progeny thereof. "Transient transformation" is intended to mean that a polynucleotide is introduced into the host cell and does not integrate into the genome of the host cell.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into a transgenic organism, such as a plant, in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Alternatively, cells that have been transformed may be introduced into an organism. These cells could have originated from the organism, wherein the cells are transformed in an ex vivo approach.

The sequences provided herein may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, *papaya*, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, *hydrangea*, hibiscus, roses, tulips, daffodils, petunias, carnation, poinsettia, and *chrysanthemum*. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processed plant product or byproduct that retains the sequences disclosed herein, including for example, soymeal.

The polynucleotides encoding the RGNs, crRNAs, and/or tracrRNAs or comprising the crRNAs and/or tracrRNAs can also be used to transform any prokaryotic species, including but not limited to, archaea and bacteria (e.g., *Bacillus* sp., *Klebsiella* sp. *Streptomyces* sp., *Rhizobium* sp., *Escherichia* sp., *Pseudomonas* sp., *Salmonella* sp., *Shigella* sp., *Vibrio* sp., *Yersinia* sp., *Mycoplasma* sp., *Agrobacterium, Lactobacillus* sp.).

The polynucleotides encoding the RGNs, crRNAs, and/or tracrRNAs or comprising the crRNAs and/or tracrRNAs can be used to transform any eukaryotic species, including but not limited to animals (e.g., mammals, insects, fish, birds, and reptiles), fungi, amoeba, algae, and yeast.

Conventional viral and non-viral based gene transfer methods can be used to introduce nucleic acids in mammalian, insect, or avian cells or target tissues. Such methods can be used to administer nucleic acids encoding components of an RGN system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6 (10): 1149-1154 (1988); Vigne, Restorative Neurology and Neuroscience 8:35-36 (1995); Kremer & Perricaudet, British Medical Bulletin 51 (1): 31-44 (1995); Haddada et al., in Current Topics in Microbiology and Immunology, Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration). The preparation of lipid: nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946, 787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Viral. 66:2731-2739 (1992); Johann et al., J. Viral. 66:1635-1640 (1992); Sommnerfelt et al., Viral. 176:58-59 (1990); Wilson et al., J. Viral. 63:2374-2378 (1989); Miller et al., 1. Viral. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Katin, Human Gene Therapy 5:793-801 (1994); Muzyczka, 1. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., 1. Viral. 63:03822-3828 (1989). Packaging cells are typically used to form virus particles that are capable of infecting a host cell. Such cells include 293 cells, which package adenovirus, and ψwJ2 cells or PA317 cells, which package retrovirus.

Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences.

The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. In some embodiments, the cell line may be mammalian, insect, or avian cells. A wide variety of cell lines for tissue culture are known in the art. Examples of cell lines include, but are not limited to, C8161, CCRF-CEM, MOLT, mIMCD-3, NHDF, HeLaS3, Huh1, Huh4, Huh7, HUVEC, HASMC, HEKn, HEKa, MiaPaCell, Panel, PC-3, TF1, CTLL-2, CIR, Rat6, CVI, RPTE, AlO, T24, 182, A375, ARH-77, Calu1, SW480, SW620, SKOV3, SK-UT, CaCo2, P388D1, SEM-K2, WEHI-231, HB56, TIB55, Jurkat, 145.01, LRMB, Bcl-1, BC-3, IC21, DLD2, Raw264.7, NRK, NRK-52E, MRC5, MEF, Hep G2, HeLa B, HeLa T4. COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-I cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr–/–, COR-L23, COR-L23/CPR, COR-L235010, CORL23/R23, COS-7, COV-434, CML T1, CMT, CT26, D17, DH82, DU145, DuCaP. EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, lurkat, IY cells, K562 cells, Ku812, KCL22, KG1, KYO1, LNCap, Ma-Me1 1-48, MC-38, MCF-7, MCF-10A, MDA-MB-231, MDA-MB-468, MDA-MB-435, MDCKII, MDCKII, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, a cell transfected with one or more vectors described herein is used to establish a new cell line comprising one or more vector-derived sequences. In some embodiments, a cell transiently transfected with the components of an RGN system as described herein (such as by transient transfection of one or more vectors, or transfection with RNA), and modified through the activity of an RGN system, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, hamster, rabbit, cow, or pig. In some embodiments, the transgenic animal is a bird, such as a chicken or a duck. In some embodiments, the transgenic animal is an insect, such as a mosquito or a tick.

V. Variants and Fragments of Polypeptides and Polynucleotides

The present disclosure provides active variants and fragments of a naturally-occurring (i.e., wild-type) RNA-guided nuclease, the amino acid sequence of which is set forth as any one of SEQ ID NOs: 1-12, as well as active variants and fragments of naturally-occurring CRISPR repeats, such as any one of the sequences set forth as SEQ ID NOs: 13-24, and active variant and fragments of naturally-occurring tracrRNAs, such as any one of the sequences set forth as SEQ ID NOs: 25-36, and polynucleotides encoding the same.

While the activity of a variant or fragment may be altered compared to the polynucleotide or polypeptide of interest, the variant and fragment should retain the functionality of the polynucleotide or polypeptide of interest. For example, a variant or fragment may have increased activity, decreased activity, different spectrum of activity or any other alteration in activity when compared to the polynucleotide or polypeptide of interest.

Fragments and variants of naturally-occurring RGN polypeptides, such as those disclosed herein, will retain sequence-specific, RNA-guided DNA-binding activity. In particular embodiments, fragments and variants of naturally-occurring RGN polypeptides, such as those disclosed herein, will retain nuclease activity (single-stranded or double-stranded).

Fragments and variants of naturally-occurring CRISPR repeats, such as those disclosed herein, will retain the ability, when part of a guide RNA (comprising a tracrRNA), to bind to and guide an RNA-guided nuclease (complexed with the guide RNA) to a target nucleotide sequence in a sequence-specific manner.

Fragments and variants of naturally-occurring tracrRNAs, such as those disclosed herein, will retain the ability, when part of a guide RNA (comprising a CRISPR RNA), to guide an RNA-guided nuclease (complexed with the guide RNA) to a target nucleotide sequence in a sequence-specific manner.

The term "fragment" refers to a portion of a polynucleotide or polypeptide sequence of the invention. "Fragments" or "biologically active portions" include polynucleotides comprising a sufficient number of contiguous nucleotides to retain the biological activity (i.e., binding to and directing an RGN in a sequence-specific manner to a target nucleotide sequence when comprised within a guide RNA). "Fragments" or "biologically active portions" include polypeptides comprising a sufficient number of contiguous amino acid residues to retain the biological activity (i.e., binding to a target nucleotide sequence in a sequence-specific manner when complexed with a guide RNA). Fragments of the RGN proteins include those that are shorter than the full-length sequences due to the use of an alternate downstream start site. A biologically active portion of an RGN protein can be a polypeptide that comprises, for example, 10, 25, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700 or more contiguous amino acid residues of any one of SEQ ID NOs: 1-12. Such biologically active portions can be prepared by recombinant techniques and evaluated for sequence-specific, RNA-guided DNA-binding activity. A biologically active fragment of a CRISPR repeat sequence can comprise at least 8 contiguous amino acids of any one of SEQ ID NOs: 13-24. A biologically active portion of a CRISPR repeat sequence can be a polynucleotide that comprises, for example, 8, 9, 10, 11, 12, 13, 14, 15, 16, 17, 18, 19, 20, 21, 22, 23, or 24 contiguous nucleotides of any one of SEQ ID NOs: 13-24. A biologically active portion of a tracrRNA can be a polynucleotide that comprises, for example, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more contiguous nucleotides of any one of SEQ ID NOs: 25-36.

In general, "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the native amino acid sequence of the gene of interest. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode the polypeptide or the polynucleotide of interest. Generally, variants of a particular polynucleotide disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide disclosed herein (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

In particular embodiments, the presently disclosed polynucleotides encode an RNA-guided nuclease polypeptide comprising an amino acid sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to any one of the amino acid sequences set forth as SEQ ID NOs: 1-12.

A biologically active variant of an RGN polypeptide of the invention may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N-terminal or a C-terminal truncation, which can comprise at least a deletion of 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700 amino acids or more from either the N or C terminus of the polypeptide.

In certain embodiments, the presently disclosed polynucleotides comprise or encode a CRISPR repeat comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to any one of the nucleotide sequences set forth as SEQ ID NOs: 13-24.

The presently disclosed polynucleotides can comprise or encode a tracrRNA comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to any one of the nucleotide sequences set forth as SEQ ID NOs: 25-36.

Biologically active variants of a CRISPR repeat or tracrRNA of the invention may differ by as few as about 1-15 nucleotides, as few as about 1-10, such as about 6-10, as few as 5, as few as 4, as few as 3, as few as 2, or as few as 1 nucleotide. In specific embodiments, the polynucleotides can comprise a 5' or 3' truncation, which can comprise at least a deletion of 10, 15, 20, 25, 30, 35, 40, 45, 50, 55, 60, 65, 70, 75, 80, 90, 95, 100, 105, 110 nucleotides or more from either the 5' or 3' end of the polynucleotide.

It is recognized that modifications may be made to the RGN polypeptides, CRISPR repeats, and tracrRNAs provided herein creating variant proteins and polynucleotides. Changes designed by man may be introduced through the application of site-directed mutagenesis techniques. Alternatively, native, as yet-unknown or as yet unidentified polynucleotides and/or polypeptides structurally and/or functionally-related to the sequences disclosed herein may also be identified that fall within the scope of the present invention. Conservative amino acid substitutions may be made in nonconserved regions that do not alter the function of the RGN proteins. Alternatively, modifications may be made that improve the activity of the RGN.

Variant polynucleotides and proteins also encompass sequences and proteins derived from a mutagenic and recombinogenic procedure such as DNA shuffling. With such a procedure, one or more different RGN proteins disclosed herein (e.g., SEQ ID NOs: 1-12) is manipulated to create a new RGN protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the RGN sequences provided herein and other known RGN genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), for example in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

As used herein. "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein. "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins." In "Atlas of Protein Sequence and Structure." Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols. The gap existence penalty is imposed for the introduction of a single amino acid gap in one of the aligned sequences, and the gap extension penalty is imposed for each additional empty amino acid position inserted into an already opened gap. The alignment is defined by the amino acid positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (www.ncbi.nlm.nih.gov). Optimal alignments, including multiple alignments, can be prepared using, e.g., PSI-BLAST, available through www.ncbi.nlm.nih.gov and described by Altschul et al. (1997) *Nucleic Acids Res.* 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

VI. Antibodies

Antibodies to the RGN polypeptides or ribonucleoproteins comprising the RGN polypeptides of the present invention, including those having any one of the amino acid sequences set forth as SEQ ID NOs: 1-12 or active variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, N. Y.; and U.S. Pat. No. 4,196,265). These antibodies can be used in kits for the detection and isolation of RGN polypeptides or ribonucleoproteins. Thus, this disclosure provides kits comprising antibodies that specifically bind to the polypeptides or ribonucleoproteins described herein, including, for example, polypeptides having any one of the amino acid sequences set forth as SEQ ID NOs: 1-12.

VII. Systems and Ribonucleoprotein Complexes for Binding a Target Sequence of Interest and Methods of Making the Same The present disclosure provides a system for binding a target sequence of interest, wherein the system comprises at least one guide RNA or a nucleotide sequence encoding the same, and at least one RNA-guided nuclease or a nucleotide sequence encoding the same. The guide RNA hybridizes to the target sequence of interest and also forms a complex with the RGN polypeptide, thereby directing the RGN polypeptide to bind to the target sequence. In some of these embodiments, the RGN comprises any one of the amino acid sequences set forth as SEQ ID NOs: 1-12, or an active variant or fragment thereof. In various embodiments, the guide RNA comprises a CRISPR repeat sequence comprising any one of the nucleotide sequences set forth as SEQ ID NOs: 13-24, or an active variant or fragment thereof. In particular embodiments, the guide RNA comprises a tracrRNA comprising any one of the nucleotide sequences set forth as SEQ ID NOs: 25-36, or an active variant or fragment thereof. The guide RNA of the system can be a single guide RNA or a dual-guide RNA. In particular embodiments, the system comprises an RNA-guided nuclease that is heterologous to the guide RNA, wherein the RGN and guide RNA are not found complexed to one another (i.e., bound to one another) in nature.

The system for binding a target sequence of interest provided herein can be a ribonucleoprotein complex, which is at least one molecule of an RNA bound to at least one protein. The ribonucleoprotein complexes provided herein comprise at least one guide RNA as the RNA component and an RNA-guided nuclease as the protein component. Such ribonucleoprotein complexes can be purified from a cell or organism that naturally expresses an RGN polypeptide and has been engineered to express a particular guide RNA that is specific for a target sequence of interest. Alternatively, the ribonucleoprotein complex can be purified from a cell or organism that has been transformed with polynucleotides that encode an RGN polypeptide and a guide RNA and cultured under conditions to allow for the expression of the RGN polypeptide and guide RNA. Thus, methods are provided for making an RGN polypeptide or an RGN ribonucleoprotein complex. Such methods comprise culturing a cell comprising a nucleotide sequence encoding an RGN polypeptide, and in some embodiments a nucleotide sequence encoding a guide RNA, under conditions in which the RGN polypeptide (and in some embodiments, the guide RNA) is expressed. The RGN polypeptide or RGN ribonucleoprotein can then be purified from a lysate of the cultured cells. In embodiments, the nucleotide sequence encoding an RGN polypeptide includes a mRNA (messenger RNA). In some embodiments, methods for assembling an RNP complex comprise combining one or more of the presently disclosed guide RNAs and one or more of the presently disclosed RGN polypeptides under conditions suitable for formation of the RNP complex.

Methods for purifying an RGN polypeptide or RGN ribonucleoprotein complex from a lysate of a biological sample are known in the art (e.g., size exclusion and/or affinity chromatography, 2D-PAGE, HPLC, reversed-phase chromatography, immunoprecipitation). In particular methods, the RGN polypeptide is recombinantly produced and comprises a purification tag to aid in its purification, including but not limited to, glutathione-S-transferase (GST), chitin binding protein (CBP), maltose binding protein, thioredoxin (TRX), poly (NANP), tandem affinity purification (TAP) tag, myc, AcV5, AU1, AUS, E, ECS, E2, FLAG (e.g., 3×FLAG tag), HA, nus, Softag 1, Softag 3, Strep, SBP, Glu-Glu, HSV, KT3, S. S1, T7, V5, VSV-G, 6×His, 10×His, biotin carboxyl carrier protein (BCCP), and calmodulin. Generally, the tagged RGN polypeptide or RGN ribonucleoprotein complex is purified using immobilized metal affinity chromatography. It will be appreciated that other similar methods known in the art may be used, including other forms of chromatography or for example immunoprecipitation, either alone or in combination.

An "isolated" or "purified" polypeptide, or biologically active portion thereof, is substantially or essentially free from components that normally accompany or interact with the polypeptide as found in its naturally occurring environment. Thus, an isolated or purified polypeptide is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals. Similarly, an "isolated" polynucleotide or nucleic acid molecule is removed from its naturally occurring environment. An isolated polynucleotide is substantially free of chemical precursors or other chemicals when chemically synthesized or has been removed from a genomic locus via the breaking of phosphodiester bonds. An isolated polynucleotide can be part of a vector, a composition of matter or can be contained within a cell so long as the cell is not the original environment of the polynucleotide.

Particular methods provided herein for binding and/or cleaving a target sequence of interest involve the use of an in vitro assembled RGN ribonucleoprotein complex. In vitro assembly of an RGN ribonucleoprotein complex can be performed using any method known in the art in which an RGN polypeptide is contacted with a guide RNA under conditions to allow for binding of the RGN polypeptide to the guide RNA. As used herein, "contact", contacting", "contacted," refer to placing the components of a desired reaction together under conditions suitable for carrying out the desired reaction. The RGN polypeptide can be purified from a biological sample, cell lysate, or culture medium, produced via in vitro translation, or chemically synthesized. The guide RNA can be purified from a biological sample, cell lysate, or culture medium, transcribed in vitro, or chemically synthesized. The RGN polypeptide and guide RNA can be brought into contact in solution (e.g., buffered saline solution) to allow for in vitro assembly of the RGN ribonucleoprotein complex.

VIII. Methods of Binding, Cleaving, or Modifying a Target Sequence

The present disclosure provides methods for binding, cleaving, and/or modifying a target nucleotide sequence of interest. The methods include delivering a system comprising at least one guide RNA or a polynucleotide encoding the same, and at least one RGN polypeptide or a polynucleotide encoding the same to the target sequence or a cell, organelle, or embryo comprising the target sequence. In some of these embodiments, the RGN comprises any one of the amino acid sequences set forth as SEQ ID NOs: 1-12, or an active variant or fragment thereof. In various embodiments, the guide RNA comprises a CRISPR repeat sequence comprising any one of the nucleotide sequences set forth as SEQ ID NOs: 13-24, or an active variant or fragment thereof. In particular embodiments, the guide RNA comprises a tracrRNA comprising any one of the nucleotide sequences set forth as SEQ ID NOs: 25-36, or an active variant or fragment thereof. The guide RNA of the system can be a single guide RNA or a dual-guide RNA.

The RGN of the system may be a nuclease dead RGN, have nickase activity, or may be a fusion polypeptide. In some embodiments, the fusion polypeptide comprises a base-editing polypeptide, for example a cytosine deaminase or an adenine deaminase. In other embodiments, the RGN fusion protein comprises a reverse transcriptase. In other embodiments, the RGN fusion protein comprises a polypeptide that recruits members of a functional nucleic acid repair complex, such as a member of the nucleotide excision repair (NER) or transcription coupled-nucleotide excision repair (TC-NER) pathway (Wei et al., 2015, PNAS USA 112 (27): E3495-504; Troelstra et al., 1992, *Cell* 71:939-953; Marnef et al., 2017, *J Mol Biol* 429 (9): 1277-1288), as described in U.S. Provisional Application No. 62/966,203, which was filed on Jan. 27, 2020, and is incorporated by reference in its entirety. In some embodiments, the RGN fusion protein comprises CSB (van den Boom et al., 2004, *J Cell Biol* 166 (1): 27-36; van Gool et al., 1997, *EMBO J* 16 (19): 5955-65; an example of which is set forth as SEQ ID NO: 324), which is a member of the TC-NER (nucleotide excision repair) pathway and functions in the recruitment of other members. In further embodiments, the RGN fusion protein comprises an active domain of CSB, such as the acidic domain of CSB which comprises amino acid residues 356-394 of SEQ ID NO: 324 (Teng et al., 2018, *Nat Commun* 9 (1): 4115).

In particular embodiments, the RGN and/or guide RNA is heterologous to the cell, organelle, or embryo to which the RGN and/or guide RNA (or polynucleotide(s) encoding at least one of the RGN and guide RNA) are introduced.

In those embodiments wherein the method comprises delivering a polynucleotide encoding a guide RNA and/or an RGN polypeptide, the cell or embryo can then be cultured under conditions in which the guide RNA and/or RGN polypeptide are expressed. In various embodiments, the method comprises contacting a target sequence with an RGN ribonucleoprotein complex. The RGN ribonucleoprotein complex may comprise an RGN that is nuclease dead or has nickase activity. In some embodiments, the RGN of the ribonucleoprotein complex is a fusion polypeptide comprising a base-editing polypeptide. In certain embodiments, the method comprises introducing into a cell, organelle, or embryo comprising a target sequence an RGN ribonucleoprotein complex. The RGN ribonucleoprotein complex can be one that has been purified from a biological sample, recombinantly produced and subsequently purified, or in vitro-assembled as described herein. In those embodiments wherein the RGN ribonucleoprotein complex that is contacted with the target sequence or a cell organelle, or embryo has been assembled in vitro, the method can further comprise the in vitro assembly of the complex prior to contact with the target sequence, cell, organelle, or embryo.

A purified or in vitro assembled RGN ribonucleoprotein complex can be introduced into a cell, organelle, or embryo using any method known in the art, including, but not limited to electroporation. Alternatively, an RGN polypeptide and/or polynucleotide encoding or comprising the guide RNA can be introduced into a cell, organelle, or embryo using any method known in the art (e.g., electroporation).

Upon delivery to or contact with the target sequence or cell, organelle, or embryo comprising the target sequence, the guide RNA directs the RGN to bind to the target sequence in a sequence-specific manner. In those embodiments wherein the RGN has nuclease activity, the RGN polypeptide cleaves the target sequence of interest upon binding. The target sequence can subsequently be modified via endogenous repair mechanisms, such as non-homologous end joining, or homology-directed repair with a provided donor polynucleotide.

Methods to measure binding of an RGN polypeptide to a target sequence are known in the art and include chromatin immunoprecipitation assays, gel mobility shift assays, DNA pull-down assays, reporter assays, microplate capture and detection assays. Likewise, methods to measure cleavage or modification of a target sequence are known in the art and include in vitro or in vivo cleavage assays wherein cleavage is confirmed using PCR, sequencing, or gel electrophoresis, with or without the attachment of an appropriate label (e.g., radioisotope, fluorescent substance) to the target sequence to facilitate detection of degradation products. Alternatively, the nicking triggered exponential amplification reaction (NTEXPAR) assay can be used (see, e.g., Zhang et al. (2016) *Chem. Sci.* 7:4951-4957). In vivo cleavage can be evaluated using the Surveyor assay (Guschin et al. (2010) *Methods Mol Biol* 649:247-256).

In some embodiments, the methods involve the use of a single type of RGN complexed with more than one guide RNA. The more than one guide RNA can target different regions of a single gene or can target multiple genes.

In those embodiments wherein a donor polynucleotide is not provided, a double-stranded break introduced by an RGN polypeptide can be repaired by a non-homologous end-joining (NHEJ) repair process. Due to the error-prone nature of NHEJ, repair of the double-stranded break can result in a modification to the target sequence. As used herein, a "modification" in reference to a nucleic acid molecule refers to a change in the nucleotide sequence of the nucleic acid molecule, which can be a deletion, insertion, or substitution of one or more nucleotides, or a combination thereof. Modification of the target sequence can result in the expression of an altered protein product or inactivation of a coding sequence.

In those embodiments wherein a donor polynucleotide is present, the donor sequence in the donor polynucleotide can be integrated into or exchanged with the target nucleotide sequence during the course of repair of the introduced double-stranded break, resulting in the introduction of the exogenous donor sequence. A donor polynucleotide thus comprises a donor sequence that is desired to be introduced into a target sequence of interest. In some embodiments, the donor sequence alters the original target nucleotide sequence such that the newly integrated donor sequence will not be recognized and cleaved by the RGN. Integration of the donor sequence can be enhanced by the inclusion within the donor polynucleotide of flanking sequences, referred to herein as "homology arms" that have substantial sequence identity with the sequences flanking the target nucleotide sequence, allowing for a homology-directed repair process. In some embodiments, homology arms have a length of at least 50 base pairs, at least 100 base pairs, and up to 2000 base pairs or more, and have at least 90%, at least 95%, or more, sequence homology to their corresponding sequence within the target nucleotide sequence.

In those embodiments wherein the RGN polypeptide introduces double-stranded staggered breaks, the donor polynucleotide can comprise a donor sequence flanked by compatible overhangs, allowing for direct ligation of the donor sequence to the cleaved target nucleotide sequence comprising overhangs by a non-homologous repair process during repair of the double-stranded break.

In those embodiments wherein the method involves the use of an RGN that is a nickase (i.e., is only able to cleave a single strand of a double-stranded polynucleotide), the method can comprise introducing two RGN nickases that target identical or overlapping target sequences and cleave different strands of the polynucleotide. For example, an RGN nickase that only cleaves the positive (+) strand of a double-stranded polynucleotide can be introduced along with a second RGN nickase that only cleaves the negative (−) strand of a double-stranded polynucleotide.

In various embodiments, a method is provided for binding a target nucleotide sequence and detecting the target sequence, wherein the method comprises introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN and further comprises a detectable label, and the method further comprises detecting the detectable label. The detectable label may be fused to the RGN as a fusion protein (e.g., fluorescent protein) or may be a small molecule conjugated to or incorporated within the RGN polypeptide that can be detected visually or by other means.

Also provided herein are methods for modulating the expression of a target sequence or a gene of interest under the regulation of a target sequence. The methods comprise introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN. In some of these embodiments, the nuclease-dead RGN is a fusion protein comprising an expression modulator domain (i.e., epigenetic modification domain, transcriptional activation domain or a transcriptional repressor domain) as described herein.

The present disclosure also provides methods for binding and/or modifying a target nucleotide sequence of interest. The methods include delivering a system comprising at least one guide RNA or a polynucleotide encoding the same, and at least one fusion polypeptide comprises an RGN of the invention and a base-editing polypeptide, for example a cytosine deaminase or an adenine deaminase, or a polynucleotide encoding the fusion polypeptide, to the target sequence or a cell, organelle, or embryo comprising the target sequence.

One of ordinary skill in the art will appreciate that any of the presently disclosed methods can be used to target a single target sequence or multiple target sequences. Thus, methods comprise the use of a single RGN polypeptide in combination with multiple, distinct guide RNAs, which can target multiple, distinct sequences within a single gene and/or multiple genes. Also encompassed herein are methods wherein multiple, distinct guide RNAs are introduced in combination with multiple, distinct RGN polypeptides. These guide RNAs and guide RNA/RGN polypeptide systems can target multiple, distinct sequences within a single gene and/or multiple genes.

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a DNA sequence encoding the crRNA sequence and one or more insertion sites for inserting a guide sequence upstream of the encoded crRNA sequence, wherein when expressed, the guide sequence directs sequence-specific binding of an RGN complex to a target sequence in a eukaryotic cell, wherein the RGN complex comprises an RGN enzyme complexed with the guide RNA polynucleotide; and/or (b) a second regulatory element operably linked to an enzyme coding sequence encoding said RGN enzyme comprising a nuclear localization sequence. Elements may be provided individually or in combinations, and may be provided in any suitable container, such as a vial, a bottle, or a tube.

In some embodiments, the kit includes instructions in one or more languages. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In one aspect, the invention provides methods for using one or more elements of an RGN system. The RGN system of the invention provides an effective means for modifying a target polynucleotide. The RGN system of the invention has a wide variety of utility including modifying (e.g., deleting, inserting, translocating, inactivating, activating, base editing) a target polynucleotide in a multiplicity of cell types. As such the RGN system of the invention has a broad spectrum of applications in, e.g., gene therapy, drug screening, disease diagnosis, and prognosis. An exemplary RGN system, or RGN complex, comprises an RGN enzyme complexed with a guide sequence hybridized to a target sequence within the target polynucleotide.

IX. Target Polynucleotides

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including microalgae) and modifying the cell or cells. Culturing may occur at any stage ex vivo. The cell or cells may even be re-introduced into the non-human animal or plant (including microalgae).

Using natural variability, plant breeders combine most useful genes for desirable qualities, such as yield, quality, uniformity, hardiness, and resistance against pests. These desirable qualities also include growth, day length preferences, temperature requirements, initiation date of floral or reproductive development, fatty acid content, insect resistance, disease resistance, nematode resistance, fungal resistance, herbicide resistance, tolerance to various environmental factors including drought, heat, wet, cold, wind, and adverse soil conditions including high salinity The sources of these useful genes include native or foreign varieties, heirloom varieties, wild plant relatives, and induced mutations, e.g., treating plant material with mutagenic agents. Using the present invention, plant breeders are provided with a new tool to induce mutations. Accordingly, one skilled in the art can analyze the genome for sources of useful genes, and in varieties having desired characteristics or traits employ the present invention to induce the rise of useful genes, with more precision than previous mutagenic agents and hence accelerate and improve plant breeding programs.

The target polynucleotide of an RGN system can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, the target sequence should be associated with a PAM (protospacer adjacent motif); that is, a short sequence recognized by the RGN system. The precise sequence and length requirements for the PAM differ depending on the RGN used, but PAMs are typically 2-7 base pair sequences adjacent to the protospacer (that is, the target sequence).

The target polynucleotide of an RGN system may include a number of disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease (e.g., a causal mutation). The causal mutation may be an expanded repeat (present at higher numbers than those in normal individuals) that leads to instability of transcribed mRNA, altered splicing, or instability of a translated product or a translated product with reduced activity. The transcribed or translated products may be known or unknown, and further may be at a normal or abnormal level. In some embodiments, the disease may be an animal disease. In some embodiments, the disease may be an avian disease. In other embodiments, the disease may be a mammalian disease. In further embodiments, the disease may be a human disease. Examples of disease-associated genes and polynucleotides in humans are provided in Table 6 and are also available from McKusick-Nathans Institute of Genetic Medicine, Johns Hopkins University (Baltimore, Md.) and National Center for Biotechnology Information, National Library of Medicine (Bethesda, Md.), available on the World Wide Web.

Although RGN systems are particularly useful for their relative ease in targeting to genomic sequences of interest, there still remains an issue of what the RGN can do to address a causal mutation. One approach is to produce a fusion protein between an RGN (preferably an inactive or nickase variant of the RGN) and a base-editing enzyme or the active domain of a base editing enzyme, such as a cytosine deaminase or an adenine deaminase base editor (U.S. Pat. No. 9,840,699, herein incorporated by reference). In some embodiments, the methods comprise contacting a DNA molecule with (a) a fusion protein comprising an RGN of the invention or a nickase variant thereof and a base-editing polypeptide such as a deaminase; and (b) a gRNA targeting the fusion protein of (a) to a target nucleotide sequence of the DNA strand; wherein the DNA molecule is contacted with the fusion protein and the gRNA in an amount effective and under conditions suitable for the deamination of a nucleobase. In some embodiments, the target DNA sequence comprises a sequence associated with a disease or disorder, and wherein the deamination of the nucleobase results in a sequence that is not associated with a disease or disorder. In some embodiments, the target DNA sequence resides in an allele of a crop plant, wherein the particular allele of the trait of interest results in a plant of lesser agronomic value. The deamination of the nucleobase results in an allele that improves the trait and increases the agronomic value of the plant.

In some embodiments, the DNA sequence comprises a T→C or A→G point mutation associated with a disease or disorder, and wherein the deamination of the mutant C or G base results in a sequence that is not associated with a disease or disorder. In some embodiments, the deamination corrects a point mutation in the sequence associated with the disease or disorder.

In some embodiments, the sequence associated with the disease or disorder encodes a protein, and wherein the deamination introduces a stop codon into the sequence associated with the disease or disorder, resulting in a truncation of the encoded protein. In some embodiments, the contacting is performed in vivo in a subject susceptible to having, having, or diagnosed with the disease or disorder. In some embodiments, the disease or disorder is a disease associated with a point mutation, or a single-base mutation, in the genome. In some embodiments, the disease is a genetic disease, a cancer, a metabolic disease, or a lysosomal storage disease.

X. Pharmaceutical Compositions and Methods of Treatment

Pharmaceutical compositions comprising the presently disclosed RGN polypeptides and active variants and fragments thereof, as well as polynucleotides encoding the same, the presently disclosed gRNAs or polynucleotides encoding the same, the presently disclosed systems, or cells comprising any of the RGN polypeptides or RGN-encoding polynucleotides, gRNA or gRNA-encoding polynucleotides, or the RGN systems, and a pharmaceutically acceptable carrier are provided.

A pharmaceutical composition is a composition that is employed to prevent, reduce in intensity, cure or otherwise treat a target condition or disease that comprises an active ingredient (i.e., RGN polypeptides, RGN-encoding polynucleotides, gRNA, gRNA-encoding polynucleotides, RGN systems, or cells comprising any one of these) and a pharmaceutically acceptable carrier.

As used herein, a "pharmaceutically acceptable carrier" refers to a material that does not cause significant irritation to an organism and does not abrogate the activity and properties of the active ingredient (i.e., RGN polypeptides, RGN-encoding polynucleotides, gRNA, gRNA-encoding polynucleotides, RGN systems, or cells comprising any one of these). Carriers must be of sufficiently high purity and of sufficiently low toxicity to render them suitable for administration to a subject being treated. The carrier can be inert, or it can possess pharmaceutical benefits. In some embodiments, a pharmaceutically acceptable carrier comprises one or more compatible solid or liquid filler, diluents or encapsulating substances which are suitable for administration to a human or other vertebrate animal. In some embodiments, the pharmaceutically acceptable carrier is not naturally-occurring. In some embodiments, the pharmaceutically acceptable carrier and the active ingredient are not found together in nature.

Pharmaceutical compositions used in the presently disclosed methods can be formulated with suitable carriers, excipients, and other agents that provide suitable transfer, delivery, tolerance, and the like. A multitude of appropriate formulations are known to those skilled in the art. See, e.g., Remington, The Science and Practice of Pharmacy (21st ed. 2005). Suitable formulations include, for example, powders, pastes, ointments, jellies, waxes, oils, lipids, lipid (cationic or anionic) containing vesicles (such as LIPOFECTIN vesicles), lipid nanoparticles, DNA conjugates, anhydrous absorption pastes, oil-in-water and water-in-oil emulsions, emulsions carbowax (polyethylene glycols of various molecular weights), semi-solid gels, and semi-solid mixtures containing carbowax. Pharmaceutical compositions for oral or parenteral use may be prepared into dosage forms in a unit dose suited to fit a dose of the active ingredients. Such dosage forms in a unit dose include, for example, tablets, pills, capsules, injections (ampoules), suppositories, etc.

In some embodiments wherein cells comprising or modified with the presently disclosed RGN, gRNAs, RGN systems or polynucleotides encoding the same are administered to a subject, the cells are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the cells described herein using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable and pharmaceutically acceptable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

The presently disclosed RGN polypeptides, guide RNAs, RGN systems or polynucleotides encoding the same can be formulated with pharmaceutically acceptable excipients such as carriers, solvents, stabilizers, adjuvants, diluents, etc., depending upon the particular mode of administration and dosage form. In some embodiments, these pharmaceutical compositions are formulated to achieve a physiologically compatible pH, and range from a pH of about 3 to a pH of about 11, about pH 3 to about pH 7, depending on the formulation and route of administration. In some embodiments, the pH can be adjusted to a range from about pH 5.0 to about pH 8. In some embodiments, the compositions can comprise a therapeutically effective amount of at least one compound as described herein, together with one or more pharmaceutically acceptable excipients. In some embodiments, the compositions comprise a combination of the compounds described herein, or include a second active ingredient useful in the treatment or prevention of bacterial growth (for example and without limitation, anti-bacterial or anti-microbial agents), or include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

In some embodiments, the formulations are provided in unit-dose or multi-dose containers, for example sealed ampules and vials, and may be stored in a freeze-dried (lyophilized) condition requiring the addition of the sterile liquid carrier, for example, saline, water-for-injection, a semi-liquid foam, or gel, immediately prior to use. Extemporaneous injection solutions and suspensions may be prepared from sterile powders, granules and tablets of the kind previously described. In some embodiments, the active ingredient is dissolved in a buffered liquid solution that is frozen in a unit-dose or multi-dose container and later thawed for injection or kept/stabilized under refrigeration until use.

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. In some embodiments, the use of a long-term sustained release implant may be particularly suitable for treatment of chronic conditions. Long-term sustained release implants are well-known to those of ordinary skill in the art.

Methods of treating a disease in a subject in need thereof are provided herein. The methods comprise administering to a subject in need thereof an effective amount of a presently disclosed RGN polypeptide or active variant or fragment thereof or a polynucleotide encoding the same, a presently disclosed gRNA or a polynucleotide encoding the same, a presently disclosed RGN system, or a cell modified by or comprising any one of these compositions.

In some embodiments, the treatment comprises in vivo gene editing by administering a presently disclosed RGN polypeptide, gRNA, or RGN system or polynucleotide(s) encoding the same. In some embodiments, the treatment comprises ex vivo gene editing wherein cells are genetically modified ex vivo with a presently disclosed RGN polypeptide, gRNA, or RGN system or polynucleotide(s) encoding the same and then the modified cells are administered to a subject. In some embodiments, the genetically modified cells originate from the subject that is then administered the modified cells, and the transplanted cells are referred to herein as autologous. In some embodiments, the genetically modified cells originate from a different subject (i.e., donor) within the same species as the subject that is administered the modified cells (i.e., recipient), and the transplanted cells are referred to herein as allogeneic. In some examples described herein, the cells can be expanded in culture prior to administration to a subject in need thereof.

In some embodiments, the disease to be treated with the presently disclosed compositions is one that can be treated with immunotherapy, such as with a chimeric antigen receptor (CAR) T cell. Such diseases include but are not limited to cancer. In some embodiments, the disease to be treated with the presently disclosed compositions is associated with a causal mutation. As used herein, a "causal mutation" refers to a particular nucleotide, nucleotides, or nucleotide sequence in the genome that contributes to the severity or presence of a disease or disorder in a subject. The correction of the causal mutation leads to the improvement of at least one symptom resulting from a disease or disorder. In some embodiments, the causal mutation is adjacent to a PAM site recognized by an RGN disclosed herein. The causal mutation can be corrected with a presently disclosed RGN or a fusion polypeptide comprising a presently disclosed RGN and a base-editing polypeptide (i.e., a base editor). Non-limiting examples of diseases associated with a causal mutation include cystic fibrosis, Hurler syndrome, Friedreich's Ataxia, Huntington's Disease, and sickle cell disease. In some embodiments, the disease to be treated with the presently disclosed RGNs is a disease listed in Table 6. Additional non-limiting examples of disease-associated genes and mutations are available from McKusick-Nathans Institute of Genetic Medicine, Johns Hopkins University (Baltimore, Md.) and National Center for Biotechnology Information, National Library of Medicine (Bethesda, Md.), available on the World Wide Web.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. In some embodiments, treatment may be administered after one or more symptoms have developed and/or after a disease has been diagnosed. In particular embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their prevention or recurrence.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific dose may vary depending on one or more of: the particular agent chosen, the dosing regimen to be followed, whether it is administered in combination with other compounds, timing of administration, and the delivery system in which it is carried.

The term "administering" refers to the placement of an active ingredient into a subject, by a method or route that results in at least partial localization of the introduced active ingredient at a desired site, such as a site of injury or repair, such that a desired effect(s) is produced. In some embodiments, the disclosure provides methods comprising delivering any of the RGN polypeptides, nucleic acid molecules, ribonucleoprotein complexes, vectors, pharmaceutical compositions and/or gRNAs described herein. In some embodiments, the disclosure further provides cells produced by such methods, and organisms (such as animals or plants) comprising or produced from such cells. In some embodiments, a RGN polypeptide and/or nucleic acid molecules as described herein in combination with (and optionally complexed with) a guide sequence is delivered to a cell.

In those embodiments wherein cells are administered, the cells can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the patient, i.e., long-term engraftment. For example, in some aspects described herein, an effective amount of photoreceptor cells or retinal progenitor cells is administered via a systemic route of administration, such as an intraperitoneal or intravenous route.

In some embodiments, the administering comprises administering by viral delivery. Viral vectors comprising a nucleic acid encoding the RGN polypeptides, ribonucleoprotein complexes, or vectors disclosed herein may be administered directly to patients (i.e., in vivo) or they may be used to treat cells in vitro, and the modified cells may optionally be administered to patients (i.e., ex vivo). Conventional viral based systems may include, without limitation, retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Lentiviral vectors are retroviral vectors that are able to transduce or infect non-dividing cells and typically produce high viral titers. In applications where transient expression is preferred, adenoviral based systems may be used. Adenoviral based vectors are capable of very high transduction efficiency in many cell types and do not require cell division.

In some embodiments, the administering comprises administering by other non-viral delivery of nucleic acids. Exemplary non-viral delivery methods, without limitation, include RNP complexes, lipofection, nucleofection, microinjection, biolistics, virosomes, liposomes, immunoliposomes, polycation or lipidmucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO1991/17424; WO 1991/16024. Delivery can be to cells (e.g., in vitro or ex vivo administration) or target tissues (e.g., in vivo administration).

In some embodiments, the administering comprises administering by a method selected from the group consisting of: intravenously, subcutaneously, intramuscularly, orally, rectally, by aerosol, parenterally, ophthalmically, pulmonarily, transdermally, vaginally, otically, nasally, and by topical administration, or any combination thereof. In some embodiments, for the delivery of cells, administration by injection or infusion is used.

As used herein, the term "subject" refers to any individual for whom diagnosis, treatment or therapy is desired. In some embodiments, the subject is an animal. In some embodiments, the subject is a mammal. In some embodiments, the subject is a human being.

The efficacy of a treatment can be determined by the skilled clinician. However, a treatment is considered an "effective treatment," if any one or all of the signs or symptoms of a disease or disorder are altered in a beneficial manner (e.g., decreased by at least 10%), or other clinically accepted symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art. Treatment includes: (1) inhibiting the disease, e.g., arresting, or slowing the progression of symptoms; or (2) relieving the disease, e.g., causing regression of symptoms; and (3) preventing or reducing the likelihood of the development of symptoms.

Pharmaceutical compositions comprising the presently disclosed RGN polypeptides or polynucleotides encoding the same, the presently disclosed gRNAs or polynucleotides encoding the same, the presently disclosed systems, the presently disclosed ribonucleoprotein complexes or cells comprising any of the RGN polypeptides or RGN-encoding polynucleotides, gRNA or gRNA-encoding polynucleotides, or the systems, and a pharmaceutically acceptable carrier are provided.

As used herein, a "pharmaceutically acceptable carrier" refers to a material that does not cause significant irritation to an organism and does not abrogate the activity and properties of the active ingredient (e.g., an RGN polypeptide or nucleic acid molecule encoding the same). Carriers must be of sufficiently high purity and of sufficiently low toxicity to render them suitable for administration to a subject being treated. The carrier can be inert, or it can possess pharmaceutical benefits. In some embodiments, a pharmaceutically acceptable carrier comprises one or more compatible solid or liquid filler, diluents or encapsulating substances which are suitable for administration to a human or other vertebrate animal. In some embodiments, the pharmaceutical composition comprises a pharmaceutically acceptable carrier that is non-naturally occurring. In some embodiments, the pharmaceutically acceptable carrier and the active ingredient are not found together in nature and are thus, heterologous.

Pharmaceutical compositions used in the presently disclosed methods can be formulated with suitable carriers, excipients, and other agents that provide suitable transfer, delivery, tolerance, and the like. A multitude of appropriate formulations are known to those skilled in the art. See, e.g., Remington, The Science and Practice of Pharmacy (21st ed. 2005). Non-limiting examples include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Administered intravenously, particular carriers are physiological saline or phosphate buffered saline (PBS). Pharmaceutical compositions for oral or parenteral use may be prepared into dosage forms in a unit dose suited to fit a dose of the active ingredients. Such dosage forms in a unit dose include, for example, tablets, pills, capsules, injections (ampoules), suppositories, etc. These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

In some embodiments wherein cells comprising or modified with the presently disclosed RGNs, gRNAs, systems, or polynucleotides encoding the same are administered to a subject, the cells are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the cells described herein using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Suitable routes of administering the pharmaceutical compositions described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration.

In some embodiments, a pharmaceutical composition described herein is administered locally to a diseased site (e.g., the lung). In some embodiments, the pharmaceutical composition described herein is administered to a subject by injection, inhalation (e.g., of an aerosol), by means of a catheter, by means of a suppository, or by means of an implant, the implant being of a porous, non-porous, or gelatinous material, including a membrane, such as a sialastic membrane, or a fiber. In some embodiments, the pharmaceutical composition is formulated for delivery to a subject, e.g., for gene editing.

In some embodiments, the pharmaceutical composition is formulated in accordance with routine procedures as a composition adapted for intravenous or subcutaneous administration to a subject, e.g., a human. In some embodiments, pharmaceutical composition for administration by injection are solutions in sterile isotonic aqueous buffer.

Where necessary, the pharmaceutical can also include a solubilizing agent and a local anesthetic such as lignocaine to ease pain at the site of the injection. Generally, the ingredients are supplied either separately or mixed together, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical composition is administered by injection, an ampoule of sterile water for injection or saline can be provided so that the ingredients can be mixed prior to administration.

In some embodiments, the pharmaceutical composition can be contained within a lipid particle or vesicle, such as a liposome or microcrystal, which is also suitable for parenteral administration.

Although the descriptions of pharmaceutical compositions provided herein are principally directed to pharmaceutical compositions which are suitable for administration to humans, it will be understood by the skilled artisan that such compositions are generally suitable for administration to animals or organisms of all sorts.

A. Modifying Causal Mutations Using Base-Editing

An example of a genetically inherited disease which could be corrected using an approach that relies on an RGN-base editor fusion protein of the invention is Hurler Syndrome. Hurler Syndrome, also known as MPS-1, is the result of a deficiency of α-L-iduronidase (IDUA) resulting in a lysosomal storage disease characterized at the molecular level by the accumulation of dermatan sulfate and heparan sulfate in lysosomes. This disease is generally an inherited genetic disorder caused by mutations in the IDUA gene encoding α-L-iduronidase. Common IDUA mutations are W402X and Q70X, both nonsense mutations resulting in premature termination of translation. Such mutations are well addressed by precise genome editing (PGE) approaches, since reversion of a single nucleotide, for example by a base-editing approach, would restore the wild-type coding sequence and result in protein expression controlled by the endogenous regulatory mechanisms of the genetic locus. Additionally, since heterozygotes are known to be asymptomatic, a PGE therapy that targets one of these mutations would be useful to a large proportion of patients with this disease, as only one of the mutated alleles needs to be corrected (Bunge et al. (1994) Hum. Mol. Genet. 3 (6): 861-866, herein incorporated by reference).

Current treatments for Hurler Syndrome include enzyme replacement therapy and bone marrow transplants (Vellodi et al. (1997) Arch. Dis. Child. 76 (2): 92-99; Peters et al. (1998) Blood 91 (7): 2601-2608, herein incorporated by reference). While enzyme replacement therapy has had a dramatic effect on the survival and quality of life of Hurler Syndrome patients, this approach requires costly and time-consuming weekly infusions. Additional approaches include the delivery of the IDUA gene on an expression vector or the insertion of the gene into a highly expressed locus such as that of serum albumin (U.S. Pat. No. 9,956,247, herein incorporated by reference). However, these approaches do not restore the original IDUA locus to the correct coding sequence. A genome-editing strategy would have a number of advantages, most notably that regulation of gene expression would be controlled by the natural mechanisms present in healthy individuals. Additionally, using base editing does not necessitate causing a double stranded DNA breaks, which could lead to large chromosomal rearrangements, cell death, or oncogenecity by the disruption of tumor suppression mechanisms. A general strategy may be directed toward using RGN-base editor fusion proteins of the invention, for example those comprising LPG10136, LPG10139, LPG10134, or LPG10145, to target and correct certain disease-causing mutations in the human genome. It will be appreciated that similar approaches to target diseases that can be corrected by base-editing may also be pursued. It will be further appreciated that similar approaches to target disease-causing mutations in other species, particularly common household pets or livestock, can also be deployed using the RGNs of the invention. Common household pets and livestock include dogs, cats, horses, pigs, cows, sheep, chickens, donkeys, snakes, ferrets, and fish including salmon and shrimp.

B. Modifying Causal Mutations by Targeted Deletion

RGNs of the invention could also be useful in human therapeutic approaches where the causal mutation is more complicated. For example, some diseases such as Friedreich's Ataxia and Huntington's Disease are the result of a significant increase in repeats of a three nucleotide motif at a particular region of a gene, which affects the ability of the expressed protein to function or to be expressed. Friedreich's Ataxia (FRDA) is an autosomal recessive disease resulting in progressive degeneration of nervous tissue in the spinal cord. Reduced levels of the frataxin (FXN) protein in the mitochondria cause oxidative damages and iron deficiencies at the cellular level. The reduced FXN expression has been linked to a GAA triplet expansion within the intron 1 of the somatic and germline FXN gene. In FRDA patients, the GAA repeat frequently consists of more than 70, sometimes even more than 1000 (most commonly 600-900) triplets, whereas unaffected individuals have about 40 repeats or less (Pandolfo et al. (2012) Handbook of Clinical Neurology 103:275-294; Campuzano et al. (1996) Science 271:1423-1427; Pandolfo (2002) Adv. Exp. Med. Biol. 516:99-118; all herein incorporated by reference).

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from *S. pyogenes* (SpCas9), are too large to be packaged into adeno-associated viral (AAV) vectors, especially when considering the length of the SpCas9 gene and the guide RNA in addition to other genetic elements required for functional expression cassettes. This makes an approach using SpCas9 more difficult. Certain RNA guided nucleases of the invention, for example, LPG10134, LPG10145, LPG10136, and LPG10139, are well suited for packaging into an AAV vector along with a guide RNA. The present invention encompasses a strategy using RGNs of the invention in which a region of genomic instability is removed. Such a strategy is applicable to other diseases and disorders which have a similar genetic basis, such as Huntington's Disease. Similar strategies using RGNs of the invention may also be applicable to similar diseases and disorders in non-human animals of agronomic or economic importance, including dogs, cats, horses, pigs, cows, sheep, chickens, donkeys, snakes, ferrets, and fish including salmon and shrimp.

C. Modifying Causal Mutations by Targeted Mutagenesis

RGNs of the invention could also be to introduce disruptive mutations that may result in a beneficial effect. Genetic defects in the genes encoding hemoglobin, particularly the beta globin chain (the HBB gene), can be responsible for a number of diseases known as hemoglobinopathies, including sickle cell anemia and thalassemias.

In adult humans, hemoglobin is a heterotetramer comprising two alpha (α)-like globin chains and two beta (β)-like globin chains and 4 heme groups. In adults the α2β2 tetramer is referred to as Hemoglobin A (HbA) or adult hemoglobin. Typically, the alpha and beta globin chains are synthesized in an approximate 1:1 ratio and this ratio seems to be critical in terms of hemoglobin and red blood cell (RBC) stabilization. In a developing fetus, a different form of hemoglobin, fetal hemoglobin (HbF), is produced which has a higher binding affinity for oxygen than Hemoglobin A such that oxygen can be delivered to the baby's system via the mother's blood stream. Fetal hemoglobin also contains two α globin chains, but in place of the adult β-globin chains, it has two fetal gamma (γ)-globin chains (i.e., fetal hemoglobin is α2γ2). The regulation of the switch from production of gamma- to beta-globin is quite complex, and primarily involves a down-regulation of gamma globin transcription with a simultaneous up-regulation of beta globin transcription. At approximately 30 weeks of gestation, the synthesis of gamma globin in the fetus starts to drop while the production of beta globin increases. By approximately 10 months of age, the newborn's hemoglobin is nearly all α2β2 although some HbF persists into adulthood (approximately 1-3% of total hemoglobin). In the majority of patients with hemoglobinopathies, the genes encoding gamma globin remain present, but expression is relatively low due to normal gene repression occurring around parturition as described above.

Sickle cell disease is caused by a V6E mutation in the β globin gene (HBB) (a GAG to GTG at the DNA level), where the resultant hemoglobin is referred to as "hemoglobinS" or "HbS." Under lower oxygen conditions, HbS molecules aggregate and form fibrous precipitates. These aggregates cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of gamma globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thalassemias (alpha thalassemias and beta thalassemia) are also diseases relating to hemoglobin and typically involve a reduced expression of globin chains. This can occur through mutations in the regulatory regions of the genes or from a mutation in a globin coding sequence that results in reduced expression or reduced levels or functional globin protein. Treatment of thalassemias usually involves blood transfusions and iron chelation therapy. Bone marrow transplants are also being used for treatment of people with severe thalassemias if an appropriate donor can be identified, but this procedure can have significant risks.

One approach that has been proposed for the treatment of both sickle cell disease (SCD) and beta thalassemias is to increase the expression of gamma globin so that HbF functionally replaces the aberrant adult hemoglobin. As mentioned above, treatment of SCD patients with hydroxyurea is thought to be successful in part due to its effect on increasing gamma globin expression (DeSimone (1982) Proc Nat'l Acad Sci USA 79 (14): 4428-31; Ley, et al., (1982) N. Engl. J. Medicine, 307:1469-1475; Ley, et al., (1983) Blood 62:370-380; Constantoulakis et al., (1988) Blood 72 (6): 1961-1967, all herein incorporated by reference). Increasing the expression of HbF involves identification of genes whose products play a role in the regulation of gamma globin expression. One such gene is BCL11A. BCL11A encodes a zinc finger protein that expressed in adult erythroid precursor cells, and down-regulation of its expression leads to an increase in gamma globin expression (Sankaran et at (2008) Science 322:1839, herein incorporated by reference). Use of an inhibitory RNA targeted to the BCL11A gene has been proposed (e.g., U.S. Patent Publication 2011/0182867, herein incorporated by reference) but this technology has several potential drawbacks, including that complete knock down may not be achieved, delivery of such RNAs may be problematic, and the RNAs must be present continuously, requiring multiple treatments for life.

RGNs of the invention, for example LPG10134, LPG10145, LPG10136, or LPG10139, may be used to target the BCL11A enhancer region to disrupt expression of BCL11A, thereby increasing gamma globin expression. This targeted disruption can be achieved by non-homologous end joining (NHEJ), whereby an RGN of the invention targets to a particular sequence within the BCL11A enhancer region, makes a double-stranded break, and the cell's machinery repairs the break, typically simultaneously introducing deleterious mutations. Similar to what is described for other disease targets, RGNs of the invention may have advantages over other known RGNs due to their relatively small size, which enables packaging expression cassettes for the RGN and its guide RNA into a single AAV vector for in vivo delivery. Similar strategies using RGNs of the invention may also be applicable to similar diseases and disorders in both humans and in non-human animals of agronomic or economic importance.

XI. Cells Comprising a Genetic Modification

Provided herein are cells and organisms comprising a target sequence of interest that has been modified using a process mediated by an RGN, crRNA, and/or tracrRNA as described herein. In some of these embodiments, the RGN comprises any one of the amino acid sequences set forth as SEQ ID NOs: 1-12, or an active variant or fragment thereof. In various embodiments, the guide RNA comprises a CRISPR repeat sequence comprising any one of the nucleotide sequences set forth as SEQ ID NOs: 13-24, or an active variant or fragment thereof. In particular embodiments, the guide RNA comprises a tracrRNA comprising any one of the nucleotide sequences set forth as SEQ ID NOs: 25-36, or an active variant or fragment thereof. The guide RNA of the system can be a single guide RNA or a dual-guide RNA.

The modified cells can be eukaryotic (e.g., mammalian, plant, insect, avian cell) or prokaryotic. Also provided are organelles and embryos comprising at least one nucleotide sequence that has been modified by a process utilizing an RGN, crRNA, and/or tracrRNA as described herein. The genetically modified cells, organisms, organelles, and embryos can be heterozygous or homozygous for the modified nucleotide sequence.

The chromosomal modification of the cell, organism, organelle, or embryo can result in altered expression (up-regulation or down-regulation), inactivation, or the expression of an altered protein product or an integrated sequence. In those embodiments wherein the chromosomal modification results in either the inactivation of a gene or the expression of a non-functional protein product, the genetically modified cell, organism, organelle, or embryo is referred to as a "knock out". The knock out phenotype can be the result of a deletion mutation (i.e., deletion of at least one nucleotide), an insertion mutation (i.e., insertion of at least one nucleotide), or a nonsense mutation (i.e., substitution of at least one nucleotide such that a stop codon is introduced).

Alternatively, the chromosomal modification of a cell, organism, organelle, or embryo can produce a "knock in", which results from the chromosomal integration of a nucleotide sequence that encodes a protein. In some of these embodiments, the coding sequence is integrated into the chromosome such that the chromosomal sequence encoding the wild-type protein is inactivated, but the exogenously introduced protein is expressed.

In other embodiments, the chromosomal modification results in the production of a variant protein product. The expressed variant protein product can have at least one amino acid substitution and/or the addition or deletion of at least one amino acid. The variant protein product encoded by the altered chromosomal sequence can exhibit modified characteristics or activities when compared to the wild-type protein, including but not limited to altered enzymatic activity or substrate specificity.

In yet other embodiments, the chromosomal modification can result in an altered expression pattern of a protein. As a non-limiting example, chromosomal alterations in the regulatory regions controlling the expression of a protein product can result in the overexpression or downregulation of the protein product or an altered tissue or temporal expression pattern.

The cells that have been modified can be grown into an organism, such as a plant, in accordance with conventional ways. See, for example, McCormick et al. (1986) *Plant Cell Reports* 5:81-84. These plants may then be grown, and either pollinated with the same modified strain or different strains, and the resulting hybrid having the genetic modification. The present invention provides genetically modified seed. Progeny, variants, and mutants of the regenerated plants are also included within the scope of the invention, provided that these parts comprise the genetic modification. Further provided is a processed plant product or byproduct that retains the genetic modification, including for example, soymeal.

The methods provided herein may be used for modification of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, *papaya*, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, *hydrangea*, hibiscus, roses, tulips, daffodils, petunias, carnation, poinsettia, and *chrysanthemum*. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

The methods provided herein can also be used to genetically modify any prokaryotic species, including but not limited to, archaea and bacteria (e.g., *Bacillus* sp., *Klebsiella* sp. *Streptomyces* sp., *Rhizobium* sp., *Escherichia* sp., *Pseudomonas* sp., *Salmonella* sp., *Shigella* sp., *Vibrio* sp., *Yersinia* sp., *Mycoplasma* sp., *Agrobacterium, Lactobacillus* sp.).

The methods provided herein can be used to genetically modify any eukaryotic species or cells therefrom, including but not limited to animals (e.g., mammals, insects, fish, birds, and reptiles), fungi, amoeba, algae, and yeast. In some embodiments, the cell that is modified by the presently disclosed methods include cells of hematopoietic origin, such as cells of the immune system including but not limited to B cells, T cells, natural killer (NK) cells, pluripotent stem cells, induced pluripotent stem cells, chimeric antigen receptor T (CAR-T) cells, monocytes, macrophages, and dendritic cells.

Cells that have been modified may be introduced into an organism. These cells could have originated from the same organism (e.g., person) in the case of autologous cellular transplants, wherein the cells are modified in an ex vivo approach. Alternatively, the cells originated from another organism within the same species (e.g., another person) in the case of allogeneic cellular transplants.

XII. Kits

Some aspects of this disclosure provide kits comprising an RGN polypeptide of the invention. In addition, in some embodiments, the kit comprises suitable reagents, buffers, and/or instructions for using the RGN polypeptide, e.g., for in vitro or in vivo DNA or RNA editing. In some embodiments, the kit comprises instructions regarding the design and use of suitable gRNAs for targeted editing of a nucleic acid sequence.

In some embodiments, the pharmaceutical composition may be provided as a pharmaceutical kit comprising (a) a container containing a composition of the disclosure in lyophilized form and (b) a second container containing a pharmaceutically acceptable diluent (e.g., sterile water) for injection. The pharmaceutically acceptable diluent can be used for reconstitution or dilution of the lyophilized compound of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration.

The article "a" and "an" are used herein to refer to one or more than one (i.e., to at least one) of the grammatical object of the article. By way of example, "a polypeptide" means one or more polypeptides.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the appended embodiments.

Non-limiting embodiments include:

1. A nucleic acid molecule comprising a polynucleotide encoding an RNA-guided nuclease (RGN) polypeptide, wherein said polynucleotide comprises a nucleotide sequence encoding an RGN polypeptide comprising an amino acid sequence having at least 90% sequence identity to any one of SEQ ID NOs: 1-12;
wherein said RGN polypeptide is capable of binding a target DNA sequence in an RNA-guided sequence specific manner when bound to a guide RNA (gRNA) capable of hybridizing to said target DNA sequence.
2. The nucleic acid molecule of embodiment 1, wherein said polynucleotide encoding an RGN polypeptide is operably linked to a promoter heterologous to said polynucleotide.
3. The nucleic acid molecule of embodiment 1 or 2, wherein said RGN polypeptide comprises an amino acid sequence having at least 95% sequence identity to any one of SEQ ID NOs: 1-12.
4. The nucleic acid molecule of embodiment 1 or 2, wherein said RGN polypeptide comprises an amino acid sequence having 100% sequence identity to any one of SEQ ID NOs: 1-12.
5. The nucleic acid molecule of any one of embodiments 1-4, wherein said RGN polypeptide is capable of cleaving said target DNA sequence upon binding.
6. The nucleic acid molecule of embodiment 5, wherein said RGN polypeptide is capable of generating a double-stranded break.
7. The nucleic acid molecule of embodiment 5, wherein said RGN polypeptide is capable of generating a single-stranded break.
8. The nucleic acid molecule of any one of embodiments 1-4, wherein said RGN polypeptide is nuclease inactive or is a nickase.
9. The nucleic acid molecule of any of embodiment 1-5, 7 and 8, wherein the RGN polypeptide is operably linked to a prime editing polypeptide.
10. The nucleic acid molecule of embodiment 9, wherein said prime editing polypeptide comprises a DNA polymerase.
11. The nucleic acid molecule of embodiment 9, wherein said prime editing polypeptide comprises a reverse transcriptase.
12. The nucleic acid molecule of any one of embodiments 1-8, wherein the RGN polypeptide is operably linked to a base-editing polypeptide.
13. The nucleic acid molecule of embodiment 12, wherein the base-editing polypeptide is a deaminase.
14. The nucleic acid molecule of embodiment 13, wherein the deaminase is a cytosine deaminase or an adenine deaminase.
15. The nucleic acid molecule of embodiment 13, wherein the deaminase has at least 90% sequence identity to an amino acid sequence of any one of SEQ ID NOs: 377-448.
16. The nucleic acid molecule of embodiment 13, wherein the deaminase has 100% sequence identity to an amino acid sequence of any one of SEQ ID NOs: 377-448.
17. The nucleic acid molecule of any one of embodiments 1-16, wherein the RGN polypeptide comprises one or more nuclear localization signals.

18. The nucleic acid molecule of any one of embodiments 1-17, wherein the RGN polypeptide is codon optimized for expression in a eukaryotic cell.
19. The nucleic acid molecule of any one of embodiments 1-18, wherein said target DNA sequence is located adjacent to a protospacer adjacent motif (PAM).
20. A vector comprising the nucleic acid molecule of any one of embodiments 1-19.
21. The vector of embodiment 20, further comprising at least one nucleotide sequence encoding said gRNA capable of hybridizing to said target DNA sequence.
22. The vector of embodiment 21, wherein the guide RNA is selected from the group consisting of:
a) a guide RNA comprising:
   i) a CRISPR RNA comprising a CRISPR repeat sequence having at least 90% sequence identity to SEQ ID NO: 13; and
   ii) a tracrRNA having at least 90% sequence identity to SEQ ID NO: 25;
   wherein said RGN polypeptide comprises an amino acid sequence having at least 90% sequence identity to SEQ ID NO: 1;
b) a guide RNA comprising:
   i) a CRISPR RNA comprising a CRISPR repeat sequence having at least 90% sequence identity to SEQ ID NO: 14; and
   ii) a tracrRNA having at least 90% sequence identity to SEQ ID NO: 26;
   wherein said RGN polypeptide comprises an amino acid sequence having at least 90% sequence identity to SEQ ID NO: 2;
c) a guide RNA comprising:
   i) a CRISPR RNA comprising a CRISPR repeat sequence having at least 90% sequence identity to SEQ ID NO: 15; and
   ii) a tracrRNA having at least 90% sequence identity to SEQ ID NO: 27;
   wherein said RGN polypeptide comprises an amino acid sequence having at least 90% sequence identity to SEQ ID NO: 3;
d) a guide RNA comprising:
   i) a CRISPR RNA comprising a CRISPR repeat sequence having at least 90% sequence identity to SEQ ID NO: 16; and
   ii) a tracrRNA having at least 90% sequence identity to SEQ ID NO: 28;
   wherein said RGN polypeptide comprises an amino acid sequence having at least 90% sequence identity to SEQ ID NO: 4;
e) a guide RNA comprising:
   i) a CRISPR RNA comprising a CRISPR repeat sequence having at least 90% sequence identity to SEQ ID NO: 17; and
   ii) a tracrRNA having at least 90% sequence identity to SEQ ID NO: 29;
   wherein said RGN polypeptide comprises an amino acid sequence having at least 90% sequence identity to SEQ ID NO: 5;
f) a guide RNA comprising:
   i) a CRISPR RNA comprising a CRISPR repeat sequence having at least 90% sequence identity to SEQ ID NO: 18; and
   ii) a tracrRNA having at least 90% sequence identity to SEQ ID NO: 30;
   wherein said RGN polypeptide comprises an amino acid sequence having at least 90% sequence identity to SEQ ID NO: 6;
g) a guide RNA comprising:
   i) a CRISPR RNA comprising a CRISPR repeat sequence having at least 90% sequence identity to SEQ ID NO: 19; and
   ii) a tracrRNA having at least 90% sequence identity to SEQ ID NO: 31;
   wherein said RGN polypeptide comprises an amino acid sequence having at least 90% sequence identity to SEQ ID NO: 7;
h) a guide RNA comprising:
   i) a CRISPR RNA comprising a CRISPR repeat sequence having at least 90% sequence identity to SEQ ID NO: 20; and
   ii) a tracrRNA having at least 90% sequence identity to SEQ ID NO: 32;
   wherein said RGN polypeptide comprises an amino acid sequence having at least 90% sequence identity to SEQ ID NO: 8;
i) a guide RNA comprising:
   i) a CRISPR RNA comprising a CRISPR repeat sequence having at least 90% sequence identity to SEQ ID NO: 21; and
   ii) a tracrRNA having at least 90% sequence identity to SEQ ID NO: 33;
   wherein said RGN polypeptide comprises an amino acid sequence having at least 90% sequence identity to SEQ ID NO: 9;
j) a guide RNA comprising:
   i) a CRISPR RNA comprising a CRISPR repeat sequence having at least 90% sequence identity to SEQ ID NO: 22; and
   ii) a tracrRNA having at least 90% sequence identity to SEQ ID NO: 34;
   wherein said RGN polypeptide comprises an amino acid sequence having at least 90% sequence identity to SEQ ID NO: 10;
k) a guide RNA comprising:
   i) a CRISPR RNA comprising a CRISPR repeat sequence having at least 90% sequence identity to SEQ ID NO: 23; and
   ii) a tracrRNA having at least 90% sequence identity to SEQ ID NO: 35;
   wherein said RGN polypeptide comprises an amino acid sequence having at least 90% sequence identity to SEQ ID NO: 11; and
l) a guide RNA comprising:
   i) a CRISPR RNA comprising a CRISPR repeat sequence having at least 90% sequence identity to SEQ ID NO: 24; and
   ii) a tracrRNA having at least 90% sequence identity to SEQ ID NO: 36;
   wherein said RGN polypeptide comprises an amino acid sequence having at least 90% sequence identity to SEQ ID NO: 12.
23. The vector of embodiment 21, wherein the guide RNA is selected from the group consisting of:
a) a guide RNA comprising:
   i) a CRISPR RNA comprising a CRISPR repeat sequence having at least 95% sequence identity to SEQ ID NO: 13; and
   ii) a tracrRNA having at least 95% sequence identity to SEQ ID NO: 25;
   wherein said RGN polypeptide comprises an amino acid sequence having at least 95% sequence identity to SEQ ID NO: 1;

b) a guide RNA comprising:
   i) a CRISPR RNA comprising a CRISPR repeat sequence having at least 95% sequence identity to SEQ ID NO: 14; and
   ii) a tracrRNA having at least 95% sequence identity to SEQ ID NO: 26;
   wherein said RGN polypeptide comprises an amino acid sequence having at least 95% sequence identity to SEQ ID NO: 2;
c) a guide RNA comprising:
   i) a CRISPR RNA comprising a CRISPR repeat sequence having at least 95% sequence identity to SEQ ID NO: 15; and
   ii) a tracrRNA having at least 95% sequence identity to SEQ ID NO: 27;
   wherein said RGN polypeptide comprises an amino acid sequence having at least 95% sequence identity to SEQ ID NO: 3;
d) a guide RNA comprising:
   i) a CRISPR RNA comprising a CRISPR repeat sequence having at least 95% sequence identity to SEQ ID NO: 16; and
   ii) a tracrRNA having at least 95% sequence identity to SEQ ID NO: 28;
   wherein said RGN polypeptide comprises an amino acid sequence having at least 95% sequence identity to SEQ ID NO: 4;
e) a guide RNA comprising:
   i) a CRISPR RNA comprising a CRISPR repeat sequence having at least 95% sequence identity to SEQ ID NO: 17; and
   ii) a tracrRNA having at least 95% sequence identity to SEQ ID NO: 29;
   wherein said RGN polypeptide comprises an amino acid sequence having at least 95% sequence identity to SEQ ID NO: 5;
f) a guide RNA comprising:
   i) a CRISPR RNA comprising a CRISPR repeat sequence having at least 95% sequence identity to SEQ ID NO: 18; and
   ii) a tracrRNA having at least 95% sequence identity to SEQ ID NO: 30;
   wherein said RGN polypeptide comprises an amino acid sequence having at least 95% sequence identity to SEQ ID NO: 6;
g) a guide RNA comprising:
   i) a CRISPR RNA comprising a CRISPR repeat sequence having at least 95% sequence identity to SEQ ID NO: 19; and
   ii) a tracrRNA having at least 95% sequence identity to SEQ ID NO: 31;
   wherein said RGN polypeptide comprises an amino acid sequence having at least 95% sequence identity to SEQ ID NO: 7;
h) a guide RNA comprising:
   i) a CRISPR RNA comprising a CRISPR repeat sequence having at least 95% sequence identity to SEQ ID NO: 20; and
   ii) a tracrRNA having at least 95% sequence identity to SEQ ID NO: 32;
   wherein said RGN polypeptide comprises an amino acid sequence having at least 95% sequence identity to SEQ ID NO: 8;
i) a guide RNA comprising:
   i) a CRISPR RNA comprising a CRISPR repeat sequence having at least 95% sequence identity to SEQ ID NO: 21; and
   ii) a tracrRNA having at least 95% sequence identity to SEQ ID NO: 33;
   wherein said RGN polypeptide comprises an amino acid sequence having at least 95% sequence identity to SEQ ID NO: 9;
j) a guide RNA comprising:
   i) a CRISPR RNA comprising a CRISPR repeat sequence having at least 95% sequence identity to SEQ ID NO: 22; and
   ii) a tracrRNA having at least 95% sequence identity to SEQ ID NO: 34;
   wherein said RGN polypeptide comprises an amino acid sequence having at least 95% sequence identity to SEQ ID NO: 10;
k) a guide RNA comprising:
   i) a CRISPR RNA comprising a CRISPR repeat sequence having at least 95% sequence identity to SEQ ID NO: 23; and
   ii) a tracrRNA having at least 95% sequence identity to SEQ ID NO: 35;
   wherein said RGN polypeptide comprises an amino acid sequence having at least 95% sequence identity to SEQ ID NO: 11; and
l) a guide RNA comprising:
   i) a CRISPR RNA comprising a CRISPR repeat sequence having at least 95% sequence identity to SEQ ID NO: 24; and
   ii) a tracrRNA having at least 95% sequence identity to SEQ ID NO: 36;
   wherein said RGN polypeptide comprises an amino acid sequence having at least 95% sequence identity to SEQ ID NO: 12.

24. The vector of embodiment 21, wherein the guide RNA is selected from the group consisting of:
a) a guide RNA comprising:
   i) a CRISPR RNA comprising a CRISPR repeat sequence having 100% sequence identity to SEQ ID NO: 13; and
   ii) a tracrRNA having 100% sequence identity to SEQ ID NO: 25;
   wherein said RGN polypeptide comprises an amino acid sequence having 100% sequence identity to SEQ ID NO: 1;
b) a guide RNA comprising:
   i) a CRISPR RNA comprising a CRISPR repeat sequence having 100% sequence identity to SEQ ID NO: 14; and
   ii) a tracrRNA having 100% sequence identity to SEQ ID NO: 26;
   wherein said RGN polypeptide comprises an amino acid sequence having 100% sequence identity to SEQ ID NO: 2;
c) a guide RNA comprising:
   i) a CRISPR RNA comprising a CRISPR repeat sequence having 100% sequence identity to SEQ ID NO: 15; and
   ii) a tracrRNA having 100% sequence identity to SEQ ID NO: 27;
   wherein said RGN polypeptide comprises an amino acid sequence having 100% sequence identity to SEQ ID NO: 3;
d) a guide RNA comprising:
   i) a CRISPR RNA comprising a CRISPR repeat sequence having 100% sequence identity to SEQ ID NO: 16; and
   ii) a tracrRNA having 100% sequence identity to SEQ ID NO: 28;

wherein said RGN polypeptide comprises an amino acid sequence having 100% sequence identity to SEQ ID NO: 4;
e) a guide RNA comprising:
  i) a CRISPR RNA comprising a CRISPR repeat sequence having 100% sequence identity to SEQ ID NO: 17; and
  ii) a tracrRNA having 100% sequence identity to SEQ ID NO: 29;
  wherein said RGN polypeptide comprises an amino acid sequence having 100% sequence identity to SEQ ID NO: 5;
f) a guide RNA comprising:
  i) a CRISPR RNA comprising a CRISPR repeat sequence having 100% sequence identity to SEQ ID NO: 18; and
  ii) a tracrRNA having 100% sequence identity to SEQ ID NO: 30;
  wherein said RGN polypeptide comprises an amino acid sequence having 100% sequence identity to SEQ ID NO: 6;
g) a guide RNA comprising:
  i) a CRISPR RNA comprising a CRISPR repeat sequence having 100% sequence identity to SEQ ID NO: 19; and
  ii) a tracrRNA having 100% sequence identity to SEQ ID NO: 31;
  wherein said RGN polypeptide comprises an amino acid sequence having 100% sequence identity to SEQ ID NO: 7;
h) a guide RNA comprising:
  i) a CRISPR RNA comprising a CRISPR repeat sequence having 100% sequence identity to SEQ ID NO: 20; and
  ii) a tracrRNA having 100% sequence identity to SEQ ID NO: 32;
  wherein said RGN polypeptide comprises an amino acid sequence having 100% sequence identity to SEQ ID NO: 8;
i) a guide RNA comprising:
  i) a CRISPR RNA comprising a CRISPR repeat sequence having 100% sequence identity to SEQ ID NO: 21; and
  ii) a tracrRNA having 100% sequence identity to SEQ ID NO: 33;
  wherein said RGN polypeptide comprises an amino acid sequence having 100% sequence identity to SEQ ID NO: 9;
j) a guide RNA comprising:
  i) a CRISPR RNA comprising a CRISPR repeat sequence having 100% sequence identity to SEQ ID NO: 22; and
  ii) a tracrRNA having 100% sequence identity to SEQ ID NO: 34;
  wherein said RGN polypeptide comprises an amino acid sequence having 100% sequence identity to SEQ ID NO: 10;
k) a guide RNA comprising:
  i) a CRISPR RNA comprising a CRISPR repeat sequence having 100% sequence identity to SEQ ID NO: 23; and
  ii) a tracrRNA having 100% sequence identity to SEQ ID NO: 35;
  wherein said RGN polypeptide comprises an amino acid sequence having 100% sequence identity to SEQ ID NO: 11; and
l) a guide RNA comprising: 1)
  i) a CRISPR RNA comprising a CRISPR repeat sequence having 100% sequence identity to SEQ ID NO: 24; and
  ii) a tracrRNA having 100% sequence identity to SEQ ID NO: 36;
  wherein said RGN polypeptide comprises an amino acid sequence having 100% sequence identity to SEQ ID NO: 12.

25. The vector of any one of embodiments 21-24, where said gRNA is a single guide RNA (sgRNA).
26. The vector of embodiment 25, wherein said sgRNA further comprises an extension comprising an edit template for prime editing.
27. The vector of any one of embodiments 21-24, wherein said gRNA is a dual-guide RNA.
28. A cell comprising the nucleic acid molecule of any one of embodiments 1-19 or the vector of any one of embodiments 20-27.
29. The cell of embodiment 28, wherein the cell is a prokaryotic cell.
30. The cell of embodiment 28, wherein the cell is a eukaryotic cell.
31. The cell of embodiment 30, wherein the eukaryotic cell is a mammalian cell.
32. The cell of embodiment 31, wherein the mammalian cell is a human cell.
33. The cell of embodiment 32, wherein the human cell is an immune cell.
34. The cell of embodiment 33, wherein the immune cell is a stem cell.
35. The cell of embodiment 34, wherein the stem cell is an induced pluripotent stem cell.
36. The cell of embodiment 30, wherein the eukaryotic cell is an insect or avian cell.
37. The cell of embodiment 30, wherein the eukaryotic cell is a fungal cell.
38. The cell of embodiment 30, wherein the eukaryotic cell is a plant cell.
39. A plant comprising the cell of embodiment 38.
40. A seed comprising the cell of embodiment 38.
41. A method for making an RGN polypeptide comprising culturing the cell of any one of embodiments 28-38 under conditions in which the RGN polypeptide is expressed.
42. A method for making an RGN polypeptide comprising introducing into a cell a heterologous nucleic acid molecule comprising a nucleotide sequence encoding an RNA-guided nuclease (RGN) polypeptide comprising an amino acid sequence having at least 90% sequence identity to any one of SEQ ID NOs: 1-12;
  wherein said RGN polypeptide is capable of binding a target DNA sequence in an RNA-guided sequence specific manner when bound to a guide RNA (gRNA) capable of hybridizing to said target DNA sequence;
  and culturing said cell under conditions in which the RGN polypeptide is expressed.
43. The method of embodiment 42, wherein said RGN polypeptide comprises an amino acid sequence having at least 95% sequence identity to any one of SEQ ID NOs: 1-12.
44. The method of embodiment 42, wherein said RGN polypeptide comprises an amino acid sequence having 100% sequence identity to any one of SEQ ID NOs: 1-12.
45. The method of any one of embodiments 41-44, further comprising purifying said RGN polypeptide.

46. The method of any one of embodiments 41-44, wherein said cell further expresses one or more guide RNAs capable of binding to said RGN polypeptide to form an RGN ribonucleoprotein complex.

47. The method of embodiment 46, further comprising purifying said RGN ribonucleoprotein complex.

48. An RNA-guided nuclease (RGN) polypeptide, wherein said RGN polypeptide comprises an amino acid sequence having at least 90% sequence identity to any one of SEQ ID NOs: 1-12; and
wherein said RGN polypeptide is capable of binding a target DNA sequence of a DNA molecule in an RNA-guided sequence specific manner when bound to a guide RNA (gRNA) capable of hybridizing to said target DNA sequence.

49. The RGN polypeptide of embodiment 48, wherein said RGN polypeptide comprises an amino acid sequence having at least 95% sequence identity to any one of SEQ ID NOs: 1-12.

50. The RGN polypeptide of embodiment 48, wherein said RGN polypeptide comprises an amino acid sequence having 100% sequence identity to any one of SEQ ID NOs: 1-12.

51. The RGN polypeptide of any one of embodiments 48-50, wherein said RGN polypeptide is an isolated RGN polypeptide.

52. The RGN polypeptide of any one of embodiments 48-51, wherein said RGN polypeptide is capable of cleaving said target DNA sequence upon binding.

53. The RGN polypeptide of embodiment 52, wherein cleavage by said RGN polypeptide generates a double-stranded break.

54. The RGN polypeptide of embodiment 52, wherein cleavage by said RGN polypeptide generates a single-stranded break.

55. The RGN polypeptide of any one of embodiments 48-51, wherein said RGN polypeptide is nuclease inactive or a nickase.

56. The RGN polypeptide of any of embodiment 48-52, 54, and 55, wherein the RGN polypeptide is operably linked to a prime editing polypeptide.

57. The RGN polypeptide of embodiment 56, wherein said prime editing polypeptide comprises a DNA polymerase.

58. The RGN polypeptide of embodiment 56, wherein said prime editing polypeptide comprises a reverse transcriptase.

59. The RGN polypeptide of any one of embodiments 48-55, wherein the RGN polypeptide is operably linked to a base-editing polypeptide.

60. The RGN polypeptide of embodiment 59, wherein the base-editing polypeptide is a deaminase.

61. The RGN polypeptide of embodiment 60, wherein the deaminase is a cytosine deaminase or an adenine deaminase.

62. The RGN polypeptide of embodiment 60, wherein the deaminase has at least 90% sequence identity to an amino acid sequence of any one of SEQ ID NOs: 377-448.

63. The RGN polypeptide of embodiment 60, wherein the deaminase has 100% sequence identity to an amino acid sequence of any one of SEQ ID NOs: 377-448.

64. The RGN polypeptide of any one of embodiments 48-63, wherein said target DNA sequence is located adjacent to a protospacer adjacent motif (PAM).

65. The RGN polypeptide of any one of embodiments 48-64, wherein the RGN polypeptide comprises one or more nuclear localization signals.

66. A ribonucleoprotein (RNP) complex comprising the RGN polypeptide of any one of embodiments 48-65 and a guide RNA (gRNA) bound to the RGN polypeptide.

67. The RNP complex of embodiment 66, wherein said gRNA is a single guide RNA (sgRNA).

68. The RNP complex of embodiment 67, wherein said gRNA comprises an extension comprising an edit template for prime editing.

69. A nucleic acid molecule comprising a CRISPR RNA (crRNA) or a polynucleotide encoding a crRNA, wherein said crRNA comprises a spacer sequence and a CRISPR repeat sequence, wherein said CRISPR repeat sequence comprises a nucleotide sequence having at least 90% sequence identity to any one of SEQ ID NOs: 13-24;
wherein a guide RNA comprising:
a) said crRNA; and
b) a trans-activating CRISPR RNA (tracrRNA) hybridized to said CRISPR repeat sequence of said crRNA;
is capable of hybridizing to a target DNA sequence in a sequence specific manner through the spacer sequence of said crRNA when said guide RNA is bound to an RNA-guided nuclease (RGN) polypeptide.

70. The nucleic acid molecule of embodiment 69, wherein said polynucleotide encoding a crRNA is operably linked to a promoter heterologous to said polynucleotide.

71. The nucleic acid molecule of embodiment 69 or 70, wherein said CRISPR repeat sequence comprises a nucleotide sequence having at least 95% sequence identity to any one of SEQ ID NOs: 13-24.

72. The nucleic acid molecule of embodiment 69 or 70, wherein said CRISPR repeat sequence comprises a nucleotide sequence having 100% sequence identity to any one of SEQ ID NOs: 13-24.

73. A vector comprising the nucleic acid molecule comprising said polynucleotide encoding said crRNA of any one of embodiments 69-72.

74. The vector of embodiment 73, wherein said vector further comprises a polynucleotide encoding said tracrRNA.

75. The vector of embodiment 74, wherein said tracrRNA is selected from the group consisting of:
a) a tracrRNA having at least 90% sequence identity to SEQ ID NO: 25, wherein said CRISPR repeat sequence has at least 90% sequence identity to SEQ ID NO: 13;
b) a tracrRNA having at least 90% sequence identity to SEQ ID NO: 26, wherein said CRISPR repeat sequence has at least 90% sequence identity to SEQ ID NO: 14;
c) a tracrRNA having at least 90% sequence identity to SEQ ID NO: 27, wherein said CRISPR repeat sequence has at least 90% sequence identity to SEQ ID NO: 15;
d) a tracrRNA having at least 90% sequence identity to SEQ ID NO: 28, wherein said CRISPR repeat sequence has at least 90% sequence identity to SEQ ID NO: 16;
e) a tracrRNA having at least 90% sequence identity to SEQ ID NO: 29, wherein said CRISPR repeat sequence has at least 90% sequence identity to SEQ ID NO: 17;
f) a tracrRNA having at least 90% sequence identity to SEQ ID NO: 30, wherein said CRISPR repeat sequence has at least 90% sequence identity to SEQ ID NO: 18;

g) a tracrRNA having at least 90% sequence identity to SEQ ID NO: 31, wherein said CRISPR repeat sequence has at least 90% sequence identity to SEQ ID NO: 19;
h) a tracrRNA having at least 90% sequence identity to SEQ ID NO: 32, wherein said CRISPR repeat sequence has at least 90% sequence identity to SEQ ID NO: 20;
i) a tracrRNA having at least 90% sequence identity to SEQ ID NO: 33, wherein said CRISPR repeat sequence has at least 90% sequence identity to SEQ ID NO: 21;
j) a tracrRNA having at least 90% sequence identity to SEQ ID NO: 34, wherein said CRISPR repeat sequence has at least 90% sequence identity to SEQ ID NO: 22;
k) a tracrRNA having at least 90% sequence identity to SEQ ID NO: 35, wherein said CRISPR repeat sequence has at least 90% sequence identity to SEQ ID NO: 23; and
l) a tracrRNA having at least 90% sequence identity to SEQ ID NO: 36, wherein said CRISPR repeat sequence has at least 90% sequence identity to SEQ ID NO: 24.

76. The vector of embodiment 74, wherein said tracrRNA is selected from the group consisting of:
a) a tracrRNA having at least 95% sequence identity to SEQ ID NO: 25, wherein said CRISPR repeat sequence has at least 95% sequence identity to SEQ ID NO: 13;
b) a tracrRNA having at least 95% sequence identity to SEQ ID NO: 26, wherein said CRISPR repeat sequence has at least 95% sequence identity to SEQ ID NO: 14;
c) a tracrRNA having at least 95% sequence identity to SEQ ID NO: 27, wherein said CRISPR repeat sequence has at least 95% sequence identity to SEQ ID NO: 15;
d) a tracrRNA having at least 95% sequence identity to SEQ ID NO: 28, wherein said CRISPR repeat sequence has at least 95% sequence identity to SEQ ID NO: 16;
e) a tracrRNA having at least 95% sequence identity to SEQ ID NO: 29, wherein said CRISPR repeat sequence has at least 95% sequence identity to SEQ ID NO: 17;
f) a tracrRNA having at least 95% sequence identity to SEQ ID NO: 30, wherein said CRISPR repeat sequence has at least 95% sequence identity to SEQ ID NO: 18;
g) a tracrRNA having at least 95% sequence identity to SEQ ID NO: 31, wherein said CRISPR repeat sequence has at least 95% sequence identity to SEQ ID NO: 19;
h a tracrRNA having at least 95% sequence identity to SEQ ID NO: 32, wherein said CRISPR repeat sequence has at least 95% sequence identity to SEQ ID NO: 20;
i) a tracrRNA having at least 95% sequence identity to SEQ ID NO: 33, wherein said CRISPR repeat sequence has at least 95% sequence identity to SEQ ID NO: 21;
j) a tracrRNA having at least 95% sequence identity to SEQ ID NO: 34, wherein said CRISPR repeat sequence has at least 95% sequence identity to SEQ ID NO: 22;
k) a tracrRNA having at least 95% sequence identity to SEQ ID NO: 35, wherein said CRISPR repeat sequence has at least 95% sequence identity to SEQ ID NO: 23; and
l) a tracrRNA having at least 95% sequence identity to SEQ ID NO: 36, wherein said CRISPR repeat sequence has at least 95% sequence identity to SEQ ID NO: 24.

77. The vector of embodiment 74, wherein said tracrRNA is selected from the group consisting of:
a) a tracrRNA having 100% sequence identity to SEQ ID NO: 25, wherein said CRISPR repeat sequence has 100% sequence identity to SEQ ID NO: 13;
b) a tracrRNA having 100% sequence identity to SEQ ID NO: 26, wherein said CRISPR repeat sequence has 100% sequence identity to SEQ ID NO: 14;
c) a tracrRNA having 100% sequence identity to SEQ ID NO: 27, wherein said CRISPR repeat sequence has 100% sequence identity to SEQ ID NO: 15;
d) a tracrRNA having 100% sequence identity to SEQ ID NO: 28, wherein said CRISPR repeat sequence has 100% sequence identity to SEQ ID NO: 16;
e) a tracrRNA having 100% sequence identity to SEQ ID NO: 29, wherein said CRISPR repeat sequence has 100% sequence identity to SEQ ID NO: 17;
f) a tracrRNA having 100% sequence identity to SEQ ID NO: 30, wherein said CRISPR repeat sequence has 100% sequence identity to SEQ ID NO: 18;
g) a tracrRNA having 100% sequence identity to SEQ ID NO: 31, wherein said CRISPR repeat sequence has 100% sequence identity to SEQ ID NO: 19;
h) a tracrRNA having 100% sequence identity to SEQ ID NO: 32, wherein said CRISPR repeat sequence has 100% sequence identity to SEQ ID NO: 20;
i) a tracrRNA having 100% sequence identity to SEQ ID NO: 33, wherein said CRISPR repeat sequence has 100% sequence identity to SEQ ID NO: 21;
j) a tracrRNA having 100% sequence identity to SEQ ID NO: 34, wherein said CRISPR repeat sequence has 100% sequence identity to SEQ ID NO: 22;
k) a tracrRNA having 100% sequence identity to SEQ ID NO: 35, wherein said CRISPR repeat sequence has 100% sequence identity to SEQ ID NO: 23; and
l) a tracrRNA having 100% sequence identity to SEQ ID NO: 36, wherein said CRISPR repeat sequence has 100% sequence identity to SEQ ID NO: 24.

78. The vector of any one of embodiments 74-77, wherein said polynucleotide encoding said crRNA and said polynucleotide encoding said tracrRNA are operably linked to the same promoter and are encoded as a single guide RNA (sgRNA).

79. The vector of embodiment 78, wherein said sgRNA comprises an extension comprising an edit template for prime editing.

80. The vector of any one of embodiments 74-77, wherein said polynucleotide encoding said crRNA and said polynucleotide encoding said tracrRNA are operably linked to separate promoters.

81. The vector of any one of embodiments 74-80, wherein said vector further comprises a polynucleotide encoding said RGN polypeptide.

82. The vector of embodiment 81, wherein said RGN polypeptide is selected from the group consisting of:
a) a RGN polypeptide having at least 90% sequence identity to SEQ ID NO: 1, wherein said CRISPR repeat sequence has at least 90% sequence identity to SEQ ID NO: 13 and said tracrRNA has at least 90% sequence identity to SEQ ID NO: 25;
b) a RGN polypeptide having at least 90% sequence identity to SEQ ID NO: 2, wherein said CRISPR repeat sequence has at least 90% sequence identity to SEQ ID NO: 14 and said tracrRNA has at least 90% sequence identity to SEQ ID NO: 26;
c) a RGN polypeptide having at least 90% sequence identity to SEQ ID NO: 3, wherein said CRISPR repeat sequence has at least 90% sequence identity to SEQ ID NO: 15 and said tracrRNA has at least 90% sequence identity to SEQ ID NO: 27;
d) a RGN polypeptide having at least 90% sequence identity to SEQ ID NO: 4, wherein said CRISPR repeat sequence has at least 90% sequence identity to SEQ ID NO: 16 and said tracrRNA has at least 90% sequence identity to SEQ ID NO: 28;

e) a RGN polypeptide having at least 90% sequence identity to SEQ ID NO: 5, wherein said CRISPR repeat sequence has at least 90% sequence identity to SEQ ID NO: 17 and said tracrRNA has at least 90% sequence identity to SEQ ID NO: 29;
f) a RGN polypeptide having at least 90% sequence identity to SEQ ID NO: 6, wherein said CRISPR repeat sequence has at least 90% sequence identity to SEQ ID NO: 18 and said tracrRNA has at least 90% sequence identity to SEQ ID NO: 30;
g) a RGN polypeptide having at least 90% sequence identity to SEQ ID NO: 7, wherein said CRISPR repeat sequence has at least 90% sequence identity to SEQ ID NO: 19 and said tracrRNA has at least 90% sequence identity to SEQ ID NO: 31;
h) a RGN polypeptide having at least 90% sequence identity to SEQ ID NO: 8, wherein said CRISPR repeat sequence has at least 90% sequence identity to SEQ ID NO: 20 and said tracrRNA has at least 90% sequence identity to SEQ ID NO: 32;
i) a RGN polypeptide having at least 90% sequence identity to SEQ ID NO: 9, wherein said CRISPR repeat sequence has at least 90% sequence identity to SEQ ID NO: 21 and said tracrRNA has at least 90% sequence identity to SEQ ID NO: 33;
j) a RGN polypeptide having at least 90% sequence identity to SEQ ID NO: 10, wherein said CRISPR repeat sequence has at least 90% sequence identity to SEQ ID NO: 22 and said tracrRNA has at least 90% sequence identity to SEQ ID NO: 34;
k) a RGN polypeptide having at least 90% sequence identity to SEQ ID NO: 11, wherein said CRISPR repeat sequence has at least 90% sequence identity to SEQ ID NO: 23 and said tracrRNA has at least 90% sequence identity to SEQ ID NO: 35; and
l) a RGN polypeptide having at least 90% sequence identity to SEQ ID NO: 12, wherein said CRISPR repeat sequence has at least 90% sequence identity to SEQ ID NO: 24 and said tracrRNA has at least 90% sequence identity to SEQ ID NO: 36.

83. The vector of embodiment 81, wherein said RGN polypeptide is selected from the group consisting of:
a) a RGN polypeptide having at least 95% sequence identity to SEQ ID NO: 1, wherein said CRISPR repeat sequence has at least 95% sequence identity to SEQ ID NO: 13 and said tracrRNA has at least 95% sequence identity to SEQ ID NO: 25;
b) a RGN polypeptide having at least 95% sequence identity to SEQ ID NO: 2, wherein said CRISPR repeat sequence has at least 95% sequence identity to SEQ ID NO: 14 and said tracrRNA has at least 95% sequence identity to SEQ ID NO: 26;
c) a RGN polypeptide having at least 95% sequence identity to SEQ ID NO: 3, wherein said CRISPR repeat sequence has at least 95% sequence identity to SEQ ID NO: 15 and said tracrRNA has at least 95% sequence identity to SEQ ID NO: 27;
d) a RGN polypeptide having at least 95% sequence identity to SEQ ID NO: 4, wherein said CRISPR repeat sequence has at least 95% sequence identity to SEQ ID NO: 16 and said tracrRNA has at least 95% sequence identity to SEQ ID NO: 28;
e) a RGN polypeptide having at least 95% sequence identity to SEQ ID NO: 5, wherein said CRISPR repeat sequence has at least 95% sequence identity to SEQ ID NO: 17 and said tracrRNA has at least 95% sequence identity to SEQ ID NO: 29;
f) a RGN polypeptide having at least 95% sequence identity to SEQ ID NO: 6, wherein said CRISPR repeat sequence has at least 95% sequence identity to SEQ ID NO: 18 and said tracrRNA has at least 95% sequence identity to SEQ ID NO: 30;
g) a RGN polypeptide having at least 95% sequence identity to SEQ ID NO: 7, wherein said CRISPR repeat sequence has at least 95% sequence identity to SEQ ID NO: 19 and said tracrRNA has at least 95% sequence identity to SEQ ID NO: 31;
h) a RGN polypeptide having at least 95% sequence identity to SEQ ID NO: 8, wherein said CRISPR repeat sequence has at least 95% sequence identity to SEQ ID NO: 20 and said tracrRNA has at least 95% sequence identity to SEQ ID NO: 32;
i) a RGN polypeptide having at least 95% sequence identity to SEQ ID NO: 9, wherein said CRISPR repeat sequence has at least 95% sequence identity to SEQ ID NO: 21 and said tracrRNA has at least 95% sequence identity to SEQ ID NO: 33;
j) a RGN polypeptide having at least 95% sequence identity to SEQ ID NO: 10, wherein said CRISPR repeat sequence has at least 95% sequence identity to SEQ ID NO: 22 and said tracrRNA has at least 95% sequence identity to SEQ ID NO: 34;
k) a RGN polypeptide having at least 95% sequence identity to SEQ ID NO: 11, wherein said CRISPR repeat sequence has at least 95% sequence identity to SEQ ID NO: 23 and said tracrRNA has at least 95% sequence identity to SEQ ID NO: 35; and
l) a RGN polypeptide having at least 95% sequence identity to SEQ ID NO: 12, wherein said CRISPR repeat sequence has at least 95% sequence identity to SEQ ID NO: 24 and said tracrRNA has at least 95% sequence identity to SEQ ID NO: 36.

84. The vector of embodiment 81, wherein said RGN polypeptide is selected from the group consisting of:
a) a RGN polypeptide having 100% sequence identity to SEQ ID NO: 1, wherein said CRISPR repeat sequence has 100% sequence identity to SEQ ID NO: 13 and said tracrRNA has 100% sequence identity to SEQ ID NO: 25;
b) a RGN polypeptide having 100% sequence identity to SEQ ID NO: 2, wherein said CRISPR repeat sequence has 100% sequence identity to SEQ ID NO: 14 and said tracrRNA has 100% sequence identity to SEQ ID NO: 26;
c) a RGN polypeptide having 100% sequence identity to SEQ ID NO: 3, wherein said CRISPR repeat sequence has 100% sequence identity to SEQ ID NO: 15 and said tracrRNA has 100% sequence identity to SEQ ID NO: 27;
d) a RGN polypeptide having 100% sequence identity to SEQ ID NO: 4, wherein said CRISPR repeat sequence has 100% sequence identity to SEQ ID NO: 16 and said tracrRNA has 100% sequence identity to SEQ ID NO: 28;
e) a RGN polypeptide having 100% sequence identity to SEQ ID NO: 5, wherein said CRISPR repeat sequence has 100% sequence identity to SEQ ID NO: 17 and said tracrRNA has 100% sequence identity to SEQ ID NO: 29;
f) a RGN polypeptide having 100% sequence identity to SEQ ID NO: 6, wherein said CRISPR repeat sequence has 100% sequence identity to SEQ ID NO: 18 and said tracrRNA has 100% sequence identity to SEQ ID NO: 30;

g) a RGN polypeptide having 100% sequence identity to SEQ ID NO: 7, wherein said CRISPR repeat sequence has 100% sequence identity to SEQ ID NO: 19 and said tracrRNA has 100% sequence identity to SEQ ID NO: 31;

h) a RGN polypeptide having 100% sequence identity to SEQ ID NO: 8, wherein said CRISPR repeat sequence has 100% sequence identity to SEQ ID NO: 20 and said tracrRNA has 100% sequence identity to SEQ ID NO: 32;

i) a RGN polypeptide having 100% sequence identity to SEQ ID NO: 9, wherein said CRISPR repeat sequence has 100% sequence identity to SEQ ID NO: 21 and said tracrRNA has 100% sequence identity to SEQ ID NO: 33;

j) a RGN polypeptide having 100% sequence identity to SEQ ID NO: 10, wherein said CRISPR repeat sequence has 100% sequence identity to SEQ ID NO: 22 and said tracrRNA has 100% sequence identity to SEQ ID NO: 34;

k) a RGN polypeptide having 100% sequence identity to SEQ ID NO: 11, wherein said CRISPR repeat sequence has 100% sequence identity to SEQ ID NO: 23 and said tracrRNA has 100% sequence identity to SEQ ID NO: 35; and l) a RGN polypeptide having 100% sequence identity to SEQ ID NO: 12, wherein said CRISPR repeat sequence has 100% sequence identity to SEQ ID NO: 24 and said tracrRNA has 100% sequence identity to SEQ ID NO: 36.

85. A nucleic acid molecule comprising a trans-activating CRISPR RNA (tracrRNA) or a polynucleotide encoding a tracrRNA comprising a nucleotide sequence having at least 90% sequence identity to any one of SEQ ID NOs: 25-36;
wherein a guide RNA comprising:
  a) said tracrRNA; and
  b) a crRNA comprising a spacer sequence and a CRISPR repeat sequence, wherein said tracrRNA hybridizes with said CRISPR repeat sequence of said crRNA;
is capable of hybridizing to a target DNA sequence in a sequence specific manner through the spacer sequence of said crRNA when said guide RNA is bound to an RNA-guided nuclease (RGN) polypeptide.

86. The nucleic acid molecule of embodiment 85, wherein said polynucleotide encoding a tracrRNA is operably linked to a promoter heterologous to said polynucleotide.

87. The nucleic acid molecule of embodiment 85 or 86, wherein said tracrRNA comprises a nucleotide sequence having at least 95% sequence identity to any one of SEQ ID NOs: 25-36.

88. The nucleic acid molecule of embodiment 85 or 86, wherein said tracrRNA comprises a nucleotide sequence having 100% sequence identity to any one of SEQ ID NOs: 25-36.

89. A vector comprising the nucleic acid molecule comprising said polynucleotide encoding said tracrRNA of any one of embodiments 85-88.

90. The vector of embodiment 89, wherein said vector further comprises a polynucleotide encoding said crRNA.

91. The vector of embodiment 90, wherein said crRNA comprises a CRISPR repeat sequence selected from the group consisting of:

a) a CRISPR repeat sequence having at least 90% sequence identity to SEQ ID NO: 13, wherein said tracrRNA has at least 90% sequence identity to SEQ ID NO: 25;

b) a CRISPR repeat sequence having at least 90% sequence identity to SEQ ID NO: 14, wherein said tracrRNA has at least 90% sequence identity to SEQ ID NO: 26;

c) a CRISPR repeat sequence having at least 90% sequence identity to SEQ ID NO: 15, wherein said tracrRNA has at least 90% sequence identity to SEQ ID NO: 27;

d) a CRISPR repeat sequence having at least 90% sequence identity to SEQ ID NO: 16, wherein said tracrRNA has at least 90% sequence identity to SEQ ID NO: 28;

e) a CRISPR repeat sequence having at least 90% sequence identity to SEQ ID NO: 17, wherein said tracrRNA has at least 90% sequence identity to SEQ ID NO: 29;

f) a CRISPR repeat sequence having at least 90% sequence identity to SEQ ID NO: 18, wherein said tracrRNA has at least 90% sequence identity to SEQ ID NO: 30;

g) a CRISPR repeat sequence having at least 90% sequence identity to SEQ ID NO: 19, wherein said tracrRNA has at least 90% sequence identity to SEQ ID NO: 31;

h) a CRISPR repeat sequence having at least 90% sequence identity to SEQ ID NO: 20, wherein said tracrRNA has at least 90% sequence identity to SEQ ID NO: 32;

i) a CRISPR repeat sequence having at least 90% sequence identity to SEQ ID NO: 21, wherein said tracrRNA has at least 90% sequence identity to SEQ ID NO: 33;

j) a CRISPR repeat sequence having at least 90% sequence identity to SEQ ID NO: 22, wherein said tracrRNA has at least 90% sequence identity to SEQ ID NO: 34;

k) a CRISPR repeat sequence having at least 90% sequence identity to SEQ ID NO: 23, wherein said tracrRNA has at least 90% sequence identity to SEQ ID NO: 35; and l) a CRISPR repeat sequence having at least 90% sequence identity to SEQ ID NO: 24, wherein said tracrRNA has at least 90% sequence identity to SEQ ID NO: 36.

92. The vector of embodiment 90, wherein said crRNA comprises a CRISPR repeat sequence selected from the group consisting of:

a) a CRISPR repeat sequence having at least 95% sequence identity to SEQ ID NO: 13, wherein said tracrRNA has at least 95% sequence identity to SEQ ID NO: 25;

b) a CRISPR repeat sequence having at least 95% sequence identity to SEQ ID NO: 14, wherein said tracrRNA has at least 95% sequence identity to SEQ ID NO: 26;

c) a CRISPR repeat sequence having at least 95% sequence identity to SEQ ID NO: 15, wherein said tracrRNA has at least 95% sequence identity to SEQ ID NO: 27;

d) a CRISPR repeat sequence having at least 95% sequence identity to SEQ ID NO: 16, wherein said tracrRNA has at least 95% sequence identity to SEQ ID NO: 28;

e) a CRISPR repeat sequence having at least 95% sequence identity to SEQ ID NO: 17, wherein said tracrRNA has at least 95% sequence identity to SEQ ID NO: 29;
f) a CRISPR repeat sequence having at least 95% sequence identity to SEQ ID NO: 18, wherein said tracrRNA has at least 95% sequence identity to SEQ ID NO: 30;
g) a CRISPR repeat sequence having at least 95% sequence identity to SEQ ID NO: 19, wherein said tracrRNA has at least 95% sequence identity to SEQ ID NO: 31;
h) a CRISPR repeat sequence having at least 95% sequence identity to SEQ ID NO: 20, wherein said tracrRNA has at least 95% sequence identity to SEQ ID NO: 32;
i) a CRISPR repeat sequence having at least 95% sequence identity to SEQ ID NO: 21, wherein said tracrRNA has at least 95% sequence identity to SEQ ID NO: 33;
j) a CRISPR repeat sequence having at least 95% sequence identity to SEQ ID NO: 22, wherein said tracrRNA has at least 95% sequence identity to SEQ ID NO: 34;
k) a CRISPR repeat sequence having at least 95% sequence identity to SEQ ID NO: 23, wherein said tracrRNA has at least 95% sequence identity to SEQ ID NO: 35; and
l) a CRISPR repeat sequence having at least 95% sequence identity to SEQ ID NO: 24, wherein said tracrRNA has at least 95% sequence identity to SEQ ID NO: 36.

93. The vector of embodiment 90, wherein said crRNA comprises a CRISPR repeat sequence selected from the group consisting of:
a) a CRISPR repeat sequence having 100% sequence identity to SEQ ID NO: 13, wherein said tracrRNA has 100% sequence identity to SEQ ID NO: 25;
b) a CRISPR repeat sequence having 100% sequence identity to SEQ ID NO: 14, wherein said tracrRNA has 100% sequence identity to SEQ ID NO: 26;
c) a CRISPR repeat sequence having 100% sequence identity to SEQ ID NO: 15, wherein said tracrRNA has 100% sequence identity to SEQ ID NO: 27;
d) a CRISPR repeat sequence having 100% sequence identity to SEQ ID NO: 16, wherein said tracrRNA has 100% sequence identity to SEQ ID NO: 28;
e) a CRISPR repeat sequence having 100% sequence identity to SEQ ID NO: 17, wherein said tracrRNA has 100% sequence identity to SEQ ID NO: 29;
f) a CRISPR repeat sequence having 100% sequence identity to SEQ ID NO: 18, wherein said tracrRNA has 100% sequence identity to SEQ ID NO: 30;
g) a CRISPR repeat sequence having 100% sequence identity to SEQ ID NO: 19, wherein said tracrRNA has 100% sequence identity to SEQ ID NO: 31;
h) a CRISPR repeat sequence having 100% sequence identity to SEQ ID NO: 20, wherein said tracrRNA has 100% sequence identity to SEQ ID NO: 32;
i) a CRISPR repeat sequence having 100% sequence identity to SEQ ID NO: 21, wherein said tracrRNA has 100% sequence identity to SEQ ID NO: 33;
j) a CRISPR repeat sequence having 100% sequence identity to SEQ ID NO: 22, wherein said tracrRNA has 100% sequence identity to SEQ ID NO: 34;
k) a CRISPR repeat sequence having 100% sequence identity to SEQ ID NO: 23, wherein said tracrRNA has 100% sequence identity to SEQ ID NO: 35; and
l) a CRISPR repeat sequence having 100% sequence identity to SEQ ID NO: 24, wherein said tracrRNA has 100% sequence identity to SEQ ID NO: 36.

94. The vector of any one of embodiments 90-93, wherein said polynucleotide encoding said crRNA and said polynucleotide encoding said tracrRNA are operably linked to the same promoter and are encoded as a single guide RNA (sgRNA).

95. The vector of embodiment 94, wherein said sgRNA comprises an extension comprising an edit template for prime editing.

96. The vector of any one of embodiments 90-93, wherein said polynucleotide encoding said crRNA and said polynucleotide encoding said tracrRNA are operably linked to separate promoters.

97. The vector of any one of embodiments 90-96, wherein said vector further comprises a polynucleotide encoding said RGN polypeptide.

98. The vector of embodiment 97, wherein said RGN polypeptide is selected from the group consisting of:
a) a RGN polypeptide having at least 90% sequence identity to SEQ ID NO: 1, wherein said crRNA comprises a CRISPR repeat sequence having at least 90% sequence identity to SEQ ID NO: 13 and said tracrRNA has at least 90% sequence identity to SEQ ID NO: 25;
b) a RGN polypeptide having at least 90% sequence identity to SEQ ID NO: 2, wherein said crRNA comprises a CRISPR repeat sequence having at least 90% sequence identity to SEQ ID NO: 14 and said tracrRNA has at least 90% sequence identity to SEQ ID NO: 26;
c) a RGN polypeptide having at least 90% sequence identity to SEQ ID NO: 3, wherein said crRNA comprises a CRISPR repeat sequence having at least 90% sequence identity to SEQ ID NO: 15 and said tracrRNA has at least 90% sequence identity to SEQ ID NO: 27;
d) a RGN polypeptide having at least 90% sequence identity to SEQ ID NO: 4, wherein said crRNA comprises a CRISPR repeat sequence having at least 90% sequence identity to SEQ ID NO: 16 and said tracrRNA has at least 90% sequence identity to SEQ ID NO: 28;
e) a RGN polypeptide having at least 90% sequence identity to SEQ ID NO: 5, wherein said crRNA comprises a CRISPR repeat sequence having at least 90% sequence identity to SEQ ID NO: 17 and said tracrRNA has at least 90% sequence identity to SEQ ID NO: 29;
f) a RGN polypeptide having at least 90% sequence identity to SEQ ID NO: 6, wherein said crRNA comprises a CRISPR repeat sequence having at least 90% sequence identity to SEQ ID NO: 18 and said tracrRNA has at least 90% sequence identity to SEQ ID NO: 30;
g) a RGN polypeptide having at least 90% sequence identity to SEQ ID NO: 7, wherein said crRNA comprises a CRISPR repeat sequence having at least 90% sequence identity to SEQ ID NO: 19 and said tracrRNA has at least 90% sequence identity to SEQ ID NO: 31;
h) a RGN polypeptide having at least 90% sequence identity to SEQ ID NO: 8, wherein said crRNA comprises a CRISPR repeat sequence having at least 90% sequence identity to SEQ ID NO: 20 and said tracrRNA has at least 90% sequence identity to SEQ ID NO: 32;
i) a RGN polypeptide having at least 90% sequence identity to SEQ ID NO: 9, wherein said crRNA comprises a CRISPR repeat sequence having at least 90% sequence identity to SEQ ID NO: 21 and said tracrRNA has at least 90% sequence identity to SEQ ID NO: 33;

j) a RGN polypeptide having at least 90% sequence identity to SEQ ID NO: 10, wherein said crRNA comprises a CRISPR repeat sequence having at least 90% sequence identity to SEQ ID NO: 22 and said tracrRNA has at least 90% sequence identity to SEQ ID NO: 34;

k) a RGN polypeptide having at least 90% sequence identity to SEQ ID NO: 11, wherein said crRNA comprises a CRISPR repeat sequence having at least 90% sequence identity to SEQ ID NO: 23 and said tracrRNA has at least 90% sequence identity to SEQ ID NO: 35; and l) a RGN polypeptide having at least 90% sequence identity to SEQ ID NO: 12, wherein said crRNA comprises a CRISPR repeat sequence having at least 90% sequence identity to SEQ ID NO: 24 and said tracrRNA has at least 90% sequence identity to SEQ ID NO: 36.

99. The vector of embodiment 97, wherein said RGN polypeptide is selected from the group consisting of:

a) a RGN polypeptide having at least 95% sequence identity to SEQ ID NO: 1, wherein said crRNA comprises a CRISPR repeat sequence having at least 95% sequence identity to SEQ ID NO: 13 and said tracrRNA has at least 95% sequence identity to SEQ ID NO: 25;

b) a RGN polypeptide having at least 95% sequence identity to SEQ ID NO: 2, wherein said crRNA comprises a CRISPR repeat sequence having at least 95% sequence identity to SEQ ID NO: 14 and said tracrRNA has at least 95% sequence identity to SEQ ID NO: 26;

c) a RGN polypeptide having at least 95% sequence identity to SEQ ID NO: 3, wherein said crRNA comprises a CRISPR repeat sequence having at least 95% sequence identity to SEQ ID NO: 15 and said tracrRNA has at least 95% sequence identity to SEQ ID NO: 27;

d) a RGN polypeptide having at least 95% sequence identity to SEQ ID NO: 4, wherein said crRNA comprises a CRISPR repeat sequence having at least 95% sequence identity to SEQ ID NO: 16 and said tracrRNA has at least 95% sequence identity to SEQ ID NO: 28;

e) a RGN polypeptide having at least 95% sequence identity to SEQ ID NO: 5, wherein said crRNA comprises a CRISPR repeat sequence having at least 95% sequence identity to SEQ ID NO: 17 and said tracrRNA has at least 95% sequence identity to SEQ ID NO: 29;

f) a RGN polypeptide having at least 95% sequence identity to SEQ ID NO: 6, wherein said crRNA comprises a CRISPR repeat sequence having at least 95% sequence identity to SEQ ID NO: 18 and said tracrRNA has at least 95% sequence identity to SEQ ID NO: 30;

g) a RGN polypeptide having at least 95% sequence identity to SEQ ID NO: 7, wherein said crRNA comprises a CRISPR repeat sequence having at least 95% sequence identity to SEQ ID NO: 19 and said tracrRNA has at least 95% sequence identity to SEQ ID NO: 31;

h) a RGN polypeptide having at least 95% sequence identity to SEQ ID NO: 8, wherein said crRNA comprises a CRISPR repeat sequence having at least 95% sequence identity to SEQ ID NO: 20 and said tracrRNA has at least 95% sequence identity to SEQ ID NO: 32;

i) a RGN polypeptide having at least 95% sequence identity to SEQ ID NO: 9, wherein said crRNA comprises a CRISPR repeat sequence having at least 95% sequence identity to SEQ ID NO: 21 and said tracrRNA has at least 95% sequence identity to SEQ ID NO: 33;

j) a RGN polypeptide having at least 95% sequence identity to SEQ ID NO: 10, wherein said crRNA comprises a CRISPR repeat sequence having at least 95% sequence identity to SEQ ID NO: 22 and said tracrRNA has at least 95% sequence identity to SEQ ID NO: 34;

k) a RGN polypeptide having at least 95% sequence identity to SEQ ID NO: 11, wherein said crRNA comprises a CRISPR repeat sequence having at least 95% sequence identity to SEQ ID NO: 23 and said tracrRNA has at least 95% sequence identity to SEQ ID NO: 35; and l) a RGN polypeptide having at least 95% sequence identity to SEQ ID NO: 12, wherein said crRNA comprises a CRISPR repeat sequence having at least 95% sequence identity to SEQ ID NO: 24 and said tracrRNA has at least 95% sequence identity to SEQ ID NO: 36.

100. The vector of embodiment 97, wherein said RGN polypeptide is selected from the group consisting of:

a) a RGN polypeptide having 100% sequence identity to SEQ ID NO: 1, wherein said crRNA comprises a CRISPR repeat sequence having 100% sequence identity to SEQ ID NO: 13 and said tracrRNA has 100% sequence identity to SEQ ID NO: 25;

b) a RGN polypeptide having 100% sequence identity to SEQ ID NO: 2, wherein said crRNA comprises a CRISPR repeat sequence having 100% sequence identity to SEQ ID NO: 14 and said tracrRNA has 100% sequence identity to SEQ ID NO: 26;

c) a RGN polypeptide having 100% sequence identity to SEQ ID NO: 3, wherein said crRNA comprises a CRISPR repeat sequence having 100% sequence identity to SEQ ID NO: 15 and said tracrRNA has 100% sequence identity to SEQ ID NO: 27;

d) a RGN polypeptide having 100% sequence identity to SEQ ID NO: 4, wherein said crRNA comprises a CRISPR repeat sequence having 100% sequence identity to SEQ ID NO: 16 and said tracrRNA has 100% sequence identity to SEQ ID NO: 28;

e) a RGN polypeptide having 100% sequence identity to SEQ ID NO: 5, wherein said crRNA comprises a CRISPR repeat sequence having 100% sequence identity to SEQ ID NO: 17 and said tracrRNA has 100% sequence identity to SEQ ID NO: 29;

f) a RGN polypeptide having 100% sequence identity to SEQ ID NO: 6, wherein said crRNA comprises a CRISPR repeat sequence having 100% sequence identity to SEQ ID NO: 18 and said tracrRNA has 100% sequence identity to SEQ ID NO: 30;

g) a RGN polypeptide having 100% sequence identity to SEQ ID NO: 7, wherein said crRNA comprises a CRISPR repeat sequence having 100% sequence identity to SEQ ID NO: 19 and said tracrRNA has 100% sequence identity to SEQ ID NO: 31;

h) a RGN polypeptide having 100% sequence identity to SEQ ID NO: 8, wherein said crRNA comprises a CRISPR repeat sequence having 100% sequence identity to SEQ ID NO: 20 and said tracrRNA has 100% sequence identity to SEQ ID NO: 32;

i) a RGN polypeptide having 100% sequence identity to SEQ ID NO: 9, wherein said crRNA comprises a CRISPR repeat sequence having 100% sequence identity to SEQ ID NO: 21 and said tracrRNA has 100% sequence identity to SEQ ID NO: 33;

j) a RGN polypeptide having 100% sequence identity to SEQ ID NO: 10, wherein said crRNA comprises a CRISPR repeat sequence having 100% sequence identity to SEQ ID NO: 22 and said tracrRNA has 100% sequence identity to SEQ ID NO: 34;

k) a RGN polypeptide having 100% sequence identity to SEQ ID NO: 11, wherein said crRNA comprises a CRISPR repeat sequence having 100% sequence identity to SEQ ID NO: 23 and said tracrRNA has 100% sequence identity to SEQ ID NO: 35; and l) a RGN polypeptide having 100% sequence identity to SEQ ID NO: 12, wherein said crRNA comprises a CRISPR repeat sequence having 100% sequence identity to SEQ ID NO: 24 and said tracrRNA has 100% sequence identity to SEQ ID NO: 36.

101. A cell comprising the nucleic acid molecule of any one of embodiments 69-72 and 85-88, the vector of any one of embodiments 73-84 and 89-100, the single guide RNA of embodiment 274 or 275, or the double guide RNA of embodiment 276.

102. The cell of embodiment 101, wherein the cell is a prokaryotic cell.

103. The cell of embodiment 101, wherein the cell is a eukaryotic cell.

104. The cell of embodiment 103, wherein the eukaryotic cell is a mammalian cell.

105. The cell of embodiment 104, wherein the mammalian cell is a human cell.

106. The cell of embodiment 105, wherein the human cell is an immune cell.

107. The cell of embodiment 106, wherein the immune cell is a stem cell.

108. The cell of embodiment 107, wherein the stem cell is an induced pluripotent stem cell.

109. The cell of embodiment 103, wherein the eukaryotic cell is an insect or avian cell.

110. The cell of embodiment 103, wherein the eukaryotic cell is a fungal cell.

111. The cell of embodiment 103, wherein the eukaryotic cell is a plant cell.

112. A plant comprising the cell of embodiment 111.

113. A seed comprising the cell of embodiment 111.

114. A system for binding a target DNA sequence of a DNA molecule, said system comprising:
a) one or more guide RNAs capable of hybridizing to said target DNA sequence or one or more polynucleotides comprising one or more nucleotide sequences encoding the one or more guide RNAs (gRNAs); and
b) an RNA-guided nuclease (RGN) polypeptide comprising an amino acid sequence having at least 90% sequence identity to any one of SEQ ID NOs: 1-12 or a polynucleotide comprising a nucleotide sequence encoding the RGN polypeptide;
wherein the one or more guide RNAs are capable of hybridizing to the target DNA sequence, and
wherein the one or more guide RNAs are capable of forming a complex with the RGN polypeptide in order to direct said RGN polypeptide to bind to said target DNA sequence of the DNA molecule.

115. The system of embodiment 114, wherein at least one of said nucleotide sequences encoding the one or more guide RNAs and said nucleotide sequence encoding the RGN polypeptide is operably linked to a promoter heterologous to said nucleotide sequence.

116. A system for binding a target DNA sequence of a DNA molecule, said system comprising:
a) one or more guide RNAs capable of hybridizing to said target DNA sequence or one or more polynucleotides comprising one or more nucleotide sequences encoding the one or more guide RNAs (gRNAs); and
b) an RNA-guided nuclease (RGN) polypeptide comprising an amino acid sequence having at least 90% sequence identity to any one of SEQ ID NOs: 1-12;
wherein the one or more guide RNAs are capable of hybridizing to the target DNA sequence, and
wherein the one or more guide RNAs are capable of forming a complex with the RGN polypeptide in order to direct said RGN polypeptide to bind to said target DNA sequence of the DNA molecule.

117. The system of any one of embodiments 114-116, wherein at least one of said nucleotides sequences encoding the one or more guide RNAs is operably linked to a promoter heterologous to said nucleotide sequence.

118. The system of any one of embodiments 114-117, wherein said RGN polypeptide comprises an amino acid sequence having at least 95% sequence identity to any one of SEQ ID NOs: 1-12.

119. The system of any one of embodiments 114-117, wherein said RGN polypeptide comprises an amino acid sequence having 100% sequence identity to any one of SEQ ID NOs: 1-12.

120. The system of any one of embodiments 114-119, wherein said RGN polypeptide and said one or more guide RNAs are not found complexed to one another in nature.

121. The system of any one of embodiments 114-120, wherein said target DNA sequence is a eukaryotic target DNA sequence.

122. The system of any one of embodiments 114-121, wherein said gRNA is a single guide RNA (sgRNA).

123. The system of embodiment 122, wherein said sgRNA comprises an extension comprising an edit template for prime editing.

124. The system of any one of embodiments 114-121, wherein said gRNA is a dual-guide RNA.

125. The system of any one of embodiments 114-124, wherein said gRNA is selected from the group consisting of:
a) a gRNA comprising a CRISPR repeat sequence having at least 90% sequence identity to SEQ ID NO: 13 and a tracrRNA having at least 90% sequence identity to SEQ ID NO: 25, wherein said RGN polypeptide comprises an amino acid sequence having at least 90% sequence identity to SEQ ID NO: 1;
b) a gRNA comprising a CRISPR repeat sequence having at least 90% sequence identity to SEQ ID NO: 14 and a tracrRNA having at least 90% sequence identity to SEQ ID NO: 26, wherein said RGN polypeptide comprises an amino acid sequence having at least 90% sequence identity to SEQ ID NO: 2;
c) a gRNA comprising a CRISPR repeat sequence having at least 90% sequence identity to SEQ ID NO: 15 and a tracrRNA having at least 90% sequence identity to SEQ ID NO: 27, wherein said RGN polypeptide comprises an amino acid sequence having at least 90% sequence identity to SEQ ID NO: 3;
d) a gRNA comprising a CRISPR repeat sequence having at least 90% sequence identity to SEQ ID NO: 16 and a tracrRNA having at least 90% sequence identity to SEQ ID NO: 28, wherein said RGN polypeptide comprises an amino acid sequence having at least 90% sequence identity to SEQ ID NO: 4;
e) a gRNA comprising a CRISPR repeat sequence having at least 90% sequence identity to SEQ ID NO: 17 and a tracrRNA having at least 90% sequence identity to SEQ ID NO: 29, wherein said RGN polypeptide comprises an amino acid sequence having at least 90% sequence identity to SEQ ID NO: 5;
f) a gRNA comprising a CRISPR repeat sequence having at least 90% sequence identity to SEQ ID NO: 18 and a tracrRNA having at least 90% sequence identity to SEQ ID NO: 30, wherein said RGN polypeptide comprises an amino acid sequence having at least 90% sequence identity to SEQ ID NO: 6;
g) a gRNA comprising a CRISPR repeat sequence having at least 90% sequence identity to SEQ ID NO: 19 and a tracrRNA having at least 90% sequence identity to SEQ ID NO: 31, wherein said RGN polypeptide comprises an amino acid sequence having at least 90% sequence identity to SEQ ID NO: 7;
h) a gRNA comprising a CRISPR repeat sequence having at least 90% sequence identity to SEQ ID NO: 20 and a tracrRNA having at least 90% sequence identity to SEQ ID NO: 32, wherein said RGN polypeptide comprises an amino acid sequence having at least 90% sequence identity to SEQ ID NO: 8;
i) a gRNA comprising a CRISPR repeat sequence having at least 90% sequence identity to SEQ ID NO: 21 and a tracrRNA having at least 90% sequence identity to SEQ ID NO: 33, wherein said RGN polypeptide comprises an amino acid sequence having at least 90% sequence identity to SEQ ID NO: 9;
j) a gRNA comprising a CRISPR repeat sequence having at least 90% sequence identity to SEQ ID NO: 22 and a tracrRNA having at least 90% sequence identity to SEQ ID NO: 34, wherein said RGN polypeptide comprises an amino acid sequence having at least 90% sequence identity to SEQ ID NOs: 10;
k) a gRNA comprising a CRISPR repeat sequence having at least 90% sequence identity to SEQ ID NO: 23 and a tracrRNA having at least 90% sequence identity to SEQ ID NO: 35, wherein said RGN polypeptide comprises an amino acid sequence having at least 90% sequence identity to SEQ ID NO: 11; and
l) a gRNA comprising a CRISPR repeat sequence having at least 90% sequence identity to SEQ ID NO: 24 and a tracrRNA having at least 90% sequence identity to SEQ ID NO: 36, wherein said RGN polypeptide comprises an amino acid sequence having at least 90% sequence identity to SEQ ID NO: 12.

126. The system of any one of embodiments 114-124, wherein said gRNA is selected from the group consisting of:
a) a gRNA comprising a CRISPR repeat sequence having at least 95% sequence identity to SEQ ID NO: 13 and a tracrRNA having at least 95% sequence identity to SEQ ID NO: 25, wherein said RGN polypeptide comprises an amino acid sequence having at least 95% sequence identity to SEQ ID NO: 1;
b) a gRNA comprising a CRISPR repeat sequence having at least 95% sequence identity to SEQ ID NO: 14 and a tracrRNA having at least 95% sequence identity to SEQ ID NO: 26, wherein said RGN polypeptide comprises an amino acid sequence having at least 95% sequence identity to SEQ ID NO: 2;
c) a gRNA comprising a CRISPR repeat sequence having at least 95% sequence identity to SEQ ID NO: 15 and a tracrRNA having at least 95% sequence identity to SEQ ID NO: 27, wherein said RGN polypeptide comprises an amino acid sequence having at least 95% sequence identity to SEQ ID NO: 3;
d) a gRNA comprising a CRISPR repeat sequence having at least 95% sequence identity to SEQ ID NO: 16 and a tracrRNA having at least 95% sequence identity to SEQ ID NO: 28, wherein said RGN polypeptide comprises an amino acid sequence having at least 95% sequence identity to SEQ ID NO: 4;
e) a gRNA comprising a CRISPR repeat sequence having at least 95% sequence identity to SEQ ID NO: 17 and a tracrRNA having at least 95% sequence identity to SEQ ID NO: 29, wherein said RGN polypeptide comprises an amino acid sequence having at least 95% sequence identity to SEQ ID NO: 5;
f) a gRNA comprising a CRISPR repeat sequence having at least 95% sequence identity to SEQ ID NO: 18 and a tracrRNA having at least 95% sequence identity to SEQ ID NO: 30, wherein said RGN polypeptide comprises an amino acid sequence having at least 95% sequence identity to SEQ ID NO: 6;
g) a gRNA comprising a CRISPR repeat sequence having at least 95% sequence identity to SEQ ID NO: 19 and a tracrRNA having at least 95% sequence identity to SEQ ID NO: 31, wherein said RGN polypeptide comprises an amino acid sequence having at least 95% sequence identity to SEQ ID NO: 7;
h) a gRNA comprising a CRISPR repeat sequence having at least 95% sequence identity to SEQ ID NO: 20 and a tracrRNA having at least 95% sequence identity to SEQ ID NO: 32, wherein said RGN polypeptide comprises an amino acid sequence having at least 95% sequence identity to SEQ ID NO: 8;
i) a gRNA comprising a CRISPR repeat sequence having at least 95% sequence identity to SEQ ID NO: 21 and a tracrRNA having at least 95% sequence identity to SEQ ID NO: 33, wherein said RGN polypeptide comprises an amino acid sequence having at least 95% sequence identity to SEQ ID NO: 9;
j) a gRNA comprising a CRISPR repeat sequence having at least 95% sequence identity to SEQ ID NO: 22 and a tracrRNA having at least 95% sequence identity to SEQ ID NO: 34, wherein said RGN polypeptide comprises an amino acid sequence having at least 95% sequence identity to SEQ ID NOs: 10;
k) a gRNA comprising a CRISPR repeat sequence having at least 95% sequence identity to SEQ ID NO: 23 and a tracrRNA having at least 95% sequence identity to SEQ ID NO: 35, wherein said RGN polypeptide comprises an amino acid sequence having at least 95% sequence identity to SEQ ID NO: 11; and
l) a gRNA comprising a CRISPR repeat sequence having at least 95% sequence identity to SEQ ID NO: 24 and a tracrRNA having at least 95% sequence identity to SEQ ID NO: 36, wherein said RGN polypeptide comprises an amino acid sequence having at least 95% sequence identity to SEQ ID NO: 12.

127. The system of any one of embodiments 114-124, wherein said gRNA is selected from the group consisting of:
a) a gRNA comprising a CRISPR repeat sequence having 100% sequence identity to SEQ ID NO: 13 and a tracrRNA having 100% sequence identity to SEQ ID NO: 25, wherein said RGN polypeptide comprises an amino acid sequence having 100% sequence identity to SEQ ID NO: 1;
b) a gRNA comprising a CRISPR repeat sequence having 100% sequence identity to SEQ ID NO: 14 and a tracrRNA having 100% sequence identity to SEQ ID NO: 26, wherein said RGN polypeptide comprises an amino acid sequence having 100% sequence identity to SEQ ID NO: 2;
c) a gRNA comprising a CRISPR repeat sequence having 100% sequence identity to SEQ ID NO: 15 and a tracrRNA having 100% sequence identity to SEQ ID NO: 27, wherein said RGN polypeptide comprises an amino acid sequence having 100% sequence identity to SEQ ID NO: 3;
d) a gRNA comprising a CRISPR repeat sequence having 100% sequence identity to SEQ ID NO: 16 and a tracrRNA having 100% sequence identity to SEQ ID NO: 28, wherein said RGN polypeptide comprises an amino acid sequence having 100% sequence identity to SEQ ID NO: 4;
e) a gRNA comprising a CRISPR repeat sequence having 100% sequence identity to SEQ ID NO: 17 and a tracrRNA having 100% sequence identity to SEQ ID NO: 29, wherein said RGN polypeptide comprises an amino acid sequence having 100% sequence identity to SEQ ID NO: 5;
f) a gRNA comprising a CRISPR repeat sequence having 100% sequence identity to SEQ ID NO: 18 and a tracrRNA having 100% sequence identity to SEQ ID NO: 30, wherein said RGN polypeptide comprises an amino acid sequence having 100% sequence identity to SEQ ID NO: 6;
g) a gRNA comprising a CRISPR repeat sequence having 100% sequence identity to SEQ ID NO: 19 and a tracrRNA having 100% sequence identity to SEQ ID NO: 31, wherein said RGN polypeptide comprises an amino acid sequence having 100% sequence identity to SEQ ID NO: 7;
h) a gRNA comprising a CRISPR repeat sequence having 100% sequence identity to SEQ ID NO: 20 and a tracrRNA having 100% sequence identity to SEQ ID NO: 32, wherein said RGN polypeptide comprises an amino acid sequence having 100% sequence identity to SEQ ID NO: 8;
i) a gRNA comprising a CRISPR repeat sequence having 100% sequence identity to SEQ ID NO: 21 and a tracrRNA having 100% sequence identity to SEQ ID NO: 33, wherein said RGN polypeptide comprises an amino acid sequence having 100% sequence identity to SEQ ID NO: 9;
j) a gRNA comprising a CRISPR repeat sequence having 100% sequence identity to SEQ ID NO: 22 and a tracrRNA having 100% sequence identity to SEQ ID NO: 34, wherein said RGN polypeptide comprises an amino acid sequence having 100% sequence identity to SEQ ID NOs: 10;
k) a gRNA comprising a CRISPR repeat sequence having 100% sequence identity to SEQ ID NO: 23 and a tracrRNA having 100% sequence identity to SEQ ID NO: 35, wherein said RGN polypeptide comprises an amino acid sequence having 100% sequence identity to SEQ ID NO: 11; and
l) a gRNA comprising a CRISPR repeat sequence having 100% sequence identity to SEQ ID NO: 24 and a tracrRNA having 100% sequence identity to SEQ ID NO: 36, wherein said RGN polypeptide comprises an amino acid sequence having 100% sequence identity to SEQ ID NO: 12.

128. The system of any one of embodiments 114-127, wherein said target DNA sequence is located adjacent to a protospacer adjacent motif (PAM).

129. The system of any one of embodiments 114-127, wherein the target DNA sequence is within a cell.

130. The system of any one of embodiments 114-129, wherein the one or more guide RNAs is capable of hybridizing to the target DNA sequence and the guide RNA is capable of forming a complex with the RGN polypeptide to direct cleavage of the target DNA sequence.

131. The system of embodiment 130, wherein the cleavage generates a double-stranded break.

132. The system of embodiment 130, wherein the cleavage generates a single-stranded break.

133. The system of any one of embodiments 114-129, wherein said RGN polypeptide is nuclease inactive or is a nickase.

134. The system of any one of embodiments 114-130, 132, and 133, wherein said RGN polypeptide is operably linked to a prime editing polypeptide.

135. The system of embodiment 134, wherein said prime editing polypeptide comprises a DNA polymerase.

136. The system of embodiment 134, wherein said prime editing polypeptide comprises a reverse transcriptase.

137. The system of any one of embodiments 114-133, wherein the RGN polypeptide is operably linked to a base-editing polypeptide.

138. The system of embodiment 137, wherein the base-editing polypeptide is a deaminase.

139. The system of embodiment 138, wherein the deaminase is a cytosine deaminase or an adenine deaminase.

140. The system of embodiment 138, wherein the deaminase has at least 90% sequence identity to an amino acid sequence of any one of SEQ ID NOs: 377-448.

141. The system of embodiment 138, wherein the deaminase has 100% sequence identity to an amino acid sequence of any one of SEQ ID NOs: 377-448.

142. The system of any one of embodiments 114-141, wherein the RGN polypeptide comprises one or more nuclear localization signals.

143. The system of any one of embodiments 114-142, wherein the RGN polypeptide is codon optimized for expression in a eukaryotic cell.

144. The system of any one of embodiments 114-143, wherein the nucleotide sequences encoding the one or more guide RNAs and the nucleotide sequence encoding the RGN polypeptide are located on one vector.

145. The system of any one of embodiments 114-144, wherein said system further comprises one or more donor polynucleotides.

146. A cell comprising the system of any one of embodiments 114-145.

147. The cell of embodiment 146, wherein the cell is a prokaryotic cell.

148. The cell of embodiment 146, wherein the cell is a eukaryotic cell.

149. The cell of embodiment 148, wherein the eukaryotic cell is a mammalian cell.

150. The cell of embodiment 149, wherein the mammalian cell is a human cell.

151. The cell of embodiment 150, wherein the human cell is an immune cell.

152. The cell of embodiment 151, wherein the immune cell is a stem cell.

153. The cell of embodiment 152, wherein the stem cell is an induced pluripotent stem cell.

154. The cell of embodiment 148, wherein the eukaryotic cell is an insect or avian cell.

155. The cell of embodiment 148, wherein the eukaryotic cell is a fungal cell.
156. The cell of embodiment 148, wherein the eukaryotic cell is a plant cell.
157. A plant comprising the cell of embodiment 156.
158. A seed comprising the cell of embodiment 156.
159. A pharmaceutical composition comprising the nucleic acid molecule of any one of embodiments 1-19, 69-72, and 85-88, the vector of any one of embodiments 20-27, 73-84, and 89-100, the cell of any one of embodiments 30-35, 103-108, and 148-153, the RGN polypeptide of any one of embodiments 48-65, the RNP complex of any one of embodiments 66-68, or the system of any one of embodiments 114-145, and a pharmaceutically acceptable carrier.
160. The pharmaceutical composition of embodiment 159, wherein the pharmaceutically acceptable carrier is heterologous to said nucleic acid molecule, said vector, said cell, said RGN polypeptide, or said system.
161. The pharmaceutical composition of embodiment 159 or 160, wherein the pharmaceutically acceptable carrier is not naturally-occurring.
162. A method for binding a target DNA sequence of a DNA molecule comprising delivering a system according to any one of embodiments 114-145, to said target DNA sequence or a cell comprising the target DNA sequence.
163. The method of embodiment 162, wherein said RGN polypeptide or said guide RNA further comprises a detectable label, thereby allowing for detection of said target DNA sequence.
164. The method of embodiment 162, wherein said guide RNA or said RGN polypeptide further comprises an expression modulator, thereby modulating expression of said target DNA sequence or a gene under transcriptional control by said target DNA sequence.
165. A method for cleaving and/or modifying a target DNA sequence of a DNA molecule comprising delivering a system according to any one of embodiments 114-145 to said target DNA sequence or a cell comprising the DNA molecule, wherein cleavage or modification of said target DNA sequence occurs.
166. The method of embodiment 165, wherein said modified target DNA sequence comprises insertion of heterologous DNA into the target DNA sequence.
167. The method of embodiment 165, wherein said modified target DNA sequence comprises deletion of at least one nucleotide from the target DNA sequence.
168. The method of embodiment 165, wherein said modified target DNA sequence comprises mutation of at least one nucleotide in the target DNA sequence.
169. A method for binding a target DNA sequence of a DNA molecule comprising:
a) assembling an RNA-guided nuclease (RGN) ribonucleotide complex by combining:
  i) one or more guide RNAs capable of hybridizing to the target DNA sequence; and
  ii) an RGN polypeptide comprising an amino acid sequence having at least 90% sequence identity to any one of SEQ ID NOs: 1-12;
  under conditions suitable for formation of the RGN ribonucleotide complex; and
b) contacting said target DNA sequence or a cell comprising said target DNA sequence with the assembled RGN ribonucleotide complex;
wherein the one or more guide RNAs hybridize to the target DNA sequence, thereby directing said RGN polypeptide to bind to said target DNA sequence.
170. The method of embodiment 169, wherein said method is performed in vitro, in vivo, or ex vivo.
171. The method of embodiment 169 or 170, wherein said RGN polypeptide or said guide RNA further comprises a detectable label, thereby allowing for detection of said target DNA sequence.
172. The method of embodiment 169 or 170, wherein said guide RNA or said RGN polypeptide further comprises an expression modulator, thereby allowing for the modulation of expression of said target DNA sequence.
173. The method of embodiment 169 or 170, wherein said RGN polypeptide is operably linked to a prime editing polypeptide, thereby allowing for the modification of said target DNA sequence.
174. The method of embodiment 173, wherein said prime editing polypeptide comprises a DNA polymerase.
175. The method of embodiment 173, wherein said prime editing polypeptide comprises a reverse transcriptase.
176. The method of embodiment 169 or 170, wherein said RGN polypeptide is operably linked to a base-editing polypeptide, thereby allowing for the modification of said target DNA sequence.
177. The method of embodiment 176, wherein said base-editing polypeptide comprises a deaminase.
178. The method of embodiment 177, wherein said deaminase is a cytosine deaminase or an adenine deaminase.
179. The method of embodiment 177, wherein the deaminase has at least 90% sequence identity to an amino acid sequence of any one of SEQ ID NOs: 377-448.
180. The method of embodiment 178, wherein the deaminase has 100% sequence identity to an amino acid sequence of any one of SEQ ID NOs: 377-448.
181. The method of embodiment 169 or 170, wherein said RGN polypeptide is capable of cleaving said target DNA sequence, thereby allowing for the cleaving and/or modifying of said target DNA sequence.
182. A method for cleaving and/or modifying a target DNA sequence of a DNA molecule, comprising contacting the DNA molecule with:
a) an RNA-guided nuclease (RGN) polypeptide, wherein said RGN comprises an amino acid sequence having at least 90% sequence identity to any one of SEQ ID NOs: 1-12; and
b) one or more guide RNAs capable of targeting the RGN of (a) to the target DNA sequence;
wherein the one or more guide RNAs hybridize to the target DNA sequence, thereby directing said RGN polypeptide to bind to said target DNA sequence and cleavage and/or modification of said target DNA sequence occurs.
183. The method of embodiment 182, wherein cleavage by said RGN polypeptide generates a double-stranded break.
184. The method of embodiment 182, wherein cleavage by said RGN polypeptide generates a single-stranded break.
185. The method of embodiment 182, wherein said RGN polypeptide is nuclease inactive or a nickase.
186. The method of any one of embodiments 182, 184, and 185, wherein said RGN is operably linked to a prime editing polypeptide, thereby allowing for the modification of said target DNA sequence.

187. The method of embodiment 186, wherein said prime editing polypeptide comprises a DNA polymerase.
188. The method of embodiment 186, wherein said prime editing polypeptide comprises a reverse transcriptase.
189. The method of any one of embodiments 182-185, wherein said RGN polypeptide is operably linked to a base-editing polypeptide.
190. The method of embodiment 189, wherein the base-editing polypeptide is a deaminase.
191. The method of embodiment 189, wherein the deaminase is a cytosine deaminase or an adenine deaminase.
192. The method of embodiment 190, wherein the deaminase has at least 90% sequence identity to an amino acid sequence of any one of SEQ ID NOs: 377-448.
193. The method of embodiment 190, wherein the deaminase has 100% sequence identity to an amino acid sequence of any one of SEQ ID NOs: 377-448.
194. The method of embodiment 182, wherein said modified target DNA sequence comprises insertion of heterologous DNA into the target DNA sequence.
195. The method of embodiment 182, wherein said modified target DNA sequence comprises deletion of at least one nucleotide from the target DNA sequence.
196. The method of embodiment 182, wherein said modified target DNA sequence comprises mutation of at least one nucleotide in the target DNA sequence.
197. The method of any one of embodiments 169-196, wherein said target DNA sequence is located adjacent to a protospacer adjacent motif (PAM).
198. The method of any one of embodiments 169-197, wherein said target DNA sequence is a eukaryotic target DNA sequence.
199. The method of any one of embodiments 169-198, wherein said gRNA is a single guide RNA (sgRNA).
200. The method of embodiment 199, wherein said sgRNA comprises an extension comprising an edit template for prime editing.
201. The method of any one of embodiments 169-198, wherein said gRNA is a dual-guide RNA.
202. The method of any one of embodiments 169-201, wherein said RGN comprises an amino acid sequence having at least 95% sequence identity to any one of SEQ ID NOs: 1-12.
203. The method of any one of embodiments 169-201, wherein said RGN comprises an amino acid sequence having 100% sequence identity to any one of SEQ ID NOs: 1-12.
204. The method of any one of embodiments 169-201, wherein:
a) said RGN has at least 90% sequence identity to SEQ ID NO: 1, said guide RNA comprises a crRNA repeat sequence having at least 90% sequence identity to SEQ ID NO: 13 and a tracrRNA having at least 90% sequence identity to SEQ ID NO: 25;
b) said RGN has at least 90% sequence identity to SEQ ID NO: 2, said guide RNA comprises a crRNA repeat sequence having at least 90% sequence identity to SEQ ID NO: 14 and a tracrRNA having at least 90% sequence identity to SEQ ID NO: 26;
c) said RGN has at least 90% sequence identity to SEQ ID NO: 3, said guide RNA comprises a crRNA repeat sequence having at least 90% sequence identity to SEQ ID NO: 15 and a tracrRNA having at least 90% sequence identity to SEQ ID NO: 27;
d) said RGN has at least 90% sequence identity to SEQ ID NO: 4, said guide RNA comprises a crRNA repeat sequence having at least 90% sequence identity to SEQ ID NO: 16 and a tracrRNA having at least 90% sequence identity to SEQ ID NO: 28;
e) said RGN has at least 90% sequence identity to SEQ ID NO: 5, said guide RNA comprises a crRNA repeat sequence having at least 90% sequence identity to SEQ ID NO: 17 and a tracrRNA having at least 90% sequence identity to SEQ ID NO: 29;
f) said RGN has at least 90% sequence identity to SEQ ID NO: 6, said guide RNA comprises a crRNA repeat sequence having at least 90% sequence identity to SEQ ID NO: 18 and a tracrRNA having at least 90% sequence identity to SEQ ID NO: 30;
g) said RGN has at least 90% sequence identity to SEQ ID NO: 7, said guide RNA comprises a crRNA repeat sequence having at least 90% sequence identity to SEQ ID NO: 19 and a tracrRNA having at least 90% sequence identity to SEQ ID NO: 31;
h) said RGN has at least 90% sequence identity to SEQ ID NO: 8, said guide RNA comprises a crRNA repeat sequence having at least 90% sequence identity to SEQ ID NO: 20 and a tracrRNA having at least 90% sequence identity to SEQ ID NO: 32;
i) said RGN has at least 90% sequence identity to SEQ ID NO: 9, said guide RNA comprises a crRNA repeat sequence having at least 90% sequence identity to SEQ ID NO: 21 and a tracrRNA having at least 90% sequence identity to SEQ ID NO: 33;
j) said RGN has at least 90% sequence identity to SEQ ID NO: 10, said guide RNA comprises a crRNA repeat sequence having at least 90% sequence identity to SEQ ID NO: 22 and a tracrRNA having at least 90% sequence identity to SEQ ID NO:34;
k) said RGN has at least 90% sequence identity to SEQ ID NO: 11, said guide RNA comprises a crRNA repeat sequence having at least 90% sequence identity to SEQ ID NO: 23 and a tracrRNA having at least 90% sequence identity to SEQ ID NO: 35; or
l) said RGN has at least 90% sequence identity to SEQ ID NO: 12, said guide RNA comprises a crRNA repeat sequence having at least 90% sequence identity to SEQ ID NO: 24 and a tracrRNA having at least 90% sequence identity to SEQ ID NO: 36.
205. The method of any one of embodiments 169-201, wherein:
a) said RGN has at least 95% sequence identity to SEQ ID NO: 1, said guide RNA comprises a crRNA repeat sequence having at least 95% sequence identity to SEQ ID NO: 13 and a tracrRNA having at least 95% sequence identity to SEQ ID NO: 25;
b) said RGN has at least 95% sequence identity to SEQ ID NO: 2, said guide RNA comprises a crRNA repeat sequence having at least 95% sequence identity to SEQ ID NO: 14 and a tracrRNA having at least 95% sequence identity to SEQ ID NO: 26;
c) said RGN has at least 95% sequence identity to SEQ ID NO: 3, said guide RNA comprises a crRNA repeat sequence having at least 95% sequence identity to SEQ ID NO: 15 and a tracrRNA having at least 95% sequence identity to SEQ ID NO: 27;
d) said RGN has at least 95% sequence identity to SEQ ID NO: 4, said guide RNA comprises a crRNA repeat sequence having at least 95% sequence identity to SEQ ID NO: 16 and a tracrRNA having at least 95% sequence identity to SEQ ID NO: 28;
e) said RGN has at least 95% sequence identity to SEQ ID NO: 5, said guide RNA comprises a crRNA repeat sequence having at least 95% sequence identity to SEQ ID NO: 17 and a tracrRNA having at least 95% sequence identity to SEQ ID NO: 29;
f) said RGN has at least 95% sequence identity to SEQ ID NO: 6, said guide RNA comprises a crRNA repeat sequence having at least 95% sequence identity to SEQ ID NO: 18 and a tracrRNA having at least 95% sequence identity to SEQ ID NO: 30;
g) said RGN has at least 95% sequence identity to SEQ ID NO: 7, said guide RNA comprises a crRNA repeat sequence having at least 95% sequence identity to SEQ ID NO: 19 and a tracrRNA having at least 95% sequence identity to SEQ ID NO: 31;
h) said RGN has at least 95% sequence identity to SEQ ID NO: 8, said guide RNA comprises a crRNA repeat sequence having at least 95% sequence identity to SEQ ID NO: 20 and a tracrRNA having at least 95% sequence identity to SEQ ID NO: 32;
i) said RGN has at least 95% sequence identity to SEQ ID NO: 9, said guide RNA comprises a crRNA repeat sequence having at least 95% sequence identity to SEQ ID NO: 21 and a tracrRNA having at least 95% sequence identity to SEQ ID NO: 33;
j) said RGN has at least 95% sequence identity to SEQ ID NO: 10, said guide RNA comprises a crRNA repeat sequence having at least 95% sequence identity to SEQ ID NO: 22 and a tracrRNA having at least 95% sequence identity to SEQ ID NO:34;
k) said RGN has at least 95% sequence identity to SEQ ID NO: 11, said guide RNA comprises a crRNA repeat sequence having at least 95% sequence identity to SEQ ID NO: 23 and a tracrRNA having at least 95% sequence identity to SEQ ID NO: 35; or
l) said RGN has at least 95% sequence identity to SEQ ID NO: 12, said guide RNA comprises a crRNA repeat sequence having at least 95% sequence identity to SEQ ID NO: 24 and a tracrRNA having at least 95% sequence identity to SEQ ID NO: 36.

206. The method of any one of embodiments 169-201, wherein:
a) said RGN has 100% sequence identity to SEQ ID NO: 1, said guide RNA comprises a crRNA repeat sequence having 100% sequence identity to SEQ ID NO: 13 and a tracrRNA having 100% sequence identity to SEQ ID NO: 25;
b) said RGN has 100% sequence identity to SEQ ID NO: 2, said guide RNA comprises a crRNA repeat sequence having 100% sequence identity to SEQ ID NO: 14 and a tracrRNA having 100% sequence identity to SEQ ID NO: 26;
c) said RGN has 100% sequence identity to SEQ ID NO: 3, said guide RNA comprises a crRNA repeat sequence having 100% sequence identity to SEQ ID NO: 15 and a tracrRNA having 100% sequence identity to SEQ ID NO: 27;
d) said RGN has 100% sequence identity to SEQ ID NO: 4, said guide RNA comprises a crRNA repeat sequence having 100% sequence identity to SEQ ID NO: 16 and a tracrRNA having 100% sequence identity to SEQ ID NO: 28;
e) said RGN has 100% sequence identity to SEQ ID NO: 5, said guide RNA comprises a crRNA repeat sequence having 100% sequence identity to SEQ ID NO: 17 and a tracrRNA having 100% sequence identity to SEQ ID NO: 29;
f) said RGN has 100% sequence identity to SEQ ID NO: 6, said guide RNA comprises a crRNA repeat sequence having 100% sequence identity to SEQ ID NO: 18 and a tracrRNA having 100% sequence identity to SEQ ID NO: 30;
g) said RGN has 100% sequence identity to SEQ ID NO: 7, said guide RNA comprises a crRNA repeat sequence having 100% sequence identity to SEQ ID NO: 19 and a tracrRNA having 100% sequence identity to SEQ ID NO: 31;
h) said RGN has 100% sequence identity to SEQ ID NO: 8, said guide RNA comprises a crRNA repeat sequence having 100% sequence identity to SEQ ID NO: 20 and a tracrRNA having 100% sequence identity to SEQ ID NO: 32;
i) said RGN has 100% sequence identity to SEQ ID NO: 9, said guide RNA comprises a crRNA repeat sequence having 100% sequence identity to SEQ ID NO: 21 and a tracrRNA having 100% sequence identity to SEQ ID NO: 33;
j) said RGN has 100% sequence identity to SEQ ID NO: 10, said guide RNA comprises a crRNA repeat sequence having 100% sequence identity to SEQ ID NO: 22 and a tracrRNA having 100% sequence identity to SEQ ID NO:34;
k) said RGN has 100% sequence identity to SEQ ID NO: 11, said guide RNA comprises a crRNA repeat sequence having 100% sequence identity to SEQ ID NO: 23 and a tracrRNA having 100% sequence identity to SEQ ID NO: 35; or
l) said RGN has 100% sequence identity to SEQ ID NO: 12, said guide RNA comprises a crRNA repeat sequence having 100% sequence identity to SEQ ID NO: 24 and a tracrRNA having 100% sequence identity to SEQ ID NO: 36.

207. The method of any one of embodiments 162-206, wherein the target DNA sequence is within a cell.
208. The method of embodiment 207, wherein the cell is a eukaryotic cell.
209. The method of embodiment 208, wherein the eukaryotic cell is a mammalian cell.
210. The method of embodiment 209, wherein said mammalian cell is a human cell.
211. The method of embodiment 210, wherein said human cell is an immune cell.
212. The method of embodiment 211, wherein said immune cell is a stem cell.
213. The method of embodiment 212, wherein said stem cell is an induced pluripotent stem cell.
214. The method of embodiment 208, wherein the eukaryotic cell is an insect or avian cell.
215. The method of embodiment 207, wherein the cell is a prokaryotic cell.
216. The method of embodiment 208, wherein the eukaryotic cell is a fungal cell.
217. The method of embodiment 208, wherein the eukaryotic cell is a plant cell.
218. The method of any one of embodiments 207-217, further comprising culturing the cell under conditions in which the RGN polypeptide is expressed and cleaves and modifies the target DNA sequence to produce a DNA molecule comprising a modified target DNA sequence; and selecting a cell comprising said modified target DNA sequence.
219. A cell comprising a modified target DNA sequence according to the method of embodiment 218.
220. The cell of embodiment 219, wherein the cell is a eukaryotic cell.

221. The cell of embodiment 220, wherein the eukaryotic cell is a mammalian cell.
222. The cell of embodiment 221, wherein said mammalian cell is a human cell.
223. The cell of embodiment 222, wherein said human cell is an immune cell.
224. The cell of embodiment 223, wherein said immune cell is a stem cell.
225. The cell of embodiment 224, wherein said stem cell is an induced pluripotent stem cell.
226. The cell of embodiment 220, wherein the eukaryotic cell is an insect or avian cell.
227. The cell of embodiment 219, wherein the cell is a prokaryotic cell.
228. The cell of embodiment 220, wherein the eukaryotic cell is a fungal cell.
229. The cell of embodiment 220, wherein the eukaryotic cell is a plant cell.
230. A plant comprising the cell of embodiment 229.
231. A seed comprising the cell of embodiment 229.
232. A pharmaceutical composition comprising the cell of any one of embodiments 220-225 and a pharmaceutically acceptable carrier.
233. A method for producing a genetically modified cell with a correction in a causal mutation for a genetically inherited disease, the method comprising introducing into the cell:
a) an RNA-guided nuclease (RGN) polypeptide, wherein the RGN polypeptide comprises an amino acid sequence having at least 90% sequence identity to any one of SEQ ID NOs: 1-12, or a polynucleotide encoding said RGN polypeptide, wherein said polynucleotide encoding the RGN polypeptide is operably linked to a promoter to enable expression of the RGN polypeptide in the cell; and
b) a guide RNA (gRNA) or a polynucleotide encoding said gRNA, wherein said polynucleotide encoding the gRNA is operably linked to a promoter to enable expression of the gRNA in the cell whereby the RGN and gRNA target to the genomic location of the causal mutation and modify the genomic sequence to remove the causal mutation.
234. The method of embodiment 233, wherein the RGN is nuclease inactive or a nickase.
235. The method of embodiment 233 or 234, wherein the RGN is operably linked to a prime editing polypeptide.
236. The method of embodiment 235, wherein the prime editing polypeptide comprises a DNA polymerase.
237. The method of embodiment 235, wherein the prime editing polypeptide comprises a reverse transcriptase.
238. The method of any one of embodiments 235-237, wherein said gRNA is a single guide RNA and comprises an extension comprising an edit template for prime editing.
239. The method of embodiment 233 or 234, wherein the RGN is operably linked to a polypeptide which has base-editing activity.
240. The method of embodiment 239, wherein the base-editing polypeptide is a deaminase.
241. The method of embodiment 240, wherein the polypeptide with base-editing activity is a cytosine deaminase or an adenine deaminase.
242. The method of embodiment 240, wherein the deaminase has at least 90% sequence identity to an amino acid sequence of any one of SEQ ID NOs: 377-448.
243. The method of embodiment 240, wherein the deaminase has 100% sequence identity to an amino acid sequence of any one of SEQ ID NOs: 377-448.
244. The method of any one of embodiments 240-243, wherein the genetically inherited disease is caused by a single nucleotide polymorphism.
245. The method of any one of embodiments 240-243, wherein the genetically inherited disease is Hurler Syndrome.
246. The method of embodiment 244, wherein the gRNA further comprises a spacer sequence that targets a region proximal to the causal single nucleotide polymorphism.
247. A method for producing a genetically modified cell with a deletion in a causal mutation, the method comprising introducing into the cell:
a) an RNA-guided nuclease (RGN) polypeptide, wherein the RGN polypeptide comprises an amino acid sequence having at least 90% sequence identity to any one of SEQ ID NOs: 1-12, or a polynucleotide encoding said RGN polypeptide, wherein said polynucleotide encoding the RGN polypeptide is operably linked to a promoter to enable expression of the RGN polypeptide in the cell; and
b) a first guide RNA (gRNA) or a polynucleotide encoding said gRNA, wherein said polynucleotide encoding the gRNA is operably linked to a promoter to enable expression of the gRNA in the cell, and further wherein the gRNA comprises a spacer sequence that targets the 5' flank of the causal mutation; and
c) a second guide RNA (gRNA) or a polynucleotide encoding said gRNA, wherein said polynucleotide encoding the gRNA is operably linked to a promoter to enable expression of the gRNA in the cell, and further wherein said second gRNA comprises a spacer sequence that targets the 3'flank of the causal mutation;
whereby the RGN and the two gRNAs target to the causal mutation and at least a portion of the causal mutation is removed.
248. The method of embodiment 247, wherein the genetically inherited disease is Friedrich's Ataxia or Huntington's Disease.
249. The method of embodiment 247, wherein the first gRNA further comprises a spacer sequence that targets a region within or proximal to the causal mutation.
250. The method of embodiment 249, wherein the second gRNA further comprises a spacer sequence that targets a region within or proximal to the causal mutation.
251. The method of any one of embodiments 233-250, wherein said RGN polypeptide has at least 95% sequence identity to any one of SEQ ID NOs: 1-12.
252. The method of any one of embodiments 233-250, wherein said RGN polypeptide has 100% sequence identity to any one of SEQ ID NOs: 1-12.
253. The method of any one of embodiments 233-250, wherein said gRNA, said first gRNA, said second gRNA, or said first gRNA and said second gRNA is selected from a gRNA selected from the group consisting of:
a) a gRNA comprising a CRISPR repeat sequence having at least 90% sequence identity to SEQ ID NO: 13 and a tracrRNA having at least 90% sequence identity to SEQ ID NO: 25, wherein said RGN polypeptide has an amino acid sequence having at least 90% sequence identity to SEQ ID NO: 1;
b) a gRNA comprising a CRISPR repeat sequence having at least 90% sequence identity to SEQ ID NO: 14 and a tracrRNA having at least 90% sequence identity to SEQ ID NO: 26, wherein said RGN polypeptide has an amino acid sequence having at least 90% sequence identity to SEQ ID NO: 2;
c) a gRNA comprising a CRISPR repeat sequence having at least 90% sequence identity to SEQ ID NO: 15 and a tracrRNA having at least 90% sequence identity to SEQ ID NO: 27, wherein said RGN polypeptide has an amino acid sequence having at least 90% sequence identity to SEQ ID NO: 3;
d) a gRNA comprising a CRISPR repeat sequence having at least 90% sequence identity to SEQ ID NO: 16 and a tracrRNA having at least 90% sequence identity to SEQ ID NO: 28, wherein said RGN polypeptide has an amino acid sequence having at least 90% sequence identity to SEQ ID NO: 4;
e) a gRNA comprising a CRISPR repeat sequence having at least 90% sequence identity to SEQ ID NO: 17 and a tracrRNA having at least 90% sequence identity to SEQ ID NO: 29, wherein said RGN polypeptide has an amino acid sequence having at least 90% sequence identity to SEQ ID NO: 5;
f) a gRNA comprising a CRISPR repeat sequence having at least 90% sequence identity to SEQ ID NO: 18 and a tracrRNA having at least 90% sequence identity to SEQ ID NO: 30, wherein said RGN polypeptide has an amino acid sequence having at least 90% sequence identity to SEQ ID NO: 6;
g) a gRNA comprising a CRISPR repeat sequence having at least 90% sequence identity to SEQ ID NO: 19 and a tracrRNA having at least 90% sequence identity to SEQ ID NO: 31, wherein said RGN polypeptide has an amino acid sequence having at least 90% sequence identity to SEQ ID NO: 7;
h) a gRNA comprising a CRISPR repeat sequence having at least 90% sequence identity to SEQ ID NO: 20 and a tracrRNA having at least 90% sequence identity to SEQ ID NO: 32, wherein said RGN polypeptide has an amino acid sequence having at least 90% sequence identity to SEQ ID NO: 8;
i) a gRNA comprising a CRISPR repeat sequence having at least 90% sequence identity to SEQ ID NO: 21 and a tracrRNA having at least 90% sequence identity to SEQ ID NO: 33, wherein said RGN polypeptide has an amino acid sequence having at least 90% sequence identity to SEQ ID NO: 9;
j) a gRNA comprising a CRISPR repeat sequence having at least 90% sequence identity to SEQ ID NO: 22 and a tracrRNA having at least 90% sequence identity to SEQ ID NO: 34, wherein said RGN polypeptide has an amino acid sequence having at least 90% sequence identity to SEQ ID NO: 10;
k) a gRNA comprising a CRISPR repeat sequence having at least 90% sequence identity to SEQ ID NO: 23 and a tracrRNA having at least 90% sequence identity to SEQ ID NO: 35, wherein said RGN polypeptide has an amino acid sequence having at least 90% sequence identity to SEQ ID NO: 11; and
l) a gRNA comprising a CRISPR repeat sequence having at least 90% sequence identity to SEQ ID NO: 24 and a tracrRNA having at least 90% sequence identity to SEQ ID NO: 36, wherein said RGN polypeptide has an amino acid sequence having at least 90% sequence identity to SEQ ID 254. The method of any one of embodiments 233-250, wherein said gRNA, said first gRNA, said second gRNA, or said first gRNA and said second gRNA is selected from a gRNA selected from the group consisting of: NO: 12.
a) a gRNA comprising a CRISPR repeat sequence having at least 95% sequence identity to SEQ ID NO: 13 and a tracrRNA having at least 95% sequence identity to SEQ ID NO: 25, wherein said RGN polypeptide has an amino acid sequence having at least 95% sequence identity to SEQ ID NO: 1;
b) a gRNA comprising a CRISPR repeat sequence having at least 95% sequence identity to SEQ ID NO: 14 and a tracrRNA having at least 95% sequence identity to SEQ ID NO: 26, wherein said RGN polypeptide has an amino acid sequence having at least 95% sequence identity to SEQ ID NO: 2;
c) a gRNA comprising a CRISPR repeat sequence having at least 95% sequence identity to SEQ ID NO: 15 and a tracrRNA having at least 95% sequence identity to SEQ ID NO: 27, wherein said RGN polypeptide has an amino acid sequence having at least 95% sequence identity to SEQ ID NO: 3;
d) a gRNA comprising a CRISPR repeat sequence having at least 95% sequence identity to SEQ ID NO: 16 and a tracrRNA having at least 95% sequence identity to SEQ ID NO: 28, wherein said RGN polypeptide has an amino acid sequence having at least 95% sequence identity to SEQ ID NO: 4;
e) a gRNA comprising a CRISPR repeat sequence having at least 95% sequence identity to SEQ ID NO: 17 and a tracrRNA having at least 95% sequence identity to SEQ ID NO: 29, wherein said RGN polypeptide has an amino acid sequence having at least 95% sequence identity to SEQ ID NO: 5;
f) a gRNA comprising a CRISPR repeat sequence having at least 95% sequence identity to SEQ ID NO: 18 and a tracrRNA having at least 95% sequence identity to SEQ ID NO: 30, wherein said RGN polypeptide has an amino acid sequence having at least 95% sequence identity to SEQ ID NO: 6;
g) a gRNA comprising a CRISPR repeat sequence having at least 95% sequence identity to SEQ ID NO: 19 and a tracrRNA having at least 95% sequence identity to SEQ ID NO: 31, wherein said RGN polypeptide has an amino acid sequence having at least 95% sequence identity to SEQ ID NO: 7;
h) a gRNA comprising a CRISPR repeat sequence having at least 95% sequence identity to SEQ ID NO: 20 and a tracrRNA having at least 95% sequence identity to SEQ ID NO: 32, wherein said RGN polypeptide has an amino acid sequence having at least 95% sequence identity to SEQ ID NO: 8;
i) a gRNA comprising a CRISPR repeat sequence having at least 95% sequence identity to SEQ ID NO: 21 and a tracrRNA having at least 95% sequence identity to SEQ ID NO: 33, wherein said RGN polypeptide has an amino acid sequence having at least 95% sequence identity to SEQ ID NO: 9;
j) a gRNA comprising a CRISPR repeat sequence having at least 95% sequence identity to SEQ ID NO: 22 and a tracrRNA having at least 95% sequence identity to SEQ ID NO: 34, wherein said RGN polypeptide has an amino acid sequence having at least 95% sequence identity to SEQ ID NO: 10;
k) a gRNA comprising a CRISPR repeat sequence having at least 95% sequence identity to SEQ ID NO: 23 and a tracrRNA having at least 95% sequence identity to SEQ ID NO: 35, wherein said RGN polypeptide has an amino acid sequence having at least 95% sequence identity to SEQ ID NO: 11; and l) a gRNA comprising a CRISPR repeat sequence having at least 95% sequence identity to SEQ ID NO: 24 and a tracrRNA having at least 95% sequence identity to SEQ ID NO: 36, wherein said RGN polypeptide has an amino acid sequence having at least 95% sequence identity to SEQ ID NO: 12.

255. The method of any one of embodiments 233-250, wherein said gRNA, said first gRNA, said second gRNA, or said first gRNA and said second gRNA is selected from a gRNA selected from the group consisting of:

a) a gRNA comprising a CRISPR repeat sequence having 100% sequence identity to SEQ ID NO: 13 and a tracrRNA having 100% sequence identity to SEQ ID NO: 25, wherein said RGN polypeptide has an amino acid sequence having 100% sequence identity to SEQ ID NO: 1;

b) a gRNA comprising a CRISPR repeat sequence having 100% sequence identity to SEQ ID NO: 14 and a tracrRNA having 100% sequence identity to SEQ ID NO: 26, wherein said RGN polypeptide has an amino acid sequence having 100% sequence identity to SEQ ID NO: 2;

c) a gRNA comprising a CRISPR repeat sequence having 100% sequence identity to SEQ ID NO: 15 and a tracrRNA having 100% sequence identity to SEQ ID NO: 27, wherein said RGN polypeptide has an amino acid sequence having 100% sequence identity to SEQ ID NO: 3;

d) a gRNA comprising a CRISPR repeat sequence having 100% sequence identity to SEQ ID NO: 16 and a tracrRNA having 100% sequence identity to SEQ ID NO: 28, wherein said RGN polypeptide has an amino acid sequence having 100% sequence identity to SEQ ID NO: 4;

e) a gRNA comprising a CRISPR repeat sequence having 100% sequence identity to SEQ ID NO: 17 and a tracrRNA having 100% sequence identity to SEQ ID NO: 29, wherein said RGN polypeptide has an amino acid sequence having 100% sequence identity to SEQ ID NO: 5;

f) a gRNA comprising a CRISPR repeat sequence having 100% sequence identity to SEQ ID NO: 18 and a tracrRNA having 100% sequence identity to SEQ ID NO: 30, wherein said RGN polypeptide has an amino acid sequence having 100% sequence identity to SEQ ID NO: 6;

g) a gRNA comprising a CRISPR repeat sequence having 100% sequence identity to SEQ ID NO: 19 and a tracrRNA having 100% sequence identity to SEQ ID NO: 31, wherein said RGN polypeptide has an amino acid sequence having 100% sequence identity to SEQ ID NO: 7;

h) a gRNA comprising a CRISPR repeat sequence having 100% sequence identity to SEQ ID NO: 20 and a tracrRNA having 100% sequence identity to SEQ ID NO: 32, wherein said RGN polypeptide has an amino acid sequence having 100% sequence identity to SEQ ID NO: 8;

i) a gRNA comprising a CRISPR repeat sequence having 100% sequence identity to SEQ ID NO: 21 and a tracrRNA having 100% sequence identity to SEQ ID NO: 33, wherein said RGN polypeptide has an amino acid sequence having 100% sequence identity to SEQ ID NO: 9;

j) a gRNA comprising a CRISPR repeat sequence having 100% sequence identity to SEQ ID NO: 22 and a tracrRNA having 100% sequence identity to SEQ ID NO: 34, wherein said RGN polypeptide has an amino acid sequence having 100% sequence identity to SEQ ID NO: 10;

k) a gRNA comprising a CRISPR repeat sequence having 100% sequence identity to SEQ ID NO: 23 and a tracrRNA having 100% sequence identity to SEQ ID NO: 35, wherein said RGN polypeptide has an amino acid sequence having 100% sequence identity to SEQ ID NO: 11; and l) a gRNA comprising a CRISPR repeat sequence having 100% sequence identity to SEQ ID NO: 24 and a tracrRNA having 100% sequence identity to SEQ ID NO: 36, wherein said RGN polypeptide has an amino acid sequence having 100% sequence identity to SEQ ID NO: 12.

256. The method of any one of embodiments 233-255, wherein the cell is an animal cell.

257. The method of embodiment 256, wherein the animal cell is a mammalian cell.

258. The method of embodiment 256, wherein the cell is derived from a dog, cat, mouse, rat, rabbit, horse, cow, pig, or human.

259. A method for producing a genetically modified mammalian hematopoietic progenitor cell having decreased BCL11A mRNA and protein expression, the method comprising introducing into an isolated human hematopoietic progenitor cell:

a) an RNA-guided nuclease (RGN) polypeptide, wherein the RGN polypeptide comprises an amino acid sequence having at least 90% sequence identity to any one of SEQ ID NOs: 1-12, or a polynucleotide encoding said RGN polypeptide, wherein said polynucleotide encoding the RGN polypeptide is operably linked to a promoter to enable expression of the RGN polypeptide in the cell; and b) a guide RNA (gRNA) or a polynucleotide encoding said gRNA, wherein said polynucleotide encoding the gRNA is operably linked to a promoter to enable expression of the gRNA in the cell, whereby the RGN and gRNA are expressed in the cell and cleave at the BCL11A enhancer region, resulting in genetic modification of the human hematopoietic progenitor cell and reducing the mRNA and/or protein expression of BCL11A.

260. The method of embodiment 259, wherein said RGN polypeptide has at least 95% sequence identity to any one of SEQ ID NOs: 1-12.

261. The method of embodiment 259, wherein said RGN polypeptide has 100% sequence identity to any one of SEQ ID NOs: 1-12.

262. The method of embodiment 259, wherein said gRNA is selected from the group consisting of:

a) a gRNA comprising a CRISPR repeat sequence having at least 90% sequence identity to SEQ ID NO: 13 and a tracrRNA having at least 90% sequence identity to SEQ ID NO: 25, wherein said RGN polypeptide has an amino acid sequence having at least 90% sequence identity to SEQ ID NO: 1;

b) a gRNA comprising a CRISPR repeat sequence having at least 90% sequence identity to SEQ ID NO: 14 and a tracrRNA having at least 90% sequence identity to SEQ ID NO: 26, wherein said RGN polypeptide has an amino acid sequence having at least 90% sequence identity to SEQ ID NO: 2;

c) a gRNA comprising a CRISPR repeat sequence having at least 90% sequence identity to SEQ ID NO: 15 and a tracrRNA having at least 90% sequence identity to SEQ ID NO: 27, wherein said RGN polypeptide has an amino acid sequence having at least 90% sequence identity to SEQ ID NO: 3;
d) a gRNA comprising a CRISPR repeat sequence having at least 90% sequence identity to SEQ ID NO: 16 and a tracrRNA having at least 90% sequence identity to SEQ ID NO: 28, wherein said RGN polypeptide has an amino acid sequence having at least 90% sequence identity to SEQ ID NO: 4;
e) a gRNA comprising a CRISPR repeat sequence having at least 90% sequence identity to SEQ ID NO: 17 and a tracrRNA having at least 90% sequence identity to SEQ ID NO: 29, wherein said RGN polypeptide has an amino acid sequence having at least 90% sequence identity to SEQ ID NO: 5;
f) a gRNA comprising a CRISPR repeat sequence having at least 90% sequence identity to SEQ ID NO: 18 and a tracrRNA having at least 90% sequence identity to SEQ ID NO: 30, wherein said RGN polypeptide has an amino acid sequence having at least 90% sequence identity to SEQ ID NO: 6;
g) a gRNA comprising a CRISPR repeat sequence having at least 90% sequence identity to SEQ ID NO: 19 and a tracrRNA having at least 90% sequence identity to SEQ ID NO: 31, wherein said RGN polypeptide has an amino acid sequence having at least 90% sequence identity to SEQ ID NO: 7;
h) a gRNA comprising a CRISPR repeat sequence having at least 90% sequence identity to SEQ ID NO: 20 and a tracrRNA having at least 90% sequence identity to SEQ ID NO: 32, wherein said RGN polypeptide has an amino acid sequence having at least 90% sequence identity to SEQ ID NO: 8;
i) a gRNA comprising a CRISPR repeat sequence having at least 90% sequence identity to SEQ ID NO: 21 and a tracrRNA having at least 90% sequence identity to SEQ ID NO: 33, wherein said RGN polypeptide has an amino acid sequence having at least 90% sequence identity to SEQ ID NO: 9;
j) a gRNA comprising a CRISPR repeat sequence having at least 90% sequence identity to SEQ ID NO: 22 and a tracrRNA having at least 90% sequence identity to SEQ ID NO: 34, wherein said RGN polypeptide has an amino acid sequence having at least 90% sequence identity to SEQ ID NO: 10;
k) a gRNA comprising a CRISPR repeat sequence having at least 90% sequence identity to SEQ ID NO: 23 and a tracrRNA having at least 90% sequence identity to SEQ ID NO: 35, wherein said RGN polypeptide has an amino acid sequence having at least 90% sequence identity to SEQ ID NO: 11; and
l) a gRNA comprising a CRISPR repeat sequence having at least 90% sequence identity to SEQ ID NO: 24 and a tracrRNA having at least 90% sequence identity to SEQ ID NO: 36, wherein said RGN polypeptide has an amino acid sequence having at least 90% sequence identity to SEQ ID NO: 12.

263. The method of embodiment 259, wherein said gRNA is selected from the group consisting of:
a) a gRNA comprising a CRISPR repeat sequence having at least 95% sequence identity to SEQ ID NO: 13 and a tracrRNA having at least 95% sequence identity to SEQ ID NO: 25, wherein said RGN polypeptide has an amino acid sequence having at least 95% sequence identity to SEQ ID NO: 1;
b) a gRNA comprising a CRISPR repeat sequence having at least 95% sequence identity to SEQ ID NO: 14 and a tracrRNA having at least 95% sequence identity to SEQ ID NO: 26, wherein said RGN polypeptide has an amino acid sequence having at least 95% sequence identity to SEQ ID NO: 2;
c) a gRNA comprising a CRISPR repeat sequence having at least 95% sequence identity to SEQ ID NO: 15 and a tracrRNA having at least 95% sequence identity to SEQ ID NO: 27, wherein said RGN polypeptide has an amino acid sequence having at least 95% sequence identity to SEQ ID NO: 3;
d) a gRNA comprising a CRISPR repeat sequence having at least 95% sequence identity to SEQ ID NO: 16 and a tracrRNA having at least 95% sequence identity to SEQ ID NO: 28, wherein said RGN polypeptide has an amino acid sequence having at least 95% sequence identity to SEQ ID NO: 4;
e) a gRNA comprising a CRISPR repeat sequence having at least 95% sequence identity to SEQ ID NO: 17 and a tracrRNA having at least 95% sequence identity to SEQ ID NO: 29, wherein said RGN polypeptide has an amino acid sequence having at least 95% sequence identity to SEQ ID NO: 5;
f) a gRNA comprising a CRISPR repeat sequence having at least 95% sequence identity to SEQ ID NO: 18 and a tracrRNA having at least 95% sequence identity to SEQ ID NO: 30, wherein said RGN polypeptide has an amino acid sequence having at least 95% sequence identity to SEQ ID NO: 6;
g) a gRNA comprising a CRISPR repeat sequence having at least 95% sequence identity to SEQ ID NO: 19 and a tracrRNA having at least 95% sequence identity to SEQ ID NO: 31, wherein said RGN polypeptide has an amino acid sequence having at least 95% sequence identity to SEQ ID NO: 7;
h) a gRNA comprising a CRISPR repeat sequence having at least 95% sequence identity to SEQ ID NO: 20 and a tracrRNA having at least 95% sequence identity to SEQ ID NO: 32, wherein said RGN polypeptide has an amino acid sequence having at least 95% sequence identity to SEQ ID NO: 8;
i) a gRNA comprising a CRISPR repeat sequence having at least 95% sequence identity to SEQ ID NO: 21 and a tracrRNA having at least 95% sequence identity to SEQ ID NO: 33, wherein said RGN polypeptide has an amino acid sequence having at least 95% sequence identity to SEQ ID NO: 9;
j) a gRNA comprising a CRISPR repeat sequence having at least 95% sequence identity to SEQ ID NO: 22 and a tracrRNA having at least 95% sequence identity to SEQ ID NO: 34, wherein said RGN polypeptide has an amino acid sequence having at least 95% sequence identity to SEQ ID NO: 10;
k) a gRNA comprising a CRISPR repeat sequence having at least 95% sequence identity to SEQ ID NO: 23 and a tracrRNA having at least 95% sequence identity to SEQ ID NO: 35, wherein said RGN polypeptide has an amino acid sequence having at least 95% sequence identity to SEQ ID NO: 11; and
l) a gRNA comprising a CRISPR repeat sequence having at least 95% sequence identity to SEQ ID NO: 24 and a tracrRNA having at least 95% sequence identity to SEQ ID NO: 36, wherein said RGN polypeptide has an amino acid sequence having at least 95% sequence identity to SEQ ID NO: 12.

264. The method of embodiment 259, wherein said gRNA is selected from the group consisting of:
a) a gRNA comprising a CRISPR repeat sequence having 100% sequence identity to SEQ ID NO: 13 and a tracrRNA having 100% sequence identity to SEQ ID NO: 25, wherein said RGN polypeptide has an amino acid sequence having 100% sequence identity to SEQ ID NO: 1;
b) a gRNA comprising a CRISPR repeat sequence having 100% sequence identity to SEQ ID NO: 14 and a tracrRNA having 100% sequence identity to SEQ ID NO: 26, wherein said RGN polypeptide has an amino acid sequence having 100% sequence identity to SEQ ID NO: 2;
c) a gRNA comprising a CRISPR repeat sequence having 100% sequence identity to SEQ ID NO: 15 and a tracrRNA having 100% sequence identity to SEQ ID NO: 27, wherein said RGN polypeptide has an amino acid sequence having 100% sequence identity to SEQ ID NO: 3;
d) a gRNA comprising a CRISPR repeat sequence having 100% sequence identity to SEQ ID NO: 16 and a tracrRNA having 100% sequence identity to SEQ ID NO: 28, wherein said RGN polypeptide has an amino acid sequence having 100% sequence identity to SEQ ID NO: 4;
e) a gRNA comprising a CRISPR repeat sequence having 100% sequence identity to SEQ ID NO: 17 and a tracrRNA having 100% sequence identity to SEQ ID NO: 29, wherein said RGN polypeptide has an amino acid sequence having 100% sequence identity to SEQ ID NO: 5;
f) a gRNA comprising a CRISPR repeat sequence having 100% sequence identity to SEQ ID NO: 18 and a tracrRNA having 100% sequence identity to SEQ ID NO: 30, wherein said RGN polypeptide has an amino acid sequence having 100% sequence identity to SEQ ID NO: 6;
g) a gRNA comprising a CRISPR repeat sequence having 100% sequence identity to SEQ ID NO: 19 and a tracrRNA having 100% sequence identity to SEQ ID NO: 31, wherein said RGN polypeptide has an amino acid sequence having 100% sequence identity to SEQ ID NO: 7;
h) a gRNA comprising a CRISPR repeat sequence having 100% sequence identity to SEQ ID NO: 20 and a tracrRNA having 100% sequence identity to SEQ ID NO: 32, wherein said RGN polypeptide has an amino acid sequence having 100% sequence identity to SEQ ID NO: 8;
i) a gRNA comprising a CRISPR repeat sequence having 100% sequence identity to SEQ ID NO: 21 and a tracrRNA having 100% sequence identity to SEQ ID NO: 33, wherein said RGN polypeptide has an amino acid sequence having 100% sequence identity to SEQ ID NO: 9;
j) a gRNA comprising a CRISPR repeat sequence having 100% sequence identity to SEQ ID NO: 22 and a tracrRNA having 100% sequence identity to SEQ ID NO: 34, wherein said RGN polypeptide has an amino acid sequence having 100% sequence identity to SEQ ID NO:10;
k) a gRNA comprising a CRISPR repeat sequence having 100% sequence identity to SEQ ID NO: 23 and a tracrRNA having 100% sequence identity to SEQ ID NO: 35, wherein said RGN polypeptide has an amino acid sequence having 100% sequence identity to SEQ ID NO: 11; and
l) a gRNA comprising a CRISPR repeat sequence having 100% sequence identity to SEQ ID NO: 24 and a tracrRNA having 100% sequence identity to SEQ ID NO: 36, wherein said RGN polypeptide has an amino acid sequence having 100% sequence identity to SEQ ID NO: 12.

265. The method of any one of embodiments 259-264, wherein the gRNA further comprises a spacer sequence that targets a region within or proximal to the BCL11A enhancer region.

266. A method of treating a disease, disorder, or condition, said method comprising administering to a subject in need thereof an effective amount of a pharmaceutical composition of any one of embodiments 159-161 and 232.

267. The method of embodiment 266, wherein said disease, disorder, or condition is associated with a causal mutation and said effective amount of said pharmaceutical composition corrects said causal mutation.

268. The method of embodiment 266 or 267, wherein said subject is at risk of developing said disease, disorder, or condition.

269. Use of the nucleic acid molecule of any one of embodiments 1-19, 69-72, and 85-88, the vector of any one of embodiments 20-27, 73-84, and 89-100, the cell of any one of embodiments 30-35, 103-108, 148-153, and 220-225, the RGN polypeptide of any one of embodiments 48-65, the RNP complex of any one of embodiments 66-68, or the system of any one of embodiments 114-145 for the treatment of a disease, disorder, or condition in a subject in need thereof.

270. The use of embodiment 269, wherein said disease, disorder, or condition is associated with a causal mutation and said treating comprises correcting said causal mutation.

271. The use of embodiment 269 or 270, wherein said subject is at risk of developing said disease, disorder, or condition.

272. Use of the nucleic acid molecule of any one of embodiments 1-19, 69-72, and 85-88, the vector of any one of embodiments 20-27, 73-84, and 89-100, the cell of any one of embodiments 30-35, 103-108, 148-153, and 220-225, the RGN polypeptide of any one of embodiments 48-65, the RNP complex of any one of embodiments 66-68, or the system of any one of embodiments 114-145 for the manufacture of a medicament useful for treating a disease, disorder, or condition.

273. The use of embodiment 272, wherein said disease is associated with a causal mutation and an effective amount of said medicament corrects said causal mutation.

274. A single guide RNA comprising the nucleic acid molecule comprising said crRNA of any one of embodiments 69-72 and the nucleic acid molecule comprising said tracrRNA of any one of embodiments 85-88.

275. The single guide RNA of embodiment 274, wherein said single guide RNA further comprises an extension comprising an edit template for prime editing.

276. A dual guide RNA comprising the nucleic acid molecule comprising said crRNA of any one of embodiments 69-72 and the nucleic acid molecule comprising said tracrRNA of any one of embodiments 85-88.

277. A nucleic acid molecule comprising a polynucleotide encoding an RNA-guided nuclease (RGN) polypeptide, wherein said polynucleotide comprises a nucleotide sequence encoding an RGN polypeptide comprising an amino acid sequence having at least 90% sequence identity to SEQ ID NO:6;
wherein said RGN polypeptide is capable of binding a target DNA sequence in an RNA-guided sequence specific manner when bound to a guide RNA (gRNA) capable of hybridizing to said target DNA sequence.

278. The nucleic acid molecule of embodiment 277, wherein said polynucleotide encoding an RGN polypeptide is operably linked to a promoter heterologous to said polynucleotide.

279. The nucleic acid molecule of embodiment 277 or 278, wherein said RGN polypeptide comprises an amino acid sequence having at least 95% sequence identity to SEQ ID NO:6.

280. The nucleic acid molecule of embodiment 277 or 278, wherein said RGN polypeptide comprises an amino acid sequence having 100% sequence identity to SEQ ID NO: 6.

281. The nucleic acid molecule of any one of embodiments 277-280, wherein said RGN polypeptide is capable of cleaving said target DNA sequence upon binding.

282. The nucleic acid molecule of embodiment 281, wherein said RGN polypeptide is capable of generating a double-stranded break.

283. The nucleic acid molecule of embodiment 281, wherein said RGN polypeptide is capable of generating a single-stranded break.

284. The nucleic acid molecule of any one of embodiments 277-280, wherein said RGN polypeptide is nuclease inactive or is a nickase.

285. The nucleic acid molecule of any of embodiment 277-280, 283 and 284, wherein the RGN polypeptide is operably linked to a prime editing polypeptide.

286. The nucleic acid molecule of embodiment 285, wherein said prime editing polypeptide comprises a DNA polymerase.

287. The nucleic acid molecule of embodiment 285, wherein said prime editing polypeptide comprises a reverse transcriptase.

288. The nucleic acid molecule of any one of embodiments 277-284, wherein the RGN polypeptide is operably linked to a base-editing polypeptide.

289. The nucleic acid molecule of embodiment 288, wherein the base-editing polypeptide is a deaminase.

290. The nucleic acid molecule of embodiment 289, wherein the deaminase is a cytosine deaminase or an adenine deaminase.

291. The nucleic acid molecule of embodiment 289, wherein the deaminase has at least 90% sequence identity to an amino acid sequence of any one of SEQ ID NOs: 377-448.

292. The nucleic acid molecule of embodiment 289, wherein the deaminase has 100% sequence identity to an amino acid sequence of any one of SEQ ID NOs: 377-448.

293. The nucleic acid molecule of any one of embodiments 277-292, wherein the RGN polypeptide comprises one or more nuclear localization signals.

294. The nucleic acid molecule of any one of embodiments 277-293, wherein the RGN polypeptide is codon optimized for expression in a eukaryotic cell.

295. The nucleic acid molecule of any one of embodiments 277-294, wherein said target DNA sequence is located adjacent to a protospacer adjacent motif (PAM).

296. The nucleic acid molecule of embodiment 295, wherein said PAM has the sequence set forth as SEQ ID NO: 78 or 465.

297. A vector comprising the nucleic acid molecule of any one of embodiments 277-296.

298. The vector of embodiment 297, further comprising at least one nucleotide sequence encoding said gRNA capable of hybridizing to said target DNA sequence.

299. The vector of embodiment 298, wherein the guide RNA comprises:
a) a CRISPR RNA comprising a CRISPR repeat sequence having at least 90% sequence identity to SEQ ID NO: 18; and
b) a tracrRNA having at least 90% sequence identity to SEQ ID NO: 30.

300. The vector of embodiment 298, wherein the guide RNA comprises:
a) a CRISPR RNA comprising a CRISPR repeat sequence having at least 95% sequence identity to SEQ ID NO: 18; and
b) a tracrRNA having at least 95% sequence identity to SEQ ID NO: 30.

301. The vector of embodiment 298, wherein the guide RNA comprises:
a) a CRISPR repeat sequence having 100% sequence identity to SEQ ID NO: 18; and
b) a tracrRNA having 100% sequence identity to SEQ ID NO: 30.

302. The vector of any one of embodiments 298-301, where said gRNA is a single guide RNA (sgRNA).

303. The vector of embodiment 302, wherein said sgRNA further comprises an extension comprising an edit template for prime editing.

304. The vector of any one of embodiments 298-301, wherein said gRNA is a dual-guide RNA.

305. A cell comprising the nucleic acid molecule of any one of embodiments 277-296 or the vector of any one of embodiments 297-304.

306. An RNA-guided nuclease (RGN) polypeptide, wherein said RGN polypeptide comprises an amino acid sequence having at least 90% sequence identity to SEQ ID NO: 6; and
wherein said RGN polypeptide is capable of binding a target DNA sequence of a DNA molecule in an RNA-guided sequence specific manner when bound to a guide RNA (gRNA) capable of hybridizing to said target DNA sequence.

307. The RGN polypeptide of embodiment 306, wherein said RGN polypeptide comprises an amino acid sequence having at least 95% sequence identity to SEQ ID NO: 6.

308. The RGN polypeptide of embodiment 306, wherein said RGN polypeptide comprises an amino acid sequence having 100% sequence identity to SEQ ID NO: 6.

309. The RGN polypeptide of any one of embodiments 306-308, wherein said RGN polypeptide is an isolated RGN polypeptide.

310. The RGN polypeptide of any one of embodiments 306-309, wherein said RGN polypeptide is capable of cleaving said target DNA sequence upon binding.

311. The RGN polypeptide of embodiment 310, wherein cleavage by said RGN polypeptide generates a double-stranded break.

312. The RGN polypeptide of embodiment 310, wherein cleavage by said RGN polypeptide generates a single-stranded break.

313. The RGN polypeptide of any one of embodiments 306-309, wherein said RGN polypeptide is nuclease inactive or a nickase.

314. The RGN polypeptide of any of embodiment 306-310, 312, and 313, wherein the RGN polypeptide is operably linked to a prime editing polypeptide.

315. The RGN polypeptide of embodiment 314, wherein said prime editing polypeptide comprises a DNA polymerase.

316. The RGN polypeptide of embodiment 314, wherein said prime editing polypeptide comprises a reverse transcriptase.

317. The RGN polypeptide of any one of embodiments 306-316, wherein the RGN polypeptide is operably linked to a base-editing polypeptide.

318. The RGN polypeptide of embodiment 317, wherein the base-editing polypeptide is a deaminase.

319. The RGN polypeptide of embodiment 318, wherein the deaminase is a cytosine deaminase or an adenine deaminase.

320. The RGN polypeptide of embodiment 318, wherein the deaminase has at least 90% sequence identity to an amino acid sequence of any one of SEQ ID NOs: 377-448.

321. The RGN polypeptide of embodiment 318, wherein the deaminase has 100% sequence identity to an amino acid sequence of any one of SEQ ID NOs: 377-448.

322. The RGN polypeptide of any one of embodiments 306-321, wherein said target DNA sequence is located adjacent to a protospacer adjacent motif (PAM).

323. The RGN polypeptide of embodiment 322, wherein said PAM has the sequence set forth as SEQ ID NO: 78 or 465.

324. The RGN polypeptide of any one of embodiments 306-323, wherein the RGN polypeptide comprises one or more nuclear localization signals.

325. A ribonucleoprotein (RNP) complex comprising the RGN polypeptide of any one of embodiments 306-324 and a guide RNA (gRNA) bound to the RGN polypeptide.

326. The RNP complex of embodiment 325, wherein said gRNA is a single guide RNA (sgRNA).

327. The RNP complex of embodiment 326, wherein said gRNA comprises an extension comprising an edit template for prime editing.

328. A system for binding a target DNA sequence of a DNA molecule, said system comprising:
a) one or more guide RNAs capable of hybridizing to said target DNA sequence or one or more polynucleotides comprising one or more nucleotide sequences encoding the one or more guide RNAs (gRNAs); and
b) an RNA-guided nuclease (RGN) polypeptide comprising an amino acid sequence having at least 90% sequence identity to SEQ ID NO: 6 or a polynucleotide comprising a nucleotide sequence encoding the RGN polypeptide;
wherein the one or more guide RNAs are capable of hybridizing to the target DNA sequence, and
wherein the one or more guide RNAs are capable of forming a complex with the RGN polypeptide in order to direct said RGN polypeptide to bind to said target DNA sequence of the DNA molecule.

329. The system of embodiment 328, wherein at least one of said nucleotide sequences encoding the one or more guide RNAs and said nucleotide sequence encoding the RGN polypeptide is operably linked to a promoter heterologous to said nucleotide sequence.

330. A system for binding a target DNA sequence of a DNA molecule, said system comprising:
a) one or more guide RNAs capable of hybridizing to said target DNA sequence or one or more polynucleotides comprising one or more nucleotide sequences encoding the one or more guide RNAs (gRNAs); and
b) an RNA-guided nuclease (RGN) polypeptide comprising an amino acid sequence having at least 90% sequence identity to SEQ ID NO: 6;
wherein the one or more guide RNAs are capable of hybridizing to the target DNA sequence, and
wherein the one or more guide RNAs are capable of forming a complex with the RGN polypeptide in order to direct said RGN polypeptide to bind to said target DNA sequence of the DNA molecule.

331. The system of any one of embodiments 328-330, wherein at least one of said nucleotides sequences encoding the one or more guide RNAs is operably linked to a promoter heterologous to said nucleotide sequence.

332. The system of any one of embodiments 328-331, wherein said RGN polypeptide comprises an amino acid sequence having at least 95% sequence identity to SEQ ID NO: 6.

333. The system of any one of embodiments 328-331, wherein said RGN polypeptide comprises an amino acid sequence having 100% sequence identity to SEQ ID NO: 6.

334. The system of any one of embodiments 328-333, wherein said RGN polypeptide and said one or more guide RNAs are not found complexed to one another in nature.

335. The system of any one of embodiments 328-334, wherein said target DNA sequence is a eukaryotic target DNA sequence.

336. The system of any one of embodiments 328-335, wherein said gRNA is a single guide RNA (sgRNA).

337. The system of embodiment 336, wherein said sgRNA comprises an extension comprising an edit template for prime editing.

338. The system of any one of embodiments 328-336, wherein said gRNA is a dual-guide RNA.

339. The system of any one of embodiments 328-338, wherein said gRNA comprises a CRISPR repeat sequence having at least 90% sequence identity to SEQ ID NO: 18 and a tracrRNA having at least 90% sequence identity to SEQ ID NO: 30.

340. The system of any one of embodiments 328-338, wherein said gRNA comprises a CRISPR repeat sequence having at least 95% sequence identity to SEQ ID NO: 18 and a tracrRNA having at least 95% sequence identity to SEQ ID NO: 30.

341. The system of any one of embodiments 328-338, wherein said gRNA comprises a CRISPR repeat sequence having 100% sequence identity to SEQ ID NO: 18 and a tracrRNA having 100% sequence identity to SEQ ID NO: 30.

342. The system of any one of embodiments 328-341, wherein said target DNA sequence is located adjacent to a protospacer adjacent motif (PAM).

343. The system of embodiment 342, wherein said PAM has the sequence set forth as SEQ ID NO: 78 or 465.

344. The system of any one of embodiments 328-341, wherein the target DNA sequence is within a cell.

345. The system of any one of embodiments 328-344, wherein the one or more guide RNAs is capable of hybridizing to the target DNA sequence and the guide RNA is capable of forming a complex with the RGN polypeptide to direct cleavage of the target DNA sequence.

346. The system of embodiment 345, wherein the cleavage generates a double-stranded break.

347. The system of embodiment 345, wherein the cleavage generates a single-stranded break.

348. The system of any one of embodiments 328-344, wherein said RGN polypeptide is nuclease inactive or is a nickase.

349. The system of any one of embodiments 328-344, 347, and 348, wherein said RGN polypeptide is operably linked to a prime editing polypeptide.

350. The system of embodiment 349, wherein said prime editing polypeptide comprises a DNA polymerase.

351. The system of embodiment 349, wherein said prime editing polypeptide comprises a reverse transcriptase.

352. The system of any one of embodiments 328-348, wherein the RGN polypeptide is operably linked to a base-editing polypeptide.

353. The system of embodiment 352, wherein the base-editing polypeptide is a deaminase.

354. The system of embodiment 353, wherein the deaminase is a cytosine deaminase or an adenine deaminase.

355. The system of embodiment 353, wherein the deaminase has at least 90% sequence identity to an amino acid sequence of any one of SEQ ID NOs: 377-448.

356. The system of embodiment 353, wherein the deaminase has 100% sequence identity to an amino acid sequence of any one of SEQ ID NOs: 377-448.

357. The system of any one of embodiments 328-355, wherein the RGN polypeptide comprises one or more nuclear localization signals.

358. The system of any one of embodiments 328-357, wherein the RGN polypeptide is codon optimized for expression in a eukaryotic cell.

359. The system of any one of embodiments 328-358, wherein the nucleotide sequences encoding the one or more guide RNAs and the nucleotide sequence encoding the RGN polypeptide are located on one vector.

360. The system of any one of embodiments 328-359, wherein said system further comprises one or more donor polynucleotides.

361. A cell comprising the system of any one of embodiments 328-360.

362. A pharmaceutical composition comprising the nucleic acid molecule of any one of embodiments 277-296, the vector of any one of embodiments 297-304, the cell of embodiment 305 or 361, the RGN polypeptide of any one of embodiments 306-324, the RNP complex of any one of embodiments 325-327, or the system of any one of embodiments 328-360, and a pharmaceutically acceptable carrier.

363. The pharmaceutical composition of embodiment 362, wherein the pharmaceutically acceptable carrier is heterologous to said nucleic acid molecule, said vector, said cell, said RGN polypeptide, or said system.

364. The pharmaceutical composition of embodiment 362 or 363, wherein the pharmaceutically acceptable carrier is not naturally-occurring.

365. A method for binding a target DNA sequence of a DNA molecule comprising delivering a system according to any one of embodiments 328-360, to said target DNA sequence or a cell comprising the target DNA sequence.

366. The method of embodiment 365, wherein said RGN polypeptide or said guide RNA further comprises a detectable label, thereby allowing for detection of said target DNA sequence.

367. The method of embodiment 365, wherein said guide RNA or said RGN polypeptide further comprises an expression modulator, thereby modulating expression of said target DNA sequence or a gene under transcriptional control by said target DNA sequence.

368. A method for cleaving and/or modifying a target DNA sequence of a DNA molecule comprising delivering a system according to any one of embodiments 328-360 to said target DNA sequence or a cell comprising the DNA molecule, wherein cleavage or modification of said target DNA sequence occurs.

369. The method of embodiment 368, wherein said modified target DNA sequence comprises insertion of heterologous DNA into the target DNA sequence.

370. The method of embodiment 368, wherein said modified target DNA sequence comprises deletion of at least one nucleotide from the target DNA sequence.

371. The method of embodiment 368, wherein said modified target DNA sequence comprises mutation of at least one nucleotide in the target DNA sequence.

372. A method for binding a target DNA sequence of a DNA molecule comprising:

a) assembling an RNA-guided nuclease (RGN) ribonucleotide complex by combining:
  i) one or more guide RNAs capable of hybridizing to the target DNA sequence; and
  ii) an RGN polypeptide comprising an amino acid sequence having at least 90% sequence identity to SEQ ID NO:6;
  under conditions suitable for formation of the RGN ribonucleotide complex; and
b) contacting said target DNA sequence or a cell comprising said target DNA sequence with the assembled RGN ribonucleotide complex;
wherein the one or more guide RNAs hybridize to the target DNA sequence, thereby directing said RGN polypeptide to bind to said target DNA sequence.

373. The method of embodiment 372, wherein said method is performed in vitro, in vivo, or ex vivo.

374. The method of embodiment 372 or 373, wherein said RGN polypeptide or said guide RNA further comprises a detectable label, thereby allowing for detection of said target DNA sequence.

375. The method of embodiment 372 or 373, wherein said guide RNA or said RGN polypeptide further comprises an expression modulator, thereby allowing for the modulation of expression of said target DNA sequence.

376. The method of embodiment 372 or 373, wherein said RGN polypeptide is operably linked to a prime editing polypeptide, thereby allowing for the modification of said target DNA sequence.

377. The method of embodiment 376, wherein said prime editing polypeptide comprises a DNA polymerase.

378. The method of embodiment 376, wherein said prime editing polypeptide comprises a reverse transcriptase.

379. The method of embodiment 372 or 373, wherein said RGN polypeptide is operably linked to a base-editing polypeptide, thereby allowing for the modification of said target DNA sequence.

380. The method of embodiment 379, wherein said base-editing polypeptide comprises a deaminase.

381. The method of embodiment 380, wherein said deaminase is a cytosine deaminase or an adenine deaminase.

382. The method of embodiment 380, wherein the deaminase has at least 90% sequence identity to an amino acid sequence of any one of SEQ ID NOs: 377-448.

383. The method of embodiment 380, wherein the deaminase has 100% sequence identity to an amino acid sequence of any one of SEQ ID NOs: 377-448.

384. The method of embodiment 372 or 373, wherein said RGN polypeptide is capable of cleaving said target DNA sequence, thereby allowing for the cleaving and/or modifying of said target DNA sequence.

385. A method for cleaving and/or modifying a target DNA sequence of a DNA molecule, comprising contacting the DNA molecule with:
  a) an RNA-guided nuclease (RGN) polypeptide, wherein said RGN comprises an amino acid sequence having at least 90% sequence identity to SEQ ID NO: 6; and
  b) one or more guide RNAs capable of targeting the RGN of (a) to the target DNA sequence;
wherein the one or more guide RNAs hybridize to the target DNA sequence, thereby directing said RGN polypeptide to bind to said target DNA sequence and cleavage and/or modification of said target DNA sequence occurs.

386. The method of embodiment 385, wherein cleavage by said RGN polypeptide generates a double-stranded break.

387. The method of embodiment 385, wherein cleavage by said RGN polypeptide generates a single-stranded break.

388. The method of embodiment 385, wherein said RGN polypeptide is nuclease inactive or a nickase.

389. The method of any one of embodiments 385, 387, and 388, wherein said RGN polypeptide is operably linked to a prime editing polypeptide, thereby allowing for the modification of said target DNA sequence.

390. The method of embodiment 389, wherein said prime editing polypeptide comprises a DNA polymerase.

391. The method of embodiment 389, wherein said prime editing polypeptide comprises a reverse transcriptase.

392. The method of any one of embodiments 385-388, wherein said RGN polypeptide is operably linked to a base-editing polypeptide.

393. The method of embodiment 392, wherein the base-editing polypeptide is a deaminase.

394. The method of embodiment 392, wherein the deaminase is a cytosine deaminase or an adenine deaminase.

395. The method of embodiment 393, wherein the deaminase has at least 90% sequence identity to an amino acid sequence of any one of SEQ ID NOs: 377-448.

396. The method of embodiment 393, wherein the deaminase has 100% sequence identity to an amino acid sequence of any one of SEQ ID NOs: 377-448.

397. The method of embodiment 385, wherein said modified target DNA sequence comprises insertion of heterologous DNA into the target DNA sequence.

398. The method of embodiment 385, wherein said modified target DNA sequence comprises deletion of at least one nucleotide from the target DNA sequence.

399. The method of embodiment 385, wherein said modified target DNA sequence comprises mutation of at least one nucleotide in the target DNA sequence.

400. The method of any one of embodiments 372-399, wherein said target DNA sequence is located adjacent to a protospacer adjacent motif (PAM).

401. The method of embodiment 400, wherein said PAM has the sequence set forth as SEQ ID NO: 78 or 465.

402. The method of any one of embodiments 372-401, wherein said target DNA sequence is a eukaryotic target DNA sequence.

403. The method of any one of embodiments 372-402, wherein said gRNA is a single guide RNA (sgRNA).

404. The method of embodiment 403, wherein said sgRNA comprises an extension comprising an edit template for prime editing.

405. The method of any one of embodiments 372-403, wherein said gRNA is a dual-guide RNA.

406. The method of any one of embodiments 372-405, wherein said RGN comprises an amino acid sequence having at least 95% sequence identity to SEQ ID NO: 6.

407. The method of any one of embodiments 372-405, wherein said RGN comprises an amino acid sequence having 100% sequence identity to SEQ ID NO: 6.

408. The method of any one of embodiments 372-405, wherein said RGN has at least 90% sequence identity to SEQ ID NO: 6, said guide RNA comprises a crRNA repeat sequence having at least 90% sequence identity to SEQ ID NO: 18 and a tracrRNA having at least 90% sequence identity to SEQ ID NO: 30.

409. The method of any one of embodiments 372-405, wherein said RGN has at least 95% sequence identity to SEQ ID NO: 6, said guide RNA comprises a crRNA repeat sequence having at least 95% sequence identity to SEQ ID NO: 18 and a tracrRNA having at least 95% sequence identity to SEQ ID NO: 30.

410. The method of any one of embodiments 372-405, wherein said RGN has 100% sequence identity to SEQ ID NO: 6, said guide RNA comprises a crRNA repeat sequence having 100% sequence identity to SEQ ID NO: 18 and a tracrRNA having 100% sequence identity to SEQ ID NO: 30.

411. The method of any one of embodiments 365-183, wherein the target DNA sequence is within a cell.

412. The method of embodiment 411, further comprising culturing the cell under conditions in which the RGN polypeptide is expressed and cleaves and modifies the target DNA sequence to produce a DNA molecule comprising a modified target DNA sequence; and selecting a cell comprising said modified target DNA sequence.

413. A cell comprising a modified target DNA sequence according to the method of embodiment 412.

414. A pharmaceutical composition comprising the cell of embodiment 413 and a pharmaceutically acceptable carrier.

415. A method for producing a genetically modified cell with a correction in a causal mutation for a genetically inherited disease, the method comprising introducing into the cell:
a) an RNA-guided nuclease (RGN) polypeptide, wherein the RGN polypeptide comprises an amino acid sequence having at least 90% sequence identity to SEQ ID NO: 6, or a polynucleotide encoding said RGN polypeptide, wherein said polynucleotide encoding the RGN polypeptide is operably linked to a promoter to enable expression of the RGN polypeptide in the cell; and
b) a guide RNA (gRNA) or a polynucleotide encoding said gRNA, wherein said polynucleotide encoding the gRNA is operably linked to a promoter to enable expression of the gRNA in the cell
whereby the RGN and gRNA target to the genomic location of the causal mutation and modify the genomic sequence to remove the causal mutation.

416. The method of embodiment 415, wherein the RGN is nuclease inactive or a nickase.

417. The method of embodiment 415 or 416, wherein the RGN is operably linked to a prime editing polypeptide.

418. The method of embodiment 417, wherein the prime editing polypeptide comprises a DNA polymerase.

419. The method of embodiment 417, wherein the prime editing polypeptide comprises a reverse transcriptase.

420. The method of any one of embodiments 417-419, wherein said gRNA comprises an extension comprising an edit template for prime editing.

421. The method of embodiment 415 or 416, wherein the RGN is operably linked to a polypeptide which has base-editing activity.

422. The method of embodiment 421, wherein the base-editing polypeptide is a deaminase.

423. The method of embodiment 422, wherein the polypeptide with base-editing activity is a cytosine deaminase or an adenine deaminase.

424. The method of embodiment 422, wherein the deaminase has at least 90% sequence identity to an amino acid sequence of any one of SEQ ID NOs: 377-448.

425. The method of embodiment 422, wherein the deaminase has 100% sequence identity to an amino acid sequence of any one of SEQ ID NOs: 377-448.

426. The method of any one of embodiments 415-425, wherein the genetically inherited disease is caused by a single nucleotide polymorphism.

427. The method of embodiment 426, wherein the gRNA further comprises a spacer sequence that targets a region proximal to the causal single nucleotide polymorphism.

428. A method for producing a genetically modified cell with a deletion in a causal mutation, the method comprising introducing into the cell:
a) an RNA-guided nuclease (RGN) polypeptide, wherein the RGN polypeptide comprises an amino acid sequence having at least 90% sequence identity to SEQ ID NO: 6, or a polynucleotide encoding said RGN polypeptide, wherein said polynucleotide encoding the RGN polypeptide is operably linked to a promoter to enable expression of the RGN polypeptide in the cell;
b) a first guide RNA (gRNA) or a polynucleotide encoding said gRNA, wherein said polynucleotide encoding the gRNA is operably linked to a promoter to enable expression of the gRNA in the cell, and further wherein the gRNA comprises a spacer sequence that targets the 5' flank of the causal mutation; and
c) a second guide RNA (gRNA) or a polynucleotide encoding said gRNA, wherein said polynucleotide encoding the gRNA is operably linked to a promoter to enable expression of the gRNA in the cell, and further wherein said second gRNA comprises a spacer sequence that targets the 3'flank of the causal mutation;
whereby the RGN and the two gRNAs target to the causal mutation and at least a portion of the causal mutation is removed.

429. The method of embodiment 428, wherein the first gRNA further comprises a spacer sequence that targets a region within or proximal to the causal mutation.

430. The method of embodiment 429, wherein the second gRNA further comprises a spacer sequence that targets a region within or proximal to the causal mutation.

431. The method of any one of embodiments 415-430, wherein said RGN polypeptide has at least 95% sequence identity to SEQ ID NO: 6.

432. The method of any one of embodiments 415-430, wherein said RGN polypeptide has 100% sequence identity to SEQ ID NO: 6.

433. The method of any one of embodiments 415-430, wherein said gRNA, said first gRNA, said second gRNA, or said first gRNA and said second gRNA comprises a CRISPR repeat sequence having at least 90% sequence identity to SEQ ID NO: 18 and a tracrRNA having at least 90% sequence identity to SEQ ID NO: 30, wherein said RGN polypeptide has an amino acid sequence having at least 90% sequence identity to SEQ ID NO: 6.

434. The method of any one of embodiments 415-430, wherein said gRNA, said first gRNA, said second gRNA, or said first gRNA and said second gRNA comprise a CRISPR repeat sequence having at least 95% sequence identity to SEQ ID NO: 18 and a tracrRNA having at least 95% sequence identity to SEQ ID NO: 30, wherein said RGN polypeptide has an amino acid sequence having at least 95% sequence identity to SEQ ID NO: 6.

435. The method of any one of embodiments 415-430, wherein said gRNA, said first gRNA, said second gRNA, or said first gRNA and said second gRNA comprise a CRISPR repeat sequence having 100% sequence identity to SEQ ID NO: 18 and a tracrRNA having 100% sequence identity to SEQ ID NO: 30, wherein said RGN polypeptide has an amino acid sequence having 100% sequence identity to SEQ ID NO: 6.

436. A method of treating a disease, disorder, or condition, said method comprising administering to a subject in need thereof an effective amount of a pharmaceutical composition of any one of embodiments 362-364 and 414.

437. The method of embodiment 436, wherein said disease, disorder, or condition is associated with a causal mutation and said effective amount of said pharmaceutical composition corrects said causal mutation.

438. The method of embodiment 436 or 437, wherein said subject is at risk of developing said disease, disorder, or condition.

439. Use of the nucleic acid molecule of any one of embodiments 277-296, the vector of any one of embodiments 297-304, the cell of embodiment 305 or 361, the RGN polypeptide of any one of embodiments 306-324, the RNP complex of any one of embodiments 325-327, or the system of any one of embodiments 328-360 for the treatment of a disease, disorder, or condition in a subject in need thereof.

440. The use of embodiment 439, wherein said disease, disorder, or condition is associated with a causal mutation and said treating comprises correcting said causal mutation.

441. The use of embodiment 439 or 440, wherein said subject is at risk of developing said disease, disorder, or condition.

442. Use of the nucleic acid molecule of any one of embodiments 277-296, the vector of any one of embodiments 297-304, the cell of embodiment 305 or 361, the RGN polypeptide of any one of embodiments 306-324, the RNP complex of any one of embodiments 325-327, or the system of any one of embodiments 328-360 for the manufacture of a medicament useful for treating a disease, disorder, or condition.

443. The use of embodiment 442, wherein said disease is associated with a causal mutation and an effective amount of said medicament corrects said causal mutation.

The following examples are offered by way of illustration and not by way of limitation.

EXAMPLES

Example 1. Identification of RNA-Guided Nuclease

Twelve distinct CRISPR-associated RNA-guided nucleases (RGNs) were identified and are described in Table 1 below. Table 1 provides the name of each RGN, its amino acid sequence, the source from which it was derived, and processed crRNA and tracrRNA sequences (see Example 2 for methods of identification). Table 1 further provides a generic single guide RNA (sgRNA) sequence, where the poly-N indicates the location of the spacer sequence which determines the nucleic acid target sequence of the sgRNA. For RGN systems LPG10134 and LPG10141, the conserved sequence in the base of the hairpin stem of the tracrRNA is CNANNA (SEQ ID NO: 322). For LPG10136, LPG10138, and LPG10139, the sequence in the same location is UNANNG (SEQ ID NO: 321). For RGN system LPG10145, the conserved sequence in the base of the hairpin stem of the tracrRNA is UNANNC (SEQ ID NO: 318). For LPG10146, LPG10147, LPG10150, LPG10155, LPG10159 and LPG10160, the sequence in the same location is UNANNA (SEQ ID NO: 319).

TABLE 1

Summary of SEQ IDs and CRISPR associated systems

| RGN ID | SEQ ID NO. | Source | crRNA repeat seq (SEQ ID NO.) | tracrRNA (SEQ ID NO.) | sgRNA backbone (SEQ ID NO) |
|---|---|---|---|---|---|
| LPG10134 | 1 | Brevundimonas vesicularis | 13 | 25 | 37 |
| LPG10136 | 2 | Bacillus_I endophyticus | 14 | 26 | 38 |
| LPG10138 | 3 | Bacillus_C megaterium | 15 | 27 | 39 |
| LPG10139 | 4 | Bacillus_C megaterium | 16 | 28 | 40 |
| LPG10141 | 5 | Bosea thiooxidans | 17 | 29 | 41 |
| LPG10145 | 6 | undetermined | 18 | 30 | 42 |
| LPG10146 | 7 | Bifidobacterium thermacidophilum | 19 | 31 | 43 |
| LPG10147 | 8 | undetermined | 20 | 32 | 44 |
| LPG10150 | 9 | undetermined | 21 | 33 | 45 |
| LPG10155 | 10 | Chryseobacterium geocarposphaerae | 22 | 34 | 46 |
| LPG10159 | 11 | Contaminated/multiple | 23 | 35 | 47 |
| LPG10160 | 12 | Chryseobacterium ureilyticum | 24 | 36 | 48 |

Example 2: Guide RNA Identification and soRNA Construction

Guide RNAs were determined through identification of tracrRNAs and crRNAs encoded in the genomic CRISPR loci. An internal database of validated and predicted tracrRNAs was used to determine a putative RNA. When no homology-based tracrRNA could be identified, the anti-repeat portion of the tracrRNA was identified using permissive BLASTn parameters using the consensus CRISPR repeat following the protocol determined in Briner, Cold Spring Harb Protoc 7: pbd. prot086785 (2016). Manual curation of RNAs was performed using secondary structure prediction by RNAfold, an RNA folding software. sgRNA cassettes were prepared by DNA synthesis and were generally designed as follows (5'->3'): 20-30 bp spacer sequence, operably linked at its 3' end to the processed repeat portion of the crRNA, operably linked to a 4 bp noncomplementary linker (AAAG; SEQ ID NO: 323), operably linked at its 3' end to the processed tracrRNA. Other 4 bp noncomplementary linkers may also be used.

For in vitro assays, sgRNAs were synthesized by in vitro transcription of the sgRNA cassettes with a GeneArt™ Precision gRNA Synthesis Kit (ThermoFisher). Processed crRNA and tracrRNA sequences for each of the RGN polypeptides are identified and are set forth in Table 1. See Example 3 for the sgRNAs constructed for PAM libraries 1 and 2.

Example 3: Determination of PAM Requirements for Each RGN

PAM requirements for each RGN were determined using an in vitro translation PAM determination assay essentially adapted from Karvelis et al. (2015) Genome Biol 253. Briefly, two plasmid libraries (L1 and L2) were generated in a pUC18 backbone (ampR), with each containing a distinct 30 bp protospacer (target) sequence flanked by 8 random nucleotides (i.e., the PAM region). The target sequence and flanking PAM region of library 1 and library 2 for each RGN are set forth in Table 2.

Briefly, the proteins were translated in vitro using the PURExpress In Vitro Protein Synthesis kit (New England Biolabs) starting from a T7 promoter driven bacterial expression plasmid.

In the presence of the appropriate sgRNA, plasmids containing a PAM that is recognizable by the RGN will be cleaved. Adapters were ligated to cleaved DNA using the NEBNext Ultra II DNA Library Prep Kit (New England Biolabs), and after cleanup, the product was PCR amplified using primers complementary to the ligated adapter and plasmid backbone sequence such that the enriched PAM sequences were contained in the amplicon. Deep sequencing (75 bp single end reads) was performed on a MiSeq (Illumina) by a service provider (MoGene, St. Louis, MO). Typically, 500,000 reads were obtained per amplicon. PAM regions were extracted, counted, and normalized to total reads for each sample. PAMs that led to plasmid cleavage were identified by being enriched when compared to controls (i.e., the starting frequencies for the PAM in the libraries). To represent PAM requirements for a novel RGN, the depletion ratios (frequency in sample/frequency in control) for all sequences in the region in question were converted to enrichment values with a −log base 2 transformation. Sufficient PAMs were defined as those with enrichment values>3.5. PAMs above this threshold in both libraries were collected and used to generate web logos, which for example can be generated using a web-based service on the internet known as "weblogo". PAM sequences were identified and reported when there was a consistent pattern in the top enriched PAMs. A consensus PAM (having an enrichment factor (EF)>3.5) for each RGN is provided in Table 2. The PAM orientation is also indicated in Table 2.

TABLE 2

PAM or PAM-like determination

| RGN ID | sgRNA L1 (SEQ ID NO.) | sgRNA L2 (SEQ ID NO.) | PAM (SEQ ID NO.) | PAM orientation |
|---|---|---|---|---|
| LPG10134 | 49 | 61 | NGG | 5'-target-PAM-3' |
| LPG10136 | 50 | 62 | NNNNCC | 5'-target-PAM-3' |
| LPG10138 | 51 | 63 | 75 | 5'-target-PAM-3' |
| LPG10139 | 52 | 64 | NNNNC | 5'-target-PAM-3' |
| LPG10141 | 53 | 65 | 77 | 5'-target-PAM-3' |
| LPG10145 | 54 | 66 | NNGG | 5'-target-PAM-3' |
| LPG10146 | 55 | 67 | 79 | 5'-target-PAM-3' |
| LPG10147 | 56 | 68 | 80 | 5'-target-PAM-3' |
| LPG10150 | 57 | 69 | 81 | 5'-target-PAM-3' |
| LPG10155 | 58 | 70 | 82 | 5'-target-PAM-3' |
| LPG10159 | 59 | 71 | 83 | 5'-target-PAM-3' |
| LPG10160 | 60 | 72 | 84 | 5'-target-PAM-3' |

Example 4: Demonstration of Gene Editing Activity in Mammalian Cells

RGN expression cassettes were produced and introduced into vectors for mammalian expression. Each RGN was codon-optimized for human expression and operably fused at the 5'end to an SV40 nuclear localization sequence (NLS; SEQ ID NO: 316) and to 3×FLAG tags (SEQ ID NO: 326), and operably fused at the 3' end to nucleoplasmin NLS sequences (SEQ ID NO: 317). Each expression cassette was under control of a cytomegalovirus (CMV) promoter (SEQ ID NO: 327). It is known in the art that the CMV transcription enhancer (SEQ ID NO: 328) may also be included in constructs comprising the CMV promoter. Guide RNA expression constructs encoding a single gRNA, each under the control of a human RNA polymerase III U6 promoter (SEQ ID NO: 329), were produced and introduced into the pTwist High Copy Amp vector. Sequences for the target sequences for each guide are provided in Table 3.

Several of the constructs described above were introduced into mammalian cells. One day prior to transfection, 1×10⁵ HEK293T cells (Sigma) were plated in 24-well dishes in Dulbecco's modified Eagle medium (DMEM) plus 10% (vol/vol) fetal bovine serum (Gibco) and 1% Penicillin-Streptomycin (Gibco). The next day when the cells were at 50-60% confluency, 500 ng of an RGN expression plasmid plus 500 ng of a single gRNA expression plasmid were co-transfected using 1.5 µL of Lipofectamine 3000 (Thermo Scientific) per well, following the manufacturer's instructions. After 48 hours of growth, total genomic DNA was harvested using a genomic DNA isolation kit (Machery-Nagel) according to the manufacturer's instructions.

The total genomic DNA was then analyzed to determine the rate of editing for each RGN for each genomic target. First, oligonucleotides were produced to be used for PCR amplification and subsequent analysis of the amplified genomic target site.

All PCR reactions were performed using 10 µL of 2× Master Mix Phusion High-Fidelity DNA polymerase (Thermo Scientific) in a 20 µL reaction including 0.5 µM of each primer. Large genomic regions encompassing each target gene were first amplified using PCR #1 primers, using a program of: 98° C., 1 min; 30 cycles of [98° C., 10 sec; 62° C., 15 sec; 72° C., 5 min]; 72° C., 5 min; 12° C., forever. One microliter of this PCR reaction was then further amplified using primers specific for each guide (PCR #2 primers), using a program of: 98° C., 1 min; 35 cycles of [98° C., 10 sec; 67° C., 15 sec; 72° C., 30 sec]; 72° C., 5 min; 12° C., forever. Primers for PCR #2 include Nextera Read 1 and Read 2 Transposase Adapter overhang sequences for Illumina sequencing.

A number of different genes in the human genome were targeted for RNA-guided cleavage. These loci are included in Table 3 below.

TABLE 3

Target and sgRNA sequences for guide RNAs used to test gene editing activity in mammalian cells

| RGN ID | Gene | Guide ID | Target Sequence (SEQ ID NO) |
|---|---|---|---|
| LPG10134 | B2M | SGN002644 | 554 |
| LPG10134 | B2M | SGN002645 | 555 |
| LPG10134 | B2M | SGN002646 | 556 |
| LPG10134 | B2M | SGN002647 | 557 |
| LPG10134 | B2M | SGN002648 | 558 |
| LPG10134 | TRAC | SGN002649 | 559 |
| LPG10134 | TRAC | SGN002650 | 560 |
| LPG10134 | TRAC | SGN002651 | 561 |
| LPG10134 | TRAC | SGN002652 | 562 |
| LPG10134 | TRAC | SGN002653 | 563 |
| LPG10136 | B2M | SGN002654 | 564 |
| LPG10136 | B2M | SGN002655 | 565 |
| LPG10136 | B2M | SGN002656 | 566 |
| LPG10136 | B2M | SGN002657 | 567 |
| LPG10136 | B2M | SGN002658 | 568 |
| LPG10136 | TRAC | SGN002659 | 569 |
| LPG10136 | TRAC | SGN002660 | 570 |
| LPG10136 | TRAC | SGN002661 | 571 |
| LPG10136 | TRAC | SGN002662 | 572 |
| LPG10136 | TRAC | SGN002663 | 573 |
| LPG10138 | B2M | SGN002664 | 574 |
| LPG10138 | B2M | SGN002665 | 575 |
| LPG10138 | B2M | SGN002666 | 576 |
| LPG10138 | B2M | SGN002667 | 577 |
| LPG10138 | B2M | SGN002668 | 578 |
| LPG10138 | TRAC | SGN002669 | 579 |
| LPG10138 | TRAC | SGN002670 | 580 |
| LPG10138 | TRAC | SGN002671 | 581 |
| LPG10138 | TRAC | SGN002672 | 582 |
| LPG10138 | TRAC | SGN002673 | 583 |
| LPG10139 | B2M | SGN002674 | 584 |
| LPG10139 | B2M | SGN002675 | 585 |
| LPG10139 | B2M | SGN002676 | 586 |
| LPG10139 | B2M | SGN002677 | 587 |
| LPG10139 | B2M | SGN002678 | 588 |
| LPG10139 | TRAC | SGN002679 | 589 |
| LPG10139 | TRAC | SGN002680 | 590 |
| LPG10139 | TRAC | SGN002681 | 591 |
| LPG10139 | TRAC | SGN002682 | 592 |
| LPG10139 | TRAC | SGN002683 | 593 |
| LPG10141 | B2M | SGN002684 | 594 |
| LPG10141 | B2M | SGN002685 | 595 |
| LPG10141 | B2M | SGN002686 | 596 |
| LPG10141 | B2M | SGN002687 | 597 |
| LPG10141 | B2M | SGN002688 | 598 |
| LPG10141 | TRAC | SGN002689 | 599 |
| LPG10141 | TRAC | SGN002690 | 600 |
| LPG10141 | TRAC | SGN002691 | 601 |
| LPG10141 | TRAC | SGN002692 | 602 |
| LPG10141 | TRAC | SGN002693 | 603 |
| LPG10145 | B2M | SGN002698 | 604 |
| LPG10145 | B2M | SGN002699 | 605 |
| LPG10145 | B2M | SGN002700 | 606 |
| LPG10145 | B2M | SGN002701 | 607 |

TABLE 3-continued

Target and sgRNA sequences for guide RNAs used to test gene editing activity in mammalian cells

| RGN ID | Gene | Guide ID | Target Sequence (SEQ ID NO) |
|---|---|---|---|
| LPG10145 | B2M | SGN002702 | 608 |
| LPG10145 | TRAC | SGN002703 | 609 |
| LPG10145 | TRAC | SGN002704 | 610 |
| LPG10145 | TRAC | SGN002705 | 611 |
| LPG10145 | TRAC | SGN002706 | 612 |
| LPG10145 | TRAC | SGN002707 | 613 |
| LPG10146 | B2M | SGN002708 | 614 |
| LPG10146 | B2M | SGN002709 | 615 |
| LPG10146 | B2M | SGN002710 | 616 |
| LPG10146 | B2M | SGN002711 | 617 |
| LPG10146 | B2M | SGN002712 | 618 |
| LPG10146 | TRAC | SGN002713 | 619 |
| LPG10146 | TRAC | SGN002714 | 620 |
| LPG10146 | TRAC | SGN002715 | 621 |
| LPG10146 | TRAC | SGN002716 | 622 |
| LPG10146 | TRAC | SGN002717 | 623 |
| LPG10147 | B2M | SGN002718 | 624 |
| LPG10147 | B2M | SGN002719 | 625 |
| LPG10147 | TRAC | SGN002720 | 626 |
| LPG10147 | TRAC | SGN002721 | 627 |
| LPG10147 | TRAC | SGN002722 | 628 |
| LPG10147 | TRAC | SGN002723 | 629 |
| LPG10150 | B2M | SGN002724 | 630 |
| LPG10150 | B2M | SGN002725 | 631 |
| LPG10150 | B2M | SGN002726 | 632 |
| LPG10150 | B2M | SGN002727 | 633 |
| LPG10150 | B2M | SGN002728 | 634 |
| LPG10150 | TRAC | SGN002729 | 635 |
| LPG10150 | TRAC | SGN002730 | 636 |
| LPG10150 | TRAC | SGN002731 | 637 |
| LPG10150 | TRAC | SGN002732 | 638 |
| LPG10150 | TRAC | SGN002733 | 639 |
| LPG10155 | B2M | SGN002734 | 640 |
| LPG10155 | B2M | SGN002735 | 641 |
| LPG10155 | TRAC | SGN002736 | 642 |
| LPG10155 | TRAC | SGN002737 | 643 |
| LPG10155 | TRAC | SGN002738 | 644 |
| LPG10155 | TRAC | SGN002739 | 645 |
| LPG10159 | B2M | SGN002740 | 646 |
| LPG10159 | B2M | SGN002741 | 647 |
| LPG10159 | B2M | SGN002742 | 648 |
| LPG10159 | B2M | SGN002743 | 649 |
| LPG10159 | B2M | SGN002744 | 650 |
| LPG10159 | TRAC | SGN002745 | 651 |
| LPG10159 | TRAC | SGN002746 | 652 |
| LPG10159 | TRAC | SGN002747 | 653 |
| LPG10159 | TRAC | SGN002748 | 654 |
| LPG10159 | TRAC | SGN002749 | 655 |
| LPG10160 | B2M | SGN002750 | 656 |
| LPG10160 | B2M | SGN002751 | 657 |
| LPG10160 | B2M | SGN002752 | 658 |
| LPG10160 | B2M | SGN002753 | 659 |
| LPG10160 | B2M | SGN002754 | 660 |
| LPG10160 | TRAC | SGN002755 | 661 |
| LPG10160 | TRAC | SGN002756 | 662 |
| LPG10160 | TRAC | SGN002757 | 663 |
| LPG10160 | TRAC | SGN002758 | 664 |
| LPG10160 | TRAC | SGN002759 | 665 |

Purified genomic DNA was subjected to PCR #1 and PCR #2 as above. Following the second PCR amplification, DNA was cleaned using a PCR cleanup kit (Zymo) according to the manufacturer's instructions and eluted in water. 200-500 ng of purified PCR #2 product was combined with 2 µL of 10×NEB Buffer 2 and water in a 20 µL reaction and annealed to form heteroduplex DNA using a program of: 95° C., 5 min; 95-85° C., cooled at a rate of 2° C./sec; 85-25° C., cooled at a rate of 0.1° C./sec.; 12° C., forever. Following annealing 5 µL of DNA was removed as a no enzyme control, and 1 µL of T7 Endonuclease I (NEB) was added and the reaction incubated at 37° C. for 1 hr. After incubation 5× FlashGel loading dye (Lonza) was added and 5 µL of each reaction and controls were analyzed by a 2.2% agarose FlashGel (Lonza) using gel electrophoresis. Following visualization of the gel, the percentage of non-homologous end joining (NHEJ) was determined using the following equation: % NHEJ events=100×[1−(1−fraction cleaved) (½)], where (fraction cleaved) is defined as: (density of digested products)/(density of digested products+undigested parental band).

For some samples, SURVEYOR® was used to analyze the results following expression in mammalian cells. Cells were incubated at 37° C. for 72 h post-transfection before genomic DNA extraction. Genomic DNA was extracted using the QuickExtract DNA Extraction Solution (Epicentre) following the manufacturer's protocol. The genomic region flanking the RGN target site was PCR amplified, and products were purified using QiaQuick Spin Column (Qiagen) following the manufacturer's protocol. 200-500 ng total of the purified PCR products were mixed with 1 µl 10× Taq DNA Polymerase PCR buffer (Enzymatics) and ultrapure water to a final volume of 10 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min.

After reannealing, products were treated with SURVEYOR® nuclease and SURVEYOR® enhancer S (Integrated DNA Technologies) following the manufacturer's recommended protocol and analyzed on 4-20% Novex TBE polyacrylamide gels (Life Technologies). Gels were stained with SYBR Gold DNA stain (Life Technologies) for 10 min and imaged with a Gel Doc gel imaging system (Bio-rad). Quantification was based on relative band intensities. Indel percentage was determined by the formula, 100×(1−(1−(b+c)/(a+b+c))½), where a is the integrated intensity of the undigested PCR product, and b and c are the integrated intensities of each cleavage product.

Additionally, products from PCR #2 containing Illumina overhang sequences underwent library preparation following the Illumina 16S Metagenomic Sequencing Library protocol. Deep sequencing was performed on an Illumina Mi-Seq platform by a service provider (MOGene). Typically, 200,000 of 250 bp paired-end reads (2×100,000 reads) are generated per amplicon. The reads were analyzed using CRISPResso (Pinello, et al. 2016 Nature Biotech, 34:695-697) to calculate the rates of editing. Output alignments were hand-curated to confirm insertion and deletion sites as well as identify microhomology sites at the recombination sites. The rates of editing are shown in Table 4. All experiments were performed in human cells. The "target sequence" is the targeted sequence within the gene target. For each target sequence, the guide RNA comprised the complementary RNA target sequence and the appropriate sgRNA depending on the RGN used. A selected breakdown of experiments by guide RNA is shown in Tables 5.1 and 5.2 and depicted in FIG. 1.

TABLE 4

Editing rate by plasmid delivery

| RGN | SGN | Rep1 | Rep2 | Rep3 |
|---|---|---|---|---|
| LPG10134 | SGN002644 | 0 | 0.06 | 1.76 |
| LPG10134 | SGN002645 | 0 | 0 | 1.43 |
| LPG10134 | SGN002646 | 0 | 0 | 0.04 |
| LPG10134 | SGN002647 | 0 | 0 | 0 |
| LPG10134 | SGN002648 | 0 | 0 | 2.15 |

TABLE 4-continued

Editing rate by plasmid delivery

| RGN | SGN | Rep1 | Rep2 | Rep3 |
|---|---|---|---|---|
| LPG10134 | SGN002649 | 0 | 0 | 0 |
| LPG10134 | SGN002650 | 0 | 0 | 0 |
| LPG10134 | SGN002651 | 0 | 0 | 0 |
| LPG10134 | SGN002652 | 0 | 0 | 0 |
| LPG10134 | SGN002653 | 0 | 0 | 0 |
| LPG10136 | SGN002654 | 5.74 | 3.57 | 8 |
| LPG10136 | SGN002655 | 5.18 | 5.36 | 6.86 |
| LPG10136 | SGN002656 | 3.4 | 2.06 | 5.7 |
| LPG10136 | SGN002657 | 4.14 | 3.01 | 6.77 |
| LPG10136 | SGN002658 | 0.05 | 0 | 0 |
| LPG10136 | SGN002659 | 0.33 | 0.15 | 0.87 |
| LPG10136 | SGN002660 | 1.89 | 0.82 | 4.38 |
| LPG10136 | SGN002661 | 3.56 | 3.81 | 4.82 |
| LPG10136 | SGN002662 | 2.53 | 1.9 | 3.99 |
| LPG10136 | SGN002663 | 0.51 | 0.33 | 0.67 |
| LPG10138 | SGN002664 | 0.47 | 0.46 | 2.75 |
| LPG10138 | SGN002665 | 0.92 | 3.79 | 4.84 |
| LPG10138 | SGN002666 | 0.12 | 0.22 | 0.88 |
| LPG10138 | SGN002667 | 0.91 | 3.13 | 3.18 |
| LPG10138 | SGN002668 | 0 | 0 | 0 |
| LPG10138 | SGN002669 | 0.14 | 0.42 | 1.92 |
| LPG10138 | SGN002670 | 0 | 0 | 0.14 |
| LPG10138 | SGN002671 | 2.54 | 2.56 | 3.21 |
| LPG10138 | SGN002672 | 0.1 | 1.11 | 0.79 |
| LPG10138 | SGN002673 | 0 | 0 | 0.87 |
| LPG10139 | SGN002674 | 0.27 | 0.56 | 2.97 |
| LPG10139 | SGN002675 | 3.95 | 3.92 | 5.99 |
| LPG10139 | SGN002676 | 0 | 0.12 | 1.36 |
| LPG10139 | SGN002677 | 0.88 | 0.24 | 3.27 |
| LPG10139 | SGN002678 | 0 | 0 | 0 |
| LPG10139 | SGN002679 | 1.68 | 0.47 | 3.26 |
| LPG10139 | SGN002680 | 0 | 0 | 0.16 |
| LPG10139 | SGN002681 | 3.53 | 4.09 | 7.03 |
| LPG10139 | SGN002682 | 0.94 | 0.51 | 3.32 |
| LPG10139 | SGN002683 | 0.35 | 0.44 | 0.93 |
| LPG10141 | SGN002684 | 0 | 0 | 0.3 |
| LPG10141 | SGN002685 | 0 | 0 | 0.43 |
| LPG10141 | SGN002686 | 0 | 0 | 0.14 |
| LPG10141 | SGN002687 | 0 | 0 | 2.1 |
| LPG10141 | SGN002688 | 0 | 0 | 0 |
| LPG10141 | SGN002689 | 0 | 0 | 0 |
| LPG10141 | SGN002690 | 0 | 0 | 0 |
| LPG10141 | SGN002691 | 0 | 0 | 0 |
| LPG10141 | SGN002692 | 0 | 0 | 0 |
| LPG10141 | SGN002693 | 0 | 0 | 0 |
| LPG10145 | SGN002698 | 9.25 | 9.03 | 13.74 |
| LPG10145 | SGN002699 | 3.19 | 4.3 | 6.29 |
| LPG10145 | SGN002700 | 1.43 | 0.31 | 4.26 |
| LPG10145 | SGN002701 | 3.9 | 5.07 | 6.85 |
| LPG10145 | SGN002702 | 9.87 | 4.92 | 11.76 |
| LPG10145 | SGN002703 | 0.08 | 0.07 | 0.61 |
| LPG10145 | SGN002704 | 3.04 | 1.09 | 4.83 |
| LPG10145 | SGN002705 | 0 | 0 | 0 |
| LPG10145 | SGN002706 | 4.36 | 1.96 | 4.7 |
| LPG10145 | SGN002707 | 8.54 | 8.09 | 7.36 |
| LPG10146 | SGN002708 | 0.85 | 0 | 1.09 |
| LPG10146 | SGN002709 | 0 | 0 | 0.19 |
| LPG10146 | SGN002710 | 0.29 | 1.08 | 1.09 |
| LPG10146 | SGN002711 | 0 | 0 | 0.71 |
| LPG10146 | SGN002712 | 2.42 | 1.57 | 3.01 |
| LPG10146 | SGN002713 | 0 | 0 | 0 |
| LPG10146 | SGN002714 | 0 | 0 | 0 |
| LPG10146 | SGN002715 | 0 | 0 | 0 |
| LPG10146 | SGN002716 | 0 | 0 | 0 |
| LPG10146 | SGN002717 | 0 | 0 | 0 |
| LPG10147 | SGN002718 | 0 | 0 | 0 |
| LPG10147 | SGN002719 | 0 | 0 | 0 |
| LPG10147 | SGN002720 | 0 | 0 | 0 |
| LPG10147 | SGN002721 | 0 | 0 | 0 |
| LPG10147 | SGN002722 | 0 | 0 | 0 |
| LPG10147 | SGN002723 | 0 | 0 | 0 |
| LPG10150 | SGN002724 | 2.15 | 3.12 | 1.25 |
| LPG10150 | SGN002725 | 1.29 | 1.1 | 0.28 |
| LPG10150 | SGN002726 | 0.05 | 0 | 0 |
| LPG10150 | SGN002727 | 0.03 | 0 | 0 |
| LPG10150 | SGN002728 | 0.06 | 0.1 | 0 |
| LPG10150 | SGN002729 | 0 | 0 | 0 |
| LPG10150 | SGN002730 | 0 | 0 | 0 |
| LPG10150 | SGN002731 | 0.08 | 0.2 | 0 |
| LPG10150 | SGN002732 | 0 | 0 | 0 |
| LPG10150 | SGN002733 | 0.72 | 0.17 | 0.09 |
| LPG10155 | SGN002734 | 0 | 0 | 0 |
| LPG10155 | SGN002735 | 0 | 0.15 | 0 |
| LPG10155 | SGN002735 | 0.42 | 0 | 0 |
| LPG10155 | SGN002736 | 0 | 0 | 0 |
| LPG10155 | SGN002737 | 0 | 0 | 0 |
| LPG10155 | SGN002738 | 0 | 0 | 0 |
| LPG10159 | SGN002738 | 0 | 0 | 0 |
| LPG10159 | SGN002739 | 0 | 0 | 0 |
| LPG10159 | SGN002740 | 0 | 0 | 0 |
| LPG10159 | SGN002741 | 0 | 0 | 0 |
| LPG10159 | SGN002742 | 0 | 0 | 0 |
| LPG10159 | SGN002744 | 0 | 0 | 0 |
| LPG10159 | SGN002745 | 0 |  | 0 |
| LPG10159 | SGN002747 |  | 0 | 0 |
| LPG10159 | SGN002748 | 0 | 0 | 0 |
| LPG10159 | SGN002749 | 0 | 0 | 0 |
| LPG10160 | SGN002750 | 0 | 0 | 0 |
| LPG10160 | SGN002751 | 0 | 0 | 0 |
| LPG10160 | SGN002752 | 0 | 0 | 0 |
| LPG10160 | SGN002753 | 0 | 0 | 0 |
| LPG10160 | SGN002754 | 0 | 0 | 0 |
| LPG10160 | SGN002755 | 0 | 0 | 0 |
| LPG10160 | SGN002756 | 0 | 0 | 0 |
| LPG10160 | SGN002757 | 0 | 0 | 0 |
| LPG10160 | SGN002758 | 0 | 0 | 0 |
| LPG10160 | SGN002759 | 0 | 0 | 0 |

LPG10136 showed an average editing rate around 3.01% across 10 guides in three independent experiments. LPG10145 showed an average editing rate around 4.63% across 10 guides in three independent editing experiments, with three guides editing around 10%. LPG10138, LPG10139, LPG10141, LPG10146, and LPG10150 also showed indel formation by amplicon sequencing with at least one guide RNA demonstrating these nucleases are active in mammalian cells.

TABLE 5.1

Example INDEL formation for LPG10136

| #Reads | Edited Sequence | Category | INDEL Size | INDEL Location | % Reads | % of INDELS |
|---|---|---|---|---|---|---|
| 261890 | CTCAGGTACTCCAAAGATTCAGG TTTACTCACGTCATCCAGCAGAGA | WT | 0 | 0 | 92.82 | 0 |
| 1935 | CTCAGGTACTCCAAAGATTCAGGT TT----ACGTCATCCAGCAGAGA | Deletion | 4 | 3 | 0.69 | 9.55 |

TABLE 5.1-continued

Example INDEL formation for LPG10136

| #Reads | Edited Sequence | Category | INDEL Size | Location | % Reads | % of INDELS |
|---|---|---|---|---|---|---|
| 1806 | CTCAGGTACTCCAAAGATTCAGGT<br>TTAC-----TCATCCAGCAGAGA | Deletion | 5 | 0 | 0.64 | 8.92 |
| 929 | CTCAGGTACTCCAAAGAT----------T<br>CACGTCATCCAGCAGAGA | Deletion | 10 | 5 | 0.33 | 4.59 |
| 828 | CTCAGGTACTCCAAAGATTCAGGT<br>TTACT-ACGTCATCCAGCAGAGA | Deletion | 1 | 3 | 0.29 | 4.09 |
| 803 | CTCAGGTACTCCAAAGATTCAGGT<br>TTACTCAACGTCATCCAGCAGAG | Insertion | 1 | 3 | 0.28 | 3.96 |
| 802 | CTCAGGTACTCCAAAGATTCAGGT<br>TTAC--------TCCAGCAGAGA | Deletion | 8 | -3 | 0.28 | 3.96 |
| 622 | CTCAGGTACTCCAAAGATTCAGGT<br>TTACT-CGTCATCCAGCAGAGA | Deletion | 2 | 2 | 0.22 | 3.07 |
| 409 | CTCAGGTACTCCAAAG--------------A<br>CGTCATCCAGCAGAGA | Deletion | 14 | 3 | 0.14 | 2.02 |
| 380 | CTCAGGTACTCCAAAGATTCAGGT<br>TTACTCCACGTCATCCAGCAGAG | Insertion | 1 | 4 | 0.13 | 1.88 |
| 373 | CTCAGGTACTCCAAAGATTCAGGT<br>TTACT---------CAGCAGAGA | Deletion | 9 | -5 | 0.13 | 1.84 |
| 342 | CTCAGGTACTCCAAAGATTCA-----<br>-------------------------<br>----ACGTCATCCAGCAGAGA | Deletion | 9 | 3 | 0.12 | 1.69 |
| 340 | CTCAGGTACTCCAAAG---------------<br>----------------------<br>------A | Deletion | 133 | -116 | 0.12 | 1.68 |
| 335 | CTCAGGTACTCCAAAGAT------------<br>---TCATCCAGCAGAGA | Deletion | 15 | 0 | 0.12 | 1.65 |
| 302 | CTCAGGTACTCCAAAGATTCAGGT<br>TTA-CACGTCATCCAGCAGAGA | Deletion | 2 | 4 | 0.11 | 1.49 |
| 302 | CTCAGGTACTCCAAAGAT------------<br>ACGTCATCCAGCAGAGA | Deletion | 12 | 3 | 0.11 | 1.49 |
| 293 | CTCAGGTACTCCAAAGATTCAG----<br>------GTCATCCAGCAGAGA | Deletion | 10 | 1 | 0.1 | 1.45 |
| 289 | CTCAGGTACTCCAAAGATTCAGGT<br>TTACTC-CGTCATCCAGCAGAGA | Deletion | 1 | 2 | 0.1 | 1.43 |
| 287 | CTCAGGTACTCCAAAGATTCAGGT<br>T-----ACGTCATCCAGCAGAGA | Deletion | 5 | 3 | 0.1 | 1.42 |
| 277 | CTCAGGTACTCCAAAGATTCAGGT<br>T-------------------------<br>-------------------------<br>---------T | Deletion | 168 | -160 | 0.1 | 1.37 |
| 271 | CTCAGGTACTCCAAAGATTCAGGT<br>TTA---ACGTCATCCAGCAGAGA | Deletion | 3 | 3 | 0.1 | 1.34 |

Edited alleles that account for >0.1% of overall editing results are shown above. Deletions are shown by dashes. The most frequent editing outcome for this guide was small deletions and insertions.

TABLE 5.2

Example INDEL formation for LPG10145

| #Reads | Edited Sequence | Category | Size | INDEL Location | % Reads | % of INDELS |
|---|---|---|---|---|---|---|
| 270438 | ATGTCTCGCTCCGTGGCCTTAGCTGT GCTCGCGCTACTCTCTCTTTC | WT | 0 | 0 | 85.84 | 0 |
| 8329 | ATGTCTCGCTCCGTGG-CTTAGCTGT GCTCGCGCTACTCTCTCTTTC | Deletion | 1 | 2 | 2.64 | 18.68 |
| 3531 | ATGTCTCGCTCCGTGGC-TAGCTGT GCTCGCGCTACTCTCTCTTTC | Deletion | 2 | 3 | 1.12 | 7.92 |
| 2595 | ATGTCTCGCTCCGTG------GCTGTGC TCGCGCTACTCTCTCTTTC | Deletion | 6 | 1 | 0.82 | 5.82 |
| 2201 | ATGTCTCGCTCCGTGGC----------CTC GCGCTACTCTCTCTTTC | Deletion | 10 | 3 | 0.7 | 4.94 |
| 1902 | ATGTCTCGCTCCGTGGCACTTAGC TGTGCTCGCGCTACTCTCTCTTT | Insertion | 1 | 3 | 0.6 | 4.27 |
| 1262 | ATGTCTCGCTCCGTG-----------GCTC GCGCTACTCTCTCTTTC | Deletion | 11 | 1 | 0.4 | 2.83 |
| 1047 | ATGTCTCG---------CTTAGCTGTGCT CGCGCTACTCTCTCTTTC | Deletion | 9 | -6 | 0.33 | 2.35 |
| 759 | ATGTCTC-------------GCTCGCGC TACTCTCTCTTTC | Deletion | 19 | -7 | 0.24 | 1.7 |
| 730 | ATGTCTCGCTCCGTGGC----GCTGT GCTCGCGCTACTCTCTCTTTC | Deletion | 4 | 3 | 0.23 | 1.64 |
| 654 | ATGTCTCGCTCCGTGGC-----CTGTG CTCGCGCTACTCTCTCTTTC | Deletion | 5 | 3 | 0.21 | 1.47 |
| 639 | ATGTCTCGCTCCGTGGC---AGCTGT GCTCGCGCTACTCTCTCTTTC | Deletion | 3 | 3 | 0.2 | 1.43 |
| 548 | ATGTCTCGCTCCGTG-------------GC GCTACTCTCTCTTTC | Deletion | 15 | 1 | 0.17 | 1.23 |
| 530 | ATGTCTCGCTCCGTGGC--------TGC TCGCGCTACTCTCTCTTTC | Deletion | 8 | 3 | 0.17 | 1.19 |
| 528 | ATGT---------------CTCGCGCT ACTCTCTCTTTC | Deletion | 23 | -10 | 0.17 | 1.18 |
| 519 | ATGTCTCGCTCCGTGGC---------GC TCGCGCTACTCTCTCTTTC | Deletion | 9 | 3 | 0.16 | 1.16 |
| 470 | ATGTCTCGCTCCGTGGCTTCTTAG CTGTGCTCGCGCTACTCTCTCTT | Insertion | 2 | 3 | 0.15 | 1.05 |
| 456 | ATGTCTCGCTCCGTGGC-------GTG CTCGCGCTACTCTCTCTTTC | Deletion | 7 | 3 | 0.14 | 1.02 |
| 431 | ATGTCTC----------GCTGTGCTCG CGCTACTCTCTCTTTC | Deletion | 14 | -7 | 0.14 | 0.97 |
| 410 | ATGTCTCGCTCCGTGGC-GAGCT GTGCTCGCGCTACTCTCTCTTTC | Deletion | 2 | 3 | 0.13 | 0.92 |
| 391 | ATGTCTCGCTCCGTGGCCGTTT CCCCCTGGAAGCTCCCTCGTGC GCT | Insertion | 41 | 3 | 0.12 | 0.88 |
| 368 | ATGTCTCGCTCCG----- TAGCTGTGCTCGCGCTACTCTC TCTTTC | Deletion | 6 | -1 | 0.12 | 0.83 |

TABLE 5.2-continued

Example INDEL formation for LPG10145

| #Reads | Edited Sequence | Category | Size | INDEL Location | % Reads | % of INDELS |
|--------|-----------------|----------|------|----------------|---------|-------------|
| 329 | ATG---------------------<br>------------------------<br>------------------------<br>------------------------<br>------------ | Deletion | 137 | -11 | 0.1 | 0.74 |
| 328 | ATGTCTCGCTCCGTG--------------<br>GCTACTCTCTCTTTC | Deletion | 17 | 1 | 0.1 | 0.74 |
| 310 | ATGTCTCGCTCCGTGGC----------<br>CGCGCTACTCTCTCTTTC | Deletion | 12 | 3 | 0.1 | 0.7 |
| 301 | ATGTCTCGCTC-----<br>CCTTAGCTGTGCTCGCGCTACTC<br>TCTCTTTC | Deletion | 5 | -3 | 0.1 | 0.67 |

Edited alleles that account for >0.1% of overall editing results are shown above. Deletions are shown by dashes. The most frequent editing outcome for this guide was small deletions and insertions.

Example 5: Testing Different Delivery Formats

To determine if the RGNs are capable of delivery in different formats, mRNA and RNP nucleofection delivery is tested with primary T-cells. Purified CD3+ T-cells or peripheral blood mononuclear cells (PBMCs) are thawed, activated using CD3/CD28 beads (ThermoFisher) for 3 days, then nucleofected using the Lonza 4D-Nucleofector X unit and Nucleocuvette strips. The P3 Primary Cell kit is used for both mRNA and RNP delivery. Cells are transfected using the EO-115 and EH-115 programs for mRNA and RNP delivery respectively. Cells are cultured in CTS OpTimizer T cell expansion medium (ThermoFisher) containing IL-2, IL-7, and IL-15 (Miltenyi Biotec) for 4 days post nucleofection before being harvested using a Nucleospin Tissue genomic DNA isolation kit (Machery Nagel).

Amplicons surrounding the editing sites are generated by PCR using primers and subjected to NGS sequencing using the Illumina Nextera platform using 2×250 bp paired end sequencing following the method in Example 4.

Example 6: Identification of Disease Targets

A database of clinical variants was obtained from NCBI Clin Var database, which is available through the world wide web at the NCBI Clin Var website. Pathogenic Single Nucleotide Polymorphisms (SNPs) were identified from this list. Using the genomic locus information, CRISPR targets in the region overlapping and surrounding each SNP were identified. A selection of SNPs that can be corrected using base editing in combination with the RGNs of the invention to target the causal mutation ("Casl Mut.") is listed in Table 6. In Table 6, only one alias of each disease is listed. The "RS #" corresponds to the RS accession number through the SNP database at the NCBI website. The AlleleID corresponds to a causal allele accession number. Table 6 also provides genomic target sequence information suitable for the RGN listed for each disease. The target sequence information also provides protospacer sequence for the production of the necessary sgRNA for the corresponding RGN of the invention.

TABLE 6

Disease Targets for RGNs

| Disease | RS# | RGN | Casl Mut. | AlleleID | Gene Symbol | Target (SEQ ID NO.) |
|---------|-----|-----|-----------|----------|-------------|---------------------|
| Stargardt disease 1 | 1800553 | LPG10134 | G > A | 22927 | ABCA4 | 85 |
| Stargardt disease 1 | 1800553 | LPG10136 | G > A | 22927 | ABCA4 | 86 |
| Stargardt disease 1 | 1800553 | LPG10138, LPG10139 | G > A | 22927 | ABCA4 | 87 |
| Stargardt disease 1 | 1800553 | LPG10145 | G > A | 22927 | ABCA4 | 88 |
| Stargardt disease 1 | 1800553 | LPG10141 | G > A | 22927 | ABCA4 | 89 |
| Stargardt disease 1 | 1800728 | LPG10134 | T > C | 98777 | ABCA4 | 90 |
| Stargardt disease 1 | 1800728 | LPG10138, LPG10139 | T > C | 98777 | ABCA4 | 91 |
| Stargardt disease 1 | 1800728 | LPG10145 | T > C | 98777 | ABCA4 | 92 |
| Stargardt disease 1 | 1800728 | LPG10146 | T > C | 98777 | ABCA4 | 93 |
| Stargardt disease 1 | 1800728 | LPG10150 | T > C | 98777 | ABCA4 | 94 |
| Stargardt disease 1 | 1800728 | LPG10159 | T > C | 98777 | ABCA4 | 95 |
| Stargardt disease 1 | 1800728 | LPG10141 | T > C | 98777 | ABCA4 | 96 |
| Medium-chain acyl-coenzyme A dehydrogenase deficiency | 121434274 | LPG10138, LPG10139 | G > A | 18627 | ACADM | 97 |
| Medium-chain acyl-coenzyme A dehydrogenase deficiency | 121434274 | LPG10160 | G > A | 18627 | ACADM | 98 |

TABLE 6-continued

Disease Targets for RGNs

| Disease | RS# | RGN | Casl Mut. | AlleleID | Gene Symbol | Target (SEQ ID NO.) |
|---|---|---|---|---|---|---|
| Very long chain acyl-CoA dehydrogenase deficiency | 113994167 | LPG10134 | T > C | 33877 | ACADVL | 99 |
| Very long chain acyl-CoA dehydrogenase deficiency | 113994167 | LPG10138, LPG10139 | T > C | 33877 | ACADVL | 100 |
| Very long chain acyl-CoA dehydrogenase deficiency | 113994167 | LPG10145 | T > C | 33877 | ACADVL | 101 |
| Very long chain acyl-CoA dehydrogenase deficiency | 113994167 | LPG10146 | T > C | 33877 | ACADVL | 102 |
| Very long chain acyl-CoA dehydrogenase deficiency | 113994167 | LPG10141 | T > C | 33877 | ACADVL | 103 |
| Adenylosuccinate lyase deficiency | 119450941 | LPG10138, LPG10139 | G > A | 17501 | ADSL | 104 |
| Primary hyperoxaluria, type I | 121908529 | LPG10134 | G > A | 38436 | AGXT | 105 |
| Primary hyperoxaluria, type I | 121908529 | LPG10136 | G > A | 38436 | AGXT | 106 |
| Primary hyperoxaluria, type I | 121908529 | LPG10138, LPG10139 | G > A | 38436 | AGXT | 107 |
| Primary hyperoxaluria, type I | 121908529 | LPG10145 | G > A | 38436 | AGXT | 108 |
| Primary hyperoxaluria, type I | 121908529 | LPG10141 | G > A | 38436 | AGXT | 109 |
| Hypophosphatasia | 121918007 | LPG10134 | G > A | 28709 | ALPL | 110 |
| Hypophosphatasia | 121918007 | LPG10136 | G > A | 28709 | ALPL | 111 |
| Hypophosphatasia | 121918007 | LPG10138, LPG10139 | G > A | 28709 | ALPL | 112 |
| Hypophosphatasia | 121918007 | LPG10145 | G > A | 28709 | ALPL | 113 |
| Metachromatic leukodystrophy | 80338815 | LPG10134 | G > A | 18090 | ARSA | 114 |
| Metachromatic leukodystrophy | 80338815 | LPG10136 | G > A | 18090 | ARSA | 115 |
| Metachromatic leukodystrophy | 80338815 | LPG10138, LPG10139 | G > A | 18090 | ARSA | 116 |
| Metachromatic leukodystrophy | 80338815 | LPG10145 | G > A | 18090 | ARSA | 117 |
| Metachromatic leukodystrophy | 80338815 | LPG10146 | G > A | 18090 | ARSA | 118 |
| Metachromatic leukodystrophy | 80338815 | LPG10141 | G > A | 18090 | ARSA | 119 |
| Breast and/or ovarian cancer | 80356962 | LPG10134 | G > A | 70247 | BRCA1 | 120 |
| Breast and/or ovarian cancer | 80356962 | LPG10134 | G > A | 70247 | BRCA1 | 121 |
| Breast and/or ovarian cancer | 80356962 | LPG10136 | G > A | 70247 | BRCA1 | 122 |
| Breast and/or ovarian cancer | 80356962 | LPG10138, LPG10139 | G > A | 70247 | BRCA1 | 123 |
| Breast and/or ovarian cancer | 80356962 | LPG10145 | G > A | 70247 | BRCA1 | 124 |
| Breast and/or ovarian cancer | 80356962 | LPG10146 | G > A | 70247 | BRCA1 | 125 |
| Breast and/or ovarian cancer | 80359003 | LPG10134 | G > A | 67069 | BRCA2 | 126 |
| Breast and/or ovarian cancer | 80359003 | LPG10145 | G > A | 67069 | BRCA2 | 127 |
| Breast and/or ovarian cancer | 80359003 | LPG10146 | G > A | 67069 | BRCA2 | 128 |
| Breast and/or ovarian cancer | 80359003 | LPG10159 | G > A | 67069 | BRCA2 | 129 |
| Breast and/or ovarian cancer | 80359003 | LPG10160 | G > A | 67069 | BRCA2 | 130 |
| Breast and/or ovarian cancer | 80359003 | LPG10141 | G > A | 67069 | BRCA2 | 131 |
| Breast and/or ovarian cancer | 80359071 | LPG10134 | G > A | 67203 | BRCA2 | 132 |
| Breast and/or ovarian cancer | 80359071 | LPG10138, LPG10139 | G > A | 67203 | BRCA2 | 133 |
| Homocystinuria | 5742905 | LPG10134 | T > C | 15159 | CBS | 134 |
| Homocystinuria | 5742905 | LPG10136 | T > C | 15159 | CBS | 135 |
| Homocystinuria | 5742905 | LPG10138, LPG10139 | T > C | 15159 | CBS | 136 |
| Homocystinuria | 5742905 | LPG10145 | T > C | 15159 | CBS | 137 |

TABLE 6-continued

Disease Targets for RGNs

| Disease | RS# | RGN | Cas1 Mut. | AlleleID | Gene Symbol | Target (SEQ ID NO.) |
|---|---|---|---|---|---|---|
| Homocystinuria | 5742905 | LPG10145 | T > C | 15159 | CBS | 138 |
| Homocystinuria | 5742905 | LPG10150 | T > C | 15159 | CBS | 139 |
| Homocystinuria | 5742905 | LPG10159 | T > C | 15159 | CBS | 140 |
| Homocystinuria | 5742905 | LPG10141 | T > C | 15159 | CBS | 141 |
| Homocystinuria | 121964962 | LPG10134 | G > A | 15156 | CBS | 142 |
| Homocystinuria | 121964962 | LPG10136 | G > A | 15156 | CBS | 143 |
| Homocystinuria | 121964962 | LPG10138, LPG10139 | G > A | 15156 | CBS | 144 |
| Homocystinuria | 121964962 | LPG10145 | G > A | 15156 | CBS | 145 |
| Homocystinuria | 121964962 | LPG10141 | G > A | 15156 | CBS | 146 |
| Cystic fibrosis | 75527207 | LPG10138, LPG10139 | G > A | 22159 | CFTR | 147 |
| Cystic fibrosis | 75527207 | LPG10160 | G > A | 22159 | CFTR | 148 |
| Cystic fibrosis | 78655421 | LPG10134 | G > A | 22148 | CFTR | 149 |
| Cystic fibrosis | 78655421 | LPG10138, LPG10139 | G > A | 22148 | CFTR | 150 |
| Cystic fibrosis | 78655421 | LPG10145 | G > A | 22148 | CFTR | 151 |
| Cystic fibrosis | 78655421 | LPG10141 | G > A | 22148 | CFTR | 152 |
| Familial dysautonomia | 111033171 | LPG10136 | T > C | 21124 | ELP1 | 153 |
| Familial dysautonomia | 111033171 | LPG10138, LPG10139 | T > C | 21124 | ELP1 | 154 |
| Familial dysautonomia | 111033171 | LPG10146 | T > C | 21124 | ELP1 | 155 |
| Tyrosinemia type I | 80338901 | LPG10134 | G > A | 26909 | FAH | 156 |
| Tyrosinemia type I | 80338901 | LPG10136 | G > A | 26909 | FAH | 157 |
| Tyrosinemia type I | 80338901 | LPG10138, LPG10139 | G > A | 26909 | FAH | 158 |
| Tyrosinemia type I | 80338901 | LPG10145 | G > A | 26909 | FAH | 159 |
| Deafness | 80338945 | LPG10134 | T > C | 32055 | GJB2 | 160 |
| Deafness | 80338945 | LPG10136 | T > C | 32055 | GJB2 | 161 |
| Deafness | 80338945 | LPG10138, LPG10139 | T > C | 32055 | GJB2 | 162 |
| Deafness | 80338945 | LPG10145 | T > C | 32055 | GJB2 | 163 |
| Deafness | 80338945 | LPG10146 | T > C | 32055 | GJB2 | 164 |
| Deafness | 80338945 | LPG10150 | T > C | 32055 | GJB2 | 165 |
| Deafness | 80338945 | LPG10159 | T > C | 32055 | GJB2 | 166 |
| Deafness | 104894396 | LPG10138, LPG10139 | G > A | 32041 | GJB2 | 167 |
| Deafness | 104894396 | LPG10145 | G > A | 32041 | GJB2 | 168 |
| Deafness | 104894396 | LPG10160 | G > A | 32041 | GJB2 | 169 |
| Deafness | 104894396 | LPG10141 | G > A | 32041 | GJB2 | 170 |
| Inclusion body myopathy | 28937594 | LPG10134 | T > C | 21064 | GNE | 171 |
| Inclusion body myopathy | 28937594 | LPG10138, LPG10139 | T > C | 21064 | GNE | 172 |
| Inclusion body myopathy | 28937594 | LPG10145 | T > C | 21064 | GNE | 173 |
| Inclusion body myopathy | 28937594 | LPG10146 | T > C | 21064 | GNE | 174 |
| Inclusion body myopathy | 28937594 | LPG10141 | T > C | 21064 | GNE | 175 |
| Mucopolysaccharidosis type I | 121965019 | LPG10134 | G > A | 26947 | IDUA | 176 |
| Mucopolysaccharidosis type I | 121965019 | LPG10136 | G > A | 26947 | IDUA | 177 |
| Mucopolysaccharidosis type I | 121965019 | LPG10138, LPG10139 | G > A | 26947 | IDUA | 178 |
| Mucopolysaccharidosis type I | 121965019 | LPG10145 | G > A | 26947 | IDUA | 179 |
| Mucopolysaccharidosis type I | 121965019 | LPG10150 | G > A | 26947 | IDUA | 180 |
| Mucopolysaccharidosis type I | 121965019 | LPG10141 | G > A | 26947 | IDUA | 181 |
| Familial hypercholesterolemia | 137929307 | LPG10134 | G > A | 171217 | LDLR | 182 |
| Familial hypercholesterolemia | 137929307 | LPG10138, LPG10139 | G > A | 171217 | LDLR | 183 |
| Familial hypercholesterolemia | 137929307 | LPG10145 | G > A | 171217 | LDLR | 184 |
| Familial hypercholesterolemia | 137929307 | LPG10146 | G > A | 171217 | LDLR | 185 |
| Familial hypercholesterolemia | 137929307 | LPG10141 | G > A | 171217 | LDLR | 186 |
| Familial Mediterranean fever | 28940579 | LPG10136 | T > C | 17579 | MEFV | 187 |
| Familial Mediterranean fever | 28940579 | LPG10138, LPG10139 | T > C | 17579 | MEFV | 188 |
| Familial Mediterranean fever | 28940579 | LPG10146 | T > C | 17579 | MEFV | 189 |
| Familial Mediterranean fever | 28940579 | LPG10159 | T > C | 17579 | MEFV | 190 |
| Familial Mediterranean fever | 28940579 | LPG10160 | T > C | 17579 | MEFV | 191 |

TABLE 6-continued

Disease Targets for RGNs

| Disease | RS# | RGN | Cas1 Mut. | AlleleID | Gene Symbol | Target (SEQ ID NO.) |
|---|---|---|---|---|---|---|
| Familial Mediterranean fever | 104895097 | LPG10136 | G > A | 17588 | MEFV | 192 |
| Familial Mediterranean fever | 104895097 | LPG10138, LPG10139 | G > A | 17588 | MEFV | 193 |
| Familial Mediterranean fever | 104895097 | LPG10145 | G > A | 17588 | MEFV | 194 |
| Familial Mediterranean fever | 104895097 | LPG10146 | G > A | 17588 | MEFV | 195 |
| Familial Mediterranean fever | 104895097 | LPG10150 | G > A | 17588 | MEFV | 196 |
| Familial Mediterranean fever | 104895097 | LPG10159 | G > A | 17588 | MEFV | 197 |
| Mevalonic aciduria | 28934897 | LPG10136 | G > A | 26968 | MVK | 198 |
| Mevalonic aciduria | 28934897 | LPG10138, LPG10139 | G > A | 26968 | MVK | 199 |
| Mevalonic aciduria | 28934897 | LPG10146 | G > A | 26968 | MVK | 200 |
| Hypertrophic cardiomyopathy | 200411226 | LPG10134 | G > A | 174776 | MYBPC3 | 201 |
| Hypertrophic cardiomyopathy | 200411226 | LPG10136 | G > A | 174776 | MYBPC3 | 202 |
| Hypertrophic cardiomyopathy | 200411226 | LPG10138, LPG10139 | G > A | 174776 | MYBPC3 | 203 |
| Hypertrophic cardiomyopathy | 200411226 | LPG10145 | G > A | 174776 | MYBPC3 | 204 |
| Hypertrophic cardiomyopathy | 200411226 | LPG10146 | G > A | 174776 | MYBPC3 | 205 |
| Hypertrophic cardiomyopathy | 200411226 | LPG10147 | G > A | 174776 | MYBPC3 | 206 |
| Hypertrophic cardiomyopathy | 200411226 | LPG10155 | G > A | 174776 | MYBPC3 | 207 |
| Hypertrophic cardiomyopathy | 200411226 | LPG10160 | G > A | 174776 | MYBPC3 | 208 |
| Hypertrophic cardiomyopathy | 397516074 | LPG10134 | G > A | 51962 | MYBPC3 | 209 |
| Hypertrophic cardiomyopathy | 397516074 | LPG10136 | G > A | 51962 | MYBPC3 | 210 |
| Hypertrophic cardiomyopathy | 397516074 | LPG10138, LPG10139 | G > A | 51962 | MYBPC3 | 211 |
| Hypertrophic cardiomyopathy | 397516074 | LPG10145 | G > A | 51962 | MYBPC3 | 212 |
| Hypertrophic cardiomyopathy | 397516074 | LPG10159 | G > A | 51962 | MYBPC3 | 213 |
| Hypertrophic cardiomyopathy | 397516074 | LPG10141 | G > A | 51962 | MYBPC3 | 214 |
| MYH7-related disorder | 3218716 | LPG10134 | G > A | 52071 | MYH7 | 215 |
| MYH7-related disorder | 3218716 | LPG10136 | G > A | 52071 | MYH7 | 216 |
| MYH7-related disorder | 3218716 | LPG10138, LPG10139 | G > A | 52071 | MYH7 | 217 |
| MYH7-related disorder | 3218716 | LPG10145 | G > A | 52071 | MYH7 | 218 |
| MYH7-related disorder | 3218716 | LPG10150 | G > A | 52071 | MYH7 | 219 |
| MYH7-related disorder | 3218716 | LPG10159 | G > A | 52071 | MYH7 | 220 |
| MYH7-related disorder | 3218716 | LPG10141 | G > A | 52071 | MYH7 | 221 |
| MYH7-related disorder | 371898076 | LPG10138, LPG10139 | G > A | 52045 | MYH7 | 222 |
| Hypertrophic cardiomyopathy | 104894368 | LPG10134 | G > A | 29104 | MYL2 | 223 |
| Hypertrophic cardiomyopathy | 104894368 | LPG10138, LPG10139 | G > A | 29104 | MYL2 | 224 |
| Hypertrophic cardiomyopathy | 104894368 | LPG10145 | G > A | 29104 | MYL2 | 225 |
| Hypertrophic cardiomyopathy | 104894368 | LPG10145 | G > A | 29104 | MYL2 | 226 |
| Hypertrophic cardiomyopathy | 104894368 | LPG10160 | G > A | 29104 | MYL2 | 227 |
| Hypertrophic cardiomyopathy | 104894368 | LPG10141 | G > A | 29104 | MYL2 | 228 |
| Niemann-Pick disease type C1 | 80358259 | LPG10136 | T > C | 18006 | NPC1 | 229 |
| Niemann-Pick disease type C1 | 80358259 | LPG10138, LPG10139 | T > C | 18006 | NPC1 | 230 |
| Niemann-Pick disease type C1 | 80358259 | LPG10146 | T > C | 18006 | NPC1 | 231 |
| Niemann-Pick disease type C1 | 80358259 | LPG10150 | T > C | 18006 | NPC1 | 232 |
| Niemann-Pick disease type C1 | 80358259 | LPG10159 | T > C | 18006 | NPC1 | 233 |
| Phenylketonuria | 5030855 | LPG10138, LPG10139 | G > A | 15646 | PAH | 234 |
| Phenylketonuria | 5030855 | LPG10146 | G > A | 15646 | PAH | 235 |

TABLE 6-continued

Disease Targets for RGNs

| Disease | RS# | RGN | Casl Mut. | AlleleID | Gene Symbol | Target (SEQ ID NO.) |
|---|---|---|---|---|---|---|
| Phenylketonuria | 62508698 | LPG10134 | G > A | 15619 | PAH | 236 |
| Phenylketonuria | 62508698 | LPG10136 | G > A | 15619 | PAH | 237 |
| Phenylketonuria | 62508698 | LPG10138, LPG10139 | G > A | 15619 | PAH | 238 |
| Phenylketonuria | 62508698 | LPG10145 | G > A | 15619 | PAH | 239 |
| Phenylketonuria | 62508698 | LPG10146 | G > A | 15619 | PAH | 240 |
| Phenylketonuria | 62508698 | LPG10150 | G > A | 15619 | PAH | 241 |
| Phenylketonuria | 62516152 | LPG10134 | G > A | 108520 | PAH | 242 |
| Phenylketonuria | 62516152 | LPG10138, LPG10139 | G > A | 108520 | PAH | 243 |
| Phenylketonuria | 62516152 | LPG10145 | G > A | 108520 | PAH | 244 |
| Phenylketonuria | 62516152 | LPG10146 | G > A | 108520 | PAH | 245 |
| Phenylketonuria | 62516152 | LPG10160 | G > A | 108520 | PAH | 246 |
| Phenylketonuria | 62516152 | LPG10141 | G > A | 108520 | PAH | 247 |
| Phenylketonuria | 62644499 | LPG10134 | G > A | 15656 | PAH | 248 |
| Phenylketonuria | 62644499 | LPG10136 | G > A | 15656 | PAH | 249 |
| Phenylketonuria | 62644499 | LPG10138, LPG10139 | G > A | 15656 | PAH | 250 |
| Phenylketonuria | 62644499 | LPG10145 | G > A | 15656 | PAH | 251 |
| Phenylketonuria | 62644499 | LPG10159 | G > A | 15656 | PAH | 252 |
| Zellweger syndrome | 61750420 | LPG10134 | G > A | 22555 | PEX1 | 253 |
| Zellweger syndrome | 61750420 | LPG10136 | G > A | 22555 | PEX1 | 254 |
| Zellweger syndrome | 61750420 | LPG10138, LPG10139 | G > A | 22555 | PEX1 | 255 |
| Zellweger syndrome | 61750420 | LPG10145 | G > A | 22555 | PEX1 | 256 |
| Zellweger syndrome | 61750420 | LPG10146 | G > A | 22555 | PEX1 | 257 |
| Zellweger syndrome | 61750420 | LPG10150 | G > A | 22555 | PEX1 | 258 |
| Zellweger syndrome | 61750420 | LPG10141 | G > A | 22555 | PEX1 | 259 |
| Immunodeficiency 14 | 397518423 | LPG10134 | G > A | 94255 | PIK3CD | 260 |
| Immunodeficiency 14 | 397518423 | LPG10136 | G > A | 94255 | PIK3CD | 261 |
| Immunodeficiency 14 | 397518423 | LPG10138, LPG10139 | G > A | 94255 | PIK3CD | 262 |
| Immunodeficiency 14 | 397518423 | LPG10145 | G > A | 94255 | PIK3CD | 263 |
| Immunodeficiency 14 | 397518423 | LPG10146 | G > A | 94255 | PIK3CD | 264 |
| Immunodeficiency 14 | 397518423 | LPG10150 | G > A | 94255 | PIK3CD | 265 |
| Immunodeficiency 14 | 397518423 | LPG10159 | G > A | 94255 | PIK3CD | 266 |
| Immunodeficiency 14 | 397518423 | LPG10141 | G > A | 94255 | PIK3CD | 267 |
| POLG-related condition | 113994095 | LPG10138, LPG10139 | G > A | 28535 | POLG | 268 |
| POLG-related condition | 113994095 | LPG10146 | G > A | 28535 | POLG | 269 |
| POLG-related condition | 113994098 | LPG10134 | G > A | 28541 | POLG | 270 |
| POLG-related condition | 113994098 | LPG10138, LPG10139 | G > A | 28541 | POLG | 271 |
| POLG-related condition | 113994098 | LPG10145 | G > A | 28541 | POLG | 272 |
| POLG-related condition | 113994098 | LPG10141 | G > A | 28541 | POLG | 273 |
| Cardiomyopathy | 121908987 | LPG10134 | G > A | 21885 | PRKAG2 | 274 |
| Cardiomyopathy | 121908987 | LPG10136 | G > A | 21885 | PRKAG2 | 275 |
| Cardiomyopathy | 121908987 | LPG10138, LPG10139 | G > A | 21885 | PRKAG2 | 276 |
| Cardiomyopathy | 121908987 | LPG10145 | G > A | 21885 | PRKAG2 | 277 |
| Cardiomyopathy | 121908987 | LPG10146 | G > A | 21885 | PRKAG2 | 278 |
| Cardiomyopathy | 121908987 | LPG10159 | G > A | 21885 | PRKAG2 | 279 |
| Cardiomyopathy | 121908987 | LPG10141 | G > A | 21885 | PRKAG2 | 280 |
| Shwachman syndrome | 113993993 | LPG10136 | T > C | 18235 | SBDS | 281 |
| Shwachman syndrome | 113993993 | LPG10138, LPG10139 | T > C | 18235 | SBDS | 282 |
| Brugada syndrome | 137854601 | LPG10134 | G > A | 24416 | SCN5A | 283 |
| Brugada syndrome | 137854601 | LPG10136 | G > A | 24416 | SCN5A | 284 |
| Brugada syndrome | 137854601 | LPG10138, LPG10139 | G > A | 24416 | SCN5A | 285 |
| Brugada syndrome | 137854601 | LPG10145 | G > A | 24416 | SCN5A | 286 |
| Brugada syndrome | 137854601 | LPG10146 | G > A | 24416 | SCN5A | 287 |
| Brugada syndrome | 137854601 | LPG10150 | G > A | 24416 | SCN5A | 288 |
| Alpha-1-antitrypsin deficiency | 28929474 | LPG10134 | G > A | 33006 | SERPINA1 | 289 |
| Alpha-1-antitrypsin deficiency | 28929474 | LPG10136 | G > A | 33006 | SERPINA1 | 290 |
| Alpha-1-antitrypsin deficiency | 28929474 | LPG10138, LPG10139 | G > A | 33006 | SERPINA1 | 291 |
| Alpha-1-antitrypsin deficiency | 28929474 | LPG10138, LPG10139 | G > A | 33006 | SERPINA1 | 292 |
| Alpha-1-antitrypsin deficiency | 28929474 | LPG10145 | G > A | 33006 | SERPINA1 | 293 |
| Alpha-1-antitrypsin deficiency | 28929474 | LPG10141 | G > A | 33006 | SERPINA1 | 294 |
| Mucopolysaccharidosis, MPS-III-A | 104894635 | LPG10134 | G > A | 20146 | SGSH | 295 |
| Mucopolysaccharidosis, MPS-III-A | 104894635 | LPG10138, LPG10139 | G > A | 20146 | SGSH | 296 |
| Mucopolysaccharidosis, MPS-III-A | 104894635 | LPG10145 | G > A | 20146 | SGSH | 297 |
| Mucopolysaccharidosis, MPS-III-A | 104894635 | LPG10141 | G > A | 20146 | SGSH | 298 |
| Tuberous sclerosis syndrome | 28934872 | LPG10134 | G > A | 27436 | TSC2 | 299 |

TABLE 6-continued

Disease Targets for RGNs

| Disease | RS# | RGN | Cas1 Mut. | AlleleID | Gene Symbol | Target (SEQ ID NO.) |
|---|---|---|---|---|---|---|
| Tuberous sclerosis syndrome | 28934872 | LPG10138, LPG10139 | G > A | 27436 | TSC2 | 300 |
| Tuberous sclerosis syndrome | 28934872 | LPG10145 | G > A | 27436 | TSC2 | 301 |
| Tuberous sclerosis syndrome | 28934872 | LPG10141 | G > A | 27436 | TSC2 | 302 |
| Amyloidogenic transthyretin amyloidosis | 76992529 | LPG10134 | G > A | 28465 | TTR | 303 |
| Amyloidogenic transthyretin amyloidosis | 76992529 | LPG10138, LPG10139 | G > A | 28465 | TTR | 304 |
| Amyloidogenic transthyretin amyloidosis | 76992529 | LPG10145 | G > A | 28465 | TTR | 305 |
| Amyloidogenic transthyretin amyloidosis | 76992529 | LPG10150 | G > A | 28465 | TTR | 306 |
| Amyloidogenic transthyretin amyloidosis | 76992529 | LPG10160 | G > A | 28465 | TTR | 307 |
| Amyloidogenic transthyretin amyloidosis | 76992529 | LPG10141 | G > A | 28465 | TTR | 308 |
| Von Willebrand disease | 41276738 | LPG10134 | G > A | 15335 | VWF | 309 |
| Von Willebrand disease | 41276738 | LPG10136 | G > A | 15335 | VWF | 310 |
| Von Willebrand disease | 41276738 | LPG10138, LPG10139 | G > A | 15335 | VWF | 311 |
| Von Willebrand disease | 41276738 | LPG10145 | G > A | 15335 | VWF | 312 |
| Von Willebrand disease | 41276738 | LPG10146 | G > A | 15335 | VWF | 313 |
| Von Willebrand disease | 41276738 | LPG10150 | G > A | 15335 | VWF | 314 |
| Von Willebrand disease | 41276738 | LPG10141 | G > A | 15335 | VWF | 330 |

Example 7: Targeting Mutations Responsible for Hurler Syndrome

The following describes a potential treatment for Hurler Syndrome, also referred to as MPS-1, using an RNA directed base editing system that corrects a mutation responsible for Hurler syndrome in a large proportion of patients with the disease. This approach utilizes a base editing fusion protein that is RNA guided and that can be packaged into a single AAV vector for delivery to a wide range of tissue types. Depending on the exact regulatory elements and base editor domain used, it may also be possible to engineer a single vector that encodes for both the base editing fusion protein and a single guide RNA to target the diseased locus.

Example 7.1: Identifying RGN with Ideal PAM

The genetic disease MPS-1 is a lysosomal storage disease characterized at the molecular level by the accumulation of dermatan sulfate and heparan sulfate in lysosomes. This disease is generally an inherited genetic disorder caused by mutations in the IDUA gene (NCBI Reference sequence NG_008103.1), which encodes α-L-iduronidase. The disease is a result of a deficiency of α-L-iduronidase. The most common IDUA mutations found in studies of individuals of Northern European background are W402X and Q70X, each nonsense mutation resulting in premature termination of translation (Bunge et al. (1994), Hum. Mol. Genet, 3 (6): 861-866, herein incorporated by reference). Reversion of a single nucleotide would restore the wild-type coding sequence and result in protein expression controlled by the endogenous regulatory mechanisms of the genetic locus.

The W402X mutation of the human Idua gene accounts for a high proportion of MPS-1H cases. Base editors can target a narrow sequence window relative to the binding site of the protospacer component of the guide RNA and thus the presence of a PAM sequence a specific distance from the target locus is essential for the success of the strategy. Given the constraints that the target mutation must be on the exposed non-target strand (NTS) during the interaction of the base editing protein and that the footprint of the RGN domain will block access to the region near the PAM, an accessible locus is thought to be 10-30 bp from the PAM. To avoid editing and mutagenesis of other nearby adenosine bases in this window, different linkers are screened. The ideal window is 12-16 bp from the PAM.

A PAM sequence compatible with LPG10134, LPG10136, LPG10139 and LPG10145 is readily apparent at the genetic locus. These nucleases have a PAM sequence of 5'-nGG-3' (SEQ ID NO: 73), 5'-nnnnCC-3' (SEQ ID NO: 74), 5'-nnnnC-3' (SEQ ID NO: 76), and 5'-nnGG-3' (SEQ ID NO: 78) respectively, and are compact in size-potentially allowing delivery via a single AAV vector. This delivery approach bestows multiple advantages relative to others, such as access to a wide range of tissues (liver, muscle, CNS) and well-established safety profile and manufacturing techniques.

Cas9 from *S. pyogenes* (SpyCas9) requires a PAM sequence of NGG (SEQ ID NO: 331), which is present near the W402X locus, but the size of SpyCas9 prevents packaging into a single AAV vector, and thus forgoes the aforementioned advantages of this approach. While a dual delivery strategy may be employed (for example, Ryu et al. (2018), Nat. Biotechnol., 36 (6): 536-539, herein incorporated by reference), it would add significant manufacturing complexity and cost. Additionally, dual viral vector delivery significantly decreases the efficiency of gene correction, since a successful edit in a given cell requires infection with both vectors and assembly of the fusion protein in the cell.

A commonly used Cas9 ortholog from *S. aureus* (SauCas9) is considerably smaller in size relative to SpyCas9 but has a more complex PAM requirement-NGRRT (SEQ ID NO: 332). This sequence is not within a range expected to be useful for base editing of the causative locus.

Example 7.2: RGN Fusion Constructs and sgRNA Sequences

A DNA sequence encoding a fusion protein with the following domains is produced using standard molecular biology techniques: 1) an RGN domain with mutations that inactivate the DNA cleavage activity ("dead" or "nickase"); 2) an adenine deaminase useful for base editing. All constructs described in Table 7 comprise a fusion protein with the base editing active domain, in this example LPG50148 (SEQ ID NO: 333), operably fused to the N-terminal end of a dead RGN LPG10134, LPG10136, LPG10139, or LPG10145. Other adenine deaminases useful for base editing DNA may also be used (see for example International Publ. No. WO 2020/139873, U.S. Provisional Appl. Nos. 63/077,089 filed Sep. 11, 2020, 63/146,840 filed Feb. 8, 2021, and 63/164,273 filed Mar. 22, 2021, and International Appl. No. PCT/US2021/049853 filed Sep. 10, 2021, each of which is herein incorporated by reference in its entirety). It is known in the art that a fusion protein could also be made with the base-editing enzyme at the C-terminal end of the RGN. Additionally, the RGN and the base editor of the fusion protein are typically separated by a linker amino acid sequence. It is known in the art that lengths of standard linkers range from 15-30 amino acids.

TABLE 7

Constructs for RNA-targeted base editing

| SEQ ID NO. | Construct | RGN | Dead (D) or Nickase (N) | Base editor |
|---|---|---|---|---|
| 334 | SV40-LPG50148-Linker-d LPG10134 -Linker-Nuc | LPG10134 | D | ADAT |
| 335 | SV40-LPG50148-Linker-d LPG10145 -Linker-Nuc | LPG10145 | D | ADAT |
| 336 | SV40-LPG50148-Linker-d LPG10136 -Linker-Nuc | LPG10136 | D | ADAT |
| 337 | SV40-LPG50148-Linker-d LPG10139 -Linker-Nuc | LPG10139 | D | ADAT |

The accessible editing sites of an RGN are determined by the PAM sequence. When combining an RGN with a base editing domain, the target residue for editing must reside on the non-target strand (NTS), since the NTS is single stranded while the RGN is associated with the locus. Evaluating a number of nucleases and corresponding guide RNAs enables the selection of the most appropriate gene editing tool for this particular locus. Several potential PAM sequences that can be targeted by the constructs described above in the human Idua gene are in the proximity of the mutant nucleotide responsible for the W402x mutation. A sequence encoding a guide RNA transcript containing 1) a "spacer" that is complementary to the non-coding DNA strand at the disease locus; and 2) RNA sequence required for association of the guide RNA with the RGN is also produced. Such a sgRNA may be, for example, SEQ ID NOs: 338-341 for LPG10134, LPG10145, LPG10136, and LPG10139, respectively. These sgRNA molecules, and similar sgRNAs that may be devised by one of skill in the art, can be evaluated for their efficiency in directing the base editors above to the locus of interest.

Example 7.3: Assay for Activity in Cells from Hurler Disease Patients

To verify the genotype strategy and evaluate the constructs described above, fibroblasts from Hurler disease patients are used. A vector is designed containing appropriate promoters upstream of the fusion protein coding sequence and the sgRNA encoding sequence for expression of these in human cells, similar to those vectors described in Example 4. It is recognized that promoters and other DNA elements (for example enhancers, or terminators) which either are known for high levels of expression in human cells or may specifically express well in fibroblast cells may also be used. The vector is transfected into the fibroblasts using standard techniques, for example transfection similar to what is described in Example 4. Alternatively, electroporation may be used. The cells are cultured for 1-3 days. Genomic DNA (gDNA) is isolated using standard techniques. The editing efficiency is determined by performing a qPCR genotyping assay and/or next generation sequencing on the purified gDNA, as described further below.

Taqman™ qPCR analysis utilizes probes specific for the wild-type and mutant allele. These probes bear fluorophores which are resolved by their spectral excitation and/or emission properties using a qPCR instrument. A genotyping kit containing PCR primers and probes can be obtained commercially (i.e. Thermo Fisher Taqman™ SNP genotyping assayID C_27862753_10 for SNP ID rs121965019) or designed. An example of a designed primer and probe set is shown in Table 8.

TABLE 8

RT-PCR primers and probes

| Description | Sequence | SEQ ID NO. |
|---|---|---|
| Forward Amplification Primer | 5'-GACTCCTTCACCAAG-3' | 342 |
| Reverse Amplification Primer | 5'-GTAGATCAGCACCG-3' | 343 |
| Wild Type Probe | 5'-CTCTGGGCCGAAGT-3' | 344 |
| W402X Probe | 5'-CTCTAGGCCGAAGT-3' | 345 |

Following the editing experiment, the gDNA is subjected to qPCR analysis using standard methods and the primers and probes described above. Expected results are shown in Table 9. This in vitro system can be used to expediently evaluate constructs and choose one with high editing efficiency for further studies. The systems will be evaluated in comparison with cells with and without the W402X mutation, and preferably with some that are heterozygous for this mutation. The Ct values will be compared to either a reference gene or the total amplification of the locus using a dye such as Sybr green.

TABLE 9

Expected qPCR results

| Genotype | Transfected with base editor | Expected PCR result |
|---|---|---|
| Idua$^{WT/WT}$ | No | Homozygous WT |
| Idua$^{WT/W402X}$ | No | Heterozygous: 50% WT, 50% W402X |
| Idua$^{W402X/W402X}$ | No | Homozygous W402X |
| Idua$^{W402X/W402X}$ | Yes | Variable |

The tissues can also be analyzed by next generation sequencing. Primer binding sites such as the ones shown below (Table 10), or other suitable primer binding sites that can be identified by a person of skill in the art, can be used. Following PCR amplification, products containing Illumina Nextera XT overhang sequences undergo library preparation following the Illumina 16S Metagenomic Sequencing Library protocol. Deep sequencing is performed on an Illumina Mi-Seq platform. Typically, 200,000 of 250 bp paired-end reads (2×100,000 reads) are generated per amplicon. The reads are analyzed using CRISPResso (Pinello et al., 2016) to calculate the rates of editing. Output alignments are hand-curated to confirm insertion and deletion sites as well as identify microhomology sites at the recombination sites.

TABLE 10

NGS primer binding sites

| Direction | Sequence | SEQ ID NO. |
|---|---|---|
| Forward | 5'-ACTTCCTCCAGCC-3' | 346 |
| Reverse | 5'-GAACCCCGGCTTA-3' | 347 |

Western blotting of cell lysate of transfected cells and control cells using an anti-IDUA antibody is performed to verify expression of the full-length protein and an enzyme activity assay on the cell lysate using substrate 4-methylumbelliferyl α-L-iduronide verifies that the enzyme is catalytically active (Hopwood et al., Clin. Chim. Acta (1979), 92 (2): 257-265, incorporated by reference herein). These experiments are performed in comparison with the original Idua$^{W402X/W402X}$ cell line (without transfection), the Idua$^{W402X/W402X}$ cell line transfected with the base editing construct and a random guide sequence, and a cell line expressing wild-type IDUA.

Example 7.4: Disease Treatment Validation in a Murine Model

To verify the efficacy of this therapeutic approach, a mouse model with a nonsense mutation in the analogous amino acid is used. The mouse strain bears a W392X mutation in its Idua gene (Gene ID: 15932) which corresponds to the homologous mutation in Hurler syndrome patients (Bunge et al., (1994), Hum. Mol. Genet. 3 (6): 861-866, incorporated by reference herein). This locus comprises a distinct nucleotide sequence relative to that in humans, which lacks the PAM sequence necessary for correction with the base editors described in the previous examples, and thus necessitates design of a distinct fusion protein to perform the nucleotide correction. Amelioration of the disease in this animal can validate the therapeutic approach of correcting the mutation in tissues accessible by a gene delivery vector.

Mice homozygous for this mutation display a number of phenotypic characteristics similar to Hurler syndrome patients. A base editing-RGN fusion protein as described above (Table 7) along with an RNA guide sequence are incorporated into an expression vector that allows protein expression and RNA transcription in mice. A study design is shown below in Table 11. The study includes groups that are treated with a high dose of the expression vector comprising the base-editing fusion protein and RNA guide sequence, a low dose of same expression vector, control which is the model mouse treated with an expression vector that does not comprise the base editing fusion protein or the guide RNA, and a second control which is a wild type mouse treated with the same empty vector.

TABLE 11

Genome editing experiment in murine model

| Group | Mouse strain | N | Treatment |
|---|---|---|---|
| 1 | Idua-W392X | ≥5 | Low dose of vector |
| 2 | Idua-W392X | ≥5 | High dose of vector |
| 3 | Idua-W392X | ≥5 | Vehicle |
| 4 | 129/Sv (WT) | 5 | Vehicle |

Endpoints to evaluate include body weight, urine GAG excretion, serum IDUA enzymatic activity, IDUA activity in tissues of interest, tissue pathology, genotyping of tissues of interest to verify correction of the SNP, and behavioral and neurological evaluation. Since some endpoints are terminal, additional groups may be added for evaluation of, for example, tissue pathology and tissue IDUA activities before the end of the study. Additional examples of endpoints can be found in published papers establishing Hurler syndrome animal models (Shull et al. (1994), Proc. Natl. Acad. Sci. U.S.A., 91 (26): 12937-12941; Wang et al. (2010), Mol. Genet. Metab., 99 (1): 62-71; Hartung et al. (2004), Mol. Ther., 9 (6): 866-875; Liu et al. (2005), Mol. Ther., 11 (1): 35-47; Clarke et al. (1997), Hum. Mol. Genet. 6 (4): 503-511; all herein incorporated by reference).

One possible delivery vector utilizes the adeno associated virus (AAV). A vector is produced to include a base editor-dRGN fusion protein coding sequence (for example, Nuc-ADAT-Linker-dAPG19748-Linker-SV40, as described above) preceded by a CMV enhancer (SEQ ID NO: 328) and promoter (SEQ ID NO: 327), or other suitable enhancer and promoter combination), optionally a Kozak sequence, and operably fused at the 3' end to a terminator sequence and a poly-adenylation sequence such as the minimal sequence described in Levitt, N.; Briggs, D.; Gil, A.; Proudfoot, N. J. Definition of an Efficient Synthetic Poly (A) Site. Genes Dev. 1989, 3 (7), 1019-1025. The vector may further comprise an expression cassette encoding for a single guide RNA operably linked at its 5' end to a human U6 promoter (SEQ ID NO: 329) or another promoter suitable for production of small non-coding RNAs, and further comprising inverted terminal repeat (ITR) sequences necessary and well-known in the art for packaging into the AAV capsid. Production and viral packaging is performed by standard methods, such as those described in U.S. Pat. No. 9,587,250, herein incorporated by reference.

Other possible viral vectors include adenovirus and lentivirus vectors, which are commonly used and would contain similar elements, with different packaging capabilities and requirements. Non-viral delivery methods also be used, such as mRNA and sgRNA encapsulated by lipid nanoparticles (Cullis, P. R. and Allen, T. M. (2013), Adv. Drug Deliv. Rev. 65 (1): 36-48; Finn et al. (2018), Cell Rep. 22 (9): 2227-2235, both incorporated by reference) hydrodynamic injection of plasmid DNA (Suda T and Liu D,) 2007) Mol. Ther. 15 (12): 2063-2069, herein incorporated by reference), or ribonucleoprotein complexes of sgRNA and associated with gold nanoparticles (Lee, K.; Conboy, M.; Park, H. M.; Jiang, F.; Kim, H. J.; Dewitt, M. A.; Mackley, V. A.; Chang, K.; Rao, A.; Skinner, C.; et al. Nanoparticle Delivery of Cas9 Ribonucleoprotein and Donor DNA in Vivo Induces Homology-Directed DNA Repair. Nat. Biomed. Eng. 2017, 1 (11), 889-90).

Example 7.5: Disease Correction in a Murine Model with a Humanized Locus

To evaluate the efficacy of an identical base editor construct as would be used for human therapy, a mouse model in which the nucleotides near W392 are altered to match the sequence in humans around W402 is needed. This can be accomplished by a variety of techniques, including use of an RGN and an HDR template to cut and replace the locus in mouse embryos.

Due to the high degree of amino acid conservation, most nucleotides in the mouse locus can be altered to those of the human sequence with silent mutations as shown in Table 12. The only base changes resulting in altered coding sequence in the resulting engineered mouse genome occur after the introduced stop codon.

TABLE 12

Nucleotide mutations to generate a humanized mouse locus

| Feature | Human (W402X) Nucleotide (SEQ ID NO: 548) | Human (W402X) Encoded AA | Mouse (W392X) Nucleotide (SEQ ID NO: 549) | Mouse (W392X) Encoded AA | Humanized Mouse Nucleotide (SEQ ID NO: 550) | Humanized Mouse Encoded AA |
|---|---|---|---|---|---|---|
| Protospacer | G | E | A | G | G | G |
| | G | E | G | E | G | E |
| | A | | A | | A | |
| | G | | A | | G | |
| | C | Q | C | Q | C | Q |
| | A | | A | | A | |
| | G | | A | | G | |
| | C | L | C | L | C | L |
| | T | | T | | T | |
| | C | | C | | C | |
| | T | STOP | T | STOP | T | STOP |
| | A | | A | | A | |
| | G | | G | | G | |
| | G | A | G | A | G | A |
| | C | | C | | C | |
| | C | | A | | C | |
| | G | E | G | E | G | E |
| | A | | A | | A | |
| | A | | G | | A | |
| | G | V | G | V | G | V |
| | T | | T | | T | |
| | G | | C | | G | |
| | T | S | T | S | T | S |
| | C | | C | | C | |
| | G | | A | | G | |
| PAM, non-critical | C | Q | A | K | C | Q |
| | A | | A | | A | |
| | G | | G | | G | |
| | G | A | G | A | G | A |
| PAM, critical | C | | C | | C | |
| | C | | T | | C | |

Upon engineering of this mouse strain, similar experiments will be performed as described in Example 7.4.

Example 8: Targeting Mutations Responsible for Friedreich's Ataxia

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from *S. pyogenes* (SpCas9), are too large to be packaged into adeno-associated viral (AAV) vectors, especially when considering the length of the SpCas9 gene and the guide RNA in addition to other genetic elements required for functional expression cassettes. This makes a viable approach using SpCas9 unlikely.

Compact RNA guided nucleases of the invention, for example LPG10134, LPG10145, LPG10136, and LPG10139, are uniquely well suited for the excision of the FRDA instability region. LPG10134, LPG10145, LPG10136, and LPG10139 have a PAM requirement that is in the vicinity of the FRDA instability region. Additionally, LPG10134, LPG10145, LPG10136, or LPG10139 can be packaged into an AAV vector along with a guide RNA.

Table 13 shows the location of genomic target sequences suitable for targeting LPG10134, LPG10145, LPG10136, or LPG10139 to the 5' and 3' flanks of the FRDA instability region. Once at the locus, the RGN would excise the FA instability region. Excision of the region can be verified with Illumina sequencing of the locus.

TABLE 13

Genomic target sequences for RGN systems

| RGN | Location relative to FRDA instability region | Genome target sequence (SEQ ID NO.) |
| --- | --- | --- |
| LPG10134 | 5' | 348 |
| LPG10134 | 5' | 349 |
| LPG10134 | 3' | 350 |
| LPG10134 | 3' | 351 |
| LPG10145 | 5' | 352 |
| LPG10145 | 5' | 353 |
| LPG10145 | 3' | 354 |
| LPG10145 | 3' | 355 |
| LPG10136 | 5' | 356 |
| LPG10136 | 5' | 357 |
| LPG10136 | 3' | 358 |
| LPG10136 | 3' | 359 |
| LPG10139 | 5' | 360 |
| LPG10139 | 5' | 361 |
| LPG10139 | 3' | 362 |
| LPG10139 | 3' | 363 |

Example 9: Targeting Mutations Responsible for Sickle Cell Diseases

Targeting sequences within the BCL11A enhancer region (SEQ ID NO: 364) may provide a mechanism for increasing fetal hemoglobulin (HbF) to either cure or alleviate the symptoms of sickle cell diseases. For example, genome wide association studies have identified a set of genetic variations at BCL11A that are associated with increased HbF levels. These variations are a collection of SNPs found in non-coding regions of BCL11A that function as a stage-specific, lineage-restricted enhancer region. Further investigation revealed that this BCL11A enhancer is required in erythroid cells for BCL11A expression (Bauer et al, (2013) Science 343:253-257, incorporated by reference herein). The enhancer region was found within intron 2 of the BCL11A gene, and three areas of DNaseI hypersensitivity (often indicative of a chromatin state that is associated with regulatory potential) in intron 2 were identified. These three areas were identified as "+62", "+58" and "+55" in accordance with the distance in kilobases from the transcription start site of BCL11A. These enhancer regions are roughly 350 (+55); 550 (+58); and 350 (+62) nucleotides in length (Bauer et al., 2013).

Example 9.1: Identifying Preferred RGN Systems

Here we describe a potential treatment for beta-hemoglobinopathies using an RGN system that disrupts BCL11A binding to its binding site within the HBB locus, which is the gene responsible for making beta-globin in adult hemoglobin. This approach uses NHEJ which is more efficient in mammalian cells. In addition, this approach uses a nuclease of sufficiently small size that can be packaged into a single AAV vector for in vivo delivery.

The GATA1 enhancer motif in the human BCL11A enhancer region (SEQ ID NO: 364) is an ideal target for disruption using RNA guided nucleases (RGNs) to reduce BCL11A expression with concurrent re-expression of HbF in adult human erythrocytes (Wu et al. (2019) Nat Med 387:2554). Several PAM sequences compatible with LPG10134, LPG10145, LPG10136, and LPG10139 are readily apparent at the genetic locus surrounding this GATA1 site. These nucleases have a PAM sequence of 5'-nGG-3' (SEQ ID NO:73), 5'-nnGG-3 (SEQ ID NO: 78)', 5'-nnnnCC-3' (SEQ ID NO: 74), and 5'-nnnnC-3' (SEQ ID NO: 76), respectively, and are compact in size, potentially allowing their delivery along with an appropriate guide RNA in a single AAV or adenoviral vector. This delivery approach bestows multiple advantages relative to others, such as access to hematopoietic stem cells and a well-established safety profile and manufacturing techniques.

The commonly used Cas9 nuclease from *S. pyogenes* (SpyCas9) requires a PAM sequence of 5'-NGG-3', (SEQ ID NO: 331) several of which are present near the GATA1 motif. However, the size of SpyCas9 prevents packaging into a single AAV or adenoviral vector and thus forgoes the aforementioned advantages of this approach. While a dual delivery strategy may be employed, it would add significant manufacturing complexity and cost. Additionally, dual viral vector delivery significantly decreases the efficiency of gene correction, since a successful edit in a given cell requires infection with both vectors.

An expression cassette encoding a human codon optimized LPG10134, LPG10145, LPG10136, or LPG10139 is produced, similar to those described in Example 4. Expression cassettes which express guide RNAs for RGNs LPG10134, LPG10145, LPG10136, and LPG10139 are also produced. These guide RNAs comprise: 1) a protospacer sequence that is complementary to either the non-coding or coding DNA strand within the BCL11A enhancer locus (the target sequence) and 2) an RNA sequence required for association of the guide RNA with the RGN. Because several potential PAM sequences for targeting by LPG10134, LPG10145, LPG10136, and LPG10139 surround the BCL11A GATA1 enhancer motif, several potential guide RNA constructs are produced to determine the best protospacer sequence that produces robust cleavage and NHEJ mediated disruption of the BCL11A GATA1 enhancer sequence. The target genomic sequences in Table 14 are evaluated to direct the RGN to this locus.

TABLE 14

Target Sequences for BCL11A GATA1 enhancer locus using LPG10134, LPG10145, LPG10136 or LPG10139

| Guide | RGN | Target genomic sequence (SEQ ID NO.) |
| --- | --- | --- |
| 1 | LPG10134 | 365 |
| 2 | LPG10134 | 366 |
| 3 | LPG10134 | 367 |
| 4 | LPG10145 | 368 |
| 5 | LPG10145 | 369 |
| 6 | LPG10145 | 370 |
| 7 | LPG10136 | 371 |
| 8 | LPG10136 | 372 |
| 9 | LPG10136 | 373 |
| 10 | LPG10139 | 374 |
| 11 | LPG10139 | 375 |
| 12 | LPG10139 | 376 |

To evaluate the efficiency with which LPG10134, LPG10145, LPG10136, or LPG10139 generates insertions or deletions that disrupt the BCL11A enhancer region, human cell lines such as human embryonic kidney cells (HEK cells) are used. A DNA vector comprising an RGN expression cassette (for example, as described in Example 4) is produced. A separate vector comprising an expression cassette comprising a coding sequence for a guide RNA sequence is also produced. Such an expression cassette may further comprise a human RNA polymerase III U6 promoter (SEQ ID NO: 329), as described in Example 4. Alternatively, a single vector comprising expression cassettes of both the RGN and guide RNA may be used. The vector is introduced into HEK cells using standard techniques such as those described in Example 4, and the cells are cultured for 1-3 days. Following this culture period, genomic DNA is isolated and the frequency of insertions or deletions is determined by using T7 Endonuclease I digestion and/or direct DNA sequencing, as described in Example 4.

A region of DNA encompassing the target BCL11A region is amplified by PCR with primers containing Illumina Nextera XT overhang sequences. These PCR amplicons are either examined for NHEJ formation using T7 Endonuclease I digestion, or undergo library preparation following the Illumina 16S Metagenomic Sequencing Library protocol or a similar Next Generation Sequencing (NGS) library preparation. Following deep sequencing, the reads generated are analyzed by CRISPResso to calculate rates of editing. Output alignments are hand-curated to confirm insertion and deletion sites. This analysis identifies the preferred RGN and the corresponding preferred guide RNA (sgRNA). The analysis may result in any of LPG10134, LPG10145, LPG10136, and LPG10139 being equally preferred. Additionally, the analysis may determine there is more than one preferred guide RNA, or that all target genomic sequences in Table 14 are equally preferred.

Example 9.2: Assay for Expression of Fetal Hemoglobin

In this example, LPG10134, LPG10145, LPG10136, or LPG10139 generated insertions or deletions disrupting the BCL11A enhancer region are assayed for expression of fetal hemoglobin. Healthy human donor CD34$^+$ hematopoietic stem cells (HSCs) are used. These HSCs are cultured and vector(s) comprising expression cassettes comprising the coding regions of the preferred RGN and the preferred sgRNA are introduced using methods similar to those described in Example 8.1. Following electroporation, these cells are differentiated in vitro into erythrocytes using established protocols (for example, Giarratana et al. (2004) Nat Biotechnology 23:69-74, herein incorporated by reference). The expression of HbF is then measured using western blotting with an anti-human HbF antibody, or quantified via High Performance Liquid Chromatography (HPLC). It is expected that successful disruption of the BCL11A enhancer locus will lead to an increase in HbF production when compared to HSCs electroporated with only the RGN but no guide.

Example 9.3: Assay for Decreased Sickle Cell Formation

In this example, LPG10134, LPG10145, LPG10136, or LPG10139-generated insertions or deletions disrupting the BCL11A enhancer region are assayed for decreased sickle-cell formation. Donor CD34$^+$ hematopoietic stem cells (HSCs) from patients afflicted with sickle cell disease are used. These HSCs are cultured and vector(s) comprising expression cassettes comprising the coding regions of preferred RGN and the preferred sgRNA are introduced using methods similar to those described in Example 8.1. Following electroporation, these cells are differentiated in vitro into erythrocytes using established protocols (Giarratana et al. (2004) Nat Biotechnology 23:69-74). The expression of HbF is then measured using western blotting with an anti-human HbF antibody, or quantified via High Performance Liquid Chromatography (HPLC). It is expected that successful disruption of the BCL11A enhancer locus will lead to an increase in HbF production when compared to HSCs electroporated with only the RGN but no guide.

Sickle cell formation is induced in these differentiated erythrocytes by the addition of metabisulfite. The numbers of sickled vs normal erythrocytes are counted using a microscope. It is expected that the numbers of sickled cells are less in cells treated with LPG10134, LPG10145, LPG10136, or LPG10139 plus sgRNAs than with cells untreated, or treated with RGNs alone.

Example 9.4: Disease Treatment Validation in a Murine Model

To evaluate the efficacy of using LPG10134, LPG10145, LPG10136, or LPG10139 for disruption of the BCL11A locus, suitable humanized mouse models of sickle cell anemia are used. Expression cassettes encoding for the preferred RGN and for the preferred sgRNA are packaged into AAV vectors or adenovirus vectors. In particular, adenovirus type Ad5/35 is effective at targeting HSCs. A suitable mouse model containing a humanized HBB locus with sickle cell alleles is chosen, such as B6; FVB-Tg (LCR-HBA2, LCR-HBB*E26K) 53Hhb/J or B6.Cg-Hbatm1Paz Hbbtm1Tow Tg (HBA-HBBs) 41Paz/HhbJ. These mice are treated with granulocyte colony-stimulating factor alone or in combination with plerixafor to mobilize HSCs into circulation. AAVs or adenoviruses carrying the RGN and guide plasmid are then injected intravenously, and the mice are allowed to recover for a week. Blood obtained from these mice is tested in an in vitro sickling assay using metabisulfite, and the mice are followed longitudinally to monitor mortality rates and hematopoietic function. It is expected that treatment with AAVs or adenoviruses carrying an RGN and guide RNA will reduce sickling, mortality, and improve hematopoietic function when compared to mice treated with viruses lacking both expression cassettes, or with viruses carrying the RGN expression cassette alone.

Example 10: Protein Purification and Biochemical Testing

The presently disclosed RGNs were expressed, purified, and tested for in vitro cleavage of a target sequence. The cut site was subsequently determined using an in vitro cleavage assay for LPG10145.

Example 10.1: Recombinant Expression and Purification of RNA-Guided Nucleases and Biochemical Cleavage Assay Plasmids containing the bacterial codon-optimized, HIS-tagged RGN coding sequences were synthesized and cloned into a pET-29b(+) vector backbone. Transformation of the RGN bacterial expression plasmid was carried out with One Shot™ BL21 Star™ (DE3) Chemically Competent *E. coli* cells using heat shock. RGNs were expressed at a 0.5 L scale using MagicMedia™ *E. coli* Expression Medium (Invitrogen) supplemented with 50 μg/mL Kanamycin. After seeding with a starter culture, expression cultures were incubated for 5 hours at 30° C. shaking at 300 rpm, then dropped to 18° C. for an additional 24 hours. The cells were then harvested by centrifugation and frozen at −80° C. Cell pellets from expression cultures were thawed at room temperature, resuspended in lysis buffer, homogenized, then lysed with an EmulsiFlex-C3 cell disruptor (Avestin). The crude lysate solution was then clarified using high speed centrifugation. Clarified lysates were then purified using immobilized metal affinity chromatography (IMAC) using an ÄKTA Pure25 Fast Protein Liquid Chromatography system (Cytiva). LPG10136, LPG10138, and LPG10139 were further purified using cation exchange chromatography. Purified RGN proteins were then concentrated and exchanged into a formulation buffer containing 20 mM sodium phosphate, 300 mM sodium chloride, 1 mM DTT, pH 7.4, and 20% glycerol then flash frozen using liquid nitrogen. Purity of purified RGNs was determined using sodium dodecyl sulfate-polyacrylamide gel electrophoresis (SDS-PAGE).

Ribonucleoprotein complexes (comprising nuclease and an sgRNA) were formed by incubation of nuclease and the RNA in a buffered solution for 20 min at room temperature. The complex was transferred to a tube containing digestion buffer and a PCR amplified target, directly linked at its 3' end to the corresponding PAM sequence for each RGN. Each RGN as a ribonucleoprotein complex was incubated with its respective target (library 1 or library 2; SEQ ID NOs: 459 and 460, respectively) polynucleotide at 37° C. for 120 mins. The digestion reaction was quenched using ethylenediaminetetraacetic acid (EDTA) and analyzed using fragment analysis to quantify cleavage products.

Ten of the twelve presently disclosed RGNs were solubly expressed and isolated from *E. coli*. The yield from recombinant expression and subsequent purification varied greatly depending on the identity of the RGN, ranging from several milligrams to greater than one-hundred milligrams. Of the ten RGN proteins that were successfully expressed and purified, eight were active in a biochemical DNA cleavage assay when tested against two different target sequences and several compatible PAM contexts. Inactivity in these in vitro assays with purified protein could be due to several factors specific to these particular expression, purification, and/or cleavage conditions and may not necessarily reflect the activity of the RGNs under other conditions or within in vivo settings.

TABLE 15

Purification purity and in vitro cleavage of dsDNA

| RGN | Isolated Yield mg/L culture | Purity (%) | Max Target Strand Cleavage Observed (%) |
|---|---|---|---|
| LPG10134 | 15 | 78 | 0 |
| LPG10136 | 34 (14) | 66 | 31 |
| LPG10138 | 67 (6) | 75 | 18 |
| LPG10139 | 79 (36) | 75 | 7 |
| LPG10141 | 0 | n/a | n/a |
| LPG10145 | 148 | 90 | 100 |
| LPG10146 | 127 | 87 | 58 |
| LPG10147 | 0 | n/a | n/a |
| LPG10150 | 148 | 70 | 32 |
| LPG10155 | 15 | 77 | 33 |
| LPG10159 | 62 | 83 | 2.6 |
| LPG10160 | 3 | 35 | 0 |

Isolated yield from IMAC purification
(isolated yield from CEX)

TABLE 16

Sequences for in vitro cleavage and perfect target cleavage

| RGN ID | Target Sequence | PAM Context | PAM SEQ ID NO | Cleavage of Target Strand (%) | Cleavage of Non-target Strand (%) |
|---|---|---|---|---|---|
| LPG10134 | Library 1 | AGGACCTC | 461 | 0 | 0 |
| LPG10134 | Library 1 | AGGAATTC | 462 | 0 | 0 |
| LPG10134 | Library 1 | AGGAAAGC | 463 | 0 | 0 |
| LPG10134 | Library 2 | AGGACCTC | 461 | 0 | 0 |
| LPG10134 | Library 2 | AGGAATTC | 462 | 0 | 0 |
| LPG10134 | Library 2 | AGGAAAGC | 463 | 0 | 0 |
| LPG10136 | Library 1 | AGGACCTC | 461 | 5.0 | 3.3 |
| LPG10136 | Library 1 | AGGACTTC | 464 | 0 | 0 |
| LPG10136 | Library 2 | AGGACCTC | 461 | 30.9 | 19.7 |
| LPG10136 | Library 2 | AGGACTTC | 464 | 11.3 | 7.5 |
| LPG10138 | Library 1 | AGGACCTC | 461 | 1.4 | 0.5 |
| LPG10138 | Library 1 | AGGAATTC | 462 | 0 | 0 |
| LPG10138 | Library 1 | AGGACTTC | 464 | 5.5 | 3.7 |
| LPG10138 | Library 2 | AGGACCTC | 461 | 4.7 | 1.5 |
| LPG10138 | Library 2 | AGGAATTC | 462 | 0 | 0 |
| LPG10138 | Library 2 | AGGACTTC | 464 | 18.0 | 9.4 |

TABLE 16-continued

Sequences for in vitro cleavage and perfect target cleavage

| RGN ID | Target Sequence | PAM Context | PAM SEQ ID NO | Cleavage of Target Strand (%) | Cleavage of Non-target Strand (%) |
|---|---|---|---|---|---|
| LPG10139 | Library 1 | AGGACCTC | 461 | 4.4 | 2.4 |
| LPG10139 | Library 2 | AGGACCTC | 461 | 7.3 | 4.5 |
| LPG10145 | Library 1 | ACGGATTC | 465 | 92.9 | 95.3 |
| LPG10145 | Library 2 | ACGGATTC | 465 | 100 | 100 |
| LPG10146 | Library 1 | AGGAAACC | 466 | 3.9 | 2.8 |
| LPG10146 | Library 1 | GGATAACC | 467 | 0 | 0 |
| LPG10146 | Library 1 | GAGTAACC | 468 | 1.5 | 1.0 |
| LPG10146 | Library 1 | CAATAACC | 469 | 0 | 0 |
| LPG10146 | Library 2 | AGGAAACC | 466 | 48.9 | 48.6 |
| LPG10146 | Library 2 | GGATAACC | 467 | 39.7 | 27.2 |
| LPG10146 | Library 2 | GAGTAACC | 468 | 57.7 | 48.2 |
| LPG10146 | Library 2 | CAATAACC | 469 | 32.7 | 25.9 |
| LPG10150 | Library 1 | AGGACCTC | 461 | 1.4 | 0.9 |
| LPG10150 | Library 1 | AGGACTTC | 464 | 2.3 | 1.7 |
| LPG10150 | Library 2 | AGGACCTC | 461 | 25.1 | 16.5 |
| LPG10150 | Library 2 | AGGACTTC | 464 | 31.8 | 26.1 |
| LPG10155 | Library 1 | AGAAATTC | 470 | 32.7 | 20.1 |
| LPG10155 | Library 2 | AGAAATTC | 470 | 7.6 | 3.5 |
| LPG10159 | Library 2 | AGAAATTC | 470 | 2.5 | 1.2 |
| LPG10160 | Library 1 | AAATATTC | 471 | 0 | 0 |
| LPG10160 | Library 2 | AAATATTC | 471 | 0 | 0 |

Example 10.2 In Vitro Cleavage Site Determination

Cleavage sites were determined using RNP (ribonucleoprotein) and an appropriate plasmid substrate. E. coli expression plasmids coding for an RGN fused to a His 10 N-terminal tag were constructed and transformed into BL21 (DE3) Star E. coli (Invitrogen) for protein expression. RGN expression was performed using autoinduction MagicMedia (Thermo). After lysis and clarification, proteins were purified with a 3-step purification method which included immobilized metal affinity chromatography, cation exchange chromatography, and anion exchange chromatography. RNP complexes were formed by incubation of the RGN with its RNA guide (SEQ ID NO: 473 for Library 1 and SEQ ID NO: 474 for Library 2) in a buffered solution for 15 min at room temperature.

The cleavage reaction was comprised of the RNP, digestion buffer and the plasmid target. The plasmid target (SEQ ID NO: 472) sequence contained two target nucleotide sequences, described as Library 1 and Library 2, (SEQ ID NO: 459 and SEQ ID NO: 460, respectively), −5' to the RGN PAM sequence. Incubation of the cleavage reaction at 37° C. for 90 min resulted in cleaved products. Cleaved products were visualized via agarose gel electrophoresis. The total cleavage reaction was cleaned up using a magnetic-bead DNA purification method with no size selection, and this clean-up was repeated after each enzymatic reaction. The cleaned DNA was end-repaired with T4 DNA polymerase (NEB) and A-tailed using the Klenow Fragment (3'-5' exo-) (NEB). Adapter oligos (SEQ ID NOs: 475 and 476) were annealed by mixing in equimolar amounts, heating to 95° C. and cooling slowly to room temperature. Adapters were annealed to A-tailed cleavage products using T4 DNA ligase in combination with T4 polynucleotide kinase. The final cleaned ligation products served as PCR templates.

PCRs to amplify the adapter-ligated cleavage products were performed using the appropriate primer pairs complementary to the adapter sequence and the plasmid backbone upstream and downstream of the anticipated cleavage site. Specifically, the PCR reactions included 2× Ultra II Q5 Master Mix (NEB) with 50-100 ng of template DNA and 0.5 µM of each primer. The PCR cycling conditions were as follows: 98° C. for 1 min, followed by 30 cycles of 98° C. for 10 sec, 62° C. for 10 sec, 72° C. for 10 sec, followed by a final step at 72° C. for 1 min, holding at 10° C. forever. PCR products were visualized by agarose gel electrophoresis and sequence verified by Sanger sequencing.

The cleavage site was determined to be blunt if there was no sequence absent or repeated in the Sanger sequence. If the cut site had a 5'-overhang, the overhang sequence would be present in both sequenced PCR products. A 3'-overhang would yield a sequence missing in both PCR products relative to the uncut plasmid substrate.

It was determined that LPG10145 has a cleavage site at the +3 position relative to the PAM, i.e., a blunt cleavage is introduced between the third and fourth nucleotides upstream (5') of the PAM sequence.

Example 11: Delivery of RNPs and mRNA to PBMCs

To determine if the RGNs are capable of delivery in different formats, RNP nucleofection delivery was tested with peripheral blood mononuclear cells (PBMCs). PBMCs were thawed, activated using CD3/CD28 beads (ThermoFisher) for 3 days, then nucleofected using the Lonza 4D-Nucleofector X unit and Nucleocuvette strips. The P3 Primary Cell kit was used for both mRNA and RNP delivery. Cells were transfected using the EO-115 and EH-115 programs for mRNA and RNP delivery, respectively. Cells were cultured in CTS OpTimizer T cell expansion medium (ThermoFisher) containing IL-2, IL-7, and IL-15 (Miltenyi Biotec) for 4 days post nucleofection before being harvested using a Nucleospin Tissue genomic DNA isolation kit (Machery Nagel).

To determine the editing efficiency, the nucleofected PBMCs were incubated with an appropriate fluorophore-conjugated antibody followed by flow cytometry or NGS. Editing efficiency by flow cytometry is reported as percent knockout of the gene of interest. An unedited control was included to ensure staining efficiency was complete. Amplicons surrounding the editing sites were generated by PCR and subjected to NGS sequencing using the Illumina Nextera platform using 2×250 bp paired end sequencing following the method in Example 4.

Figure 2:
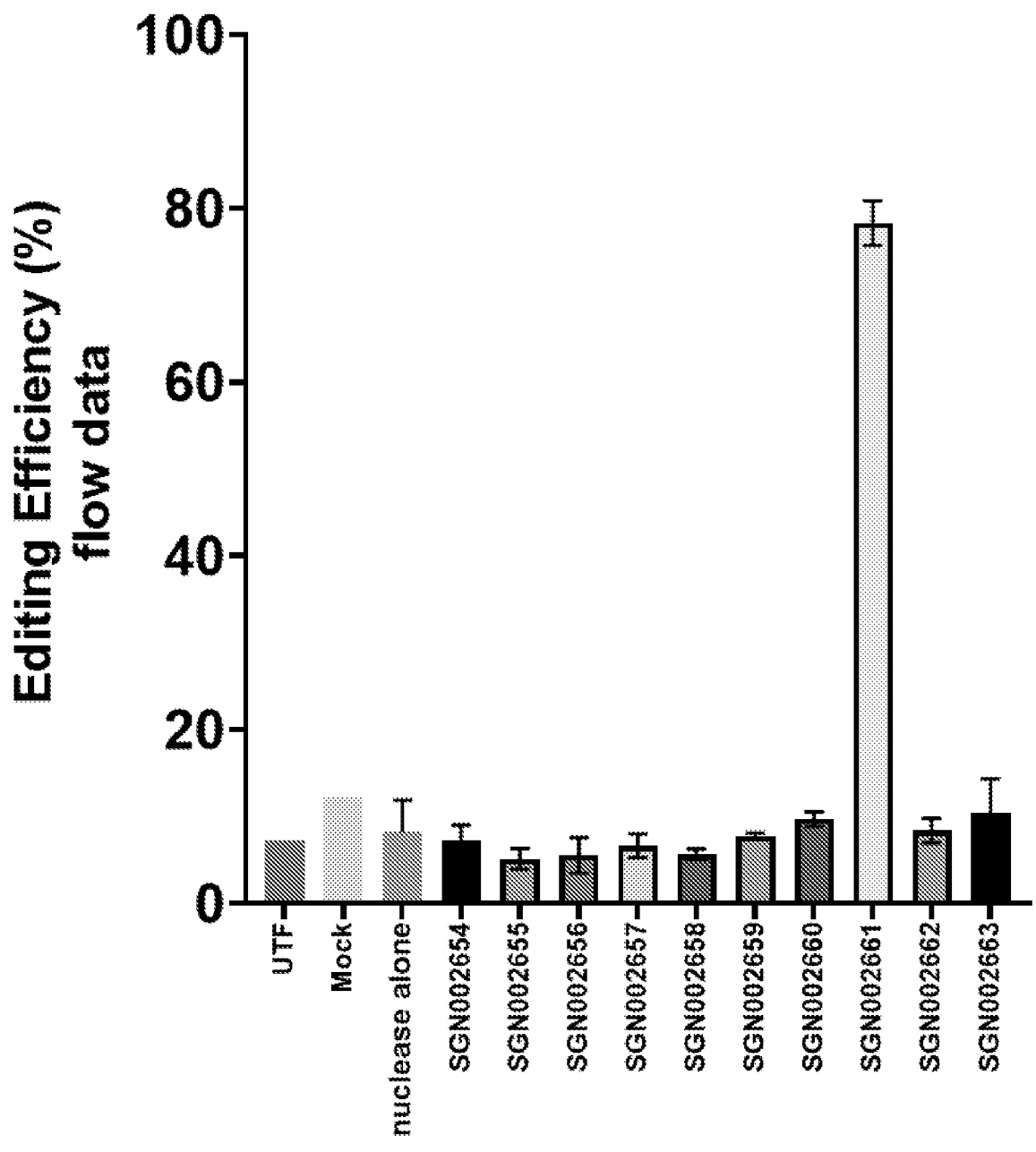
FIG. 2 shows that the single-guide RNA (sgRNA) SGN002661, along with the LPG10136 RNA-guided nuclease (RGN), provides for over 75% of editing of the T cell receptor alpha (TRAC) gene as measured by flow cytometry when the RGN and sgRNA are delivered as a ribonucleoprotein (RNP) complex in activated human peripheral blood mononuclear cells (PBMCs). B2M: beta-2-microglobulin.

Using RNP delivery of LPG10136, RNPs were formed to test 10 different guides (see FIG. 2 and Table 17). Of the 9 guides tested, only one guide, SGN002661, showed high levels of editing as measured by protein knockout via flow cytometry. SGN002661 showed over 75% protein knockout as measured by flow cytometry.

TABLE 17

| sgRNAs used for RNP delivery of LPG10136 | |
| --- | --- |
| sgRNA name | sgRNA target sequence SEQ ID NO |
| SGN002654 | 505 |
| SGN002655 | 506 |
| SGN002656 | 507 |
| SGN002657 | 508 |
| SGN002658 | 509 |

TABLE 17-continued

| sgRNAs used for RNP delivery of LPG10136 | |
| --- | --- |
| sgRNA name | sgRNA target sequence SEQ ID NO |
| SGN002659 | 510 |
| SGN002660 | 511 |
| SGN002661 | 512 |
| SGN002662 | 513 |
| SGN002663 | 514 |

Example 11.1 Optimization of Target Length

For delivery of LPG10145 as ribonucleoproteins (RNP: RNA-guided nuclease complexed with single guide RNAs) in PBMCs, nucleofection was utilized, which is an electroporation-based method that allows for the transfer of DNA, RNA, and/or protein into the cell nucleus. The TRAC and B2M genes were targeted due to their clinical relevance and because these genes control cell surface proteins, which provided the convenience of utilizing high throughput flow cytometry-based analysis. For this experiment, the length of the spacer sequence was shortened from 25 to 20 nucleotides to determine the effects of spacer length on editing efficiency for two targets of interest. Isolated peripheral blood mononuclear cells (PBMC) were thawed, activated with CD3/CD28 beads, and incubated at 37° C. with 5% $CO_2$. After 3 days, the beads were removed from the cells. The cells were then concentrated via centrifugation and resuspended in nucleofection buffer (P3 Solution Lonza) so that 1×10^6 cells could be used for each reaction. The RNP (60 pmol RGN and 120 pmol guide) incubated at room temperature for at least 10 minutes prior to addition of the PBMC. The cells+LPG10145+sgRNA reactions were nucleofected according to the manufacturer's instructions using Program EH-115 (Lonza). After nucleofection, the cells rested for 10 minutes, followed by incubation in media for 1-4 days. To determine the editing efficiency, the nucleofected cells were incubated with an appropriate fluorophore-conjugated antibody followed by flow cytometry. Editing efficiency is reported as percent knockout of the gene of interest. An unedited control was included to ensure staining efficiency was complete.

In addition, spacer length optimization was confirmed by mRNA delivery of LPG10145 while expanding the length of the spacers from 27 to 17 nucleotides using the same guides that targeted TRAC and B2M. For delivery of LPG10145 as mRNA, 2 µg of LPG10145 mRNA and 4 µg of sgRNA was resuspended in nucleofection buffer (P3 solution) along with 3.0×10^4 cells per reaction. The cells were added to the reaction, and nucleofected according to the manufacturer's instructions using program EO-115 (Lonza). After nucleofection, cells were transferred to culture vessel and incubated in media for 4 days. Evaluation of editing efficiency by flow cytometry was conducted as described above.

TABLE 18

| RNP delivery of LPG10145 to cells testing effects of target length on editing | | | | | | |
| --- | --- | --- | --- | --- | --- | --- |
| Nuclease | SGN | Spacer length | Target SEQ ID NO | Editing Rate by flow cytometry (Replicate #1) | Editing Rate by flow cytometry (Replicate #2) | Editing Rate by flow cytometry (Replicate #3) |
| None | Unedited Control | | | 10.3 | 18.1 | |
| LPG10145 | SGN002702 | 25 | 516 | 77.1 | 68.8 | 80.7 |
| | SGN005121 | 24 | 491 | 90.01 | 89.3 | 76.2 |

TABLE 18-continued

RNP delivery of LPG10145 to cells testing effects of target length on editing

| Nuclease | SGN | Spacer length | Target SEQ ID NO | Editing Rate by flow cytometry (Replicate #1) | Editing Rate by flow cytometry (Replicate #2) | Editing Rate by flow cytometry (Replicate #3) |
|---|---|---|---|---|---|---|
| | SGN005122 | 23 | 492 | 88.9 | 90 | 87.4 |
| | SGN005123 | 22 | 493 | 90.1 | 91.38 | 85.2 |
| | SGN005124 | 21 | 494 | 92.61 | 91.26 | 85.5 |
| | SGN003018 | 20 | 481 | 83.2 | 83.6 | 55.2 |
| LPG10145 | SGN002707 | 25 | 517 | 50.4 | 53 | 20.6 |
| | SGN005117 | 24 | 487 | 50.1 | 52.5 | 19.9 |
| | SGN005118 | 23 | 488 | 50.5 | 58 | 22.8 |
| | SGN005119 | 22 | 489 | NT | NT | 21.7 |
| | SGN005120 | 21 | 490 | NT | NT | 19.2 |
| | SGN003023 | 20 | 486 | 57.3 | 51.5 | 15.7 |

NT: not tested

TABLE 19 mRNA delivery of LPG10145 to cells testing effects of target length on editing

| Nuclease | SGN | Spacer Length | Target SEQ ID NO | Editing Rate by FLOW Cytometry (Replicate 1) | Editing Rate by FLOW Cytometry (Replicate 2) |
|---|---|---|---|---|---|
| None | Unedited | | | 1.1 | .8 |
| LPG10145 | SGN007076 | 17 | 495 | 1.1 | 1.3 |
| | SGN007077 | 18 | 496 | 1.1 | 1.3 |
| | SGN007078 | 19 | 497 | 18.1 | 22.8 |
| | SGN003018 | 20 | 481 | 84.8 | 91.0 |
| | SGN005124 | 21 | 494 | 94.1 | 89.5 |
| | SGN005123 | 22 | 493 | 93.58 | 94.72 |
| | SGN005122 | 23 | 492 | 93.61 | 92.61 |
| | SGN005121 | 24 | 491 | 91.85 | 95.83 |
| | SGN002702 | 25 | 557 | 93.40 | 94.81 |
| | SGN007079 | 26 | 498 | 86.8 | 89.7 |
| | SGN007080 | 27 | 499 | 82.3 | 87.2 |
| None | Unedited | | | 1.4 | .8 |
| LPG10145 | SGN007081 | 17 | 500 | 1.3 | 1.6 |
| | SGN007082 | 18 | 501 | 1.3 | 1.9 |
| | SGN007083 | 19 | 502 | 23.7 | 27.7 |
| | SGN003023 | 20 | 486 | 51.4 | 56.8 |
| | SGN005120 | 21 | 490 | 55.0 | 58.4 |
| | SGN005119 | 22 | 489 | 56.7 | 61.6 |
| | SGN005118 | 23 | 488 | 69.8 | 73.7 |
| | SGN005117 | 24 | 487 | 69.7 | 58.9 |
| | SGN002707 | 25 | 558 | 55.1 | 56.9 |
| | SGN007084 | 26 | 503 | 56.1 | 63.8 |
| | SGN007085 | 27 | 504 | 49.1 | 57.7 |

Analysis

Using RNP delivery and testing the spacer lengths from 20 to 25 nucleotides, all spacer lengths demonstrated similar levels of editing for each target. The best editing, although slight, was seen with spacer lengths of 21-24 nucleotides. Because there were small differences in editing between 20-25 nucleotides, the spacer lengths tested for each target were expanded and tested with mRNA. These data corroborated the RNP data and helped to define that the highest editing was when using spacer lengths between 21-24 nucleotides.

Example 11.2 RNP Dose Dependence

Figure 3A:
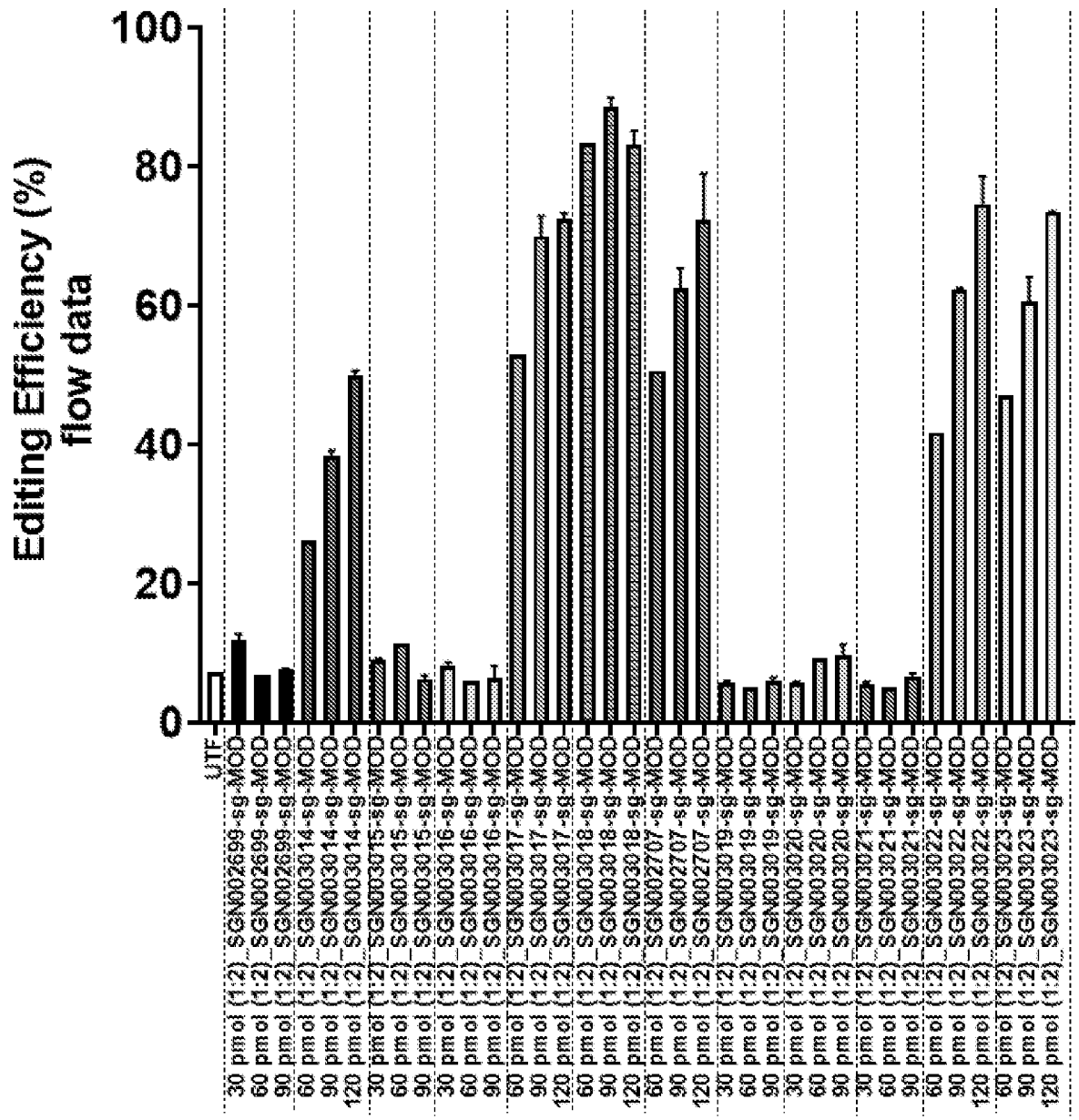
FIGS. 3A and 3B demonstrate that increasing concentrations of RNPs improve editing. The figures show the editing efficiency of increasing concentrations of RNPs comprised of LPG10145 and various sgRNAs at a protein: RNA ratio of 1:2 through the measurement of levels of beta-2-microglobulin (B2M) or T cell receptor alpha (TRAC) by flow cytometry in activated human PBMCs.
Figure 3B:
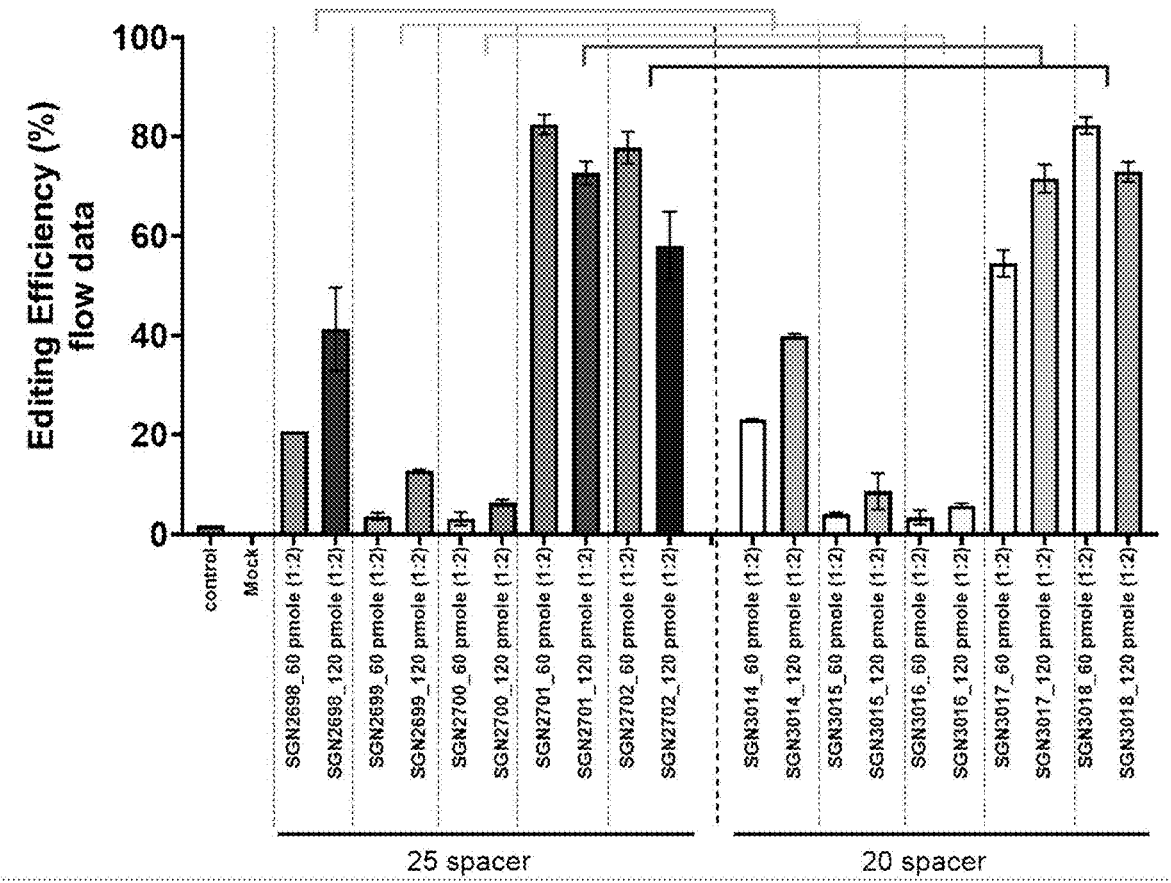

To understand if increasing concentration of RGN can effectively improve editing, different concentrations of RNP were provided in a PBMC cell editing experiment. The RNP concentrations tested were 60 pmole, 90 pmole and 120 pmole, with a protein:RNA ratio of 1:2. The results showed that with a working gRNA, the editing rate on the desired target can be improved with higher amounts of RGN (see Table 20 and FIGS. 3A and 3B).

TABLE 20 sgRNAs used for RNP dose dependence experiments

| SGN name | SGN target sequence SEQ ID NO |
|---|---|
| SGN002699 | 515 |
| SGN003014 | 477 |
| SGN003015 | 478 |
| SGN003016 | 479 |
| SGN003017 | 480 |
| SGN003018 | 481 |
| SGN002707 | 517 |
| SGN003019 | 482 |
| SGN003020 | 483 |
| SGN003021 | 484 |
| SGN003022 | 485 |
| SGN003023 | 486 |

Example 12: Off Target Analysis

To assess the specificity of the nucleases, off target editing was determined at potential sites identified via bioinformatics. Potential off target sites for LPG10145 were identified by targets with less than five mismatches in the target sequence and at least one residue match in the PAM sequence.

The same methods as those described in Example 11.1 for RNP delivery to mammalian cells and amplicon sequencing were used to test the specificity and off target editing of LPG10145. In samples with high editing rates for SGN003017 and SGN003023, the potential off target locations in Table 21 were assayed for potential editing. The primers in Table 22 were used to amplify potential off target sites with sequence similarity to the on target site to look for off target editing.

TABLE 21

Off target sequences assayed

| SGN | Off target Number | Off target seq | SEQ ID |
|---|---|---|---|
| SGN003017 | 3017-1 | TGTCCACGGAGCGAGACAGGGAGG | 518 |
| SGN003023 | 3023-1 | ATAGGCAGACAAACTTGTATAGG | 519 |

TABLE 21-continued

Off target sequences assayed

| SGN | Off target Number | Off target seq | SEQ ID |
|---|---|---|---|
| SGN003023 | 3023-2 | ATAGGCAGACAGACTTGCAGAGG | 520 |
| SGN003023 | 3023-3 | ACAGGCAGACAGATTTGTCAGAGG | 521 |
| SGN003023 | 3023-4 | AAAGGCAGACAGACATGTCAGTGG | 522 |
| SGN003023 | 3023-5 | CTAGGCAGACAGACTTCCTTCCTAGG | 523 |
| SGN003023 | 3023-6 | ATGGGGCAGACAGACTTGTCACAGG | 524 |
| SGN003023 | 3023-7 | ACAGGCAGACAGACTTGCATTTGG | 525 |
| SGN003023 | 3023-8 | ATAGGCAGACAGACTTGTTAGAAG | 526 |
| SGN003023 | 3023-9 | ATAGGTAGACAGACTTGTCAGTGA | 527 |

TABLE 22

Primers used to amplify off target regions

| Description | Primer sequence | SEQ ID |
|---|---|---|
| 3017-1 FWD | TCTTCGCCTGTGATCTCTGA | 528 |
| 3023-1 FWD | GCTAGTTCCAGCTGCCTAGG | 530 |
| 3023-2 FWD | TGAGCCCTTCTTCTGTGCTG | 532 |
| 3023-3 FWD | AGTGCTAGAGTGATGTGGGA | 534 |
| 3023-4 FWD | ATCTCCCTCAGTCCAGTCCC | 536 |
| 3023-5 FWD | CCAGAACATCAGCAGCAAGC | 538 |
| 3023-6 FWD | AAGGTGGGACTCACTCTGAA | 540 |
| 3023-7 FWD | CCCTCAGCTCTGACTCCTCT | 542 |
| 3023-8 FWD | CCTGTCAAGGGAGTGTTTCT | 544 |
| 3023-9 FWD | ATGCTCCGCTCCTTGATCTG | 546 |
| 3017-1 REV | TTGGATGGGATGTCCTGAGG | 529 |
| 3023-1 REV | CAGTGCGTTTCTCTGGTCCT | 531 |
| 3023-2 REV | CCTCCAGATCCCCACTACCA | 533 |
| 3023-3 REV | AGGTCACCTTTGTTGCCATC | 535 |
| 3023-4 REV | CCATCTCATCCAGTGCCCTC | 537 |
| 3023-5 REV | CCTGGGTCACTTCCTGTCAC | 539 |
| 3023-6 REV | ATTTTACTCAAGGCCCAGGC | 541 |
| 3023-7 REV | TGAACTCAGGACCACATGGC | 543 |
| 3023-8 REV | ATCCTTGCAATCCTCTGAAA | 545 |
| 3023-9 REV | TCATTCCCTCCCCACTTTCTC | 547 |

Using RNP delivery, there was no detectable off target editing at the two guides tested. Two off target locations showed low levels of background indels that were also seen in amplicons from unedited control cells. These off target locations were 3023-5 and 3023-9; denoted with an asterisks in Table 23.

TABLE 23

Off target editing for SGN003017 and SGN003023

| Delivery | Guide | On-Target Efficiency | Off-target Site | Off-target Editing |
|---|---|---|---|---|
| RNP | SGN003017 - B2M | 59% | 1 | 0% |
| RNP | SGN003023 - TRAC | 54% | 1 | 0% |
|  |  |  | 2 | 0% |
|  |  |  | 3 | 0% |
|  |  |  | 4 | 0.11% |
|  |  |  | 5 | 0.07%* |
|  |  |  | 6 | 0.49% |
|  |  |  | 7 | 0% |
|  |  |  | 8 | 0% |
|  |  |  | 9 | 0.14* |

Example 13: Glycine Scanning of LPG10145

Determination of Glycine Mutations and Insertions

The protein sequence of LPG10145 was run through the DynaMine webserver which provided an S2 prediction score for each residue, estimating rigidity and flexibility of that residue's backbone. Scores range from 1 (rigid) to 0 (highly dynamic). Residues with a score of <0.72 were mutated to glycine unless a nearby residue was a glycine rich region (defined as two glycines next to each other). Insertion sites for glycine were chosen as flexible regions with a score higher than 0.72 but less than 0.75 and that were adjacent to a glycine. These insertions sites were also mapped onto a LPG10145 homology model to check if they were predicted to be in flexible regions.

Screening Activity of LPG10145 Glycine Mutants in Mammalian Cells

Glycine mutants were compared with parental LPG10145 in their ability to edit exon 1 of beta-2-microglobulin (B2M) in HEK293T cells using two different guides (SGN003014 and SGN003018). These guides were chosen for their moderate to low levels of editing with the parental LPG10145 and were tested on saturating (optimal) editing conditions as well as non-saturating (sub-optimal) conditions. Optimal editing conditions were performed with plasmid lipofection using Lipofectamine 3000 of cells seeded the previous day at 10,000 cells and using 160 ng of plasmid encoding LPG10145 or LPG10145 variant and 40 ng of guide-encoding plasmid. Sub-optimal editing conditions were performed with plasmid lipofection of cells seeded the previous day at 10,000 cells using 40 ng of plasmid DNA encoding LPG10145 or LPG10145 variant and 40 ng of guide-encoding plasmid. Cells were incubated at 37° C. and 5% $CO_2$ for 2 days, genomic DNA extracted, and the target region amplified by PCR and submitted for NGS sequencing.

TABLE 24

Activity of LPG10145 Glycine Mutants

| LPG10145 Construct | Editing Normalized to WT (WT = 1) | | % Editing | |
| --- | --- | --- | --- | --- |
| | SGN003014 | SGN003018 | SGN003014 | SGN003018 |
| pLEM145v3.1 | 1 | 1 | 48.1* | 47.99* |
| S44G | 0.417464 | 0.760913 | 20.08 | 36.52 |
| S46G | 0.533056 | 0.715908 | 25.64 | 34.36 |
| A47G | 0.582952 | 0.86384 | 28.04 | 41.46 |
| S48G | 0.470686 | 0.784665 | 22.64 | 37.66 |
| R49G | 0.427651 | 0.663611 | 20.57 | 31.85 |
| N50G | 0.486071 | 0.823627 | 23.38 | 39.53 |
| E51G | 0.437006 | 0.816543 | 21.02 | 39.19 |
| E52G | 0.497089 | 0.779039 | 23.91 | 37.39 |
| F82G | 0.356133 | 0.97531 | 17.13 | 46.81 |
| P83G | 0.588773 | 0.879675 | 28.32 | 42.22 |
| F84G | 0.363825 | 0.711741 | 17.5 | 34.16 |
| P85G | 0.530977 | 0.590895 | 25.54 | 28.36 |
| N87G | 0.512266 | 0.661527 | 24.64 | 31.75 |
| T88G | 0.848233 | 1.050526 | 40.8 | 50.42 |
| A90G | 0.809979 | 1.05636 | 38.96 | 50.7 |
| N91G | 0.613929 | 0.94864 | 29.53 | 45.53 |
| S133G | 0.728067 | 0.943223 | 35.02 | 45.27 |
| N138G | 0.59106 | 0.89926 | 28.43 | 43.16 |
| L176G | 0.735759 | 0.831128 | 35.39 | 39.89 |
| E178G | 0.681289 | 0.979685 | 32.77 | 47.02 |
| P234G | 0.499376 | 1.005521 | 24.02 | 48.26 |
| S236G | 0.641372 | 0.921763 | 30.85 | 44.24 |
| E237G | 0.66736 | 0.874883 | 32.1 | 41.99 |
| K238G | 0.449688 | 0.653401 | 21.63 | 31.36 |
| S239G | 0.434719 | 0.699865 | 20.91 | 33.59 |
| S334G | 0.642204 | 0.965934 | 30.89 | 46.36 |
| P335G | 0.571102 | 0.891134 | 27.47 | 42.77 |
| A336G | 0.567775 | 0.996562 | 27.31 | 47.83 |
| P349G | 0.81684 | 1.158871 | 39.29 | 55.62 |
| V428G | 0.892931 | 1.282217 | 42.95 | 61.54 |
| K544G | 0.645946 | 0.936973 | 31.07 | 44.97 |
| Q623G | 0.72578 | 1.020106 | 34.91 | 48.96 |
| N624G | 0.645114 | 0.765496 | 31.03 | 36.74 |
| S647G | 0.707069 | 0.950099 | 34.01 | 45.6 |
| N740G | 0.798753 | 0.892385 | 38.42 | 42.83 |
| K741G | 0.124116 | 0.379623 | 5.97 | 18.22 |
| S742G | 0.57131 | 0.806126 | 27.48 | 38.69 |
| R743G | 0.44657 | 0.729243 | 21.48 | 35 |
| E744G | 0.975468 | 1.079487 | 46.92 | 51.81 |
| T745G | 0.66736 | 0.931972 | 32.1 | 44.73 |
| H746G | 0.646778 | 0.87905 | 31.11 | 42.19 |
| M827G | 0.804366 | 1.009063 | 38.69 | 48.43 |
| N828G | 0.573181 | 0.736118 | 27.57 | 35.33 |
| V844G | 0.811019 | 1.010314 | 39.01 | 48.49 |
| P910G | 0.778794 | 1.091572 | 37.46 | 52.39 |
| N911G | 0.862162 | 1.035733 | 41.47 | 49.71 |
| N939G | 0.69605 | 0.981561 | 33.48 | 47.11 |
| N940G | 0.478378 | 0.624857 | 23.01 | 29.99 |
| P942G | 0.418295 | 0.652985 | 20.12 | 31.34 |
| N1044G | 0.632848 | 1.013647 | 30.44 | 48.65 |
| N1058G | 0.980873 | 0.905928 | 47.18 | 43.48 |
| P1059G | 0.597713 | 0.925721 | 28.75 | 44.43 |
| A1060G | 0.755094 | 1.068236 | 36.32 | 51.27 |
| G429 | 0.822661 | 1.020523 | 39.57 | 48.98 |
| G473 | 0.707692 | 1.057819 | 34.04 | 50.77 |
| G592 | 0.729314 | 0.777164 | 35.08 | 37.3 |
| G845 | 0.834096 | 0.945515 | 40.12 | 45.38 |
| G930 | 0.797089 | 1.009689 | 38.34 | 48.46 |

*Editing for the parental WT control is an average of two replicates

Example 14: Robustness Testing of LPG10145

Example 14.1: Screening LPG10145 Editing at Multiple Target Loci in Mammalian Cells by Plasmid Delivery Guides targeting several genes were designed for robustness testing in HEK293T cells by plasmid delivery. These guides were tested under optimal editing conditions for HEK293T cells in a 96-well plate which involved seeding 10,000 cells on day 1, lipofection using Lipofectamine 3000 on day 2, and genomic DNA extraction on day 4. Lipofections were performed by mixing 160 ng of LPG10145-encoding plasmid and 40 ng of guide-encoding plasmid, and 0.4 µl of p3000 in Opti-MEM. Then, 0.3 µl of Lipofectamine 3000 diluted in Opti-MEM was added to the plasmid mixture and incubated for 15 mins before adding to cells. Regions around the editing site for each guide are amplified from the extracted genomic DNA and sequenced by NGS as described in Example 4. The editing efficiency of LPG10145 with each guide is reported as percent editing (percent of INDELS at the target site). Out of 32 guides tested, LPG10145 exhibited editing greater than 20% with 43.7% of the guides (14/32 guides) and had editing over 10% at 53% of guides tested (17/32 guides).

TABLE 25

Robust editing by LPG10145 by plasmid delivery in HEK293T cells

| Guide | Gene Name | % Editing | Replicates per guide |
| --- | --- | --- | --- |
| SGN006164 | Gene A | 0.6 | 1 |
| SGN006165 | Gene A | 1.07 | 1 |
| SGN006166 | Gene A | 17.83 | 1 |
| SGN006167 | Gene A | 4.86 | 1 |
| SGN006168 | Gene A | 0.78 | 1 |
| SGN006169 | Gene A | 6.315 | 2 |
| SGN006170 | Gene A | 40.59 | 2 |
| SGN002707 | TRAC | 34.87 | 2 |
| SGN002703 | TRAC | 6.555 | 2 |
| SGN006172 | TRAC | 29.745 | 2 |
| SGN006173 | TRAC | 31.86 | 2 |
| SGN006174 | TRAC | 26.595 | 2 |
| SGN006175 | TRAC | 20.83 | 2 |
| SGN006176 | B2M | 9.61 | 2 |
| SGN002700 | B2M | 10.615 | 2 |
| SGN006178 | B2M | 23.975 | 2 |
| SGN006179 | B2M | 45.445 | 2 |
| SGN006180 | B2M | 0.895 | 2 |
| SGN006181 | B2M | 4.465 | 2 |
| SGN006182 | B2M | 32.365 | 2 |
| SGN006183 | Gene B | 5.595 | 2 |
| SGN006184 | Gene B | 11.065 | 2 |
| SGN006185 | Gene B | 9.09 | 2 |
| SGN006186 | Gene B | 22.7 | 2 |
| SGN006187 | Gene C | 31.87 | 2 |
| SGN006188 | Gene C | 0.065 | 2 |
| SGN006189 | Gene C | 35.725 | 2 |
| SGN006190 | Gene C | 4.325 | 2 |
| SGN006192 | Gene C | 3.4 | 2 |
| SGN006193 | Gene C | 2.24 | 1 |
| SGN003014 | B2M | 34.41 | 2 |
| SGN003018 | B2M | 56.51 | 2 |

Example 15: LPG10145 Reproducibility Screening

Figure 4:
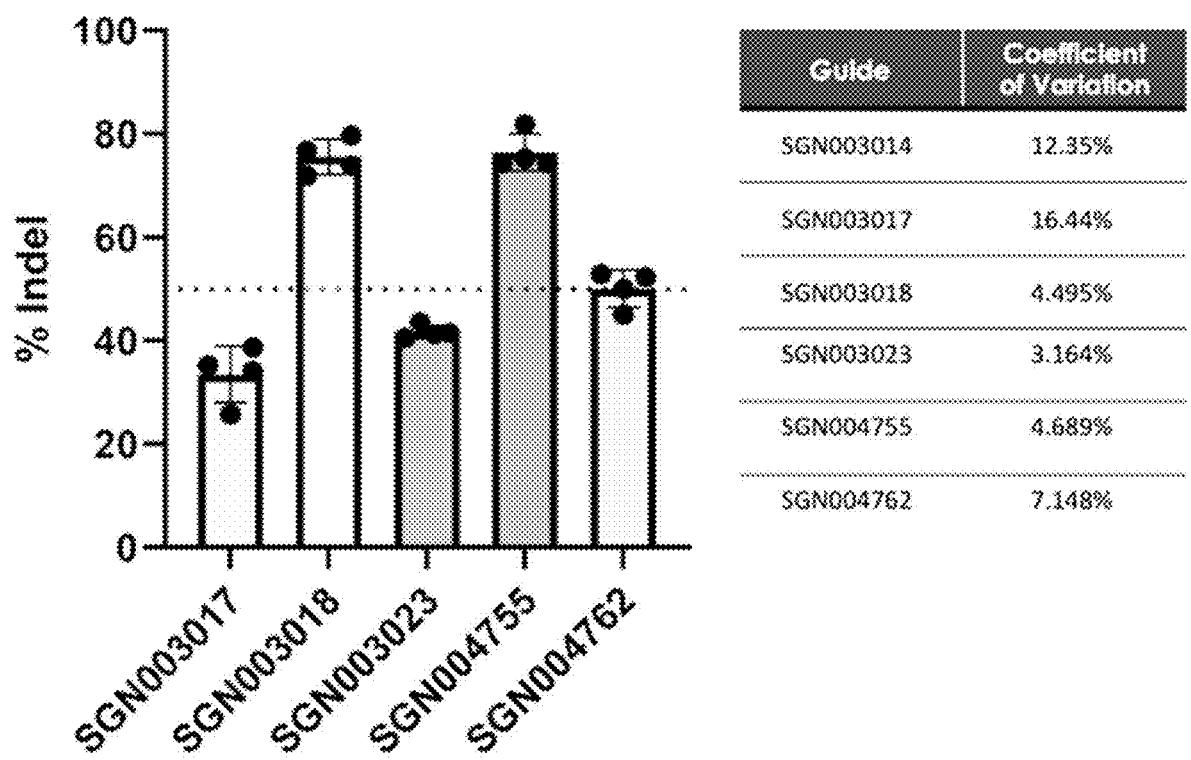
FIG. 4 shows that LPG10145 can edit targets in multiple genes. LPG10145 was delivered as an RNP to T cells through nucleofection. All guides exhibited a coefficient of variation (CV) of less than 50%.

To evaluate LPG10145 editing reproducibility, LPG10145 was delivered as a ribonucleoprotein complex in T cells through nucleofection. Methods for RNP delivery and experimental read out through amplicon sequencing were carried out as described in Example 11. Here, multiple sgRNA targeting different genes were utilized to show the reproducibility of LPG10145 editing with all guides returning a coefficient of variation (CV) value of less than 50% (FIG. 4).

That which is claimed:

1. A nucleic acid molecule comprising a polynucleotide encoding an RNA-guided nuclease (RGN) polypeptide, wherein said RGN polypeptide comprises an amino acid sequence having at least 90% sequence identity to SEQ ID NO: 2;
wherein said polynucleotide encoding an RGN polypeptide is operably linked to a regulatory region heterologous to said polynucleotide.

2. The nucleic acid molecule of claim 1, wherein said RGN polypeptide comprises an amino acid sequence having at least 95% sequence identity to SEQ ID NO: 2.

3. The nucleic acid molecule of claim 1, wherein said RGN polypeptide comprises the amino acid sequence set forth as SEQ ID NO: 2.

4. The nucleic acid molecule of claim 1, wherein said RGN polypeptide is nuclease inactive or is a nickase.

5. The nucleic acid molecule of claim 1, wherein said RGN polypeptide comprises an amino acid other than D at amino acid position 11 and/or comprises an amino acid other than H at amino acid position 603 corresponding to the amino acid positions of SEQ ID NO: 2, when said RGN polypeptide is aligned to SEQ ID NO: 2 for maximum sequence identity.

6. The nucleic acid molecule of claim 1, wherein the RGN polypeptide is operably fused to an effector domain.

7. The nucleic acid molecule of claim 6, wherein the effector domain comprises a cleavage domain, a deaminase domain, or an expression modulator domain.

8. The nucleic acid molecule of claim 6, wherein the effector domain is operably fused at the N-terminus, the C-terminus, or at an internal location of said RGN polypeptide.

9. The nucleic acid molecule of claim 1, wherein the RGN polypeptide is operably linked to a prime editing polypeptide or a base-editing polypeptide, optionally wherein said prime editing polypeptide comprises a DNA polymerase or a reverse transcriptase, or optionally wherein said base-editing polypeptide comprises a deaminase.

10. A vector comprising the nucleic acid molecule of claim 1.

11. The vector of claim 10, further comprising at least one nucleotide sequence encoding a guide RNA capable of hybridizing to a target DNA sequence.

12. The vector of claim 11, wherein the guide RNA comprises:
  i) a CRISPR RNA comprising a CRISPR repeat sequence having at least 90% sequence identity to SEQ ID NO: 14; and
  ii) a tracrRNA having at least 90% sequence identity to SEQ ID NO: 26;
  wherein said RGN polypeptide comprises an amino acid sequence having at least 90% sequence identity to SEQ ID NO: 2.

13. A cell comprising the nucleic acid molecule of claim 1.

14. A system for binding a target DNA sequence of a DNA molecule, said system comprising:
  a) one or more guide RNAs (gRNAs), or one or more polynucleotides comprising one or more nucleotide sequences encoding the one or more gRNAs; and
  b) the nucleic acid molecule of claim 1;
  wherein at least one of said one or more nucleotide sequences encoding the one or more gRNAs is operably linked to a promoter heterologous to said nucleotide sequence.

15. The system of claim 14, wherein said RGN polypeptide is nuclease inactive or is a nickase.

16. The system of claim 14, wherein the RGN polypeptide is operably linked to a prime editing polypeptide or a base-editing polypeptide, optionally wherein said prime editing polypeptide comprises a DNA polymerase or a reverse transcriptase, or optionally wherein said base-editing polypeptide comprises a deaminase.

17. A cell comprising the system of claim 14.

18. A method for binding a target DNA sequence of a DNA molecule comprising delivering a system of claim 2 to a cell comprising the target DNA sequence.

19. The nucleic acid molecule of claim 1, wherein said regulatory region comprises a promoter.

20. The nucleic acid molecule of claim 1, wherein said regulatory region comprises a transcriptional regulatory region or a translational termination region.

21. The nucleic acid molecule of claim 1, wherein said polynucleotide encoding an RGN polypeptide is an mRNA.

22. The method of claim 18, wherein said RGN polypeptide is capable of cleaving said target DNA sequence to produce a modified target DNA sequence.

23. The method of claim 22, wherein cleavage by said RGN polypeptide generates a double-stranded break.

24. The method of claim 22, wherein cleavage by said RGN polypeptide generates a single-stranded break.

25. The method of claim 22, wherein said modified target DNA sequence comprises:
  insertion of heterologous DNA into the target DNA sequence; or
  deletion of at least one nucleotide from the target DNA sequence.

26. The method of claim 22, wherein said modified target DNA sequence comprises mutation of at least one nucleotide in the target DNA sequence.

27. The method of claim 18, wherein said cell is a eukaryotic cell.

28. The method of claim 18, wherein said one or more gRNAs is a single guide RNA.

29. The method of claim 28, wherein said single guide RNA further comprises an extension comprising an edit template for prime editing.

* * * * *